United States Patent
Wang et al.

(10) Patent No.: US 9,422,271 B2
(45) Date of Patent: Aug. 23, 2016

(54) PYRIMIDINE COMPOUNDS AS TUBERCULOSIS INHIBITORS

(71) Applicant: Vertex Pharmaceuticals Incorporated, Cambridge, MA (US)

(72) Inventors: Tiansheng Wang, Concord, MA (US); Brian Hanzelka, Iowa City, IA (US); Ute Muh, Iowa City, IA (US); Guy Bemis, Arlington, MA (US); Harmon J. Zuccola, Westwood, MA (US)

(73) Assignee: Vertex Pharmaceuticals Incorporated, Boston, MA (US)

( * ) Notice: Subject to any disclaimer, the term of this patent is extended or adjusted under 35 U.S.C. 154(b) by 178 days.

(21) Appl. No.: 14/068,606

(22) Filed: Oct. 31, 2013

(65) Prior Publication Data

US 2014/0249137 A1 Sep. 4, 2014

Related U.S. Application Data

(63) Continuation of application No. 12/855,263, filed on Aug. 12, 2010, now abandoned.

(60) Provisional application No. 61/234,063, filed on Aug. 14, 2009.

(51) Int. Cl.

| | |
|---|---|
| *C07D 403/12* | (2006.01) |
| *A61K 31/519* | (2006.01) |
| *C07D 403/14* | (2006.01) |
| *C07D 409/14* | (2006.01) |
| *C07D 487/04* | (2006.01) |
| *A61K 31/506* | (2006.01) |
| *A61K 31/5377* | (2006.01) |
| *A61K 31/551* | (2006.01) |
| *C07D 401/14* | (2006.01) |
| *C07D 405/14* | (2006.01) |
| *C07D 417/14* | (2006.01) |
| *C07D 487/14* | (2006.01) |
| *C07D 487/16* | (2006.01) |

(52) U.S. Cl.
CPC ............ *C07D 403/12* (2013.01); *A61K 31/506* (2013.01); *A61K 31/519* (2013.01); *A61K 31/5377* (2013.01); *A61K 31/551* (2013.01); *C07D 401/14* (2013.01); *C07D 403/14* (2013.01); *C07D 405/14* (2013.01); *C07D 409/14* (2013.01); *C07D 417/14* (2013.01); *C07D 487/04* (2013.01); *C07D 487/14* (2013.01); *C07D 487/16* (2013.01)

(58) Field of Classification Search
None
See application file for complete search history.

(56) References Cited

FOREIGN PATENT DOCUMENTS

| | | |
|---|---|---|
| WO | 0222602 A1 | 3/2002 |
| WO | 0222607 A1 | 3/2002 |
| WO | 2004078733 A1 | 9/2004 |
| WO | 2005040159 A1 | 5/2005 |
| WO | 2006074057 A1 | 7/2006 |
| WO | 2006106306 A1 | 10/2006 |
| WO | 2006106307 A1 | 10/2006 |
| WO | 2007023382 A1 | 3/2007 |
| WO | 2007129195 | * 11/2007 |

OTHER PUBLICATIONS

International Search Report, PCT/US2010/002244, mailed Oct. 6, 2010.
Written Opinion of the International Searching Authority (PCT Rule 43bis.1), PCT/US2010/002244, mailed Feb. 23, 2012.
Bebbington, D., et al., "The discovery of the potent aurora inhibitor MK-0457 (VX-680)", Bioorg. & Med. Chem. Ltrs., vol. 19, No. 13, Jul. 1, 2009, pp. 3586-3592.

* cited by examiner

*Primary Examiner* — Noble Jarrell
(74) *Attorney, Agent, or Firm* — Michael C. Badia

(57) ABSTRACT

The present invention relates to compounds useful as inhibitors of treating tuberculosis. The invention also provides processes for preparing compounds of the invention.

16 Claims, No Drawings

PYRIMIDINE COMPOUNDS AS TUBERCULOSIS INHIBITORS

CROSS-REFERENCE TO RELATED APPLICATIONS

The present application claims priority under 35 U.S.C. §119 to U.S. Provisional Application No. 61/234,063, filed Aug. 14, 2009 and entitled "PYRIMIDINE COMPOUNDS AS TUBERCULOSIS INHIBITORS," the entire contents of which is incorporated herein by reference.

FIELD OF THE INVENTION

This invention relates to pyrimine compound and their derivatives and to the use of these compounds as an inhibitor for human and non-humans against *Mycobacterium tuberculosis*.

BACKGROUND OF THE INVENTION

The infectious disease, tuberculosis (TB), is the leading cause of death worldwide from a single human pathogen, claiming more adult lives than diseases such as acquired immunodeficiency syndrome (AIDS), malaria, diarrhea, leprosy and all other tropical diseases combined (Zumla A, Grange J. B M J (1998) 316, 1962-1964). About one third of the world's population is currently infected with *M. tuberculosis*; 10% of those infected will develop clinical diseases, particularly those who also have the human immunodeficiency virus (HIV) infection (Zumla A, Grange J. B M J (1998) 316, 1962-1964). With the discovery of effective anti-mycobacterial agents (including ethambutol, isoniazid, pyrazinamide, rifampicin and streptomycin) and a reduction in poverty, there was a drastic decline in the number of TB cases, especially in developed nations. However, since the late 1980s, the number of cases of TB throughout the world has been increasing rapidly partly due to the emergence of multi-drug resistant *M. tuberculosis* (C. E. Barry, III, Biochemical Pharmacology (1997) 54, 1165-1172). According to the World Health Organization (World Health Organization. 1993 92. per Besra G S, Brennan P J. 1997. J Pharm Pharmacol 49 (Suppl. 1):25-30.s), it is expected that the annual death rate caused by TB will reach an overwhelming 3.5 million by the year 2000.

Thus, the TB problem requires urgent attention. Short course anti-TB regiments initially using at least three first-line drugs (including isoniazid, rifampicin and pyrazinamide) are often not effective due to an increase in the number of tuberculosis strains that have become resistant to current drugs. For example the World Health Organization (WHO) recently reported that the death rate of patients with multi-drug resistant (MDR) tuberculosis in the US was approximately 70%. Current treatment is also very expensive: a 3 drugs regimen is needed (more than $500/month cost per patient). Thus the major problems faced in tuberculosis control are poor infrastructures for diagnosis and drug supply. The failure of patients to complete therapy as well as inappropriate monotherapy has led to the emergence and distribution of strains of *Mycobacterium tuberculosis* resistant to every available chemotherapy (Bloom B R and Murray C J L, Science (1992) 257, 1055-1064). Such organisms will not remain confined to the Third World or to the poor and indigent of developed countries. The recent documentation of the spread of a single clone of multi-drug-resistant *Mycobacterium tuberculosis* (the "W" strain) throughout the continental United States and Europe highlights the danger of an airborne pathogen in our global society (Bifani P J, et al., JAMA (1996) 275, 452-457).

Consequently, there is a need for an anti-mycobacteria drug for humans and non-humans which are effective against human and non-human mycobacteria.

SUMMARY OF THE INVENTION

This invention provides, in general, compounds that are useful treating tuberculosis. In one embodiment, the present invention provides a method of treating tuberculosis, comprising the step of administering a patient a therapeutically effective amount of a compound of formula I

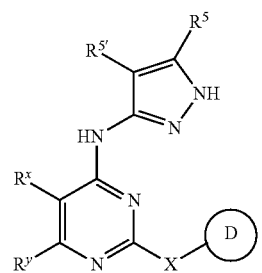

or a pharmaceutically acceptable salt thereof.

X is a bond or —N(R)—.

Ring D is a 5-7 membered monocyclic ring or 8-10 membered bicyclic ring selected from aryl, heteroaryl, heterocyclyl or carbocyclyl, said heteroaryl or heterocyclyl ring having 1-4 ring heteroatoms selected from nitrogen, oxygen or sulfur. Ring D is independently substituted at any substitutable ring carbon by oxo or —$R^5$, and at any substitutable ring nitrogen by —$R^4$, provided that when Ring D is a six-membered aryl or heteroaryl ring, —$R^5$ is hydrogen at each ortho carbon position of Ring D.

$R^x$ and $R^y$ are independently selected from T-$R^3$, or $R^x$ and $R^y$ are taken together with their intervening atoms to form a fused, unsaturated or partially unsaturated, 5-8 membered ring having 1-3 ring heteroatoms selected from oxygen, sulfur, or nitrogen. Any substitutable carbon on said fused ring is optionally and independently substituted by T-$R^3$, and any substitutable nitrogen on said ring is substituted by $R^4$.

T is a valence bond or a $C_{1-4}$ alkylidene chain.

$R^2$ and $R^{2'}$ are independently selected from —R, -T-W—$R^6$, or $R^2$ and $R^{2'}$ are taken together with their intervening atoms to form a fused, 5-8 membered, unsaturated or partially unsaturated, ring containing 0-3 ring heteroatoms selected from nitrogen, oxygen, or sulfur. The fused ring is optionally substituted by up to three groups independently selected from halo, oxo, —CN, —$NO_2$, —$R^7$, or —V—$R^6$.

$R^3$ is selected from —R, -halo, =O, —OR, —C(=O)R, —$CO_2$R, —COCOR, —$COCH_2$COR, —$NO_2$, —CN, —S(O)R, —$S(O)_2$R, —SR, —$N(R^4)_2$, —$CON(R^4)_2$, —$SO_2N(R^4)_2$, —OC(=O)R, —$N(R^4)$COR, —$N(R^4)CO_2$ (optionally substituted $C_{1-6}$ aliphatic), —$N(R^4)N(R^4)_2$, —C=$NN(R^4)_2$, —C=N—OR, —$N(R^4)CON(R^4)_2$, —$N(R^4)SO_2N(R^4)_2$, —$N(R^4)S$ $O_2$R, or —OC(=O)$N(R^4)_2$.

Each R is independently selected from hydrogen or an optionally substituted group selected from $C_{1-6}$ aliphatic, $C_{6-10}$ aryl, a heteroaryl ring having 5-10 ring atoms, or a heterocyclyl ring having 5-10 ring atoms.

Each $R^4$ is independently selected from —$R^7$, —$COR^7$, —$CO_2$ (optionally substituted $C_{1-6}$ aliphatic), —$CON(R^7)_2$, or —$SO_2R^7$, or two $R^4$ on the same nitrogen are taken together to form a 5-8 membered heterocyclyl or heteroaryl ring.

Each $R^5$ is independently selected from —R, halo, —OR, —C(=O)R, —$CO_2R$, —COCOR, —$NO_2$, —CN, —S(O)R, —$SO_2R$, —SR, —$N(R^4)_2$, —$CON(R^4)_2$, —$SO_2N(R^4)_2$, —OC(=O)R, —$N(R^4)COR$, —$N(R^4)CO_2$ (optionally substituted $C_{1-6}$ aliphatic), —$N(R^4)N(R^4)_2$, —C=$NN(R^4)_2$, —C=N—OR, —$N(R^4)CON(R^4)_2$, —$N(R^4)SO_2N(R^4)_2$, —$N(R^4)S$ $O_2R$, or —OC(=O)$N(R^4)_2$.

V is —O—, —S—, —SO—, —$SO_2$—, —$N(R^6)SO_2$—, —$SO_2N(R^6)$—, —$N(R^6)$—, —CO—, —$CO_2$—, —$N(R^6)$CO—, —$N(R^6)C(O)$ O—, —$N(R^6)CON(R^6)$—, —$N(R^6)SO_2N(R^6)$—, —$N(R^6)N(R^6)$—, —$C(O)N(R^6)$—, —OC(O)$N(R^6)$—, —$C(R^6)_2O$—, —$C(R^6)_2S$—, —$C(R^6)_2SO$—, —$C(R^6)_2SO_2$—, —$C(R^6)_2SO_2N(R^6)$—, —$C(R^6)_2N(R^6)$—, —$C(R^6)_2N(R^6)C(O)$—, —$C(R^6)_2N(R^6)C(O)O$—, —$C(R^6)$=$NN(R^6)$—, —$C(R^6)$=N—O—, —$C(R^6)_2N(R^6)N(R^6)$—, —$C(R^6)_2N(R^6)SO_2N(R^6)$—, or —$C(R^6)_2N(R^6)CON(R^6)$—.

W is —$C(R^6)_2O$—, —$C(R^6)_2S$—, —$C(R^6)_2SO$—, —$C(R^6)_2SO_2$—, —$C(R^6)_2SO_2N(R^6)$—, —$C(R^6)_2N(R^6)$—, —CO—, —$CO_2$—, —$C(R^6)OC(O)$—, —$C(R^6)OC(O)N(R^6)$—, —$C(R^6)_2N(R^6)CO$—, —$C(R^6)_2N(R^6)C(O)O$—, —$C(R^6)$=$NN(R^6)$—, —$C(R^6)$=N—O—, —$C(R^6)_2N(R^6)N(R^6)$—, —$C(R^6)_2N(R^6)SO_2N(R^6)$—, —$C(R^6)_2N(R^6)CON(R^6)$—, or —$CON(R^6)$—.

Each $R^6$ is independently selected from hydrogen or an optionally substituted $C_{1-4}$ aliphatic group, or two $R^6$ groups on the same nitrogen atom are taken together with the nitrogen atom to form a 5-6 membered heterocyclyl or heteroaryl ring.

Each $R^7$ is independently selected from hydrogen or an optionally substituted $C_{1-6}$ aliphatic group, or two $R^7$ on the same nitrogen are taken together with the nitrogen to form a 5-8 membered heterocyclyl ring or heteroaryl.

In one embodiment, the compounds of the present invention are represented by structural formula II:

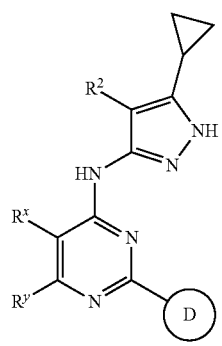

II or a pharmaceutically acceptable salt thereof, wherein.

Ring D is a 5-7 membered monocyclic ring or 8-10 membered bicyclic ring selected from aryl, heteroaryl, heterocyclyl or carbocyclyl, said heteroaryl or heterocyclyl ring having 1-4 ring heteroatoms selected from nitrogen, oxygen or sulfur. Ring D is independently substituted at any substitutable ring carbon by oxo or —$R^5$, and at any substitutable ring nitrogen by —$R^4$.

$R^x$ and $R^y$ are independently selected from T-$R^3$, or $R^x$ and $R^y$ are taken together with their intervening atoms to form a fused, unsaturated or partially unsaturated, 5-8 membered ring having 1-3 ring heteroatoms selected from oxygen, sulfur, or nitrogen. Any substitutable carbon on said fused ring is optionally and independently substituted by T-$R^3$, and any substitutable nitrogen on said ring is substituted by $R^4$.

T is a valence bond or a $C_{1-4}$ alkylidene chain.

$R^2$ is independently selected from —R, -T-W—$R^6$.

$R^3$ is selected from —R, -halo, =O, —OR, —C(=O)R, —$CO_2R$, —COCOR, —$COCH_2COR$, —$NO_2$, —CN, —S(O)R, —$S(O)_2R$, —SR, —$N(R^4)_2$, —$CON(R^4)_2$, —$SO_2N(R^4)_2$, —OC(=O)R, —$N(R^4)COR$, —$N(R^4)CO_2$ (optionally substituted $C_{1-6}$ aliphatic), —$N(R^4)N(R^4)_2$, —C=$NN(R^4)_2$, —C=N—OR, —$N(R^4)CON(R^4)_2$, —$N(R^4)SO_2N(R^4)_2$, —$N(R^4)S$ $O_2R$, or —OC(=O)$N(R^4)_2$.

Each R is independently selected from hydrogen or an optionally substituted group selected from $C_{1-6}$ aliphatic, $C_{6-10}$ aryl, a heteroaryl ring having 5-10 ring atoms, or a heterocyclyl ring having 5-10 ring atoms.

Each $R^4$ is independently selected from —$R^7$, —$COR^7$, —$CO_2$ (optionally substituted $C_{1-6}$ aliphatic), —$CON(R^7)_2$, or —$SO_2R^7$, or two $R^4$ on the same nitrogen are taken together to form a 5-8 membered heterocyclyl or heteroaryl ring.

Each $R^5$ is independently selected from —R, halo, —OR, —C(=O)R, —$CO_2R$, —COCOR, —$NO_2$, —CN, —S(O)R, —$SO_2R$, —SR, —$N(R^4)_2$, —$CON(R^4)_2$, —$SO_2N(R^4)_2$, —OC(=O)R, —$N(R^4)COR$, —$N(R^4)CO_2$ (optionally substituted $C_{1-6}$ aliphatic), —$N(R^4)N(R^4)_2$, —C=$NN(R^4)_2$, —C=N—OR, —$N(R^4)CON(R^4)_2$, —$N(R^4)SO_2N(R^4)_2$, —$N(R^4)S$ $O_2R$, or —OC(=O)$N(R^4)_2$.

V is —O—, —S—, —SO—, —$SO_2$—, —$N(R^6)SO_2$—, —$SO_2N(R^6)$—, —$N(R^6)$—, —CO—, —$CO_2$—, —$N(R^6)$CO—, —$N(R^6)C(O)$ O—, —$N(R^6)CON(R^6)$—, —$N(R^6)SO_2N(R^6)$—, —$N(R^6)N(R^6)$—, —$C(O)N(R^6)$—, —OC(O)$N(R^6)$—, —$C(R^6)_2O$—, —$C(R^6)_2S$—, —$C(R^6)_2SO$—, —$C(R^6)_2SO_2$—, —$C(R^6)_2SO_2N(R^6)$—, —$C(R^6)_2N(R^6)$—, —$C(R^6)_2N(R^6)C(O)$—, —$C(R^6)_2N(R^6)C(O)O$—, —$C(R^6)$=$NN(R^6)$—, —$C(R^6)$=N—O—, —$C(R^6)_2N(R^6)N(R^6)$—, —$C(R^6)_2N(R^6)SO_2N(R^6)$—, or —$C(R^6)_2N(R^6)CON(R^6)$—.

W is —$C(R^6)_2O$—, —$C(R^6)_2S$—, —$C(R^6)_2SO$—, —$C(R^6)_2SO_2$—, —$C(R^6)_2SO_2N(R^6)$—, —$C(R^6)_2N(R^6)$—, —CO—, —$C(R^6)OC(O)$—, —$C(R^6)OC(O)N(R^6)$—, —$C(R^6)_2N(R^6)CO$—, —$C(R^6)_2N(R^6)C(O)O$—, —$C(R^6)$=$NN(R^6)$—, —$C(R^6)$=N—O—, —$C(R^6)_2N(R^6)N(R^6)$—, —$C(R^6)_2N(R^6)SO_2N(R^6)$—, —$C(R^6)_2N(R^6)CON(R^6)$—, or —$CON(R^6)$—.

Each $R^6$ is independently selected from hydrogen or an optionally substituted $C_{1-4}$ aliphatic group, or two $R^6$ groups on the same nitrogen atom are taken together with the nitrogen atom to form a 5-6 membered heterocyclyl or heteroaryl ring.

Each $R^7$ is independently selected from hydrogen or an optionally substituted $C_{1-6}$ aliphatic group, or two $R^7$ on the same nitrogen are taken together with the nitrogen to form a 5-8 membered heterocyclyl ring or heteroaryl.

In one embodiment the present invention is the manufacture of a compound, a pharmaceutically acceptable salt thereof, or composition of the present invention for use in treating or preventing a protein kinase-mediated condition in a subject.

In another embodiment, the compounds, pharmaceutically acceptable salts thereof, and compositions of the present invention are also useful for the study of kinases in biological and pathological phenomena; the study of intracellular signal transduction pathways mediated by such kinases; and the comparative evaluation of new kinase inhibitors.

DETAILED DESCRIPTION OF THE INVENTION

This invention relates to compounds, pharmaceutically acceptable salts thereof, and compositions (such as, pharmaceutical compositions) useful as protein kinase inhibitors.

In one embodiment, the compounds, pharmaceutically acceptable salts thereof, and compositions of the present invention are effective as inhibitors of PKCtheta.

Compounds of this invention include those described generally herein, and are further illustrated by the classes, subclasses, and species disclosed herein. As used herein, the definitions defined herein shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5th Ed., Ed.: Smith, M. B. and March, J., John Wiley & Sons, New York: 2001, the entire contents of which are hereby incorporated by reference.

The present invention provides a first method of treating tuberculosis, comprising the step of administering a patient a therapeutically effective amount of a compound of formula I

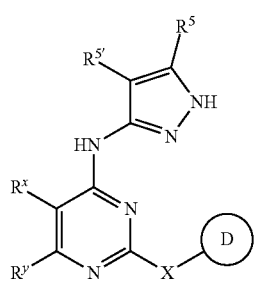

I or a pharmaceutically acceptable salt thereof.

X is a bond or —N(R)—.

Ring D is a 5-7 membered monocyclic ring or 8-10 membered bicyclic ring selected from aryl, heteroaryl, heterocyclyl or carbocyclyl, said heteroaryl or heterocyclyl ring having 1-4 ring heteroatoms selected from nitrogen, oxygen or sulfur. Ring D is independently substituted at any substitutable ring carbon by oxo or —R$^5$, and at any substitutable ring nitrogen by —R$^4$, provided that when Ring D is a six-membered aryl or heteroaryl ring, —R$^5$ is hydrogen at each ortho carbon position of Ring D.

R$^x$ and R$^y$ are independently selected from T-R$^3$, or R$^x$ and R$^y$ are taken together with their intervening atoms to form a fused, unsaturated or partially unsaturated, 5-8 membered ring having 1-3 ring heteroatoms selected from oxygen, sulfur, or nitrogen. Any substitutable carbon on said fused ring is optionally and independently substituted by T-R$^3$, and any substitutable nitrogen on said ring is substituted by R$^4$.

T is a valence bond or a C$_{1-4}$ alkylidene chain.

R$^2$ and R$^{2'}$ are independently selected from —R, -T-W—R$^6$, or R$^2$ and R$^{2'}$ are taken together with their intervening atoms to form a fused, 5-8 membered, unsaturated or partially unsaturated, ring containing 0-3 ring heteroatoms selected from nitrogen, oxygen, or sulfur. The fused ring is optionally substituted by up to three groups independently selected from halo, oxo, —CN, —NO$_2$, —R$^7$, or —V—R$^6$.

R$^3$ is selected from —R, -halo, =O, —OR, —C(=O)R, —CO$_2$R, —COCOR, —COCH$_2$COR, —NO$_2$, —CN, —S(O)R, —S(O)$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$ (optionally substituted C$_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)S O$_2$R, or —OC(=O)N(R$^4$)$_2$.

Each R is independently selected from hydrogen or an optionally substituted group selected from C$_{1-6}$ aliphatic, C$_{6-10}$ aryl, a heteroaryl ring having 5-10 ring atoms, or a heterocyclyl ring having 5-10 ring atoms.

Each R$^4$ is independently selected from —R$^7$, —COR$^7$, —CO$_2$ (optionally substituted C$_{1-6}$ aliphatic), —CON(R$^7$)$_2$, or —SO$_2$R$^7$, or two R$^4$ on the same nitrogen are taken together to form a 5-8 membered heterocyclyl or heteroaryl ring.

Each R$^5$ is independently selected from —R, halo, —OR, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$ (optionally substituted C$_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)S O$_2$R, or —OC(=O)N(R$^4$)$_2$.

V is —O—, —S—, —SO—, —SO$_2$—, —N(R$^6$)SO$_2$—, —SO$_2$N(R$^6$)—, —N(R$^6$)—, —CO—, —CO$_2$—, —N(R$^6$)CO—, —N(R$^6$)C(O) O—, —N(R$^6$)CON(R$^6$)—, —N(R$^6$)SO$_2$N(R$^6$)—, —N(R$^6$)N(R$^6$)—, —C(O)N(R$^6$)—, —OC(O)N(R$^6$)—, —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —C(R$^6$)$_2$N(R$^6$)C(O)—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, or —C(R$^6$)$_2$N(R$^6$)CON(R$^6$)—.

W is —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —CO—, —CO$_2$—, —C(R$^6$)OC(O)—, —C(R$^6$)OC(O)N(R$^6$)—, —C(R$^6$)$_2$N(R$^6$)CO—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, —C(R$^6$)$_2$N(R$^6$)CON(R$^6$)—, or —CON(R$^6$)—.

In certain embodiment of the method, X is a bond.

In certain embodiment of the method, the compound has one or more features selected from the group consisting of:

(a) Ring D is an optionally substituted ring selected from a phenyl, pyridinyl, piperidinyl, piperazinyl, pyrrolidinyl, thienyl, azepanyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl ring;

(b) R$^x$ is hydrogen or C$_{1-4}$ aliphatic and R$^y$ is T-R$^3$, or R$^x$ and R$^y$ are taken together with their intervening atoms to form an optionally substituted 5-7 membered unsaturated or partially unsaturated ring having 1-2 ring heteroatoms; and (c) R$^2$ is hydrogen or methyl and R$^{2'}$ is T-W—R$^6$ or R, wherein W is —C(R$^6$)$_2$O—, —C(R$^6$)$_2$N(R$^6$)—, —CO—, —C(R$^6$)OC(O)—, —C(R$^6$)$_2$N(R$^6$)CO—, —C(R$^6$)$_2$N(R$^6$)C(O)O—, or —CON(R$^6$)—, and R is an optionally substituted group selected from C$_{1-6}$ aliphatic or phenyl, or R$^2$ and R$^{2'}$ are taken together with their intervening atoms to form a substituted or unsubstituted benzo, pyrido, pyrimido, or partially unsaturated 6-membered carbocyclo ring.

In certain embodiment, the compound has the features of (a), (b) and (c).

In certain embodiment of the method, the compound has one or more features selected from the group consisting of:

(a) Ring D is an optionally substituted ring selected from a phenyl, pyridinyl, piperidinyl, piperazinyl, pyrrolidinyl, morpholinyl, 1,2,3,4-tetrahydroisoquinolinyl, 1,2,3,4-tetrahydroquinolinyl, 2,3-dihydro-1H-isoindolyl, 2,3-dihydro-1H-indolyl, isoquinolinyl, quinolinyl, or naphthyl ring;

(b) $R^x$ is hydrogen or methyl and $R^y$ is —R, $N(R^4)_2$, or —OR, or $R^x$ and $R^y$ are taken together with their intervening atoms to form a 5-7 membered unsaturated or partially unsaturated ring having 1-2 ring nitrogens, wherein said ring is optionally substituted with —R, halo, oxo, —OR, —C(=O)R, —$CO_2R$, —COCOR, —$NO_2$, —CN, —S(O)R, —$SO_2R$, —SR, —$N(R^4)_2$, —$CON(R^4)_2$, —$SO_2N(R^4)_2$, —OC(=O)R, —$N(R^4)COR$, —$N(R^4)CO_2$ (optionally substituted $C_{1-6}$ aliphatic), —$N(R^4)N(R^4)_2$, —C=$NN(R^4)_2$, —C=N—OR, —$N(R^4)CON(R^4)_2$, —$N(R^4)SO_2N(R^4)_2$, —$N(R^4)S O_2R$, or —OC(=O)$N(R^4)_2$; and (c) each $R^5$ is independently selected from halo, oxo, CN, $NO_2$, —$N(R^4)_2$, —$CO_2R$, —$CONH(R^4)$, —$N(R^4)COR$, —$SO_2N(R^4)_2$, —$N(R^4)SO_2R$, —SR, —OR, —C(O)R, or a substituted or unsubstituted group selected from 5-6 membered heterocyclyl, $C_{6-10}$ aryl, or $C_{1-6}$ aliphatic.

In certain embodiment, the compound has the features of (a), (b) and (c).

In certain embodiment of the method, compound has one or more features selected from the group consisting of:
- (a) IV and $R^y$ are taken together with their intervening atoms to form a 6-membered unsaturated or partially unsaturated ring having 1-2 ring nitrogens, optionally substituted with halo, CN, oxo, $C_{1-6}$ alkyl, $C_{1-6}$ alkoxy, ($C_{1-6}$ alkyl)carbonyl, ($C_{1-6}$ alkyl)sulfonyl, mono- or dialkylamino, mono- or dialkylaminocarbonyl, mono- or dialkylaminocarbonyloxy, or 5-6 membered heteroaryl;
- (b) each $R^5$ is independently selected from -halo, —CN, -oxo, —SR, —OR, —$N(R^4)_2$, —C(O)R, or a substituted or unsubstituted group selected from 5-6 membered heterocyclyl, $C_{6-10}$ aryl, and $C_{1-6}$ aliphatic; and
- (c) $R^{2'}$ is hydrogen and $R^2$ is T-W—$R^6$ or R, wherein W is —$C(R^6)_2O$—, —$C(R^6)_2N(R^6)$—, —CO—, —$C(R^6)OC(O)$—, —$C(R^6)_2N(R^6)CO$—, or —$CON(R^6)$—, and R is an optionally substituted group selected from $C_{1-6}$ aliphatic or phenyl, or $R^2$ and $R^{2'}$ are taken together with their intervening atoms to form a substituted or unsubstituted benzo, pyrido, or partially unsaturated 6-membered carbocyclo ring optionally substituted with -halo, oxo, —$N(R^4)_2$, —$C_{1-4}$ alkyl, —$C_{1-4}$ haloalkyl, —$NO_2$, —O($C_{1-4}$ alkyl), —$CO_2(C_{1-4}$ alkyl), —CN, —$SO_2(C_{1-4}$ alkyl), —$SO_2NH_2$, —OC(O)$NH_2$, —$NH_2SO_2(C_{1-4}$ alkyl), —NHC(O)($C_{1-4}$ alkyl), —C(O)$NH_2$, or —CO($C_{1-4}$ alkyl), wherein the ($C_{1-4}$ alkyl) is a straight, branched, or cyclic alkyl group.

In certain embodiment, the compound has the features of (a), (b) and (c).

In certain embodiment of the method, compound has one or both features selected from the group consisting of:
- (a) $R^{2'}$ is hydrogen and $R^2$ is R; and
- (b) Ring D is a 5-7 membered monocyclic ring selected from aryl, heteroaryl, heterocyclyl or carbocyclyl, said heteroaryl or heterocyclyl ring having 1-4 ring heteroatoms selected from nitrogen, oxygen or sulfur, wherein Ring D is independently substituted at any substitutable ring carbon by oxo or —$R^5$, and at any substitutable ring nitrogen by —$R^4$, provided that when Ring D is a six-membered aryl or heteroaryl ring, —$R^5$ is hydrogen at each ortho carbon position of Ring D.

In certain embodiment, the compound has the features of (a) and (b).

In certain embodiment of the method, the compound has one or both features selected from the group consisting of:
- (a) $R^{2'}$ is hydrogen and $R^2$ is $C_{1-6}$ aliphatic; and
- (b) Ring D is an optionally substituted ring selected from a phenyl, pyridinyl, piperidinyl, piperazinyl, furanyl, pyrrolidinyl, thienyl, 1,4-diazepane, 1,2,3,4-tetrahydropyridinyl, azepanyl, morpholinyl, 1,2,3,4-tetrahydroisoquinolinyl, 1,2,3,4-tetrahydroquinolinyl, 2,3-dihydro-1H-isoindolyl, 1H-indolyl, 2,3-dihydro-1H-indolyl, isoquinolinyl, quinolinyl, or naphthyl ring.

In certain embodiment, the compound has the features of (a) and (b).

In certain embodiment of the method, the compound has one or both features selected from the group consisting of:
- (a) $R^{2'}$ is hydrogen and $R^2$ is $C_{1-6}$ aliphatic; and
- (b) Ring D is an optionally substituted ring selected from a phenyl, pyridinyl, piperidinyl, piperazinyl, furanyl, pyrrolidinyl, thienyl, 1,4-diazepane, 1,2,3,4-tetrahydropyridinyl and 1H-indolyl.

In certain embodiment, the compound has the features of (a) and (b).

In certain embodiment of the method, Ring D is optionally substituted —($C_{1-6}$ aliphatic) or —$R^8SO_2N(R^9)_2$, wherein $R^8$ is a bond, —NR—, or —($C_{1-6}$ aliphatic)N(R)—; and $R^9$ is H or $C_{1-6}$ aliphatic or two $R^9$ are taken together with their intervening atoms to form a substituted or unsubstituted unsaturated 5 or 6-membered heterocyclic ring.

In certain embodiment of the method the compound has one or both features selected from the group consisting of:
- (a) $R^8$ is a bond; and
- (b) $R^9$ is H.

In certain embodiment, the compound has the features of (a) and (b).

In certain embodiment of the method, Ring D is thiazolyl.

In certain embodiment of the method, Ring D is thienyl.

In certain embodiment of the method, Ring D is piperidinyl.

In certain embodiment of the method, $R^2$ is cyclopropyl.

In certain embodiment of the method, the compound has one or more features selected from the group consisting of:
a) $R^{2'}$ is hydrogen and $R^2$ is cyclopropyl;
b) $R^x$ is halogen or $C_{1-4}$ aliphatic;
c) $R^y$ is hydrogen; and
d) Ring D is a ring selected from a phenyl, pyridinyl, piperidinyl, piperazinyl, furanyl, pyrrolidinyl, thienyl, 1,4-diazepane, 1,2,3,4-tetrahydropyridinyl and 1H-indolyl, wherein the ring is optionally substituted —($C_{1-6}$ aliphatic) or —$R^8SO_2N(R^1)_2$, wherein $R^8$ is a bond, —NR—, or —($C_{1-6}$ aliphatic)N(R)—; and $R^9$ is H or $C_{1-6}$ aliphatic or two $R^9$ are taken together with their intervening atoms to form a substituted or unsubstituted unsaturated 5 or 6-membered heterocyclic ring.

In certain embodiment, the compound has the features of (a), (b), (c) and (d).

In one embodiment, the present invention provides a second method of treating tuberculosis, comprising the step of administering a patient a therapeutically effective amount of a compound of formula I

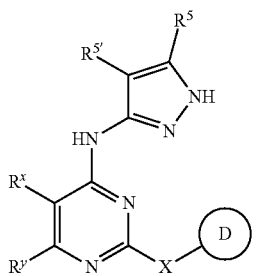

II

Wherein:

X is a bond or —N(R)—.

Ring D is a 5-7 membered monocyclic ring from aryl, heteroaryl, heterocyclyl or carbocyclyl, said heteroaryl or heterocyclyl ring having 1-4 ring heteroatoms selected from nitrogen, oxygen or sulfur, a) the 5-7 membered monocyclic ring is optionally substituted at any substitutable ring carbon by A, wherein:

A is independently selected from one, more or a combination of the follow groups: —($C_{1-6}$ aliphatic), —$R^8SO_2N(R^1)_2$, —$R^8SO_2N(R^1)_2NR$, —$R^8SO_2OR$, —$R^8SO_2R$, —$R^8SOR$, —$R^8NR_2$, —C(O)R, —C(R)$_2$—OH, —C(OH)($C_{1-6}$ aliphatic)C(O)$_2$R, —C(=O)$R^8N(R)_2$, —($C_{1-3}$ aliphatic)-O—C(O)R, —NO$_2$, —$R^8C(O)_2R$, —C(NH)(NH$_2$), —$R^3$, —C(=O)C(=O)$R^4$R and —C(=O)C(=O)OR;

b) the 5-7 membered monocyclic ring is substituted at any substitutable ring carbon by B and A, wherein:

B is a halogen, —O($C_{1-6}$ aliphatic), or —$C_{1-3}$ aliphatic, provided that when Ring D is phenyl, the maximum number of the substitution at any substitutable ring carbon is 2; or c) the 8-10 membered ring is optionally independently substituted by —OH or -oxo group at any substitutable ring carbon;

R is H or $C_{1-6}$ aliphatic;

$R^1$ is H or $C_{1-6}$ aliphatic or two $R^1$ are taken together with their intervening atoms to form a substituted or unsubstituted unsaturated 5 or 6-membered heterocyclic ring;

$R^3$ is —($C_{1-6}$ aliphatic) independently substituted one or multiples of the following groups: —CN, —OH and —O($C_{1-6}$ aliphatic); and $R^4$ is a bond or —O—;

$R^5$ and $R^{5'}$ are:

a) independently H or —$C_{1-6}$ aliphatic; or b) taken together with their intervening atoms to form a fused, unsaturated or partially unsaturated, 5-8 membered ring, provided that Ring D is heteroaryl;

$R^x$ is H, halogen, —($C_{1-6}$ aliphatic), —N(R)$_2$ or —OR; and $R^y$ is H, —$C_{1-6}$ aliphatic or —CN, $R^8$ is a bond, —NR—, or —($C_{1-6}$ aliphatic)N(R)—, wherein $C_{1-3}$ aliphatic or $C_{1-6}$ aliphatic group is optionally and independently substituted with halogen, $R^2OR$, —(OH)$_{1-3}$, —CN, -oxo, =S, —NHCR, —NHC(=O)R or —NHC(O)$_2$R.

In certain embodiment of the second method, a) the 5-7 membered monocyclic ring is optionally substituted at any substitutable ring carbon by A; and b) X is a bond.

In certain embodiment, Ring D is a 5- or 6-membered ring.

In certain embodiment, A is —($C_{1-6}$ aliphatic) or —$R^2SO_2N(R^1)_2$. In certain embodiment, A is —($C_{1-6}$ aliphatic). In certain embodiment, A is —$R^8SO_2N(R^1)_2$.

In certain embodiment, $R^8$ is a bond.

In certain embodiment, IV is H, halogen or $C_{1-6}$ aliphatic. In certain embodiment, IV is H. In certain embodiment, IV is —($C_{1-6}$ aliphatic).

In certain embodiment, $R^5$ and $R^{5'}$ are independently H or —$C_{1-6}$ aliphatic.

In certain embodiment, the compound has one or both features selected from the group consisting of:

a) $R^5$ is —$C_{1-6}$ aliphatic; and b) $R^{5'}$ is H.

In certain embodiment, the compound has the features of (a) and (b).

In certain embodiment, $R^5$ is methyl, ethyl, propyl, isopropyl, cyclopropyl, butyl, isobutyl or tert-butyl. In certain embodiment, $R^5$ is methyl. In certain embodiment, $R^5$ is ethyl. In certain embodiment, $R^5$ is propyl. In certain embodiment, $R^5$ is isopropyl. In certain embodiment, $R^5$ is cyclopropyl. In certain embodiment, $R^5$ is butyl. In certain embodiment, $R^5$ is isobutyl. In certain embodiment, $R^5$ is tert-butyl.

In certain embodiment, $R^1$ is H. In certain embodiment, $R^1$ is $C_{1-6}$ aliphatic.

In certain embodiment, the compound has one or more features selected from the group consisting of:

a) X is a bond;

b) Ring D is phenyl, furanyl, pyrindinyl, thienyl, or thiazolyl;

c) A is —($C_{1-6}$ aliphatic) or —$R^2SO_2N(R^1)_2$; and d) IV is H or —($C_{1-6}$ aliphatic).

In certain embodiment, the compound has the features of (a), (b), (c) and (d).

In certain embodiment, the compound has one or both features selected from the group consisting of:

a) $R^2$ is a bond; and b) $R^1$ is H or $C_{1-6}$ aliphatic.

In certain embodiment, the compound has the features of (a) and (b). In certain embodiment, $R^1$ is H. In certain embodiment, $R^1$ is $C_{1-6}$ aliphatic.

In certain embodiment, the compound has one or more features selected from the group consisting of:

a) $R^5$ is —$C_{1-6}$ aliphatic; and b) $R^{5'}$ is H.

In certain embodiment, the compound has the features of (a) and (b).

In certain embodiment, Ring D is phenyl, furanyl, pyrindinyl, thienyl, or thiazolyl. In certain embodiment, Ring D is phenyl. In certain embodiment, Ring D is furanyl. In certain embodiment, Ring D is pyrindinyl. In certain embodiment, Ring D is thienyl. In certain embodiment, Ring D is thiazolyl.

In certain embodiment, IV is H, halogen or $C_{1-6}$ aliphatic. In certain embodiment, IV is H. In certain embodiment, IV is $C_{1-6}$ aliphatic. In certain embodiment, IV is halogen.

In certain embodiment, the compound has one or both features selected from the group consisting of:

a) X is —N(R)—; and b) Ring D is phenyl.

In certain embodiment, the compound has the features of (a) and (b).

In certain embodiment, the compound has one or both features selected from the group consisting of:

a) A is —($C_{1-6}$ aliphatic) or —$R^2SO_2N(R^1)_2$; and b) $R^x$ is H or —($C_{1-6}$ aliphatic).

In certain embodiment, the compound has the features of (a) and (b).

In certain embodiment, the compound has one or both features selected from the group consisting of:

a) $R^2$ is a bond; and b) $R^1$ is H or $C_{1-6}$ aliphatic.

In certain embodiment, the compound has the features of (a) and (b).

In certain embodiment, $R^1$ is H. In certain embodiment, $R^1$ is $C_{1-6}$ aliphatic.

In certain embodiment, $R^5$ is methyl, ethyl, propyl, isopropyl, cyclopropyl, butyl or tert-butyl. In certain embodiment, $R^5$ is methyl. In certain embodiment, $R^5$ is ethyl. In certain embodiment, $R^5$ is propyl. In certain embodiment, $R^5$ is isopropyl. In certain embodiment, $R^5$ is cyclopropyl.

In certain embodiment, $R^2$ is a bond.

In certain embodiment, $R^1$ is H. In certain embodiment, $R^1$ is $C_{1-6}$ aliphatic.

In one embodiment, the compounds of the present invention are represented by structural formula II:

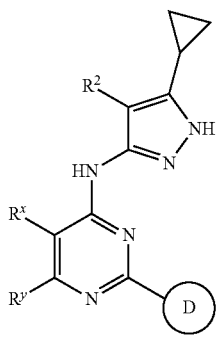

III or a pharmaceutically acceptable salt thereof, wherein.

Ring D is a 5-7 membered monocyclic ring or 8-10 membered bicyclic ring selected from aryl, heteroaryl, heterocyclyl or carbocyclyl, said heteroaryl or heterocyclyl ring having 1-4 ring heteroatoms selected from nitrogen, oxygen or sulfur. Ring D is independently substituted at any substitutable ring carbon by oxo or $—R^5$, and at any substitutable ring nitrogen by $—R^4$.

$R^x$ and $R^y$ are independently selected from T-$R^3$, or $R^x$ and $R^y$ are taken together with their intervening atoms to form a fused, unsaturated or partially unsaturated, 5-8 membered ring having 1-3 ring heteroatoms selected from oxygen, sulfur, or nitrogen. Any substitutable carbon on said fused ring is optionally and independently substituted by T-$R^3$, and any substitutable nitrogen on said ring is substituted by $R^4$.

T is a valence bond or a $C_{1-4}$ alkylidene chain.

$R^2$ is independently selected from —R, -T-W—$R^6$.

$R^3$ is selected from —R, -halo, =O, —OR, —C(=O)R, —$CO_2$R, —COCOR, —$COCH_2$COR, —$NO_2$, —CN, —S(O)R, —S(O)$_2$R, —SR, —N($R^4$)$_2$, —CON($R^4$)$_2$, —$SO_2$N($R^4$)$_2$, —OC(=O)R, —N($R^4$)COR, —N($R^4$)$CO_2$ (optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)$SO_2$N($R^4$)$_2$, —N($R^4$)S $O_2$R, or —OC(=O)N($R^4$)$_2$.

Each R is independently selected from hydrogen or an optionally substituted group selected from $C_{1-6}$ aliphatic, $C_{6-10}$ aryl, a heteroaryl ring having 5-10 ring atoms, or a heterocyclyl ring having 5-10 ring atoms.

Each $R^4$ is independently selected from —$R^7$, —$COR^7$, —$CO_2$ (optionally substituted $C_{1-6}$ aliphatic), —CON($R^7$)$_2$, or —$SO_2R^7$, or two $R^4$ on the same nitrogen are taken together to form a 5-8 membered heterocyclyl or heteroaryl ring.

Each $R^5$ is independently selected from —R, halo, —OR, —C(=O)R, —$CO_2$R, —COCOR, —$NO_2$, —CN, —S(O)R, —$SO_2$R, —SR, —N($R^4$)$_2$, —CON($R^4$)$_2$, —$SO_2$N($R^4$)$_2$, —OC(=O)R, —N($R^4$)COR, —N($R^4$)$CO_2$ (optionally substituted $C_{1-6}$ aliphatic), —N($R^4$)N($R^4$)$_2$, —C=NN($R^4$)$_2$, —C=N—OR, —N($R^4$)CON($R^4$)$_2$, —N($R^4$)$SO_2$N($R^4$)$_2$, —N($R^4$)S $O_2$R, or —OC(=O)N($R^4$)$_2$.

V is —O—, —S—, —SO—, —$SO_2$—, —N($R^6$)$SO_2$—, —$SO_2$N($R^6$)—, —N($R^6$)—, —CO—, —$CO_2$—, —N($R^6$)CO—, —N($R^6$)C(O) O—, —N($R^6$)CON($R^6$)—, —N($R^6$)$SO_2$N($R^6$)—, —N($R^6$)N($R^6$)—, —C(O)N($R^6$)—, —OC(O)N($R^6$)—, —C($R^6$)$_2$O—, —C($R^6$)$_2$S—, —C($R^6$)$_2$SO—, —C($R^6$)$_2$$SO_2$—, —C($R^6$)$_2$$SO_2$N($R^6$)—, —C($R^6$)$_2$N($R^6$)—, —C($R^6$)$_2$N($R^6$)C(O)—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)$SO_2$N($R^6$)—, or —C($R^6$)$_2$N($R^6$)CON($R^6$)—.

W is —C($R^6$)$_2$O—, —C($R^6$)$_2$S—, —C($R^6$)$_2$SO—, —C($R^6$)$_2$$SO_2$—, —C($R^6$)$_2$$SO_2$N($R^6$)—, —C($R^6$)$_2$N($R^6$)—, —CO—, —C($R^6$)OC(O)—, —C($R^6$)OC(O)N($R^6$)—, —C($R^6$)$_2$N($R^6$)CO—, —C($R^6$)$_2$N($R^6$)C(O)O—, —C($R^6$)=NN($R^6$)—, —C($R^6$)=N—O—, —C($R^6$)$_2$N($R^6$)N($R^6$)—, —C($R^6$)$_2$N($R^6$)$SO_2$N($R^6$)—, —C($R^6$)$_2$N($R^6$)CON($R^6$)—, or —CON($R^6$)—.

Each $R^6$ is independently selected from hydrogen or an optionally substituted $C_{1-4}$ aliphatic group, or two $R^6$ groups on the same nitrogen atom are taken together with the nitrogen atom to form a 5-6 membered heterocyclyl or heteroaryl ring.

Each $R^7$ is independently selected from hydrogen or an optionally substituted $C_{1-6}$ aliphatic group, or two $R^7$ on the same nitrogen are taken together with the nitrogen to form a 5-8 membered heterocyclyl ring or heteroaryl.

In certain embodiment, Ring D is a phenyl, pyridinyl, piperidinyl, piperazinyl, furanyl, pyrrolidinyl, thienyl, 1,4-diazepane, 1,2,3,4-tetrahydropyridinyl, azepanyl, morpholinyl, thiazolyl, 1,2,3,4-tetrahydroisoquinolinyl, 1,2,3,4-tetrahydroquinolinyl, 2,3-dihydro-1H-isoindolyl, 1H-indolyl, 2,3-dihydro-1H-indolyl, isoquinolinyl, quinolinyl, or naphthyl ring.

In certain embodiment, Ring D is pyridinyl, piperidinyl, piperazinyl, furanyl, pyrrolidinyl, thienyl, 1,4-diazepane, 1,2,3,4-tetrahydropyridinyl, azepanyl, morpholinyl, thiazolyl, 1,2,3,4-tetrahydroisoquinolinyl, 1,2,3,4-tetrahydroquinolinyl, 2,3-dihydro-1H-isoindolyl, 1H-indolyl, 2,3-dihydro-1H-indolyl, isoquinolinyl, quinolinyl, or naphthyl ring.

In certain embodiment, Ring D is a 5-7 membered monocyclic ring selected from heteroaryl, heterocyclyl or carbocyclyl, said heteroaryl or heterocyclyl ring having 1-4 ring heteroatoms selected from nitrogen, oxygen or sulfur, wherein Ring D is independently substituted at any substitutable ring carbon by oxo or —$R^5$, and at any substitutable ring nitrogen by —$R^4$.

In certain embodiment, Ring D is pyridinyl, piperidinyl, piperazinyl, furanyl, thiazolyl, pyrrolidinyl, thienyl, 1,4-diazepane or 1,2,3,4-tetrahydropyridinyl.

In certain embodiment, Ring D is a 5-7 membered monocyclic heteroaryl ring.

In certain embodiment, Ring D is pyridinyl, thienyl, thiazolyl or furanyl. In certain embodiment, Ring D is Ring D is thienyl or thiazolyl. In certain embodiment, Ring D is thienyl.

In certain embodiment, Ring D is substituted with —($C_{1-6}$ aliphatic), —$R^8$$SO_2$N($R^1$)$_2$, —$R^8$$SO_2$N($R^1$)$_2$NR, —$R^8$$SO_2$OR, —$R^8$$SO_2$R, —$R^8$SOR, —$R^8$$NR_2$, —C(O)R, —C(R)$_2$—OH, —C(OH)($C_{1-6}$ aliphatic)C(O)$_2$R, —C(=O)$R^8$N(R)$_2$, —($C_{1-3}$ aliphatic)-O—C(O)R, —$NO_2$, —$R^8$C(O)$_2$R, —C(NH)(NH$_2$), —$R^3$, —C(=O)C(=O)$R^4$R and —C(=O)C(=O)OR, wherein $R^8$ is a bond, —NR— or —($C_{1-6}$ aliphatic)N(R)—.

In certain embodiment, Ring D is substituted with —R$^8$SO$_2$N(R$^1$)$_2$, —C(O)R or —C(R)$_2$—OH and R$^8$ is a bond.

In certain embodiment, Ring D is substituted with —R$^8$SO$_2$N(R$^1$)$_2$ and R$^8$ is a bond.

In certain embodiment, Ring D is substituted with —C(R)$_2$—OH and R$^8$ is a bond.

In one embodiment, the present invention provides a composition for treating tuberculosis comprising a compound according to the disclosure of the present patent application and a pharmaceutically acceptable excipient.

In one embodiment, the present invention provides a method for treating tuberculosis in a mammal which comprises administering to the mammal a therapeutically effective amount of the compound and/or the composition according to the disclosure of the present patent application.

In certain embodiment, the compound inhibits PKnB kinase activity. In certain embodiment, the compound inhibits phosphorylation of a kinase substrate by PknB kinase.

In certain embodiment, the present invention provides a method for inhibiting phosphorylation of a kinase substrate by PknB kinase in a subject comprising administering the subject a therapeutically effective amount of the compound and or a composition.

As described herein, a specified number range of atoms includes any integer therein. For example, a group having from 1-4 atoms could have 1, 2, 3, or 4 atoms.

As used here the terms "absent" and "a bond" can be used interchangeably to mean the variable does not exits in that embodiment, that is the variable does not represent an atom or groups of atoms.

The term "stable", as used herein, refers to compounds that are not substantially altered when subjected to conditions to allow for their production, detection, recovery, storage, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

Unless otherwise specified, aliphatic groups contain 1-20 aliphatic carbon atoms. In some embodiments, aliphatic groups contain 1-10 aliphatic carbon atoms. In other embodiments, aliphatic groups contain 1-8 aliphatic carbon atoms. In still other embodiments, aliphatic groups contain 1-6 aliphatic carbon atoms, and in yet other embodiments aliphatic groups contain 1-4 aliphatic carbon atoms. Aliphatic groups may be linear, branched or cyclic alkyl, alkenyl, or alkynyl groups. Specific examples include, but are not limited to, methyl, ethyl, isopropyl, n-propyl, cyclopropyl, sec-butyl, vinyl, n-butanol, cyclobutyl, thinly, and tert-butyl.

The term "alkyl" as used herein means a saturated straight or branched chain hydrocarbon. The term "alkenyl" as used herein means a straight or branched chain hydrocarbon comprising one or more double bonds. The term "alkynyl" as used herein means a straight or branched chain hydrocarbon comprising one or more triple bonds.

The term "heterocycle" (or "heterocyclyl", or "heterocyclic") as used herein means refers to a non-aromatic monocyclic ring which can be saturated or contain one or more units of unsaturation, having three to fourteen ring atoms in which one or more ring carbons is replaced by a heteroatom such as, N, S, or O. The term includes polycyclic fused, spiro or bridged heterocyclic ring systems. The term also includes polycyclic ring systems in which the heterocyclic ring can be fused to one or more non-aromatic carbocyclic or heterocyclic rings or one or more aromatic rings or combination thereof, wherein the radical or point of attachment is on the heterocyclic ring. Examples of heterocycles include, but are not limited to, piperidinyl, piperizinyl, pyrrolidinyl, pyrazolidinyl, imidazolidinyl, azepanyl, diazepanyl, triazepanyl, azocanyl, diazocanyl, triazocanyl, oxazolidinyl, isoxazolidinyl, thiazolidinyl, isothiazolidinyl, oxazocanyl, oxazepanyl, thiazepanyl, thiazocanyl, benzimidazolonyl, tetrahydrofuranyl, tetrahydrothiophenyl, tetrahydrothiophenyl, morpholino, including, for example, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-piperazinyl, 2-piperazinyl, 3-piperazinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolanyl, benzodithianyl, dihydro-benzimidazol-2-onyl, and 1,3-dihydro-imidazol-2-onyl, azabicyclopentyl, azabicyclohexyl, azabicycloheptyl, azabicyclooctyl, azabicyclononyl, azabicyclodecyl, diazabicyclohexyl, diazabicycloheptyl, dihydroindazolyl, dihydrobenzimidazolyl, tetrahydropyridyl, dihydropyridyl, tetrahydropyrazinyl, dihydropyrazinyl, tetrahydropyrimidinyl, dihydropyrimidinyl, dihydropyrrolyl, dihydropyrazolyl, dihydroimidazolyl, octahydropyrrolopyrazyl, octahydropyrrolopyridyl, octahydropyridopyrazyl, octahydropyridopyridyl, di azabicyclooctyl, diazabicyclononyl, and diazabicyclodecyl.

As used herein, unless stated otherwise, bicyclic rings can be fused, spiro and bridged.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated", as used herein, means that a moiety has one or more units of unsaturation.

The term "alkoxy", or "thioalkyl", as used herein, refers to an alkyl group, as previously defined, attached to the molecule through an oxygen ("alkoxy" e.g., —O-alkyl) or sulfur ("thioalkyl" e.g., —S-alkyl) atom.

The terms "haloalkyl", "haloalkenyl", "halo aliphatic", and "haloalkoxy" (or "aminoalkyl", "hydroxyalkyl" etc.,) mean alkyl, alkenyl or alkoxy, as the case may be, substituted with one or more halogen atoms. This term includes perfluorinated alkyl groups, such as —CF$_3$ and —CF$_2$CF$_3$.

The terms "halogen", "halo", and "hal" mean F, Cl, Br, or I. The term halo aliphatic and —O(halo aliphatic) include, mono- di- and tri-halo substituted aliphatic groups.

The term "aryl" used alone or as part of a larger moiety as in "a alkyl", "aralkoxy", "aryloxyalkyl", or "heteroaryl" refers to carbocyclic and or heterocyclic aromatic ring systems. The term "aryl" may be used interchangeably with the term "aryl ring".

Carbocyclic aromatic ring groups have only carbon ring atoms (typically six to fourteen) and include monocyclic aromatic rings such as phenyl and fused polycyclic aromatic ring systems in which two or more carbocyclic aromatic rings are fused to one another. Examples include 1-naphthyl, 2-naphthyl, 1-anthracyl and 2-anthracyl. Also included within the scope of the term "carbocyclic aromatic ring", as it is used herein, is a group in which an aromatic ring is fused to one or more non-aromatic rings (carbocyclic or heterocyclic), such as in an indanyl, phthalimidyl, naphthimidyl, phenanthridinyl, or tetrahydronaphthyl, where the radical or point of attachment is on the aromatic ring.

The term "heteroaryl", "heteroaromatic", "heteroaryl ring", "heteroaryl group" and "heteroaromatic group", used alone or as part of a larger moiety as in "heteroaralkyl" or "heteroarylalkoxy", refers to heteroaromatic ring groups having five to fourteen members, including monocyclic heteroaromatic rings and polycyclic aromatic rings in which a monocyclic aromatic ring is fused to one or more other aromatic ring. Heteroaryl groups have one or more ring heteroatoms. Also included within the scope of the term "heteroaryl", as it is used herein, is a group in which an aromatic ring is fused to one or more non-aromatic rings (carbocyclic or heterocyclic), where the radical or point of attachment is on the aromatic ring. Bicyclic 6,5 heteroaromatic ring, as used herein, for example, is a six membered heteroaromatic ring fused to a second five membered ring, wherein the radical or point of attachment is on the six membered ring. Examples of heteroaryl groups include pyridyl, pyrazinyl, pyrimidinyl, pyridazinyl, imidazolyl, pyrrolyl, pyrazolyl, triazolyl, tetrazolyl, oxazolyl, isoxazolyl, oxadiazolyl, thiazolyl, isothiazolyl or thiadiazolyl including, for example, 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 3-pyrazolyl, 4-pyrazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, tetrazolyl, 2-thienyl, 3-thienyl, carbazolyl, benzimidazolyl, benzothienyl, benzofuranyl, indolyl, benzotriazolyl, benzothiazolyl, benzoxazolyl, benzimidazolyl, isoquinolinyl, indolyl, isoindolyl, acridinyl, benzisoxazolyl, isothiazolyl, 1,2,3-oxadiazolyl, 1,2,5-oxadiazolyl, 1,2,4-oxadiazolyl, 1,2,3-triazolyl, 1,2,3-thiadiazolyl, 1,3,4-thiadiazolyl, 1,2,5-thiadiazolyl, purinyl, pyrazinyl, 1,3, 5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "protecting group" and "protective group" as used herein, are interchangeable and refer to an agent used to temporarily block one or more desired functional groups in a compound with multiple reactive sites. In certain embodiments, a protecting group has one or more, or preferably all, of the following characteristics: a) is added selectively to a functional group in good yield to give a protected substrate that is b) stable to reactions occurring at one or more of the other reactive sites; and c) is selectively removable in good yield by reagents that do not attack the regenerated, deprotected functional group. As would be understood by one skilled in the art, in some cases, the reagents do not attack other reactive groups in the compound. In other cases, the reagents may also react with other reactive groups in the compound. Examples of protecting groups are detailed in Greene, T. W., Wuts, P. Gin "Protective Groups in Organic Synthesis", Third Edition, John Wiley & Sons, New York: 1999 (and other editions of the book), the entire contents of which are hereby incorporated by reference. The term "nitrogen protecting group", as used herein, refers to an agent used to temporarily block one or more desired nitrogen reactive sites in a multifunctional compound. Preferred nitrogen protecting groups also possess the characteristics exemplified for a protecting group above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

Only those replacement and combinations of groups that result in a stable structure are contemplated. Optional replacements can occur both within the chain and/or at either end of the chain; i.e. both at the point of attachment and/or also at the terminal end. Two optional replacements can also be adjacent to each other within a chain so long as it results in a chemically stable compound.

In some embodiments the optional replacements can also completely replace all of the carbon atoms in a chain. For example, a $C_3$ aliphatic can be optionally replaced by —N(R')—, —C(O)—, and —N(R')— to form —N(R')OC(O)N(R')— (a urea), or a $C_1$ aliphatic can be optionally be replaced by, for example, —O—, NH— etc. In certain instances of these embodiments the chain is a linker.

Unless otherwise indicated, if the replacement occurs at the terminal end, the replacement atom is bound to an H on the terminal end. For example, if —$CH_2CH_2CH_3$ were optionally replaced with —O—, the resulting compound could be —$OCH_2CH_3$, —$CH_2OCH_3$, or —$CH_2CH_2OH$, or if —$CH_2CH_3$ were optionally replaced with —O—, the resulting compound could be —$OCH_3$, or —$CH_2CH_2OH$, or if —$CH_2CH_3$ were optionally replaced with —C(O)—, the resulting compound could be —$C(O)CH_3$, or —$CH_2C(O)H$.

Unless otherwise indicated, structures depicted herein are also meant to include all isomeric (e.g., enantiomeric, diastereomeric, geometric, conformational, and rotational) forms of the structure. For example, the R and S configurations for each asymmetric center, (Z) and (E) double bond isomers, and (Z) and (E) conformational isomers are included in this invention. As would be understood to one skilled in the art, a substituent can freely rotate around any rotatable bonds. For example, a substituent drawn as

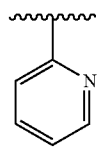

also represents

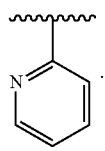

Therefore, single stereochemical isomers as well as enantiomeric, diastereomeric, geometric, conformational, and rotational mixtures of the present compounds are within the scope of the invention.

Unless otherwise indicated, all tautomeric forms of the compounds of the invention are within the scope of the invention.

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}C$- or $^{14}C$-enriched carbon are within the scope of this invention. Such compounds are useful, for example, as analytical tools or probes in biological assays.

As described herein, where indicated compounds of the invention may optionally be substituted with one or more substituents, such as are illustrated generally herein, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position.

Only those choices and combinations of substituents that result in a stable structure are contemplated. Such choices and combinations will be apparent to those of ordinary skill in the art and may be determined without undue experimentation.

The term "ring atom" is an atom such as C, N, O or S that is in the ring of an aromatic group, cycloalkyl group or non-aromatic heterocyclic ring.

A "substitutable ring atom" in an aromatic or non-aromatic ring group is a ring carbon or nitrogen atom bonded to a hydrogen atom. The hydrogen can be optionally replaced with a suitable substituent group. Thus, the term "substitutable ring atom" does not include ring nitrogen or carbon atoms which are shared when two rings are fused. In addition, "substitutable ring atom" does not include ring carbon or nitrogen atoms when the structure depicts that they are already attached to a moiety other than hydrogen.

An optionally substituted aryl group as defined herein may contain one or more substitutable ring atoms, which may be bonded to a suitable substituent. Examples of suitable substituents on a substitutable ring carbon atom of an aryl group includes $R^{11}$. $R^{11}$ is —Ra, —Br, —Cl, —I, —F, —ORa, —SRa, —O—CORa, —CORa, —CSRa, —CN, —NO$_2$, —NCS, —SO$_3$H, —N(RaRb), —COORa, —NRcNRc-CORa, —NRcNRcCO$_2$Ra, —CHO, —CON(RaRb), —OC(O)N(RaRb), —CSN(RaRb), —NRcCORa, —NRcCOORa, —NRcCSRa, —NRcCON(RaRb), —NRcNRcC(O)N(RaRb), —NRcCSN(RaRb), —C(=NRc)-N(RaRb), —C(=S)N(RaRb), —NRd-C(=NRc)-N(RaRb), —NRcN-RaRb, —S(O)$_p$NRaRb, —NRcSO$_2$N(RaRb), —NRcS(O)$_p$Ra, —S(O)$_p$Ra, —OS(O)$_p$NRaRb or —OS(O)$_p$Ra; wherein p is 1 or 2.

Ra-Rd are each independently —H, an aliphatic group, aromatic group, non-aromatic carbocyclic or heterocyclic group or —N(RaRb), taken together, form a non-aromatic heterocyclic group. The aliphatic, aromatic and non-aromatic heterocyclic group represented by Ra-Rd and the non-aromatic heterocyclic group represented by —N(RaRb) are each optionally and independently substituted with one or more groups represented by $R^{12}$. Preferably Ra-Rd are unsubstituted.

$R^{12}$ is halogen, $R^{13}$, —OR$^{13}$, —SR$^{13}$, —NO$_2$, —CN, —N(R$^{13}$)$_2$, —COR$^{13}$, —COOR$^{13}$, —NHCO$_2$R$^{13}$, —NHC(O)R$^{13}$, —NHNHC(O)R$^{13}$, —NHC(O)N(R$^{13}$)$_2$, —NHNHC(O)N(R$^{13}$)$_2$, —NHNHCO$_2$R$^{13}$, —C(O)N(R$^{13}$)$_2$, —OC(O)R$^{13}$, —OC(O)N(R$^{13}$)$_2$, —S(O)$_2$R$^{13}$, —SO$_2$N(R$^{13}$)$_2$, —S(O)R$^{13}$, —NHSO$_2$N(R$^{13}$)$_2$, —NHSO$_2$R$^{13}$, —C(=S)N(R$^{13}$)$_2$, or —C(=NH)—N(R$^{13}$)$_2$.

$R^{13}$ is —H, a $C_{1-4}$ alkyl group, a monocyclic aryl group, a non-aromatic carbocyclic or heterocyclic group each optionally substituted with alkyl, haloalkyl, alkoxy, haloalkoxy, halogen, —CN, —NO$_2$, amine, alkylamine or dialkylamine. Preferably $R^{13}$ is unsubstituted.

An optionally substituted aliphatic or a non-aromatic heterocyclic or carbocyclic group as used herein may contain one or more substituents. Examples of suitable substituents for an aliphatic group or a ring carbon of a non-aromatic heterocyclic group is $R^{14}$. $R^{14}$ includes those substituents listed above for $R^{11}$ and =O, =S, =NNHR$^{15}$, =NN(R$^{15}$2, =NNHC(O)R$^{15}$, =NNHCO2 (alkyl), =NNHSO2 (alkyl), =NR$^{15}$, spiro cycloalkyl group or fused cycloalkyl group. Each $R^{15}$ is independently selected from hydrogen, an unsubstituted alkyl group or a substituted alkyl group. Examples of substituents on the alkyl group represented by $R^{15}$ include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

When a heterocyclyl, heteroaryl, or heteroaralkyl group contains a nitrogen atom, it may be substituted or unsubstituted. When a nitrogen atom in the aromatic ring of a heteroaryl group has a substituent the nitrogen may be a quaternary nitrogen.

A preferred position for substitution of a non-aromatic nitrogen-containing heterocyclic group is the nitrogen ring atom. Suitable substituents on the nitrogen of a non-aromatic heterocyclic group or heteroaryl group include —R$^{16}$, —N(R$^{16}$)$_2$, C(O)R$^{16}$, CO$_2$R$^{16}$, —C(O)C(O)R$^{16}$, —SO$_2$R$^{16}$, SO$_2$N(R$^{16}$)$_2$, C(=S)N(R$^{16}$)$_2$, C(=NH)—N(R$^{16}$)$_2$, and —NR$^{16}$SO$_2$R$^{16}$; wherein R$^{16}$ is hydrogen, an aliphatic group, a substituted aliphatic group, aryl, substituted aryl, heterocyclic or carbocyclic ring or a substituted heterocyclic or carbocyclic ring. Examples of substituents on the group represented by R$^{16}$ include alkyl, haloalkoxy, haloalkyl, alkoxyalkyl, sulfonyl, alkylsulfonyl, halogen, nitro, cyano, hydroxy, aryl, carbocyclic or heterocyclic ring, oxo, amino, alkylamino, dialkylamino, aminocarbonyl, alkylaminocarbonyl, dialkylaminocarbonyloxy, alkoxy, carboxy, alkoxycarbonyl, or alkylcarbonyl. Preferably R^ is not substituted.

Non-aromatic nitrogen containing heterocyclic rings that are substituted on a ring nitrogen and attached to the remainder of the molecule at a ring carbon atom are said to be N substituted. For example, an N alkyl piperidinyl group is attached to the remainder of the molecule at the two, three or four position of the piperidinyl ring and substituted at the ring nitrogen with an alkyl group. Non-aromatic nitrogen containing heterocyclic rings such as pyrazinyl that are substituted on a ring nitrogen and attached to the remainder of the molecule at a second ring nitrogen atom are said to be N' substituted-N-heterocycles. For example, an N' acyl N-pyrazinyl group is attached to the remainder of the molecule at one ring nitrogen atom and substituted at the second ring nitrogen atom with an acyl group.

As used herein an optionally substituted aralkyl can be substituted on both the alkyl and the aryl portion. Unless otherwise indicated as used herein optionally substituted aralkyl is optionally substituted on the aryl portion.

The compounds of the invention are defined herein by their chemical structures and/or chemical names. Where a compound is referred to by both a chemical structure and a chemical name, and the chemical structure and chemical name conflict, the chemical structure is determinative of the compound's identity.

The compounds of this invention can exist in free form for treatment, or where appropriate, as a pharmaceutically acceptable salt.

As used herein, the term "pharmaceutically acceptable salt" refers to salts of a compound which are, within the scope of sound medical judgment, suitable for use in contact with the tissues of humans and lower animals without undue side effects, such as, toxicity, irritation, allergic response and the like, and are commensurate with a reasonable benefit/risk ratio.

Pharmaceutically acceptable salts are well known in the art. For example, S. M. Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, glycolate, gluconate, glycolate, hemisulfate, heptanoate, hexanoate, hydrochloride, hydrobromide, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, palmoate, pectinate, persulfate, 3-phenyl-propionate, phosphate, picrate, pivalate, propionate, salicylate, stearate, succinate, sulfate, tartrate, thiocyanate, p-toluenesulfonate, undecanoate, valerate salts, and the like.

Base addition salts can be prepared by 1) reacting the purified compound in its acid form with a suitable organic or inorganic base and 2) isolating the salt thus formed. Salts derived from appropriate bases include alkali metal (e.g., sodium, lithium, and potassium), alkaline earth metal (e.g., magnesium and calcium), ammonium and $N^+(C_{1-4}alkyl)_4$ salts. This invention also envisions the quaternization of any basic nitrogen-containing groups of the compounds disclosed herein. Water or oil-soluble or dispersible products may be obtained by such quaternization.

Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

It should be understood that this invention includes mixtures/combinations of different pharmaceutically acceptable salts and also mixtures/combinations of compounds in free form and pharmaceutically acceptable salts.

In addition to the compounds of this invention, pharmaceutically acceptable solvates (e.g., hydrates) and clathrates of the compounds of this invention may also be employed in compositions to treat or prevent the herein identified disorders.

As used herein, the term "pharmaceutically acceptable solvate," is a solvate formed from the association of one or more pharmaceutically acceptable solvent molecules to one of the compounds the invention. The term solvate includes hydrates (e.g., hemihydrate, monohydrate, dihydrate, trihydrate, tetrahydrate, and the like).

As used herein, the term "hydrate" means a compound of the present invention or a salt thereof, that further includes a stoichiometric or non-stoichiometric amount of water bound by non-covalent intermolecular forces.

As used herein, the term "clathrate" means a compound of the present invention or a salt thereof in the form of a crystal lattice that contains spaces (e.g., channels) that have a guest molecule (e.g., a solvent or water) trapped within.

In addition to the compounds of this invention, pharmaceutically acceptable derivatives or prodrugs, and esters, of the compounds of this invention may also be employed in compositions to treat or prevent the herein identified disorders.

As used herein and unless otherwise indicated, the term "prodrug" means a derivative of a compound that can hydrolyze, oxidize, or otherwise react under biological conditions (in vitro or in vivo) to provide a compound of this invention. Prodrugs may become active upon such reaction under biological conditions, or they may have activity in their unreacted forms. Examples of prodrugs contemplated in this invention include, but are not limited to, analogs or derivatives of compounds of the invention that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of compounds of the invention that comprise —NO, —NO2, —ONO, or —ONO2 moieties. Prodrugs can typically be prepared using well-known methods, such as those described by BURGER'S MEDICINAL CHEMISTRY AND DRUG DISCOVERY (1995) 172-178, 949-982 (Manfred E. Wolff ed., 5th ed).

A "pharmaceutically acceptable derivative" is an adduct or derivative which, upon administration to a patient in need, is capable of providing, directly or indirectly, a compound as otherwise described herein, or a metabolite or residue thereof. Examples of pharmaceutically acceptable derivatives include, but are not limited to, esters and salts of such esters.

A "pharmaceutically acceptable derivative or prodrug" includes any pharmaceutically acceptable ester, salt of an ester or other derivative or salt thereof of a compound, of this invention which, upon administration to a recipient, is capable of providing, either directly or indirectly, a compound of this invention or an inhibitorily active metabolite or residue thereof. Particularly favoured derivatives or prodrugs are those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Pharmaceutically acceptable prodrugs of the compounds of this invention include, without limitation, esters, amino acid esters, phosphate esters, metal salts and sulfonate esters.

As used herein, the phrase "side effects" encompasses unwanted and adverse effects of a therapy (e.g., a prophylactic or therapeutic agent). Side effects are always unwanted, but unwanted effects are not necessarily adverse. An adverse effect from a therapy (e.g., prophylactic or therapeutic agent) might be harmful or uncomfortable or risky. Side effects include, but are not limited to fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

In one embodiment the present invention is a pharmaceutical composition comprising a compound of the present invention and a pharmaceutically acceptable carrier, diluent, adjuvant or vehicle. In one embodiment the present invention is a pharmaceutical composition comprising an effective amount of compound of the present invention and a pharmaceutically acceptable carrier, diluent, adjuvant or vehicle. Pharmaceutically acceptable carriers include, for example, pharmaceutical diluents, excipients or carriers suitably selected with respect to the intended form of administration, and consistent with conventional pharmaceutical practices.

A pharmaceutically acceptable carrier may contain inert ingredients which do not unduly inhibit the biological activity of the compounds. The pharmaceutically acceptable carriers should be biocompatible, e.g., non-toxic, non-inflammatory, non-immunogenic or devoid of other undesired reactions or side-effects upon the administration to a subject. Standard pharmaceutical formulation techniques can be employed.

The pharmaceutically acceptable carrier, adjuvant, or vehicle, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention.

Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The protein kinase inhibitors or pharmaceutical salts thereof may be formulated into pharmaceutical compositions for administration to a subject as defined herein. These pharmaceutical compositions, which comprise an amount of the protein inhibitor effective to treat or prevent a protein kinase-mediated condition and a pharmaceutically acceptable carrier, are another embodiment of the present invention.

In one embodiment the present invention is a method of treating or preventing a protein kinase-mediated disorder in a subject in need thereof, comprising administering to the subject an effective amount of a compound composition or a pharmaceutically acceptable salt of the present invention as described herein. In another embodiment, the present invention is the use of an effective amount of a compound, composition or a pharmaceutically acceptable salt described herein for treating or preventing a disease or disorder, described herein, in a subject in need thereof. In yet another embodiment, the present invention is the use of an effective amount of a compound, composition or a pharmaceutically acceptable salt described herein for the manufacture of a medicament method for the treatment or prevention of a disease or disorder, described herein, in a subject in need thereof. In one embodiment the protein kinase mediated disease is a protein kinase C (PKC) mediated disease. In another embodiment the protein kinase mediated disease is a protein kinase C theta (PKCtheta)-mediated disease.

As used herein, the terms "subject", "patient" and "mammal" are used interchangeably. The terms "subject" and "patient" refer to an animal (e.g., a bird such as a chicken, quail or turkey, or a mammal), preferably a mammal including a non-primate (e.g., a cow, pig, horse, sheep, rabbit, guinea pig, rat, cat, dog, and mouse) and a primate (e.g., a monkey, chimpanzee and a human), and more preferably a human. In one embodiment, the subject is a non-human animal such as a farm animal (e.g., a horse, cow, pig or sheep), or a pet (e.g., a dog, cat, guinea pig or rabbit). In a preferred embodiment, the subject is a human.

As used herein, an "effective amount" refers to an amount sufficient to elicit the desired biological response. In the present invention the desired biological response is to reduce or ameliorate the severity, duration, progression, or onset of a protein kinase-mediated condition, prevent the advancement of a protein kinase-mediated condition, cause the regression of a protein kinase-mediated condition, prevent the recurrence, development, onset or progression of a symptom associated with a protein kinase-mediated condition, or enhance or improve the prophylactic or therapeutic effect(s) of another therapy. The precise amount of compound administered to a subject will depend on the mode of administration, the type and severity of the disease or condition and on the characteristics of the subject, such as general health, age, sex, body weight and tolerance to drugs. It will also depend on the degree, severity and type of protein kinase-mediated condition, and the mode of administration. The skilled artisan will be able to determine appropriate dosages depending on these and other factors. When co-administered with other agents, e.g., when co-administered with an protein kinase-mediated condition agent, an "effective amount" of the second agent will depend on the type of drug used. Suitable dosages are known for approved agents and can be adjusted by the skilled artisan according to the condition of the subject, the type of condition(s) being treated and the amount of a compound of the invention being used. In cases where no amount is expressly noted, an effective amount should be assumed.

As used herein, the terms "treat", "treatment" and "treating" refer to the reduction or amelioration of the progression, severity and/or duration of a protein kinase-mediated condition, or the amelioration of one or more symptoms (preferably, one or more discernible symptoms) of a protein kinase-mediated condition resulting from the administration of one or more therapies (e.g., one or more therapeutic agents such as a compound of the invention). In specific embodiments, the terms "treat", "treatment" and "treating" refer to the amelioration of at least one measurable physical parameter of a protein kinase-mediated condition. In other embodiments the terms "treat", "treatment" and "treating" refer to the inhibition of the progression of a protein kinase-mediated condition, either physically by, e.g., stabilization of a discernible symptom, physiologically by, e.g., stabilization of a physical parameter, or both. In other embodiments the terms "treat", "treatment" and "treating" refer to the reduction or stabilization of a protein kinase-mediated condition.

As used herein, the terms "prevent", "prevention" and "preventing" refer to the reduction in the risk of acquiring or developing a given protein kinase-mediated condition, or the reduction or inhibition of the recurrence or a protein kinase-mediated condition. In one embodiment, a compound of the invention is administered as a preventative measure to a patient, preferably a human, having a genetic predisposition to any of the conditions, diseases or disorders described herein.

As used herein, the terms, "disease", "disorder" and "condition" may be used interchangeably here to refer to a protein kinase-mediated condition.

In one aspect, the present invention provides a method for treating or lessening the severity of tuberculosis by inhibiting a serine-threonine protein protease kinase. The essential serine-threonine protein kinases (STPK) of *M. tuberculosis*, PknA and PknB, are found to be effective targets for novel anti-tuberculosis chemotherapeutic agents. Inhibition of *M. tuberculosis* growth is achieved by pharmacological inhibition of STPKs, resulting from anti-mycobacterial activity of the compounds disclosed herein that inhibits mycobacterial STPKs. In another aspect of the present invention, the compounds disclosed herein are bactericidal.

In one aspect, the present invention provides a method of inhibiting growth of live *Mycobacterium* cells by inhibiting phosphorylation of kinase substrate(s) by the STPKs.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly (orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The compositions of the present invention may be administered orally, parenterally, by inhalation spray, topically, rectally, nasally, buccally, vaginally or via an implanted reservoir. The term "parenteral" as used herein includes, but is not limited to, subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used include, but are not limited to, lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include, but are not limited to, cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2 octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The dosage regimen utilizing the compounds of Structural Formula I, II or III can be selected in accordance with a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the renal and hepatic function of the subject; and the particular compound or salt thereof employed, the duration of the treatment; drugs used in combination or coincidental with the specific compound employed, and like factors well known in the medical arts. The skilled artisan can readily determine and prescribe the effective amount of the compound of Structural Formula I, II or III required to treat, for example, to prevent, inhibit (fully or partially) or arrest the progress of the disease.

Dosages of the compounds of Structural Formula I, II or III can range from between about 0.01 to about 100 mg/kg body weight/day, about 0.01 to about 50 mg/kg body weight/day, about 0.1 to about 50 mg/kg body weight/day, or about 1 to about 25 mg/kg body weight/day. It is understood that the total amount per day can be administered in a single dose or can be administered in multiple dosings such as twice, three or four times per day.

The compounds for use in the method of the invention can be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form can be for a single daily dose or one of multiple daily doses (e.g., about 1 to 4 or more times per day). When multiple daily doses are used, the unit dosage form can be the same or different for each dose.

An effective amount can be achieved in the method or pharmaceutical composition of the invention employing a compound of Structural Formula I, II or III or a pharmaceutically acceptable salt or solvate (e.g., hydrate) thereof alone or in combination with an additional suitable therapeutic agent, for example, a cancer-therapeutic agent. When combination therapy is employed, an effective amount can be achieved using a first amount of a compound of Structural Formula I, II or III or a pharmaceutically acceptable salt or solvate (e.g., hydrate) thereof and a second amount of an additional suitable therapeutic agent.

In one embodiment, the compound of Structural Formula I, II or III and the additional therapeutic agent, are each administered in an effective amount (i.e., each in an amount which would be therapeutically effective if administered alone). In another embodiment, the compound of Structural Formula I, II or III and the additional therapeutic agent, are each administered in an amount which alone does not provide a therapeutic effect (a sub-therapeutic dose). In yet another embodiment, the compound of Structural Formula I, II or III be administered in an effective amount, while the additional therapeutic agent is administered in a sub-therapeutic dose. In still another embodiment, the compound of Structural Formula I, II or III can be administered in a sub-therapeutic dose, while the additional therapeutic agent, for example, a suitable cancer-therapeutic agent is administered in an effective amount.

As used herein, the terms "in combination" or "coadministration" can be used interchangeably to refer to the use of more than one therapies (e.g., one or more prophylactic and/or therapeutic agents). The use of the terms does not restrict the order in which therapies (e.g., prophylactic and/or therapeutic agents) are administered to a subject.

Coadministration encompasses administration of the first and second amounts of the compounds of the coadministration in an essentially simultaneous manner, such as in a single pharmaceutical composition, for example, capsule or tablet having a fixed ratio of first and second amounts, or in multiple, separate capsules or tablets for each. In addition, such coadministration also encompasses use of each compound in a sequential manner in either order.

When coadministration involves the separate administration of the first amount of a compound of Structural Formula I, II or III and a second amount of an additional therapeutic agent, the compounds are administered sufficiently close in time to have the desired therapeutic effect. For example, the period of time between each administration which can result in the desired therapeutic effect, can range from minutes to hours and can be determined taking into account the properties of each compound such as potency, solubility, bioavailability, plasma half-life and kinetic profile. For example, a compound of Structural Formula I, II or III and the second therapeutic agent can be administered in any order within about 24 hours of each other, within about 16 hours of each other, within about 8 hours of each other, within about 4 hours of each other, within about 1 hour of each other or within about 30 minutes of each other.

More, specifically, a first therapy (e.g., a prophylactic or therapeutic agent such as a compound of the invention) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a prophylactic or therapeutic agent such as an anti-cancer agent) to a subject.

It is understood that the method of coadministration of a first amount of a compound of Structural Formula I, II or III and a second amount of an additional therapeutic agent can result in an enhanced or synergistic therapeutic effect, wherein the combined effect is greater than the additive effect that would result from separate administration of the first amount of the compound of Structural Formula I, II or III and the second amount of the additional therapeutic agent.

As used herein, the term "synergistic" refers to a combination of a compound of the invention and another therapy (e.g., a prophylactic or therapeutic agent), which is more effective than the additive effects of the therapies. A synergistic effect of a combination of therapies (e.g., a combination of prophylactic or therapeutic agents) permits the use of lower dosages of one or more of the therapies and/or less frequent administration of said therapies to a subject. The ability to utilize lower dosages of a therapy (e.g., a prophylactic or therapeutic agent) and/or to administer said therapy less frequently reduces the toxicity associated with the administration of said therapy to a subject without reducing the efficacy of said therapy in the prevention, management or treatment of a disorder. In addition, a synergistic effect can result in improved efficacy of agents in the prevention, management or treatment of a disorder. Finally, a synergistic effect of a combination of therapies (e.g., a combination of prophylactic or therapeutic agents) may avoid or reduce adverse or unwanted side effects associated with the use of either therapy alone.

The presence of a synergistic effect can be determined using suitable methods for assessing drug interaction. Suitable methods include, for example, the Sigmoid-Emax equation (Holford, N. H. G. and Scheiner, L. B., Clin. Pharmacokinet. 6: 429-453 (1981)), the equation of Loewe additivity (Loewe, S. and Muischnek, H., Arch. Exp. Pathol Pharmacol. 114: 313-326 (1926)) and the median-effect equation (Chou, T. C. and Talalay, P., Adv. Enzyme Regul. 22: 27-55 (1984)). Each equation referred to above can be applied with experimental data to generate a corresponding graph to aid in assessing the effects of the drug combination. The corresponding graphs associated with the equations referred to above are the concentration-effect curve, isobologram curve and combination index curve, respectively.

In some embodiments, said additional therapeutic agent is selected from a anti-HIV agent, such as reverse transcriptase inhibitors, protease inhibitors, and fusion inhibitors.

Other examples of agents the compounds of this invention may also be combined with include, without limitation: treatments for Alzheimer's Disease such as Aricept® and Excelon®; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; and agents for treating immunodeficiency disorders such as gamma globulin.

As inhibitors of protein kinases, the compounds and compositions of this invention are also useful in biological samples. One aspect of the invention relates to inhibiting protein kinase activity in a biological sample, which method comprises contacting said biological sample with a compound of formula I, II or III or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof.

Inhibition of STPK activity in a biological sample is useful for a variety of purposes that are known to one of skill in the art. Examples of such purposes include, but are not limited to, blood transfusion, organ-transplantation, and biological specimen storage.

Another aspect of this invention relates to the study of protein kinases in biological and pathological phenomena; the study of intracellular signal transduction pathways mediated by such protein kinases; and the comparative evaluation of new protein kinase inhibitors. Examples of such uses include, but are not limited to, biological assays such as enzyme assays and cell-based assays.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands. Detailed conditions for assaying a compound utilized in this invention are set forth in the Examples below.

Another aspect of this invention relates to the use of the compounds described here (in particular those with moderate observed affinity for biochemical targets (IC50 1-10 μM)) as start points for chemistry optimization. In particular, one aspect of this invention relates to routine inhibition studies against a target enzyme for chemical optimization.

Another aspect of this invention relates to the use of the compounds described herein for crystallography (in particular those with moderate observed affinity for biochemical targets): In particular, the one aspect of this invention relates to the generation of co-complex crystal structures with compounds described herein.

Another aspect of this invention relates to the use of the compounds described herein as chemical tools to probe target biology in vitro and in vivo: In particular inhibitors with moderate affinity in biochemical assays can be used to probe the biological impact of inhibiting a target enzyme in cells and in whole animal models of disease.

Another aspect of the invention provides a method for modulating enzyme activity by contacting a compound of formula I, II or III with a STPK.

Abbreviations

The following abbreviations are used:
DMSO dimethyl sulfoxide
TCA trichloroacetic acid
ATP adenosine triphosphate
BSA bovine serum albumin
DTT dithiothreitol
MOPS 4-morpholinepropanesulfonic acid
NMR nuclear magnetic resonance
HPLC high performance liquid chromatography
LCMS liquid chromatography-mass spectrometry
TLC thin layer chromatography
Rt retention time In some embodiments, the compounds of this invention are represented in Table 1. In certain embodiments, the variables used herein are as defined in the specific embodiments as shown in Tables 1.

TABLE 1
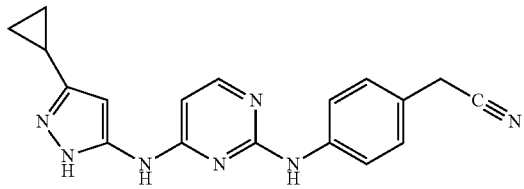 [SMILES: N#CCc1ccc(Nc2nccc(Nc3cc(C4CC4)n[nH]3)n2)cc1]
1
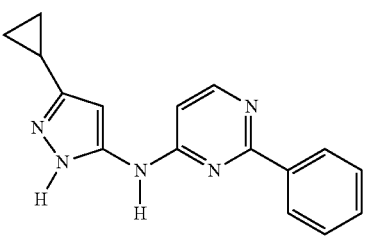 [SMILES: c1ccc(-c2nccc(Nc3cc(C4CC4)n[nH]3)n2)cc1]
2
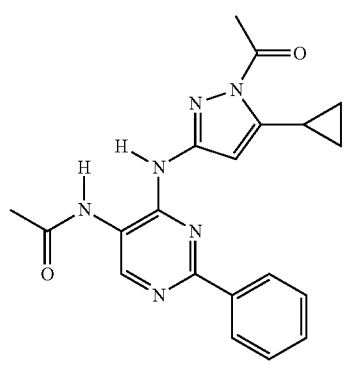 [SMILES: CC(=O)Nc1cnc(-c2ccccc2)nc1Nc1cc(C2CC2)n(C(C)=O)n1]
3
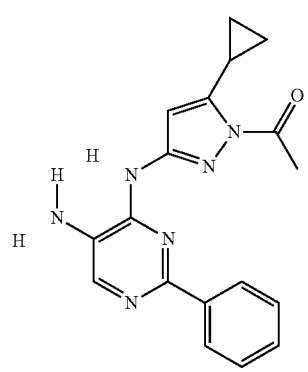
4
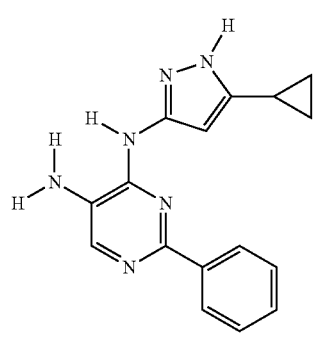
5

TABLE 1-continued
| | |
|---|---|
| 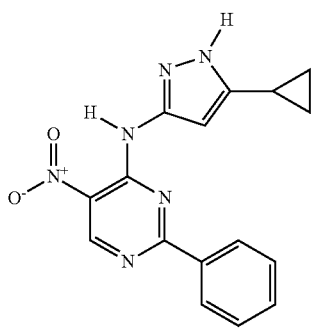 [SMILES: O=[N+]([O-])c1cnc(-c2ccccc2)nc1Nc1cc(C2CC2)[nH]n1] | 6 |
| 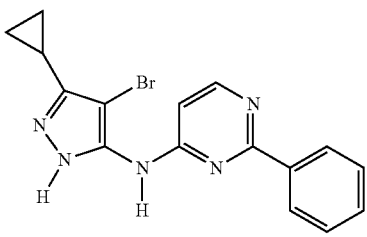 [SMILES: Brc1c(C2CC2)n[nH]c1Nc1ccnc(-c2ccccc2)n1] | 7 |
| 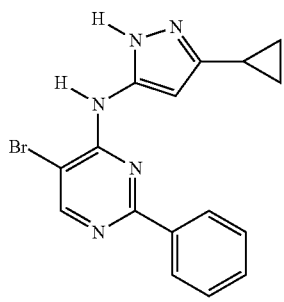 [SMILES: Brc1cnc(-c2ccccc2)nc1Nc1cc(C2CC2)n[nH]1] | 8 |
| 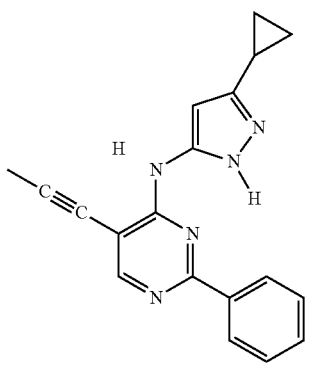 | 9 |
| 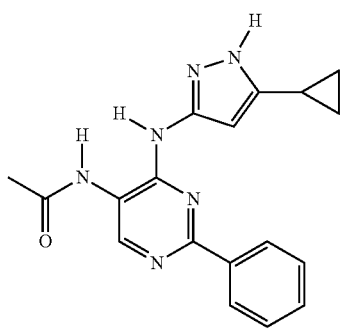 [SMILES: CC(=O)Nc1cnc(-c2ccccc2)nc1Nc1cc(C2CC2)[nH]n1] | 10 |

TABLE 1-continued
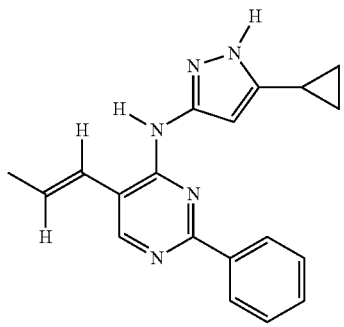 [SMILES: C/C=C/c1cnc(-c2ccccc2)nc1Nc1cc(C2CC2)[nH]n1]
11
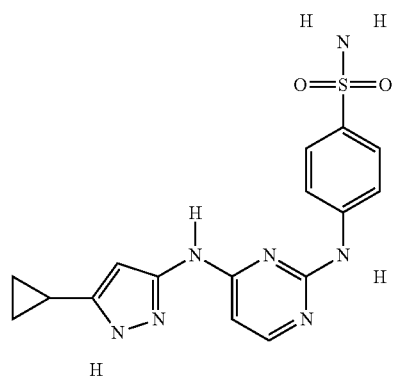
12
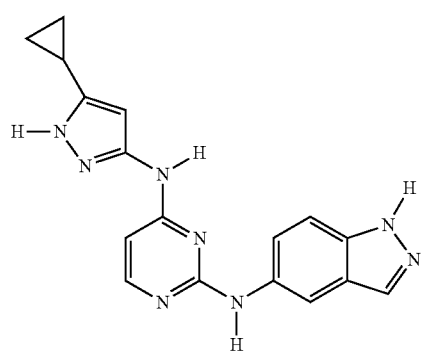 [SMILES: c1cc(Nc2cc(C3CC3)[nH]n2)nc(Nc2ccc3[nH]ncc3c2)n1]
13
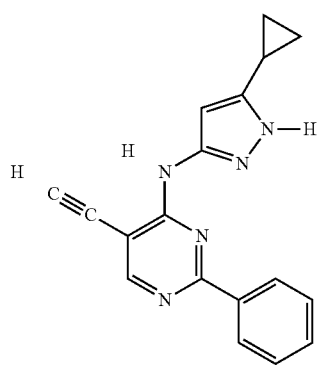
14

TABLE 1-continued
15
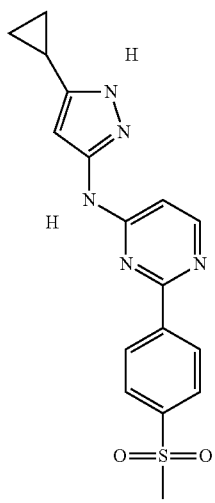
16
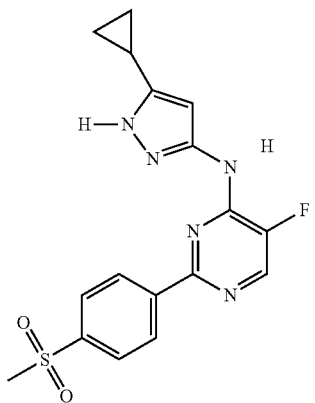
17
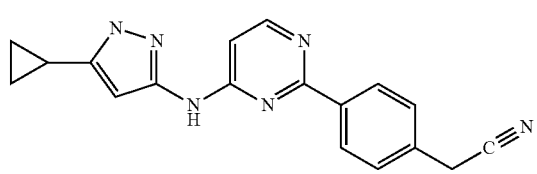
18
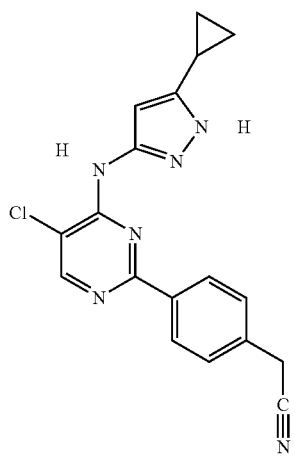

TABLE 1-continued
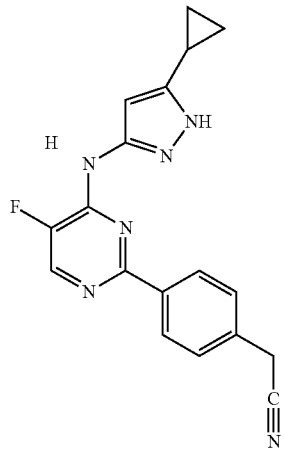
19
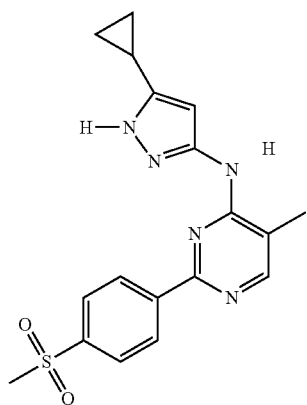
20
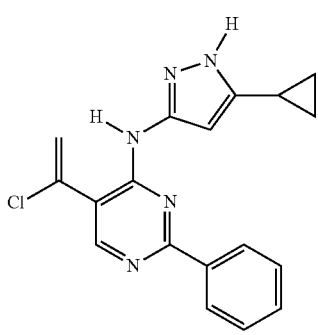 [SMILES: C=C(Cl)c1cnc(-c2ccccc2)nc1Nc1cc(C2CC2)[nH]n1]
21
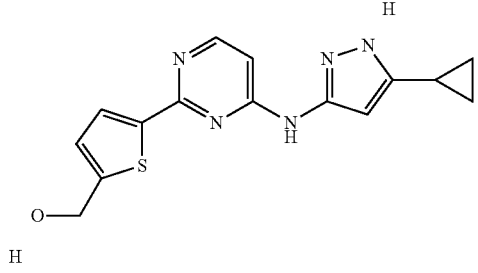
22

TABLE 1-continued
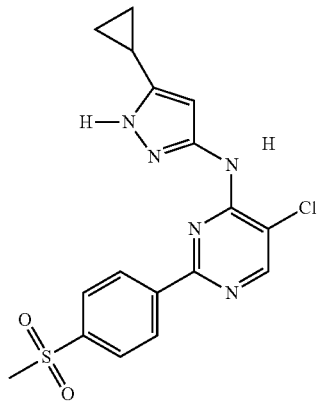
23
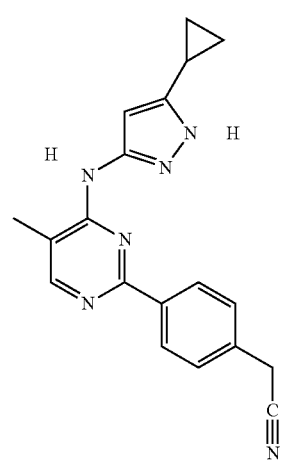
24
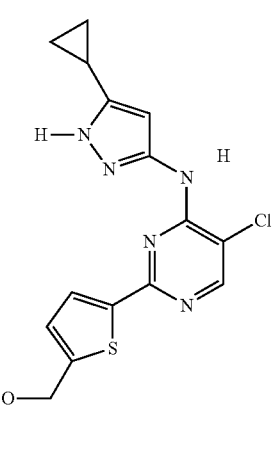
25

TABLE 1-continued
| | |
|---|---|
| 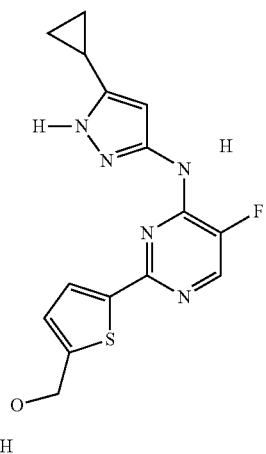 | 26 |
| 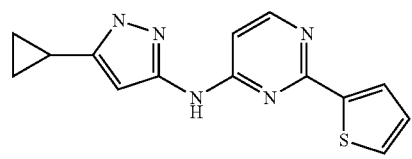 | 27 |
| 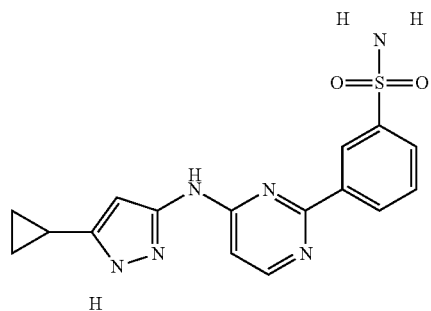 | 28 |
| 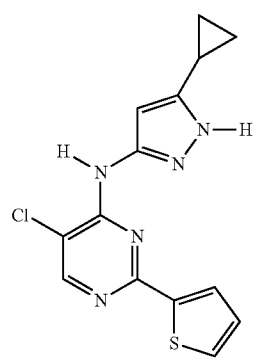 [SMILES: Clc1cnc(-c2cccs2)nc1Nc1cc(C2CC2)[nH]n1] | 29 |

TABLE 1-continued
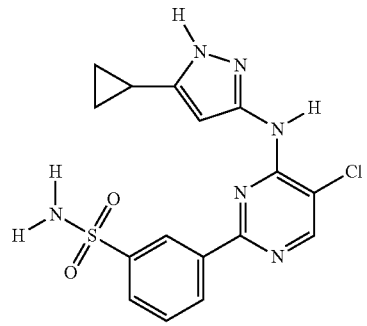 [SMILES: NS(=O)(=O)c1cccc(-c2ncc(Cl)c(Nc3cc(C4CC4)[nH]n3)n2)c1]
30
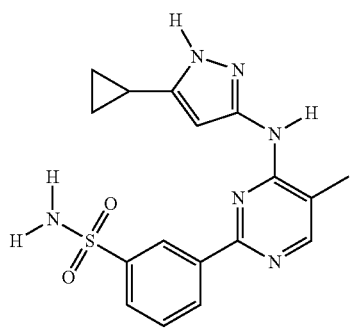 [SMILES: Cc1cnc(-c2cccc(S(N)(=O)=O)c2)nc1Nc1cc(C2CC2)[nH]n1]
31
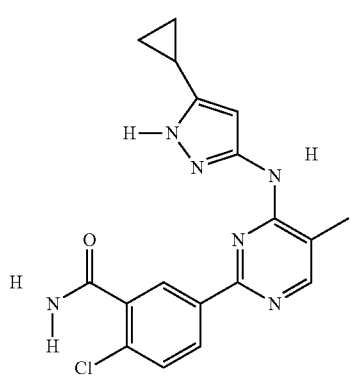
32
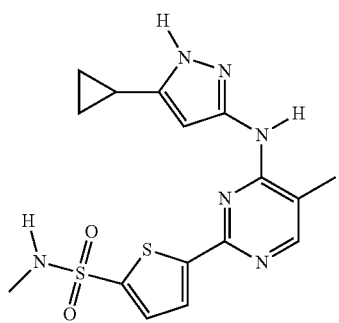
33

TABLE 1-continued
| | |
|---|---|
| 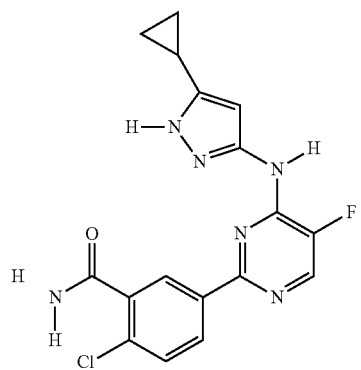 | 34 |
| 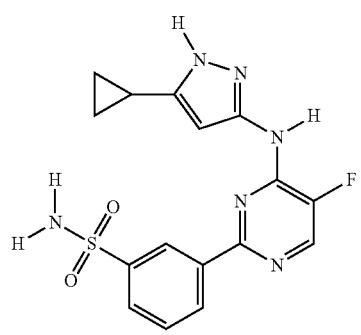 [SMILES: NS(=O)(=O)c1cccc(-c2ncc(F)c(Nc3cc(C4CC4)[nH]n3)n2)c1] | 35 |
| 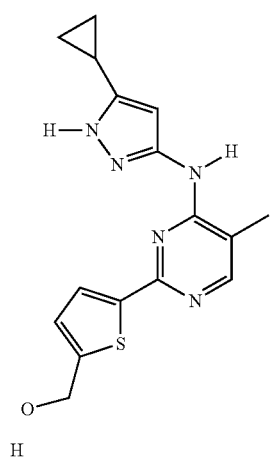 | 36 |
| 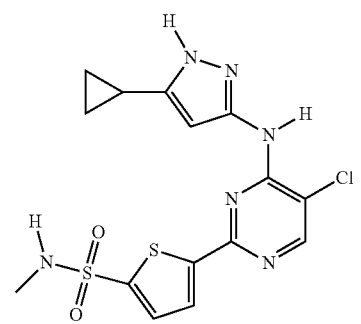 | 37 |

TABLE 1-continued
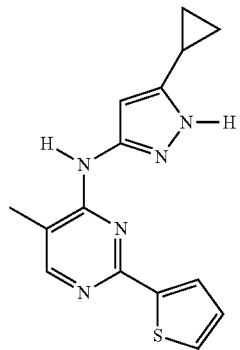 [SMILES: Cc1cnc(-c2cccs2)nc1Nc1cc(C2CC2)[nH]n1]
38
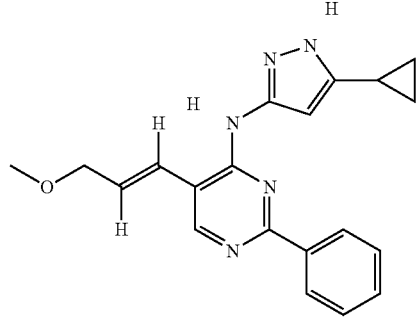
39
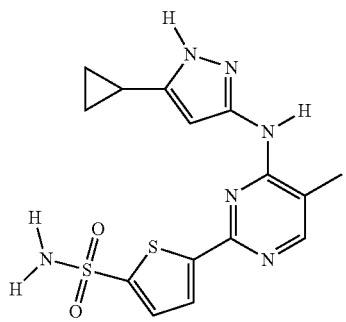 [SMILES: Cc1cnc(-c2ccc(S(N)(=O)=O)s2)nc1Nc1cc(C2CC2)[nH]n1]
40
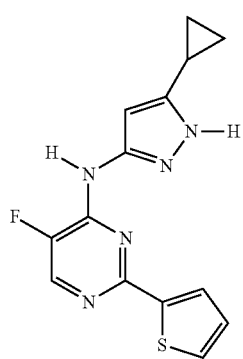 [SMILES: Fc1cnc(-c2cccs2)nc1Nc1cc(C2CC2)[nH]n1]
41

TABLE 1-continued
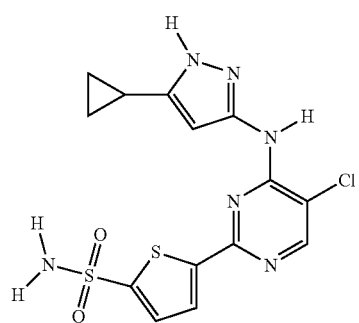 [SMILES: NS(=O)(=O)c1ccc(-c2ncc(Cl)c(Nc3cc(C4CC4)[nH]n3)n2)s1]
42
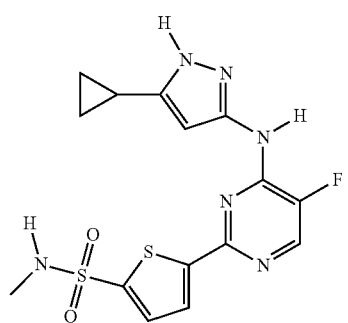 [SMILES: CNS(=O)(=O)c1ccc(-c2ncc(F)c(Nc3cc(C4CC4)[nH]n3)n2)s1]
43
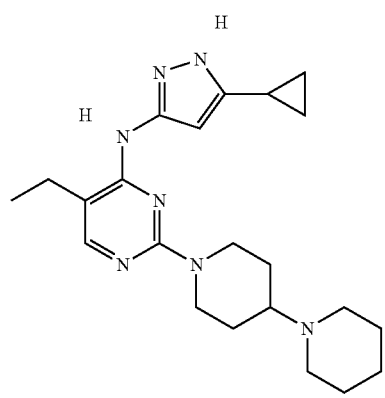
44
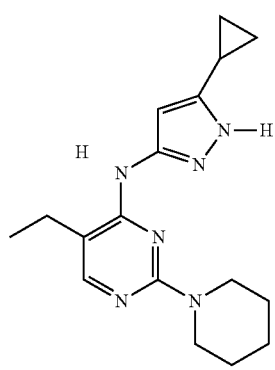
45

TABLE 1-continued
| | |
|---|---|
| 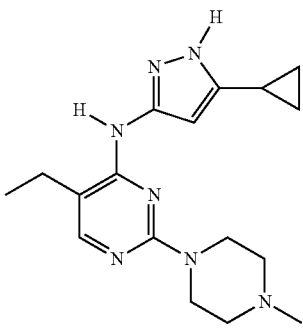 [SMILES: CCc1cnc(N2CCN(C)CC2)nc1Nc1cc(C2CC2)[nH]n1] | 46 |
| 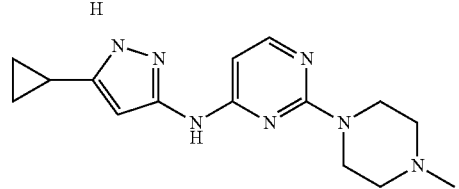 | 47 |
| 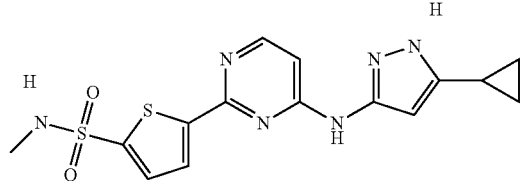 | 48 |
| 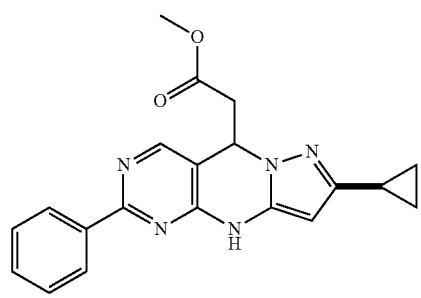 | 49 |
| 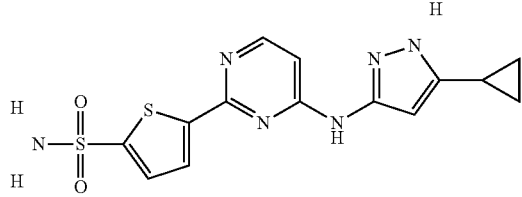 | 50 |
| 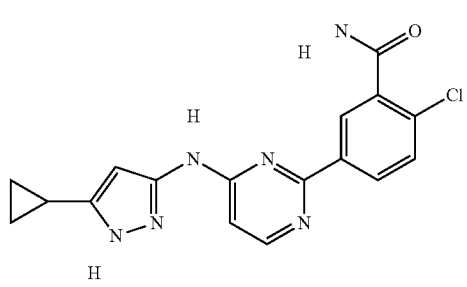 | 51 |

TABLE 1-continued
| | |
|---|---|
| 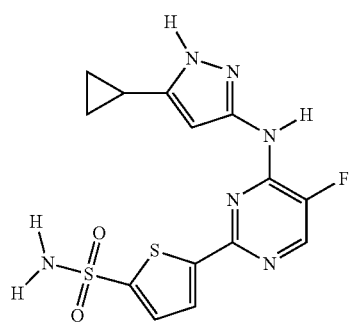 [SMILES: NS(=O)(=O)c1ccc(-c2ncc(F)c(Nc3cc(C4CC4)[nH]n3)n2)s1] | 52 |
| 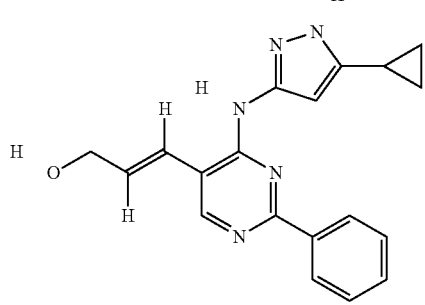 | 53 |
| 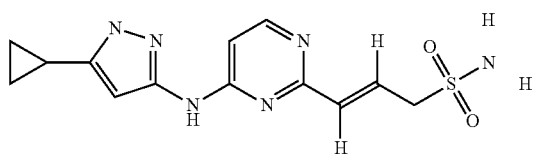 | 54 |
| 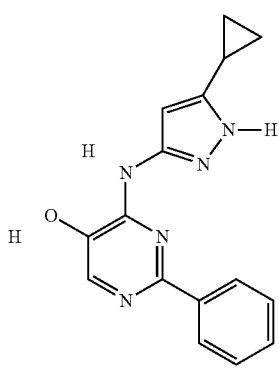 | 55 |
| 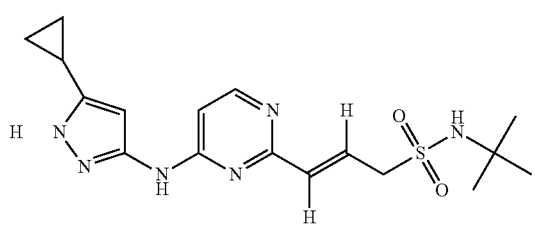 | 56 |

TABLE 1-continued
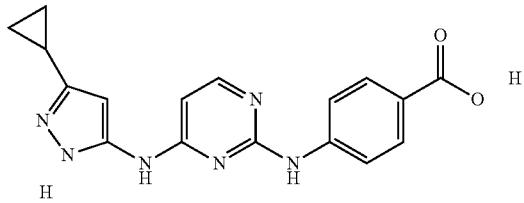
57
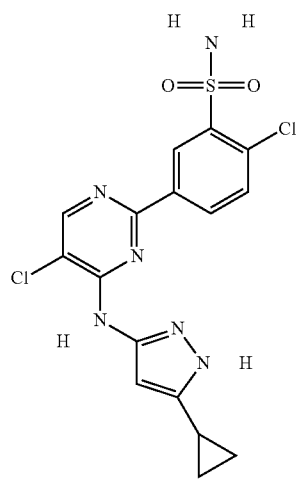
58
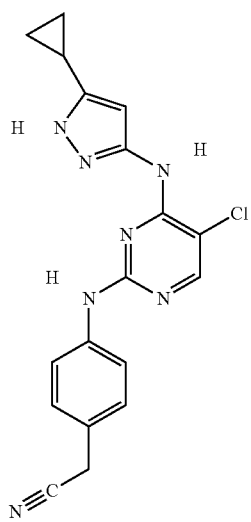
59
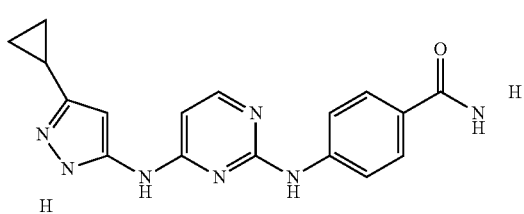
60

TABLE 1-continued
| | |
|---|---|
| 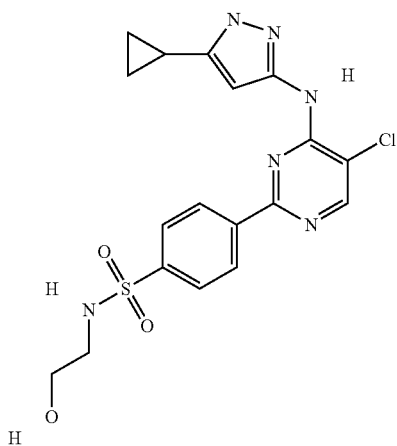 | 61 |
| 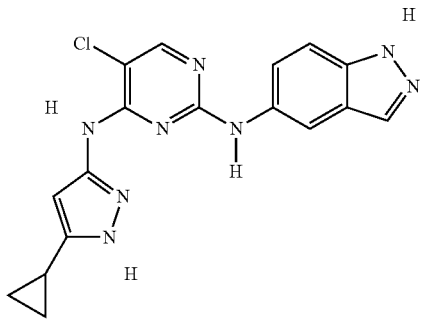 | 62 |
| 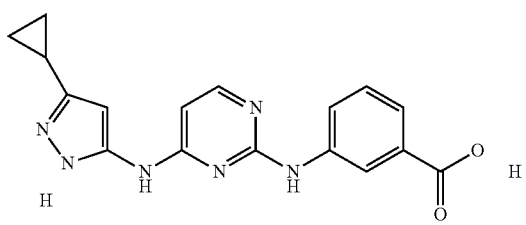 | 63 |
| 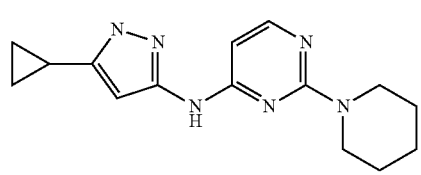 | 64 |
| 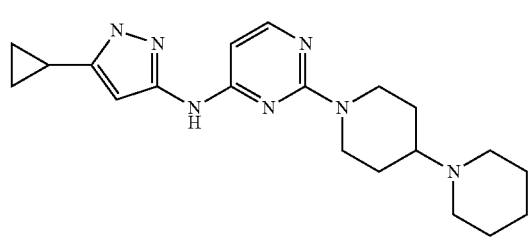 | 65 |

TABLE 1-continued
| | |
|---|---|
| 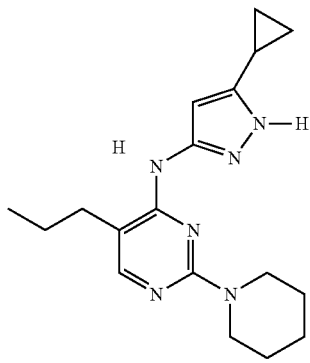 | 66 |
| 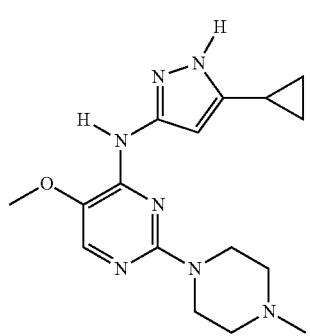 | 67 |
| 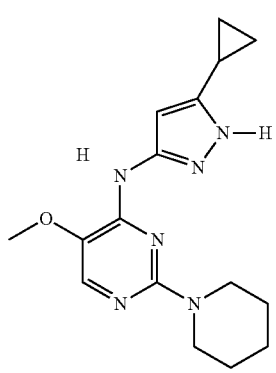 | 68 |
| 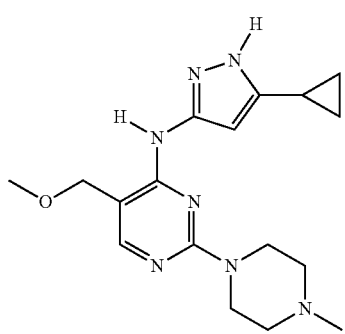 | 69 |

TABLE 1-continued
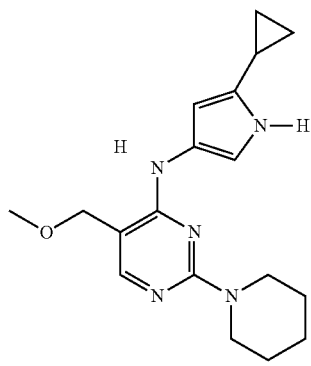
70
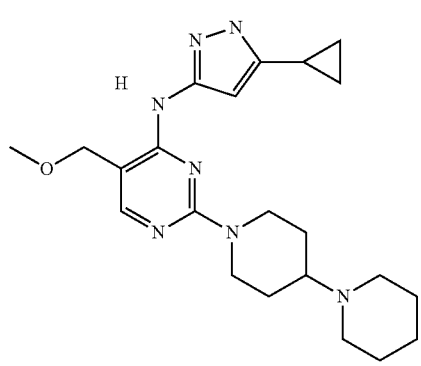
71
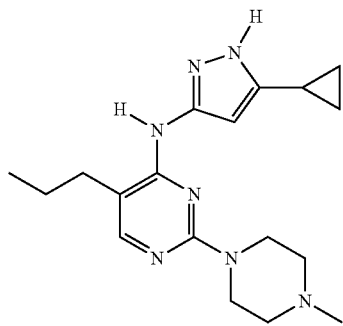 [SMILES: CCCc1cnc(N2CCN(C)CC2)nc1Nc1cc(C2CC2)[nH]n1]
72
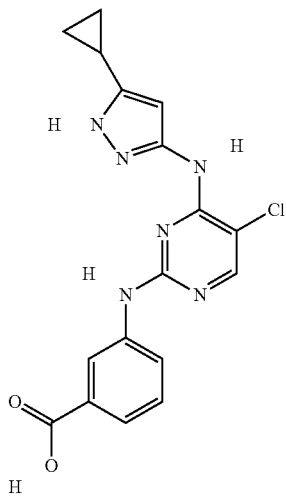
73

TABLE 1-continued
74
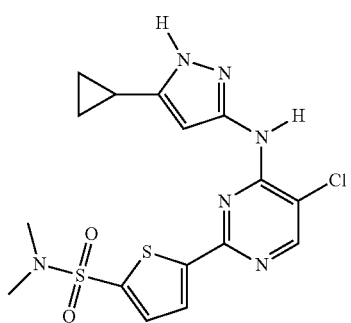 [SMILES: CN(C)S(=O)(=O)c1ccc(-c2ncc(Cl)c(Nc3cc(C4CC4)[nH]n3)n2)s1]
75
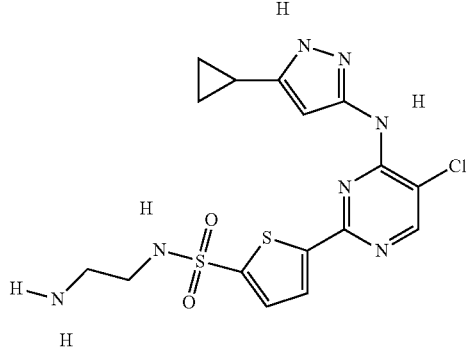
76
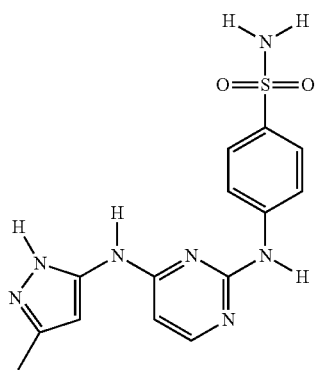 [SMILES: Cc1cc(Nc2ccnc(Nc3ccc(S(N)(=O)=O)cc3)n2)[nH]n1]
77
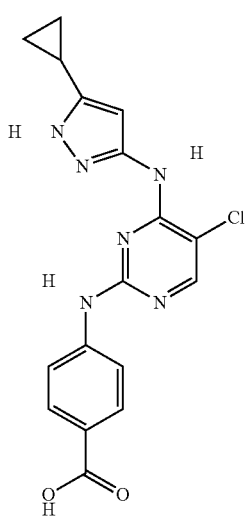

TABLE 1-continued
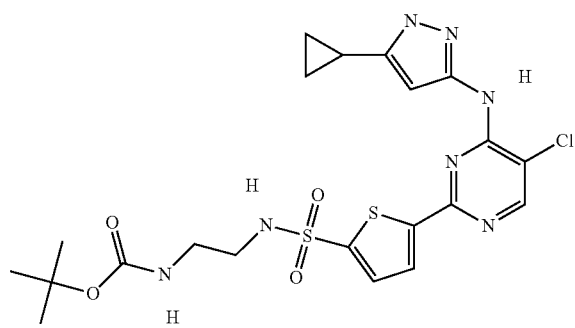
78
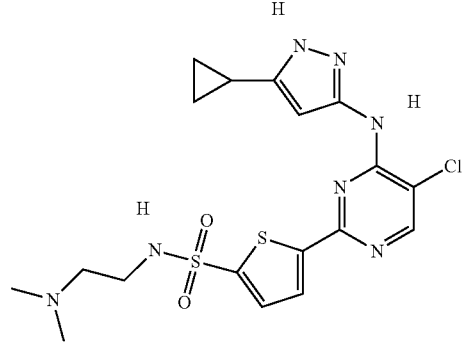
79
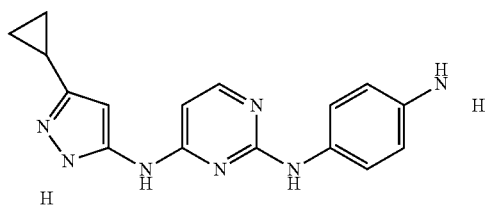
80
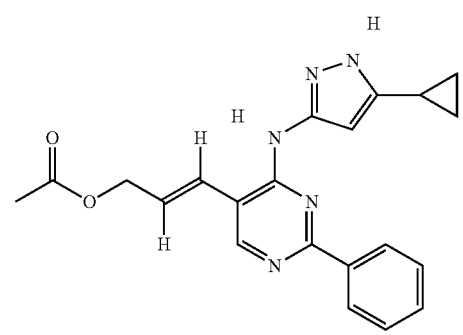
81

TABLE 1-continued
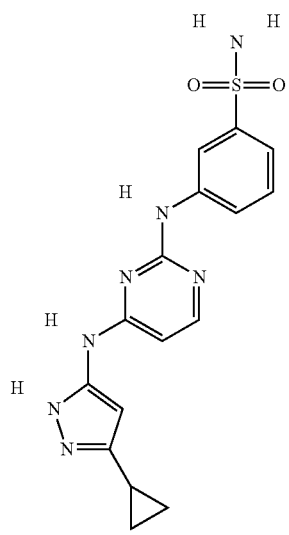
82
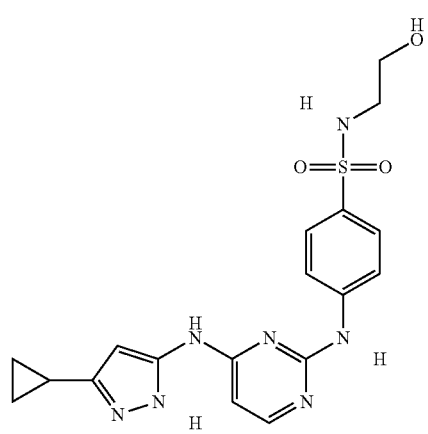
83
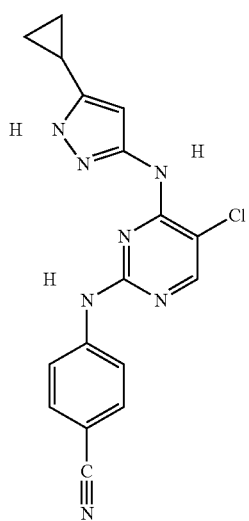
84

TABLE 1-continued
| | |
|---|---|
| 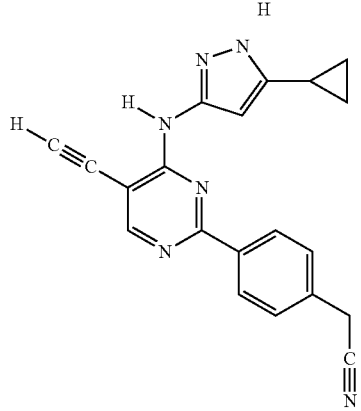 | 85 |
| 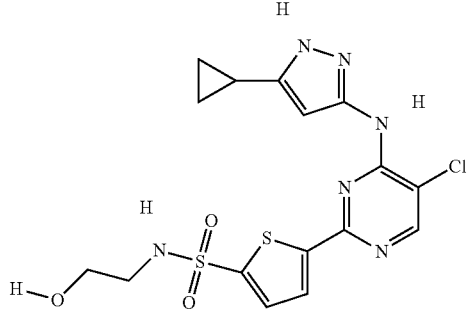 | 86 |
| 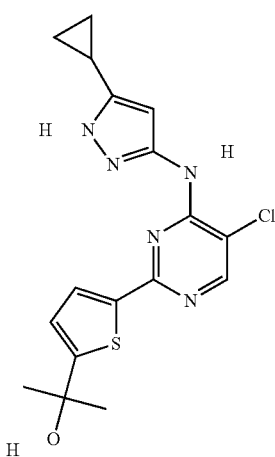 | 87 |
| 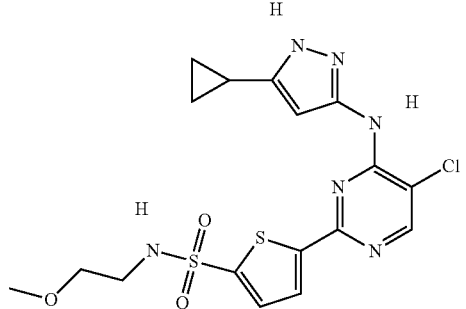 | 88 |

TABLE 1-continued
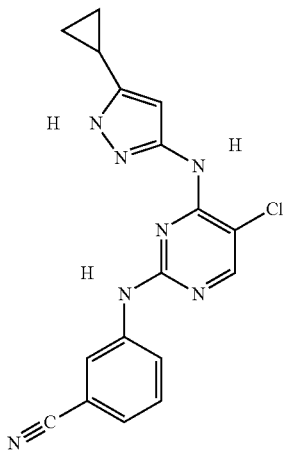
89
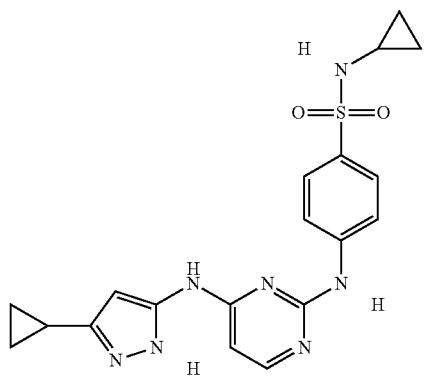
90
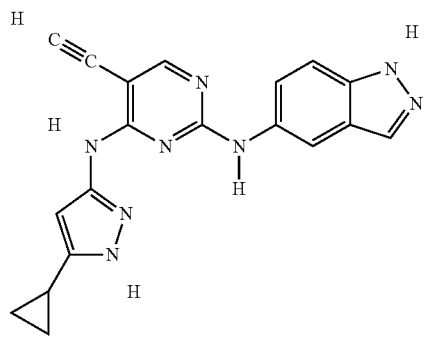
91
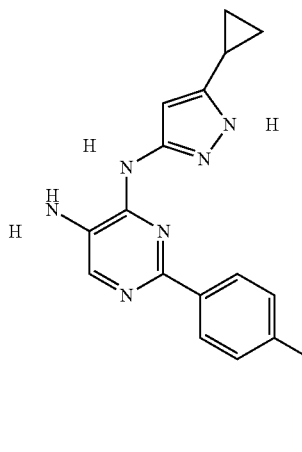
92

TABLE 1-continued
| | |
|---|---|
| 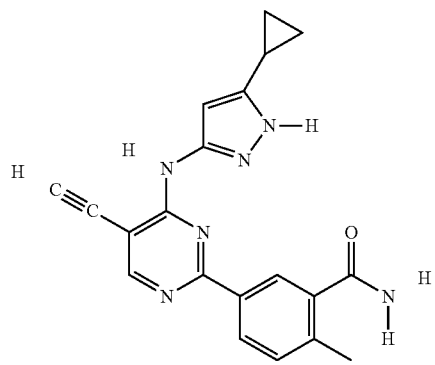 | 93 |
| 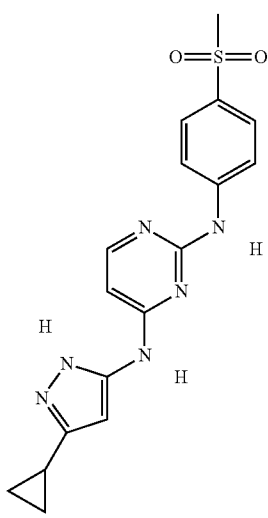 | 94 |
| 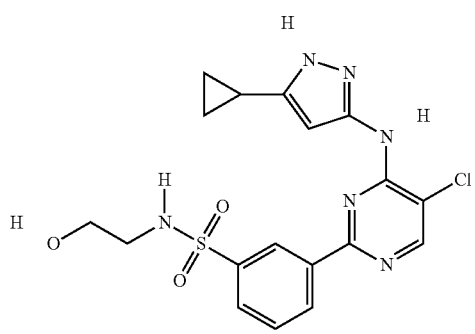 | 95 |
| 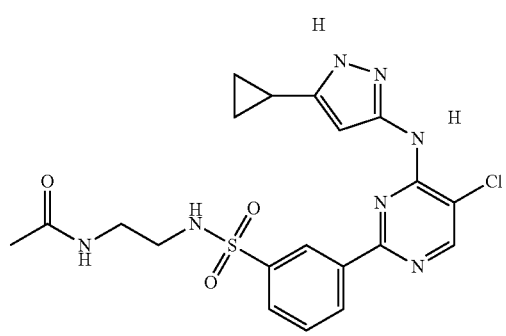 | 96 |

TABLE 1-continued
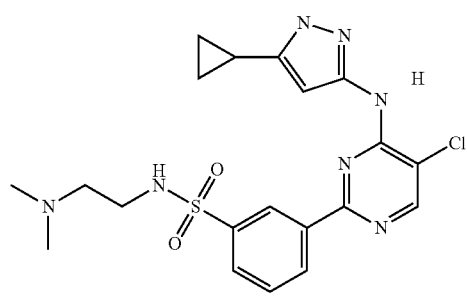
97
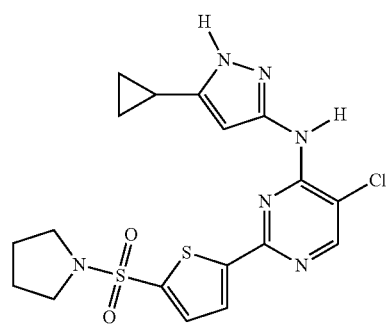 [SMILES: O=S(=O)(c1ccc(-c2ncc(Cl)c(Nc3cc(C4CC4)[nH]n3)n2)s1)N1CCCC1]
98
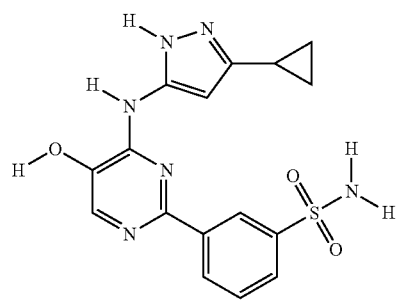 [SMILES: NS(=O)(=O)c1cccc(-c2ncc(O)c(Nc3cc(C4CC4)n[nH]3)n2)c1]
99
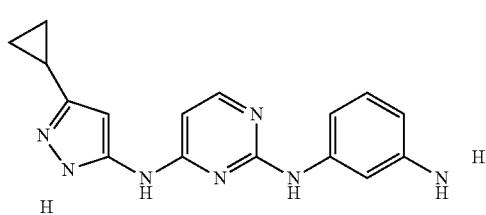
100

TABLE 1-continued
101
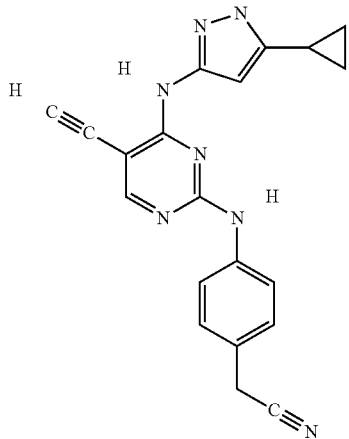
102
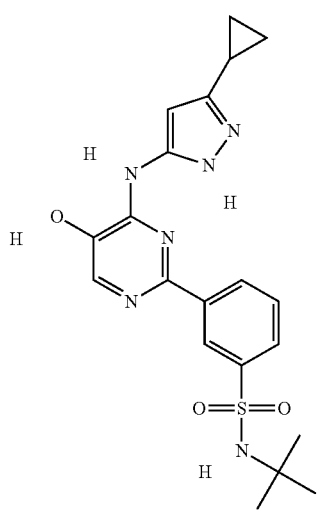
103
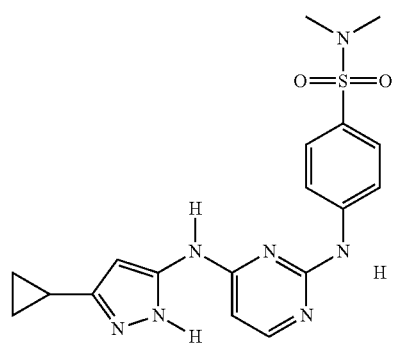

TABLE 1-continued
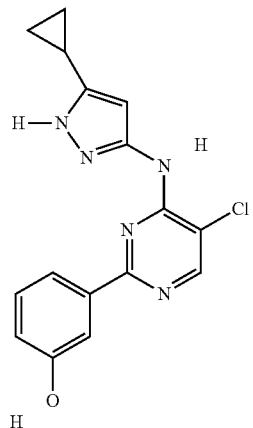
104
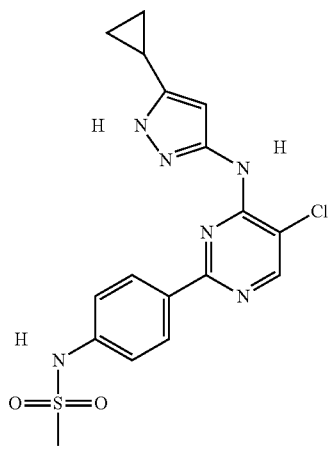
105
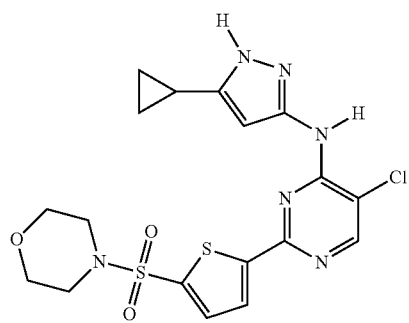 [SMILES: O=S(=O)(c1ccc(-c2ncc(Cl)c(Nc3cc(C4CC4)[nH]n3)n2)s1)N1CCOCC1]
106

TABLE 1-continued
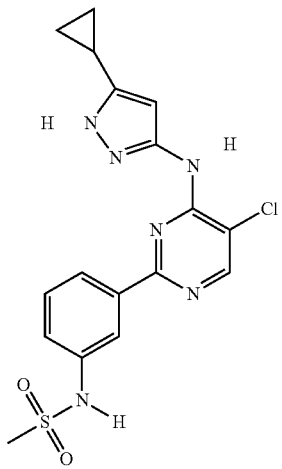 107
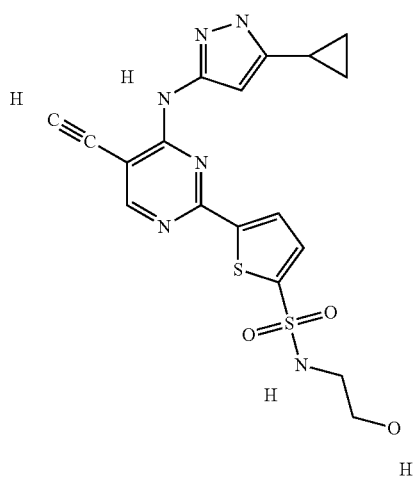 108
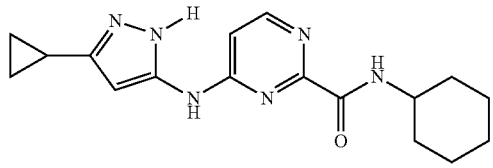 [SMILES: O=C(NC1CCCCC1)c1nccc(Nc2cc(C3CC3)n[nH]2)n1] 109
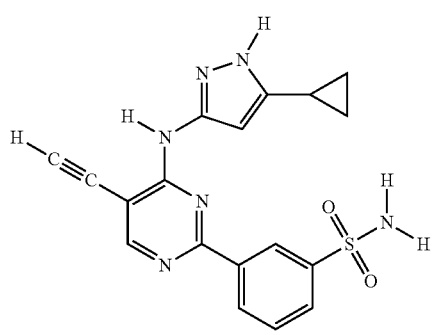 [SMILES: C#Cc1cnc(-c2cccc(S(N)(=O)=O)c2)nc1Nc1cc(C2CC2)[nH]n1] 110

TABLE 1-continued
| | |
|---|---|
| 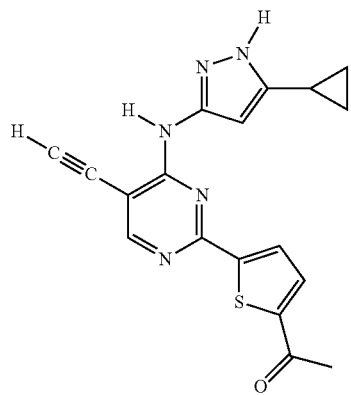 [SMILES: C#Cc1cnc(-c2ccc(C(C)=O)s2)nc1Nc1cc(C2CC2)[nH]n1] | 111 |
| 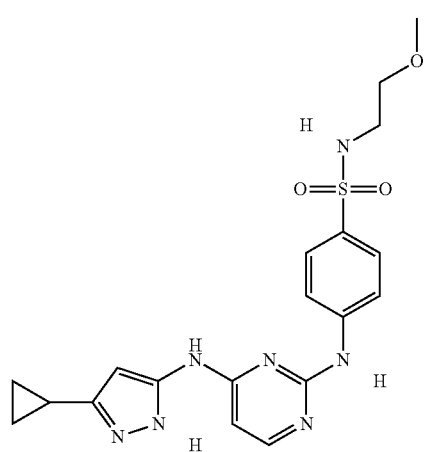 | 112 |
| 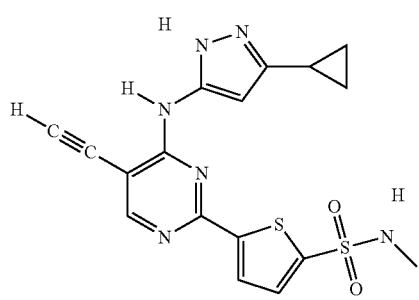 | 113 |
| 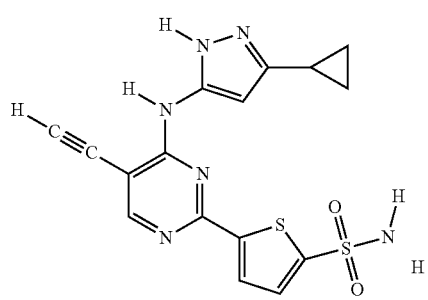 | 114 |

TABLE 1-continued
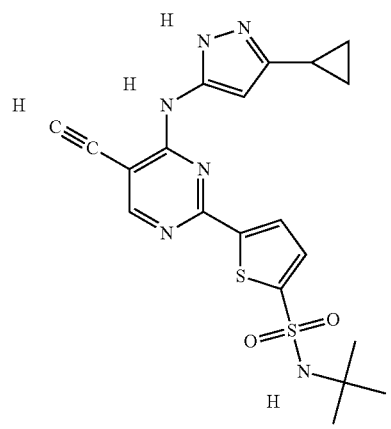
115
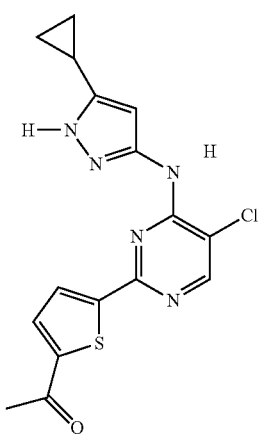
116
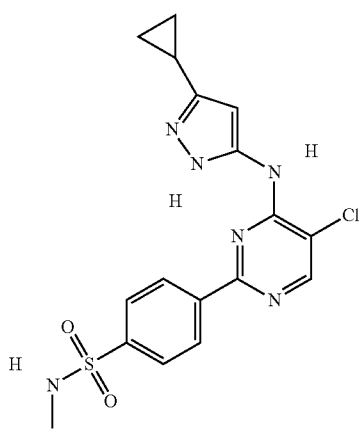
117

TABLE 1-continued
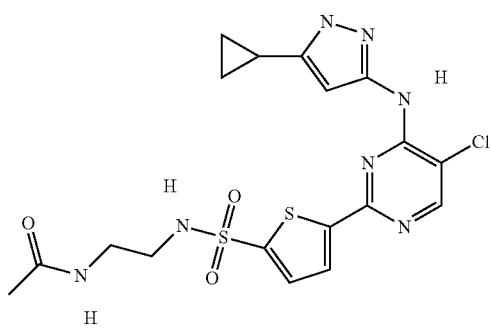
118
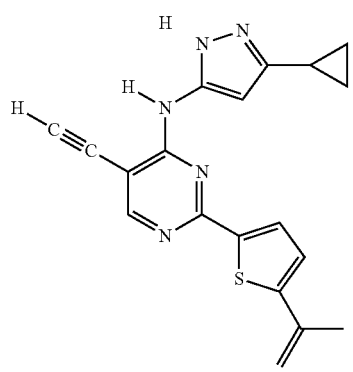
119
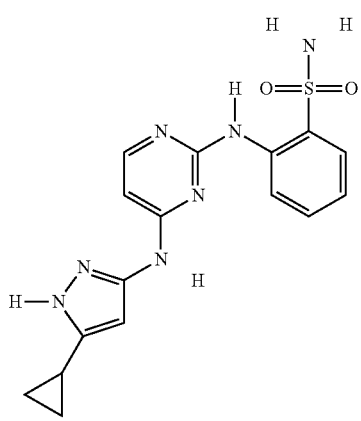
120
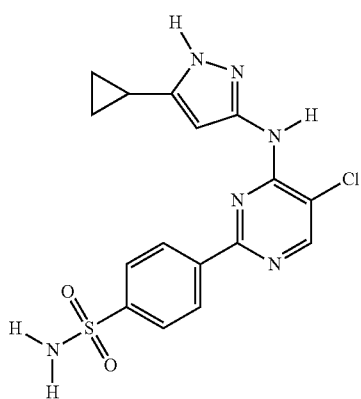 [SMILES: NS(=O)(=O)c1ccc(-c2ncc(Cl)c(Nc3cc(C4CC4)[nH]n3)n2)cc1]
121

TABLE 1-continued
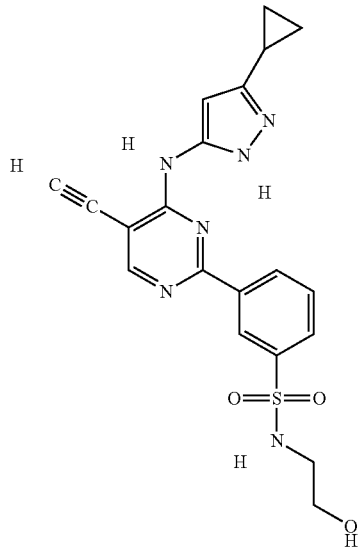
122
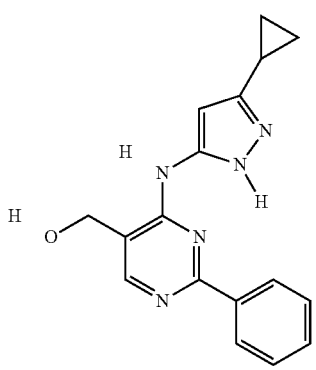
123
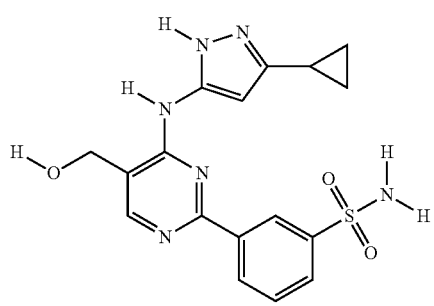 [SMILES: NS(=O)(=O)c1cccc(-c2ncc(CO)c(Nc3cc(C4CC4)n[nH]3)n2)c1]
124
125

TABLE 1-continued
126
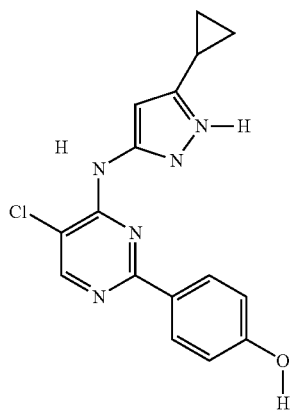
127
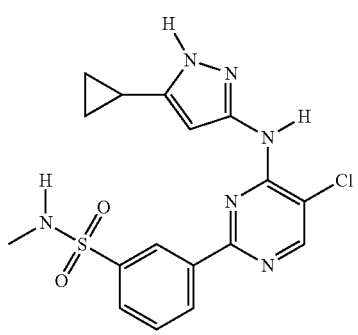 [SMILES: CNS(=O)(=O)c1cccc(-c2ncc(Cl)c(Nc3cc(C4CC4)[nH]n3)n2)c1]
128
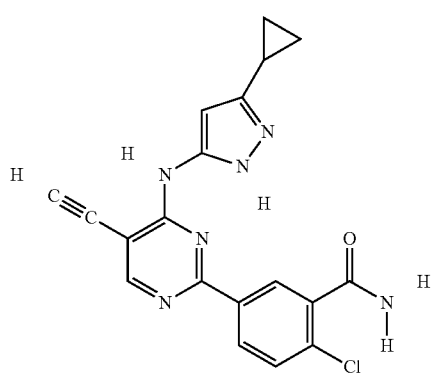
129
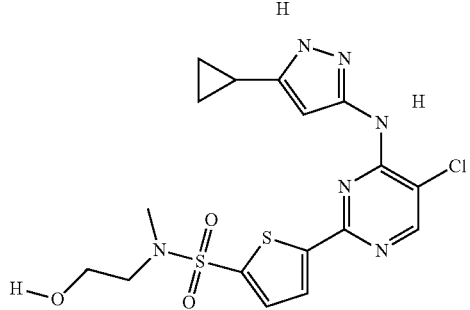

TABLE 1-continued
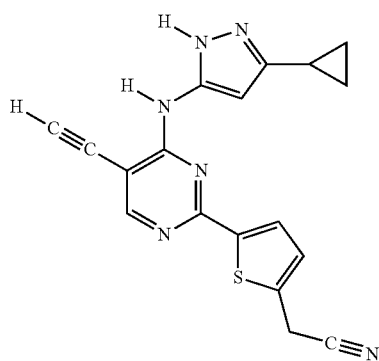 [SMILES: C#Cc1cnc(-c2ccc(CC#N)s2)nc1Nc1cc(C2CC2)n[nH]1]
130
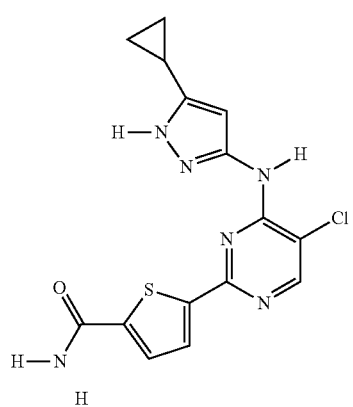
131
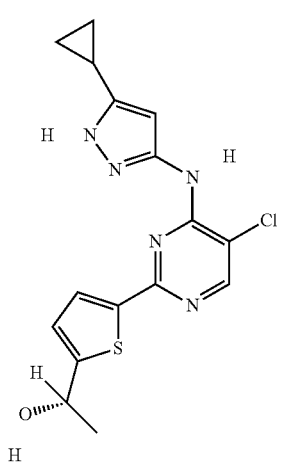
132

TABLE 1-continued
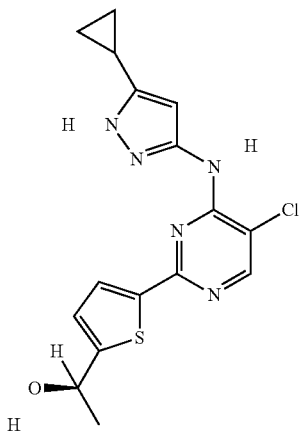
133
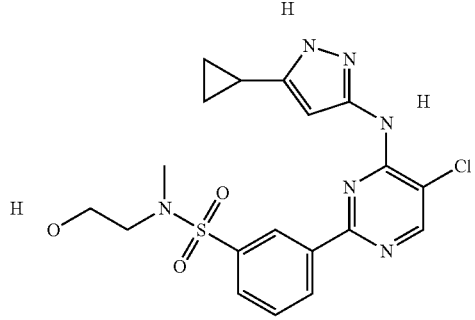
134
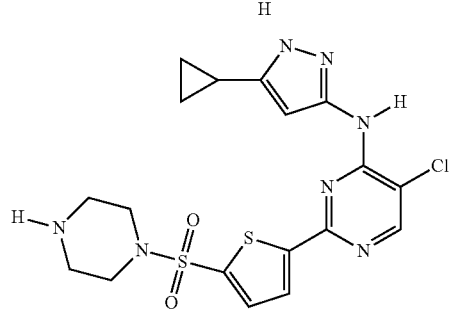
135
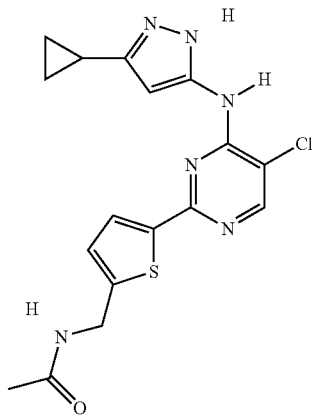
136

TABLE 1-continued
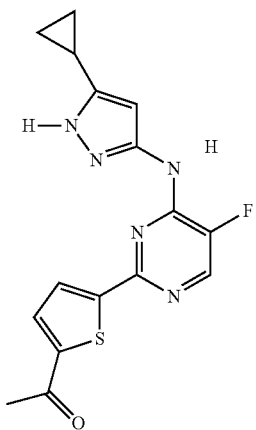
137
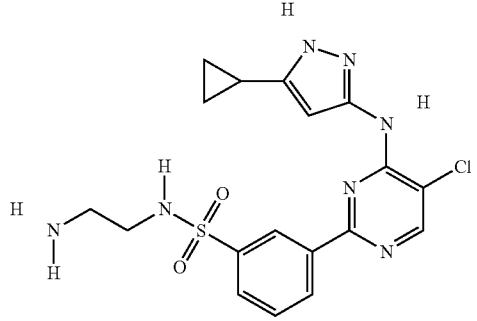
138
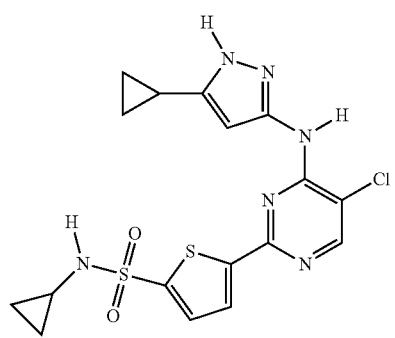 [SMILES: O=S(=O)(NC1CC1)c1ccc(-c2ncc(Cl)c(Nc3cc(C4CC4)[nH]n3)n2)s1]
139
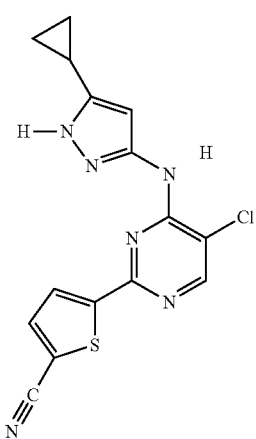
140

TABLE 1-continued
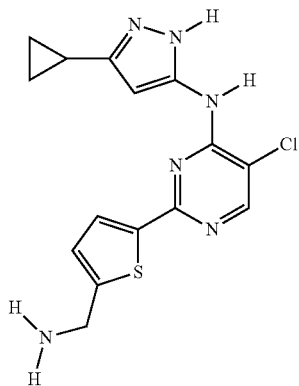 [SMILES: NCc1ccc(-c2ncc(Cl)c(Nc3cc(C4CC4)n[nH]3)n2)s1]
141
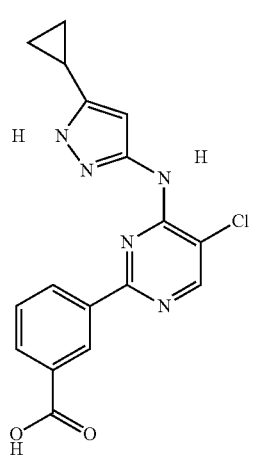
142
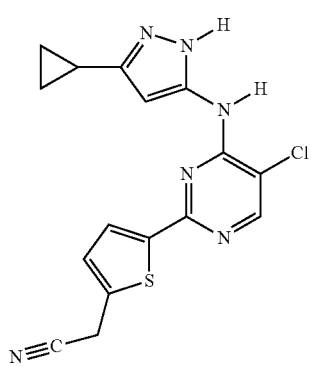 [SMILES: N#CCc1ccc(-c2ncc(Cl)c(Nc3cc(C4CC4)n[nH]3)n2)s1]
143

TABLE 1-continued
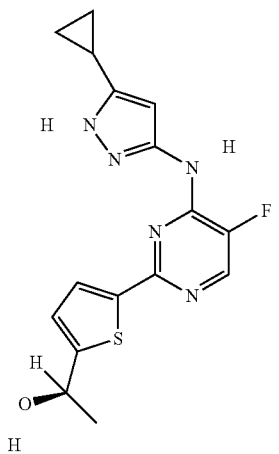
144
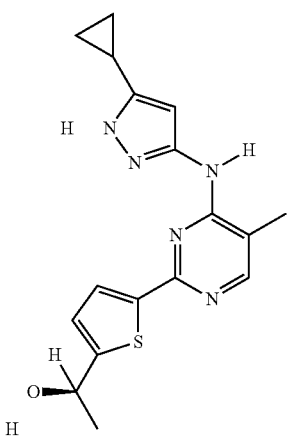
145
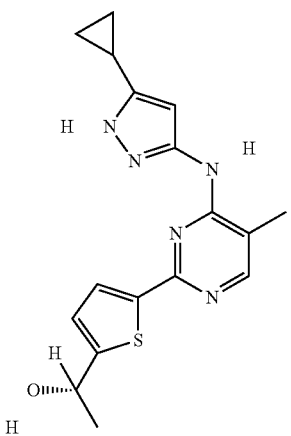
146

TABLE 1-continued
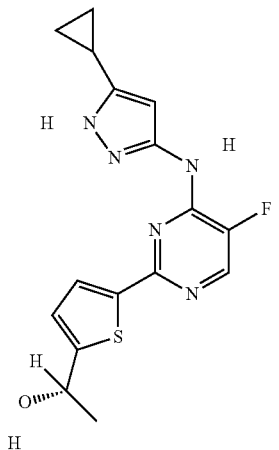
147
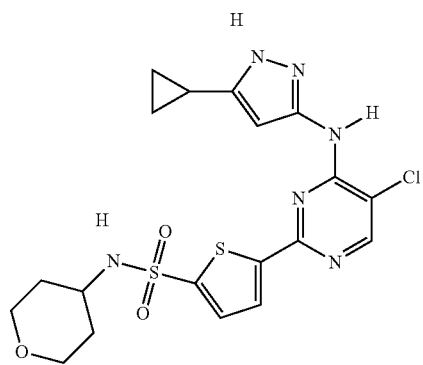
148
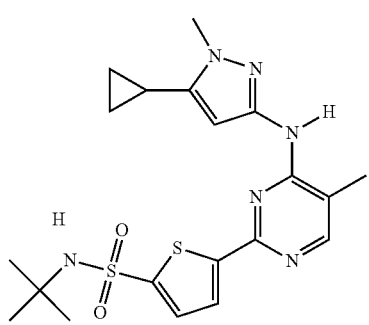
149
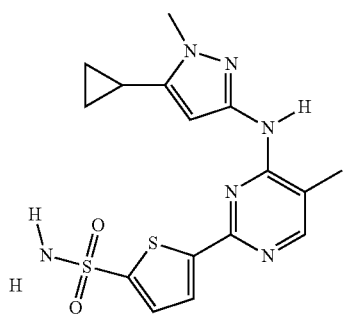
150

TABLE 1-continued
| | |
|---|---|
| 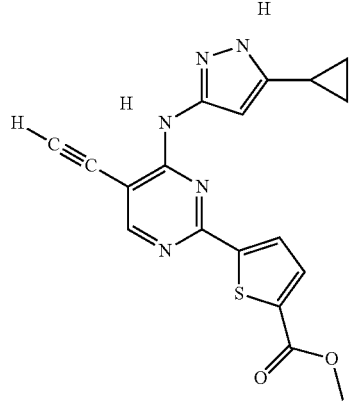 | 151 |
| 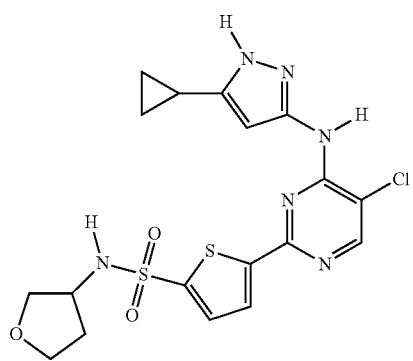 [SMILES: O=S(=O)(NC1CCOC1)c1ccc(-c2ncc(Cl)c(Nc3cc(C4CC4)[nH]n3)n2)s1] | 152 |
| 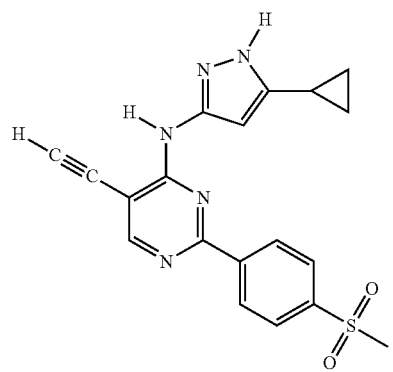 [SMILES: C#Cc1cnc(-c2ccc(S(C)(=O)=O)cc2)nc1Nc1cc(C2CC2)[nH]n1] | 153 |
| 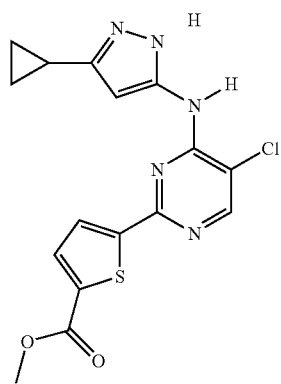 | 154 |

TABLE 1-continued
| | |
|---|---|
| 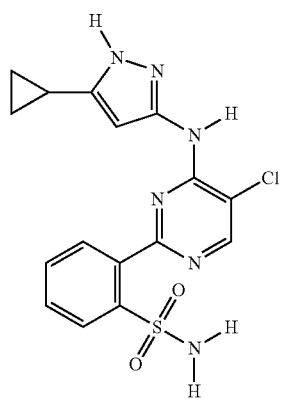 | 155 |
| 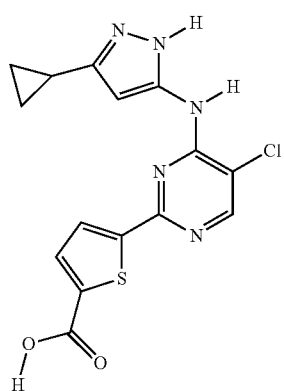 [SMILES: O=C(O)c1ccc(-c2ncc(Cl)c(Nc3cc(C4CC4)n[nH]3)n2)s1] | 156 |
| 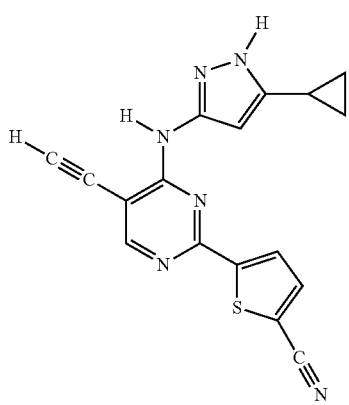 [SMILES: C#Cc1cnc(-c2ccc(C#N)s2)nc1Nc1cc(C2CC2)[nH]n1] | 157 |
| 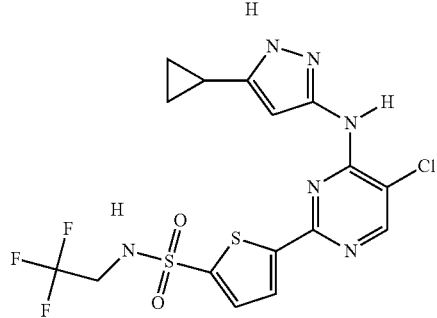 | 158 |

TABLE 1-continued
| | |
|---|---|
| 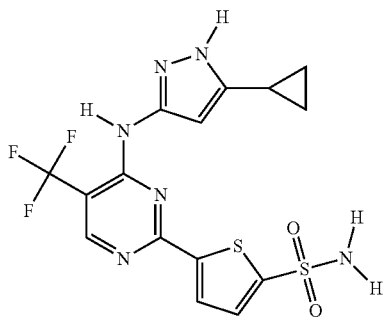 [SMILES: NS(=O)(=O)c1ccc(-c2ncc(C(F)(F)F)c(Nc3cc(C4CC4)[nH]n3)n2)s1] | 159 |
| 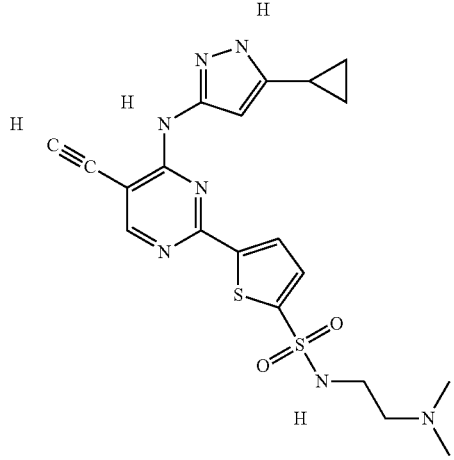 | 160 |
| 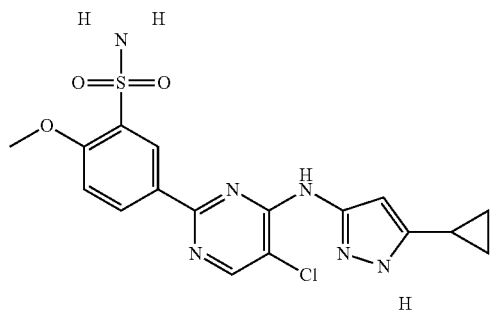 | 161 |
| 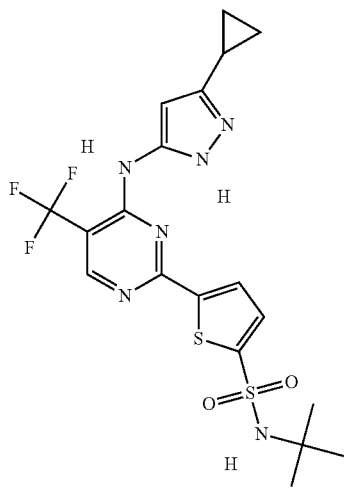 | 162 |

TABLE 1-continued
| | |
|---|---|
| 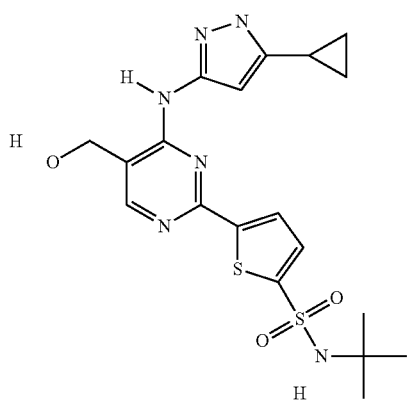 | 163 |
| 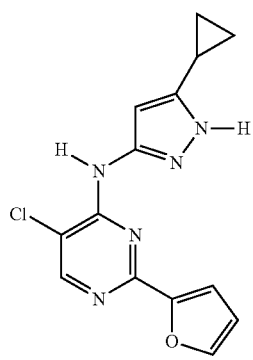 [SMILES: Clc1cnc(-c2ccco2)nc1Nc1cc(C2CC2)[nH]n1] | 164 |
| 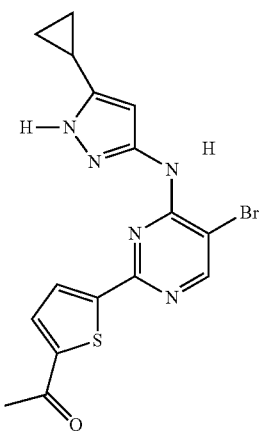 | 165 |
| 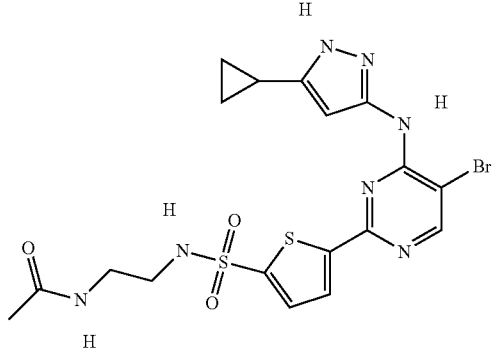 | 166 |

TABLE 1-continued
| | |
|---|---|
| 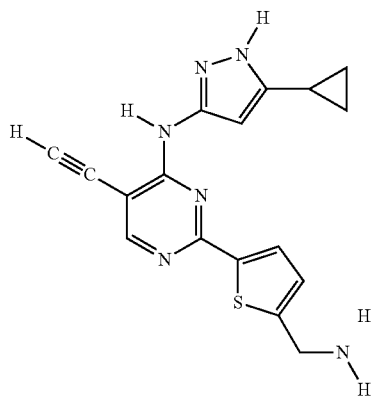 | 167 |
| 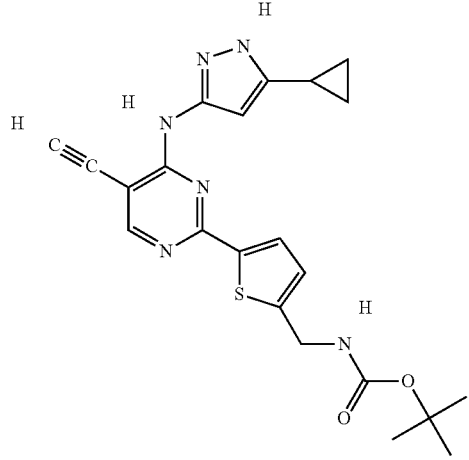 | 168 |
| 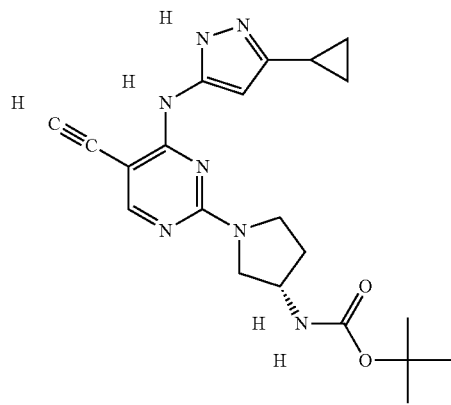 | 169 |
| 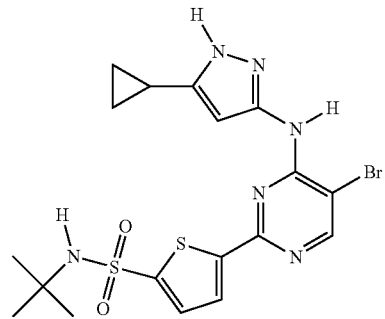 [SMILES: CC(C)(C)NS(=O)(=O)c1ccc(-c2ncc(Br)c(Nc3cc(C4CC4)[nH]n3)n2)s1] | 170 |

TABLE 1-continued
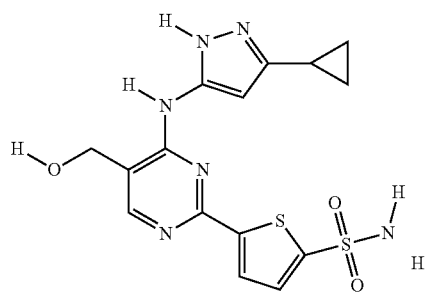
171
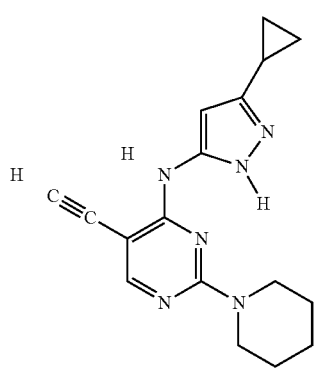
172
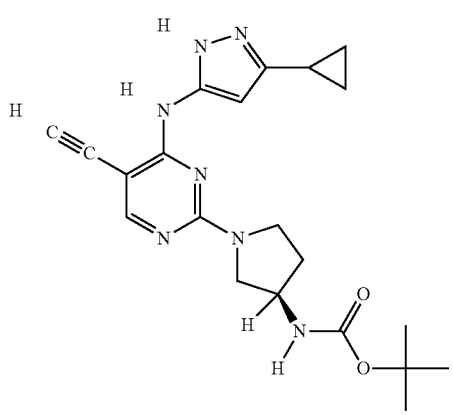
173
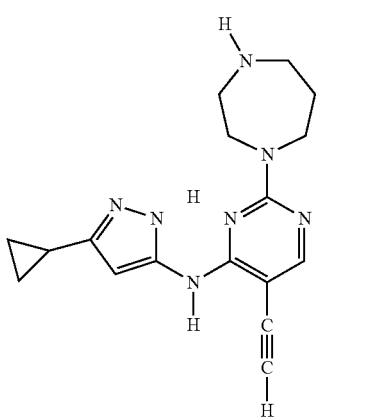
174

TABLE 1-continued
| | |
|---|---|
| 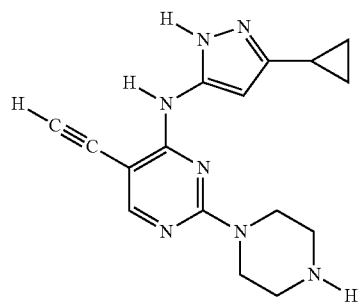 [SMILES: C#Cc1cnc(N2CCNCC2)nc1Nc1cc(C2CC2)n[nH]1] | 175 |
| 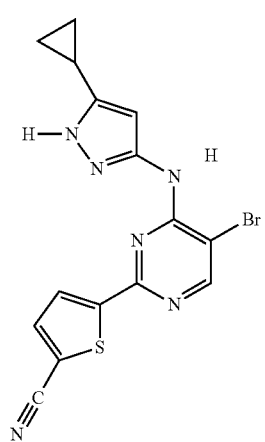 | 176 |
| 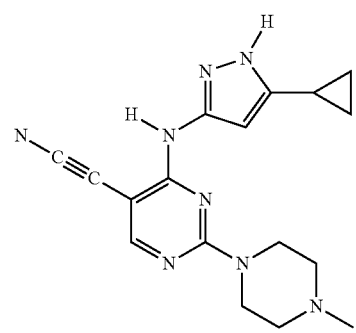 | 177 |
| 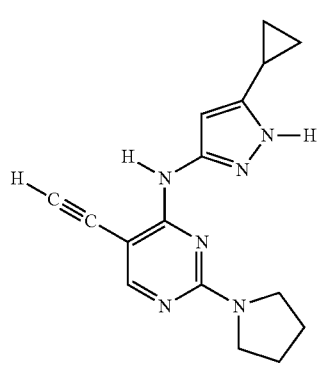 [SMILES: C#Cc1cnc(N2CCCC2)nc1Nc1cc(C2CC2)[nH]n1] | 178 |

TABLE 1-continued
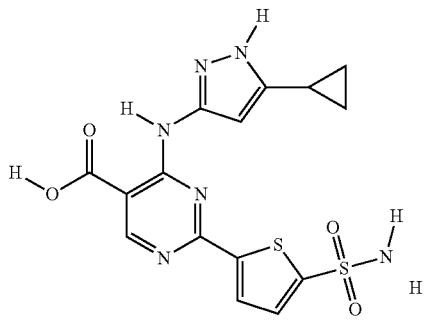
179
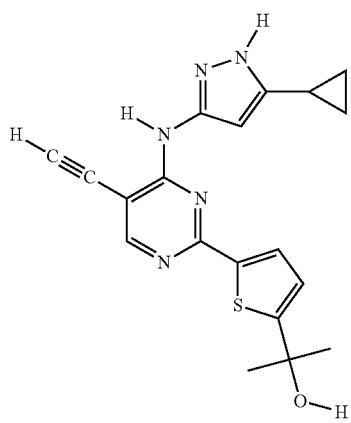 [SMILES: C#Cc1cnc(-c2ccc(C(C)(C)O)s2)nc1Nc1cc(C2CC2)[nH]n1]
180
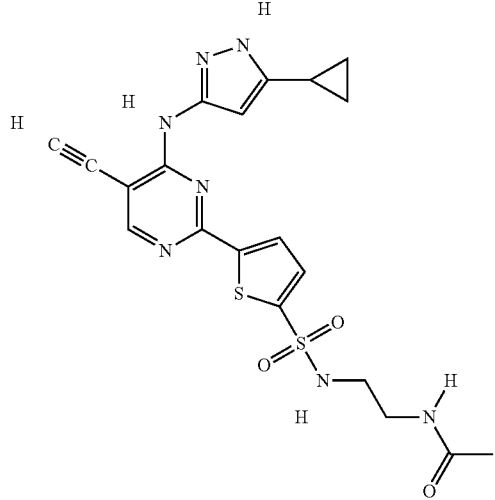
181
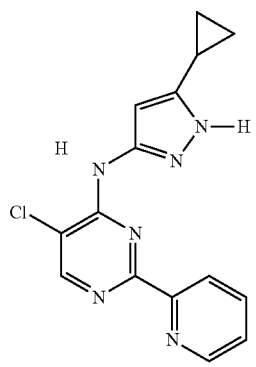
182

TABLE 1-continued
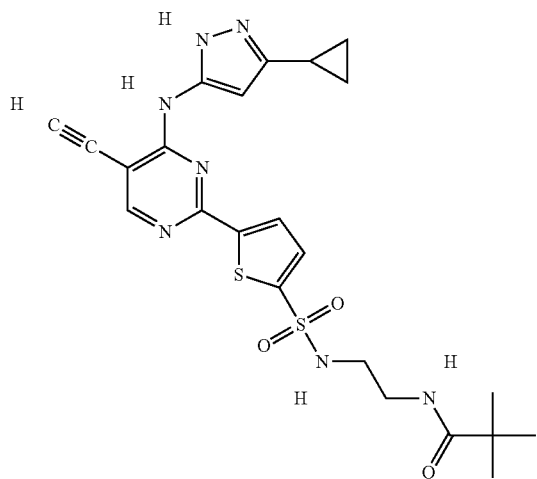
183
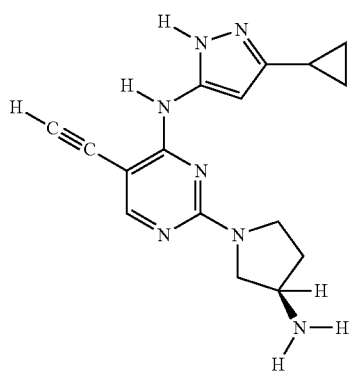 [SMILES: C#Cc1cnc(N2CC[C@@H](N)C2)nc1Nc1cc(C2CC2)n[nH]1]
184
185
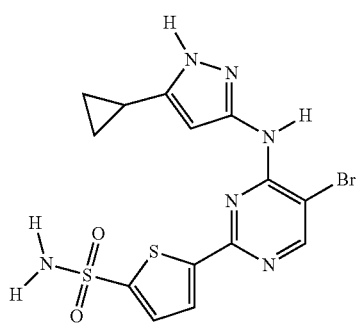 [SMILES: NS(=O)(=O)c1ccc(-c2ncc(Br)c(Nc3cc(C4CC4)[nH]n3)n2)s1]
186

TABLE 1-continued
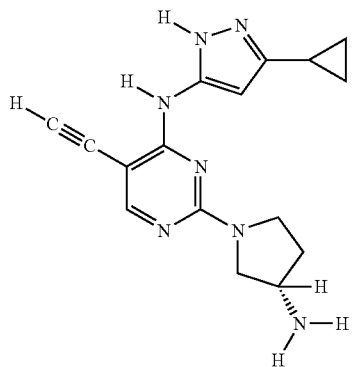 [SMILES: C#Cc1cnc(N2CC[C@H](N)C2)nc1Nc1cc(C2CC2)n[nH]1]
187
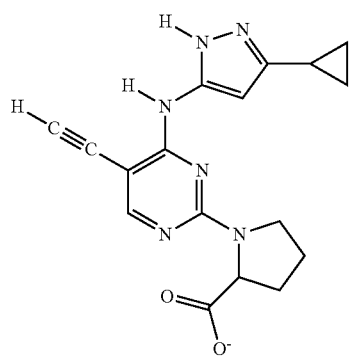 [SMILES: C#Cc1cnc(N2CCCC2C(=O)[O-])nc1Nc1cc(C2CC2)n[nH]1]
188
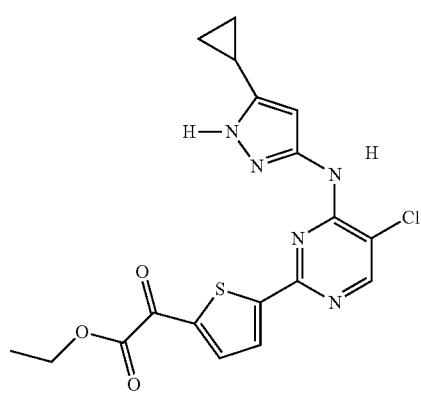
189
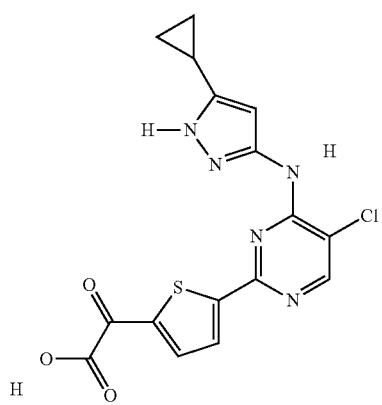
190

TABLE 1-continued
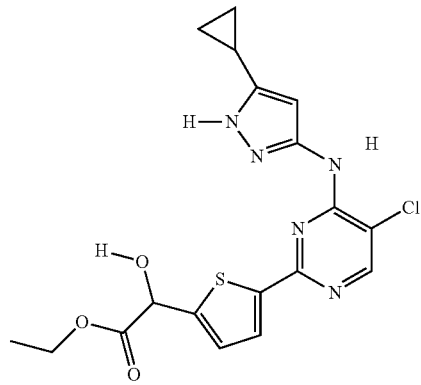
191
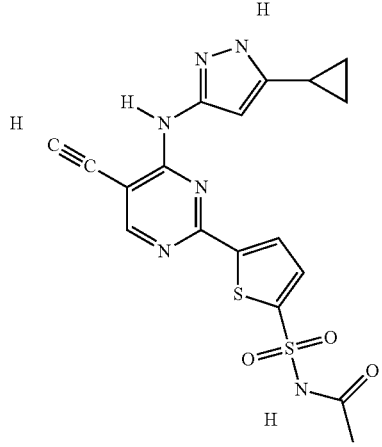
192
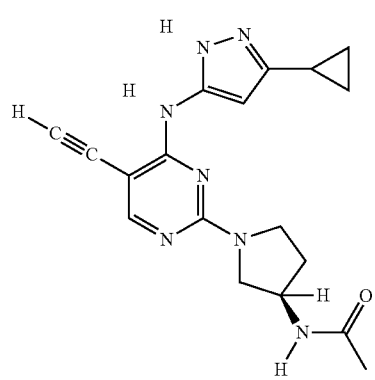
193
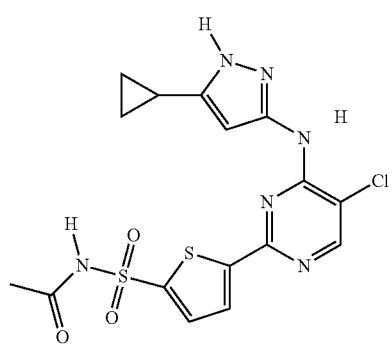
194

TABLE 1-continued
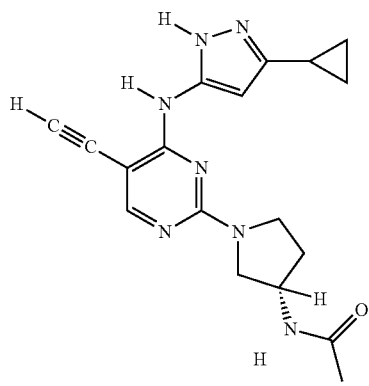 195
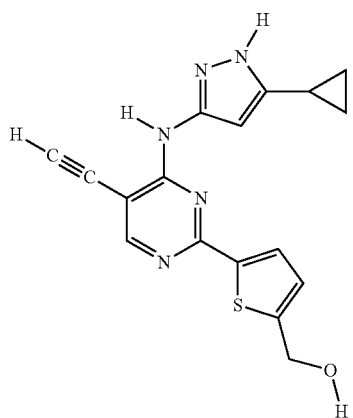 [SMILES: C#Cc1cnc(-c2ccc(CO)s2)nc1Nc1cc(C2CC2)[nH]n1] 196
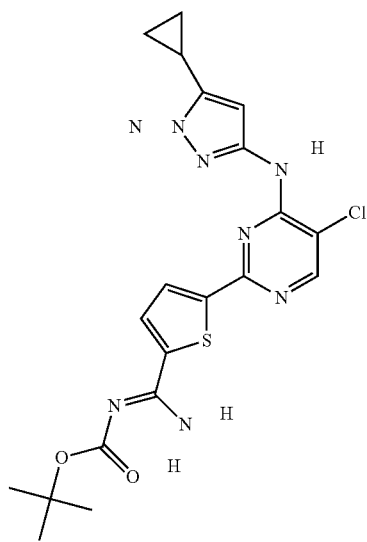 197

TABLE 1-continued
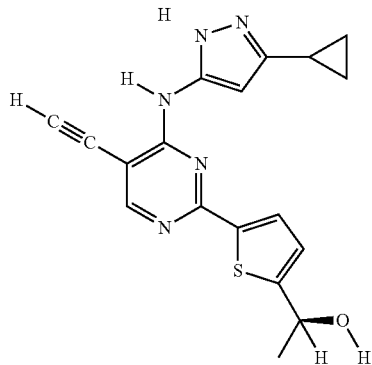
198
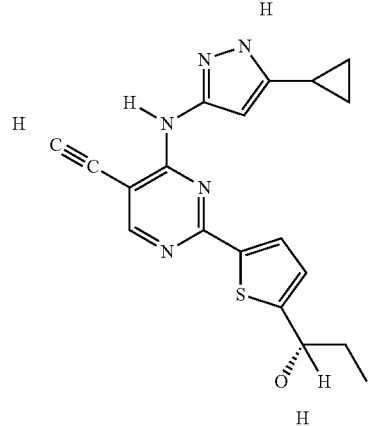
199
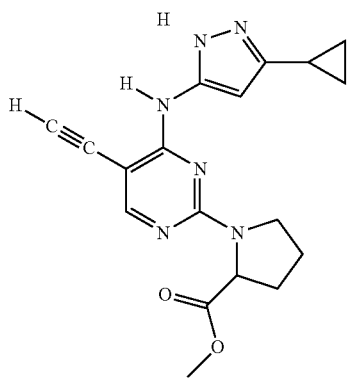
200

TABLE 1-continued
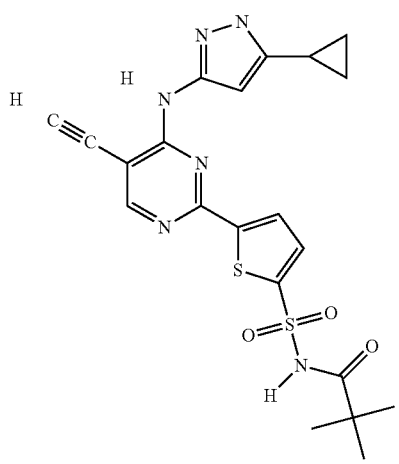
201
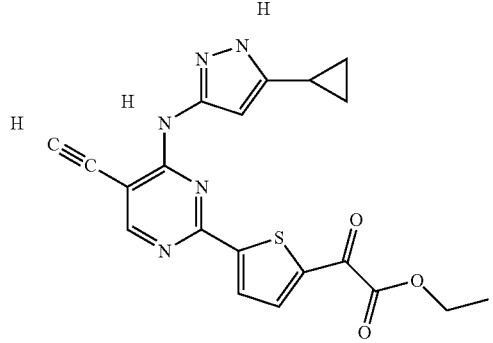
202
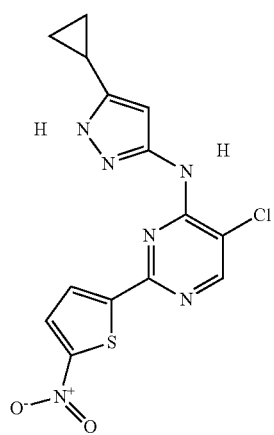
203

TABLE 1-continued

| | |
|---|---|
| 204 | (structure) |
| 205 | (structure) |
| 206 | (structure) |
| 207 | (structure) |

TABLE 1-continued
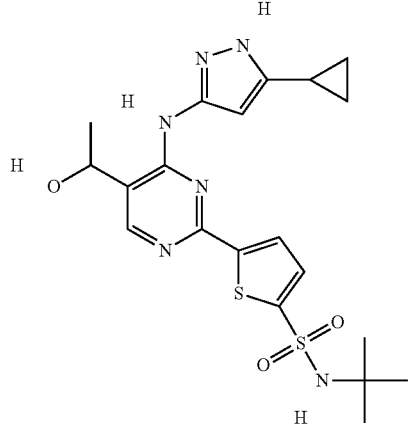
208
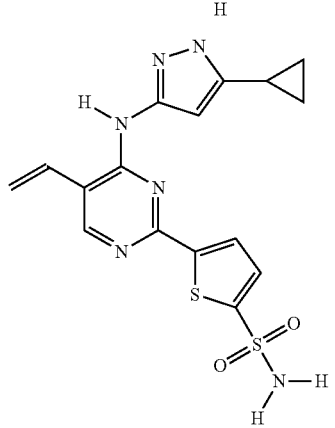
209
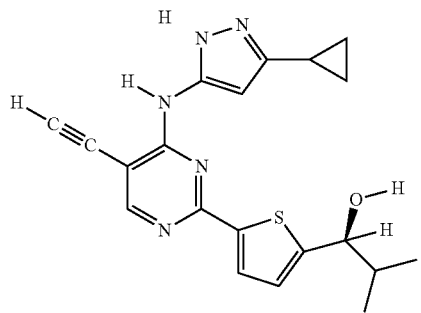
210
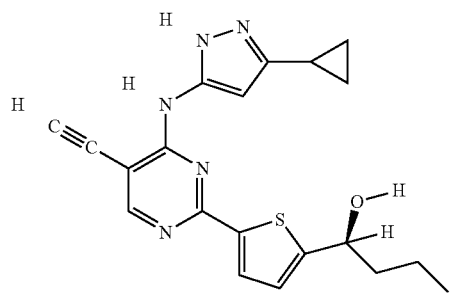
211

TABLE 1-continued
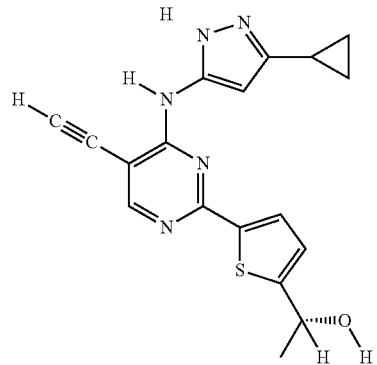
212
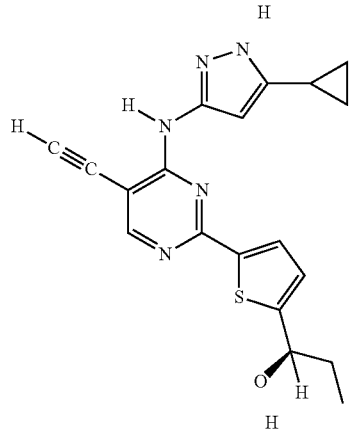
213
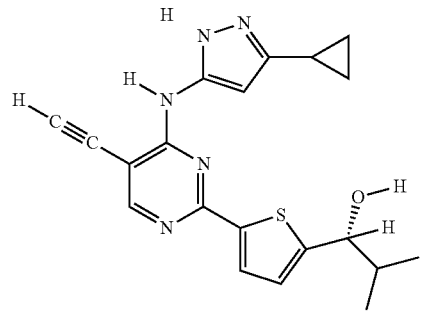
214
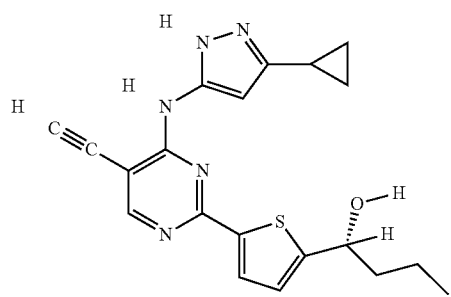
215

TABLE 1-continued
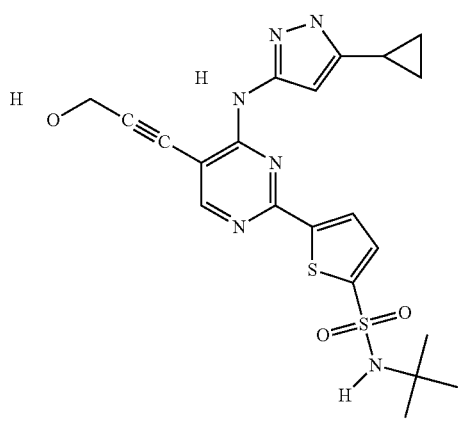
216
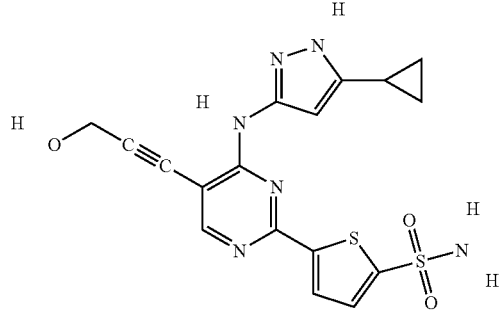
217
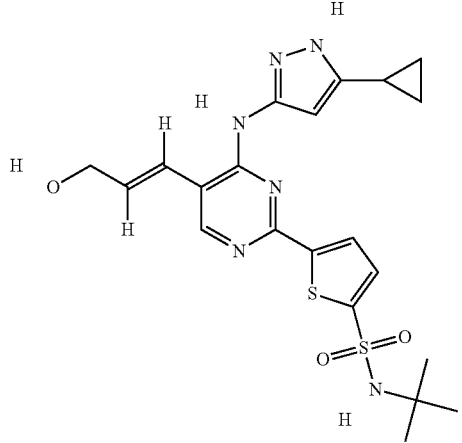
218

TABLE 1-continued
| | |
|---|---|
| 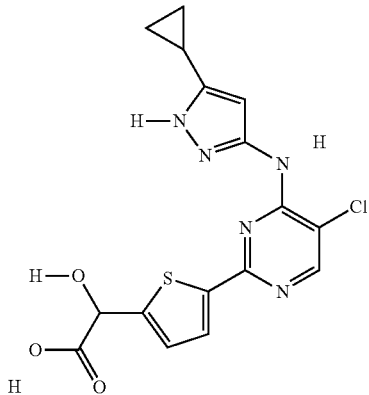 | 219 |
| 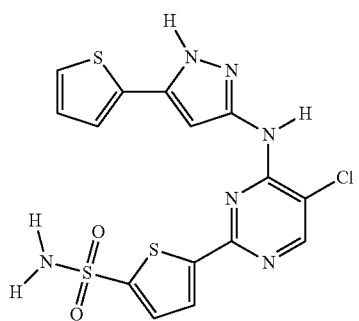 [SMILES: NS(=O)(=O)c1ccc(-c2ncc(Cl)c(Nc3cc(-c4cccs4)[nH]n3)n2)s1] | 220 |
| 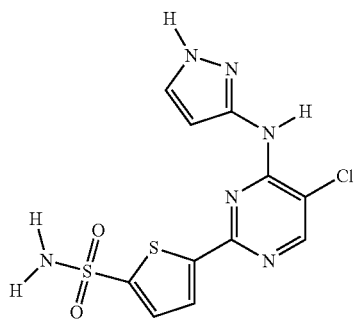 [SMILES: NS(=O)(=O)c1ccc(-c2ncc(Cl)c(Nc3cc[nH]n3)n2)s1] | 221 |
| 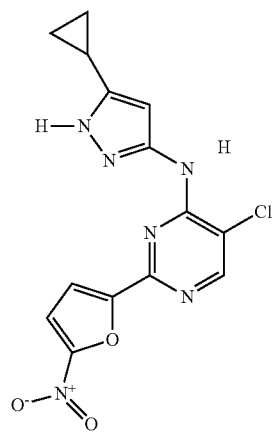 | 222 |

TABLE 1-continued
223
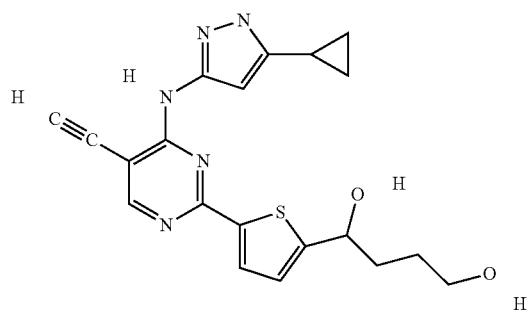
224
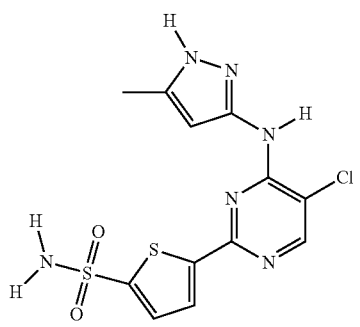 [SMILES: Cc1cc(Nc2nc(-c3ccc(S(N)(=O)=O)s3)ncc2Cl)n[nH]1]
225
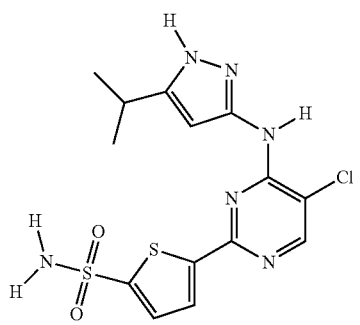 [SMILES: CC(C)c1cc(Nc2nc(-c3ccc(S(N)(=O)=O)s3)ncc2Cl)n[nH]1]
226
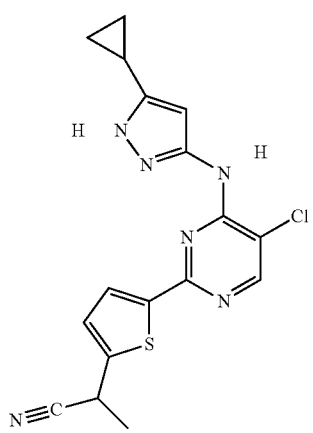

TABLE 1-continued
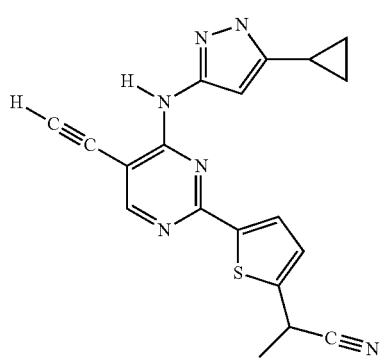
227
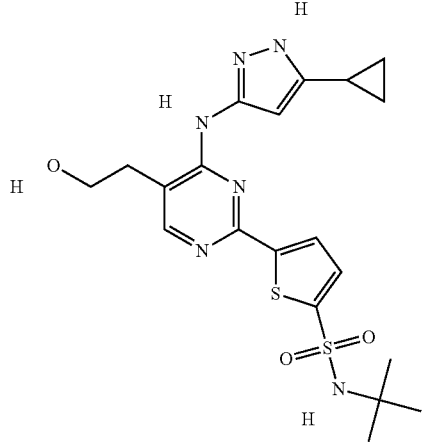
228
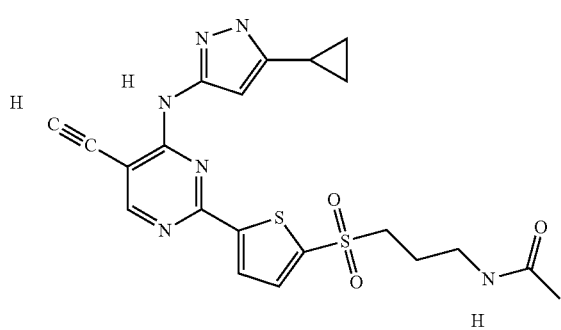
229
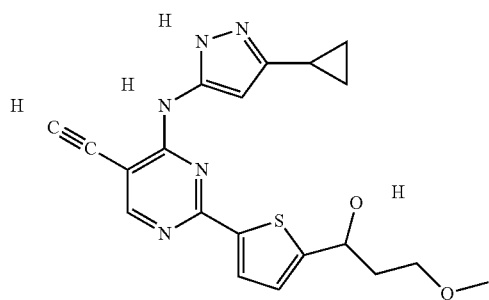
230

TABLE 1-continued
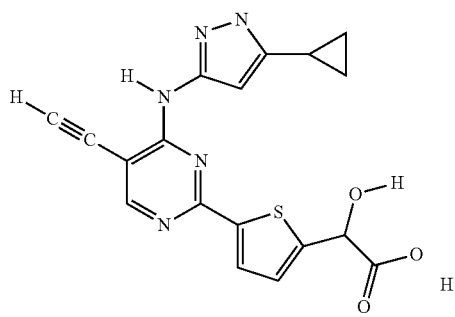
231
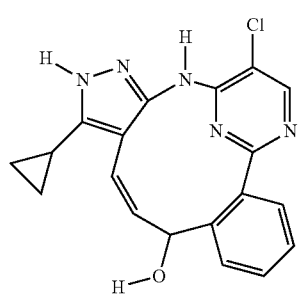 [SMILES: OC1/C=C\c2c(n[nH]c2C2CC2)Nc2nc(ncc2Cl)-c2ccccc21]
232
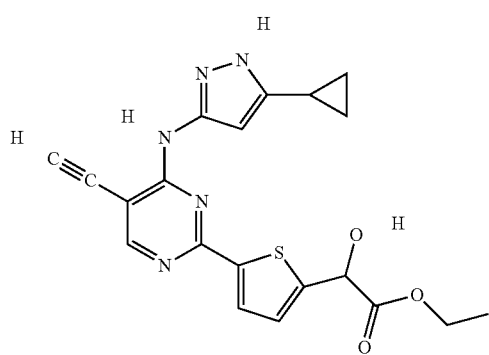
233
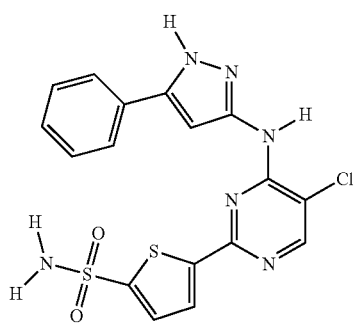 [SMILES: NS(=O)(=O)c1ccc(-c2ncc(Cl)c(Nc3cc(-c4ccccc4)[nH]n3)n2)s1]
234

TABLE 1-continued
235
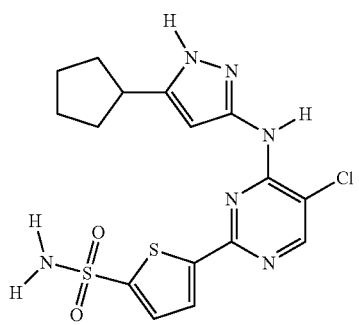 [SMILES: NS(=O)(=O)c1ccc(-c2ncc(Cl)c(Nc3cc(C4CCCC4)[nH]n3)n2)s1]
236
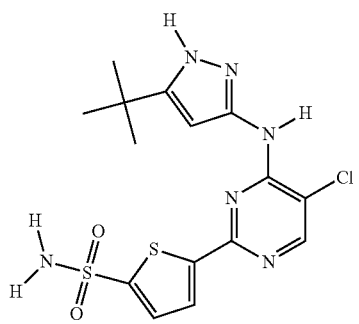 [SMILES: CC(C)(C)c1cc(Nc2nc(-c3ccc(S(N)(=O)=O)s3)ncc2Cl)n[nH]1]
237
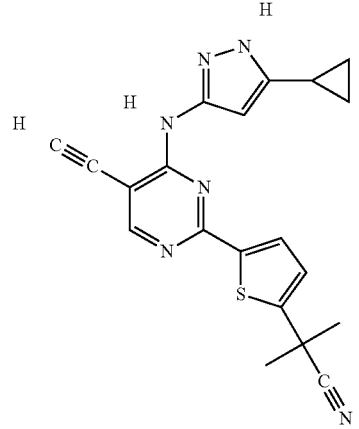
238
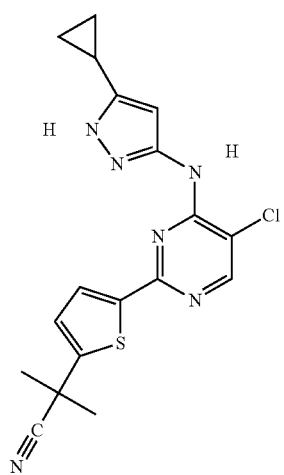

TABLE 1-continued
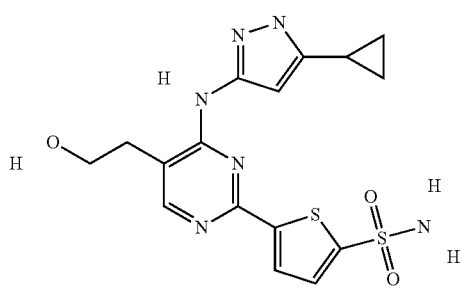
239
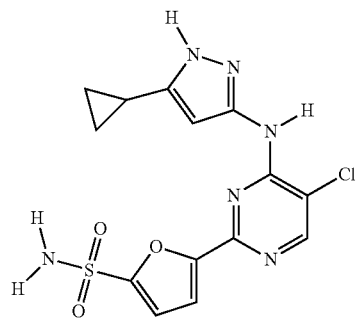 [SMILES: NS(=O)(=O)c1ccc(-c2ncc(Cl)c(Nc3cc(C4CC4)[nH]n3)n2)o1]
240
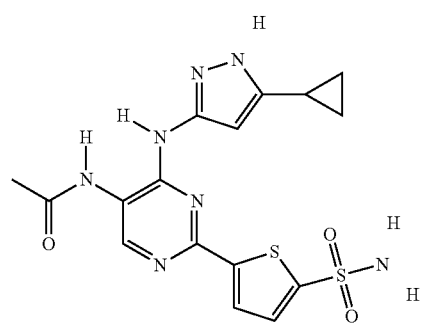
241
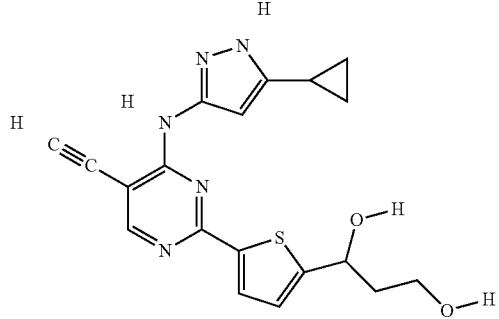
242

TABLE 1-continued
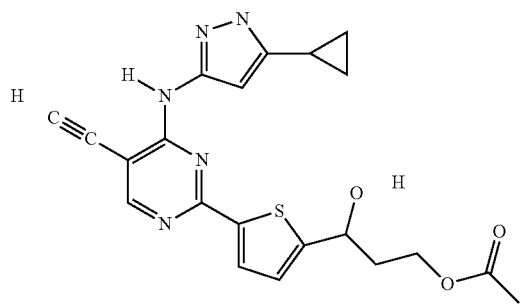
243
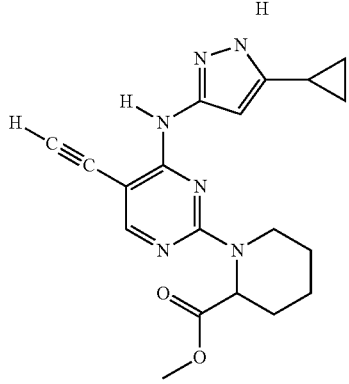
244
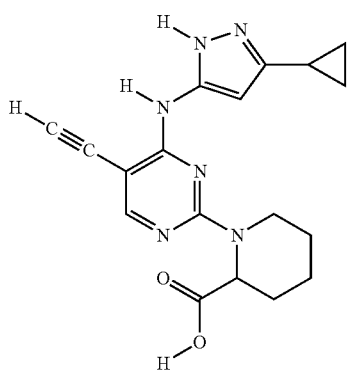 [SMILES: C#Cc1cnc(N2CCCCC2C(=O)O)nc1Nc1cc(C2CC2)n[nH]1]
245
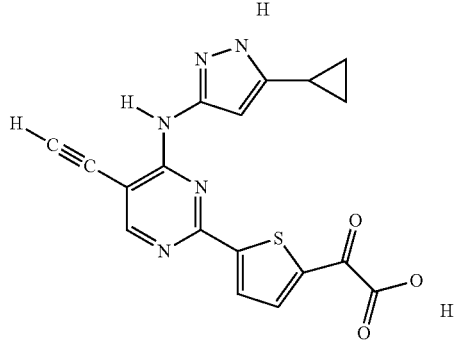
246

TABLE 1-continued
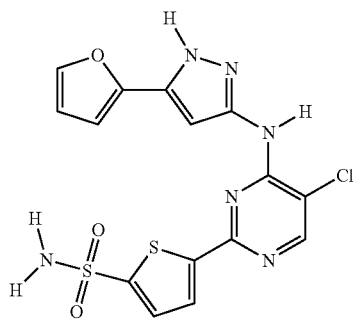 [SMILES: NS(=O)(=O)c1ccc(-c2ncc(Cl)c(Nc3cc(-c4ccco4)[nH]n3)n2)s1]
247
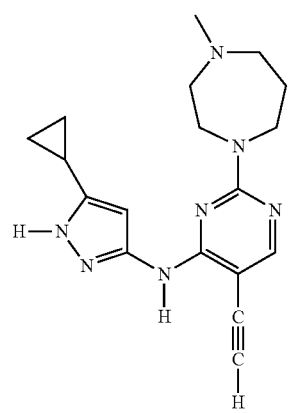 [SMILES: C#Cc1cnc(N2CCCN(C)CC2)nc1Nc1cc(C2CC2)[nH]n1]
248
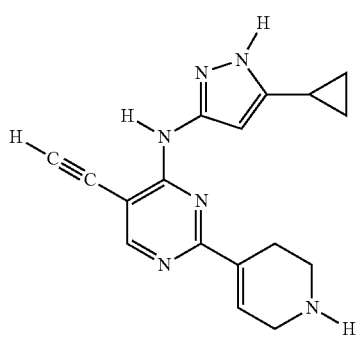 [SMILES: C#Cc1cnc(C2=CCNCC2)nc1Nc1cc(C2CC2)[nH]n1]
249
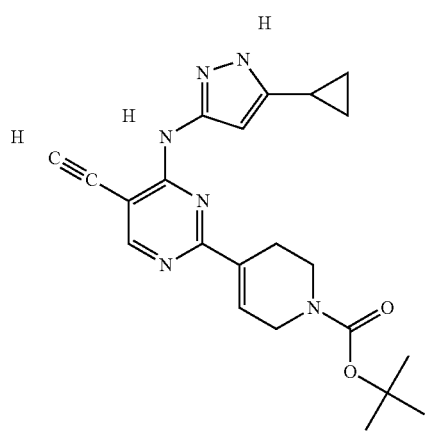
250

TABLE 1-continued
251
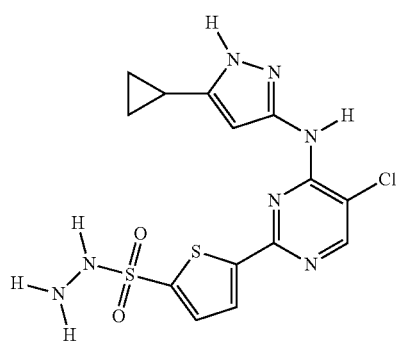 [SMILES: NNS(=O)(=O)c1ccc(-c2ncc(Cl)c(Nc3cc(C4CC4)[nH]n3)n2)s1]
252
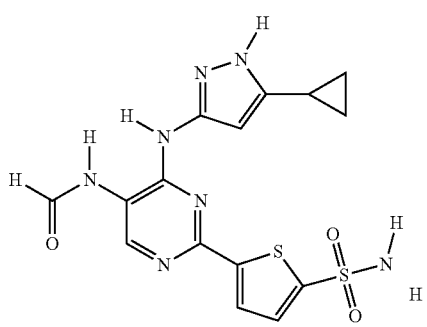
253
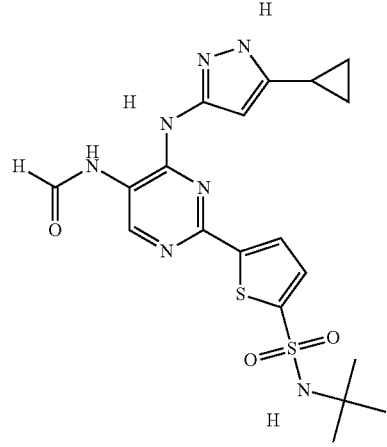
254
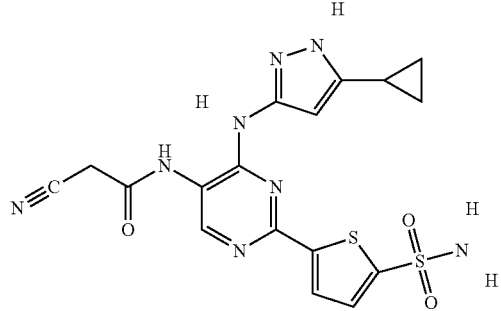

TABLE 1-continued
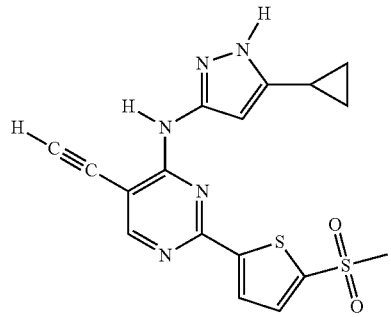 [SMILES: C#Cc1cnc(-c2ccc(S(C)(=O)=O)s2)nc1Nc1cc(C2CC2)[nH]n1]
255
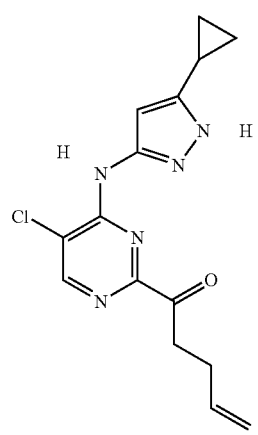
256
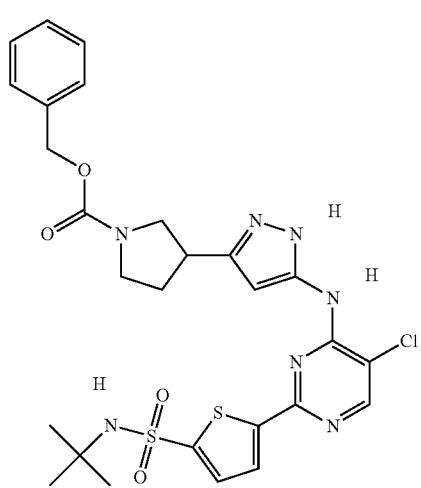
257

TABLE 1-continued
| | |
|---|---|
| 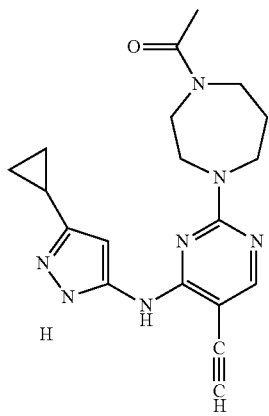 | 258 |
| 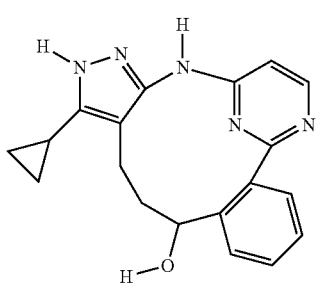 [SMILES: OC1CCc2c(n[nH]c2C2CC2)Nc2ccnc(n2)-c2ccccc21] | 259 |
| 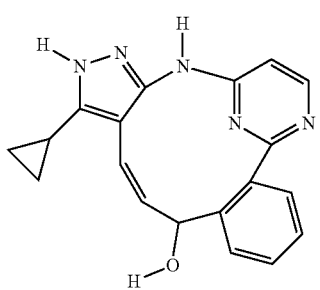 [SMILES: OC1/C=C\c2c(n[nH]c2C2CC2)Nc2ccnc(n2)-c2ccccc21] | 260 |
| 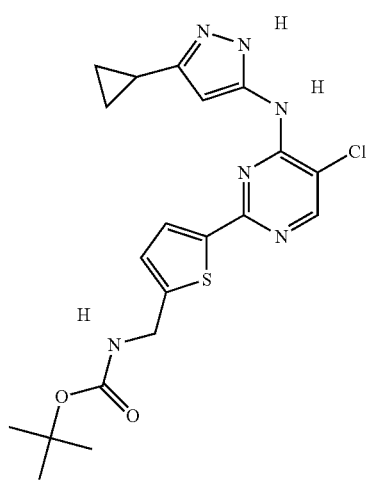 | 261 |

TABLE 1-continued
262
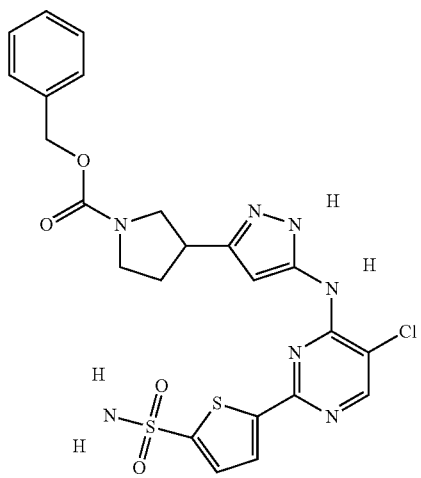
263
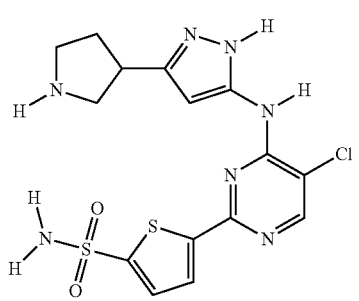 [SMILES: NS(=O)(=O)c1ccc(-c2ncc(Cl)c(Nc3cc(C4CCNC4)n[nH]3)n2)s1]
264
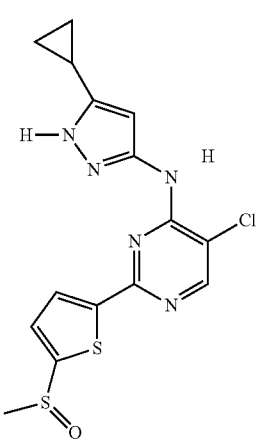
265
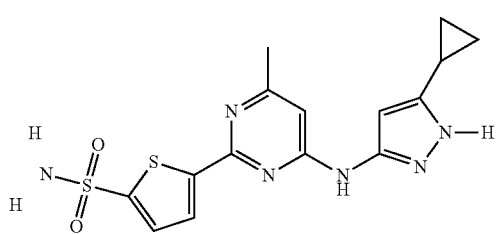

TABLE 1-continued
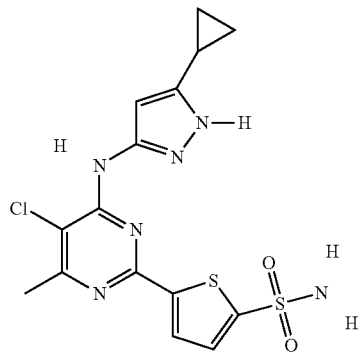
266
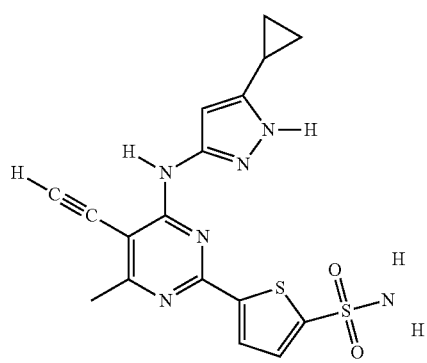
267
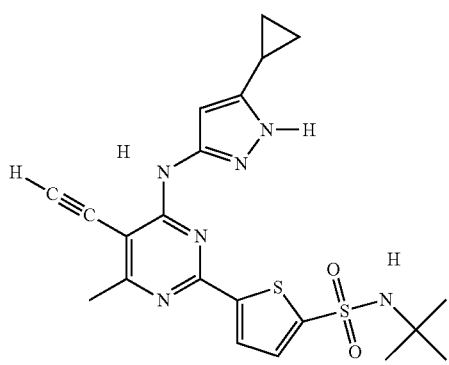
268
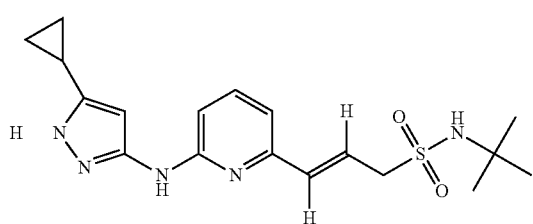
269
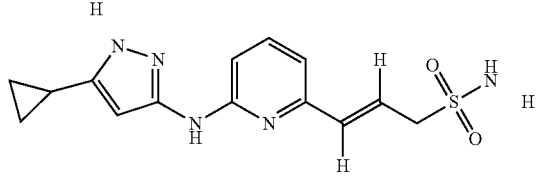
270

TABLE 1-continued
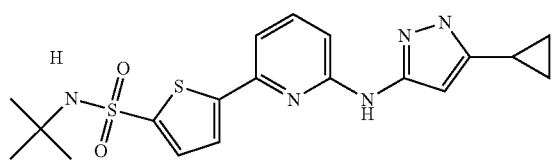 271
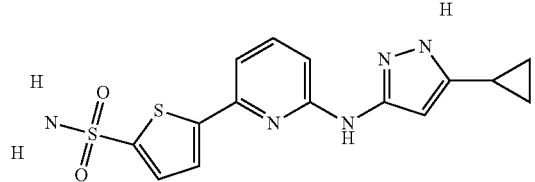 272
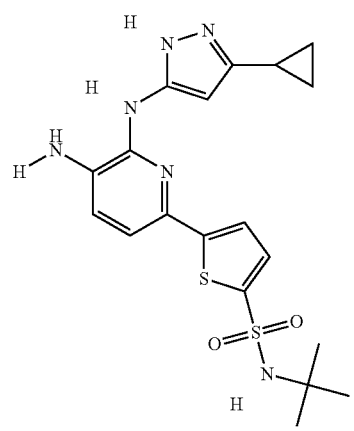 273
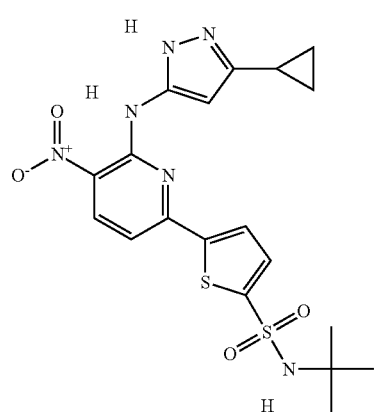 274
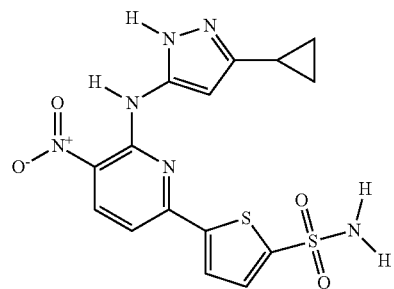 [SMILES: NS(=O)(=O)c1ccc(-c2ccc([N+](=O)[O-])c(Nc3cc(C4CC4)n[nH]3)n2)s1] 275

TABLE 1-continued
| | |
|---|---|
| 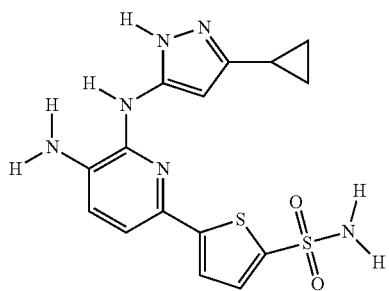 [SMILES: Nc1ccc(-c2ccc(S(N)(=O)=O)s2)nc1Nc1cc(C2CC2)n[nH]1] | 276 |
| 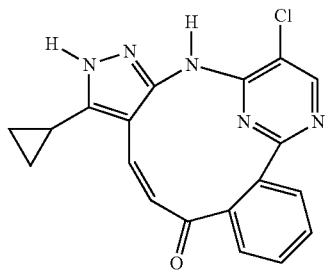 [SMILES: O=C1/C=C\c2c(n[nH]c2C2CC2)Nc2nc(ncc2Cl)-c2ccccc21] | 277 |
| 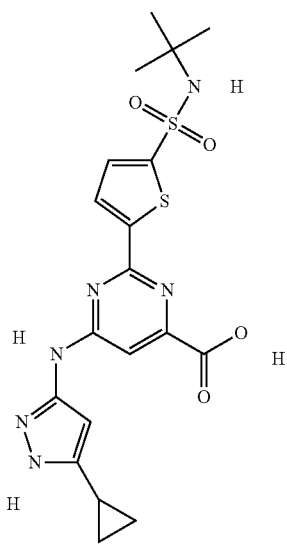 | 278 |
| 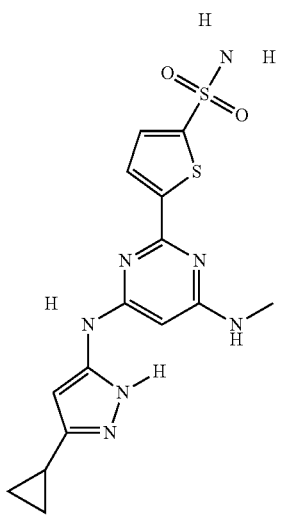 | 279 |

TABLE 1-continued
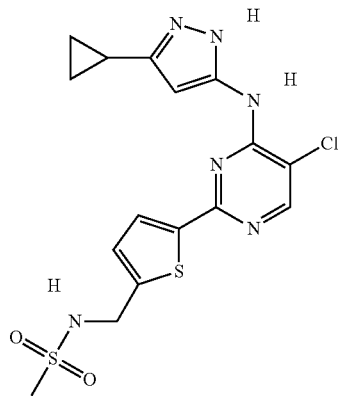
280
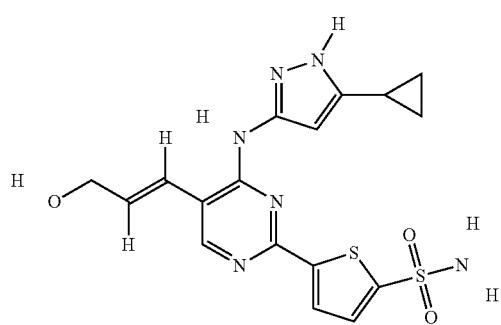
281
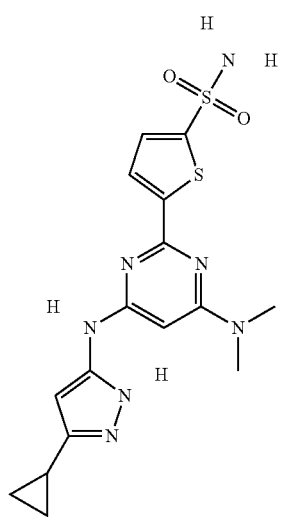
282

TABLE 1-continued
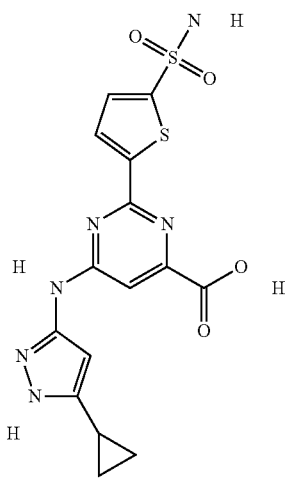
283
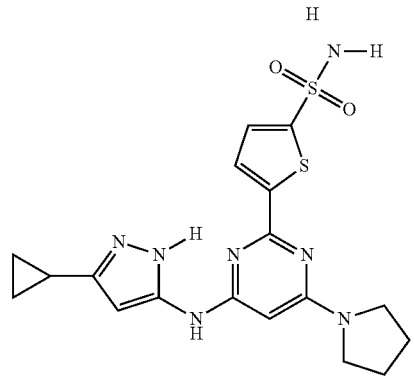
284
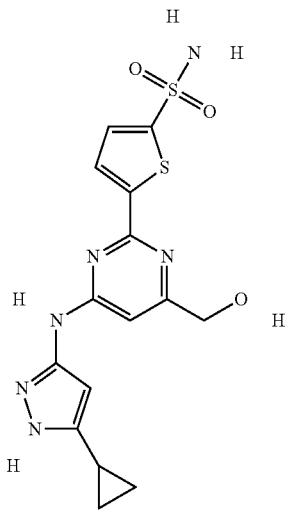
285

TABLE 1-continued
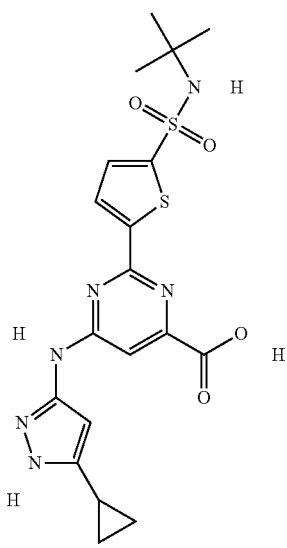
286
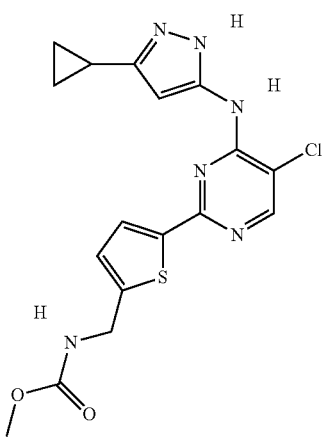
287
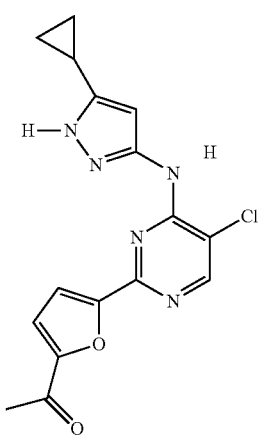
288

TABLE 1-continued
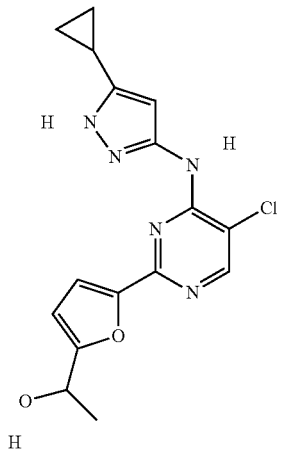
289
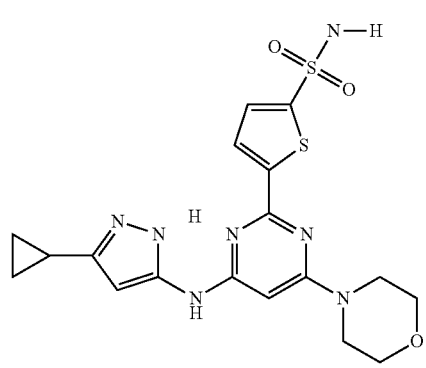
290
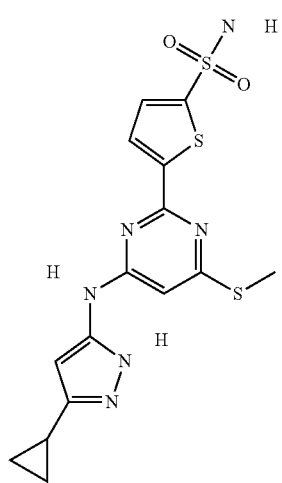
291

TABLE 1-continued
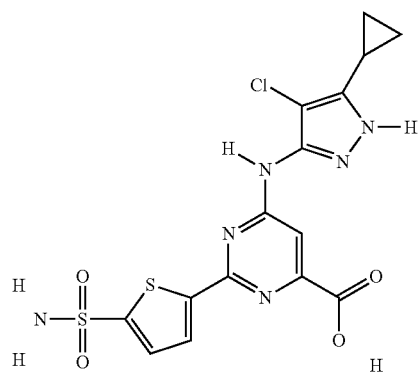
292
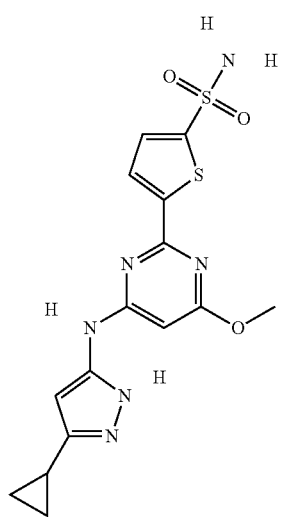
293
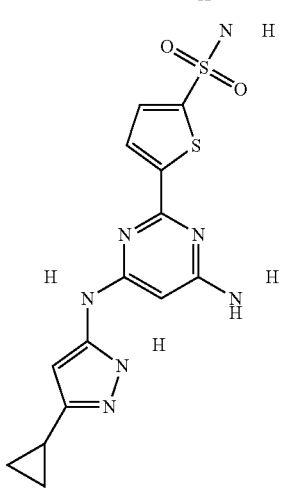
294

TABLE 1-continued
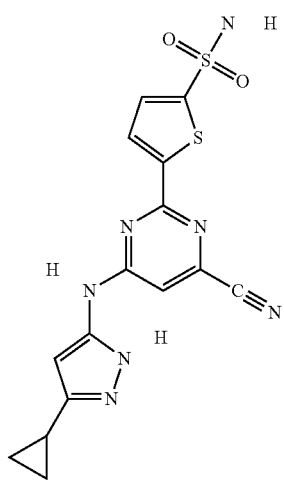
295
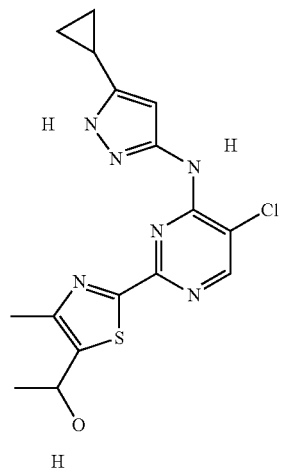
296
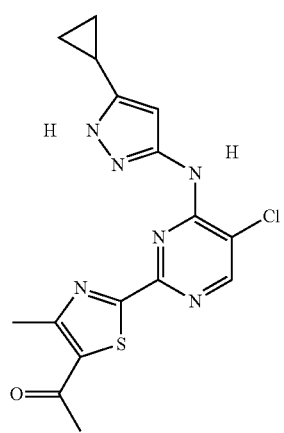
297

TABLE 1-continued
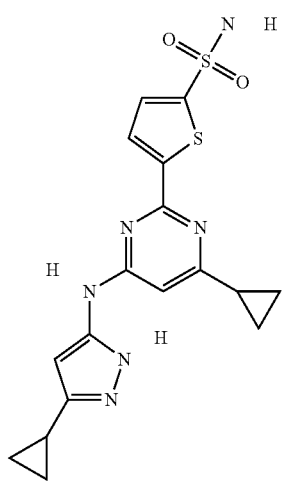
298
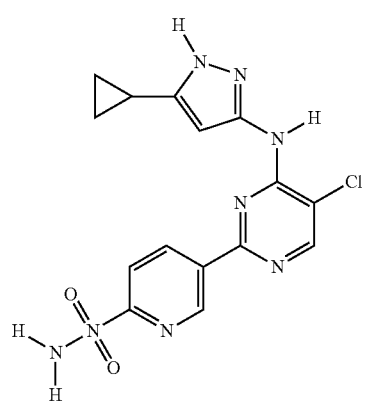
299
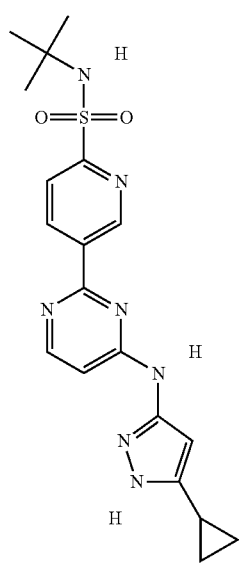
300

TABLE 1-continued
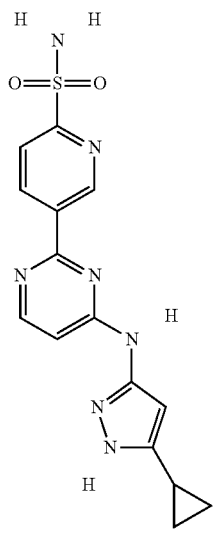
301
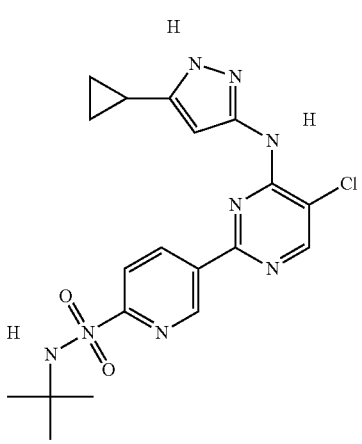
302
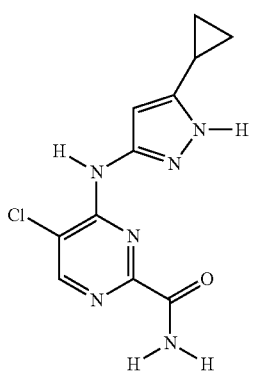 [SMILES: NC(=O)c1ncc(Cl)c(Nc2cc(C3CC3)[nH]n2)n1]
303

TABLE 1-continued
| | |
|---|---|
| 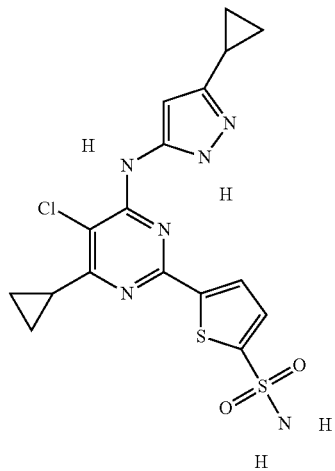 | 304 |
| 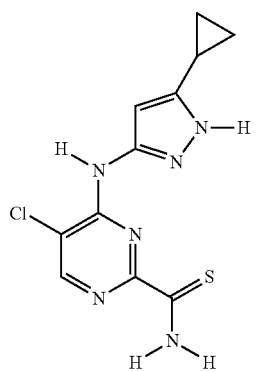 [SMILES: NC(=S)c1ncc(Cl)c(Nc2cc(C3CC3)[nH]n2)n1] | 305 |
| 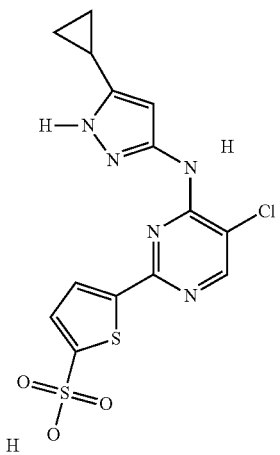 | 306 |
| 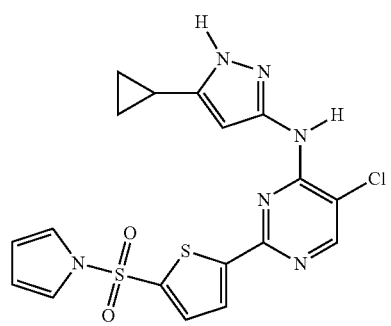 [SMILES: O=S(=O)(c1ccc(-c2ncc(Cl)c(Nc3cc(C4CC4)[nH]n3)n2)s1)n1cccc1] | 307 |

TABLE 1-continued
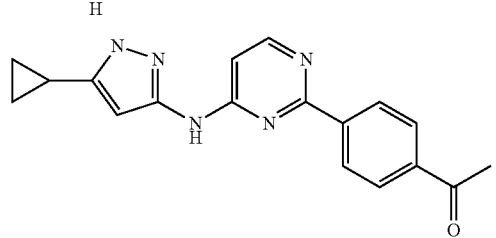
308
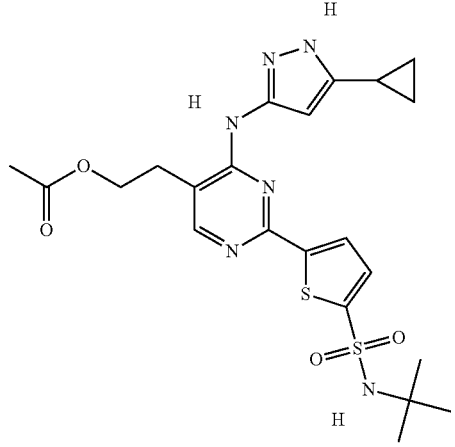
309
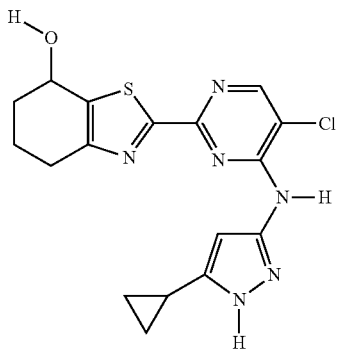 [SMILES: OC1CCCc2nc(-c3ncc(Cl)c(Nc4cc(C5CC5)[nH]n4)n3)sc21]
310
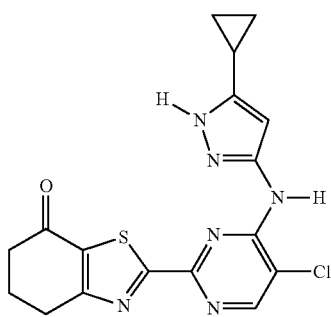 [SMILES: O=C1CCCc2nc(-c3ncc(Cl)c(Nc4cc(C5CC5)[nH]n4)n3)sc21]
311

TABLE 1-continued
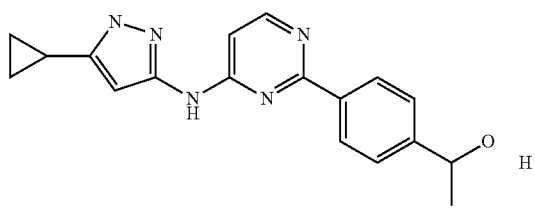
312
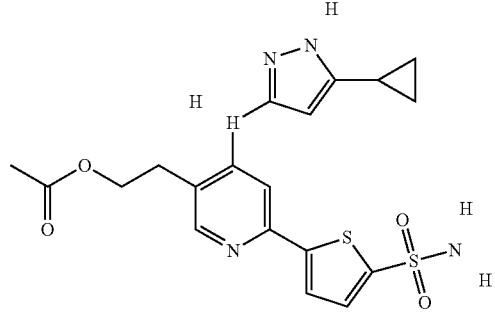
313
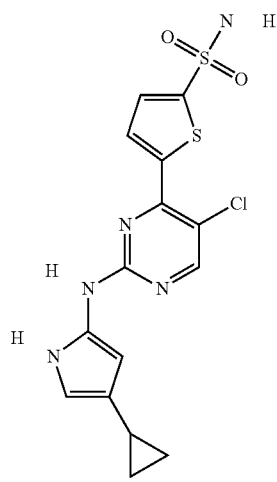
314
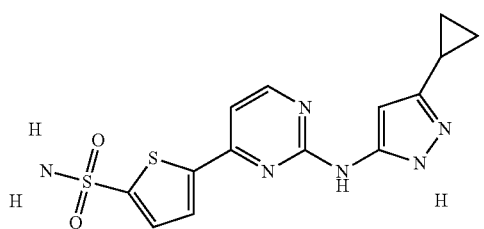
315
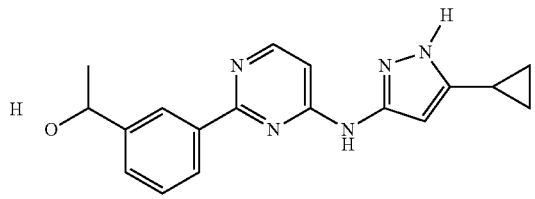
316

TABLE 1-continued
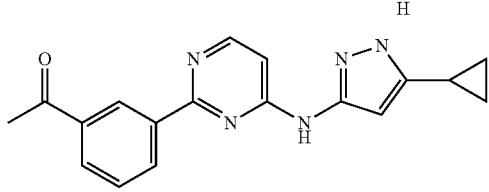
317
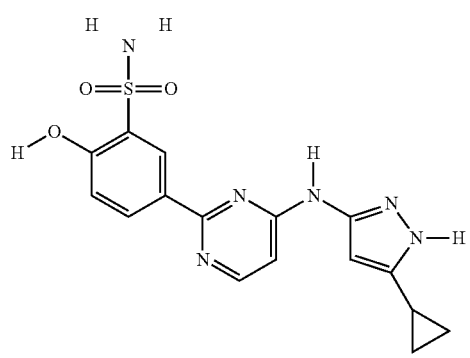
318
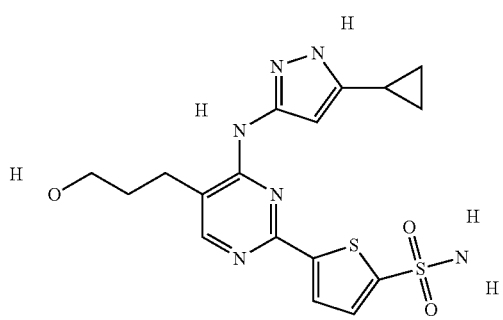
319
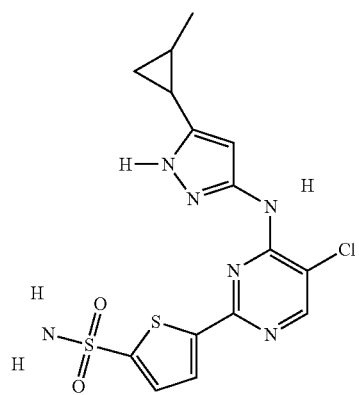
320

TABLE 1-continued
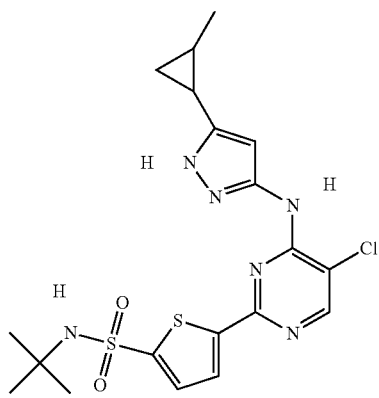
321
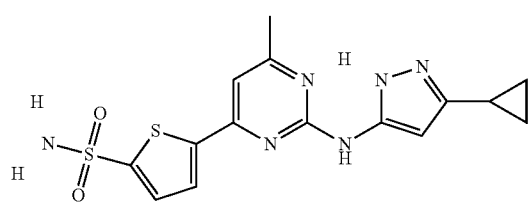
322
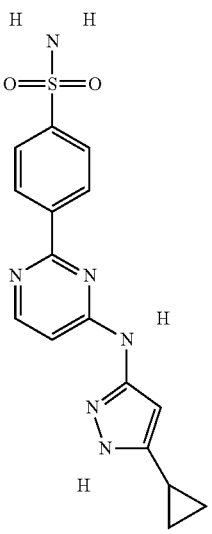
323
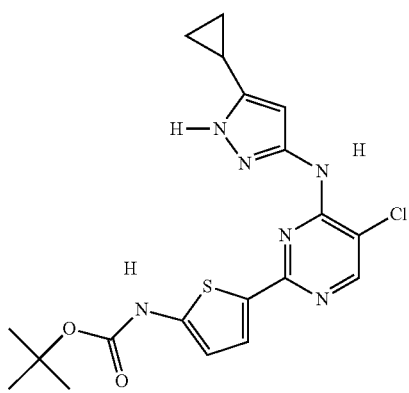
324

TABLE 1-continued
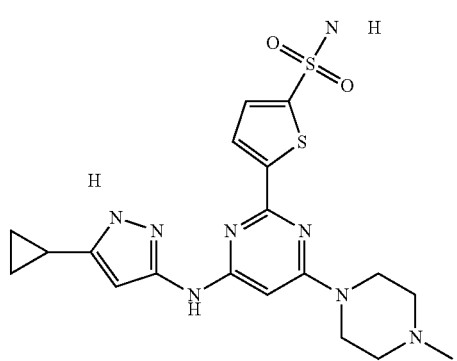
325
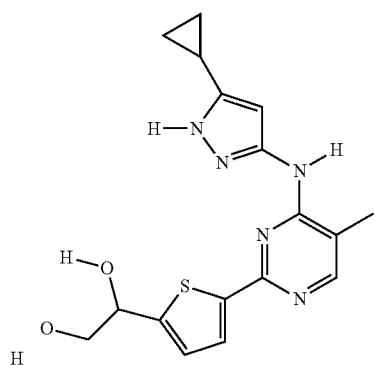
326
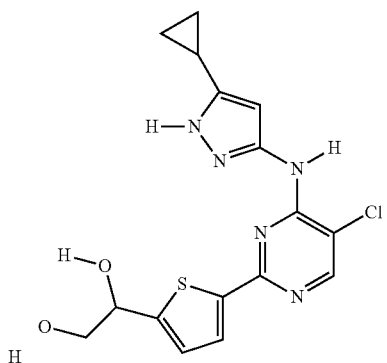
327
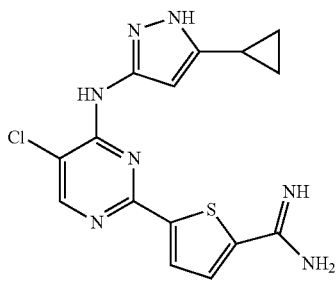 [SMILES: N=C(N)c1ccc(-c2ncc(Cl)c(Nc3cc(C4CC4)[nH]n3)n2)s1]
328

TABLE 2

| Compound # | Name | NMR |
|---|---|---|
| 1 | 2-[4-[[4-[(5-cyclopropyl-2H-pyrazol-3-yl)amino]pyrimidin-2-yl]amino]phenyl]acetonitrile | d (300 MHz, DMSO-d6); 0.54 (2H, m), 0.93-0.99 (2H, m), 1.84-1.87 (1H, m), 2.53 (6H, s), 4.14 (2H, s), 6.12 (1H, s), 6.45-6.47 (1H, m), 7.44-7.54 (4H, m), 7.94 (1H, s), 10.4 (1H, s), 11.3 (1H, s), 12.34 (1H, bs). |
| 2 | N-(5-cyclopropyl-2H-pyrazol-3-yl)-2-phenyl-pyrimidin-4-amine | d (300 MHz, DMSO-d6); 0.71-0.76 (m, 2H), 0.94-1.01 (m, 2H), 1.90-1.99 (m, 1H), 6.18-6.28 (bs, 1H), 7.06-7.10 (bs, 1H), 7.51-7.53 (m, 3H), 8.34-8.39 (m, 3H), 9.86 (s, 1H), 12.10 (s, 1H). |
| 3 | N-[4-[(1-acetyl-5-cyclopropyl-pyrazol-3-yl)amino]-2-phenyl-pyrimidin-5-yl]acetamide | d (300 MHz, DMSO-d6); 0.79-0.85 (2H, m), 0.99-1.05 (2H, m), 2.00-2.03 (1H, m), 2.04 (3H, s), 2.62 (3H, s), 6.85 (1H, s), 7.54-7.58 (3H, m), 8.30-8.34 (2H, m), 8.43 (1H, s), 10.03 (1H, s), 10.49 (1H, s). |
| 4 | 1-[3-[(5-amino-2-phenyl-pyrimidin-4-yl)amino]-5-cyclopropyl-pyrazol-1-yl]ethanone | d (300 MHz, DMSO-d6); 0.80-0.84 (2H, m), 0.98-1.05 (2H, m), 1.96-2.00 (1 H, m), 2.63 (3H, s), 5.17 (2H, s), 6.83 (1H, s), 7.40-7.50 (3H, m), 8.12 (1H, s), 8.19-8.22 (2H, m), 10.17 (1H, s). |
| 5 | N-(5-cyclopropyl-1H-pyrazol-3-yl)-2-phenyl-pyrimidine-4,5-diamine | d (300 MHz, DMSO-d6); 0.71-0.72 (2H, m), 0.95-1.00 (2H, m), 1.92-1.95 (1 H, m), 5.29 (2H, s), 6.59 (1H, s), 7.31-7.43 (3H, m), 7.81 (1H, s), 8.18 (2H, d, J = 6.9 Hz), 8.81 (1H, s), 12.02 (1H, s). |
| 6 | N-(5-cyclopropyl-1H-pyrazol-3-yl)-5-nitro-2-phenyl-pyrimidin-4-amine | d (300 MHz, DMSO-d6); 0.73-0.78 (2H, m), 0.96-1.01 (2H, m), 1.96-2.01 (1H, m), 6.53 (1H, s), 7.55-7.63 (3H, m), 8.35-8.38 (m, 1H), 9.33 (1H, s), 10.26 (1H, s), 12.50 (1H, s). |
| 7 | N-(4-bromo-5-cyclopropyl-2H-pyrazol-3-yl)-2-phenyl-pyrimidin-4-amine | d (300 MHz, DMSO-d6); 0.90-0.94 (m, 2H), 0.99-1.04 (m, 2H), 1.87-1.96 (m, 1H), 6.67-6.69 (d, 1H, J = 6 Hz), 7.47-7.50 (m, 3H), 8.31-8.34 (m, 2H), 8.37-8.39 (d, 1H, J = 6 Hz), 9.20 (s, 1H), 12.65 (s, 1H). |
| 8 | 5-bromo-N-(5-cyclopropyl-2H-pyrazol-3-yl)-2-phenyl-pyrimidin-4-amine | d (300 MHz, DMSO-d6); 0.74-0.77 (m, 2H), 0.98-1.02 (m, 2H), 1.96-2.01 (m, 1H), 6.40 (s, 2H), 7.50-7.54 (m, 3H), 8.27-8.30 (m, 2H), 8.63 (s, 1H), 8.88 (s, 2H), 12.32(s, 1H). |
| 9 | N-(5-cyclopropyl-2H-pyrazol-3-yl)-2-phenyl-5-prop-1-ynyl-pyrimidin-4-amine | d (300 MHz, DMSO-d6): 0.83-0.86 (m, 2H), 1.03-1.06 (m, 2H), 2.03-2.09 (m, 1H), 2.44(s, 3H), 6.39 (d, J = 2.1 Hz, 1H), 6.56 (s, 1H), 7.45-7.52 (m, 3H), 8.35-8.38 (m, 2H), 9.03 (s, 1H), 12.86(s, 1H). |
| 10 | N-[4-[(5-cyclopropyl-1H-pyrazol-3-yl)amino]-2-phenyl-pyrimidin-5-yl]acetamide | d (300 MHz, DMSO-d6); 0.68-0.75 (2H, m), 0.91-1.00 (2H, m), 1.90-1.97 (1H, m), 2.10 (3H, s), 6.51 (1H, s), 7.49 (3H, s), 8.24-8.29 (2H, m), 8.51 (1H, s), 9.24 (1H, s), 9.44 (1H, s), 12.15 (1H, s). |
| 11 | N-(5-cyclopropyl-1H-pyrazol-3-yl)-2-phenyl-5-prop-1-enyl-pyrimidin-4-amine | d (300 MHz, DMSO-d6): 0.71-0.72 (m, 2H), 0.94-1.02 (m, 2H), 1.74-1.80 (m, 3H), 1.87-1.96 (m, 1H), 5.98 (d, J = 11.4 Hz, 1H), 6.48 (d, J = 11.4 Hz, 1H), 7.47-7.49 (m, 3H), 8.24-8.32 (m, 2H), 8.71 (s, 1H), 12.12 (s, 1H). |
| 12 | 4-[[4-[(5-cyclopropyl-1H-pyrazol-3-yl)amino]pyrimidin-2-yl]amino]benzenesulfonamide | d (300 MHz, DMSO-d6); 0.68-0.69 (m, 2H), 0.90-0.92 (m, 2H), 1.85-1.87 (m, 1H), 6.21 (s, 1H), 6.51 (s, 1H), 7.13 (s, 1H), 7.67 (d, J = 9 Hz, 2H), 7.92 (d, J = 7.2 Hz, 2H), 8.02 (d, J = 5.4 Hz, 1H), 9.53 (d, J = 32.4 Hz, 2H), 12.02 (s, 1H). |
| 13 | N'-(5-cyclopropyl-1H-pyrazol-3-yl)-N-(1H-indazol-5-yl)pyrimidine-2,4-diamine | d (300 MHz, DMSO-d6); 0.39-0.45 (m, 2H), 0.82-0.84 (m, 2H), 1.71-1.75 (m, 1H), 6.00 (s, 1H), 6.37 (s, 1H), 7.44-7.57 (m, 2H), 7.90-7.92 (m, 1H), 8.03 (s, 2H), 9.69 (s, 1H), 10.36 (s, 1H), 11.74 (bs, 1H), 12.95 (bs, 1H). |
| 14 | N-(5-cyclopropyl-1H-pyrazol-3-yl)-5-ethynyl-2-phenyl-pyrimidin-4-amine | d (300 MHz, CDCl3-d): 0.78-0.82 (m, 2H), 0.97-1.01 (m, 2H), 1.88-1.94 (m, 1H), 3.65 (s, 1H), 5.68 (s, 1H), 6.51 (s, 1H), 7.47-7.49 (m, 3H), 7.81 (s, 1H), 8.34-8.36 (m, 2H), 8.54 (s, 1H). |
| 15 | N-(5-cyclopropyl-1H-pyrazol-3-yl)-2-(4-methylsulfonylphenyl)-pyrimidin-4-amine | |
| 16 | N-(5-cyclopropyl-1H-pyrazol-3-yl)-5-fluoro-2-(4-methylsulfonylphenyl)-pyrimidin-4-amine | |
| 17 | 2-[4-[4-[(5-cyclopropyl-1H-pyrazol-3-yl)amino]pyrimidin-2-yl]phenyl]acetonitrile | d (400 MHz, DMSO-d6); 0.73 (m, 2H), 0.96 (m, 2H), 1.93 (m, 1H), 4.14 (s, 2H), 6.25 (bs, 1H), 7.11 (bs, 1H), 7.49 (d, J = 8.4 Hz, 2H), 8.35 (m, 3H), 9.89 (s, 1H), 12.09 (s, 1H). |

TABLE 2-continued

| Compound # | Name | NMR |
|---|---|---|
| 18 | 2-[4-[5-chloro-4-[(5-cyclopropyl-1H-pyrazol-3-yl)amino]-pyrimidin-2-yl]phenyl]acetonitrile | d (400 MHz, DMSO-d6); 0.75 (m, 2H), 1.00 (m, 2H), 1.98 (m, 1H), 4.13 (s, 2H), 6.41 (s, 1H), 7.48 (d, J = 8.0 Hz, 2H), 8.27 (d, J = 8.4 Hz, 2H), 8.50 (s, 1H), 9.26 (s, 1H), 12.29 (s, 1H). |
| 19 | 2-[4-[4-[(5-cyclopropyl-1H-pyrazol-3-yl)amino]-5-fluoro-pyrimidin-2-yl]phenyl]acetonitrile | d (300 MHz, DMSO-d6); 0.73 (m, 2H), 0.97 (m, 2H), 1.94 (m, 1H), 4.11 (s, 2H), 6.4 (s, 1H), 7.46 (d, J = 8.4 Hz, 2H), 8.24 (d, J = 8.1 Hz, 2H), 8.37 (d, J = 3.9 Hz, 2H), 10.00 (s, 1H), 12.20 (s, 1H). |
| 20 | N-(5-cyclopropyl-1H-pyrazol-3-yl)-5-methyl-2-(4-methylsulfonylphenyl)-pyrimidin-4-amine | d (300 MHz, DMSO-d6); 0.77 (m, 2H), 1.01 (m, 2H), 1.75 (m, 1H), 1.96 (s, 3H), 3.28 (s, 3H), 6.49 (s, 1H), 8.05 (d, J = 8.4 Hz, 2H), 8.26 (s, 1H), 8.50 (d, J = 8.4 Hz, 2H), 9.07 (s, 1H), 12.18 (s, 1H). |
| 21 | 5-(1-chlorovinyl)-N-(5-cyclopropyl-1H-pyrazol-3-yl)-2-phenyl-pyrimidin-4-amine | d (300 MHz, DMSO-d6): 0.79-0.83 (m, 2H), 1.00-1.05 (m, 2H), 1.91-2.05 (m, 1H), 5.72 (s, 1H), 5.82 (s, 1H), 6.51 (bs, 1H), 7.49-7.52 (m, 3H), 7.58 (bs, 1H), 8.36-8.39 (m, 2H), 8.42 (m, 1H). |
| 22 | [5-[4-[(5-cyclopropyl-1H-pyrazol-3-yl)amino]pyrimidin-2-yl]-2-thienyl]methanol | d (400 MHz, DMSO-d6); 0.71 (m, 2H), 0.94 (m, 2H), 1.90 (m, 1H), 4.65 (d, J = 5.6 Hz, 2H), 5.56 (t, J = 5.6 Hz, 1H), 6.34 (bs, 1H), 6.86 (bs, 1H), 6.99 (d, J = 2 Hz, 1H), 7.67 (d, J = 2.8 Hz, 1H), 8.21 (d, J = 4.8, 1H), 9.86 (s, 1H), 12.05 (s, 1H). |
| 23 | 5-chloro-N-(5-cyclopropyl-1H-pyrazol-3-yl)-2-(4-methylsulfonylphenyl)-pyrimidin-4-amine | d (400 MHz, DMSO-d6); 0.77 (m, 2H), 1.00 (m, 2H), 1.99 (m, 1H), 3.28 (s, 3H), 6.39 (s, 1H), 8.07 (d, J = 8.4 Hz, 2H), 8.48 (d, J = 8 Hz, 2H), 8.58 (s, 2H), 9.41 (s, 1H), 12.31 (s,1H). |
| 24 | 2-[4-[4-[(5-cyclopropyl-1H-pyrazol-3-yl)amino]-5-methyl-pyrimidin-2-yl]phenyl]acetonitrile | d (400 MHz, DMSO-d6); 0.74 (m, 2H), 1.01 (m, 2H), 1.96 (m, 1H), 2.19 (s, 3H), 3.34 (s, 2H), 6.50 (s, 1H), 7.46 (d, J = 8 Hz, 2H), 8.91 (s, 1H), 8.30 (d, J = 8.4 Hz, 1H), 8.95 (s, 1H), 12.11 (s, 1H). |
| 25 | [5-[5-chloro-4-[(5-cyclopropyl-1H-pyrazol-3-yl)amino]-pyrimidin-2-yl]-2-thienyl]methanol | d (400 MHz, DMSO-d6); 0.74 (s, 2H), 0.97 (m, 2H), 1.94 (m, 1H), 4.65 (d, J = 5.6 Hz, 2H), 5.61 (t, J = 5.2 Hz, 1H), 6.48 (s, 1H), 7.00 (d, J = 3.2 Hz, 1H), 7.65 (d, J = 2.8 Hz, 1H), 8.37 (s, 1H), 9.24 (s, 1H), 12.26 (s, 1H). |
| 26 | [5-[4-[(5-cyclopropyl-1H-pyrazol-3-yl)amino]-5-fluoro-pyrimidin-2-yl]-2-thienyl]methanol | d (400 MHz, DMSO-d6); 0.73 (m, 2H), 0.94 (m, 2H), 1.94 (m, 1H), 4.64 (d, J = 5.2 Hz, 2H), 5.59 (t, J = 5.2 Hz, 1H), 6.55 (s, 1H), 6.98 (d, J = 3.6 Hz, 1H), 7.59 (d, J = 2.8 Hz, 1H), 8.26 (d, J = 3.2 Hz, 1H), 10.04 (s, 1H), 12.19 (s, 1H). |
| 27 | N-(5-cyclopropyl-1H-pyrazol-3-yl)-2-(2-thienyl)pyrimidin-4-amine | d (400 MHz, DMSO-d6); 0.71 (m, 2H), 0.95 (m, 2H), 1.94 (m, 1H), 6.35 (bs, 1H), 6.87 (bs, 1H), 7.17 (m, 1H), 7.70 (m, 1H), 7.83 (d, J = 2.8 Hz, 1H), 8.23 (d, J = 5.6 Hz, 1H), 9.91 (s, 1H), 12.08 (s, 1H). |
| 28 | 3-[4-[(5-cyclopropyl-1H-pyrazol-3-yl)amino]pyrimidin-2-yl]benzenesulfonamide | d (400 MHz, DMSO-d6); 0.75 (m, 2H), 0.93 (m, 2H), 1.90 (m, 1H), 6.23 (bs, 1H), 7.09 (bs, 1H), 7.43 (s, 2H), 7.71 (t, J = 7.6 Hz, 1H), 7.93 (d, J = 7.6 Hz, 1H), 8.39 (d, J = 4.8, 1H), 8.51 (d, J = 7.6 Hz, 1H), 8.82 (s, 1H), 9.99 (s, 1H), 12.11 (s, 1H). |
| 29 | 5-chloro-N-(5-cyclopropyl-1H-pyrazol-3-yl)-2-(2-thienyl)pyrimidin-4-amine | d (400 MHz, DMSO-d6); 0.73 (m, 2H), 0.97 (m, 2H), 1.94 (m, 1H), 6.48 (s, 1H), 7.19 (s, 1H), 7.00 (d, J = 20 Hz, 2H), 8.39 (s, 1H), 9.29 (s, 1H), 12.28 (s, 1H). |
| 30 | 3-[5-chloro-4-[(5-cyclopropyl-1H-pyrazol-3-yl)amino]-pyrimidin-2-yl]benzenesulfonamide | d (400 MHz, DMSO-d6); 0.81 (m, 2H), 0.95 (m, 2H), 1.93 (m, 1H), 6.41 (s, 1H), 7.43 (s, 2H), 7.71 (t, J = 7.2 Hz, 1H), 7.94 (d, J = 7.6 Hz, 1H), 8.43 (d, J = 8.0 Hz, 1H), 8.54 (s, 1H), 8.76 (s, 1H), 9.36 (s, 1H), 12.31 (s, 1H). |
| 31 | 3-[4-[(5-cyclopropyl-1H-pyrazol-3-yl)amino]-5-methyl-pyrimidin-2-yl]benzenesulfonamide | d (400 MHz, DMSO-d6); 0.79-0.80 (m, 2H), 0.93-0.95 (m, 2H), 1.91-1.92 (m, 1H), 2.20 (s, 3H), 6.49 (s, 1H), 7.40 (s, 2H), 7.68 (t, J = 8.0 Hz, 7.6 Hz, 1H), 7.90 (d, J = 7.6 Hz, 1H), 8.22 (s, 1H), 8.46 (d, J = 8 Hz, 1H), 8.79 (s, 1H), 9.00 (s, 1H), 12.15 (s, 1H). |
| 32 | 2-chloro-5-[4-[(5-cyclopropyl-1H-pyrazol-3-yl)amino]-5-methyl-pyrimidin-2-yl]-benzamide | d (400 MHz, DMSO-d6); 0.72-0.73 (m, 2H), 0.96-0.97 (m, 2H), 1.87-1.93 (m, 1H), 2.18 (s, 3H), 6.40 (s, 1H), 7.58 (d, J = 8.4 Hz, 1H), 7.67 (s, 1H), 8.02 (s, 1H), 8.20 (s, 1H), 8.28 (d, J = 8 Hz, 1H), 8.32 (s, 1H), 9.06 (s, 1H), 12.17 (s, 1H). |

TABLE 2-continued

| Compound # | Name | NMR |
|---|---|---|
| 33 | 5-[4-[(5-cyclopropyl-1H-pyrazol-3-yl)amino]-5-methyl-pyrimidin-2-yl]-N-methyl-thiophene-2-sulfonamide | d (400 MHz, DMSO-d6); 0.74-0.75 (m, 2H), 0.98-0.99 (m, 2H), 1.92-1.95 (m, 1H), 2.19 (s, 3H), 2.56 (d, J = 4.8 Hz, 3H), 6.50 (s, 1H), 7.59 (d, J = 4.0 Hz, 1H), 7.76-7.77 (m, 2H), 8.15 (s, 1H), 9.15 (s, 1H), 12.19 (s, 1H). |
| 34 | 2-chloro-5-[4-[(5-cyclopropyl-1H-pyrazol-3-yl)amino]-5-fluoro-pyrimidin-2-yl]-benzamide | d (400 MHz, DMSO-d6); 0.73-0.75 (m, 2H), 0.95-0.98 (m, 2H), 1.87-1.93 (m, 1H), 6.41 (s, 1H), 7.61 (d, J = 8.4 Hz, 1H), 7.72 (s, 1H), 8.05 (s, 1H), 8.23-8.27 (m, 2H), 8.41 (d, J = 3.2 Hz, 1H), 10.13 (s, 1H), 12.27 (s, 1H). |
| 35 | 3-[4-[(5-cyclopropyl-1H-pyrazol-3-yl)amino]-5-fluoro-pyrimidin-2-yl]benzenesulfonamide | d (400 MHz, DMSO-d6); 0.83 (m, 2H), 0.98 (m, 2H), 1.95 (m, 1H), 6.51 (s, 1H), 7.44 (s, 2H), 7.73 (t, J = 7.2 Hz, 1H), 7.95 (d, J = 7.6 Hz, 1H), 8.45 (d, J = 4.8 Hz, 2H), 8.78 (s, 1H), 10.12 (s, 1H), 12.26 (s, 1H). |
| 36 | [5-[4-[(5-cyclopropyl-1H-pyrazol-3-yl)amino]-5-methyl-pyrimidin-2-yl]-2-thienyl]methanol | d (400 MHz, DMSO-d6); 0.74-0.75 (m, 2H), 0.97-0.98 (m, 2H), 1.93-1.95 (m, 1H), 2.15 (s, 3H), 4.65 (d, J = 5.6 Hz, 2H), 5.57 (t, J = 5.6 Hz, 1H), 6.59 (s, 1H), 6.99 (d, J = 3.6 Hz, 1H), 7.62 (d, J = 3.2 Hz, 1H), 8.08 (s, 1H), 8.97 (s, 1H), 12.12 (s, 1H). |
| 37 | 5-[5-chloro-4-[(5-cyclopropyl-1H-pyrazol-3-yl)amino]-pyrimidin-2-yl]-N-methyl-thiophene-2-sulfonamide | d (400 MHz, DMSO-d6); 0.74 (m, 2H), 0.98 (m, 2H), 1.95 (m, 1H), 2.54 (d, J = 4.8 Hz, 3H), 6.39 (s, 1H), 7.59 (d, J = 4 Hz, 1H), 7.79 (m, 2H), 8.45 (s, 1H), 9.48 (s, 1H), 12.33 (s, 1H). |
| 38 | N-(5-cyclopropyl-1H-pyrazol-3-yl)-5-methyl-2-(2-thienyl)pyrimidin-4-amine | d (400 MHz, DMSO-d6); 0.74 (m, 2H), 0.98-1.00 (m, 2H), 1.94 (m, 1H), 2.17 (s, 3H), 6.60 (s, 1H), 7.17 (t, J = 4.4 Hz, 1H), 7.67 (d, J = 4.4 Hz, 1H), 7.78 (s, 1H), 8.09 (s, 1H), 8.99 (s, 1H), 12.14 (s, 1H). |
| 39 | N-(5-cyclopropyl-1H-pyrazol-3-yl)-5-(3-methoxyprop-1-enyl)-2-phenyl-pyrimidin-4-amine | d (400 MHz, DMSO-d6): 0.72~0.78 (m, 2H), 0.96~0.98 (m, 2H), 1.94~2.02 (m, 1H), 3.30 (s, 3H), 4.06 (d, J = 5.2 Hz, 2H), 6.33 (m, 1H), 6.46 (s, 1H), 7.02 (d, J = 15.6 Hz, 1H), 7.48 (m, 3H), 8.29 (d, J = 4.4 Hz, 2H), 8.53 (s, 1H), 9.26 (s, 1H), 12.15 (s, 1H). |
| 40 | 5-[4-[(5-cyclopropyl-1H-pyrazol-3-yl)amino]-5-methyl-pyrimidin-2-yl]thiophene-2-sulfonamide | d (400 MHz, DMSO-d6); 0.75-0.76 (m, 2H), 0.97-0.99 (m, 2H), 1.93-1.95 (m, 1H), 2.18 (s, 3H), 6.51 (s, 1H), 7.57 (d, J = 3.6 Hz, 1H), 7.73 (d, J = 3.2 Hz, 1H), 7.78 (s, 2H), 8.14 (s, 1H), 9.13 (s, 1H), 12.17 (s, 1H). |
| 41 | N-(5-cyclopropyl-1H-pyrazol-3-yl)-5-fluoro-2-(2-thienyl)pyrimidin-4-amine | d (400 MHz, DMSO-d6); 0.77 (m, 2H), 1.01 (m, 2H), 1.97 (m, 1H), 6.58 (s, 1H), 7.21 (t, J = 4.2 Hz, 1H), 7.76 (m, 2H), 8.32 (d, J = 3.2 Hz, 1H), 10.12 (s, 1H), 12.24 (s, 1H). |
| 42 | 5-[5-chloro-4-[(5-cyclopropyl-1H-pyrazol-3-yl)amino]-pyrimidin-2-yl]thiophene-2-sulfonamide | d (400 MHz, DMSO-d6); 0.78-0.79 (m, 2H), 1.00-1.02 (m, 2H), 1.97-1.99 (m, 1H), 6.42 (s, 1H), 7.59 (d, J = 4.4 Hz, 1H), 7.78 (d, J = 3.6 Hz, 1H), 7.84 (s, 2H), 8.50 (s, 1H), 9.65 (s, 1H). |
| 43 | 5-[4-[(5-cyclopropyl-1H-pyrazol-3-yl)amino]-5-fluoro-pyrimidin-2-yl]-N-methyl-thiophene-2-sulfonamide | d (400 MHz, DMSO-d6); 0.76 (m, 2H), 1.00 (m, 2H), 1.96 (m, 1H), 2.57 (d, J = 4.4 Hz, 3H), 6.49 (s, 1H), 7.16 (d, J = 4 Hz, 1H), 7.79 (m, 2H), 8.38 (s, 1H), 10.24 (s, 1H), 12.27 (s, 1H). |
| 44 | N-(5-cyclopropyl-1H-pyrazol-3-yl)-5-ethyl-2-[4-(1-piperidyl)-1-piperidyl]-pyrimidin-4-amine | |
| 45 | N-(5-cyclopropyl-1H-pyrazol-3-yl)-5-ethyl-2-(1-piperidyl)pyrimidin-4-amine | |
| 46 | N-(5-cyclopropyl-1H-pyrazol-3-yl)-5-ethyl-2-(4-methylpiperazin-1-yl)-pyrimidin-4-amine | d (400 MHz, CD3OD); 0.71 (2H, m), 0.99 (2H, brs), 1.21(3H, t, J = 7.6 Hz), 1.92(1H, br s), 2.34(3H, s), 2.49 (6H, m), 3.73(4H, m), 6.29(1H, s), 7.75(1H, s) |
| 47 | N-(5-cyclopropyl-1H-pyrazol-3-yl)-2-(4-methylpiperazin-1-yl)-pyrimidin-4-amine | d (400 MHz, CDCl3); 0.73 (2H, dd, J1 = 8.8 Hz, J2 = 2.0 Hz), 0.98 (2H, J1 = 8.8 Hz, J2 = 2.0 Hz), 1.86(1H, m), 2.36(3H, s), 2.49 (4H, t, J = 4.8 Hz), 3.82(4H, t, J = 4.8 Hz), 5.90(1H, brs), 6.10(1H, brs), 6.94(1H, s), 8.02(1H, d, J = 2.0 Hz) |
| 48 | 5-[4-[(5-cyclopropyl-1H-pyrazol-3-yl)amino]pyrimidin-2-yl]-N-methyl-thiophene-2-sulfonamide | d (400 MHz, DMSO-d6); 0.71 (m, 2H), 0.95 (m, 2H), 1.90 (m, 1H), 2.54 (s, 3H), 6.35 (bs, 1H), 6.85 (bs, 1H), 7.59 (s, 1H), 7.82 (s, 2H), 8.28 (s, 1H), 10.13 (s, 1H), 12.15 (bs, 1H). |
| 49 | methyl 2-(cyclopropyl-phenyl-BLAHyl)acetate | d (400 MHz, DMSO-d6); 0.60-0.61 (m, 2H), 0.81-0.83 (m, 2H), 1.75-1.82 (m, 1H), 3.06 (dd, J1 = 4.4 Hz, J2 = 16 Hz, 1H), 3.22 (dd, J1 = 4.4 Hz, J2 = 16 Hz, 1H), 5.33 (s, 1H), 5.83 (t, J = 4.4 Hz, 1H), 7.51 (m, 3H), 8.30-8.32 (m, 2H), 8.55 (s, 1H), 10.94 (s, 1H). |

TABLE 2-continued

| Compound # | Name | NMR |
|---|---|---|
| 50 | 5-[4-[(5-cyclopropyl-1H-pyrazol-3-yl)amino]pyrimidin-2-yl]thiophene-2-sulfonamide | d (400 MHz, DMSO-d6); 0.72-0.74 (m, 2H), 0.94-0.99 (m, 2H), 1.89-1.94 (m, 1H), 6.41 (bs, 1H), 6.84 (bs, 1H), 7.58 (d, J = 4 Hz, 1H), 7.49-7.81 (m, 3H), 8.29 (d, J = 5.2 Hz, 1H), 10.08 (s, 1H), 12.14 (s, 1H). |
| 51 | 2-chloro-5-[4-[(5-cyclopropyl-1H-pyrazol-3-yl)amino]pyrimidin-2-yl]-benzamide | d (400 MHz, DMSO-d6); 0.72-0.73 (m, 2H), 0.95-0.97 (m, 2H), 1.87-1.92 (m, 1H), 6.20 (bs, 1H), 7.05 (bs, 1H), 7.67 (d, J = 8 Hz, 1H), 7.74 (s, 1H), 8.06 (s, 1H), 8.32 (d, J = 8.4 Hz, 1H), 8.38(s, 2H), 10.28 (s, 1H), 12.24 (bs, 1H). |
| 52 | 5-[4-[(5-cyclopropyl-1H-pyrazol-3-yl)amino]-5-fluoro-pyrimidin-2-yl]thiophene-2-sulfonamide | d (400 MHz, DMSO-d6); 0.75-0.76 (m, 2H), 0.98-0.99 (m, 2H), 1.94-1.97 (m, 1H), 6.49 (s, 1H), 7.57 (d, J = 4 Hz, 1H), 7.71 (d, J = 3.6 Hz, 1H), 7.82 (s, 2H), 8.36(s, 1H), 10.23 (s, 1H), 12.25 (s, 1H). |
| 53 | 3-[4-[(5-cyclopropyl-1H-pyrazol-3-yl)amino]-2-phenyl-pyrimidin-5-yl]prop-2-en-1-ol | d (400 MHz, DMSO-d6); 0.71-0.72 (m, 2H), 0.96-0.98 (m, 2H), 1.91-1.98 (m, 1H), 4.15 (t, J = 5.2 Hz, 2H), 4.87 (m, 1H), 6.34 (dt, J1 = 4.8 Hz, J2 = 15.6 Hz, 1H), 6.48 (s, 1H), 6.80 (d, J = 16 Hz, 1H), 7.48-7.51 (m, 3H), 8.28-8.30 (m, 2H), 8.47 (s, 1H), 9.05 (s, 1H), 12.15 (s, 1H). |
| 54 | 3-[4-[(5-cyclopropyl-1H-pyrazol-3-yl)amino]pyrimidin-2-yl]prop-2-ene-1-sulfonamide | d (400 MHz, DMSO-d6): 0.69-0.75 (m, 2H), 0.95~0.97 (m, 2H), 1.92~1.96 (m, 1H), 4.17 (d, J = 7.6 Hz, 2H), 6.45 (bs, 1H), 6.86 (d, J = 15.2 Hz, 1H), 6.98 (bs, 1H), 7.17 (s, 2H), 7.27 (td, J = 15.2 Hz, 7.6 Hz, 1H), 8.33 (bs, 1H), 11.66 (bs, 1H), 12.66 (bs, 1H). |
| 55 | 4-[(5-cyclopropyl-1 H-pyrazol-3-yl)amino]-2-phenyl-pyrimidin-5-ol | d (400 MHz, DMSO-d6): 0.69~0.74 (m, 2H), 0.93~0.98 (m, 2H), 1.85~1.89 (m, 1H), 6.52 (bs, 1H), 7.40~7.47 (m, 3H), 7.93 (s, 1H), 8.22 (d, J = 7.6 Hz, 2H), 8.41 (bs, 1H), 10.43 (bs, 1H), 12.09 (bs, 1H). |
| 56 | 3-[4-[(5-cyclopropyl-1H-pyrazol-3-yl)amino]pyrimidin-2-yl]-N-tert-butyl-prop-2-ene-1-sulfonamide | d (400 MHz, DMSO-d6): 0.64~0.69 (m, 2H), 0.77~0.83 (m, 2H), 1.30 (s, 9H), 1.80~1.92 (m, 1H), 4.02 (d, J = 7.6 Hz, 2H), 6.17 (bs, 1H), 6.60 (d, J = 15.2 Hz, 1H), 6.93 (td, J = 15.2 Hz, 7.6 Hz, 1H), 7.02 (bs, 1H), 7.08 (s, 1H), 8.23 (s, 1H), 9.84 (bs, 1H), 12.26 (bs, 1H). |
| 57 | 4-[[4-[(5-cyclopropyl-2H-pyrazol-3-yl)amino]pyrimidin-2-yl]amino]benzoic acid | d (400 MHz, DMSO-d6); 0.57-0.58 (m, 2H), 0.90-0.94 (m, 2H), 1.84-1.85 (m, 1 H), 6.04 (s, 1H), 6.51 (bs, 1H), 7.71-7.72 (m, 2H), 7.97-8.05 (m, 3H), 10.93 (s, 1H), 12.62 (bs, 1H). |
| 58 | 2-chloro-5-[5-chloro-4-[(5-cyclopropyl-1H-pyrazol-3-yl)amino]-pyrimidin-2-yl]-benzenesulfonamide | d (400 MHz, DMSO-d6); 0.81 (m, 2H), 0.95 (m, 2H), 1.94 (m, 1H), 6.40 (s, 1H), 7.69 (s, 2H), 7.78 (d, J = 8.4 Hz, 1H), 8.40 (d, J = 8.4 Hz, 1H) 8.54 (s, 1H), 8.94 (s, 1H), 9.35 (s, 1H), 12.30 (s, 1H). |
| 59 | 2-[4-[[5-chloro-4-[(5-cyclopropyl-1H-pyrazol-3-yl)amino]-pyrimidin-2-yl]amino]phenyl]acetonitrile | d (400 MHz, DMSO-d6); 0.68 (m, 2H), 0.99 (m, 2H), 1.93 (m, 2H), 4.00 (s, 2H), 6.12 (s, 1H), 7.29 (d, J = 8 Hz, 2H), 7.59 (d, J = 7.2 Hz, 2H) 8.27 (s, 1H), 10.07 (m, 2H), 10.65 (bs, 1H). |
| 60 | 4-[[4-[(5-cyclopropyl-2H-pyrazol-3-yl)amino]pyrimidin-2-yl]amino]benzamide | d (400 MHz, DMSO-d6); 0.55-0.55 (m, 2H), 0.88-0.90 (m, 2H), 1.82-1.83 (m, 1H), 6.04 (s, 1H), 6.49 (bs, 1H), 7.34 (s, 1H), 7.62 (s, 2H), 7.92-7.96 (m, 4H), 10.73 (s, 1H), 11.17 (bs, 1H), 12.48 (bs, 1H). |
| 61 | 4-[5-chloro-4-[(5-cyclopropyl-1H-pyrazol-3-yl)amino]-pyrimidin-2-yl]-N-(2-hydroxyethyl)benzenesulfonamide | d (400 MHz, DMSO-d6); 0.77 (m, 2H), 1.00 (m, 2H), 2.00 (m, 1H), 2.83 (q, J = 6.0 Hz, 2H), 3.37 (q, J = 6.0 Hz, 2H), 4.71 (t, J = 5.6 Hz, 1H), 6.41 (s, 1H), 7.72 (t, J = 6.0 Hz, 1H), 7.92 (d, J = 8.8 Hz, 2H), 8.42 (d, J = 8.4 Hz, 2H), 8.56 (s, 1 H), 9.40 (s, 1H), 12.32 (s, 1H) |
| 62 | 5-chloro-N'-(5-cyclopropyl-1H-pyrazol-3-yl)-N-(1H-indazol-5-yl)pyrimidine-2,4-diamine | d (400 MHz, DMSO-d6); 0.59 (m, 2H), 0.86 (m, 2H), 1.84 (m, 2H), 6.03 (bs, 1H), 7.43 (s, 2H), 7.95 (s, 1H), 8.08 (s, 1H), 8.63 (s, 1H), 9.25 (s, 1H), 9.70 (bs, 1H), 12.22 (s, 1H), 12.89 (s, 1H). |
| 63 | 3-[[4-[(5-cyclopropyl-2H-pyrazol-3-yl)amino]pyrimidin-2-yl]amino]benzoic acid | d (400 MHz, DMSO-d6); 0.49-0.49 (m, 2H), 0.86-0.89 (m, 2H), 1.78-1.78 (m, 1H), 5.98 (s, 1H), 6.47 (s, 1H), 7.57 (t, J = 4.0 Hz, 1H), 7.83 (m, 2H), 8.00 (m, 2H), 10.76 (s,1H), 11.24 (s, 1H), 12.52 (bs, 2H). |

TABLE 2-continued

| Compound # | Name | NMR |
|---|---|---|
| 64 | N-(5-cyclopropyl-1H-pyrazol-3-yl)-2-(1-piperidyl)pyrimidin-4-amine | d (400 MHz, CDCl3); 0.71 (2H, m), 0.98 (2H, m), 1.60 (4H, m), 1.71(2H, m), 1.90(1H, m), 3.746(4H, t, J = 5.6 Hz), 6.14(1H, s), 7.83(1H, d, J = 4.4 Hz) |
| 65 | N-(5-cyclopropyl-1H-pyrazol-3-yl)-2-[4-(1-piperidyl)-1-piperidyl]-pyrimidin-4-amine | d (400 MHz, CD3OD); 0.71 (2H, m), 0.99 (2H, m), 1.31(4H, m), 1.62(4H, m), 1.92(3H, m), 2.62(5H, brs), 2.85 (2H, t, J = 12.0 Hz), 4.73(2H, d, J = 13.2 Hz), 6.09(1H, s), 6.17(1H, s), 7.86(1H, d, J = 5.6 Hz) |
| 66 | N-(5-cyclopropyl-1H-pyrazol-3-yl)-2-(1-piperidyl)-5-propyl-pyrimidin-4-amine | d (400 MHz, CD3OD); 0.69(2H, m), 0.98 (5H, m), 1.58 (8H, m), 1.88(1H, m), 2.40 (2H, m), 3.67 (4H, m), 6.17(1H, s), 7.69(1H, s) |
| 67 | N-(5-cyclopropyl-1H-pyrazol-3-yl)-5-methoxy-2-(4-methylpiperazin-1-yl)-pyrimidin-4-amine | |
| 68 | N-(5-cyclopropyl-1H-pyrazol-3-yl)-5-methoxy-2-(1-piperidyl)pyrimidin-4-amine | d (400 MHz, CD3OD); 0.71 (2H, d, J = 5.2 Hz), 0.99 (2H, m), 1.68 (6H, m), 1.91(1H, m), 3.67(4H, m), 3.85(3H, s), 6.41(1H, s), 7.59(1H, s) |
| 69 | N-(5-cyclopropyl-1H-pyrazol-3-yl)-5-(methoxymethyl)-2-(4-methylpiperazin-1-yl)-pyrimidin-4-amine | |
| 70 | N-(5-cyclopropyl-1H-pyrazol-3-yl)-5-(methoxymethyl)-2-(1-piperidyl)pyrimidin-4-amine | |
| 71 | N-(5-cyclopropyl-1H-pyrazol-3-yl)-5-(methoxymethyl)-2-[4-(1-piperidyl)-1-piperidyl]-pyrimidin-4-amine | d (400 MHz, CD3OD); 0.71 (2H, m), 0.99 (2H, m), 1.49(4H, m), 1.64(4H, m), 1.93(3H, m), 2.63(5H, br s), 2.88 (2H, t, J = 12.4 Hz), 3.38 (3H, s), 4.38 (2H, s), 4.74(2H, d, J = 13.2 Hz), 6.39(1H, brs), 7.82 (1H, s) |
| 72 | N-(5-cyclopropyl-1H-pyrazol-3-yl)-2-(4-methylpiperazin-1-yl)-5-propyl-pyrimidin-4-amine | d (400 MHz, CD3OD); 0.71 (2H, m), 0.98 (5H, m), 1.59 (2H, m), 1.90(1H, m), 2.33 (3H, s), 2.42 (2H, m), 2.50(4H, m), 3.73 (4H, m), 6.30 (1H, br s), 7.73 (1H, s) |
| 73 | 3-[[5-chloro-4-[(5-cyclopropyl-1H-pyrazol-3-yl)amino]-pyrimidin-2-yl]amino]benzoic acid | d (400 MHz, DMSO-d6); 0.66 (m, 2H), 0.95 (m, 2H), 1.89 (m, 1H), 6.13 (s, 1H), 7.42 (t, J = 7.8 Hz, 1H), 7.62 (d, J = 8.0 Hz, 1H), 7.92 (d, J = 8.4 Hz, 1H), 8.11 (s, 1H), 8.27 (s, 1H), 9.89 (s, 1H), 9.99 (s, 1H), 10.78 (bs, 2H). |
| 74 | 5-[5-chloro-4-[(5-cyclopropyl-1H-pyrazol-3-yl)amino]-pyrimidin-2-yl]-N,N-dimethyl-thiophene-2-sulfonamide | d (400 MHz, DMSO-d6); 0.73 (m, 2H), 0.99 (m, 2H), 1.94 (m, 1H), 2.72 (s, 6H), 6.40 (s, 1H), 7.67 (d, J = 3.2 Hz, 1H), 7.85 (d, J = 3.6 Hz, 1H), 8.48 (s, 1H), 9.55 (s, 1H), 12.37 (s, 1H) |
| 75 | N-(2-aminoethyl)-5-[5-chloro-4-[(5-cyclopropyl-1H-pyrazol-3-yl)amino]-pyrimidin-2-yl]-thiophene-2-sulfonamide | d (400 MHz, DMSO-d6); 0.82 (m, 2H), 1.03 (m, 2H), 2.01 (m, 1H), 2.90 (q, J = 5.6 Hz, 2H), 3.15 (q, J = 6.0 Hz, 2H), 6.43 (s, 1H), 7.71 (d, J = 4.0 Hz, 1H), 7.85 (d, J = 3.6 Hz, 1H), 8.18 (s, 1H), 8.48 (d, J = 5.6 Hz, 1H), 8.55 (s, 1H), 9.83 (bd, J = 20.8 Hz, 1H) |
| 76 | 4-[[4-[(5-methyl-2H-pyrazol-3-yl)amino]pyrimidin-2-yl]amino]benzenesulfonamide | d (400 MHz, DMSO-d6); 2.22 (s, 3H), 6.21 (bs, 1H), 6.58 (bs, 1H), 7.32 (s, 2H), 7.79 (m, 4H), 8.02 (d, J = 3 Hz, 1H), 10.34 (s, 1H), 10.70 (bs, 1H), 12.33 (bs, 1H). |
| 77 | 4-[[5-chloro-4-[(5-cyclopropyl-1H-pyrazol-3-yl)amino]-pyrimidin-2-yl]amino]benzoic acid | d (400 MHz, DMSO-d6); 0.77 (m, 2H), 1.03 (m, 2H), 2.00 (m, 1H), 6.19 (s, 1H), 7.76 (d, J = 7.6 Hz, 2H), 7.95 (d, J = 8.4 Hz, 2H), 8.33 (s, 1H), 9.31 (s, 1H), 9.95 (m, 1H), 10.20 (s, 1H). |
| 78 | tert-butyl [2-[[5-[5-chloro-4-[(5-cyclopropyl-1H-pyrazol-3-yl)amino]-pyrimidin-2-yl]-2-thienyl]sulfonylamino]ethylamino]formate | d (400 MHz, DMSO-d6); 0.74 (mz, 2H), 0.98 (m, 2H), 1.94 (s, 9H), 1.96 (m, 1H), 2.89 (q, J = 6.0 Hz, 2H), 2.99 (q, J = 6.0 Hz, 2H), 6.39 (s, 1H), 6.83 (t, J = 5.2 Hz, 1H), 7.60 (d, J = 4.0 Hz, 1H), 7.77 (d, J = 3.6 Hz, 1H), 8.03 (t, J = 5.6 Hz, 1H), 8.47 (s, 1H), 9.50 (s, 1H), 12.33 (s, 1H) |
| 79 | 5-[5-chloro-4-[(5-cyclopropyl-1H-pyrazol-3-yl)amino]-pyrimidin-2-yl]-N-(2-dimethylaminoethyl)thiophene-2-sulfonamide | d (400 MHz, DMSO-d6); 0.75 (m, 2H), 0.98 (m, 2H), 1.95 (m, 1H), 2.09 (s, 6H), 2.30 (t, J = 6.8 Hz, 2H), 2.97 (t, J = 6.8 Hz, 2H), 6.39 (s, 1H), 7.62 (d, J = 3.6 Hz, 1H), 7.77 (d, J = 3.6 Hz, 1H), 7.96 (bs, 1H), 8.47 (s, 1H), 9.50 (s, 1H), 12.34 (s, 1H) |
| 80 | N-(4-aminophenyl)-N'-(5-cyclopropyl-2H-pyrazol-3-yl)-pyrimidine-2,4-diamine | d (400 MHz, DMSO-d6); 0.61-0.61 (m, 2H), 0.90-0.94 (m, 2H), 1.81-1.82 (m, 1H), 6.11 (bs, 1H), 6.34 (bs, 1H), 6.60-6.79 (m, 3H), 7.04-7.17 (m, 3H), 7.82 (s, 1H), 9.90 (s, 1H), 10.79 (bs, 1H), 12.32 (s, 1H). |

TABLE 2-continued

| Compound # | Name | NMR |
|---|---|---|
| 81 | 3-[4-[(5-cyclopropyl-1H-pyrazol-3-yl)amino]-2-phenyl-pyrimidin-5-yl]prop-2-enyl acetate | d (400 MHz, DMSO-d6); 0.72-0.73 (m, 2H), 0.96-0.98 (m, 2H), 1.91-1.98 (m, 1H), 2.07 (s, 3H), 4.70 (d, J = 5.6 Hz, 2H), 6.35 (d, J = 15.2 Hz, 1H), 6.46 (s, 1H), 7.10 (d, J = 15.2 Hz, 1H), 7.47-7.49 (m, 3H), 8.29-8.30 (m, 2H), 8.54 (s, 1H), 9.29 (s, 1H), 12.16(s, 1H). |
| 82 | 3-[[4-[(5-cyclopropyl-2H-pyrazol-3-yl)amino]pyrimidin-2-yl]amino]benzenesulfonamide | d (400 MHz, DMSO-d6); 0.62-0.63 (m, 2H), 0.88-0.92 (m, 2H), 1.82-1.86 (m, 1H), 6.06 (bs, 1H), 6.49 (bs, 1H), 7.39 (s, 2H), 7.52 (d, J = 1.8 Hz, 2H), 7.97 (s, 3H), 10.02 (s, 1H), 10.45 (bs, 1H), 12.27 (bs, 1H). |
| 83 | 4-[[4-[(5-cyclopropyl-2H-pyrazol-3-yl)amino]pyrimidin-2-yl]amino]-N-(2-hydroxyethyl)benzenesulfonamide | d (400 MHz, DMSO-d6); 0.63-0.64 (m, 2H), 0.92-0.95 (m, 2H), 1.83-1.87 (m, 1H), 2.79 (q, J = 6.0 Hz, 2H), 3.368 (t, J = 6.0 Hz, 2H), 6.10 (bs, 1H), 6.53 (bs, 1H), 7.59 (m, 1H), 7.78 (m, 4H), 8.03 (s, 1H), 10.88 (s, 1H), 11.11 (bs, 1H), 12.49 (bs, 1H). |
| 84 | 4-[[5-chloro-4-[(5-cyclopropyl-1H-pyrazol-3-yl)amino]-pyrimidin-2-yl]amino]benzonitrile | d (400 MHz, DMSO-d6); 0.76 (m, 2H), 1.01 (m, 2H), 1.99 (m, 1H), 6.16 (s, 1H), 7.68 (t, J = 9.8 Hz, 2H), 7.83 (d, J = 8.0 Hz, 2H), 8.30 (s, 1H), 9.90 (s, 1H), 10.26 (s, 1H), 11.08 (bs, 1H). |
| 85 | 2-[4-[4-[(5-cyclopropyl-1H-pyrazol-3-yl)amino]-5-ethynyl-pyrimidin-2-yl]phenyl]acetonitrile | d (400 MHz, DMSO-d6); 0.75-0.76 (m, 2H), 0.98-1.06 (m, 2H), 1.96-2.00 (m, 1H), 4.15 (s, 2H), 4.87 (s, 1H), 6.47 (s, 1H), 7.51 (d, J = 8.4 Hz, 2H), 8.32 (d, J = 8.0 Hz, 2H), 8.57 (s, 1H), 8.65 (s, 1H), 12.29 (s, 1H). |
| 86 | 5-[5-chloro-4-[(5-cyclopropyl-1H-pyrazol-3-yl)amino]-pyrimidin-2-yl]-N-(2-hydroxyethyl)thiophene-2-sulfonamide | d (400 MHz, DMSO-d6); 0.76 (s, 2H), 1.00 (d, J = 4.4 Hz, 2H), 1.98 (s, 1H), 2.95 (s, 2H), 3.43 (d, J = 4.8 Hz, 2H), 4.76 (s, 1H), 6.41 (s, 1H), 7.62 (s, 1H), 7.78 (s, 1H), 8.01 (s, 1H), 8.47 (s, 1H), 9.49 (s, 1H), 12.34 (s, 1H) |
| 87 | 2-[5-[5-chloro-4-[(5-cyclopropyl-1H-pyrazol-3-yl)amino]-pyrimidin-2-yl]-2-thienyl]propan-2-ol | d (400 MHz, DMSO-d6); 0.76 (d, J = 3.2 Hz, 2H), 1.00 (d, J = 6.4 Hz, 2H), 1.54 (s, 6H), 1.95 (t, J = 4.0 Hz, 1H), 5.60 (s, 1H), 6.51 (s, 1H), 6.98 (d, J = 4.0 Hz, 1H), 7.63 (t, J = 4.0 Hz, 1H), 8.38 (s, 1H), 9.26 (s, 1H), 12.30 (s, 1H) |
| 88 | 5-[5-chloro-4-[(5-cyclopropyl-1H-pyrazol-3-yl)amino]-pyrimidin-2-yl]-N-(2-methoxyethyl)thiophene-2-sulfonamide | d (400 MHz, DMSO-d6); 0.75 (d, J = 3.6 Hz, 2H), 0.99 (d, J = 6.4 Hz, 2H), 1.94 (m, 1H), 3.04 (t, J = 5.2 Hz, 2H), 3.20 (s, 3H), 3.37 (t, J = 5.0 Hz, 2H), 6.39 (s, 1H), 7.61 (d, J = 3.2 Hz, 1H), 7.77 (d, J = 3.6 Hz, 1H), 8.15 (bs, 1H), 8.46 (s, 1H), 9.49 (bs, 1H), 12.35 (s, 1H). |
| 89 | 3-[[5-chloro-4-[(5-cyclopropyl-1H-pyrazol-3-yl)amino]-pyrimidin-2-yl]amino]benzonitrile | d (400 MHz, DMSO-d6); 0.72 (t, J = 5.6 Hz, 2H), 0.98 (m, 2H), 1.96 (m, 1H), 6.15 (s, 1H), 7.46 (m, 2H), 7.90 (d, J = 8.4 Hz, 1H), 8.13 (s, 1H), 8.30 (s, 1H), 9.87 (s, 1H), 10.09 (s, 1H), 10.63 (bs, 1H). |
| 90 | N-cyclopropyl-4-[[4-[(5-cyclopropyl-2H-pyrazol-3-yl)amino]pyrimidin-2-yl]amino]-benzenesulfonamide | d (400 MHz, DMSO-d6); 0.38-0.39 (m, 2H), 0.46-0.51 (m, 2H), 0.65-0.65 (m, 2H), 0.93-0.97 (m, 2H), 1.87-1.89 (m, 1H), 2.11-2.13 (m, 1H), 6.12 (bs, 1H), 6.55 (bs, 1H), 7.80-7.91 (m, 5H), 8.06 (s, 1H), 11.00 (s, 1H), 11.19 (bs, 1H), 12.59 (bs, 1H). |
| 91 | N'-(5-cyclopropyl-1H-pyrazol-3-yl)-5-ethynyl-N-(1H-indazol-5-yl)pyrimidine-2,4-diamine | d (400 MHz, DMSO-d6); 0.57 (s, 2H), 0.86 (s, 2H), 1.82 (s, 1H), 4.60 (s, 1 H), 5.63~6.23 (m, 1H), 7.47 (s, 2H), 7.99~8.21 (m, 4H), 9.46 (s, 1H), 12.20 (s, 1H), 12.95 (s, 1H). |
| 92 | 2-[4-[5-amino-4-[(5-cyclopropyl-1H-pyrazol-3-yl)amino]-pyrimidin-2-yl]phenyl]acetonitrile | d (400 MHz, DMSO-d6); 0.71 (s, 2H), 0.93 (s, 2H), 1.92 (s, 1H), 3.83 (s, 2H), 5.30 (s, 2H), 6.21 (s, 1H), 7.04 (s, 1H), 7.21 (d, J = 6.0 Hz, 1H), 7.53 (s, 1H), 7.70 (s, 1H), 8.30 (s, 1H), 9.78 (s, 1H), 12.03 (s, 1H). |
| 93 | 5-[4-[(5-cyclopropyl-1H-pyrazol-3-yl)amino]-5-ethynyl-pyrimidin-2-yl]-2-methyl-benzamide | d (400 MHz, DMSO-d6); 0.74-0.78 (m, 2H), 0.95-1.00 (m, 2H), 1.91-1.95 (m, 1H), 2.43 (s, 3H), 4.88 (s, 1H), 6.47 (s, 1H), 7.39 (d, J = 8.0 Hz, 1H), 7.49 (s, 1H), 7.91 (s, 1H), 8.24 (d, J = 8.0 Hz, 1H), 8.33 (d, J = 1.2 Hz, 1H), 8.57 (s, 1H), 8.73 (s, 1H), 12.37 (bs, 1H). |
| 94 | N'-(5-cyclopropyl-2H-pyrazol-3-yl)-N-(4-methylsulfonylphenyl)-pyrimidine-2,4-diamine | d (400 MHz, DMSO-d6); 0.63-0.64 (m, 2H), 0.92-0.97 (m, 2H), 1.87-1.91 (m, 1H), 3.21 (s, 3H), 6.09 (bs, 1H), 6.57 (bs, 1H), 7.92-7.94 (m, 4H), 8.07 (s, 1H), 10.92-11.14 (m, 2H), 12.59 (bs, 1H). |

TABLE 2-continued

| Compound # | Name | NMR |
|---|---|---|
| 95 | 3-[5-chloro-4-[(5-cyclopropyl-1H-pyrazol-3-yl)amino]-pyrimidin-2-yl]-N-(2-hydroxyethyl)benzenesulfonamide | d (400 MHz, DMSO-d6); 0.81 (m, 2H), 0.96 (m, 2H), 1.94 (m, 1H), 2.83 (m, 2H), 3.39 (m, 2H), 4.70 (t, J = 5.4 Hz, 1H), 6.40 (s, 1H), 7.31 (m, 1H), 7.74 (m, 1H), 7.93 (d, J = 7.6 Hz, 1H), 8.48 (d, J = 8 Hz, 1H), 8.56 (s, 1H), 8.72 (s, 1H), 9.40 (s, 1H) 12.33 (s, 1H). |
| 96 | N-[2-[[3-[5-chloro-4-[(5-cyclopropyl-1H-pyrazol-3-yl)amino]-pyrimidin-2-yl]phenyl]sulfonylamino]ethyl]acetamide | d (400 MHz, DMSO-d6); 0.79 (m, 2H), 0.95 (m, 2H), 1.72 (s, 3H), 1.93 (m, 1H), 2.78 (q, J = 6.4 Hz, 2H), 3.05 (q, J = 6.4 Hz, 2H), 6.40 (s, 1H), 7.74 (t, J = 7.6 Hz, 2H), 7.86 (m, 2H), 8.47 (d, J = 7.6 Hz, 1H), 8.54 (s, 1H), 8.70 (s, 1H), 9.36 (s, 1H), 12.31 (s, 1H) |
| 97 | 3-[5-chloro-4-[(5-cyclopropyl-1H-pyrazol-3-yl)amino]-pyrimidin-2-yl]-N-(2-dimethylaminoethyl)benzenesulfonamide | d (400 MHz, DMSO-d6); 0.79 (m, 2H), 0.95 (m, 2H), 1.93 (m, 1H), 2.03 (s, 6H), 2.24 (t, J = 6.4 Hz, 2H), 2.85 (d, J = 5.6 Hz, 2H), 6.40 (s, 1H), 7.61 (s, 1H), 7.73 (t, J = 8.0 Hz, 1H), 7.92 (d, J = 7.6 Hz, 1H), 8.47 (d, J = 7.6 Hz, 1H), 8.54 (s, 1H), 8.71 (s, 1H), 9.36 (s, 1H), 12.32 (s, 1H). |
| 98 | 5-chloro-N-(5-cyclopropyl-1H-pyrazol-3-yl)-2-(5-pyrrolidin-1-ylsulfonyl-2-thienyl)-pyrimidin-4-amine | d (400 MHz, DMSO-d6); 0.75 (m, 2H), 0.98 (m, 2H), 1.94 (m, 1H), 1.72 (t, J = 6.6 Hz, 4H), 3.24 (t, J = 6.6 Hz, 4H), 6.39 (s, 1H), 7.71 (d, J = 4.0 Hz, 1H), 7.83 (d, J = 3.6 Hz, 1H), 8.48 (s, 1H), 9.57 (s, 1H), 12.38 (s, 1H). |
| 99 | 3-[4-[(5-cyclopropyl-2H-pyrazol-3-yl)amino]-5-hydroxy-pyrimidin-2-yl]benzenesulfonamide | d (400 MHz, DMSO-d6): 0.75~0.83 (m, 2H), 0.92~0.99 (m, 2H), 1.87~1.99 (m, 1H), 6.47 (s, 1H), 7.47 (s, 2H), 7.76 (dd, J = 8.0 Hz, 8.0 Hz, 1H), 7.95~7.98 (m, 2H), 7.76 (d, J = 8.0 Hz, 1H), 8.67 (s, 1H), 9.88 (bs, 1H), 11.54 (bs, 1H). |
| 100 | N-(3-aminophenyl)-N'-(5-cyclopropyl-2H-pyrazol-3-yl)-pyrimidine-2,4-diamine | d (400 MHz, DMSO-d6); 0.64-0.68 (m, 2H), 0.89-0.93 (m, 2H), 1.82-1.87 (m, 1H), 6.23-6.29 (m, 2H), 6.43 (d, J = 4 Hz, 2H), 6.77-6.83 (m, 2H), 6.94 (t, J = 8 Hz, 1H), 7.04 (t, J = 8 Hz, 2H), 7.92 (d, J = 2.8 Hz, 1H), 9.86 (bs, 1H), 10.63 (bs, 1H), 12.30 (bs, 1H). |
| 101 | 2-[4-[[4-[(5-cyclopropyl-1H-pyrazol-3-yl)amino]-5-ethynyl-pyrimidin-2-yl]amino]phenyl]acetonitrile | d (400 MHz, DMSO-d6); 0.68 (s, 2H), 0.94 (s, 2H), 1.89 (s, 1H), 3.97 (s, 2H), 4.61 (s, 1H), 6.31 (bs, 1H), 7.24 (d, J = 7.2 Hz, 2H), 7.68 (d, J = 7.6 Hz, 2H), 8.16 (bs, 1H), 8.23 (s, 1H), 9.57 (s, 1H), 12.24 (s, 1H),. |
| 102 | 3-[4-[(5-cyclopropyl-2H-pyrazol-3-yl)amino]-5-hydroxy-pyrimidin-2-yl]-N-tert-butyl-benzenesulfonamide | d (400 MHz, DMSO-d6): 0.76~0.80 (m, 2H), 0.92~0.97 (m, 2H), 1.11 (s, 9H), 1.90~1.94 (m, 1H), 6.48 (s, 1H), 7.60 (s, 1H), 7.68 (dd, J = 7.6 Hz, 7.6 Hz, 1H), 7.88 (d, J = 7.6 Hz, 1H), 7.95 (s, 1H), 8.47 (d, J = 7.6 Hz, 1H), 8.70 (s, 1H), 8.90 (bs, 1H), 10.76 (bs, 1H). |
| 103 | 4-[[4-[(5-cyclopropyl-2H-pyrazol-3-yl)amino]pyrimidin-2-yl]amino]-N,N-dimethyl-benzenesulfonamide | d (400 MHz, DMSO-d6); 0.69-0.73 (m, 2H), 0.91-0.96 (m, 2H), 1.86-1.90 (m, 1H), 2.58 (s, 6H), 6.28 (bs, 1H), 6.54 (bs, 1H), 7.60 (d, J = 4 Hz, 2H), 8.04 (d, J = 4 Hz, 3H), 9.66 (s, 2H), 12.08 (s, 1H). |
| 104 | 3-[5-chloro-4-[(5-cyclopropyl-1H-pyrazol-3-yl)amino]-pyrimidin-2-yl]phenol | d (400 MHz, DMSO-d6); 0.75 (s, 2H), 0.98 (s, 2H), 1.96 (s, 1H), 6.41 (s, 1H), 6.90 (d, J = 7.6 Hz, 1H), 7.28 (t, J = 7.8 Hz, 1H), 7.70 (s, 2H), 8.48 (s, 1H), 9.19 (s, 1H), 9.60 (s, 1H), 12.27 (s, 1H). |
| 105 | N-[4-[5-chloro-4-[(5-cyclopropyl-1H-pyrazol-3-yl)amino]-pyrimidin-2-yl]phenyl]methanesulfonamide | d (400 MHz, DMSO-d6); 0.73 (m, 2H), 0.97-0.99 (m, 2H), 1.98 (s, 1H), 3.07 (s, 3H), 6.41 (s, 1H), 7.29 (d, J = 8.0 Hz, 2H), 8.21 (d, J = 8.4 Hz, 2H), 8.45 (s, 1H), 9.19 (s, 1H), 10.10 (s, 1H), 12.26 (s, 1H). |
| 106 | 5-chloro-N-(5-cyclopropyl-1H-pyrazol-3-yl)-2-(5-morpholinosulfonyl-2-thienyl)-pyrimidin-4-amine | d (400 MHz, DMSO-d6); 0.73-0.74 (m, 2H), 0.98-1.00 (m, 2H), 1.94 (m, 1H), 2.99 (s, 4H), 3.69 (s, 4H), 6.38 (s, 1H), 7.68-7.69 (d, J = 3.2 Hz, 1H), 7.86-7.87 (d, J = 3.6 Hz, 1H), 8.49 (s, 1H), 9.58 (s, 1H), 12.37 (bs, 1H). |
| 107 | N-[3-[5-chloro-4-[(5-cyclopropyl-1H-pyrazol-3-yl)amino]-pyrimidin-2-yl]phenyl]methanesulfonamide | d (400 MHz, DMSO-d6); 0.76 (s, 2H), 0.95-0.96 (m, 2H), 1.97 (m, 1H), 3.00 (s, 3H), 6.47 (s, 1H), 7.31 (d, J = 8.0 Hz, 1H), 7.44 (t, J = 8.0 Hz, 1H), 7.99 (t, J = 7.6 Hz, 1H), 8.23 (s, 1H), 8.50 (s, 1H), 9.22 (s, 1H), 9.90 (s, 1H), 12.27 (s, 1H). |

TABLE 2-continued

| Compound # | Name | NMR |
|---|---|---|
| 108 | 5-[4-[(5-cyclopropyl-1H-pyrazol-3-yl)amino]-5-ethynyl-pyrimidin-2-yl]-N-(2-hydroxyethyl)thiophene-2-sulfonamide | d (400 MHz, DMSO-d6); 0.75-0.76 (m, 2H), 0.98-1.00 (m, 2H), 1.95 (m, 1H), 2.95 (q, J = 5.2 Hz, 2H), 3.42 (q, J = 6.0 Hz, 2H), 4.75 (t, J = 5.2 Hz, 1H), 4.89 (s, 1H), 6.44 (s, 1H), 7.62 (d, J = 3.6 Hz, 1H), 7.83 (d, J = 3.6 Hz, 1H), 8.02 (s, 1H), 8.52 (s, 1H), 8.81 (s, 1H), 12.32 (s, 1H). |
| 109 | N-cyclohexyl-4-[(5-cyclopropyl-2H-pyrazol-3-yl)amino]-pyrimidine-2-carboxamide | d (400 MHz, DMSO-d6); 0.66-0.70 (m, 2H), 0.92-0.97 (m, 2H), 1.16-1.18 (m, 1H), 1.34-1.37 (m, 4H), 1.58-1.61 (m, 1H), 1.72 (m, 2H), 1.80 (m, 2H), 1.85-1.91 (m, 1H), 3.74 (t, J = 4.4 Hz, 1H), 5.97 (m, 1H), 7.41 (m, 1H), 8.29 (d, J = 8.4 Hz, 1H), 8.35 (d, J = 4.8 Hz, 1H), 10.16 (s, 1H), 12.12 (s, 1H). |
| 110 | 3-[4-[(5-cyclopropyl-1H-pyrazol-3-yl)amino]-5-ethynyl-pyrimidin-2-yl]benzenesulfonamide | d (400 MHz, DMSO-d6); 0.82 (m, 2H), 0.96-0.98 (m, 2H), 1.94 (m, 1H), 4.90 (s, 1H), 6.47 (s, 1H), 7.45 (s, 2H), 7.74 (t, J = 8.0 Hz, 1H), 7.97 (d, J = 7.6 Hz, 1H), 8.49 (d, J = 8.0 Hz, 1H), 8.62 (s, 1H), 8.70 (s, 1H), 8.82 (s, 1H), 12.31 (s, 1H). |
| 111 | 1-[5-[4-[(5-cyclopropyl-1H-pyrazol-3-yl)amino]-5-ethynyl-pyrimidin-2-yl]-2-thienyl]ethanone | d (400 MHz, DMSO-d6); 0.74-0.75 (m, 2H), 0.98-0.99 (m, 2H), 1.90-1.98 (m, 1H), 2.57 (s, 3H), 4.90 (s, 1H), 6.46 (s, 1H), 7.87 (d, J = 3.6 Hz, 1H), 7.97 (d, J = 4.0 Hz, 1H), 8.52 (s, 1H), 8.78 (bs, 1H), 12.31 (s, 1H). |
| 112 | 4-[[4-[(5-cyclopropyl-2H-pyrazol-3-yl)amino]pyrimidin-2-yl]amino]-N-(2-methoxyethyl)benzenesulfonamide | d (400 MHz, DMSO-d6); 0.70 (m, 2H), 0.93-0.94 (m, 2H), 1.03-1.04 (m, 2H), 1.87-1.89 (m, 1H), 2.86-2.90 (m, 2H), 3.17 (s, 3H), 3.29-3.32(m, 2H), 6.25(bs, 1H), 6.55 (bs, 1H), 7.47-7.50 (m, 1H), 7.66 (d, J = 8.4 Hz, 2H), 7.97 (d, J = 7.6 Hz, 2H), 7.04 (d, J = 3.6 Hz, 1H), 9.56-10.23 (m, 2H), 12.06 (s, 0.8H), 12.46 (s, 0.2H) |
| 113 | 5-[4-[(5-cyclopropyl-2H-pyrazol-3-yl)amino]-5-ethynyl-pyrimidin-2-yl]-N-methyl-thiophene-2-sulfonamide | d (400 MHz, DMSO-d6); 0.76 (m, 2H), 0.98-1.00 (m, 2H), 1.90-1.98 (m, 1H), 2.56 (d, J = 4.0 Hz, 3H), 4.89 (s, 1H), 6.44 (s, 1H), 7.62 (d, J = 4.0 Hz, 1H), 7.84 (d, J = 2.8 Hz, 2H), 8.52 (s, 1H), 8.81 (s, 1H), 12.32 (s, 1H). |
| 114 | 5-[4-[(5-cyclopropyl-2H-pyrazol-3-yl)amino]-5-ethynyl-pyrimidin-2-yl]thiophene-2-sulfonamide | d (400 MHz, DMSO-d6); 0.73-0.77 (m, 2H), 0.97-0.99 (m, 2H), 1.91-1.98 (m, 1H), 4.90 (s, 1H), 6.44 (s, 1H), 7.60 (d, J = 4.0 Hz, 1H), 7.81 (d, J = 4.0 Hz, 1H), 7.84 (s, 2H), 8.52 (s, 1H), 8.80 (bs, 1H), 12.30 (bs, 1H). |
| 115 | 5-[4-[(5-cyclopropyl-2H-pyrazol-3-yl)amino]-5-ethynyl-pyrimidin-2-yl]-N-tert-butyl-thiophene-2-sulfonamide | d (400 MHz, DMSO-d6); 0.75-0.76 (m, 2H), 0.97-1.00 (m, 2H), 1.20 (s, 9H), 1.91-1.98 (m, 1H), 4.89 (s, 1H), 6.45 (s, 1H), 7.61 (d, J = 3.6 Hz, 1H), 7.79 (d, J = 4.0 Hz, 1H), 7.93 (s, 1H), 8.51 (s, 1H), 8.78 (s, 1H), 12.31 (s, 1H). |
| 116 | 1-[5-[5-chloro-4-[(5-cyclopropyl-1H-pyrazol-3-yl)amino]-pyrimidin-2-yl]-2-thienyl]ethanone | d (400 MHz, DMSO-d6); 0.75 (m, 2H), 1.00 (m, 2H), 1.96 (m, 1H), 2.57 (s, 3H), 6.44 (s, 1H), 7.83 (d, J = 3.6 Hz, 1H), 7.96 (d, J = 4 Hz, 1H), 8.47 (s, 1H), 9.47 (s, 1H), 12.34 (s, 1H). |
| 117 | 4-[5-chloro-4-[(5-cyclopropyl-2H-pyrazol-3-yl)amino]-pyrimidin-2-yl]-N-methyl-benzenesulfonamide | d (400 MHz, DMSO-d6); 1.70-1.77 (m, 2H), 0.98-1.02 (m, 2H), 1.95-2.02 (m, 1H), 2.45 (d, J = 4.8 Hz, 3H), 6.41 (s, 1H), 7.54-7.58 (q, J = 5.2 Hz, 1H), 7.89-7.92 (m, 2H), 8.43-8.45 (m, 2H), 8.56 (s, 1H), 9.41 (s, 1H), 12.32 (s, 1H). |
| 118 | N-[2-[[5-[5-chloro-4-[(5-cyclopropyl-1H-pyrazol-3-yl)amino]-pyrimidin-2-yl]-2-thienyl]sulfonylamino]ethyl]acetamide | d (400 MHz, DMSO-d6); 0.75 (m, 2H), 0.98 (m, 2H), 1.76 (s, 3H), 1.95 (m, 1H), 2.92 (q, J = 6.4 Hz, 2H), 3.11 (q, J = 6.4 Hz, 2H), 6.38 (s, 1H), 7.61 (d, J = 4.0 Hz, 1H), 7.78 (d, J = 4.0 Hz, 1H), 7.92 (t, J = 5.6 Hz, 1H), 8.06 (t, J = 5.6 Hz, 1H), 8.48 (s, 1H), 9.54 (s, 1H) |
| 119 | N-(5-cyclopropyl-2H-pyrazol-3-yl)-5-ethynyl-2-(5-isopropenyl-2-thienyl)-pyrimidin-4-amine | d (400 MHz, DMSO-d6); 0.74-0.75 (m, 2H), 0.99-1.01 (m, 2H), 1.92-1.98 (m, 1H), 2.14 (s, 1H), 4.85 (s, 1H), 5.13 (s, 1H), 5.50 (s, 1H), 6.53 (s, 1H), 7.26 (d, J = 3.6 Hz, 1H), 7.76 (d, J = 4.0 Hz, 1H), 8.46 (s, 1H), 8.64 (s, 1H), 12.30 (s, 1H). |
| 120 | 2-[[4-[(5-cyclopropyl-1H-pyrazol-3-yl)amino]pyrimidin-2-yl]amino]benzenesulfonamide | |
| 121 | 4-[5-chloro-4-[(5-cyclopropyl-1H-pyrazol-3-yl)amino]-pyrimidin-2-yl]benzenesulfonamide | d (400 MHz, DMSO-d6); 0.74-0.78 (m, 2H), 0.98-1.02 (m, 2H), 1.96-2.01 (m, 1H), 6.41 (d, J = 1.6 Hz, 1H), 7.47 (s, 1H), 7.95 (d, J = 8.4 Hz, 2H), 8.40 (d, J = 8.8 Hz, 2H), 8.55 (s, 1H), 9.39 (s, 1H), 12.32 (s, 1H). |

TABLE 2-continued

| Compound # | Name | NMR |
|---|---|---|
| 122 | 3-[4-[(5-cyclopropyl-2H-pyrazol-3-yl)amino]-5-ethynyl-pyrimidin-2-yl]-N-(2-hydroxyethyl)benzenesulfonamide | |
| 123 | [4-[(5-cyclopropyl-2H-pyrazol-3-yl)amino]-2-phenyl-pyrimidin-5-yl]methanol | d (400 MHz, DMSO-d6): 0.74-0.75 (m, 2H), 0.97-0.99 (m, 2H), 1.96-1.98 (m, 1H), 4.59 (s, 2H), 5.63 (bs, 1H), 6.56 (bs, 1H), 7.50-7.52 (m, 3H), 8.31-8.34 (m, 3H), 8.83 (s, 1H), 12.15 (bs, 1H). |
| 124 | 3-[4-[(5-cyclopropyl-2H-pyrazol-3-yl)amino]-5-(hydroxymethyl)pyrimidin-2-yl]benzenesulfonamide | |
| 125 | 3-[[4-[(5-cyclopropyl-1H-pyrazol-3-yl)amino]pyrimidin-2-yl]amino]benzamide | d (400 MHz, DMSO-d6): 0.68 (s, 2H), 0.90 (s, 2H), 1.86 (m, 1H), 6.28 (bs, 1H), 6.45 (bs, 1H), 7.32 (d, J = 12.4 Hz, 2H), 7.40 (d, J = 7.6 Hz, 1H), 7.85 (s, 1H), 7.99 (d, J = 8.0 Hz, 2H), 8.06 (s, 1H), 9.15 (s, 1H), 9.54 (s, 1H), 11.98 (s, 1H) |
| 126 | 4-[5-chloro-4-[(5-cyclopropyl-1H-pyrazol-3-yl)amino]-pyrimidin-2-yl]phenol | d (400 MHz, DMSO-d6): 0.72-0.74 (m, 2H), 0.98-1.03 (m, 2H), 1.96-1.98 (m, 1H), 6.38 (s, 1H), 6.85 (d, J = 7.2 Hz, 2H), 8.11 (d, J = 6.8 Hz, 2H), 8.42 (s, 1H), 9.14 (bs, 1H), 9.96 (s, 1H), 12.26 (bs, 1H). |
| 127 | 3-[5-chloro-4-[(5-cyclopropyl-1H-pyrazol-3-yl)amino]-pyrimidin-2-yl]-N-methyl-benzenesulfonamide | d (400 MHz, DMSO-d6): 0.79-0.82 (m, 2H), 0.94-0.99 (m, 2H), 1.92-1.96 (m, 1H), 2.45 (d, J = 5.2 Hz, 3H), 6.40 (s, 1H), 7.54 (q, J = 4.8 Hz, 1H), 7.76 (t, J = 7.6 Hz, 1H), 7.89-7.91 (m, 1H), 8.48-8.51 (m, 1H), 8.56 (s, 1H), 8.70 (t, J = 1.2 Hz, 1H), 9.42 (s, 1H). |
| 128 | 2-chloro-5-[4-[(5-cyclopropyl-2H-pyrazol-3-yl)amino]-5-ethynyl-pyrimidin-2-yl]-benzamide | d (400 MHz, DMSO-d6): 0.75-0.76 (m, 2H), 0.98-0.99 (m, 2H), 1.89-1.97 (m, 1H), 4.87 (s, 1H), 6.41 (s, 1H), 7.65 (d, J = 8.4 Hz, 1H), 7.72 (s, 1H), 8.05 (s, 1H), 8.31 (d, J = 8.4 Hz, 1H), 8.33 (d, J = 1.6 Hz, 1H), 8.58 (s, 1H), 8.75 (s, 1H), 12.33 (s, 1H). |
| 129 | 5-[5-chloro-4-[(5-cyclopropyl-1H-pyrazol-3-yl)amino]-pyrimidin-2-yl]-N-(2-hydroxyethyl)-N-methyl-thiophene-2-sulfonamide | d (400 MHz, DMSO-d6): 0.73-0.74 (m, 2H), 0.98-1.00 (m, 2H), 1.90-1.98 (m, 2H), 2.82 (s, 3H), 3.08 (t, J = 6.0 Hz, 2H), 3.56 (q, J = 4.8 Hz, 2H), 4.87 (t, J = 5.6 Hz, 1H), 6.40 (s, 1H), 7.67 (d, J = 4.4 Hz, 1H), 7.82 (d, 4.0 Hz, 1H), 8.47 (s, 1H), 9.54 (s, 1H), 12.36 (s, 1H). |
| 130 | 2-[5-[4-[(5-cyclopropyl-2H-pyrazol-3-yl)amino]-5-ethynyl-pyrimidin-2-yl]-2-thienyl]acetonitrile | d (400 MHz, DMSO-d6): 0.75-0.77 (m, 2H), 0.98-0.99 (m, 2H), 1.92-1.98 (m, 1H), 4.39 (s, 2H), 4.86 (s, 1H), 6.49 (s, 1H), 7.16 (d, J = 3.6 Hz, 1H), 7.74 (d, J = 3.6 Hz, 1H), 8.46 (s, 1H), 8.61 (s, 1H), 12.28 (s, 1H). |
| 131 | 5-[5-chloro-4-[(5-cyclopropyl-1H-pyrazol-3-yl)amino]-pyrimidin-2-yl]thiophene-2-carboxamide | d (400 MHz, DMSO-d6): 0.70-0.76 (m, 2H), 0.92-0.99 (m, 2H), 1.93-1.97 (m, 1H), 6.46 (s, 1H), 7.73-7.46 (m, 1H), 7.76 (s, 1H), 8.07-8.18 (m, 1H), 8.34 (m, 1H), 8.45 (d, J = 6.4 Hz, 1H), 9.19-9.35 (m, 1H), 12.23-12.29 (m, 1H). |
| 132 | 1-[5-[5-chloro-4-[(5-cyclopropyl-1H-pyrazol-3-yl)amino]-pyrimidin-2-yl]-2-thienyl]ethanol | |
| 133 | 1-[5-[5-chloro-4-[(5-cyclopropyl-1H-pyrazol-3-yl)amino]-pyrimidin-2-yl]-2-thienyl]ethanol | |
| 134 | 3-[5-chloro-4-[(5-cyclopropyl-1H-pyrazol-3-yl)amino]-pyrimidin-2-yl]-N-(2-hydroxyethyl)-N-methyl-benzenesulfonamide | d (400 MHz, DMSO-d6): 0.79-0.80 (m, 2H), 0.96-0.98 (m, 2H), 1.92-1.96 (m, 1H), 2.78 (s, 3H), 3.05 (t, J = 6.4 Hz, 2H), 3.53 (q, J = 6.0 Hz, 2H), 4.80 (t, J = 5.6 Hz, 1H), 6.40 (s, 1H), 7.78 (t, J = 7.6 Hz, 1H), 7.90 (t, J = 6.4 Hz, 1H), 8.55 (d, J = 9.2 Hz, 2H), 8.63 (s, 1H), 9.37 (s, 1H), 12.32 (s, 1H). |
| 135 | 5-chloro-N-(5-cyclopropyl-1H-pyrazol-3-yl)-2-(5-piperazin-1-ylsulfonyl-2-thienyl)-pyrimidin-4-amine | d (400 MHz, DMSO-d6): 0.73-0.77 (m, 2H), 0.99-1.03 (m, 2H), 1.93-2.00 (m, 1H), 3.25 (s, 8H), 6.38 (s, 1H), 7.76 (d, J = 5.2 Hz, 1H), 7.90 (d, J = 4.0 Hz, 1H), 8.51 (s, 1H), 9.17 (s, 2H), 9.67 (s, 1H). |
| 136 | N-[[5-[5-chloro-4-[(5-cyclopropyl-2H-pyrazol-3-yl)amino]-pyrimidin-2-yl]-2-thienyl]methyl]acetamide | d (500 MHz, DMSO-d6): 0.75-0.76 (m, 2H), 0.98~1.00 (m, 2H), 1.89 (s, 3H), 4.44 (d, J = 6.0 Hz, 2H), 6.46 (s, 1H), 7.01 (d, J = 3.5 Hz, 1H), 7.54 (d, J = 3.0 Hz, 2H), 8.38 (s, 1H), 8.57 (t, J = 5.5 Hz, 1H), 9.27 (s, 1H), 12.29 (s, 1H). |
| 137 | 1-[5-[4-[(5-cyclopropyl-1H-pyrazol-3-yl)amino]-5-fluoro-pyrimidin-2-yl]-2-thienyl]ethanone | d (500 MHz, DMSO-d6): 0.74-0.77 (m, 2H), 0.99-1.02 (m, 2H), 1.94-1.97 (m, 1H), 2.57 (s, 3H), 6.52 (s, 1H), 7.79 (d, J = 4.0 Hz, 1H), 7.96 (d, J = 4.5 Hz, 1H), 8.36 (d, J = 4.0 Hz, 1H),, 10.23 (s, 1H), 12.27 (s, H). |

TABLE 2-continued

| Compound # | Name | NMR |
|---|---|---|
| 138 | N-(2-aminoethyl)-3-[5-chloro-4-[(5-cyclopropyl-1H-pyrazol-3-yl)amino]-pyrimidin-2-yl]-benzenesulfonamide | d (400 MHz, DMSO-d6): 0.79-0.82 (m, 2H), 0.95-0.99 (m, 2H), 1.93-1.97 (m, 1H), 2.87 (q, J = 5.6 Hz, 2H), 2.96 (q, J = 5.6 Hz, 2H), 6.40 (s, 1H), 7.76-7.82 (m, 3H), 7.94-7.98 (m, 2H), 8.52 (d, J = 8 Hz, 1H), 8.58 (s, 1H), 8.74 (t, J = 1.6 Hz, 1H), 9.45 (s, 1H). |
| 139 | 5-[5-chloro-4-[(5-cyclopropyl-1H-pyrazol-3-yl)amino]-pyrimidin-2-yl]-N-cyclopropyl-thiophene-2-sulfonamide | d (400 MHz, DMSO-d6): 0.45-0.48 (m, 2H), 0.52-0.59 (m, 2H), 0.73-0.77 (m, 2H), 0.96-1.00 (m, 2H), 1.92-1.95 (m, 1H), 2.28-2.31 (m, 1H), 6.38 (s, 1H), 7.62 (d, J = 4 Hz, 1H), 7.80 (d, J = 4 Hz, 1H), 8.26 (d, J = 2.8 Hz, 1H), 8.47 (s, 1H), 9.49 (s, 1H), 12.34 (bs, 1H). |
| 140 | 5-[5-chloro-4-[(5-cyclopropyl-1H-pyrazol-3-yl)amino]-pyrimidin-2-yl]thiophene-2-carbonitrile | d (500 MHz, DMSO-d6): 0.76-0.79 (m, 2H), 0.95-0.99 (m, 2H), 1.96-1.99 (m, 1H), 6.37 (s, 1H), 8.33 (s, 1H), 8.48 (s, 1H), 8.60 (s, 1H), 9.37 (s, 1H), 12.28 (bs, 1H). |
| 141 | 2-[5-(aminomethyl)-2-thienyl]-5-chloro-N-(5-cyclopropyl-2H-pyrazol-3-yl)-pyrimidin-4-amine | d (500 MHz, DMSO-d6); 0.83~0.86 (m, 2H), 1.03~1.06 (m, 2H), 2.04~2.09 (m, 1H), 4.27 (d, J = 5.0 Hz, 2H), 6.50 (s, 1H), 7.37 (d, J = 3.5 Hz, 1H), 7.82 (d, J = 3.5 Hz, 1H), 8.51 (s, 1H), 8.71 (s, 2H), 9.83 (s, 1H). |
| 142 | 3-[5-chloro-4-[(5-cyclopropyl-1H-pyrazol-3-yl)amino]-pyrimidin-2-yl]benzoic acid | d (500 MHz, DMSO-d6): 0.81-0.84 (m, 2H), 0.97-1.01 (m, 2H), 1.94-1.97 (m, 1H), 6.44 (s, 1H), 7.65 (t, J = 8.0 Hz, 1H), 8.08 (dt, J = 1.5 Hz, 8.0Hz, 1H), 8.50 (dt, J = 1.0 Hz, 7.0 Hz, 1H), 8.56 (s, 1H), 8.90 (t, J = 1.0 Hz, 1H), 9.50 (s, 1H). |
| 143 | 2-[5-[5-chloro-4-[(5-cyclopropyl-2H-pyrazol-3-yl)amino]-pyrimidin-2-yl]-2-thienyl]acetonitrile | d (500 MHz, DMSO-d6); 0.76 (m, 2H), 0.98~0.99 (m, 2H), 1.93~1.98 (m, 1H), 4.38 (s, 2H), 6.44 (s, 1H), 7.14 (d, J = 4.0 Hz, 1H), 7.69 (d, J = 4.0 Hz, 1H), 8.41 (s, 1H), 9.33 (s, 1H), 12.29 (s, 1H). |
| 144 | 1-[5-[4-[(5-cyclopropyl-1H-pyrazol-3-yl)amino]-5-fluoro-pyrimidin-2-yl]-2-thienyl]ethanol | d (500 MHz, DMSO-d6): 0.73-0.76 (m, 2H), 0.97-1.01 (m, 2H), 1.45 (d, J = 6.5 Hz, 3H), 1.92-1.96 (m, 1H), 4.95-4.98 (m, 1H), 5.66 (d, J = 4.5 Hz, 1H), 6.55 (bs, 1H), 6.97 (d, J = 3.5 Hz, 1H), 7.59 (d, J = 3.5 Hz, 1H), 8.28 (d, J = 3.5 Hz, 1H), 10.05 (bs, 1H), 12.20 (bs, 1H). |
| 145 | 1-[5-[4-[(5-cyclopropyl-1H-pyrazol-3-yl)amino]-5-methyl-pyrimidin-2-yl]-2-thienyl]ethanol | d (500 MHz, DMSO-d6): 0.72-0.75 (m, 2H), 0.96-0.99 (m, 2H), 1.44 (d, J = 6.0 Hz, 3H), 1.90-1.95 (m, 1H), 2.15 (s, 3H), 4.92-4.97 (m, 1H), 5.62 (d, J = 4.5 Hz, 1H), 6.55 (bs, 1H), 6.95 (d, J = 4.0 Hz, 1H), 7.60 (d, J = 3.5 Hz, 1H), 8.07 (s, 1H), 8.97 (bs, 1H), 12.09 (bs, 1H). |
| 146 | 1-[5-[4-[(5-cyclopropyl-1H-pyrazol-3-yl)amino]-5-methyl-pyrimidin-2-yl]-2-thienyl]ethanol | d (500 MHz, DMSO-d6): 0.74-0.77 (m, 2H), 0.97-1.00 (m, 2H), 1.45 (d, J = 6.0 Hz, 3H), 1.92-1.95 (m, 1H), 2.16 (s, 3H), 4.93-4.98 (m, 1H), 5.63 (d, J = 4.5 Hz, 1H), 6.56 (bs, 1H), 6.96 (d, J = 3.5 Hz, 1H), 7.62 (d, J = 4.0 Hz, 1H), 8.08 (s, 1H), 8.99 (bs, 1H), 12.10 (bs, 1H). |
| 147 | 1-[5-[4-[(5-cyclopropyl-1H-pyrazol-3-yl)amino]-5-fluoro-pyrimidin-2-yl]-2-thienyl]ethanol | d (500 MHz, DMSO-d6): 0.72-0.76 (m, 2H), 0.96-1.00 (m, 2H), 1.44 (d, J = 6.0 Hz, 3H), 1.91-1.97 (m, 1H), 4.93-4.97 (m, 1H), 5.66 (d, J = 5.0 Hz, 1H), 6.54 (bs, 1H), 6.96 (d, J = 4.0 Hz, 1H), 7.59 (d, J = 4.0 Hz, 1H), 8.27 (d, J = 3.5 Hz, 1H), 10.04 (bs, 1H), 12.20 (bs, 1H). |
| 148 | 5-[5-chloro-4-[(5-cyclopropyl-1H-pyrazol-3-yl)amino]-pyrimidin-2-yl]-N-tetrahydropyran-4-yl-thiophene-2-sulfonamide | d (400 MHz, DMSO-d6): 0.75-0.76 (m, 2H), 0.99-1.00 (m, 2H), 1.38-1.46 (m, 2H), 1.59-1.63 (m, 2H), 1.93-1.98 (m, 1H), 3.24-3.30 (m, 3H), 3.73-3.76 (m, 2H), 6.39 (s, 1H), 7.64 (d, J = 4.0 Hz, 1H), 7.76 (d, J = 3.6 Hz, 1H), 8.19 (d, J = 7.2 Hz, 1H), 8.46 (s, 1H), 9.47 (s, 1H), 12.33 (s, 1H). |
| 149 | 5-[4-[(5-cyclopropyl-1-methyl-pyrazol-3-yl)amino]-5-methyl-pyrimidin-2-yl]-N-tert-butyl-thiophene-2-sulfonamide | d (400 MHz, DMSO-d6); 0.68-0.72 (m, 2H), 1.00-1.03 (m, 2H), 1.20 (s, 9H), 1.91-1.98 (m, 1H), 2.17 (s, 3H), 3.79 (s, 3H), 6.46 (s, 1H), 7.58 (d, J = 4.4 Hz, 1H), 7.69 (d, J = 4.0 Hz, 1H), 7.86 (s, 1H), 8.13 (d, J = 0.8 Hz, 1H), 9.21 (s, 1H). |
| 150 | 5-[4-[(5-cyclopropyl-1-methyl-pyrazol-3-yl)amino]-5-methyl-pyrimidin-2-yl]thiophene-2-sulfonamide | d (400 MHz, DMSO-d6); 0.70-0.71 (m, 2H), 1.00-1.03 (m, 2H), 1.91-1.98 (m, 1H), 2.17 (s, 3H), 3.79 (s, 3H), 6.46 (s, 1H), 7.56 (d, J = 3.6 Hz, 1H), 7.71 (d, J = 3.6 Hz, 1H), 7.78 (s, 1H), 8.14 (d, J = 0.8 Hz, 1H), 9.21 (s, 1H). |

TABLE 2-continued

| Compound # | Name | NMR |
|---|---|---|
| 151 | methyl 5-[4-[(5-cyclopropyl-1H-pyrazol-3-yl)amino]-5-ethynyl-pyrimidin-2-yl]thiophene-2-carboxylate | d (400 MHz, DMSO-d6); 0.75-0.79 (m, 2H), 0.99-1.02 (m, 2H), 1.95-1.99 (m, 1H), 3.87 (s, 3H), 4.92 (s, 1H), 6.46 (s, 1H), 7.85 (dd, J = 4.0 Hz,3.6 Hz, 2H), 8.54 (s, 1H), 8.99 (s, 1H). |
| 152 | 5-[5-chloro-4-[(5-cyclopropyl-1H-pyrazol-3-yl)amino]-pyrimidin-2-yl]-N-tetrahydrofuran-3-yl-thiophene-2-sulfonamide | d (500 MHz, DMSO-d6): 0.73-0.76 (m, 2H), 0.96-1.00 (m, 2H), 1.66-1.72 (m, 1H), 1.93-2.01 (m, 2H), 3.59-3.63 (m, 2H), 3.69-3.74 (m, 2H), 3.82-3.88 (m, 1H), 6.38 (s, 1H), 7.64 (d, J = 4.0 Hz, 1H), 7.78 (d, J = 3.5 Hz, 1H), 8.34 (d, J = 6.5 Hz, 1H), 8.47 (s, 1H), 9.51 (s, 1H). |
| 153 | N-(5-cyclopropyl-1H-pyrazol-3-yl)-5-ethynyl-2-(4-methylsulfonylphenyl)-pyrimidin-4-amine | d (400 MHz, DMSO-d6); 0.78~0.79 (m, 2H), 0.99~1.01 (m, 2H), 1.95~2.02 (m, 1H), 3.29 (s, 3H), 4.91 (s, 1H), 6.45 (s, 1H), 8.09 (d, J = 8.4 Hz, 2H), 8.51 (d, J = 8.4 Hz, 2H), 8.63 (s, 1H), 8.78 (s, 1H), 12.31 (s, 1H). |
| 154 | methyl 5-[5-chloro-4-[(5-cyclopropyl-2H-pyrazol-3-yl)amino]-pyrimidin-2-yl]thiophene-2-carboxylate | d (400 MHz, DMSO-d6); 0.77~0.81 (m, 2H), 1.00~1.05 (m, 2H), 1.95-2.02 (m, 1 H), 3.86 (s, 3H), 6.43 (s, 1H), 7.81~7.84 (m, 2H), 8.51 (s, 1H), 9.67 (s, 1H). |
| 155 | 2-[5-chloro-4-[(5-cyclopropyl-1H-pyrazol-3-yl)amino]-pyrimidin-2-yl]benzenesulfonamide | d (400 MHz, DMSO-d6): 0.65-0.69 (m, 2H), 0.88-0.93 (m, 2H), 1.85-1.89 (m, 1H), 6.10 (s, 1H), 7.33 (bs, 2H), 7.65-7.73 (m, 3H), 7.99 (d, J = 8.0 Hz, 1H), 8.59 (s, 1H), 9.58 (s, 1H). |
| 156 | 5-[5-chloro-4-[(5-cyclopropyl-2H-pyrazol-3-yl)amino]-pyrimidin-2-yl]thiophene-2-carboxylic acid | d (400 MHz, DMSO-d6); 0.75~0.78 (m, 2H), 0.97~1.01 (m, 2H), 1.92~1.99 (m, 1H), 6.44 (s, 1H), 7.73 (d, J = 3.6 Hz, 1H), 7.79 (d, J = 3.6 Hz, 1H), 8.46 (s, 1H), 9.47 (s, 1H), 12.84 (bs, 2H). |
| 157 | 5-[4-[(5-cyclopropyl-1H-pyrazol-3-yl)amino]-5-ethynyl-pyrimidin-2-yl]thiophene-2-carbonitrile | d (400 MHz, DMSO-d6); 0.75-0.76 (m, 2H), 0.97-0.99 (m, 2H), 1.96-1.99 (m, 1H), 4.91 (s, 3H), 6.43 (s, 1H), 7.88 (d, J = 4.0 Hz, 1H), 8.03 (d, J = 4.0 Hz, 1H), 8.52 (s, 1H), 8.86 (s, 1H), 12.30 (s, 1H). |
| 158 | 5-[5-chloro-4-[(5-cyclopropyl-1H-pyrazol-3-yl)amino]-pyrimidin-2-yl]-N-(2, 2, 2-trifluoroethyl)thiophene-2-sulfonamide | d (400 MHz, DMSO-d6); 0.73-0.77 (m, 2H), 0.96-1.01 (m, 2H), 1.93-1.97 (m, 1H), 3.77-3.85 (m, 2H), 6.38 (s, 1H), 7.70 (d, J = 3.6 Hz, 1H), 7.78 (d, J = 4.0 Hz, 1H), 8.48 (s, 1H), 9.04 (t, J = 6.8 Hz, 1H), 9.52 (s, 1H), 12.36 (bs, 1H). |
| 159 | 5-[4-[(5-cyclopropyl-1H-pyrazol-3-yl)amino]-5-(trifluoromethyl)pyrimidin-2-yl]thiophene-2-sulfonamide | d (400 MHz, DMSO-d6): 0.75-0.76 (m, 2H), 0.98-1.00 (m, 2H), 1.91-1.98 (m, 1H), 6.28 (s, 1H), 7.61 (d, J = 4.0 Hz, 1H), 7.82 (d, J = 4.4 Hz, 1H), 7.86 (s, 2H), 8.69 (s, 1H), 9.23 (s, 1H), 12.41 (s, 1H). |
| 160 | 5-[4-[(5-cyclopropyl-1H-pyrazol-3-yl)amino]-5-ethynyl-pyrimidin-2-yl]-N-(2-dimethylaminoethyl)thiophene-2-sulfonamide | d (400 MHz, DMSO-d6): 0.68~0.77 (m, 2H), 0.91~0.99 (m, 2H), 1.88~1.97 (m, 1H), 2.09 (s, 6H), 2.30 (t, J = 7.2 Hz, 2H), 2.97 (t, J = 7.2 Hz, 2H), 4.85 (bs, 1H), 6.39 (bs, 1H), 7.62 (d, J = 4.0 Hz, 1H), 7.80 (d, J = 3.2 Hz, 1H), 8.46 (bs, 1H), 8.80 (bs, 1H), 12.40 (bs, 1H). |
| 161 | 5-[5-chloro-4-[(5-cyclopropyl-1H-pyrazol-3-yl)amino]-pyrimidin-2-yl]-2-methoxy-benzenesulfonamide | d (400 MHz, DMSO-d6); 0.82-0.86 (m, 2H), 0.95-1.00 (m, 2H), 1.94-2.00 (m, 1H), 3.97 (s, 3H), 6.42 (s, 1H), 7.14 (s, 1H), 7.35 (d, J = 8.8 Hz, 1H), 8.46 (dd, J = 2.4 Hz, 8.8 Hz, 1H), 8.51 (s, 1H), 8.74 (d, J = 2.8 Hz, 1H), 9.39 (s, 1H). |
| 162 | 5-[4-[(5-cyclopropyl-2H-pyrazol-3-yl)amino]-5-(trifluoromethyl)pyrimidin-2-yl]-N-tert-butyl-thiophene-2-sulfonamide | d (400 MHz, DMSO-d6): 0.74-0.76 (m, 2H), 0.98-1.00 (m, 2H), 1.19 (s, 9H), 1.91-1.97 (m, 1H), 6.28 (s, 1H), 7.62 (d, J = 4.0 Hz, 1H), 7.80 (d, J = 4.0 Hz, 1H), 7.95 (s, 1H), 8.69 (s, 1H), 9.22 (s, 1H), 12.41 (s, 1H). |
| 163 | 5-[4-[(5-cyclopropyl-1H-pyrazol-3-yl)amino]-5-(hydroxymethyl)pyrimidin-2-yl]-N-tert-butyl-thiophene-2-sulfonamide | d (400 MHz, DMSO-d6); 0.75 (m, 2H), 0.96-0.98 (m, 2H), 1.20 (s, 9H), 1.93 (m, 1H), 4.56 (d, J = 4.4 Hz, 2H), 5.62 (s, 1H), 6.52(s, 1H), 7.59 (d, J = 3.6 Hz, 1H), 7.76 (d, J = 3.6 Hz, 1H), 7.86 (s, 2H), 8.23 (s, 1H), 8.96 (s, 1H), 12.18 (s, 1H) |
| 164 | 5-chloro-N-(5-cyclopropyl-1H-pyrazol-3-yl)-2-(2-furyl)pyrimidin-4-amine | d (400 MHz, DMSO-d6): 0.73-0.76 (m, 2H), 0.95-0.98 (m, 2H), 1.93-1.97 (m, 1H), 6.53 (s, 1 H), 6.68-6.70 (m, 1H), 7.15 (d, J = 2.8 Hz, 1H), 7.91 (s, 1H), 8.41 (s, 1H), 9.24 (s, 1H), 12.24 (s, 1 Hz). |
| 165 | 1-[5-[5-bromo-4-[(5-cyclopropyl-1H-pyrazol-3-yl)amino]-pyrimidin-2-yl]-2-thienyl]ethanone | d (400 MHz, DMSO-d6): 0.73-0.76 (m, 2H), 0.98-1.02 (m, 2H), 1.94-1.97 (m, 1H), 2.57 (s, 3H), 6.42 (s, 1H), 7.84 (d, J = 3.6 Hz, 1H), 7.96 (d, J = 4 Hz, 1H), 8.58 (s, 1H), 9.05 (s, 1H). |

TABLE 2-continued

| Compound # | Name | NMR |
|---|---|---|
| 166 | N-[2-[[5-[5-bromo-4-[(5-cyclopropyl-1H-pyrazol-3-yl)amino]-pyrimidin-2-yl]-2-thienyl]sulfonylamino]ethyl]acetamide | d (400 MHz, DMSO-d6): 0.73~0.76 (m, 2H), 0.97~1.02 (m, 2H), 1.76 (s, 3H), 1.93~1.97 (m, 1H), 2.89~2.94 (m, 2H), 3.09~3.13 (m, 2H), 6.38 (s, 1H), 7.60 (d, J = 4.0 Hz, 1H), 7.78 (d, J = 4.0 Hz, 1H), 7.91 (t, J = 6.0 Hz, 1H), 8.05 (t, J = 6.0 Hz, 1H), 8.57 (s, 1H), 9.04 (s, 1H), 12.35 (s, 1H). |
| 167 | 2-[5-(aminomethyl)-2-thienyl]-N-(5-cyclopropyl-1H-pyrazol-3-yl)-5-ethynyl-pyrimidin-4-amine | d (400 MHz, DMSO-d6); 0.80-0.84 (m, 2H), 1.00-1.05 (m, 2H), 2.01-2.04 (m, 1H), 4.28 (d, J = 5.2 Hz, 2H), 4.92 (s, 1H), 6.52 (s, 1H), 7.38 (d, J = 3.6 Hz, 1H), 7.87 (d, J = 4.0 Hz, 1H), 8.53 (s, 1H), 8.65 (bs, 2H), 9.13 (s, 1H). |
| 168 | tert-butyl [[5-[4-[(5-cyclopropyl-1H-pyrazol-3-yl)amino]-5-ethynyl-pyrimidin-2-yl]-2-thienyl]methylamino]formate | d (400 MHz, DMSO-d6); 0.76-0.77 (m, 2H), 0.97-0.98 (m, 2H), 1.41 (s, 9H), 1.92-1.96 (m, 1H), 4.32 (d, J = 5.6 Hz, 2H), 4.84 (s, 1H), 6.51 (s, 1H), 7.00 (d, J = 3.2 Hz, 1H), 7.57 (t, J = 5.6 Hz, 1H), 7.71 (d, J = 3.6 Hz, 1H), 8.45 (s, 1H), 8.51 (bs, 1H), 12.24 (bs, 1H). |
| 169 | tert-butyl [[1-[4-[(5-cyclopropyl-2H-pyrazol-3-yl)amino]-5-ethynyl-pyrimidin-2-yl]pyrrolidin-3-yl]amino]formate | d (400 MHz, DMSO-d6): 0.66 (d, J = 3.2 Hz, 2H), 0.91 (d, J = 5.6 Hz, 2H), 1.38 (s, 9H), 1.84-1.87 (m, 2H), 2.08-2.13 (m, 1H), 3.47-3.52 (m, 1H), 3.61-3.65 (m, 2H), 3.70-3.73 (m, 1H), 4.06 (s, 1H), 4.54 (s, 1H), 6.39 (d, J = 25.2 Hz, 1H), 7.18(s, 1H), 7.85 (bs, 1H), 8.11 (s, 1H), 12.13 (bs, 1H). |
| 170 | 5-[5-bromo-4-[(5-cyclopropyl-1H-pyrazol-3-yl)amino]-pyrimidin-2-yl]-N-tert-butyl-thiophene-2-sulfonamide | d (400 MHz, DMSO-d6); 0.74-0.76 (m, 2H), 0.98-1.00 (m, 2H), 1.20 (s, 9H), 1.92-1.97 (m, 1H), 6.38 (s, 1H), 7.60 (d, J = 4.4 Hz, 1H), 7.75 (d, J = 4.0 Hz, 1H), 7.91 (s, 1H), 8.56 (s, 1H), 8.99 (s, 1H), 12.34 (s, 1H). |
| 171 | 5-[4-[(5-cyclopropyl-2H-pyrazol-3-yl)amino]-5-(hydroxymethyl)pyrimidin-2-yl]thiophene-2-sulfonamide | d (400 MHz, DMSO-d6); 0.75-0.76 (m, 2H), 0.97-0.99 (m, 2H), 1.92-1.96 (m, 1H), 4.56 (d, J = 5.2 Hz, 2H), 5.61 (t, J = 5.2 Hz, 1H), 6.53 (d, J = 10.4 Hz, 1H), 7.58 (d, J = 3.6 Hz, 1H), 7.78 (s, 3H), 8.24 (s, 1H), 8.95 (s, 1H), 12.16 (s, 1H). |
| 172 | N-(5-cyclopropyl-2H-pyrazol-3-yl)-5-ethynyl-2-(1-piperidyl)pyrimidin-4-amine | d (400 MHz, DMSO-d6): 0.66-0.68 (m, 2H), 0.95 (d, J = 6.8 Hz, 2H), 1.53 (d, J = 3.6 Hz, 4H), 1.63-1.66 (m, 2H), 1.89-1.93 (m, 1H), 3.75 (t, J = 5.4 Hz, 4H), 4.54 (s, 1H), 6.25 (bs, 1H), 7.94 (bs, 1H), 8.14 (s, 1H), 12.17 (bs, 1H). |
| 173 | tert-butyl [[1-[4-[(5-cyclopropyl-2H-pyrazol-3-yl)amino]-5-ethynyl-pyrimidin-2-yl]pyrrolidin-3-yl]amino]formate | d (400 MHz, DMSO-d6): 0.66 (d, J = 3.2 Hz, 2H), 0.92 (d, J = 6.4 Hz, 2H), 1.38 (s, 9H), 1.86-1.89 (m, 2H), 2.10-2.14 (m, 1H), 3.47-3.53 (m, 1H), 3.63-3.67 (m, 2H), 3.72-3.76 (m, 1H), 4.08 (s, 1H), 4.55 (s, 1H), 6.41 (d, J = 2.0 Hz, 1H), 7.21 (s, 1H), 7.88 (bs, 1H), 8.12 (s, 1H), 12.13 (bs, 1H). |
| 174 | N-(5-cyclopropyl-2H-pyrazol-3-yl)-2-(1,4-diazepan-1-yl)-5-ethynyl-pyrimidin-4-amine | d (400 MHz, DMSO-d6): 0.63-0.64 (m, 2H), 0.93-0.95 (m, 2H), 1.71-1.77 (m, 2H), 1.87-1.90 (m, 1H), 2.67 (s, 2H), 2.84 (d, J = 26.0 Hz, 2H), 3.71-3.77 (m, 4H), 4.55 (s, 1H), 6.27 (d, J = 23.6 Hz, 1H), 7.85 (bs, 1H), 8.12(s, 1H), 12.16(s, 1H). |
| 175 | N-(5-cyclopropyl-2H-pyrazol-3-yl)-5-ethynyl-2-piperazin-1-yl-pyrimidin-4-amine | d (400 MHz, DMSO-d6): 0.65-0.67 (m, 2H), 0.92-0.94 (m, 2H), 1.88-1.93 (m, 1H), 2.72 (t, J = 4.8 Hz, 4H), 3.66 (t, J = 4.4 Hz, 4H), 4.53 (s, 1H), 6.22 (s, 1H), 7.97 (bs, 1H), 8.12 (s, 1H), 12.16 (bs, 1H). |
| 176 | 5-[5-bromo-4-[(5-cyclopropyl-1H-pyrazol-3-yl)amino]-pyrimidin-2-yl]thiophene-2-carbonitrile | d (400 MHz, DMSO-d6); 0.75-0.76 (m, 2H), 0.98-1.00 (m, 2H), 1.97-1.99 (m, 1H), 6.38 (s, 1H), 7.83 (d, J = 3.6 Hz, 1H), 8.01 (d, J = 3.6 Hz, 1H), 8.58 (s, 1H), 9.05 (s, 1H), 12.32 (s, 1H). |
| 177 | N-(5-cyclopropyl-1H-pyrazol-3-yl)-5-ethynyl-2-(4-methylpiperazin-1-yl)-pyrimidin-4-amine | d (400 MHz, DMSO-d6): 0.66 (d, J = 4.0 Hz, 2H), 0.92 (d, J = 6.8 Hz, 2H), 1.85-1.93 (m, 1H), 2.20 (s, 3H), 2.34 (t, J = 4.8 Hz, 4H), 3.72 (t, J = 4.8 Hz, 4H), 4.54 (s, 1H), 6.22 (s, 1H), 7.95 (bs, 1H), 8.13 (s, 1H), 12.19 (bs, 1H). |
| 178 | N-(5-cyclopropyl-1H-pyrazol-3-yl)-5-ethynyl-2-pyrrolidin-1-yl-pyrimidin-4-amine | d (400 MHz, DMSO-d6): 0.65-0.67 (m, 2H), 0.91-0.93 (m, 2H), 1.85-1.93 (m, 5H), 3.50 (s, 4H), 4.55 (s, 1H), 6.41 (s, 2H), 7.87 (bs, 1H), 8.11 (s, 1H), 12.11 (bs, 1H). |
| 179 | 4-[(5-cyclopropyl-1H-pyrazol-3-yl)amino]-2-(5-sulfamoyl-2-thienyl)-pyrimidine-5-carboxylic acid | d (400 MHz, DMSO-d6): 0.77~0.80 (m, 2H), 0.98~1.03 (m, 2H), 1.95~2.00 (m, 1H), 6.60 (s, 1H), 7.65 (d, J = 4.0 Hz, 1H), 7.92 (s, 2H), 7.95 (d, J = 4.0 Hz, 1H), 8.92 (s, 1H), 10.74 (s, 1H). |

TABLE 2-continued

| Compound # | Name | NMR |
|---|---|---|
| 180 | 2-[5-[4-[(5-cyclopropyl-1H-pyrazol-3-yl)amino]-5-ethynyl-pyrimidin-2-yl]-2-thienyl]propan-2-ol | d (400 MHz, DMSO-d6); 0.73~0.77 (m, 2H), 0.96~1.01 (m, 2H), 1.54 (s, 6H), 1.91~1.97 (m, 1H), 4.83 (s, 1H), 5.60 (s, 1H), 6.52 (s, 1H), 7.01 (d, J = 4.0 Hz, 1H), 7.69 (d, J = 4.0 Hz, 1H), 8.63 (s, 1H), 8.45 (s, 1H), 8.56 (bs, 1H), 12.24 (bs, 1H). |
| 181 | N-[2-[[5-[4-[(5-cyclopropyl-1H-pyrazol-3-yl)amino]-5-ethynyl-pyrimidin-2-yl]-2-thienyl]sulfonylamino]ethyl]acetamide | d (400 MHz, DMSO-d6): 0.75~0.76 (m, 2H), 0.98~1.00 (m, 2H), 1.76 (s, 3H), 1.94~1.95 (m, 1H), 2.90~2.93 (m, 2H), 3.09~3.14 (m, 2H), 4.90 (s, 1H), 6.44 (s, 1H), 7.62 (d, J = 4.0 Hz, 1H), 7.83 (d, J = 4.0 Hz, 1H), 7.92 (t, J = 5.6 Hz, 1H), 8.07 (s, 1H), 8.52 (s, 1H), 8.83 (s, 1H), 12.32 (s, 1H). |
| 182 | 5-chloro-N-(5-cyclopropyl-1H-pyrazol-3-yl)-2-(2-pyridyl)pyrimidin-4-amine | d (400 MHz, DMSO-d6); 0.75-0.78 (m, 2H), 0.97-1.02 (m, 2H), 1.96-2.02 (m, 1H), 6.44-6.45 (m, 1H), 7.92-7.93 (m, 1H), 8.44 (s, 2H), 8.73 (d, J = 2.8 Hz, 1H), 8.87 (d, J = 3.6 Hz, 1H), 10.20 (bs, 1H) |
| 183 | N-[2-[[5-[4-[(5-cyclopropyl-2H-pyrazol-3-yl)amino]-5-ethynyl-pyrimidin-2-yl]-2-thienyl]sulfonylamino]ethyl]-2,2-dimethyl-propanamide | d (400 MHz, DMSO-d6): 0.75 (m, 2H), 0.98-1.00 (m, 2H), 1.04 (s, 9H), 1.91-1.98 (m, 1H), 2.90-2.93 (m, 2H), 3.14 (dd, J = 6.4 Hz, 12.4 Hz, 2H), 4.88 (s, 1H), 6.44 (s, 1H), 7.48 (t, J = 5.2 Hz, 1H), 7.62 (d, J = 4.0 Hz, 1H), 7.83 (d, J = 3.6 Hz, 1H), 8.06 (s, 1H), 8.52 (s, 1H), 8.79 (s, 1H), 12.30 (s, 1H) |
| 184 | 2-(3-aminopyrrolidin-1-yl)-N-(5-cyclopropyl-2H-pyrazol-3-yl)-5-ethynyl-pyrimidin-4-amine | d (400 MHz, DMSO-d6): 0.69 (m, 2H), 0.94 (m, 2H), 1.90-1.97 (m, 2H), 2.22 (s, 1H), 3.48-3.51 (m, 2H), 3.60-3.64 (m, 2H), 3.69-3.83 (m, 2H), 3.83 (s, 1H), 4.58 (s, 1H), 6.42 (bs, 1H), 7.92 (bs, 1H), 8.16 (s, 1H), 12.14 (bs, 1H). |
| 185 | 1-[4-[4-[(5-cyclopropyl-2H-pyrazol-3-yl)amino]-5-ethynyl-pyrimidin-2-yl]piperazin-1-yl]ethanone | d (400 MHz, DMSO-d6): 0.68 (m, 2H), 0.93 (m, 2H), 1.88-1.91 (m, 1H), 2.04 (s, 3H), 3.49-3.52 (m, 4H), 3.68-3.70 (m, 2H), 3.75-3.77 (m, 2H), 4.53 (s, 1H), 6.24 (s, 1H), 7.99 (bs, 1H), 8.14(s, 1H), 12.13 (s, 1H). |
| 186 | 5-[5-bromo-4-[(5-cyclopropyl-1H-pyrazol-3-yl)amino]-pyrimidin-2-yl]thiophene-2-sulfonamide | d (400 MHz, DMSO-d6): 0.71~0.79 (m, 2H), 0.93~1.03 (m, 2H), 1.91~1.98 (m, 1H), 6.38 (s, 1H), 7.58 (d, J = 3.6 Hz, 1H), 7.76 (d, J = 3.6 Hz, 1H), 7.80 (s, 1H), 8.56 (s, 1H), 8.97 (bs, 1H), 12.32 (bs, 1H). |
| 187 | 2-(3-aminopyrrolidin-1-yl)-N-(5-cyclopropyl-2H-pyrazol-3-yl)-5-ethynyl-pyrimidin-4-amine | d (400 MHz, DMSO-d6): 0.68 (m, 2H), 0.93 (m, 2H), 1.72 (m, 1H), 1.88-1.90 (m, 1H), 2.02-2.05 (s, 1H), 3.23 (s, 2H), 3.58-3.62 (m, 5H), 4.56 (s, 1H), 6.46 (bs, 1H), 7.85 (bs, 1H), 8.12 (s, 1H), 12.11 (bs, 1H). |
| 188 | 1-[4-[(5-cyclopropyl-2H-pyrazol-3-yl)amino]-5-ethynyl-pyrimidin-2-yl]pyrrolidine-2-carboxylate | d (400 MHz, DMSO-d6): 0.67-0.78 (m, 2H), 0.81-0.97 (m, 2H), 1.79-1.81 (m, 1H), 1.98-2.01 (m, 4H), 3.51-3.57 (m, 2H), 4.16-4.24 (m, 1H), 4.46 (s, 1H), 6.18 (bs, 1H), 8.00 (s, 1H), 8.07 (s, 1H), 12.32 (bs, 1H). |
| 189 | ethyl 2-[5-[5-chloro-4-[(5-cyclopropyl-1H-pyrazol-3-yl)amino]-pyrimidin-2-yl]-2-thienyl]-2-oxo-acetate | d (400 MHz, DMSO-d6); 0.75-0.79 (m, 2H), 0.99-1.01 (m, 2H), 1.35 (t, J = 7.0 Hz, 3H), 1.93-1.97 (m, 1H), 4.40 (q, J = 6.4 Hz, 2H), 6.43 (s, 1H), 7.89 (d, J = 3.6 Hz, 1H), 8.14 (d, J = 3.6 Hz, 1H), 8.51 (s, 1H), 9.50 (s, 1H), 12.35 (s, 1H). |
| 190 | 2-[5-[5-chloro-4-[(5-cyclopropyl-1H-pyrazol-3-yl)amino]-pyrimidin-2-yl]-2-thienyl]-2-oxo-acetic acid | d (400 MHz, DMSO-d6); 0.74-0.78 (m, 2H), 0.96-1.01 (m, 2H), 1.92-1.96 (m, 1H), 6.42 (s, 1H), 7.87 (d, J = 4.0 Hz, 1H), 8.07 (d, J = 4.4 Hz, 1H), 8.49 (s, 1H), 9.51 (s, 1H), 13.28 (bs, 1H). |
| 191 | ethyl 2-[5-[5-chloro-4-[(5-cyclopropyl-1H-pyrazol-3-yl)amino]-pyrimidin-2-yl]-2-thienyl]-2-hydroxy-acetate | d (400 MHz, DMSO-d6); 0.73-0.77 (m, 2H), 0.96-1.01 (m, 2H), 1.21 (t, J = 7.0 Hz, 3H), 1.91-1.98 (m, 1H), 4.14-4.19 (m, 2H), 5.42 (d, J = 4.8 Hz, 1H), 6.44 (s, 1H), 6.52 (d, J = 5.6 Hz, 1H), 7.13 (d, J = 4.0 Hz, 1H), 7.67 (d, J = 4.0 Hz, 1H), 8.40 (s, 1H), 9.29 (s, 1H), 12.30 (bs, 1H). |
| 192 | N-[[5-[4-[(5-cyclopropyl-1H-pyrazol-3-yl)amino]-5-ethynyl-pyrimidin-2-yl]-2-thienyl]sulfonyl]acetamide | d (400 MHz, DMSO-d6): 0.74-0.77 (m, 2H), 0.97-0.99 (m, 2H), 1.71 (s, 3H), 1.92-1.99 (m, 1H), 4.87 (s, 1H), 6.49 (s, 1H), 7.41 (d, J = 4.0 Hz, 1H), 7.66 (d, J = 3.6 Hz, 1H), 8.47 (s, 1H), 8.57 (bs, 1H), 12.31 (bs, 1H). |
| 193 | N-[1-[4-[(5-cyclopropyl-2H-pyrazol-3-yl)amino]-5-ethynyl-pyrimidin-2-yl]pyrrolidin-3-yl]acetamide | d (400 MHz, DMSO-d6): 0.68 (d, J = 2.8 Hz, 2H), 0.95 (d, J = 6.8 Hz, 2H), 1.82 (s, 3H), 1.88-1.90 (m, 2H), 2.14-2.17 (m, 1H), 3.40-3.42 (m, 2H), 3.58-3.72 (m, 3H), 4.33 (s, 1H), 4.57 (s, 1H), 6.44 (d, J = 25.2 Hz, 1H), 7.88 (s, 1H), 8.14(s, 1H), 12.13 (s, 1H). |

TABLE 2-continued

| Compound # | Name | NMR |
|---|---|---|
| 194 | N-[[5-[5-chloro-4-[(5-cyclopropyl-1H-pyrazol-3-yl)amino]-pyrimidin-2-yl]-2-thienyl]sulfonyl]acetamide | d (400 MHz, DMSO-d6): 0.76-0.77 (m, 2H), 0.97-0.99 (m, 2H), 1.70 (s, 3H), 1.94-1.98 (m, 1H), 6.45 (s, 1H), 7.39 (d, J = 3.6 Hz, 1H), 7.61 (d, J = 4.0 Hz, 1H), 8.40 (s, 1H), 9.27 (s, 1H), 12.29 (s, 1H). |
| 195 | N-[1-[4-[(5-cyclopropyl-2H-pyrazol-3-yl)amino]-5-ethynyl-pyrimidin-2-yl]pyrrolidin-3-yl]acetamide | d (400 MHz, DMSO-d6): 0.67 (d, J = 3.6 Hz, 2H), 0.93 (d, J = 5.2 Hz, 2H), 1.81 (s, 3H), 1.87-1.89 (m, 2H), 2.12-2.16 (m, 1H), 3.38-3.39 (m, 2H), 3.58-3.69 (m, 3H), 4.31 (s, 1H), 4.57 (s, 1H), 6.43 (d, J = 21.6 Hz, 1H), 7.88 (bs, 1H), 8.13(s, 1H), 12.13 (s, 1H). |
| 196 | [5-[4-[(5-cyclopropyl-1H-pyrazol-3-yl)amino]-5-ethynyl-pyrimidin-2-yl]-2-thienyl]methanol | d (400 MHz, DMSO-d6): 0.74 (m, 2H), 0.92~0.97 (m, 2H), 1.94 (m, 1H), 4.67 (d, J = 5.2 Hz, 2H), 4.83 (s, 1H), 5.61~5.63 (m, 1H), 6.52 (s, 1H), 7.03 (d, J = 1.2 Hz, 1H), 7.72 (d, J = 2.4 Hz, 1H), 8.45~8.50 (m, 2H), 12.24 (s, 1H). |
| 197 | tert-butyl [[amino-[5-[5-chloro-4-[(5-cyclopropyl-1H-pyrazol-3-yl)amino]-pyrimidin-2-yl]-2-thienyl]-methylene]amino]formate | d (400 MHz, DMSO-d6); 0.80 (d, J = 4.0 Hz, 2H), 1.00 (d, J = 6.8 Hz, 2H), 1.49 (s, 9H), 1.96 (m, 1H), 6.47 (s, 1H), 7.80 (d, J = 4.4 Hz, 1H), 8.01 (d, J = 4.0 Hz, 1H), 8.46 (s, 1H), 9.09 (s, 2H), 9.39 (s, 1H), 12.33 (s, 1H) |
| 198 | 1-[5-[4-[(5-cyclopropyl-2H-pyrazol-3-yl)amino]-5-ethynyl-pyrimidin-2-yl]-2-thienyl]ethanol | d (400 MHz, DMSO-d6); 0.74~0.75 (m, 2H), 0.98~1.03 (m, 2H), 1.45 (d, J = 6.4 Hz, 3H), 1.94 (m, 1H), 4.83 (s, 1H), 4.94~5.00 (m, 1H), 5.70 (d, J = 4.8 Hz, 1H), 6.54 (s, 1H), 7.01 (d, J = 3.6 Hz, 1H), 7.71 (d, J = 3.6 Hz, 1H), 8.46 (s, 1H), 8.52 (s, 1H), 12.26 (s, 1H). |
| 199 | 1-[5-[4-[(5-cyclopropyl-1H-pyrazol-3-yl)amino]-5-ethynyl-pyrimidin-2-yl]-2-thienyl]propan-1-ol | d (400 MHz, DMSO-d6); 0.74-0.75 (m, 2H), 0.90 (t, J = 7.2 Hz, 3H), 0.98-1.00 (m, 2H), 1.73 (q, J = 7.2 Hz, 2H), 1.98 (m, 1H), 4.72 (q, J = 6.0 Hz, 1H), 4.84 (s, 1H), 5.69 (d, J = 4.8 Hz, 1H), 6.54 (s, 1H), 7.10 (d, J = 3.6 Hz, 1H), 7.72 (d, J = 3.6 Hz, 1H), 8.45 (s, 1H), 8.53 (s, 1H), 12.26 (s, 1H). |
| 200 | methyl 1-[4-[(5-cyclopropyl-2H-pyrazol-3-yl)amino]-5-ethynyl-pyrimidin-2-yl]pyrrolidine-2-carboxylate | d (400 MHz, DMSO-d6): 0.68-0.76(m, 2H), 0.94-0.95 (m, 2H), 1.87-1.99 (m, 4H), 2.27-2.39 (m, 1H), 3.59-3.68 (m, 5H), 4.51-4.60 (m, 2H), 6.22 (bs, 0.54H), 6.45 (bs, 0.28H), 7.83 (s, 0.47H), 7.95 (s, 0.28H), 8.08 (s, 0.31H), 8.16 (s, 0.5H), 12.14 (s, 1H). |
| 201 | N-[[5-[4-[(5-cyclopropyl-1H-pyrazol-3-yl)amino]-5-ethynyl-pyrimidin-2-yl]-2-thienyl]sulfonyl]-2, 2-dimethyl-propanamide | d (400 MHz, DMSO-d6); 0.77 (m, 2H), 0.97 (m, 2H), 1.04 (s, 9H), 1.95 (m, 1H), 4.87 (s, 1H), 6.48 (s, 1H), 7.53 (bs, 1H), 7.72 (s, 1H), 8.49 (s, 1H), 8.64 (bs, 1H), 12.02 (bs, 1H), 12.27(s, 1H). |
| 202 | ethyl 2-[5-[4-[(5-cyclopropyl-1H-pyrazol-3-yl)amino]-5-ethynyl-pyrimidin-2-yl]-2-thienyl]-2-oxo-acetate | d (400 MHz, DMSO-d6); 0.77 (m, 2H), 0.99-1.01 (m, 2H), 1.35 (t, J = 7.2 Hz, 3H), 1.94-1.99 (m, 1H), 4.37-4.42 (m, 2H), 4.92 (s, 1H), 6.47 (s, 1H), 7.93 (d, J = 4.0 Hz, 1H), 8.16 (d, J = 4.0 Hz, 1H), 8.55 (s, 1H), 8.84 (s, 1H), 12.33 (s, 1H). |
| 203 | 5-chloro-N-(5-cyclopropyl-1H-pyrazol-3-yl)-2-(5-nitro-2-thienyl)-pyrimidin-4-amine | d (400 MHz, DMSO-d6): 0.69~0.80 (m, 2H), 0.95~1.06 (m, 2H), 1.89~2.01 (m, 1H), 6.37 (s, 1H), 7.77 (d, J = 4.4 Hz, 1H), 8.15 (d, J = 4.4 Hz, 1H), 8.51 (s, 1H), 9.58 (s, 1H), 12.36 (s, 1H). |
| 204 | 5-chloro-N-(5-cyclopropyl-1H-pyrazol-3-yl)-2-(4-nitro-2-thienyl)-pyrimidin-4-amine | d (400 MHz, DMSO-d6): 0.66~0.78 (m, 2H), 0.93~1.05 (m, 2H), 1.93~1.96 (m, 1H), 6.38 (s, 1H), 8.12 (s, 1H), 8.47 (s, 1H), 8.92 (d, J = 1.6 Hz, 1H), 9.52 (s, 1H), 12.36 (s, 1H). |
| 205 | 5-[5-chloro-4-[(5-cyclopropyl-1H-pyrazol-3-yl)amino]-pyrimidin-2-yl]thiophene-2-carboxamidine | d (400 MHz, DMSO-d6); 0.77-0.81 (m, 2H), 0.97-1.01 (m, 2H), 1.97-2.01 (m, 1H), 6.43 (s, 1H), 7.90 (d, J = 4.0 Hz, 1H), 8.01 (d, J = 4.0 Hz, 1H), 8.50 (s, 1H), 9.34 (s, 2H), 9.44 (s, 2H), 9.56 (s, 1H) |
| 206 | N-(2-acetamidoethyl)-5-[4-[(5-cyclopropyl-2H-pyrazol-3-yl)amino]-5-ethynyl-pyrimidin-2-yl]-thiophene-2-carboxamide | d (400 MHz, DMSO-d6); 0.74-0.78 (m, 2H), 0.97-1.01 (m, 2H), 1.82 (s, 3H), 1.93-1.99 (m, 1H), 3.20-3.23 (m, 2H), 3.27-3.30 (m, 2H), 4.87 (m, 1H), 6.49 (s, 1H), 7.76 (d, J = 4.4 Hz, 1H), 7.84 (d, J = 4.0 Hz, 1H), 8.01 (t, J = 5.2 Hz, 1H), 8.50 (s, 1H), 8.70 (t, J = 5.2 Hz, 1H), 8.76 (s, 1H) |

TABLE 2-continued

| Compound # | Name | NMR |
|---|---|---|
| 207 | 5-[4-[(5-cyclopropyl-1H-pyrazol-3-yl)amino]-5-prop-1-enyl-pyrimidin-2-yl]thiophene-2-sulfonamide | d (400 MHz, DMSO-d6); 0.75-0.76 (m, 2H), 0.95-1.00 (m, 2H), 1.79-1.81 (m, 2H), 1.90 (d, J = 6.0 Hz, 1H), 1.93-1.97 (m, 1H), 5.60-6.04 (m, 0.6H), 6.26-6.31 (m, 0.4H), 6.46-6.49 (s, 1.5H), 6.79 (d, J = 15.2 Hz, 0.4H), 7.57-7.59 (m, 1H), 7.74-7.79 (m, 3H), 8.19 (s, 0.6H), 8.39 (s, 0.4H), 8.94 (s, 0.5H), 9.33 (s, 0.3H) |
| 208 | 5-[4-[(5-cyclopropyl-1H-pyrazol-3-yl)amino]-5-(1-hydroxyethyl)pyrimidin-2-yl]-N-tert-butyl-thiophene-2-sulfonamide | d (400 MHz, DMSO-d6): 0.75-0.76 (m, 2H), 0.97-0.99 (m, 2H), 1.21 (s, 9H), 1.42 (d, J = 6.8 Hz, 3H), 1.92-1.96 (m, 1H), 4.95-4.97 (m, 1H), 6.07 (d, J = 3.6 Hz, 1H), 6.53 (s, 1H), 7.59 (d, J = 4.4 Hz, 1H), 7.76 (d, J = 4.0 Hz, 1H), 7.86 (s, 1H), 8.22 (s, 1H), 9.27 (s, 1H), 12.16 (s, 1H). |
| 209 | 5-[4-[(5-cyclopropyl-1H-pyrazol-3-yl)amino]-5-vinyl-pyrimidin-2-yl]thiophene-2-sulfonamide | d (400 MHz, DMSO-d6): 0.80-0.81 (m, 2H), 1.01-1.04 (m, 2H), 1.96-2.02 (m, 1H), 5.50 (d, J = 11.6 Hz, 1H), 5.96 (d, J = 17.2 Hz, 1H), 6.43 (s, 1H), 7.08-7.15 (m, 1H), 7.63 (d, J = 4 Hz, 1H), 7.87 (bs, 2H), 8.00 (bs, 1H), 8.56 (s, 1H), 10.13 (bs, 1H). |
| 210 | 1-[5-[4-[(5-cyclopropyl-2H-pyrazol-3-yl)amino]-5-ethynyl-pyrimidin-2-yl]-2-thienyl]-2-methyl-propan-1-ol | d (400 MHz, DMSO-d6): 0.76 (d, J = 3.2 Hz, 2H), 0.89 (d, J = 6.8 Hz, 3H), 0.93 (d, J = 6.4 Hz, 3H), 0.99 (d, J = 6.8 Hz, 2H), 1.88-1.96 (m, 2H), 4.60 (t, J = 4.8 Hz, 1H), 4.86 (s, 1H), 5.71 (d, J = 4.4 Hz, 1H), 6.55 (s, 1H), 7.02 (d, J = 3.6 Hz, 1H), 7.75 (d, J = 4.0 Hz, 1H), 8.47 (s, 1H), 8.55 (bs, 1H), 12.28 (bs, 1H). |
| 211 | 1-[5-[4-[(5-cyclopropyl-2H-pyrazol-3-yl)amino]-5-ethynyl-pyrimidin-2-yl]-2-thienyl]butan-1-ol | d (400 MHz, DMSO-d6): 0.75 (m, 2H), 0.91 (t, J = 7.2 Hz, 3H), 0.99 (m, 2H), 1.31-1.43 (m, 2H), 1.67-1.72 (m, 2H), 1.93-1.96 (m, 1H), 4.78-4.81 (m, 1H), 4.83 (s, 1H), 5.67 (d, J = 4.4 Hz, 1H), 7.01 (d, J = 3.2 Hz, 1H), 7.71 (d, J = 2.8 Hz, 1H), 8.45 (s, 1H), 8.53 (bs, 1H), 12.27 (bs, 1H). |
| 212 | 1-[5-[4-[(5-cyclopropyl-2H-pyrazol-3-yl)amino]-5-ethynyl-pyrimidin-2-yl]-2-thienyl]ethanol | d (400 MHz, DMSO-d6); 0.75~0.76 (m, 2H), 0.98~1.00 (m, 2H), 1.45 (d, J = 6.4 Hz, 3H), 1.94~1.95 (m, 1H), 4.83 (s, 1H), 4.94~5.00 (m, 1H), 5.70 (d, J = 4.8 Hz, 1H), 6.54 (s, 1H), 7.01 (d, J = 3.6 Hz, 1H), 7.71 (d, J = 3.2 Hz, 1H), 8.45 (s, 1H), 8.52 (s, 1H), 12.26 (s, 1H). |
| 213 | 1-[5-[4-[(5-cyclopropyl-1H-pyrazol-3-yl)amino]-5-ethynyl-pyrimidin-2-yl]-2-thienyl]propan-1-ol | d (400 MHz, DMSO-d6); 0.74-0.75 (m, 2H), 0.90 (t, J = 7.2 Hz, 3H), 0.98-1.00 (m, 2H), 1.73 (q, J = 7.2 Hz, 2H), 1.98 (m, 1H), 4.72 (q, J = 5.6 Hz, 1H), 4.83 (s, 1H), 5.69 (d, J = 4.4 Hz, 1H), 6.54 (s, 1H), 7.10 (d, J = 3.2 Hz, 1H), 7.72 (d, J = 3.2 Hz, 1H), 8.45 (s, 1H), 8.52 (s, 1H), 12.26 (s, 1H). |
| 214 | 1-[5-[4-[(5-cyclopropyl-2H-pyrazol-3-yl)amino]-5-ethynyl-pyrimidin-2-yl]-2-thienyl]-2-methyl-propan-1-ol | d (400 MHz, DMSO-d6): 0.75 (d, J = 3.2 Hz, 2H), 0.88 (d, J = 6.8 Hz, 3H), 0.92 (d, J = 6.4 Hz, 3H), 0.99 (d, J = 6.8 Hz, 2H), 1.88-1.95 (m, 2H), 4.58 (t, J = 4.8 Hz, 1H), 4.84 (s, 1H), 5.69 (d, J = 4.4 Hz, 1H), 6.54 (s, 1H), 7.00 (d, J = 3.2 Hz, 1H), 7.73 (d, J = 3.6 Hz, 1H), 8.46 (s, 1H), 8.53 (bs, 1H), 12.27 (bs, 1H). |
| 215 | 1-[5-[4-[(5-cyclopropyl-2H-pyrazol-3-yl)amino]-5-ethynyl-pyrimidin-2-yl]-2-thienyl]butan-1-ol | d (400 MHz, DMSO-d6): 0.75 (m, 2H), 0.90-0.93 (m, 3H), 1.00 (m, 2H), 1.32-1.44 (m, 2H), 1.67-1.74 (m, 2H), 1.95-1.96 (m, 1H), 4.78-4.81 (m, 1H), 4.84 (s, 1H), 5.67 (d, J = 4.4 Hz, 1H), 6.54 (s, 1H), 7.02 (d, J = 3.2 Hz, 1H), 7.72 (d, J = 3.6 Hz, 1H), 8.46 (s, 1H), 8.52 (bs, 1H), 12.27 (bs, 1H). |
| 216 | 5-[4-[(5-cyclopropyl-1H-pyrazol-3-yl)amino]-5-(3-hydroxyprop-1-ynyl)pyrimidin-2-yl]-N-tert-butyl-thiophene-2-sulfonamide | d (400 MHz, DMSO-d6): 0.75-0.76 (m, 2H), 0.98-1.00 (m, 2H), 1.20 (s, 9H), 1.92-1.99 (m, 1H), 4.40 (d, J = 5.6 Hz, 2H), 5.43 (t, J = 5.6 Hz, 1H), 6.46 (s, 1H), 7.61 (d, J = 4.0 Hz, 1H), 7.77 (d, J = 3.6 Hz, 1H), 7.91 (s, 1H), 8.43 (s, 1H), 8.98 (s, 1H), 12.32 (s, 1H). |
| 217 | 5-[4-[(5-cyclopropyl-1H-pyrazol-3-yl)amino]-5-(3-hydroxyprop-1-ynyl)pyrimidin-2-yl]thiophene-2-sulfonamide | d (400 MHz, DMSO-d6): 0.76-0.77 (m, 2H), 0.98-1.00 (m, 2H), 1.94-1.98 (m, 1H), 4.40 (d, J = 5.6 Hz, 2H), 5.43 (t, J = 5.6 Hz, 1H), 6.47 (s, 1H), 7.60 (d, J = 4.4 Hz, 1H), 7.79 (d, J = 4.0 Hz, 1H), 7.83 (s, 2H), 8.44 (s, 1H), 8.97 (s, 1H), 12.31 (s, 1H). |

TABLE 2-continued

| Compound # | Name | NMR |
|---|---|---|
| 218 | 5-[4-[(5-cyclopropyl-1H-pyrazol-3-yl)amino]-5-(3-hydroxyprop-1-enyl)pyrimidin-2-yl]-N-tert-butyl-thiophene-2-sulfonamide | d (400 MHz, DMSO-d6): 0.74-0.75 (m, 2H), 0.96-0.97 (m, 2H), 1.20 (s, 9H), 1.90-1.95 (m, 1H), 4.16 (m, 2H), 4.85 (s, 1H), 6.38 (d, J = 16.0 Hz, 1H), 6.46 (s, 1H), 6.89 (d, J = 15.2 Hz, 1H), 7.59 (d, J = 3.6 Hz, 1H), 7.73 (d, J = 4.0 Hz, 1H), 7.87 (bs, 1H), 8.42 (s, 1H), 9.26 (bs, 1H), 12.18 (bs, 1H). |
| 219 | 2-[5-[5-chloro-4-[(5-cyclopropyl-1H-pyrazol-3-yl)amino]-pyrimidin-2-yl]-2-thienyl]-2-hydroxy-acetic acid | d (400 MHz, DMSO-d6): 0.75-0.76 (m, 2H), 0.97-0.99 (m, 2H), 1.92-1.96 (m, 1H), 5.31 (s, 1H), 6.45 (s, 1H), 7.13 (d, J = 3.2 Hz, 1H), 7.67 (d, J = 3.6 Hz, 1H), 8.39 (s, 1H), 9.30 (s, 1H), 12.59 (bs, 1H). |
| 220 | 5-[5-chloro-4-[[5-(2-thienyl)-1H-pyrazol-3-yl]amino]-pyrimidin-2-yl]thiophene-2-sulfonamide | d (400 MHz, DMSO-d6): 6.76 (s, 0.3H), 6.99 (s, 0.7H), 7.11 (s, 0.3H), 7.18 (s, 0.7H), 7.42 (s, 0.3H), 7.50 (s, 0.7H), 7.59 (d, J = 4.0 Hz, 1.3H), 7.63 (d, J = 4.8 Hz, 0.7H), 7.77 (s, 0.75H), 7.81 (s, 2.2H), 8.50 (s, 0.65H), 8.59 (s, 0.35H), 9.71 (s, 0.7H), 10.00 (s, 0.3H), 12.41 (s, 0.3H), 13.13 (s, 0.7H). |
| 221 | 5-[5-chloro-4-(1H-pyrazol-3-ylamino)-pyrimidin-2-yl]thiophene-2-sulfonamide | d (400 MHz, DMSO-d6): 6.75 (s, 1H), 7.57 (d, J = 3.2 Hz, 1H), 7.77 (d, J = 3.2 Hz, 1H), 7.80 (s, 2H), 8.48 (s, 1H), 9.56 (s, 1H), 12.60 (s, 1H). |
| 222 | 5-chloro-N-(5-cyclopropyl-1H-pyrazol-3-yl)-2-(5-nitro-2-furyl)-pyrimidin-4-amine | d (400 MHz, DMSO-d6): 0.78~0.82 (m, 2H), 0.96~1.01 (m, 2H), 1.90~1.97 (m, 1H), 6.61 (s, 1H), 7.43 (d, J = 4.0 Hz, 1H), 7.82 (d, J = 4.0 Hz, 1H), 8.54 (s, 1H), 9.64 (bs, 1H), 12.36 (bs, 1H). |
| 223 | 1-[5-[4-[(5-cyclopropyl-1H-pyrazol-3-yl)amino]-5-ethynyl-pyrimidin-2-yl]-2-thienyl]butane-1,4-diol | d (400 MHz, DMSO-d6); 0.75 (s, 2H), 0.98 (s, 2H), 1.47-1.55 (m, 2H), 1.74 (s, 2H), 1.94 (s, 1H), 3.41 (s, 2H), 4.43 (s, 1H), 4.81-4.84 (m, 2H), 5.71 (s, 1H), 6.53 (s, 1H), 7.01 (s, 1H), 7.72 (s, 1H), 8.45-8.54 (m, 2H), 12.27 (s, 1H). |
| 224 | 5-[5-chloro-4-[(5-methyl-1H-pyrazol-3-yl)amino]-pyrimidin-2-yl]thiophene-2-sulfonamide | d (400 MHz, DMSO-d6): 2.31 (s, 3H), 3.17 (s, 1H), 6.52 (s, 1H), 7.58 (d, J = 4.0 Hz, 1H), 7.79 (d, J = 3.6 Hz, 1H), 7.85 (s, 2H), 8.49 (s, 1H), 9.55 (bs, 1H). |
| 225 | 5-[5-chloro-4-[(5-isopropyl-1H-pyrazol-3-yl)amino]-pyrimidin-2-yl]thiophene-2-sulfonamide | d (400 MHz, DMSO-d6): 1.29 (d, J = 6.8 Hz, 6H), 3.00 (t, J = 6.8 Hz, 1H), 6.56 (s, 1H), 7.58 (d, J = 4.0 Hz, 1H), 7.75 (d, J = 4.0 Hz, 1H), 7.80 (s, 2H), 8.46 (s, 1H), 9.47 (s, 1H), 12.29 (s, 1H). |
| 226 | 2-[5-[5-chloro-4-[(5-cyclopropyl-1H-pyrazol-3-yl)amino]-pyrimidin-2-yl]-2-thienyl]propanenitrile | d (400 MHz, DMSO-d6); 0.75-0.76 (m, 2H), 0.98-1.00 (m, 2H), 1.66 (d, J = 7.2 Hz, 3H), 1.92-1.99 (m, 1H), 4.73 (dd, J = 7.2 Hz, 14.0 Hz, 1H), 6.45 (s, 1H), 7.20 (d, J = 3.6 Hz, 1H), 7.69 (d, J = 3.6 Hz, 1H), 8.40 (s, 1H), 9.34 (s, 1H), 12.31 (s, 1H) |
| 227 | 2-[5-[4-[(5-cyclopropyl-1H-pyrazol-3-yl)amino]-5-ethynyl-pyrimidin-2-yl]-2-thienyl]propanenitrile | d (400 MHz, DMSO-d6): 0.75-0.76 (m, 2H), 0.98-1.00 (m, 2H), 1.67 (d, J = 7.2 Hz, 3H), 1.92-1.98 (m, 1H), 4.74 (dd, J = 7.2 Hz, 14.0 Hz, 1H), 4.85 (s, 1H), 6.49 (s, 1H), 7.22 (d, J = 3.6 Hz, 1H), 7.75 (d, J = 3.6 Hz, 1H), 8.47 (s, 1H), 8.65 (s, 1H), 12.29 (s, 1H) |
| 228 | 5-[4-[(5-cyclopropyl-1H-pyrazol-3-yl)amino]-5-(2-hydroxyethyl)pyrimidin-2-yl]-N-tert-butyl-thiophene-2-sulfonamide | d (400 MHz, DMSO-d6): 0.72-0.76 (m, 2H), 0.96-1.00 (m, 2H), 1.23 (s, 9H), 1.90-1.97 (m, 1H), 2.79 (t, J = 6.0 Hz, 2H), 3.66 (t, J = 5.6 Hz, 2H), 6.47 (s, 1H), 7.60 (d, J = 4.0 Hz, 1H), 7.77 (d, J = 3.6 Hz, 1H), 7.87 (s, 1H), 8.15 (s, 1H), 9.60 (s, 1H). |
| 229 | N-[3-[[5-[4-[(5-cyclopropyl-1H-pyrazol-3-yl)amino]-5-ethynyl-pyrimidin-2-yl]-2-thienyl]sulfonyl]propyl]acetamide | d (400 MHz, DMSO-d6); 0.74-0.75 (m, 2H), 0.98-1.00 (m, 2H), 1.72-1.79 (m, 5H), 1.92-1.99 (m, 1H), 3.10 (dd, J = 7.2 Hz, 12.8 Hz, 2H), 3.47 (t, J = 8.0 Hz, 2H), 4.90 (s, 1H), 6.43 (s, 1H), 7.82 (d, J = 4.0 Hz, 1H), 7.87-7.90 (m, 2H), 8.54 (s, 1H), 8.87 (s, 1H), 12.32 (s, 1H) |
| 230 | 1-[5-[4-[(5-cyclopropyl-2H-pyrazol-3-yl)amino]-5-ethynyl-pyrimidin-2-yl]-2-thienyl]-3-methoxy-propan-1-ol | d (400 MHz, DMSO-d6); 0.75 (m, 2H), 0.98-0.99 (m, 2H), 1.94-1.95 (m, 3H), 3.24 (s, 3H), 3.33-3.37 (m, 1H), 3.46-3.54 (m, 1H), 4.84 (s, 1H), 4.85-4.91 (m, 1H), 5.79 (d, J = 5.2 Hz, 1H), 6.53 (s, 1H), 7.02 (d, J = 3.6 Hz, 1H), 7.72 (d, J = 3.2 Hz, 1H), 8.45 (s, 1H), 8.54 (s, 1H), 12.27 (s, 1H). |
| 231 | 2-[5-[4-[(5-cyclopropyl-1H-pyrazol-3-yl)amino]-5-ethynyl-pyrimidin-2-yl]-2-thienyl]-2-hydroxy-acetic acid | d (400 MHz, DMSO-d6); 0.73-0.77 (m, 2H), 0.95-1.00 (m, 2H), 1.91-1.97 (m, 1H), 4.84 (s, 1H), 5.28 (s, 1H), 6.49 (s, 1H), 7.14 (d, J = 3.2 Hz, 1H), 7.30 (d, J = 3.6 Hz, 1H), 8.46 (s, 1H), 8.62 (s, 1H). |

TABLE 2-continued

| Compound # | Name | NMR |
|---|---|---|
| 232 | chloro-cyclopropyl-BLAHol | d (400 MHz, DMSO-d6): 0.81~0.86 (m, 2H), 1.01~1.04 (m, 2H), 2.02~2.06 (m, 1H), 5.18 (d, J = 6.4 Hz, 1H), 5.46 (dd, J = 9.2 Hz, 10.0 Hz, 1H), 6.07~6.12 (m, 2H), 7.33-7.38 (m, 1H), 7.49-7.53 (m, 1H), 8.01 (d, J = 7.6 Hz, 1H), 8.40 (s, 1H), 8.49 (dd, J = 1.2 Hz, 8.0 Hz, 1H), 9.41 (s, 1H), 12.17 (s, 1H). |
| 233 | ethyl 2-[5-[4-[(5-cyclopropyl-1H-pyrazol-3-yl)amino]-5-ethynyl-pyrimidin-2-yl]-2-thienyl]-2-hydroxy-acetate | d (400 MHz, DMSO-d6); 0.75-0.76 (m, 2H), 0.98-1.00 (m, 2H), 1.21 (t, J = 7.0 Hz, 3H), 1.93-1.97 (m, 1H), 4.14-4.20 (m, 2H), 4.85 (s, 1H), 5.44 (d, J = 5.6 Hz, 1H), 6.51 (s, 1H), 6.54 (d, J = 5.6 Hz, 1H), 7.16 (d, J = 3.6 Hz, 1H), 7.73 (d, J = 3.6 Hz, 1H), 8.46 (s, 1H), 8.57 (s, 1H), 12.27 (s, 1H). |
| 234 | 5-[5-chloro-4-[(5-phenyl-1H-pyrazol-3-yl)amino]-pyrimidin-2-yl]thiophene-2-sulfonamide | d (400 MHz, DMSO-d6); 7.14 (s, 1H), 7.39 (t, J = 7.2 Hz, 1H), 7.49 (t, J = 7.6 Hz, 2H), 7.59 (d, J = 4.4 Hz, 1H), 7.79 (m, 5H), 8.52 (s, 1H), 9.72 (s, 1H), 11.11 (s, 1H) |
| 235 | 5-[5-chloro-4-[(5-cyclopentyl-1H-pyrazol-3-yl)amino]-pyrimidin-2-yl]thiophene-2-sulfonamide | d (400 MHz, DMSO-d6): 1.60-1.69 (m, 4H), 1.74-1.77 (m, 2H), 2.02-2.09 (m, 2H), 3.08-3.12 (m, 1H), 6.56 (s, 1H), 7.58 (d, J = 4.0 Hz, 1H), 7.75 (d, J = 3.6 Hz, 1H), 7.81 (s, 2H), 8.46 (s, 1H), 9.48 (s, 1H), 12.30 (s, 1H). |
| 236 | 5-[5-chloro-4-[(5-tert-butyl-1H-pyrazol-3-yl)amino]-pyrimidin-2-yl]thiophene-2-sulfonamide | d (400 MHz, DMSO-d6): 1.34 (s, 9H), 6.57 (s, 1H), 7.58 (d, J = 4.0 Hz, 1H), 7.75 (d, J = 3.6 Hz, 1H), 7.81 (s, 2H), 8.47 (s, 1H), 9.52 (s, 1H). |
| 237 | 2-[5-[4-[(5-cyclopropyl-1H-pyrazol-3-yl)amino]-5-ethynyl-pyrimidin-2-yl]-2-thienyl]-2-methyl-propanenitrile | d (400 MHz, DMSO-d6); 0.75-0.76 (m, 2H), 0.95-1.00 (m, 2H), 1.81 (s, 6H), 1.92-1.98 (m, 1H), 4.86 (s, 1H), 6.49 (s, 1H), 7.29 (d, J = 3.6 Hz, 1H), 7.75 (d, J = 3.6 Hz, 1H), 8.47 (s, 1H), 8.70 (s, 1H), 12.32 (s, 1H) |
| 238 | 2-[5-[5-chloro-4-[(5-cyclopropyl-1H-pyrazol-3-yl)amino]-pyrimidin-2-yl]-2-thienyl]-2-methyl-propanenitrile | d (400 MHz, DMSO-d6); 0.73-0.74 (m, 2H), 0.98-0.99 (m, 2H), 1.79 (s, 6H), 1.90-1.97 (m, 1H), 6.44 (s, 1H), 7.25 (d, J = 4.0 Hz, 1H), 7.68 (d, J = 3.6 Hz, 1H), 8.39 (s, 1H), 9.37 (s, 1H), 12.32 (s, 1H) |
| 239 | 5-[4-[(5-cyclopropyl-1H-pyrazol-3-yl)amino]-5-(2-hydroxyethyl)pyrimidin-2-yl]thiophene-2-sulfonamide | d (400 MHz, DMSO-d6): 0.74-0.75 (m, 2H), 0.96-0.98 (m, 2H), 1.91-1.94 (m, 1H), 2.77 (t, J = 6.0 Hz, 2H), 3.66 (s, 2H), 5.11 (s, 1H), 6.47 (s, 1H), 7.57 (d, J = 4.0 Hz, 1H), 7.74 (d, J = 4.0 Hz, 1H), 7.76 (s, 2H), 8.14 (s, 1H), 9.41 (s, 1H), 12.10 (s, 1H). |
| 240 | 5-[5-chloro-4-[(5-cyclopropyl-1H-pyrazol-3-yl)amino]-pyrimidin-2-yl]furan-2-sulfonamide | d (400 MHz, DMSO-d6): 0.73~0.81 (m, 2H), 0.91~1.00 (m, 2H), 1.91~1.97 (m, 1H), 6.50 (s, 1H), 7.12 (d, J = 3.2 Hz, 1H), 7.21 (d, J = 2.8 Hz, 1H), 7.93 (s, 2H), 8.48 (s, 1H), 9.44 (s, 1H), 12.28 (s, 1H). |
| 241 | N-[4-[(5-cyclopropyl-1H-pyrazol-3-yl)amino]-2-(5-sulfamoyl-2-thienyl)-pyrimidin-5-yl]acetamide | d (400 MHz, DMSO-d6); 0.75-0.79 (m, 2H), 0.97-1.01 (m, 2H), 1.91-1.98 (m, 1H), 2.12 (s, 3H), 6.53 (s, 1H), 7.49 (s, 2H), 8.02 (s, 1H), 8.20 (s, 1H), 8.49 (s, 1H), 9.49 (s, 1H), 9.55 (s, 1H) |
| 242 | 1-[5-[4-[(5-cyclopropyl-1H-pyrazol-3-yl)amino]-5-ethynyl-pyrimidin-2-yl]-2-thienyl]propane-1,3-diol | d (400 MHz, DMSO-d6); 0.75 (m, 2H), 0.98-1.00 (m, 2H), 1.84-1.88(m, 2H), 1.93-1.98 (m, 1H), 3.47-3.59 (m, 2H), 4.53 (t, J = 4.8 Hz, 1H), 4.84 (s, 1H), 4.92-4.96 (m, 1H), 5.72 (d, J = 4.8 Hz, 1H), 6.54 (s, 1H), 7.02 (d, J = 3.6 Hz, 1H), 7.72 (d, J = 3.2 Hz, 1H), 8.45 (s, 1H), 8.55 (s, 1H), 12.27 (s, 1H) |
| 243 | [3-[5-[4-[(5-cyclopropyl-1H-pyrazol-3-yl)amino]-5-ethynyl-pyrimidin-2-yl]-2-thienyl]-3-hydroxy-propyl] acetate | d (400 MHz, DMSO-d6); 0.74-0.75 (m, 2H), 0.98-0.99 (m, 2H), 1.91-1.97(m, 1H), 2.01-2.06 (m, 5H), 4.06-4.17 (m, 2H), 4.85 (s, 1H), 4.85-4.94 (m, 1H), 5.94 (d, J = 4.8 Hz, 1H), 6.53 (s, 1H), 7.05 (d, J = 3.6 Hz, 1H), 7.72 (d, J = 4.0 Hz, 1H), 8.46 (s, 1H), 8.57 (s, 1H), 12.27 (s, 1H) |
| 244 | methyl 1-[4-[(5-cyclopropyl-1H-pyrazol-3-yl)amino]-5-ethynyl-pyrimidin-2-yl]piperidine-2-carboxylate | d (400 MHz, DMSO-d6); 0.67 (m, 2H), 0.93-0.95 (m, 2H), 1.23-1.26 (m, 2H), 1.36-1.42 (m, 1H), 1.68-1.74 (m, 3H), 1.86 (m, 1H), 2.15-2.19 (m, 1H), 2.98-3.04 (m, 1H), 3.65 (s, 3H), 4.50-4.63 (m, 2H), 5.29 (s, 0.5H), 5.47 (s, 0.3H), 6.01 (s, 0.5H), 6.24 (s, 0.3H), 8.05-8.17 (m, 2H), 12.20 (s, 1H) |

TABLE 2-continued

| Compound # | Name | NMR |
|---|---|---|
| 245 | 1-[4-[(5-cyclopropyl-2H-pyrazol-3-yl)amino]-5-ethynyl-pyrimidin-2-yl]piperidine-2-carboxylic acid | d (400 MHz, DMSO-d6); 0.67-0.67 (m, 2H), 0.91-0.93 (m, 2H), 1.23-1.28 (m, 1H), 1.38-1.45 (m, 1H), 1.68-1.71 (m, 3H), 1.83-1.91 (m, 1H), 2.18-2.20 (m, 1H), 2.98-3.05 (m, 1H), 4.45-4.62 (m, 2H), 5.21 (s, 0.5H), 5.37 (s, 0.3H), 6.1 (s, 0.5H), 6.3 (s, 0.3H), 8.1-8.2 (m, 2H), 12.46 (s, 1H). |
| 246 | 2-[5-[4-[(5-cyclopropyl-1H-pyrazol-3-yl)amino]-5-ethynyl-pyrimidin-2-yl]-2-thienyl]-2-oxo-acetic acid | d (400 MHz, DMSO-d6); 0.78 (m, 2H), 0.99-1.00 (m, 2H), 1.96 (m, 1H), 4.91 (s, 1H), 6.51 (s, 1H), 7.76 (d, J = 3.2 Hz, 1H), 7.85 (d, J = 3.6 Hz, 1H), 8.52 (s, 1H), 8.71 (s, 1H), 12.34 (s, 1H). |
| 247 | 5-[5-chloro-4-[[5-(2-furyl)-1H-pyrazol-3-yl]amino]-pyrimidin-2-yl]thiophene-2-sulfonamide | d (400 MHz, DMSO-d6); 6.66 (s, 1H), 6.87 (s, 1H), 6.97 (s, 1H), 7.59 (d, J = 4.0 Hz, 1H), 7.77 (d, J = 3.6 Hz, 1H), 7.82 (s, 1H), 8.50 (s, 1H), 9.69 (s, 1H), 13.16 (s, 1H). |
| 248 | N-(5-cyclopropyl-1H-pyrazol-3-yl)-5-ethynyl-2-(4-methyl-1,4-diazepan-1-yl)-pyrimidin-4-amine | d (400 MHz, DMSO-d6); 0.64-0.65 (m, 2H), 0.94 (m, 2H), 1.87 (m, 3H), 2.25 (s, 3H), 2.46 (m, 2H), 2.58-2.61 (m, 2H), 3.73-3.80 (m, 4H), 4.56 (s, 1H), 6.24-6.32 (m, 1H), 7.88 (s, 1H), 8.12 (s, 1H), 12.17 (s, 1H) |
| 249 | N-(5-cyclopropyl-1H-pyrazol-3-yl)-5-ethynyl-2-(1,2,3,6-tetrahydropyridin-4-yl)pyrimidin-4-amine | d (400 MHz, DMSO-d6): 0.69-0.72 (m, 2H), 0.93-0.95 (m, 2H), 1.91 (m, 1H), 2.73 (m, 2H), 3.32 (m, 2H), 3.87 (m, 2H), 4.86 (s, 1H), 6.31 (s, 1H), 7.05 (s, 1H), 8.48 (s, 1H), 8.67 (bs, 1H), 8.88 (bs, 1H). |
| 250 | tert-butyl 4-[4-[(5-cyclopropyl-1H-pyrazol-3-yl)amino]-5-ethynyl-pyrimidin-2-yl]-3,6-dihydro-2H-pyridine-1-carboxylate | d (400 MHz, DMSO-d6): 0.71-0.72 (m, 2H), 0.95-1.04 (m, 2H), 1.43 (s, 9H), 1.91-1.97 (m, 1H), 2.56 (m, 2H), 3.52 (t, J = 5.6 Hz, 2H), 4.10 (bs, 2H), 4.84 (s, 1H), 6.40 (s, 1H), 7.10 (s, 1H), 8.44-8.45 (m, 2H), 12.21 (s, 1H). |
| 251 | 5-[5-chloro-4-[(5-cyclopropyl-1H-pyrazol-3-yl)amino]-pyrimidin-2-yl]thiophene-2-sulfonohydrazide | d (400 MHz, DMSO-d6): 0.75-0.76 (m, 2H), 0.98-0.99 (m, 2H), 1.91-1.95 (m, 1 H), 4.23 (d, J = 7.2 Hz, 2H), 6.41 (s, 1H), 7.94 (s, 1H), 8.30 (d, J = 1.2 Hz, 1H), 8.46 (s, 2H), 9.47 (d, J = 7.6 Hz, 1H), 12.37 (s, 1H). |
| 252 | N-[4-[(5-cyclopropyl-1H-pyrazol-3-yl)amino]-2-(5-sulfamoyl-2-thienyl)-pyrimidin-5-yl]formamide | d (400 MHz, DMSO-d6); 0.76 (m, 2H), 0.98 (m, 2H), 1.95 (m, 1H), 6.53 (s, 1H), 7.49 (bs, 2H), 8.01 (s, 1H), 8.18 (d, J = 1.2 Hz, 1H), 8.35 (s, 1H), 8.57 (s, 1H), 9.49 (bs, 2H), 12.21 (bs, 1H) |
| 253 | N-[4-[(5-cyclopropyl-1H-pyrazol-3-yl)amino]-2-[5-(tert-butylsulfamoyl)-2-thienyl]-pyrimidin-5-yl]formamide | d (400 MHz, DMSO-d6); 0.74-0.76 (m, 2H), 0.97-1.02 (m, 2H), 1.20 (s, 9H), 1.92-1.98 (m, 1H), 6.54 (s, 1H), 7.57 (s, 1H), 7.96 (d, J = 1.6 Hz, 1H), 8.22 (d, J = 1.2 Hz, 1H), 8.34 (d, J = 4.0 Hz, 1H), 8.58 (d, J = 5.6 Hz, 1H), 9.39 (d, J = 7.2 Hz, 1H), 9.83 (d, J = 6.4 Hz, 1H), 12.22 (s, 1H) |
| 254 | 2-cyano-N-[4-[(5-cyclopropyl-1H-pyrazol-3-yl)amino]-2-(5-sulfamoyl-2-thienyl)-pyrimidin-5-yl]-acetamide | d (400 MHz, DMSO-d6); 0.76 (m, 2H), 0.98 (m, 2H), 1.94 (m, 1H), 3.93 (s, 2H), 6.53 (s, 1H), 7.48 (s, 1H), 8.02 (s, 1H), 8.20 (s, 1H), 8.29 (s, 1H), 9.58 (s, 1H), 9.76 (s, 1H), 12.23 (bs, 1H) |
| 255 | N-(5-cyclopropyl-1H-pyrazol-3-yl)-5-ethynyl-2-(5-methylsulfonyl-2-thienyl)-pyrimidin-4-amine | d (400 MHz, DMSO-d6): 0.73-0.77 (m, 2H), 0.96-1.01 (m, 2H), 1.93-1.99 (m, 1H), 3.41 (s, 3H), 4.91 (s, 1H), 6.42 (s, 1H), 7.87 (dd, J1 = 4.0 Hz, J2 = 7.2 Hz, 2H), 8.54 (s, 1H), 8.94 (s, 1H). |
| 256 | 1-[5-chloro-4-[(5-cyclopropyl-1H-pyrazol-3-yl)amino]-pyrimidin-2-yl]pent-4-en-1-one | d (400 MHz, DMSO-d6): 0.63~0.73 (m, 2H), 0.88~0.99 (m, 2H), 1.91~1.97 (m, 1H), 2.35 (q, J = 7.2 Hz, 2H), 3.18 (t, J = 7.2 Hz, 2H), 4.99 (d, J = 10.4 Hz, 1H), 5.06 (d, J = 17.2 Hz, 1H), 5.83~5.93 (m, 1H), 6.47 (bs, 1H), 8.57 (s, 1H), 9.58 (bs, 1H), 12.31 (bs, 1H). |
| 257 | benzyl 3-[5-[[5-chloro-2-[5-(tert-butylsulfamoyl)-2-thienyl]-pyrimidin-4-yl]amino]-1H-pyrazol-3-yl]pyrrolidine-1-carboxylate | d (400 MHz, DMSO-d6); 1.17 (s, 9H), 2.05-2.10 (m, 1H), 2.28-2.33 (m, 1H), 3.41-3.60 (m, 4H), 3.77-3.84 (m, 1H), 5.09 (s, 2H), 6.63 (s, 1H), 7.35 (m, 5H), 7.58 (s, 1H), 7.73 (s, 1H), 7.89 (s, 1H), 8.47 (s, 1H), 9.58 (s, 1H), 12.50 (s, 1H) |
| 258 | 1-[4-[4-[(5-cyclopropyl-2H-pyrazol-3-yl)amino]-5-ethynyl-pyrimidin-2-yl]-1,4-diazepan-1-yl]ethanone | d (400 MHz, DMSO-d6); 0.64-0.66 (m, 2H), 0.93-0.95 (m, 2H), 1.67-1.90 (m, 4H), 1.99 (m, 2H), 3.37-3.42 (m, 2H), 3.55-3.62 (m, 2H), 3.70-3.78 (m, 3H), 3.85-3.89 (m, 1H), 4.58 (s, 1H), 6.23-6.27 (m, 1H), 7.96 (bs, 1H), 8.13 (s, 1H), 12.20 (bs, 1H). |

TABLE 2-continued

| Compound # | Name | NMR |
|---|---|---|
| 259 | cyclopropylBLAHol | d (400 MHz, MeOD): 0.60~0.63 (m, 1H), 0.65~0.75 (m, 1H), 0.80~0.88 (m, 2H), 1.60~1.63 (m, 1H), 1.78~1.84 (m, 2H), 1.95~1.97 (m, 2H), 2.63 (s, 1H), 6.60 (d, J = 6.0 Hz, 1H), 7.22 (t, J = 7.6 Hz, 1H), 7.37 (t, J = 7.6 Hz, 1H), 7.63 (d, J = 7.6 Hz, 1H), 7.68 (bs, 1H), 8.18 (d, J = 6.0 Hz, 1H). |
| 260 | cyclopropylBLAHol | d (400 MHz, DMSO-d6): 0.75~0.81 (m, 2H), 0.87~0.93 (m, 2H), 1.90~1.93 (m, 1H), 5.31~5.34 (m, 0.5H), 6.66 (d, J = 5.6 Hz, 1H), 7.26~7.28 (m, 1H), 7.49~7.51 (m, 1H), 8.17 (bs, 1H), 8.31 (d, J = 6.0 Hz, 1H), 9.00 (bs, 1H), 9.55 (s, 1H), 11.91 (bs, 1H). |
| 261 | tert-butyl [[5-[5-chloro-4-[(5-cyclopropyl-2H-pyrazol-3-yl)amino]-pyrimidin-2-yl]-2-thienyl]methylamino]formate | d (400 MHz, DMSO-d6): 0.72~0.81 (m, 2H), 0.95~1.01 (m, 2H), 1.41 (s, 9H), 1.93~1.97 (m, 1H), 4.30 (d, J = 6.0 Hz, 1H), 6.48 (s, 1H), 6.98 (d, J = 3.6 Hz, 1H), 7.59 (t, J = 6.0 Hz, 1H), 7.64 (d, J = 3.6 Hz, 1H), 8.38 (s, 1H), 9.26 (s, 1H), 12.28 (s, 1H). |
| 262 | benzyl 3-[5-[[5-chloro-2-(5-sulfamoyl-2-thienyl)-pyrimidin-4-yl]amino]-1H-pyrazol-3-yl]pyrrolidine-1-carboxylate | d (400 MHz, DMSO-d6): 2.05-2.15 (m, 1H), 2.25-2.37 (m, 1H), 3.47-3.53 (m, 4H), 3.75-3.85 (m, 1H), 5.08 (s, 2H), 6.58 (s, 1H), 7.30-7.35 (m, 5H), 7.57 (s, 1H), 7.73 (s, 1H), 8.47 (s, 1H), 12.50(s, 1H) |
| 263 | 5-[5-chloro-4-[(5-pyrrolidin-3-yl-2H-pyrazol-3-yl)amino]-pyrimidin-2-yl]thiophene-2-sulfonamide | d (400 MHz, DMSO-d6); 1.89-2.04 (m, 1H), 2.25-2.35 (m, 1H), 3.08-3.25 (m, 3H), 3.41-3.56 (m, 2H), 6.63 (s, 1H), 7.57 (s, 1H), 7.78 (s, 1H), 8.36 (bs, 1H), 8.48 (s, 1H) |
| 264 | 5-chloro-N-(5-cyclopropyl-1H-pyrazol-3-yl)-2-(5-methylsulfinyl-2-thienyl)-pyrimidin-4-amine | d (400 MHz, DMSO-d6); 0.75-0.76 (m, 2H), 0.98-1.00 (m, 2H), 1.95-1.99 (m, 1H), 2.98 (s, 3H), 6.43 (s, 1H), 7.61 (d, J = 3.6 Hz, 1H), 7.81 (d, J = 3.6 Hz, 1H), 8.47 (s, 1H), 9.51 (s, 1H) |
| 265 | 5-[4-[(5-cyclopropyl-1H-pyrazol-3-yl)amino]-6-methyl-pyrimidin-2-yl]thiophene-2-sulfonamide | d (400 MHz, DMSO-d6); 0.72 (d, J = 3.6 Hz, 2H), 0.95 (d, J = 6.8 Hz, 2H), 1.88-1.93 (m, 1H), 2.33 (s, 3H), 6.26 (bs, 1H), 6.85 (bs, 1H), 7.56 (d, J = 4 Hz, 1H), 7.76-7.77 (m, 1H), 9.90 (bs, 1H), 12.08 (s, 1H). |
| 266 | 5-[5-chloro-4-[(5-cyclopropyl-1H-pyrazol-3-yl)amino]-6-methyl-pyrimidin-2-yl]thiophene-2-sulfonamide | d (400 MHz, DMSO-d6); 0.71-0.75 (m, 2H), 0.95 (d, J = 6.4 Hz, 2H), 1.90-1.94 (m, 1H), 2.45 (s, 3H), 6.32 (s, 1H), 7.55 (d, J = 4 Hz, 1H), 8.50 (d, J = 4 Hz, 1H), 8.19 (bs, 1H), 12.19 (bs, 1H). |
| 267 | 5-[4-[(5-cyclopropyl-1H-pyrazol-3-yl)amino]-5-ethynyl-6-methyl-pyrimidin-2-yl]thiophene-2-sulfonamide | d (400 MHz, DMSO-d6); 0.81-0.85 (m, 2H), 1.03-1.07 (m, 2H), 1.99-2.04 (m, 1H), 2.55 (s, 3H), 5.17 (s, 1H), 6.49 (s, 1H), 7.61 (d, J = 3.6 Hz, 1H), 7.88 (s, 2H), 7.91 (d, J = 3.6 Hz, 1H), 9.21 (s, 1H) |
| 268 | 5-[4-[(5-cyclopropyl-1H-pyrazol-3-yl)amino]-5-ethynyl-6-methyl-pyrimidin-2-yl]-N-tert-butyl-thiophene-2-sulfonamide | d (400 MHz, DMSO-d6); 0.75-0.76 (m, 2H), 0.98-1.00 (m, 2H), 1.20 (s, 9H), 1.92-1.97 (m, 1H), 2.51 (s, 3H), 5.10 (s, 1H), 6.46 (s, 1H), 7.61 (d, J = 4.4 Hz, 1H), 7.79 (d, J = 4.4 Hz, 1H), 7.92 (s, 1H), 8.51 (s, 1H), 12.29 (s, 1H) |
| 269 | 3-[6-[(5-cyclopropyl-1H-pyrazol-3-yl)amino]-2-pyridyl]-N-tert-butyl-prop-2-ene-1-sulfonamide | d (400 MHz, DMSO-d6): 0.60~0.74 (m, 2H), 0.81~0.89 (m, 2H), 1.29 (s, 9H), 1.81~1.89 (m, 1H), 3.95 (d, J = 6.0 Hz, 2H), 6.17 (bs, 1H), 6.59~6.70 (m, 3H), 7.00 (s, 2H), 7.48 (t, J = 8.0 Hz, 1H), 9.14 (bs, 1H), 11.84 (bs, 1H). |
| 270 | 3-[6-[(5-cyclopropyl-1H-pyrazol-3-yl)amino]-2-pyridyl]prop-2-ene-1-sulfonamide | d (400 MHz, DMSO-d6): 0.78~0.82 (m, 2H), 0.99~1.04 (m, 2H), 1.96~1.99 (m, 1H), 4.03 (d, J = 7.6 Hz, 2H), 5.99 (s, 1H), 6.68 (td, J = 16.0 Hz, 7.6 Hz, 1H), 6.81 (d, J = 16.0 Hz, 1H), 7.06 (s, 2H), 7.14 (d, J = 7.6 Hz, 1H), 7.23 (d, J = 9.2 Hz, 1H), 7.92 (t, J = 8.0 Hz, 1H), 11.36 (bs, 1H). |
| 271 | 5-[6-[(5-cyclopropyl-1H-pyrazol-3-yl)amino]-2-pyridyl]-N-tert-butyl-thiophene-2-sulfonamide | d (400 MHz, DMSO-d6): 0.69~0.73 (m, 2H), 0.91~0.99 (m, 2H), 1.20 (s, 9H), 1.86~1.90 (m, 1H), 6.33 (s, 1H), 7.02 (d, J = 8.4 Hz, 1H), 7.29 (d, J = 7.2 Hz, 1H), 7.55 (d, J = 4.0 Hz, 1H), 7.59 (dd, J = 8.0 Hz, 7.6 Hz, 1H), 7.68 (d, J = 4.0 Hz, 1H), 7.78 (s, 1H), 9.38 (s, 1H), 11.90 (s, 1H). |
| 272 | 5-[6-[(5-cyclopropyl-1H-pyrazol-3-yl)amino]-2-pyridyl]thiophene-2-sulfonamide | d (400 MHz, DMSO-d6): 0.72~0.76 (m, 2H), 0.94~0.99 (m, 2H), 1.86~1.92 (m, 1H), 6.32 (s, 1H), 7.00 (d, J = 8.4 Hz, 1H), 7.32 (d, J = 7.6 Hz, 1H), 7.54 (d, J = 4.0 Hz, 1H), 7.61 (dd, J = 8.0 Hz, 7.6 Hz, 1H), 7.71 (d, J = 4.4 Hz, 1H), 7.72 (s, 2H), 9.50 (s, 1H). |

TABLE 2-continued

| Compound # | Name | NMR |
|---|---|---|
| 273 | 5-[5-amino-6-[(5-cyclopropyl-2H-pyrazol-3-yl)amino]-2-pyridyl]-N-tert-butyl-thiophene-2-sulfonamide | d (400 MHz, DMSO-d6); 0.73-0.74 (m, 2H), 0.94-0.96 (m, 2H), 1.19 (s, 9H), 1.85-1.91 (m, 1H), 5.55 (s, 2H), 5.58 (s, 1H), 6.84 (d, J = 7.2 Hz, 1H), 7.19 (d, J = 7.2 Hz, 1H), 7.37-7.36 (m, 1H), 7.45-7.46 (m, 1H), 7.64 (s, 1H), 8.40 (s, 1H), 11.91 (s, 1H). |
| 274 | 5-[6-[(5-cyclopropyl-2H-pyrazol-3-yl)amino]-5-nitro-2-pyridyl]-N-tert-butyl-thiophene-2-sulfonamide | d (400 MHz, DMSO-d6); 0.76-0.77 (m, 2H), 1.00-1.02 (m, 2H), 1.22 (s, 9H), 1.91-1.98 (m, 1H), 6.56 (s, 1H), 7.60 (d, J = 8.4 Hz, 1H), 7.66 (d, J = 4.0 Hz, 1H), 7.98 (s, 1H), 8.04 (d, J = 3.6 Hz, 1H), 8.62 (d, J = 8.8 Hz, 1H), 10.29 (s, 1H), 12.42 (s, 1H). |
| 275 | 5-[6-[(5-cyclopropyl-2H-pyrazol-3-yl)amino]-5-nitro-2-pyridyl]thiophene-2-sulfonamide | d (400 MHz, DMSO-d6); 0.77-0.78 (m, 2H), 1.00-1.02 (m, 2H), 1.91-1.96 (m, 1H), 6.58 (s, 1H), 7.60 (d, J = 8.4 Hz, 1H), 7.65 (d, J = 4.0 Hz, 1H), 7.90 (s, 2H), 8.05 (d, J = 4.0 Hz, 1H), 8.62 (d, J = 8.4 Hz, 1H), 10.30 (s, 1H), 12.40 (s, 1H). |
| 276 | 5-[5-amino-6-[(5-cyclopropyl-2H-pyrazol-3-yl)amino]-2-pyridyl]thiophene-2-sulfonamide | d (400 MHz, DMSO-d6); 0.74 (s, 2H), 0.95 (s, 2H), 1.89 (s, 1H), 5.53 (s, 2H), 6.57 (s, 1H), 6.85 (d, J = 6.0 Hz, 1H), 7.19 (d, J = 5.6 Hz, 1H), 7.38 (s, 1H), 7.45 (s, 1H), 7.59 (s, 2H), 8.41 (s, 1H), 11.87 (s, 1H). |
| 277 | chloro-cyclopropyl-BLAHone | d (400 MHz, DMSO-d6): 0.75-0.81 (m, 1H), 0.83~0.94 (m, 2H), 0.98~1.04 (m, 1H), 1.89~1.96 (m, 1H), 6.54 (s, 2H), 7.32~7.35 (m, 1H), 7.57~7.61 (m, 2H), 8.34~8.36 (m, 1H), 8.48 (s, 1H), 9.45 (s, 1H), 12.29 (s, 1H). |
| 278 | 6-[(5-cyclopropyl-1H-pyrazol-3-yl)amino]-2-[5-(tert-butylsulfamoyl)-2-thienyl]-pyrimidine-4-carboxylic acid | d (400 MHz, DMSO-d6); 0.72-0.73 (m, 2H), 0.96-0.97 (m, 2H), 1.20 (s, 9H), 1.89-1.96 (m, 2H), 6.50 (bs, 1H), 7.31 (bs, 1H), 7.60 (d, J = 3.6 Hz, 1H), 7.85 (m , 1H), 7.91 (s, 1H), 10.34 (bs, 1H), 12.28 (bs, 1H). |
| 279 | 5-[4-[(5-cyclopropyl-2H-pyrazol-3-yl)amino]-6-methylamino-pyrimidin-2-yl]thiophene-2-sulfonamide | d (400 MHz, DMSO-d6): 0.68-0.69 (m, 2H), 0.91-0.92 (m, 2H), 1.85-1.87 (m, 1H), 2.84 (d, J = 4.8 Hz, 3H), 6.28 (bs, 1H), 6.81 (bs, 2H), 7.51-7.54 (m, 2H), 7.73 (s, 2H), 9.56 (s, 1H), 11.99 (s, 1H). |
| 280 | N-[[5-[5-chloro-4-[(5-cyclopropyl-2H-pyrazol-3-yl)amino]-pyrimidin-2-yl]-2-thienyl]methyl]metnanesulfonamide | d (400 MHz, DMSO-d6): 0.74~0.78 (m, 2H), 0.96~1.01 (m, 2H), 1.91~1.97 (m, 1H), 2.92 (s, 3H), 4.38 (d, J = 6.4 Hz, 2H), 6.47 (d, J = 1.6 Hz, 1H), 7.09 (d, J = 4.0 Hz, 1H), 7.66 (d, J = 3.2 Hz, 1H), 7.82 (t, J = 6.4 Hz, 1H), 8.39 (s, 1H), 9.30 (s, 1H), 12.29 (s, 1H). |
| 281 | 5-[4-[(5-cyclopropyl-1H-pyrazol-3-yl)amino]-5-(3-hydroxyprop-1-enyl)pyrimidin-2-yl]thiophene-2-sulfonamide | d (400 MHz, DMSO-d6): 0.73-0.77 (m, 2H), 0.95-1.00 (m, 2H), 1.90-1.96 (m, 1H), 4.16 (d, J = 4.4 Hz, 2H), 6.37 (dt, J = 15.6 Hz, 4.8 Hz, 1H), 6.45 (s, 1H), 6.88 (d, J = 15.6 Hz, 1H), 7.57 (d, J = 4.4 Hz, 1H), 7.76 (d, J = 4.0 Hz, 1H), 7.78 (s, 2H), 8.43 (s, 1H), 9.27 (s, 1H). |
| 282 | 5-[4-[(5-cyclopropyl-2H-pyrazol-3-yl)amino]-6-dimetnylamino-pyrimidin-2-yl]thiophene-2-sulfonamide | d (400 MHz, DMSO-d6): 0.65-0.69 (m, 2H), 0.90-0.95 (m, 2H), 1.84-1.91 (m, 1H), 3.14 (s, 6H), 6.22 (bs, 1H), 6.72 (bs, 1H), 7.54 (d, J = 3.6 Hz, 2H), 7.72 (s, 2H), 9.61 (bs, 1H), 12.00 (s, 1H). |
| 283 | 6-[(5-cyclopropyl-1 H-pyrazol-3-yl)amino]-2-(5-sulfamoyl-2-thienyl)-pyrimidine-4-carboxylic acid | d (400 MHz, DMSO-d6): 0.74 (m, 2H), 0.96-0.98 (m, 2H), 1.90-1.96 (m, 1H), 6.57 (bs, 1H), 7.26 (bs, 1H), 7.60 (d, J = 3.6 Hz, 1H), 7.83 (s, 2H), 7.87 (d, J = 4.0 Hz, 1H), 10.50 (bs, 1H), 12.23 (bs, 1H), 13.53 (bs, 1H), |
| 284 | 5-[4-[(5-cyclopropyl-2H-pyrazol-3-yl)amino]-6-pyrrolidin-1-yl-pyrimidin-2-yl]thiophene-2-sulfonamide | d (400 MHz, DMSO-d6): 0.65-0.69 (m, 2H), 0.90-0.94 (m, 2H), 1.84-1.94 (m, 5H), 3.33-3.53 (m, 4H), 6.27 (bs, 1H), 6.70 (bs, 1H), 7.51-7.54 (m, 2H), 7.69 (s, 2H), 9.57 (s, 1H), 11.96 (bs, 1H). |
| 285 | 5-[4-[(5-cyclopropyl-1H-pyrazol-3-yl)amino]-6-(hydroxymethyl)pyrimidin-2-yl]thiophene-2-sulfonamide | d (400 MHz, DMSO-d6): 0.72-0.73 (m, 2H), 0.95-0.98 (m, 2H), 1.88-1.95 (m, 1 H), 4.43 (d, J = 5.2 Hz, 2H), 5.52 (t, J = 6.0 Hz, 1H), 6.50 (bs, 1H), 6.87 (bs, 1H), 7.56 (d, J = 4.0 Hz, 1H), 7.75 (d, J = 4.0 Hz, 1H), 7.83 (s, 2H), 10.05 (bs, 1H), 12.12 (s, 1H). |
| 286 | 5-[4-[(5-cyclopropyl-1H-pyrazol-3-yl)amino]-6-(hydroxymethyl)pyrimidin-2-yl]-N-tert-butyl-thiophene-2-sulfonamide | d (400 MHz, DMSO-d6): 0.72-0.73 (m, 2H), 0.95-0.98 (m, 2H), 1.19 (s, 9H), 1.88-1.93 (m, 1H), 4.43 (d, J = 5.2 Hz, 2H), 5.52 (t, J = 5.2 Hz, 1H), 6.52 (bs, 1H), 6.91 (bs, 1H), 7.57 (d, J = 4.0 Hz, 1H), 7.74 (d, J = 3.6 Hz, 1H), 7.87 (s, 1H), 10.03 (bs, 1H), 12.12 (s, 1H). |

TABLE 2-continued

| Compound # | Name | NMR |
|---|---|---|
| 287 | methyl [[5-[5-chloro-4-[(5-cyclopropyl-2H-pyrazol-3-yl)amino]-pyrimidin-2-yl]-2-thienyl]methylamino]formate | d (400 MHz, DMSO-d6): 0.75~0.76 (m, 2H), 0.98~1.00 (m, 2H), 1.93~1.95 (m, 1H), 3.58 (s, 3H), 4.37 (d, J = 5.6 Hz, 2H), 6.45 (s, 1H), 7.00 (d, J = 3.2 Hz, 1H), 7.65 (d, J = 3.2 Hz, 1H), 7.90 (t, J = 5.6 Hz, 1H), 8.39 (s, 1H), 9.40 (s, 1H). |
| 288 | 1-[5-[5-chloro-4-[(5-cyclopropyl-1H-pyrazol-3-yl)amino]-pyrimidin-2-yl]-2-furyl]ethanone | d (400 MHz, DMSO-d6): 0.77-0.81 (m, 2H), 0.95-0.98 (m, 2H), 1.91-1.94 (m, 1H), 2.52 (s, 3H), 6.65 (s, 1H), 7.30 (d, J = 4.0 Hz, 1H), 7.56 (d, J = 3.6 Hz, 1H), 8.49 (s, 1H), 9.48 (s, 1H), 12.31 (s, H). |
| 289 | 1-[5-[5-chloro-4-[(5-cyclopropyl-1H-pyrazol-3-yl)amino]-pyrimidin-2-yl]-2-furyl]ethanol | d (400 MHz, DMSO-d6): 0.74-0.75 (m, 2H), 0.96-0.98 (m, 2H), 1.45 (d, J = 6.4 Hz, 3H), 1.91-1.94 (m, 1H), 4.75-4.81 (m, 1H), 5.46 (d, J = 4.8 Hz, 1H), 6.45 (d, J = 3.2 Hz, 1H), 6.62 (s, 1H), 7.09 (d, J = 2.4 Hz, 1H), 8.39 (s, 1H), 9.27 (s, 1H), 12.26 (s, H). |
| 290 | 5-[4-[(5-cyclopropyl-2H-pyrazol-3-yl)amino]-6-morpholino-pyrimidin-2-yl]thiophene-2-sulfonamide | d (400 MHz, DMSO-d6): 0.66-0.69 (m, 2H), 0.91-0.94 (m, 2H), 1.86-1.90 (m, 1H), 3.69 (d, J = 3.6 Hz, 8H), 6.10 (bs, 1H), 6.81 (bs, 1H), 7.54 (d, J = 4.0 Hz, 2H), 7.73 (s, 2H), 9.67 (s, 1H), 12.03 (s, 1H). |
| 291 | 5-[4-[(5-cyclopropyl-2H-pyrazol-3-yl)amino]-6-methylsulfanyl-pyrimidin-2-yl]thiophene-2-sulfonamide | d (400 MHz, DMSO-d6): 0.66-0.70 (m, 2H), 0.91-0.96 (m, 2H), 1.88-1.90 (m, 1H), 2.53 (s, 3H), 6.11 (bs, 1H), 7.58 (d, J = 4.0 Hz, 1H), 7.64 (d, J = 4.0 Hz, 1H), 7.80 (s, 2H), 10.11 (s, 1H), 12.19 (bs, 1H). |
| 292 | 6-[(4-chloro-5-cyclopropyl-1H-pyrazol-3-yl)amino]-2-(5-sulfamoyl-2-thienyl)-pyrimidine-4-carboxylic acid | d (400 MHz, DMSO-d6): 0.91 (m, 2H), 1.00 (m, 2H), 1.91 (m, 1H), 7.28 (s, 1H), 7.57 (bs, 1H), 7.81 (bs, 3H), 9.92 (bs, 1H), 12.68 (bs, 1H), 13.61 (bs, 1H). |
| 293 | 5-[4-[(5-cyclopropyl-2H-pyrazol-3-yl)amino]-6-methoxy-pyrimidin-2-yl]thiophene-2-sulfonamide | d (400 MHz, DMSO-d6): 0.67-0.71 (m, 2H), 0.91-0.95 (m, 2H), 1.87-1.91 (m, 1H), 3.90 (s, 3H), 6.22 (bs, 1H), 7.08 (bs, 1H), 7.57 (d, J = 4.4 Hz, 1H), 7.63 (d, J = 4.0 Hz, 1H), 7.80 (s, 2H), 10.11 (bs, 1H), 12.15 (bs, 1H). |
| 294 | 5-[4-amino-6-[(5-cyclopropyl-2H-pyrazol-3-yl)amino]-pyrimidin-2-yl]thiophene-2-sulfonamide | d (400 MHz, DMSO-d6): 0.69-0.70 (m, 2H), 0.86-0.90 (m, 2H), 1.81-1.86 (m, 1H), 6.44 (m, 2H), 6.69 (bs, 1H), 7.53 (d, J = 3.6 Hz, 8.20 (s, 2H), 9.59 (bs, 1H), 12.06 (bs, 1H). |
| 295 | 5-[4-cyano-6-[(5-cyclopropyl-2H-pyrazol-3-yl)amino]-pyrimidin-2-yl]thiophene-2-sulfonamide | d (400 MHz, DMSO-d6): 0.69-0.73 (m, 2H), 0.92-0.97 (m, 2H), 1.89-1.93 (m, 1H), 5.74 (bs, 1H), 7.61 (s, J = 4.0 Hz, 1H), 7.76 (d, J = 4.0 Hz, 1H), 7.89 (s, 2H), 8.30 (bs, 1H), 10.67 (s, 1H), 12.34 (s, 1H). |
| 296 | 1-[2-[5-chloro-4-[(5-cyclopropyl-1H-pyrazol-3-yl)amino]-pyrimidin-2-yl]-4-methyl-thiazol-5-yl]ethanol | d (400 MHz, DMSO-d6): 0.70~0.78 (m, 2H), 0.95~1.03 (m, 2H), 1.41 (d, J = 5.2 Hz, 3H), 1.89~1.96 (m, 1H), 2.38 (s, 3H), 5.04~5.08 (m, 1H), 5.75 (d, J = 2.8 Hz, 1H), 6.62 (s, 1H), 8.47 (s, 1H), 9.51 (s, 1H), 12.33 (s, 1H). |
| 297 | 1-[2-[5-chloro-4-[(5-cyclopropyl-1H-pyrazol-3-yl)amino]-pyrimidin-2-yl]-4-methyl-thiazol-5-yl]ethanone | d (400 MHz, DMSO-d6): 0.67~0.80 (m, 2H), 0.92~1.05 (m, 2H), 1.91~1.97 (m, 1H), 2.60 (s, 3H), 2.73 (s, 3H), 6.60 (s, 1H), 8.54 (s, 1H), 9.69 (s, 1H), 12.37 (s, 1H). |
| 298 | 5-[4-cyclopropyl-6-[(5-cyclopropyl-2H-pyrazol-3-yl)amino]-pyrimidin-2-yl]thiophene-2-sulfonamide | d (400 MHz, DMSO-d6): 0.71-0.74 (m, 2H), 0.93-1.02 (m, 6H), 1.88-2.00 (m, 2H), 6.19 (bs, 1H), 6.93 (bs, 1H), 7.46 (s, 2H), 8.01 (s, 1H), 8.14 (b, 1H), 9.86 (s, 1H) |
| 299 | 5-[5-chloro-4-[(5-cyclopropyl-1H-pyrazol-3-yl)amino]-pyrimidin-2-yl]pyridine-2-sulfonamide | d (400 MHz, DMSO-d6): 0.67~0.80 (m, 2H), 0.92~1.06 (m, 2H), 1.87~2.03 (m, 1H), 6.41 (s, 1H), 7.61 (s, 2H), 8.07 (d, J = 8.0 Hz, 1H), 8.59 (s, 1H), 8.75 (d, J = 7.6 Hz, 1H), 9.44 (s, 1H), 9.51 (s, 1H), 12.34 (s, 1H). |
| 300 | 5-[4-[(5-cyclopropyl-1H-pyrazol-3-yl)amino]pyrimidin-2-yl]-N-tert-butyl-pyridine-2-sulfonamide | d (400 MHz, DMSO-d6): 0.68~0.76 (m, 2H), 0.94~0.98 (m, 2H), 1.12 (s, 9H), 1.88~1.99 (m, 1H), 6.25 (bs, 1H), 7.08 (bs, 1H), 7.85 (s, 1H), 8.12 (d, J = 8.4 Hz, 1H), 8.43 (d, J = 5.6 Hz, 1H), 8.82 (dd, J = 8.4 Hz, 1.6 Hz, 1H), 9.52 (d, J = 1.6 Hz, 1H), 10.08 (bs, 1H), 12.15 (s, 1H). |
| 301 | 5-[4-[(5-cyclopropyl-1H-pyrazol-3-yl)amino]pyrimidin-2-yl]pyridine-2-sulfonamide | d (400 MHz, DMSO-d6): 0.67~0.77 (m, 2H), 0.91~1.00 (m, 2H), 1.88~1.99 (m, 1H), 6.19 (bs, 1H), 7.04 (bs, 1H), 7.60 (s, 2H), 8.09 (d, J = 8.0 Hz, 1H), 8.43 (d, J = 4.4 Hz, 1H), 8.83 (d, J = 8.4 Hz, 1H), 9.52 (s, 1H), 10.09 (bs, 1H), 12.15 (s, 1H). |

TABLE 2-continued

| Compound # | Name | NMR |
|---|---|---|
| 302 | 5-[5-chloro-4-[(5-cyclopropyl-1H-pyrazol-3-yl)amino]-pyrimidin-2-yl]-N-tert-butyl-pyridine-2-sulfonamide | d (400 MHz, DMSO-d6): 0.70~0.79 (m, 2H), 0.93~1.03 (m, 2H), 1.11 (s, 9H), 1.94~2.02 (m, 1H), 6.39 (s, 1H), 7.87 (s, 1H), 8.11 (d, J = 8.4 Hz, 1H), 8.60 (s, 1H), 8.75 (dd, J = 8.4 Hz, 1.6 Hz, 1H), 9.44 (d, J = 1.6 Hz, 1H), 9.52 (s, 1H), 12.33 (s, 1H). |
| 303 | 5-chloro-4-[(5-cyclopropyl-1H-pyrazol-3-yl)amino]-pyrimidine-2-carboxamide | d (400 MHz, DMSO-d6): 0.61~0.75 (m, 2H), 0.85~0.99 (m, 2H), 1.84~1.95 (m, 1H), 6.52 (s, 1H), 7.72 (s, 1H), 7.85 (s, 1H), 8.49 (s, 1H), 9.46 (s, 1H), 12.25 (s, 1H). |
| 304 | 5-[5-chloro-4-cyclopropyl-6-[(5-cyclopropyl-2H-pyrazol-3-yl)amino]-pyrimidin-2-yl]thiophene-2-sulfonamide | d (400 MHz, DMSO-d6); 0.73-0.77 (m, 2H), 0.96-0.99 (m, 2H), 1.12-1.14 (m, 4H), 1.91 (m, 1H), 2.43-2.47 (m, 1H), 6.39 (s, 1H), 7.48 (s, 2H), 7.96 (d, J = 1.6 Hz, 1H), 8.18 (d, J = 1.2 Hz, 1H), 9.18(s, 1H) |
| 305 | 5-chloro-4-[(5-cyclopropyl-1H-pyrazol-3-yl)amino]-pyrimidine-2-carbothioamide | d (400 MHz, DMSO-d6): 0.68-0.71 (m, 2H), 0.91-0.96 (m, 2H), 1.86-1.93 (m, 1H), 6.73 (s, 1H), 8.50 (s, 1H), 9.77 (s, 2H), 10.34 (s, 1H) |
| 306 | 5-[5-chloro-4-[(5-cyclopropyl-1H-pyrazol-3-yl)amino]-pyrimidin-2-yl]thiophene-2-sulfonic acid | d (400 MHz, DMSO-d6), 0.77 (d, J = 3.6 Hz, 2H), 1.01 (d, J = 5.2 Hz, 2H), 1.96-1.98 (m, 1H), 6.44 (s, 1H), 7.15 (d, J = 2.8 Hz, 1H), 7.62 (d, J = 2.8 Hz, 1H), 8.45 (s, 1H), 9.55 (s, 1H). |
| 307 | 5-chloro-N-(5-cyclopropyl-1H-pyrazol-3-yl)-2-(5-pyrrol-1-ylsulfonyl-2-thienyl)-pyrimidin-4-amine | d (400 MHz, DMSO-d6), 0.75 (d, J = 3.6 Hz, 2H), 1.04 (d, J = 5.2 Hz, 2H), 1.94-1.97 (m, 1H), 6.33 (s, 1H), 6.43 (t, J = 1.6 Hz, 2H), 7.36 (t, J = 1.6 Hz, 2H), 7.76 (d, J = 2.8 Hz, 1H), 7.93 (d, J = 3.2 Hz, 1H), 8.46 (s, 1H), 9.59 (s, 1H), 12.37 (s, 1H). |
| 308 | 1-[4-[4-[(5-cyclopropyl-1H-pyrazol-3-yl)amino]pyrimidin-2-yl]phenyl]ethanone | d (400 MHz, DMSO-d6): 0.73 (d, J = 3.2 Hz, 2H), 0.96 (d, J = 6.8 Hz, 2H), 1.93~1.95 (m, 1H), 2.65 (s, 3H), 6.26 (bs, 1H), 7.15 (bs, 1H), 8.09 (d, J = 8 Hz, 2H), 8.41~8.47 (m, 3H), 9.98 (s, 1H), 12.13 (s, 1H). |
| 309 | 2-[4-[(5-cyclopropyl-1H-pyrazol-3-yl)amino]-2-[5-(tert-butylsulfamoyl)-2-thienyl]-pyrimidin-5-yl]ethyl acetate | d (400 MHz, DMSO-d6); 0.73-0.74 (m, 2H), 0.96-0.97 (m, 2H), 1.16 (s, 9H), 1.90-1.94 (m, 1H), 1.97 (s, 3H), 2.96 (t, J = 5.6 Hz, 2H), 4.17 (t, J = 5.6 Hz, 2H), 6.47 (s, 1H), 7.58 (d, J = 4.0 Hz, 1H), 7.72 (d, J = 4.0 Hz, 1H), 7.87 (s, 1H), 8.13 (s, 1H), 9.37 (s, 1H), 12.19 (s, 1H) |
| 310 | 2-[5-chloro-4-[(5-cyclopropyl-1H-pyrazol-3-yl)amino]-pyrimidin-2-yl]-4,5,6,7-tetrahydrobenzothiazol-7-ol | d (400 MHz, DMSO-d6); 0.73 (s, 2H), 0.98 (s, 2H), 1.23 (s, 1H), 1.68-1.78 (m, 2H), 1.93-2.02 (m, 3H), 2.75 (d, J = 5.2 Hz, 2H), 4.48 (d, J = 4.4 Hz, 1H), 5.65 (d, J = 6.4 Hz, 1H), 6.62 (s, 1H), 8.48 (bs, 1H), 9.49 (bs, 1H), 12.31 (s, 1H). |
| 311 | 2-[5-chloro-4-[(5-cyclopropyl-1H-pyrazol-3-yl)amino]-pyrimidin-2-yl]-5,6-dihydro-4H-benzothiazol-7-one | d (400 MHz, DMSO-d6): 0.71-0.75 (m, 2H), 0.97-1.02 (m, 2H), 1.92-1.96 (m, 1H), 2.16-2.19 (m, 2H), 2.63 (t, J = 6.4 Hz, 2H), 3.08 (t, J = 6 Hz, 2H), 6.55 (s, 1H), 8.57 (bs, 1H), 9.72 (bs, 1H). |
| 312 | 1-[4-[4-[(5-cyclopropyl-1H-pyrazol-3-yl)amino]pyrimidin-2-yl]phenyl]ethanol | d (400 MHz, DMSO-d6): 0.70~0.74 (m, 2H), 0.94~0.98 (m, 2H), 1.35 (d, J = 6.4 Hz, 3H), 1.89~1.96 (m, 1H), 4.77~4.82 (m, 1H), 5.25 (d, J = 4 Hz, 1H), 6.22 (bs, 1H), 7.03 (bs, 1H), 7.46 (d, J = 11.2 Hz, 2H), 8.27 (d, J = 8.4 Hz, 2H), 8.34 (d, J = 5.6 Hz, 1H), 9.86 (s, 1H), 12.09 (s, 1H). |
| 313 | 2-[4-[(5-cyclopropyl-1H-pyrazol-3-yl)amino]-2-(5-sulfamoyl-2-thienyl)-pyrimidin-5-yl]ethyl acetate | d (400 MHz, DMSO-d6); 0.76 (m, 2H), 0.98-0.99 (m, 2H), 1.94 (m, 1H), 1.99 (s, 3H), 2.98 (s, 2H), 4.20 (s, 2H), 6.47 (s, 1H), 7.59 (s, 1H), 7.76 (d, J = 2.8 Hz, 1H), 7.81 (s, 2H), 8.16 (s, 1H), 9.44 (s, 1H) |
| 314 | 5-[5-chloro-2-[(5-cyclopropyl-2H-pyrazol-3-yl)amino]-pyrimidin-4-yl]thiophene-2-sulfonamide | d (400 MHz, DMSO-d6): 0.70-0.74 (m, 2H), 0.92-0.97 (m, 2H), 1.86-1.93 (m, 1H), 6.31 (s, 1H), 7.65 (d, J = 4.4 Hz, 1H), 7.90 (s, 2H), 8.18 (d, J = 4.0 Hz, 1H), 8.58 (s, 1H), 10.08 (s, 1H), 12.09 (bs, 1H). |
| 315 | 5-[2-[(5-cyclopropyl-2H-pyrazol-3-yl)amino]pyrimidin-4-yl]thiophene-2-sulfonamide | d (400 MHz, DMSO-d6): 0.71-0.71 (m, 2H), 0.93-0.95 (m, 2H), 1.86-1.93 (m, 1H), 6.39 (bs, 1H), 7.36 (d, J = 4.0 Hz, 1H), 7.61 (d, J = 3.6 Hz, 1H), 7.85 (s, 2H), 7.83 (d, J = 4.0 Hz, 1H), 8.50 (d, J = 5.2 Hz, 1H), 9.79 (bs, 1H), 11.98 (bs, 1H). |

TABLE 2-continued

| Compound # | Name | NMR |
|---|---|---|
| 316 | 1-[3-[4-[(5-cyclopropyl-1H-pyrazol-3-yl)amino]pyrimidin-2-yl]phenyl]ethanol | d (400 MHz, DMSO-d6): 0.73 (d, J = 4 Hz, 2H), 0.94~0.98 (m, 2H), 1.38 (d, J = 6.4 Hz, 3H), 1.88~1.94 (m, 1H), 4.78~4.84 (m, 1H), 5.26 (d, J = 4 Hz, 1H), 6.31 (bs, 1H), 6.97 (bs, 1H), 7.41~7.46 (m, 2H), 8.19 (d, J = 6.8 Hz, 1H), 8.35~8.38 (m, 2H), 9.88 (s, 1H), 12.10 (s, 1H). |
| 317 | 1-[3-[4-[(5-cyclopropyl-1H-pyrazol-3-yl)amino]pyrimidin-2-yl]phenyl]ethanone | d (400 MHz, DMSO-d6): 0.76 (d, J = 3.2 Hz, 2H), 0.94~0.98 (m, 2H), 1.88~1.95 (m, 1H), 2.67 (s, 3H), 6.34 (bs, 1H), 7.05 (bs, 1H), 7.65~7.69 (m, 1H), 8.09 (d, J = 7.6 Hz, 1H), 8.39 (d, J = 5.6 Hz, 1H), 8.57 (d, J = 7.6 Hz, 1H), 8.94 (s, 1H), 9.98 (s, 1H), 12.13 (s, 1H). |
| 318 | 5-[4-[(5-cyclopropyl-1H-pyrazol-3-yl)amino]pyrimidin-2-yl]-2-hydroxy-benzenesulfonamide | d (400 MHz, DMSO-d6): 0.76 (d, J = 3.6 Hz, 2H), 0.92~0.96 (m, 2H), 1.87~1.93 (m, 1H), 6.21 (bs, 1H), 6.84~7.19 (m, 3H), 8.29~8.35 (m, 2H), 8.73 (s, 1H), 9.84 (s, 1H), 12.07 (s, 1H). |
| 319 | 5-[4-[(5-cyclopropyl-1H-pyrazol-3-yl)amino]-5-(3-hydroxypropyl)pyrimidin-2-yl]thiophene-2-sulfonamide | d (400 MHz, DMSO-d6): 0.75-0.79 (m, 2H), 0.99-1.03 (m, 2H), 1.71 (q, J = 6.4 Hz, 2H), 1.94-1.99 (m, 1H), 2.71 (t, J = 6.4 Hz, 2H), 3.47 (t, J = 6.4 Hz, 2H), 6.45 (s, 1H), 7.64 (d, J = 4.0 Hz, 1H), 7.80 (s, 2H), 8.05 (d, J = 3.2 Hz, 1H), 8.22 (s, 1H), 10.06 (bs, 1H). |
| 320 | 5-[5-chloro-4-[[5-(2-methylcyclopropyl)-1H-pyrazol-3-yl]amino]-pyrimidin-2-yl]thiophene-2-sulfonamide | d (400 MHz, DMSO-d6); 0.78-0.81 (m, 1H), 0.92-0.95 (m, 1H), 1.16 (m, 4H), 1.64-1.65 (m, 1H), 6.37 (s, 1H), 7.58 (d, J = 4.0 Hz, 1H), 7.75 (d, J = 3.6 Hz, 1H), 7.81 (s, 2H), 8.45 (s, 1H), 9.42 (s, 1H), 12.26 (s, 1H). |
| 321 | 5-[5-chloro-4-[[5-(2-methylcyclopropyl)-1H-pyrazol-3-yl]amino]-pyrimidin-2-yl]-N-tert-butyl-thiophene-2-sulfonamide | d (400 MHz, DMSO-d6); 0.78-0.81 (m, 1H), 0.93-0.94 (m, 1H), 1.16 (m, 4H), 1.20 (s, 9H), 1.64-1.66 (m, 1H), 6.38 (s, 1H), 7.60 (d, J = 3.6 Hz, 1H), 7.74 (d, J = 4.0 Hz, 1H), 7.90 (s, 1H), 8.45 (s, 1H), 9.44 (s, 1H), 12.27 (s, 1H). |
| 322 | 5-[2-[(5-cyclopropyl-2H-pyrazol-3-yl)amino]-6-methyl-pyrimidin-4-yl]thiophene-2-sulfonamide | d (400 MHz, DMSO-d6); 0.68-0.72 (m, 2H), 0.91-0.96 (m, 2H), 1.85-1.92 (m, 1H), 2.31 (s, 3H), 6.32 (s, 1H), 7.28 (s, 1H), 7.60 (d, J = 3.6 Hz, 1H), 7.82 (s, 2H), 7.91 (d, J = 3.6 Hz, 1H), 9.68 (s, 1H), 11.93 (bs, 1H). |
| 323 | 4-[4-[(5-cyclopropyl-1H-pyrazol-3-yl)amino]pyrimidin-2-yl]benzenesulfonamide | d (400 MHz, DMSO-d6): 0.77~0.74 (m, 2H), 0.93~0.97 (m, 2H), 1.89~1.96 (m, 1H), 6.17 (bs, 1H), 7.01 (bs, 1H), 7.44 (s, 2H), 7.94 (d, J = 8.4 Hz, 2H), 8.39 (d, J = 5.6 Hz, 1H), 8.46 (d, J = 8.4 Hz, 2H), 9.96 (s, 1H), 12.11 (s, 1H). |
| 324 | tert-butyl [[5-[5-chloro-4-[(5-cyclopropyl-1H-pyrazol-3-yl)amino]-pyrimidin-2-yl]-2-thienyl]amino]formate | d (400 MHz, DMSO-d6); 0.57-0.62 (m, 2H), 0.71-0.76 (m, 2H), 1.28 (s, 9H), 1.65-1.72 (m, 1H), 6.24 (s, 1H), 6.31 (d, J = 4.0 Hz, 1H), 7.30 (d, J = 4.0 Hz, 1H), 8.08 (s, 1H), 8.95 b(s, 1H), 10.54 (bs, 1H) |
| 325 | 5-[4-[(5-cyclopropyl-1H-pyrazol-3-yl)amino]-6-(4-methylpiperazin-1-yl)-pyrimidin-2-yl]thiophene-2-sulfonamide | d (400 MHz, DMSO-d6); 0.67-0.68 (m, 2H), 0.93-0.94 (m, 2H), 1.89-1.92 (m, 1H), 2.23 (s, 3H), 2.39 (s, 4H), 3.75 (s, 4H), 6.08 (bs, 1H), 6.78 (bs, 1H), 7.55 (s, 2H), 7.23 (s, 2H), 9.63 (bs, 1H), 12.11 (bs, 1H) |
| 326 | 1-[5-[4-[(5-cyclopropyl-1H-pyrazol-3-yl)amino]-5-methyl-pyrimidin-2-yl]-2-thienyl]ethane-1,2-diol | d (400 MHz, DMSO-d6); 0.74-0.78 (m, 2H), 0.98-1.02 (m, 2H), 1.91-1.98 (m, 1H), 2.21 (s, 3H), 3.50-3.59 (m, 4H), 4.81 (t, J = 6.0 Hz, 1H), 6.53 (s, 1H), 7.10 (t, J = 3.6 Hz, 1H), 7.87 (t, J = 3.6 Hz, 1H), 8.16 (s, 1H), 9.90 (bs, 1H) |
| 327 | 1-[5-[5-chloro-4-[(5-cyclopropyl-1H-pyrazol-3-yl)amino]-pyrimidin-2-yl]-2-thienyl]ethane-1,2-diol | d (400 MHz, DMSO-d6); 0.75 (m, 2H), 0.98-0.99 (m, 2H), 1.94 (m, 1H), 3.33 (m, 2H), 4.77 (m, 1H), 4.96 (t, J = 5.2 Hz, 1H), 5.80 (t, J = 0.4 Hz, 1H), 6.49 (s, 1H), 7.03 (d, J = 2.8 Hz, 1H), 7.66 (d, J = 2.0 Hz, 1H), 8.37 (s, 1H), 9.24 (s, 1H), 12.28 (s, 1H) |

General Synthetic Methodology

The compounds of this invention may be prepared in light of the specification using steps generally known to those of ordinary skill in the art. Those compounds may be analyzed by known methods, including but not limited to LCMS (liquid chromatography mass spectrometry) HPLC and NMR (nuclear magnetic resonance). It should be understood that the specific conditions shown below are only examples, and are not meant to limit the scope of the conditions that can be used for making compounds of this invention. Instead, this invention also includes conditions that would be apparent to those skilled in that art in light of this specification for making the compounds of this invention. Unless otherwise indicated, all variables in the following schemes are as defined herein.

time on a ACE5C8 4.6×150 mm column. Flow rate was 1.5 mL/min. As used herein, the term "Rt(min)" refers to the LCMS retention time, in minutes, associated with the compound. Unless otherwise indicated, the LCMS method utilized to obtain the reported retention time is as detailed above. If the Rt(min) is <5 min method A was used, if the Rt(min) is >5 min then method B was used.

1H-NMR spectra were recorded at 400 MHz using a Bruker DPX 400 instrument.

The following compounds of formula I, II or III, can be prepared and analyzed as follows:

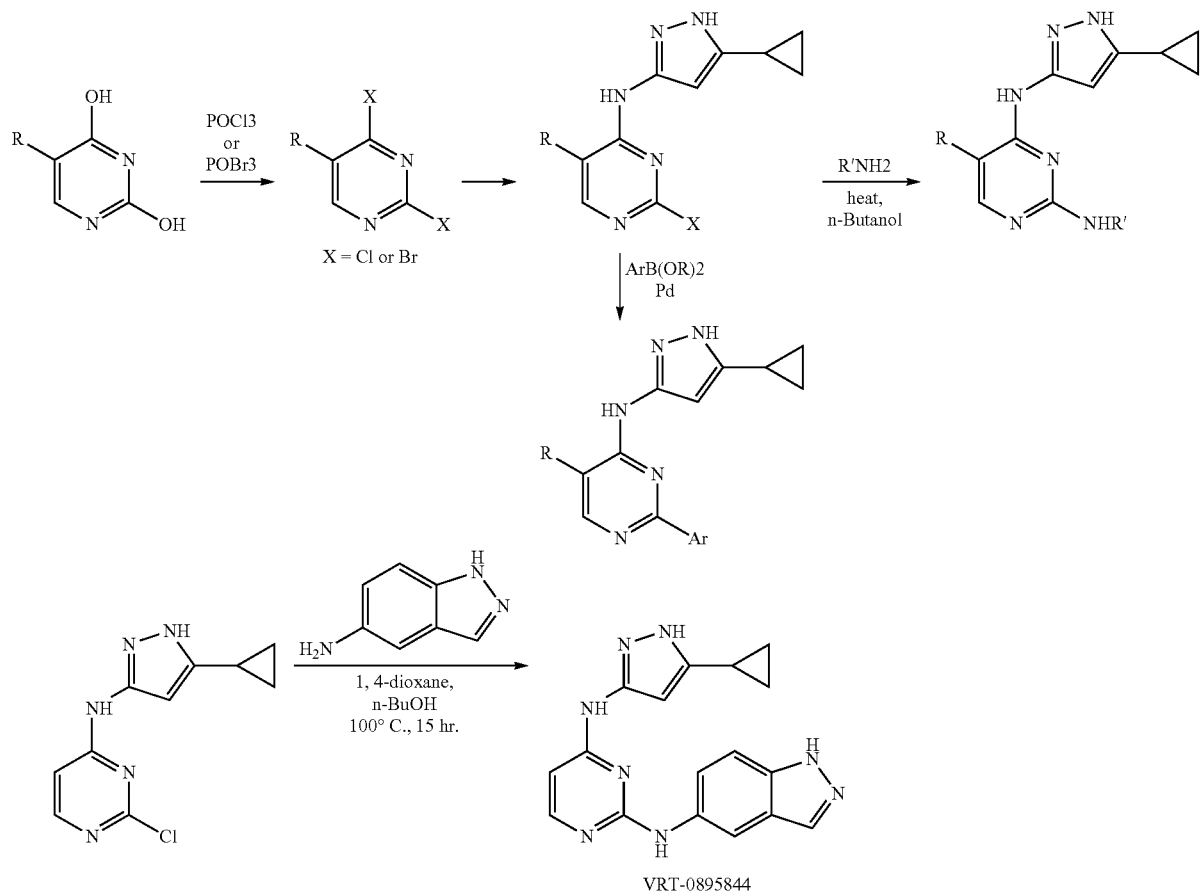

General synthesis 1

VRT-0895844

EXAMPLES

Mass spec. samples were analyzed on a MicroMass Quattro Micro mass spectrometer operated in single MS mode with electrospray ionization. Samples were introduced into the mass spectrometer using chromatography. Mobile phase for all mass spec. analyses consisted of 10 mM pH 7 ammonium acetate and a 1:1 acetonitrile-methanol mixture. Method A: Column gradient conditions were 5%-400% acetonitrile-methanol over 3.5 mins gradient time and 4.8 mins run time on an ACE5C8 3.0×75 mm column. Flow rate was 1.2 ml/min. Method B: Column gradient were 5%-400% acetonitrile-methanol over 10 mins gradient time and 12 mins run N4-(5-cyclopropyl-1H-pyrazol-3-yl)-N2-(1H-indazol-5-yl)pyrimidine-2,4-diamine (Compound 13)

A mixture of 2-chloro-N-(5-cyclopropyl-1H-pyrazol-3-yl)pyrimidin-4-amine (200 mg, 0.8 5 mmol, 1 equiv.) and 1H-indazol-5-amine (340 mg, 2.55 mmol, 3 equiv.) in 1,4-dioxane (1 ml) and n-BuOH (0.5 ml) was heated to 100° C. The mixture was allowed to react overnight (about 15 hr). The mixture was filtered under reduced pressure to afford title compound N4-(5-cyclopropyl-1H-pyrazol-3-yl)-N2-(1H-indazol-5-yl)pyrimidine-2,4-diamine (Compound 13) (44.5 mg, 15.8%) as solid. LC-MS (m/z)=333.1 [M+H]$^+$; $^1$H NMR (400 MHz, DMSO-$d_6$): δ 0.44 (s, J=17.7 Hz, 2H), 0.82 (t, J=17.7 Hz, 2H), 1.758 (s, 1H), 6.02 (s, 1H), 6.41 (s, 1H), 7.46 (d, J=8.7 Hz, 1H), 7.56 (d, J=9 Hz, 1H), 7.92 (d, J=6.6 Hz, 1H), 8.04 (d, J=9.6 Hz, 2H), 9.71 (s, 1H), 10.38 (s, 1H), 11.77 (s, 1H), 13.05 (s, 1H).

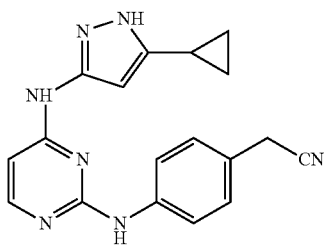

Compound 1

2-(4-(4-(5-cyclopropyl-1H-pyrazol-3-ylamino)pyrimidin-2-ylamino)phenyl) acetonitrile (Compound 1)

Compound 1 (50.2 mg, 17.8%) was prepared as described in Compound 13.

LC-MS (m/z)=332.1 [M+H]$^+$; $^1$H NMR (300 MHz, DMSO-$d_6$): δ 0.54 (s, 2H), 0.96 (d, J=6.0 Hz, 2H), 1.86 (s, 1H), 2.53 (s, 6H), 4.1 (s, 1H), 6.1 (s, 1H), 6.46 (m, 1H), 7.49 (m, 4H), 7.94 (s, 1H), 10.4 (s, 1H), 11.3 (s, 1H).

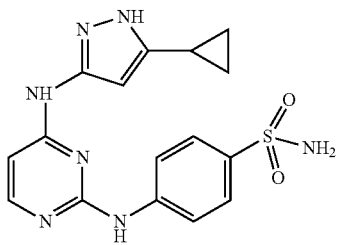

Compound 12

4-(4-(5-cyclopropyl-1H-pyrazol-3-ylamino)pyrimidin-2-ylamino)benzene sulfonamide (Compound 12)

Compound 12 (50.5 16%) was prepared as described in Compound 13. LC-MS (m/z)=372.1 [M+H]$^+$; $^1$H NMR (400 MHz, DMSO-$d_6$): δ 0.69 (m, 2H), 0.91 (m, 2H), 1.86 (m, 1H), 6.21 (s, 1H), 6.51 (s, 1H), 7.13 (s, 1H), 7.67 (d, J=9 Hz, 2H), 7.92 (d, J=7.2 Hz, 2H), 8.02 (d, J=5.4 Hz, 1H), 9.53 (d, J=3.3 Hz, 2H), 12.02 (s, 1H).

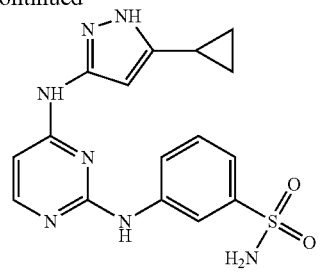

VRT-0904589

3-(4-(3-cyclopropyl-1H-pyrazol-5-ylamino) pyrimidin-2-ylamino) benzenesulfonamide (Compound 82)

The mixture of 2,4-dichloropyrimidine (2.0 g, 13.5 mmol, 1.0 equiv.), EtOH (6 mL) and 3-cyclopropyl-1H-pyrazol-5-amine (20.3 g, 20.3 mmol, 1.5 equiv.) was stirred at room temperature for 8 h. The reaction mixture was filtered to afford compound 2-chloro-N-(5-cyclopropyl-1H-pyrazol-3-yl)pyrimidin-4-amine (1.4 g, 45%).

The mixture of 2-chloro-N-(5-cyclopropyl-1H-pyrazol-3-yl)pyrimidin-4-amine (150 mg, 0.64 mmol, 1.0 equiv.), 3-aminobenzenesulfonamide (329 mg, 1.91 mmol, 3.0 equiv.), butan-1-ol (1 mL) and dioxane (0.5 mL) was stirred at 95° C. for 8 h. Then, the reaction mixture was cooled to room temperature and filtered. The residue was crystallized with methane/water/isopropyl ether to afford Compound 82 (7.7 mg, 3%). LC-MS (m/z): 372.1 [M+H]$^+$; $^1$H NMR (400 MHz, DMSO-$d_6$): δ 0.62-0.63 (m, 2H), 0.88-0.92 (m, 2H), 1.82-1.86 (m, 1H), 6.06 (bs, 1H), 6.49 (bs, 1H), 7.39 (s, 2H), 7.52 (d, J=1.8 Hz, 2H), 7.97 (s, 3H), 10.02 (s, 1H), 10.45 (bs, 1H), 12.27 (bs, 1H).

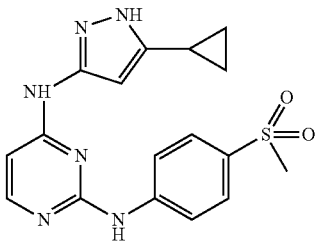

Compound 94

The procedure for preparing Compound 82 was used for the following compounds: Compounds 94, 120, 63, 57, 125, 60 and other structurally similar compounds.

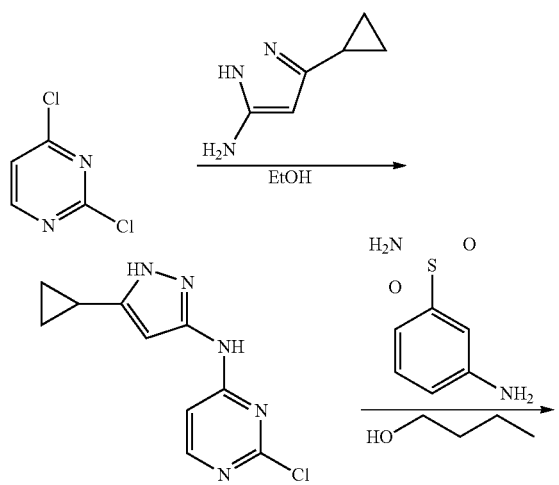

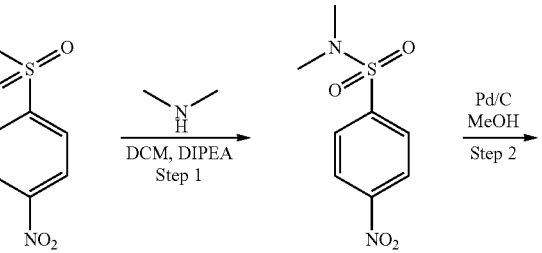

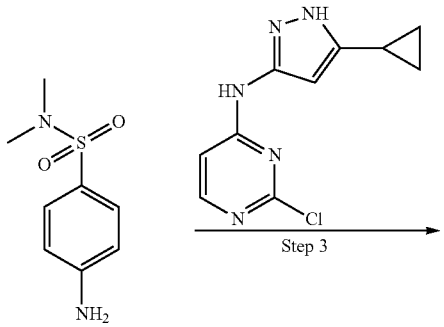
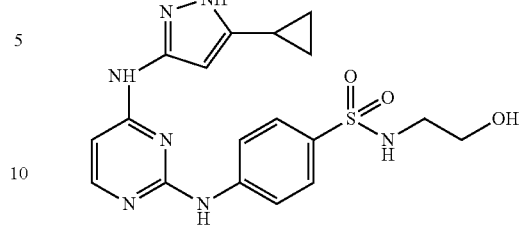

Compound 83

The procedure for preparing Compound 103 was used for the following compounds: Compounds 83, 112, 90, 100, 80, 76 and other structurally similar compounds.

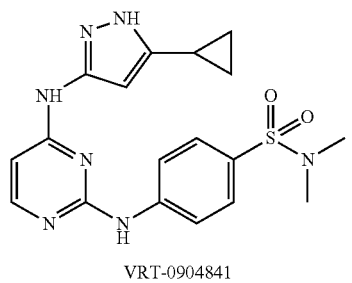

VRT-0904841

4-(4-(3-cyclopropyl-1H-pyrazol-5-ylamino)pyrimidin-2-ylamino)N,N-dimethylbenzenesulfonamide (Compound 103)

Step 1. To the solution of dimethylamine (284 mg, 6.3 mmol, 1.5 equiv.) and DIPEA (1 mL) in DCM (15 mL) was added dropwise a solution of 4-nitrobenzene-1-sulfonyl chloride (800 mg, 4.2 mmol, 1.0 equiv.) in DCM (5 mL). The reaction mixture was stirred at room temperature for 2 h. Then, the reaction mixture was washed with water and brine. The organic layers was dried ($Na_2SO_4$) and concentrated to get the residue, which was washed with isopropyl ether to afford compound N,N-dimethyl-4-nitrobenzenesulfonamide (879 mg, 91%).

Step 2. Under $H_2$, N,N-dimethyl-4-nitrobenzenesulfonamide (879 mg, 3.8 mmol, 1.0 equiv.) was catalytically hydrogenated in the presence of Pd/C (40 mg) in MeOH (25 mL). When no more $H_2$ was consumed, the reaction mixture was filtered. The filtrate was concentrated and crystallized to afford compound 4-amino-N,N-dimethyl benzenesulfonamide (722 mg, 95%).

Step 3. Compound 103 (25.0 mg, 9.8%) was prepared from 4-amino-N,N-dimethylbenzenesulfonamide as described in Compound 82 and purified by prep HPLC. LC-MS (m/z): 400.1 [M+H]$^+$; $^1$H NMR (400 MHz, DMSO-d$_6$): δ 0.69-0.73 (m, 2H), 0.91-0.96 (m, 2H), 1.86-1.90 (m, 1H), 2.58 (s, 6H), 6.28 (bs, 1H), 6.54 (bs, 1H), 7.60 (d, J=4.0 Hz, 2H), 8.04 (d, J=4.0 Hz, 3H), 9.66 (s, 2H), 12.08 (s, 1H).

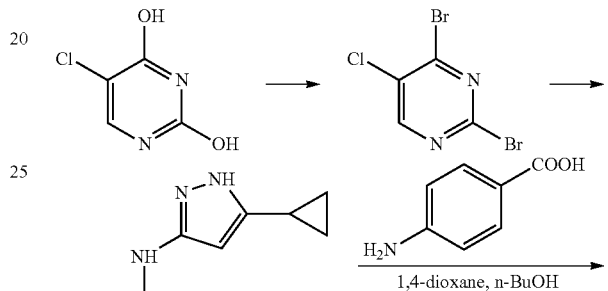

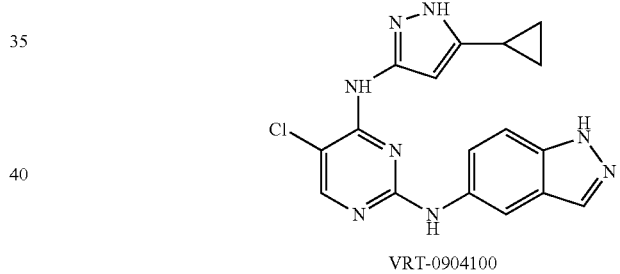

VRT-0904100

5-chloro-N4-(5-cyclopropyl-1H-pyrazol-3-yl)-N2-(1H-indazol-5-yl)pyrimidine-2,4-diamine (Compound 62)

Step 3. A mixture of 2-bromo-5-chloro-N-(5-cyclopropyl-1H-pyrazol-3-yl)pyrimidin-4-amine (300 mg, 0.95 mmol, 1 equiv.) and 1H-indazol-5-amine (380 mg, 2.86 mmol, 3 equiv.) in 1,4-dioxane (1 mL) and n-BuOH (0.5 mL) was heated to 100° C. The mixture was allowed over night (about 15 h). The mixture was filtered under reduced pressure to afford title compound 5-chloro-N4-(5-cyclopropyl-1H-pyrazol-3-yl)-N2-(1H-indazol-5-yl)pyrimidine-2,4-diamine (Compound 62) (60.5 mg, 17.3%) as solid. LC-MS (m/z) =350.0 [M+H]$^+$; $^1$H NMR (400 MHz, DMSO-d$_6$): δ 0.59 (s, 2H), 0.86 (d, J=6.4 Hz, 2H), 1.84 (m, 2H), 6.03 (m, 1H), 7.43 (s, 2H), 7.95 (s, 1H), 8.08 (s, 1H), 8.63 (s, 1H), 9.25 (s, 1H), 9.70 (s, 1H), 12.22 (s, 1H), 12.89 (s, 1H).

The procedure for preparing Compound 62 was used for the following compounds: Compounds 59, 73, 77, 84, 89 and other structurally similar compounds.

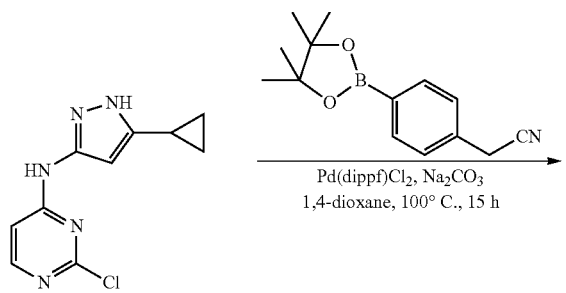

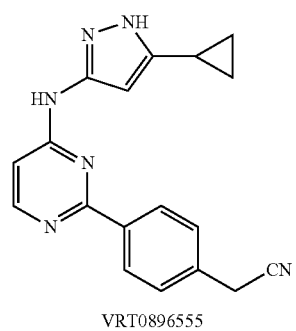

VRT0896555

2-(4-(4-(5-cyclopropyl-1H-pyrazol-3-ylamino)pyrimidin-2-yl)phenyl)acetonitrile (Compound 17)

A mixture of 2-chloro-N-(5-cyclopropyl-1H-pyrazol-3-yl)pyrimidin-4-amine (200 mg, 0.85 mmol, 1.0 equiv.), 2-(4-(4,4,5,5-tetramethyl-1,3,2-dioxaborolan-2-yl)phenyl)acetonitrile (250 mg, 1.0 mmol, 1.2 equiv.), Pd(dippf)Cl₂ (69.5 mg, 0.085 mmol, 0.1 equiv.), Na₂CO₃ (360.4 mg, 3.4 mmol, 4.0 equiv.), dioxane (5 ml) and water (1 ml) was added to the filtrate. The reaction mixture was heated to 100° C. for 15 h under nitrogen atmosphere. The residue was purified by silica gel chromatography (CH₂Cl₂/methanol 500:1 to 60:1) to afford title compound 2-(4-(4-(5-cyclopropyl-1H-pyrazol-3-ylamino)pyrimidin-2-yl)phenyl)acetonitrile (Compound 17) (28.6 mg, 10%) as solid. LC-MS (m/z)=317.1 [M+H]⁺;

¹H NMR (400 MHz, DMSO-d₆): δ 0.73 (m, 2H), 0.96 (m, 2H), 1.93 (m, 1H), 4.14 (s, 1H), 6.25 (s, 1H), 7.11 (s, 1H), 7.49 (d, J=8.4 Hz, 2H), 8.35 (m, 3H), 9.89 (s, 1H), 12.09 (s, 1H).

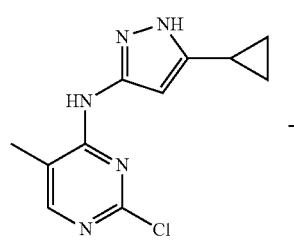

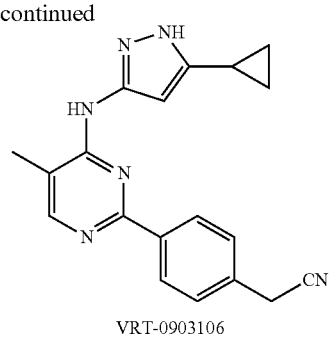

VRT-0903106

2-(4-(4-(5-cyclopropyl-1H-pyrazol-3-ylamino)-5-methylpyrimidin-2-yl)phenyl)acetonitrile (Compound 24)

Starting from 2-chloro-N-(5-cyclopropyl-1H-pyrazol-3-yl)-5-methylpyrimidin-4-amine, 2-(4-(4-(5-cyclopropyl-1H-pyrazol-3-ylamino)-5-methylpyrimidin-2-yl)phenyl)acetonitrile (Compound 24 (48.5 mg, 31.9%) was prepared as described in Compound 17. LC-MS (m/z)=331.1 [M+H]⁺; ¹H NMR (400 MHz, DMSO-d₆): δ 0.74 (d, J=3.6 Hz, 2H), 1.01 (m, 2H), 1.96 (d, J=4.8 Hz, 1H), 2.19 (s, 3H), 3.34 (s, 2H), 6.50 (s, 1H), 7.46 (d, J=8 Hz, 1H), 8.91 (s, 1H), 8.30 (d, J=8.4 Hz, 1H), 8.95 (s, 1H), 12.11 (s, 1H).

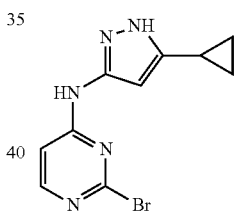

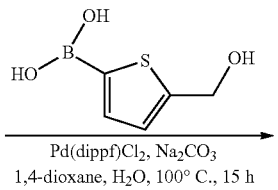

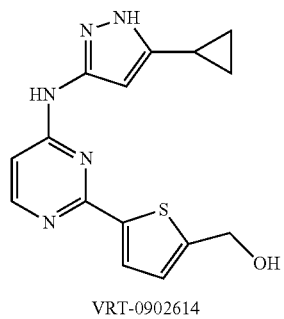

VRT-0902614

(5-(4-(5-cyclopropyl-1H-pyrazol-3-ylamino)pyrimidin-2-yl)thiophen-2-yl)methanol (Compound 22)

(5-(4-(5-cyclopropyl-1H-pyrazol-3-ylamino)pyrimidin-2-yl)thiophen-2-yl)methanol (Compound 22) (48.5 mg, 31.9%) was prepared as described in Compound 22. LC-MS (m/z)=314.1 [M+H]⁺; ¹H NMR (400 MHz, DMSO-d₆): δ 0.71 (m, 2H), 0.94 (m, 2H), 1.90 (m, 1H), 4.65 (d, J=5.6 Hz, 2H), 5.56 (t, J=5.6 Hz, 1H), 6.34 (s, 1H), 6.86 (s, 1H), 6.99 (d, J=2 Hz, 1H), 7.67 (d, J=2.8 Hz, 1H), 8.21 (d, J=4.8 Hz, 1H), 9.86 (s, 1H), 12.05 (s, 1H).

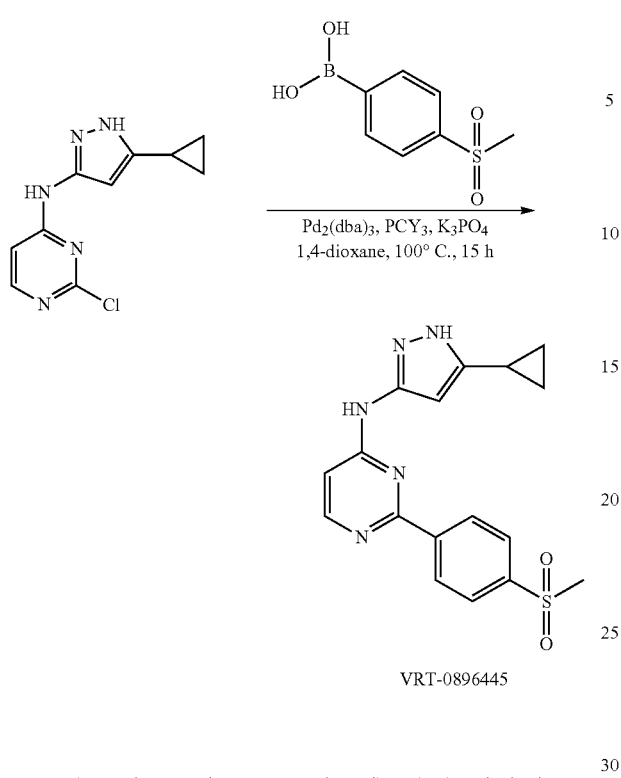

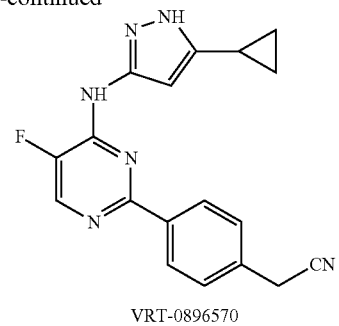

VRT-0896570

2-(4-(4-(5-cyclopropyl-1H-pyrazol-3-ylamino)-5-fluoropyrimidin-2-yl)phenyl)acetonitrile (Compound 19)

Starting from 2-chloro-N-(5-cyclopropyl-1H-pyrazol-3-yl)-5-fluoropyrimidin-4-amine, 2-(4-(4-(5-cyclopropyl-1H-pyrazol-3-ylamino)-5-fluoropyrimidin-2-yl)phenyl)acetonitrile (Compound 19) (18.9 mg, 14.3%) was prepared as described in Compound 15. LC-MS (m/z)=335.1[M+H]$^+$; $^1$H NMR (300 MHz, DMSO-d$_6$): δ 0.73 (m, 2H), 0.97 (m, 2H), 1.94 (m, 1H), 4.11 (s, 1H), 6.4 (s, 1H), 7.46 (d, J=8.4 Hz, 2H), 8.24 (d, J=8.1 Hz, 2H), 8.37 (d, J=3.9 Hz, 2H), 10.00 (s, 1H), 12.20 (s, 1H).

VRT-0896445

N-(5-cyclopropyl-1H-pyrazol-3-yl)-2-(4-(methylsulfonyl)phenyl)pyrimidin-4-amine (Compound 15)

A mixture of 2-chloro-N-(5-cyclopropyl-1H-pyrazol-3-yl)pyrimidin-4-amine (200 mg, 0.85 mmol, 1.0 equiv.), 4-(methylsulfonyl)phenylboronic acid (187 mg, 0.93 mmol, 1.1 equiv.), Pcy$_3$ (57 mg, 0.204 mmol, 0.24 equiv.), Pd$_2$(dpa)$_3$ (78 mg, 0.085 mmol, 0.1 equiv.), K$_3$PO$_4$ (722 mg, 3.4 mmol, 4 equiv.), dioxane (5 ml) and water (1 ml) was added to the filtrate. The reaction mixture was heated to 100° C. for 15 h under nitrogen atmosphere. The residue was purified by silica gel chromatography (CH$_2$Cl$_2$/methanol 500:1 to 100:1) to afford title compound N-(5-cyclopropyl-1H-pyrazol-3-yl)-2-(4-(methylsulfonyl)phenyl) pyrimidin-4-amine (Compound 15) (16.2 mg, 5.4%) as white solid. LC-MS (m/z)=356.0 [M+H]$^+$; $^1$H NMR (300 MHz, DMSO-d$_6$): δ 0.73 (m, 2H), 0.94 (m, 2H), 1.91 (m, 1H), 3.26 (s, 3H), 8.06 (d, J=8.7 Hz, 2H), 8.40 (d, J=6 Hz, 2H), 8.53 (d, J=8.4 Hz, 2H), 9.99 (s, 1H), 12.10 (s, 1H).

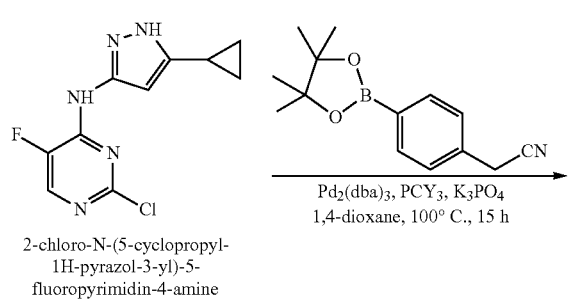

2-chloro-N-(5-cyclopropyl-1H-pyrazol-3-yl)-5-fluoropyrimidin-4-amine

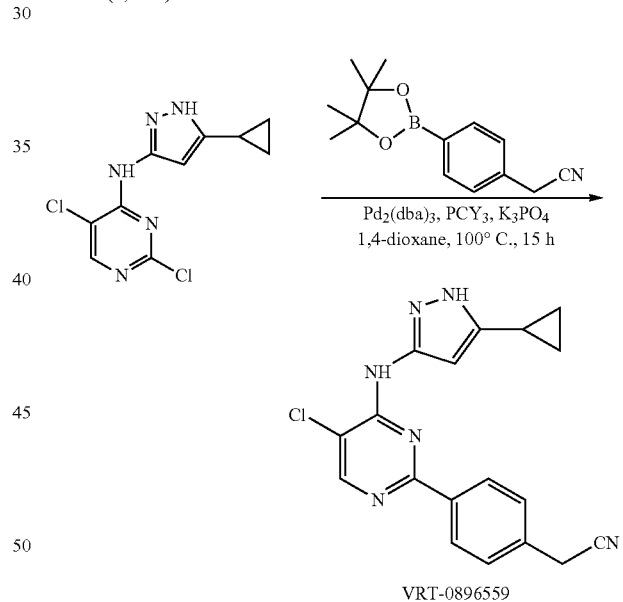

VRT-0896559

2-(4-(5-chloro-4-(5-cyclopropyl-1H-pyrazol-3-ylamino)pyrimidin-2-yl)phenyl) acetonitrile (Compound 18)

Starting from 2,5-dichloro-N-(5-cyclopropyl-1H-pyrazol-3-yl)pyrimidin-4-amine, 2-(4-(5-chloro-4-(5-cyclopropyl-1H-pyrazol-3-ylamino)pyrimidin-2-yl)phenyl) acetonitrile (Compound 18) (20 mg, 7.7%) was prepared as described in Compound 15. LC-MS (m/z)=351.0[M+H]$^+$; $^1$H NMR (400 MHz, DMSO-d$_6$): δ 0.75 (m, 2H), 1.00 (m, 2H), 1.98 (m, 1H), 4.13 (s, 1H), 6.41 (s, 1H), 7.48 (d, J=8.0 Hz, 2H), 8.27 (d, J=8.4 Hz, 2H), 8.49 (m, 3H), 9.26 (s, 1H), 12.29 (s, 1H).

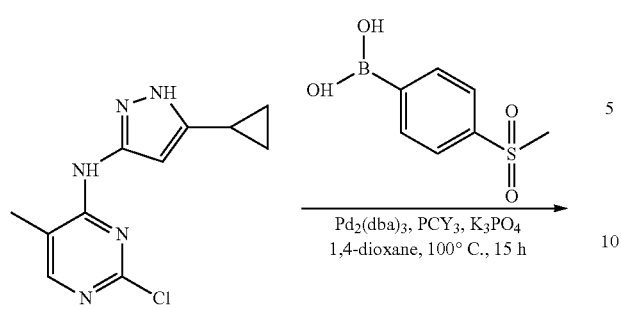

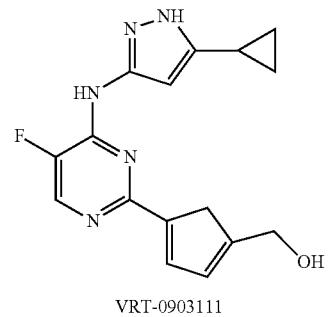

5-(4-(5-cyclopropyl-1H-pyrazol-3-ylamino)-5-fluoropyrimidin-2-yl)thiophen-2-yl)methanol (Compound 26)

A mixture of 2-chloro-N-(5-cyclopropyl-1H-pyrazol-3-yl)pyrimidin-4-amine (170 mg, 0.57 mmol, 1.0 equiv.), 5-(hydroxymethyl)thiophen-2-ylboronic acid (117 mg, 0.74 mmol, 1.3 equiv.), Pd(PPh$_3$)$_4$ (132.6 mg, 0.114 mmol, 0.2 equiv.), Na$_2$CO$_3$ (211 mg, 2 mmol, 3.5 equiv.), dioxane (5 ml) and water (1 ml) was added to the filtrate. The reaction mixture was heated to 100° C. for 15 h under nitrogen atmosphere. The residue was purified by silica gel chromatography (CH$_2$Cl$_2$/methanol 500:1 to 40:1) to afford title compound (5-(4-(5-cyclopropyl-1H-pyrazol-3-ylamino)-5-fluoropyrimidin-2-yl)thiophen-2-yl)methanol (Compound 26) (35.3 mg, 18.7%) as solid. LC-MS (m/z)=332.1 [M+H]$^+$; $^1$H NMR (400 MHz, DMSO-d$_6$): δ 0.73 (d, J=4 Hz, 2H), 0.94 (d, J=6.8 Hz, 2H), 1.94 (m, 1H), 4.64 (d, J=5.2 Hz, 2H), 5.59 (t, J=5.2 Hz, 1H), 6.55 (s, 1H), 6.98 (d, J=3.6 Hz, 1H), 7.59 (d, J=2.8 Hz, 1H), 8.26 (d, J=3.2 Hz, 1H), 10.04 (s, 1H), 12.19 (s, 1H).

The procedure for preparing Compound 26 was used for the following compounds: Compounds 36, 25 and other structurally similar compounds.

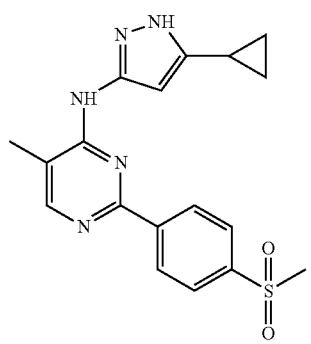

VRT-0896576

N-(5-cyclopropyl-1H-pyrazol-3-yl)-5-methyl-2-(4-(methylsulfonyl)phenyl)pyrimidin-4-amine Starting from 2-chloro-N-(5-cyclopropyl-1H-pyrazol-3-yl)-5-methylpyrimidin-4-amine, N-(5-cyclopropyl-1H-pyrazol-3-yl)-5-methyl-2-(4-(methylsulfonyl)phenyl)pyrimidin-4-amine (Compound 20) (57.3 mg, 19.4%) was prepared as described in Compound 15. LC-MS (m/z)=370.1[M+H]$^+$ $^1$H NMR (300 MHz, DMSO-d$_6$): δ 0.77 (d, J=3.6 Hz, 2H), 1.01 (m, 2H), 1.97 (m, 1H), 2.22 (s, 3H), 3.28 (s, 3H), 6.49 (s, 1H), 8.51 (d, J=8.4 Hz, 2H), 8.26 (s, 1H), 8.50 (d, J=8.4 Hz, 2H), 9.07 (s, 1H), 12.18 (s, 1H).

The procedure for preparing Compound 15 was used for the following compounds: Compounds 16, 23, and other structurally similar compounds.

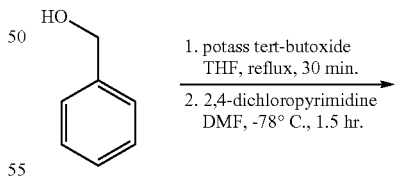

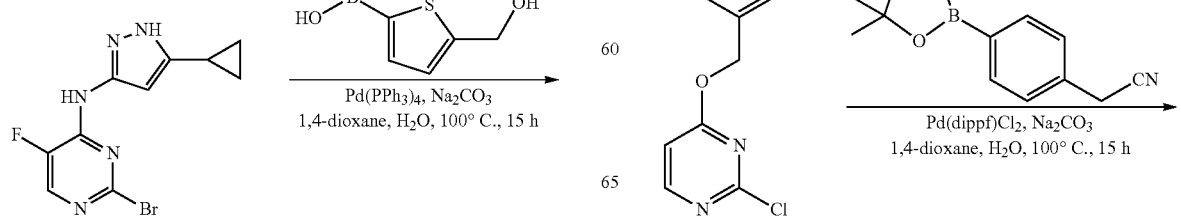

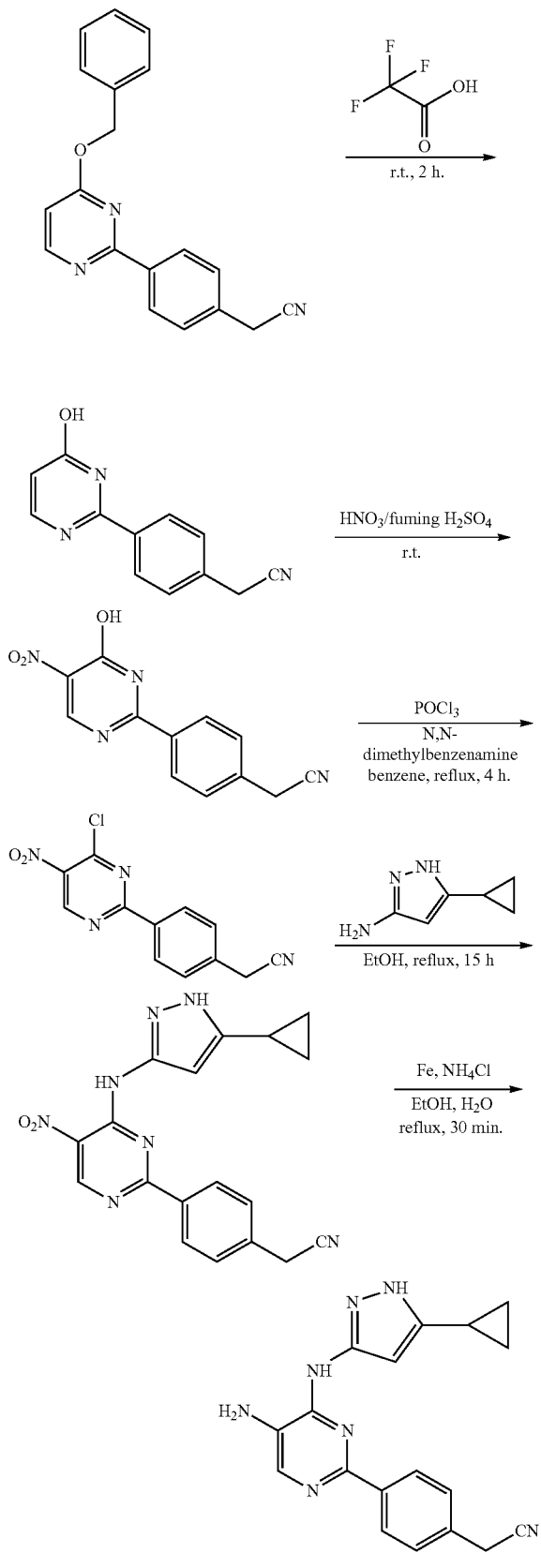

2-(4-(5-amino-4-(5-cyclopropyl-1H-pyrazol-3-ylamino)pyrimidin-2-yl)phenyl) acetonitrile (Compound 92)

Step 1. A mixture formed by 2.26 g (20.1 mmol, 1 equiv.) of potass tert-butoxide and 4.3 g (40.2 mmol, 2 equiv.) of compound phenylmethanol in 10 ml of THF was heated under reflux temperature for half an hour. The reaction mixture was cooled down to 0° C. and slowly added drop-wise to 3 g (20.1 mmol, 1 equiv.) of 2,4-dichloropyrimidine dissolved in 15 ml of N,N-dimethyl formamide, maintaining the temperature below −78° C. After stirring for one hour, it was left to reach room temperature. The mixture was added drop-wise to 100 ml of cold water, obtaining white solid 4-(benzyloxy)-2-chloropyrimidine (3.3 g, 75%). The compound was determination by LC-MS (LC-MS (m/z)=222.0 [M+H]$^+$)

Step 2. A mixture of 4-(benzyloxy)-2-chloropyrimidine (3.2 g, 14.5 mmol, 1.0 equiv.), 2-(4-(4,4,5,5-tetramethyl-1,3,2-dioxaborolan-2-yl)phenyl)acetonitrile (4.2 g, 17.4 mmol, 1.2 equiv.), Pd(dippf)Cl$_2$ (1.18 g, 1.45 mmol, 0.1 equiv.), Na$_2$CO$_3$ (6.1 g, 58 mmol, 4.0 equiv.), dioxane (5 ml) and water (1 ml) was added to the filtrate. The reaction mixture was heated to 100° C. for 15 h under nitrogen atmosphere. The residue was purified by silica gel chromatography (CH$_2$Cl$_2$/methanol 500:1 to 200:1) to afford 2-(4-(4-(benzyloxy)pyrimidin-2-yl)phenyl)acetonitrile (1.3 g, 31%) as white solid. The title compound was determination by LC-MS (LC-MS (m/z)=302.1 [M+H]$^+$).

Step 3. A mixture of 2-(4-(4-(benzyloxy)pyrimidin-2-yl)phenyl)acetonitrile (1.2 g) in 2,2,2-trifluoroacetic acid (15 ml) was stirred at room temperature for 2 h. Then, the solvent was removed under reduce pressure. The product was washed by ether to afford 2-(4-(4-hydroxypyrimidin-2-yl)phenyl)acetonitrile (1.02 g, 85%) as white solid. The title compound was determination by LC-MS (LC-MS (m/z)=212.1 [M+H]$^+$)

Step 4. A mixture of fuming nitric acid (5 ml), and concentrated sulphuric acid (5 ml) was cooled down in an ice/salt bath to 0° C. 2-(4-(4-hydroxypyrimidin-2-yl)phenyl)acetonitrile (1 g) was added portion-wise over about 45 min. and maintained the temperature below 10° C. After stirring for a further 3 h at room temperature, the mixture was poured onto crushed ice. The product was filtered under reduce pressure. The resulting 2-(4-(4-hydroxy-5-nitropyrimidin-2-yl)phenyl)acetonitrile (70 mg, 5.8%) was purified by pre-HPLC to afford title compound as white solid. (LC-MS (m/z)=257.1 [M+H]$^+$)

Step 5. A mixture of phosphorous oxychloride (126 mg, 0.819 mmol, 3 equiv.) and N,N-dimethylaniline in benzene (66 mg, 546 mmol, 2 equiv.) were stirred in a round-bottomed flask. 2-(4-(4-Hydroxy-5-nitropyrimidin-2-yl)phenyl)acetonitrile (70 mg, 0.273 mmol, 1 equiv.) was added slowly over about 15-30 min. The mixture was refluxed for 4 h. Then, the reaction mixture was cooled down and poured onto crushed ice and the mixture extracted with ethyl acetate (10 ml×3). The combined extracts were washed with brine, dried over Na$_2$SO$_4$ and filtered. Ethyl acetate was removed under reduce pressure. The target compound 2-(4-(4-chloro-5-nitropyrimidin-2-yl)phenyl)acetonitrile (55 mg, 73.3%) was determination by LC-MS (LC-MS (m/z)=276.0 [M+H]$^+$).

Step 6. A mixture of 2-(4-(4-chloro-5-nitropyrimidin-2-yl)phenyl)acetonitrile (55 mg, 0.2 mmol, 1 equiv.) and 5-cyclopropyl-1H-pyrazol-3-amine (37 mg, 0.3 mmol, 1.5 equiv.) in ethanol (2 ml) was stirred at 85° C. for 15 h. Ethanol was remove under reduce pressure. The residue was purified by silica gel chromatography (CH$_2$Cl$_2$/methanol 500:1 to 100:1) to afford 2-(4-(4-(5-cyclopropyl-1H-pyrazol-3-ylamino)-5-nitropyrimidin-2-yl)phenyl)acetonitrile (45 mg, 62%) as solid. The compound was determination by LC-MS (LC-MS (m/z)=362.1 [M+H]$^+$).

Step 7. To a solid mixture of 2-(4-(4-(5-cyclopropyl-1H-pyrazol-3-ylamino)-5-nitropyrimidin-2-yl)phenyl)acetonitrile 45 mg, 0.125 mmol, 1 equivalent) and NH$_4$Cl (3.6 g, 1.375 mmol, 11 equiv) was added EtOH (4 ml) and H$_2$O (2 mL). The reaction mixture was heated to reflux under nitrogen atmosphere and iron powder (25 mg, 0.438 mmol, 3.5 equiv.) was added. The resulting mixture was continued to reflux for 0.5 h. The mixture was filtered immediately with a hot filter under reduced pressure. EtOH and water were removed under reduce pressure. The residue was washed by water. The title compound 2-(4-(5-amino-4-(5-cyclopropyl-1H-pyrazol-3-ylamino)pyrimidin-2-yl)phenyl) acetonitrile (Compound 92) (10 mg, 24.4%) was obtained. LC-MS (m/z) =332.1 [M+H]$^+$; $^1$H NMR (400 MHz, DMSO-d$_6$): δ 0.71 (s, 2H), 0.93 (s, 2H), 1.92 (s, 1H), 3.83 (s, 2H), 5.30 (s, 2H), 6.21 (s, 2H), 7.04 (s, 1H), 7.21 (d, J=6.0 Hz, 1H), 7.53 (s, 1H), 7.70 (s, 1H), 8.30 (s, 1H), 9.78 (s, 1H), 12.03 (s, 1H).

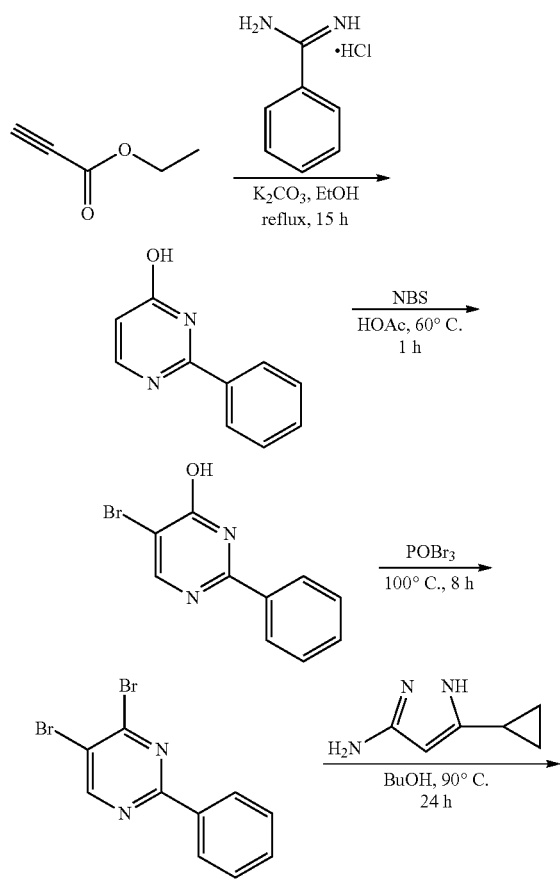

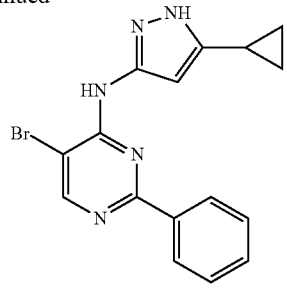

VRT-0895496

5-Bromo-N-(5-cyclopropyl-1H-pyrazol-3-yl)-2-phenylpyrimidin-4-amine (Compound 8)

Benzamide hydrochloride (10 g, 64 mmol, 1 equiva.), ethyl propioloate (6.26 g, 64 mmol, 1 eq), potassium carbonate (8.85 g, 64 mmol, 1 eq) and ethanol (200 mL) were mixed and heated to reflux for 15 h under nitrogen atmosphere. After cooling to rt, the mixture was filtered. The filtrate was concentrated under vacuum and the residue was dissolved in water (75 mL). The solution was taken to pH with conc.HCl and filtered, the solid was washed with water and dried to give 2-phenylpyrimidin-4-ol (6.2 g, 56.1%) as white solid. LC-MS (m/z): 173 [M+H]$^+$.

To a solution of 2-phenylpyrimidin-4-ol (1.0 g, 5.8 mmol, 1 eq) in acetic acid (20 mL) was added NBS (1.0 g, 5.8 mmol, 1 eq) and heated at 60° C. for 1 h. The reaction solution was concentrated in vacuo and the residue was purified by silica gel chromatography (CH$_2$Cl$_2$/MeOH=97/3 as eluant) to obtain 5-bromo-2-phenylpyrimidin-4-ol (1.1 g, 75.8%) as a white solid. LC-MS (m/z): 251.1 [M+H]$^+$. $^1$H NMR (400 MHz, DMSO-d$_6$): δ 7.35-7.51 (m, 3H), 8.10-8.18 (m, 2H), 8.46 (s, 1H), 13.32 (s, 1H).

A mixture of 5-bromo-2-phenylpyrimidin-4-ol (1.67 g, 6.67 mmol, 1.0 equiv.) and POBr$_3$ (100 g) was heated at 100° C. for 8 hours. The solution was cooled down to 55° C. and poured into ice-water while stirring vigorously. The mixture was maintained below 25° C. during the quench. The reaction mixture was extracted with CH$_2$Cl$_2$. The combined organic layer was washed (cold water), dried (Na$_2$SO$_4$), evaporated and the residue was purified by silica gel chromatography (hexane) to afford 4,5-dibromo-2-phenyl pyrimidine (1.3 g, 70.5%). LC-MS (m/z): 315.1 [M+H]$^+$. $^1$H NMR (400 MHz, CDCl$_3$): δ 7.47-7.50 (m, 3H), 8.37-8.40 (m, 2H), 8.91 (s, 1H).

To a solution of 4,5-dibromo-2-phenylpyrimidine (0.82 g, 3.29 mmol, 1.0 eq) in n-BuOH (20 mL), 3-cyclopropyl-1H-pyrazol-5-amine (0.811 g, 6.58 mmol, 2 equiv.) was added and the reaction mixture was heated to 90° C. for 24 hours, filtered to produce 5-Bromo-N-(5-cyclopropyl-1H-pyrazol-3-yl)-2-phenylpyrimidin-4-amine (Compound 8) (0.75 g, 64.1%). LC-MS (m/z): 357.2 [M+H]$^+$. $^1$H NMR (300 MHz, DMSO-d$_6$): δ 0.74-0.77 (m, 2H), 0.98-1.02 (m, 2H), 1.96-2.01 (m, 1H), 6.40 (s, 2H), 7.50-7.54 (m, 3H), 8.27-8.30 (m, 2H), 8.63 (s, 1H), 8.88 (s, 2H), 12.32 (s, 1H).

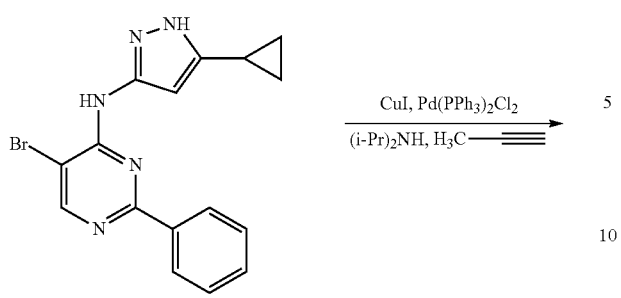

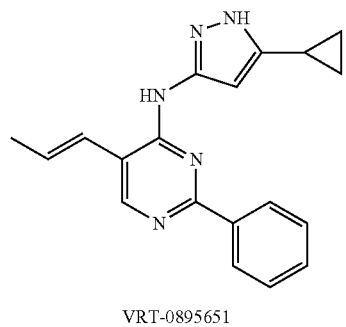

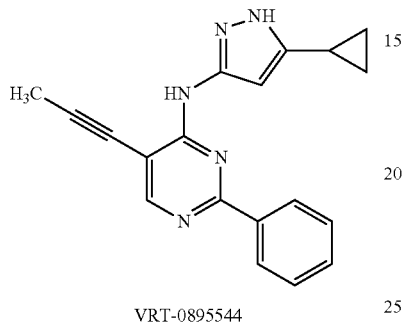

VRT-0895544

VRT-0895651

N-(5-cyclopropyl-1H-pyrazol-3-yl)-2-phenyl-5-(prop-1-ynyl)pyrimidin-4-amine (Compound 9)

Under nitrogen, prop-1-yne was bubbled into a mixture of 5-bromo-N-(5-cyclopropyl-1H-pyrazol-3-yl)-2-phenylpyrimidin-4-amine (0.2 g, 0.56 mmol, 1 equiv.), PdCl$_2$(PPh$_3$)$_2$ (0.02 g, 0.028 mmol, 0.05 equiv.), CuI (0.011 g, 0.056 mmol, 0.1 equiv.), i-Pr$_2$NH (0.125 g, 1.29 mmol, 2.3 equiv.) and DMF (10 mL). The reaction mixture was heated at 65° C. for 13 h. Without further workup, the reaction mixture was purified by silica gel chromatography (CH$_2$Cl$_2$/MeOH=20:1 as eluent) to get afford N-(5-cyclopropyl-1H-pyrazol-3-yl)-2-phenyl-5-(prop-1-ynyl)pyrimidin-4-amine (Compound 9) (25 mg, 14.2%) as white solid. LC-MS (m/z):316.1 [M+H]$^+$. $^1$H NMR (300 MHz, DMSO-d$_6$): δ 0.83-0.86 (m, 2H), 1.03-1.06 (m, 2H), 2.03-2.09 (m, 1H), 2.44 (s, 3H), 6.39 (d, J=2.1 Hz, 1H), 6.56 (s, 1H), 7.45-7.52 (m, 3H), 8.35-8.38 (m, 2H), 9.03 (s, 1H), 12.86 (s, 1H).

(E)-N-(5-cyclopropyl-1H-pyrazol-3-yl)-2-phenyl-5-(prop-1-enyl)pyrimidin-4-amine (Compound 11)

The mixture of 5-bromo-N-(5-cyclopropyl-1H-pyrazol-3-yl)-2-phenylpyrimidin-4-amine (0.3 g, 0.84 mmol, 1.0 equiv.), (E)-tributyl(prop-1-enyl)stannane (0.5 g, 1.5 mmol, 1.5 eq), Bu$_4$NBr (0.32 g, 0.84 mmol, 1.0 eq), Pd(PPh$_3$)$_2$Cl$_2$ (0.1 g, 0.034 mmol, 0.04 eq) and dioxane (10 mL) was heated to reflux for 18 h. Then, silica gel was added to the reaction mixture and evaporated to dry. The residue was purified by silica gel chromatography (hexane/EtOAc/Et$_3$N=100:100:1 as eluent) to generate (E)-N-(5-cyclopropyl-1H-pyrazol-3-yl)-2-phenyl-5-(prop-1-enyl)pyrimidin-4-amine (Compound 11) (0.1 g, 37.5%). LC-MS (m/z): 357.2 [M+H]$^+$. $^1$H NMR (300 MHz, DMSO-d$_6$): δ 0.71-0.72 (m, 2H), 0.94-1.02 (m, 2H), 1.74-1.80 (m, 3H), 1.87-1.96 (m, 1H), 5.98 (d, J=11.4 Hz, 1H), 6.48 (d, J=11.4 Hz, 1H), 7.47-7.49 (m, 3H), 8.24-8.32 (m, 2H), 8.71 (s, 1H), 12.12 (s, 1H).

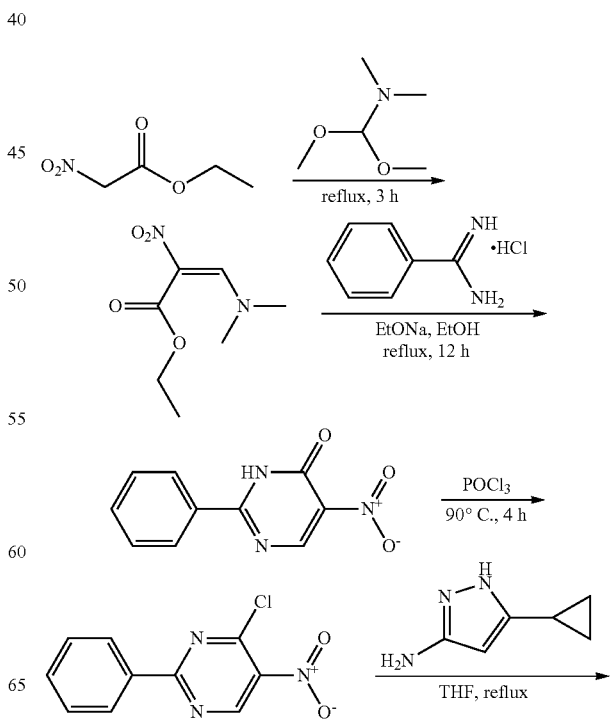

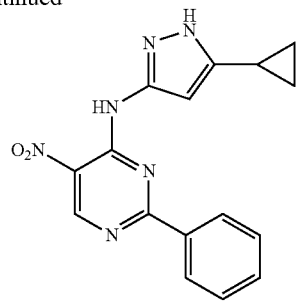

VRT-0895221

N-(5-cyclopropyl-1H-pyrazol-3-yl)-5-nitro-2-phenylpyrimidin-4-amine (Compound 6)

To a mixture of EtONa (10.1 g, 148.2 mmol, 2.0 eq) and anhydrous ethanol (150 mL) was added benzamidine hydrochloride (11.7 g, 74.7 mmol, 1.0 eq) at 0° C. The mixture was stirred at 0° C. for 30 minutes, and thereto was added dropwise a solution of (E)-ethyl 3-(dimethylamino)-2-nitroacrylate (14.0 g), which was obtained by heating a mixture of ethyl nitroacetate (10 g, 75.1 mmol, 1.0 equiv.) and dimethoxy-N,N-dimethylmethanamine (14 g, 117.5 mmol, 1.6 equiv.) under reflux for 3 hours, followed by concentrating the mixture under reduced pressure in anhydrous ethanol (35 mL) at the same temperature. After the addition, the mixture was stirred at room temperature for 30 minutes and refluxed for 12 hours. The reaction mixture is concentrated under reduced pressure, and the resultant was added water (135 mL). To the mixture, was added dropwise conc. hydrochloric acid at 0° C., until the pH value of the mixture is adjusted to 4. The precipitate are collected by filtration, washed with water, and recrystallized from ethanol to give the desired compound 5-nitro-2-phenylpyrimidin-4(3H)-one (4.95 g, 30.2%). LC-MS (m/z):218.1 [M+H]$^+$.

A mixture of 5-nitro-2-phenylpyrimidin-4(3H)-one (1.0 g) and phosphorus oxychloride (10 mL) was stirred at 90° C. for 4 hours. After cooling, the reaction mixture was concentrated under reduced pressure, and the residue was dissolved in chloroform. The mixture was neutralized with 1 N aqueous sodium hydroxide solution. The chloroform layer was separated, dried over anhydrous sodium sulfate and concentrated under reduced pressure. The residue is recrystalized from ethanol to give the desired product 4-chloro-5-nitro-2-phenylpyrimidine (800 mg, 73.7%). LC-MS (m/z):236.5 [M+H]$^+$.

To a suspension of 4-chloro-5-nitro-2-phenylpyrimidine (800 mg, 3.40 mmol, 1.0 eq) in CHCl$_3$ (20 mL) was added 5-cyclopropyl-1H-pyrazol-3-amine (832 mg, 6.80 mmol, 2.0 eq). The reaction mixture was stirred for 6 hours at 23° C. The precipitate was filtered and recrystallized to give the desired product N-(5-cyclopropyl-1H-pyrazol-3-yl)-5-nitro-2-phenylpyrimidin-4-amine (Compound 6) (500 mg, 45.7%). LC-MS (m/z): 323.0 [M+H]$^+$. $^1$H-NMR (300 MHz, DMSO-d$_6$): δ 0.73-0.78 (m, 2H), 0.96-1.01 (m, 2H), 1.96-2.01 (m, 1H), 6.53 (s, 1H), 7.55-7.63 (m, 3H), 8.35-8.38 (m, 2H), 9.33 (s, 1H), 10.26 (s, 1H), 12.50 (s, 1H).

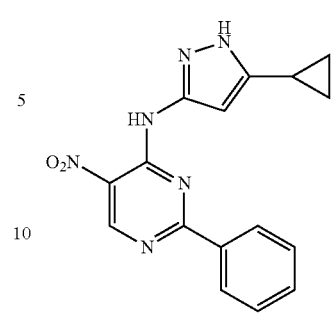

NH$_4$Cl, EtOH, THF
H$_2$O, Fe, reflux, 1 h

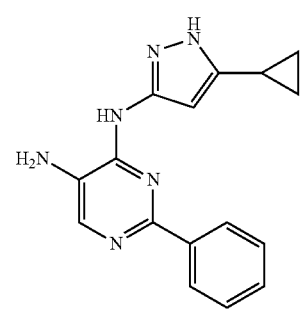

VRT-0895220

N-(5-cyclopropyl-1H-pyrazol-3-yl)-2-phenylpyrimidine-4,5-diamine (Compound 5)

A mixture of N-(5-cyclopropyl-1H-pyrazol-3-yl)-5-nitro-2-phenylpyrimidin-4-amine (500 mg, 1.55 mmol, 1.0 eq), NH$_4$Cl (1.0 g, 19.39 mmol, 12.5 eq), EtOH (12 mL), THF (12 mL) and H$_2$O (5 mL) was heated to reflux. Iron powder (0.59 g, 10.54 mmol, 6.8 eq) was added in three portions over 15 minutes under N$_2$ atmosphere. The resulting mixture was continued to reflux for 1 hour, cooled down to 23° C., diluted with CH$_2$Cl$_2$ and filtered through celite. The organic phase was washed (brine), dried (Na2SO4), filtered and concentrated to give target product N-(5-cyclopropyl-1H-pyrazol-3-yl)-2-phenylpyrimidine-4,5-diamine (Compound 5) (350 mg, 38.6%). LC-MS (m/z)=293.1 [M+H]$^+$. $^1$H-NMR (300 MHz, DMSO-d$_6$): δ 0.71-0.72 (m, 2H), 0.95-1.00 (m, 2H), 1.92-1.95 (m, 1H), 5.29 (s, 2H), 6.59 (s, 1H), 7.31-7.43 (m, 3H), 7.81 (s, 1H), 8.18 (d, J=6.9 Hz, 2H), 8.81 (s, 1H), 12.02 (s, 1H).

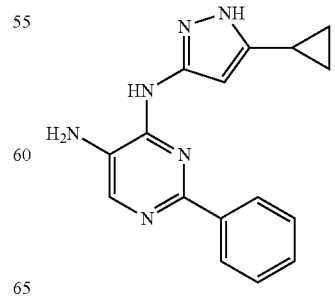

VRT-0895220

Ac$_2$O
r.t., 10 h

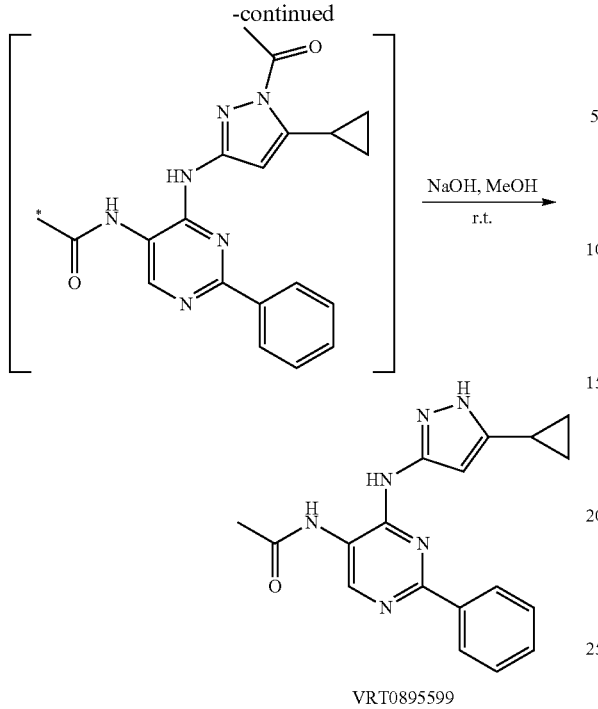

VRT0895599

N-(4-(5-cyclopropyl-1H-pyrazol-3-ylamino)-2-phenylpyrimidin-5-yl)acetamide (Compound 10)

A mixture of N-(5-cyclopropyl-1H-pyrazol-3-yl)-2-phenylpyrimidine-4,5-diamine (350 mg, 1.19 mmol, 1.0 eq) and Ac$_2$O (12 mL) was stirred at rt for 3 h and concentrated. The residue was dissolved in MeOH (3 mL). Sat. aqueous NaOH was added dropwise until pH=12 and stirred for 10 minutes. The final mixture was concentrated and purified by silica gel chromatography (hexane/EtOAc=10:1 as eluent)) to obtain target product N-(4-(5-cyclopropyl-1H-pyrazol-3-ylamino)-2-phenylpyrimidin-5-yl)acetamide.

(Compound 10) (101 mg, 25.4%). LC-MS (m/z)=335.2 [M+H]$^+$. $^1$H-NMR (300 MHz, DMSO-d$_6$): δ 0.68-0.75 (m, 2H), 0.91-1.00 (m, 2H), 1.90-1.97 (m, 1H), 2.10 (s, 3H), 6.51 (s, 1H), 7.49 (s, 3H), 8.24-8.29 (m, 2H), 8.51 (s, 1H), 9.24 (s, 1H), 9.44 (s, 1H), 12.15 (s, 1H).

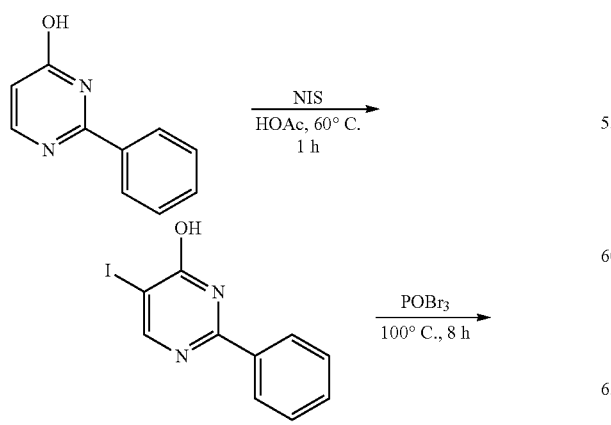

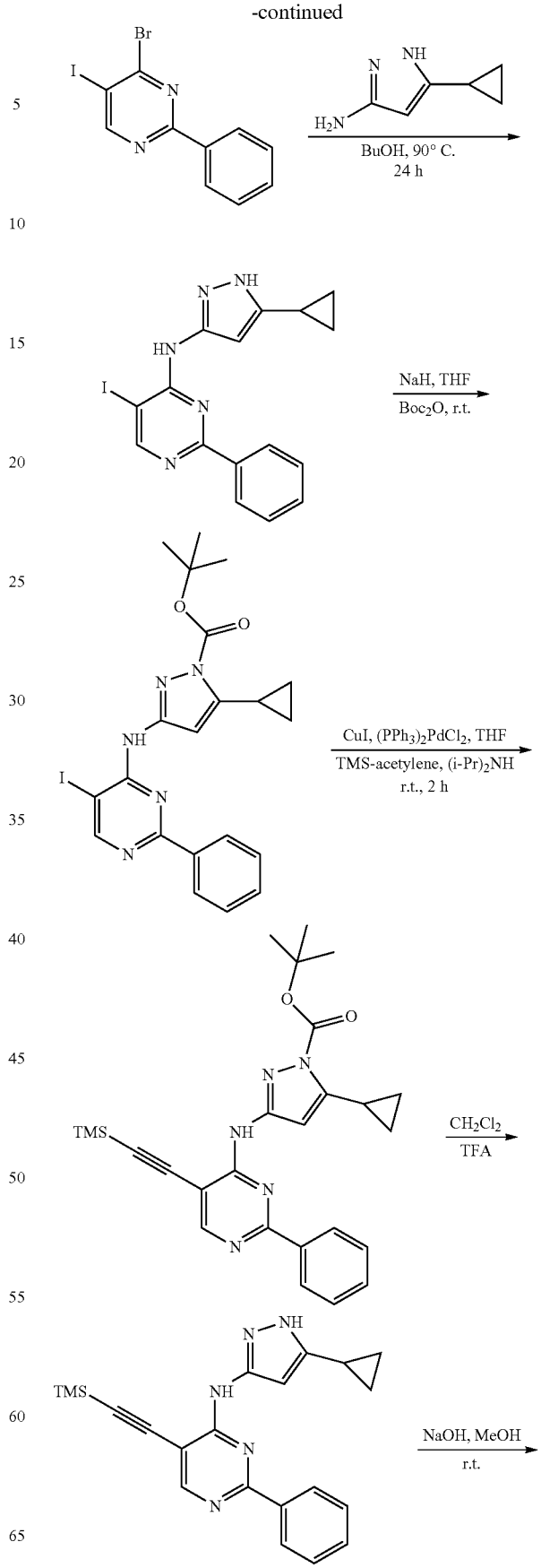

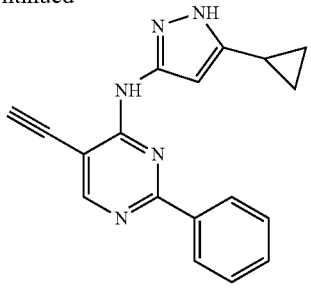

VRT-0895847

N-(5-cyclopropyl-1H-pyrazol-3-yl)-5-ethynyl-2-phenylpyrimidin-4-amine (Compound 14)

To a solution of 2-phenylpyrimidin-4-ol (1.0 g, 5.8 mmol, 1 eq) in acetic acid (20 mL), was added NIS (1.3 g, 5.8 mmol, 1 eq), then heated at 50° C. for 1 h. The reaction solution was concentrated in vacuo and the residue was purified by silica gel chromatography (CH$_2$Cl$_2$/MeOH=97/3 as eluant) to obtain 5-iodo-2-phenylpyrimidin-4-ol (1.2 g, 69.8%) as a white solid. LC-MS (m/z): 298.9 [M+H]$^+$. $^1$H NMR (400 MHz, DMSO-d$_6$): δ 7.35-7.51 (m, 3H), 8.10-8.18 (m, 2H), 8.43 (s, 1H), 13.32 (s, 1H).

A mixture of 5-iodo-2-phenylpyrimidin-4-ol (1.97 g, 6.67 mmol, 1.0 eq) and POBr$_3$ (100 g) was heated to 100° C. for 8 hours. The solution was cooled down to 55° C. and poured into ice-water while stirring vigorously. The mixture was maintained below 25° C. during the quench. The reaction mixture was extracted with CH$_2$Cl$_2$. The organic layer was washed (cold water), dried (Na$_2$SO$_4$), evaporated and purified by silica gel chromatography (hexane as eluent) to afford 4-bromo-5-iodo-2-phenylpyrimidine (1.5 g, 62.5%). LC-MS (m/z): 360.8 [M+H]$^+$. $^1$H NMR (400 MHz, CDCl$_3$): δ 7.47-7.50 (m, 3H), 8.37-8.40 (m, 2H), 8.91 (s, 1H).

To a solution of 4-bromo-5-iodo-2-phenylpyrimidine (1.18 g, 3.29 mmol, 1.0 equiv.) in n-BuOH (20 mL) was added 3-cyclopropyl-1H-pyrazol-5-amine (0.811 g, 6.58 mmol, 2 equ). After heating at 90° C. for 24 hours, the reaction was filtered to afford N-(5-cyclopropyl-1H-pyrazol-3-yl)-5-iodo-2-phenylpyrimidin-4-amine (0.85 g, 88.7%). LC-MS (m/z): 404.1 [M+H]$^+$. $^1$H NMR (300 MHz, DMSO-d$_6$): δ 0.74-0.77 (m, 2H), 0.98-1.02 (m, 2H), 1.96-2.01 (m, 1H), 6.40 (s, 2H), 7.50-7.54 (m, 3H), 8.27-8.30 (m, 2H), 8.63 (s, 1H), 8.88 (s, 2H), 12.32 (s, 1H).

To the solution of N-(5-cyclopropyl-1H-pyrazol-3-yl)-5-iodo-2-phenylpyrimidin-4-amine (0.4 g, 0.99 mmol, 1.0 eq) in dry THF (50 mL), NaH (0.4 g, 60% dispersion in oil, 10.0 mmol, 10.0 eq) was added by portions. The reaction mixture was stirred at rt for 1 h. Then, BOC$_2$O (0.26 mL, 1.19 mmol, 1.2 eq) was added to the reaction mixture and the resulting reaction was stirred at rt for 2 h. CH$_2$Cl$_2$ was added and organic layer was washed (water), dried and concentrated. The residue was purified by silica gel chromatography (hexane as eluent) to afford tert-butyl 5-cyclopropyl-3-(5-iodo-2-phenylpyrimidin-4-ylamino)-1H-pyrazole-1-carboxylate (0.32 g, 60.3%). LC-MS (m/z): 504.1 [M+H]$^+$. $^1$H NMR (400 MHz, CDCl$_3$): δ 0.81-0.85 (m, H), 1.09-1.15 (m, 2H), 1.67 (s, 1H), 2.49 (m, 1H), 6.86 (s, 2H), 7.50-7.60 (m, 3H), 8.41-8.44 (m, 2H), 9.40 (s, 1H), 10.46 (s, 2H).

Under nitrogen, to the mixture of tert-butyl 5-cyclopropyl-3-(5-iodo-2-phenylpyrimidin-4-ylamino)-1H-pyrazole-1-carboxylate (245 mg, 0.49 mmol, 1.0 equiv), PdCl$_2$(PPh$_3$)$_2$ (40 mg, 0.057 mmol, 0.12 equiv.), CuI (22 mg, 0.115 mmol, 0.23 equiv.), i-Pr$_2$NH (1.7 mL, 11.78 mmol, 24 equiv.) and THF (10 mL), TMS-acetylene (3.5 mL, 25 mmol, 51 equiv.) were added. After stirring at r.t. for 2 h, silica gel was added to the reaction mixture and the solvents were removed. The residue was purified by silica gel chromatography (hexane/EtOAc=3:1 as eluant) afford tert-butyl 5-cyclopropyl-3-(2-phenyl-5-((trimethylsilyl)ethynyl) pyrimidin-4-ylamino)-1H-pyrazole-1-carboxylate (276 mg, 98%). LC-MS (m/z): 474.2 [M+H]$^+$. To the solution of tert-butyl 5-cyclopropyl-3-(2-phenyl-5-((trimethylsilyl)ethynyl)pyrimidin-4-ylamino)-1H-pyrazole-1-carboxylate (276 mg, 0.58 mmol, 1 equiv.) in CH$_2$Cl$_2$ (2 mL) was added TFA (2 mL). After 10 min at rt, the reaction mixture was concentrated to generate crude N-(5-cyclopropyl-1H-pyrazol-3-yl)-2-phenyl-5-((trimethylsilyl)ethynyl)pyrimidin-4-amine, which was used in next step without further purification. LC-MS (m/z): 374.2 [M+H]$^+$.

To the solution of crude N-(5-cyclopropyl-1H-pyrazol-3-yl)-2-phenyl-5-((trimethylsilyl)ethynyl) pyrimidin-4-amine in MeOH (3 mL), 20% NaOH was added until the pH was adjusted to 12. After stirring at rt for 15 min, the reaction mixture was evaporated to dryness and purified by silica gel chromatography (hexane/EtOAc=3:1-1:1 as eluent) to afford N-(5-cyclopropyl-1H-pyrazol-3-yl)-5-ethynyl-2-phenylpyrimidin-4-amine (Compound 14) (71 mg, 48%). LC-MS (m/z): 302.1 [M+H]$^+$. $^1$H NMR (300 MHz, DMSO-d$_6$): δ 0.71-0.76 (m, 2H), 0.94-1.01 (m, 2H), 1.90-1.99 (m, 1H), 6.18-6.28 (bs, 1H), 7.06-7.10 (bs, 1H), 7.51-7.53 (m, 3H), 8.34-8.39 (m, 3H), 9.86 (s, 1H), 12.10 (s, 1H).

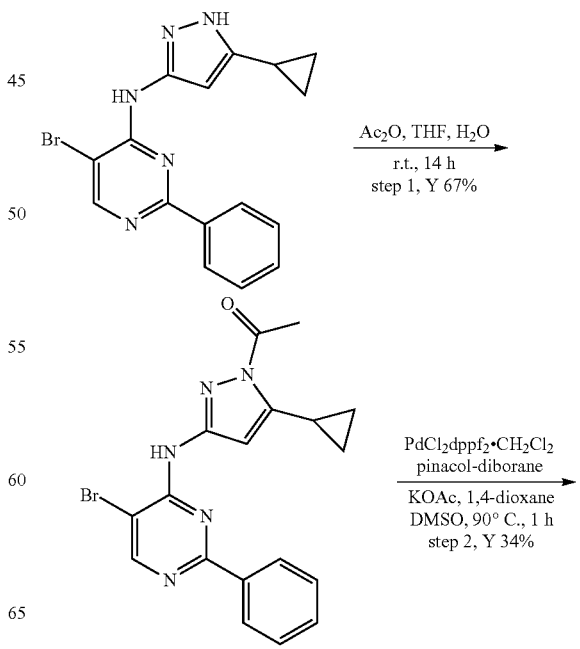

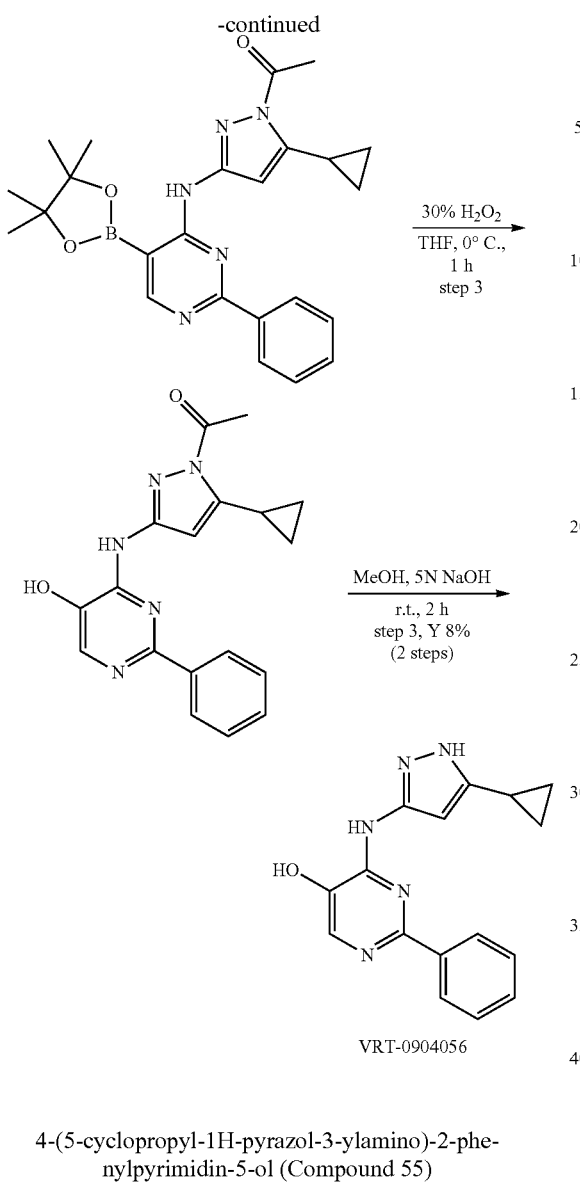

4-(5-cyclopropyl-1H-pyrazol-3-ylamino)-2-phenylpyrimidin-5-ol (Compound 55)

Step 1. To the mixture of 5-bromo-N-(5-cyclopropyl-1H-pyrazol-3-yl)-2-phenylpyrimidin-4-amine (200 mg, 0.56 mmol, 1.0 eq) in THF (8 mL) and water (5 mL) was added a solution of Ac₂O (0.18 mL, 1.68 mmol, 3.0 eq) in THF (2 mL). The reaction mixture was stirred for 14 hours and water was added. The mixture was filtered and the solid was washed with water and dried by co-evaporated with ethanol to give 1-(3-(5-bromo-2-phenylpyrimidin-4-ylamino)-5-cyclopropyl-1H-pyrazol-1-yl)ethanone (150 mg, 67%). LC-MS (m/z)=398.0, 400.0 [M+H]⁺.

Step 2. A flask charged with 1-(3-(5-bromo-2-phenylpyrimidin-4-ylamino)-5-cyclopropyl-1H-pyrazol-1-yl)ethanone (600 mg, 1.51 mmol), pinacol-dibrane (765 mg, 3.01 mmol, 2.0 eq), KOAc (440 mg, 4.52 mmol, 3.0 eq) and Pd(dppf)₂Cl₂ (369 mg, 0.45 mmol, 0.3 eq) was flushed with nitrogen followed by the addition of 1,4-dioxane (12 mL). The mixture was stirred at 90° C. for 2 hours, cooled to room temperature and diluted with EtOAc. The mixture was filtered over a pad of silica gel. The filtrate was concentrated. To the residue, petroleum ether was added. The solid was filtered off. The filtrate was concentrated. The residue was recrystallized with methanol to produce 1-(5-cyclopropyl-3-(2-phenyl-5-(4,4,5,5-tetramethyl-1,3,2-dioxaborolan-2-yl)pyrimidin-4-ylamino)-1H-pyrazol-1-yl)ethanone (230 mg, 34%). LC-MS (m/z)=446.2 [M+H]⁺.

Step 3. 30% H₂O₂ (10 mL) was added to the solution of 1-(5-cyclopropyl-3-(2-phenyl-5-(4,4,5,5-tetramethyl-1,3,2-dioxaborolan-2-yl)pyrimidin-4-ylamino)-1H-pyrazol-1-yl)ethanone (200 mg, 0.45 mmol, 1.0 eq) in THF (5 mL) at 0° C. The mixture was stirred for 1 h and water was added. The solid was collected and dissolved in methanol (8 mL). To the solution was added 5 N NaOH (4 mL). The mixture was stirred for 2 h at room temperature and concentrated. To the residue was added ethanol and EtOAc. The emerged solid was filtered off. The filtrate was concentrated and the residue was recrystallized with CH₂Cl₂ and ethyl ether to give 4-(5-cyclopropyl-1H-pyrazol-3-ylamino)-2-phenylpyrimidin-5-ol (Compound 55) (10 mg, 8% over 2 steps). LC-MS (m/z)=294.0 [M+H]⁺. ¹H NMR (400 MHz, DMSO-d₆): δ 0.69-0.74 (m, 2H), 0.93-0.98 (m, 2H), 1.85-1.89 (m, 1H), 6.52 (bs, 1H), 7.40-7.47 (m, 3H), 7.93 (s, 1H), 8.22 (d, J=7.6 Hz, 2H), 8.41 (bs, 1H), 10.43 (bs, 1H), 12.09 (bs, 1H).

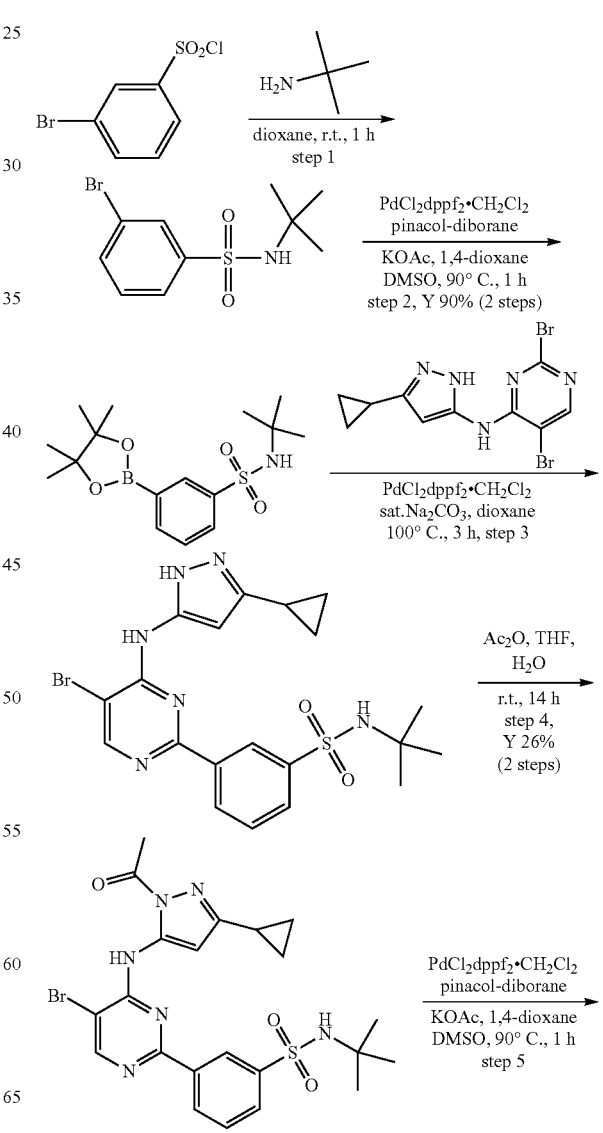

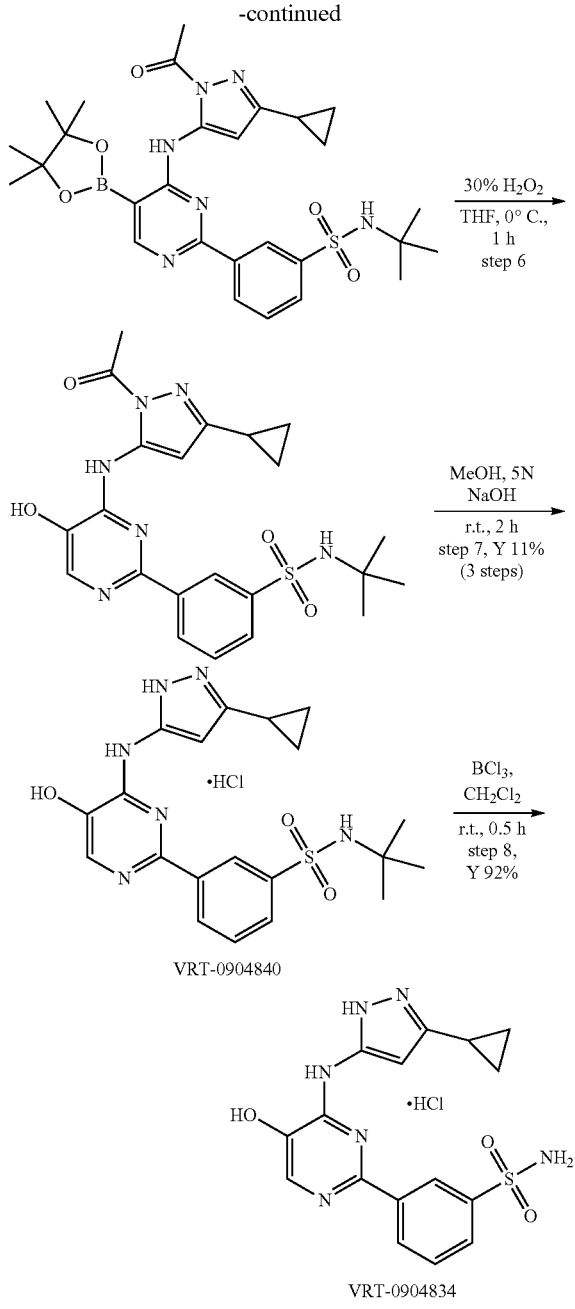

N-tert-butyl-3-(4-(3-cyclopropyl-1H-pyrazol-5-ylamino)-5-hydroxypyrimidin-2-yl)benzene sulfonamide (Compound 102) and 3-(4-(3-cyclopropyl-1H-pyrazol-5-ylamino)-5-hydroxypyrimidin-2-yl) benzenesulfonamide (Compound 99)

Step 1. A mixture of 3-bromobenzene-1-sulfonyl chloride (2 g, 7.83 mmol, 1.0 eq) and 2-methylpropan-2-amine (1.72 g, 23.5 mmol, 3.0 eq) in dioxane (50 mL) was stirred at room temperature for 1 hours and filtered. The filtrate was concentrated in vacuo to afford 3-bromo-N-tert-butylbenzenesulfonamide (all for the next step). LCMS: 291.9, 293.9 [M+H]+.

Step 2. A flask charged with 3-bromo-N-tert-butylbenzenesulfonamide obtained in step 1 (2.3 g, 7.83 mmol, 1.0 eq), pinacol-dibrane (3.98 g, 15.66 mmol, 2.0 eq), KOAc (2.31 g, 23.49 mmol, 3.0 eq) and Pd (dppf)$_2$Cl$_2$ (640 mg, 0.78 mmol, 0.1 eq) was flushed with nitrogen followed by the addition of 1,4-dioxane (20 mL). The mixture was stirred and heated to 90° C. for 2 hours, cooled to room temperature and diluted with EtOAc. The mixture was filtered over a pad of silica gel. The filtrate was concentrated. To the residue, petroleum ether was added. The emerged solid was filtered off. The filtrate was concentrated. The residue was purified by silica gel chromatography to give N-tert-butyl-3-(4,4,5,5-tetramethyl-1,3,2-dioxaborolan-2-yl)benzenesulfonamide (2.32 g, 90% over 2 steps). LC-MS (m/z)=284.1 [M−56+H]+.

Step 3. The mixture of N-tert-butyl-3-(4,4,5,5-tetramethyl-1,3,2-dioxaborolan-2-yl)benzenesulfonamide (1.49 g, 4.4 mmol, 1.1 eq), 2,5-dibromo-N-(3-cyclopropyl-1H-pyrazol-5-yl)pyrimidin-4-amine (1.44 g, 4.0 mmol, 1.0 eq), Pd (dppf)$_2$Cl$_2$ (640 mg, 0.78 mmol, 0.1 eq) and saturated aqueous Na$_2$CO$_3$ (4 mL) in 1,4-dioxane (20 mL) was stirred at 100° C. for 3 hours under N$_2$. The reaction mixture was cooled down to room temperature and partitioned between EtOAc and water. The organic layer was concentrated and the residue was purified by silica gel chromatography to give the compound 4 (all for the next step). LC-MS (m/z)=491.1 [M+H]+.

Step 4. 3-(4-(1-acetyl-3-cyclopropyl-1H-pyrazol-5-ylamino)-5-bromopyrimidin-2-yl)-N-tert-butylbenzene sulfonamide (550 mg, 26% over 2 steps) was prepared as described in step 1 of the previous example. LC-MS (m/z)=533.0, 535.0 [M+H]+.

Step 5. 3-(4-(1-acetyl-3-cyclopropyl-1H-pyrazol-5-ylamino)-5-(4,4,5, 5-tetramethyl-1,3,2-dioxaborolan-2-yl) pyrimidin-2-yl)-N-tert-butylbenzenesulfonamide (all for the next step) was prepared as described in step 2 of the previous example. LC-MS (m/z)=581.3 [M+H]+.

Step 6. 3-(4-(1-acetyl-3-cyclopropyl-1H-pyrazol-5-ylamino)-5-hydroxypyrimidin-2-yl)-N-tert-butylbenzenesulfonamide (all for the next step) was prepared as described in step 3 of the previous example. LC-MS (m/z)=471.2 [M+H]+.

Step 7. N-tert-butyl-3-(4-(3-cyclopropyl-1H-pyrazol-5-ylamino)-5-hydroxypyrimidin-2-yl)benzenesulfonamide (Compound 102) (50 mg, 11% over 3 steps) was prepared as described in step 3 of the previous example. LC-MS (m/z)=429.1 [M+H]+. $^1$H NMR (400 MHz, DMSO-d$_6$): δ 0.76-0.80 (m, 2H), 0.92-0.97 (m, 2H), 1.11 (s, 9H), 1.90-1.94 (m, 1H), 6.48 (s, 1H), 7.60 (s, 1H), 7.68 (dd, J=7.6 Hz, 7.6 Hz, 1H), 7.88 (d, J=7.6 Hz, 1H), 7.95 (s, 1H), 8.47 (d, J=7.6 Hz, 1H), 8.70 (s, 1H), 8.90 (bs, 1H), 10.76 (bs, 1H).

Step 8. To a solution of N-tert-butyl-3-(4-(3-cyclopropyl-1H-pyrazol-5-ylamino)-5-hydroxypyrimidin-2-yl)benzenesulfonamide (Compound 102) (25 mg, 0.053 mmol, 1.0 equiv.) in CH$_2$Cl$_2$ (5 mL) was added BCl$_3$ (1.5 mL, 1.48 mmol, 28.0 equiv.) at room temperature. The mixture was stirred for 0.5 hours, then, concentrated. The residue was recrystallized with methanol and isopropyl ether to give 3-(4-(3-cyclopropyl-1H-pyrazol-5-ylamino)-5-hydroxypyrimidin-2-yl)benzenesulfonamide (Compound 99) (20 mg, 92%). LC-MS (m/z)=373.1 [M+H]+. $^1$H NMR (400 MHz, DMSO-d$_6$): δ 0.75-0.83 (m, 2H), 0.92-0.99 (m, 2H), 1.87-1.99 (m, 1H), 6.47 (s, 1H), 7.47 (s, 2H), 7.76 (dd, J=8.0 Hz, 8.0 Hz, 1H), 7.95-7.98 (m, 2H), 7.76 (d, J=8.0 Hz, 1H), 8.67 (s, 1H), 9.88 (bs, 1H), 11.54 (bs, 1H).

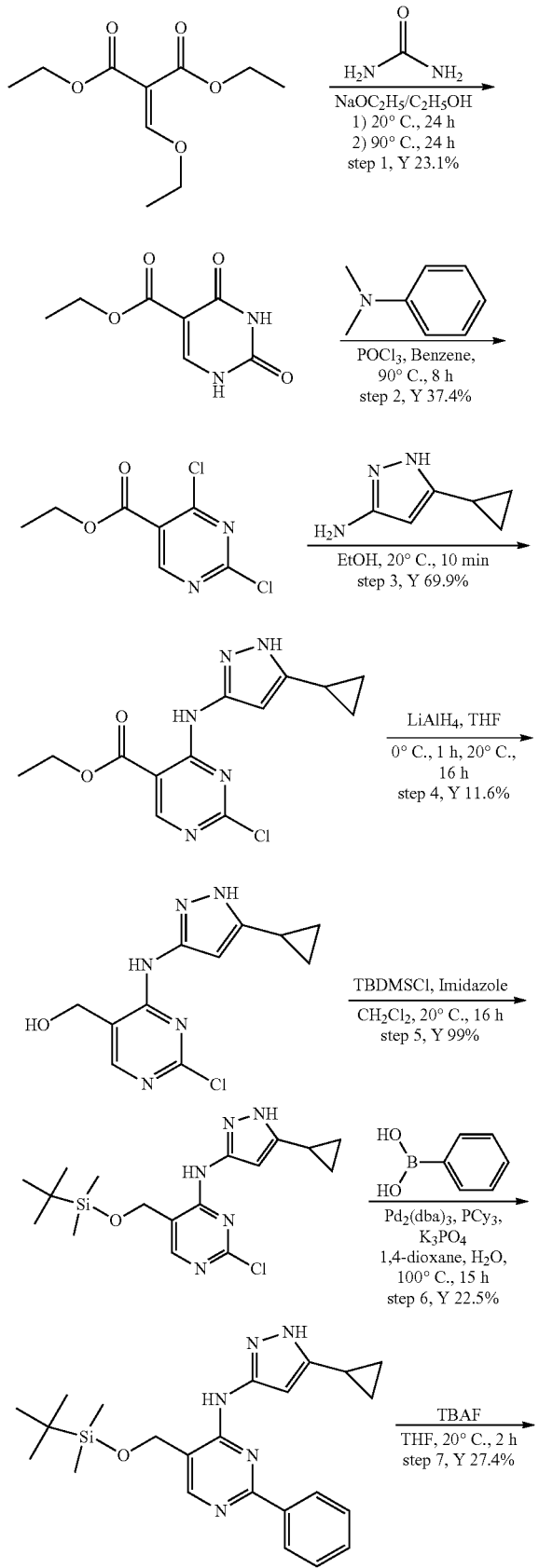

4-(5-cyclopropyl-1H-pyrazol-3-ylamino)-2-phenylpyrimidin-5-yl)methanol (Compound 123)

Step 1. Urea (12 g, 200 mmol) was added to EtOH (300 mL) containing NaOC$_2$H$_5$ previously prepared from sodium (5.52 g, 240 mmol, 1.2 eq). Diethyl 2-(ethoxymethylene) malonate (43.2 g, 200 mmol, 1.0 eq) was added and the solution was stirred at 20° C. for 24 h, and then stirred at 90° C. for 24 h. The alcohol was removed by reduced pressure distillation. Ice-water (100 mL) was added to dissolve the residue. The product was precipitated by adding cold dilute hydrochloric acid. The solid was filtered off to afford ethyl 2,4-dioxo-1,2,3,4-tetrahydropyrimidine-5-carboxylate (8.5 g, 23%), which was used in next step without further purification.

Step 2. A mixture of ethyl 2,4-dioxo-1,2,3,4-tetrahydropyrimidine-5-carboxylate obtained in step 1 (8.5 g, 46.2 mmol, 1.0 eq), N,N-dimethylbenzenamine (1.12 g, 9.24 mmol, 0.2 eq), POCl$_3$ (21.25 g, 138.6 mmol, 3.0 eq) in benzene (300 mL) was stirred at 90° C. under a nitrogen atmosphere for 8 h. The reaction mixture was allowed to cool to room temperature and throw into ice (300 g). The mixture was extracted by EtOAc (2×300 mL). The combined organic phases were washed (brine), dried (Na$_2$SO$_4$), filtered and concentrated. The residue was purified by silica gel chromatography (PE/EtOAc=500:1 to 15:1 as eluent) to afford ethyl 2,4-dichloropyrimidine-5-carboxylate (3.83 g, 37%) as white solid. LC-MS (m/z)=220.9 [M+H]$^+$.

Step 3. A mixture of ethyl 2,4-dichloropyrimidine-5-carboxylate (3.6 g, 16.3 mmol, 1.0 equiv.) and 5-cyclopropyl-1H-pyrazol-3-amine (3.0 g, 24.45 mmol, 1.5 equiv.) in EtOH (6 mL) was stirred at 20° C. under a nitrogen atmosphere for 10 min. The reaction mixture was filtered and the solid was washed by EtOH (10 mL) and MeOH (3 mL) to afford ethyl 2-chloro-4-(5-cyclopropyl-1H-pyrazol-3-ylamino)pyrimidine-5-carboxylate (3.5 g, 70%) as a white solid. LC-MS (m/z)=308.1 [M+H]$^+$.

Step 4. To a solution of ethyl 2-chloro-4-(5-cyclopropyl-1H-pyrazol-3-ylamino)pyrimidine-5-carboxylate (3.5 g, 11.4 mmol, 1.0 eq) in anhydrous THF (50 mL), LiAlH$_4$ (1.3 g, 34.2 mmol, 3.0 eq) was added portionwise under 0° C. (ice bath). The mixture was stirred at 0° C. for 1 h and 20° C. for 16 h. Ice-water (50 mL) was added and the resulting mixture was extracted by EtOAc (4×50 mL). The combined organic phases were washed (brine), dried (Na$_2$SO$_4$), filtered and concentrated. The residue was purified by silica gel chromatography (CH$_2$Cl$_2$/MeOH 500:1 to 15:1 as eluent) to afford (2-chloro-4-(5-cyclopropyl-1H-pyrazol-3-ylamino)pyrimidin-5-yl)methanol (350 mg, 12%) as white solid. LC-MS (m/z)=266.0 [M+H]$^+$.

Step 5. A mixture of (2-chloro-4-(5-cyclopropyl-1H-pyrazol-3-ylamino)pyrimidin-5-yl)methanol (350 mg, 1.32 mmol), imidazole (107.6 mg, 1.58 mmol, 1.2 eq), TBDMSCl (238 mg, 1.58 mmol, 1.2 eq) in CH$_2$Cl$_2$ (10 mL) was stirred at 20° C. for 16 h. Water (30 mL) was added and the reaction was extracted with CH$_2$Cl$_2$ (4×30 mL). The combined organic phases were washed (brine), dried (Na$_2$SO$_4$), filtered and concentrated to afford 5-((tert-butyldimethylsilyloxy)methyl)-2-chloro-N-(5-cyclopropyl-1H-pyrazol-3-yl)pyrimidin-4-amine (500 mg, 99%). LC-MS (m/z)=380.0 [M+H]$^+$.

Step 6. A mixture of 5-((tert-butyldimethylsilyloxy)methyl)-2-chloro-N-(5-cyclopropyl-1H-pyrazol-3-yl)pyrimidin-4-amine (200 mg, 0.53 mmol, 1.0 eq), phenylboronic acid (90.5 mg, 0.742 mmol, 1.4 eq), Pd$_2$(dba)$_3$ (48.5 mg, 0.053 mmol, 0.1 equiv.), tricyclohexylphosphine (35.7 mg, 0.127 mmol, 0.24 equiv.), K$_3$PO$_4$ (450 mg, 2.12 mmol, 4 eq) in 1,4-dioxane (20 mL) and water (4 mL) was stirred at 100° C. under a nitrogen atmosphere for 15 h. The reaction mixture was allowed to cool to room temperature and concentrated to give a residue, which was purified by silica gel chromatography (CH$_2$Cl$_2$/MeOH 500:1 to 100:1 as eluent) to afford 5-((tert-butyldimethylsilyloxy)methyl)-N-(5-cyclopropyl-1H-pyrazol-3-yl)-2-phenylpyrimidin-4-amine (50 mg, 22.5%) as a solid. LC-MS (m/z)=422.2 [M+H]$^+$.

Step 7. To a solution of 5-((tert-butyldimethylsilyloxy)methyl)-N-(5-cyclopropyl-1H-pyrazol-3-yl)-2-phenylpyrimidin-4-amine (50 mg, 0.119 mmol, 1.0 eq) in anhydrous THF (2 mL), TBAF (0.5 mL, 0.5 mmol, 4.2 equiv., 1M in THF) was added dropwise. The reaction mixture was stirred at 20° C. for 2 h and then concentrated to give a residue. The residue was purified by silica gel chromatography (CH$_2$Cl$_2$/MeOH 500:1 to 20:1 as eluent) to afford title compound (4-(5-cyclopropyl-1H-pyrazol-3-ylamino)-2-phenylpyrimidin-5-yl)methanol (Compound 123) (10 mg, 27.4%) as yellowish solid. LC-MS (m/z)=308.1 [M+H]$^+$. $^1$H NMR (400 MHz, DMSO-d$_6$): δ 0.74-0.75 (m, 2H), 0.97-0.99 (m, 2H), 1.96-1.98 (m, 1H), 4.59 (s, 2H), 5.63 (s, 1H), 6.56 (s, 1H), 7.51 (m, 3H), 8.32 (m, 3H), 8.83 (s, 1H), 12.15 (s, 1H).

3-(4-(5-cyclopropyl-1H-pyrazol-3-ylamino)-5-(hydroxymethyl)pyrimidin-2-yl)benzenesulfonamide (Compound 124)

N-tert-butyl-3-(5-(((tert-butyldimethylsilyloxy)methyl)-4-(5-cyclopropyl-1H-pyrazol-3-ylamino)pyrimidin-2-yl)benzenesulfonamide (400 mg, 91%) was prepared as described in Step 6 of the previous example. LC-MS (m/z)=557.2 [M+H]$^+$.

A mixture of N-tert-butyl-3-(5-(((tert-butyldimethylsilyloxy)methyl)-4-(5-cyclopropyl-1H-pyrazol-3-ylamino)pyrimidin-2-yl)benzenesulfonamide (400 mg, 0.718 mmol), BCl$_3$/CH$_2$Cl$_2$ (10 mL, 10 mmol, 13.9 eq, 1 M) in CH$_2$Cl$_2$ (10 mL) was stirred at 20° C. under a nitrogen atmosphere for 30 h. Water (50 mL) was added into the mixture. The mixture was extracted with EtOAc (3×50 mL). The combined organic phases were washed (sat NaHCO$_3$, brine), dried (Na$_2$SO$_4$), filtered and concentrated. The residue was purified by silica gel chromatography (CH$_2$Cl$_2$/MeOH 500:1 to 15:1 as eluent) to afford compound 3-(4-(5-cyclopropyl-1H-pyrazol-3-ylamino)-5-(hydroxymethyl)pyrimidin-2-yl)benzenesulfonamide (Compound 124) (28 mg, 10%) as yellowish solid. LC-MS (m/z)=387.1 [M+H]$^+$. $^1$H NMR (400 MHz, DMSO-d$_6$): δ 0.81-0.82 (m, 2H), 0.94-0.98 (m, 2H), 1.92-1.95 (m, 1H), 4.61 (d, J=5.2 Hz, 2H), 5.65 (t, J=5.2 Hz, 1H), 6.54 (s, 1H), 7.44 (s, 2H), 7.72 (t, J=8 Hz, 1H), 7.95 (d, J=7.6 Hz, 1H), 8.35 (d, J=5.6 Hz, 1H), 8.51 (d, J=7.6 Hz, 1H), 8.84 (s, 1H), 8.92 (s, 1H), 12.18 (s, 1H).

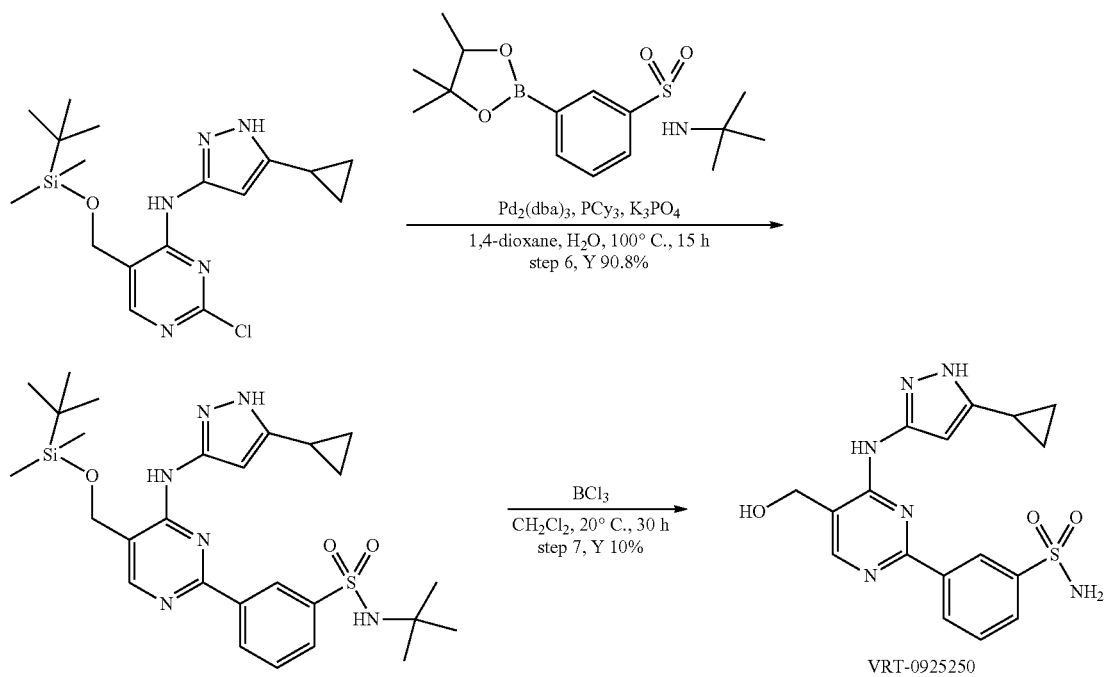

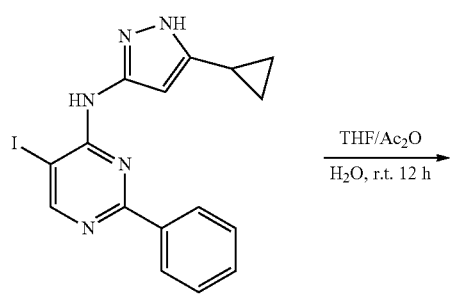

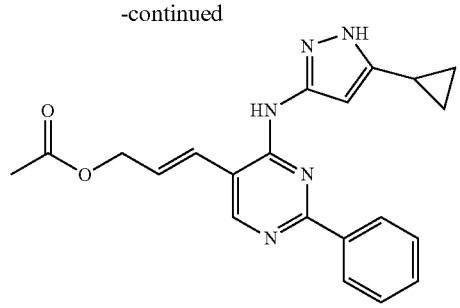

VRT-0904583

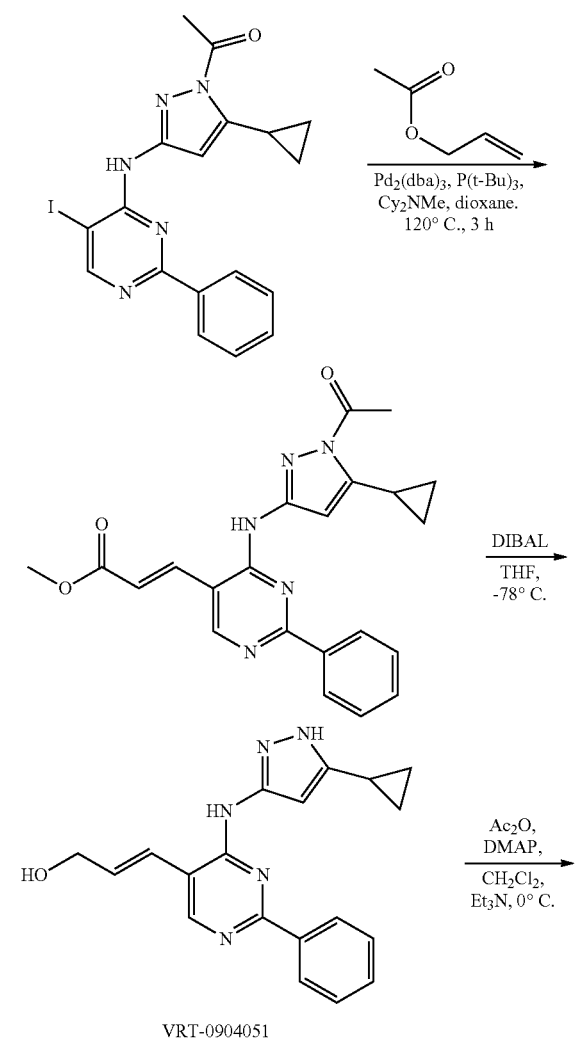

VRT-0904051

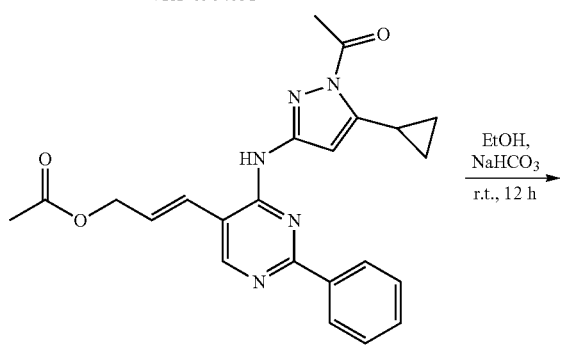

(E)-3-(4-(5-cyclopropyl-1H-pyrazol-3-ylamino)-2-phenylpyrimidin-5-yl)prop-2-en-1-ol (Compound 53) and (E)-3-(4-(5-cyclopropyl-1H-pyrazol-3-ylamino)-2-phenylpyrimidin-5-yl)allyl acetate (Compound 81)

To the solution of N-(5-cyclopropyl-1H-pyrazol-3-yl)-5-iodo-2-phenylpyrimidin-4-amine (3 g, 7.44 mmol) in THF/H₂O (50 mL/25 mL), a solution of Ac₂O (1.5 g, 14.88 mmol, 2.0 equiv.) in THF (5 mL) was added dropwise. The reaction mixture was stirred at room temperature for 12 h. The reaction mixture was filtered to afford compound 1-(5-cyclopropyl-3-(5-iodo-2-phenylpyrimidin-4-ylamino)-1H-pyrazol-1-yl)ethanone (2.2 g, 66%). LC-MS (m/z): 446.0 [M+H]⁺.

A mixture of 1-(5-cyclopropyl-3-(5-iodo-2-phenylpyrimidin-4-ylamino)-1H-pyrazol-1-yl)ethanone (3 g, 6.72 mmol, 1.0 equiv.), methyl acrylate (2.28 g, 26.8 mmol, 4.0 equiv.), Pd₂(dba)₃ (600 mg, 0.6 mmol, 0.1 equiv.), Cy₂NMe (1.35 g, 7.2 mmol, 1.1 equiv.) and P(t-Bu)₃ (540 mg, 2.4 mmol, 0.4 equiv.) in dioxane (100 mL) was heated to 120° C. for 3 h under nitrogen atmosphere. Then, the reaction mixture was cooled to room temperature and filtered. The residue was crystallized with methane/diisopropyl ether to afford (E)-methyl 3-(4-(1-acetyl-5-cyclopropyl-1H-pyrazol-3-ylamino)-2-phenylpyrimidin-5-yl)acrylate (200 mg, 7.3%). LC-MS (m/z): 404.1 [M+H]⁺. ¹H NMR: (400 MHz, DMSO-d₆) δ 0.83-0.84 (m, 2H), 1.03-1.04 (m, 2H), 2.04 (m, 1H), 2.64 (s, 3H), 3.77 (s, 3H), 6.83 (d, J=16.0 Hz, 1H), 6.84 (s, 1H), 7.57-7.58 (m, 3H), 7.71 (d, J=16.0 Hz, 1H), 8.34 (m, 2H), 8.97 (s, 1H), 10.74 (s, 1H).

A hexane solution of diisobutylaluminum hydride (1 mL of a 1.0M solution, 1.0 mmol, 4.0 equiv.) was added to a cooled (−78° C.) solution of (E)-methyl 3-(4-(1-acetyl-5-cyclopropyl-1H-pyrazol-3-ylamino)-2-phenylpyrimidin-5-yl)acrylate (100 mg, 0.248 mmol, 1.0 equiv.) in THF (2 mL). After stirring for 1 h at −78° C., additional disobutylalumium hydride solution (0.25 mL of a 1.0M solution, 0.25 mmol, 1.0 equiv.) was added. After another 30 min, NaOH solution (1N) was added and the reaction mixture was allowed to warm slowly to room temperature for 10 min. The organic layers were separated and the aqueous phase was extracted with CH₂Cl₂. The combined organic layers were washed with water, brine, dried (Na₂SO₄) and filtered. The filtrate was concentrated to afford crude. The crude was crystallized with ethanol to afford compound (E)-3-(4-(5-cyclopropyl-1H-pyrazol-3-ylamino)-2-phenylpyrimidin-5-yl)prop-2-en-1-ol (Compound 53) (80 mg, 96%). LC-MS (m/z): 334.1 [M+H]⁺. ¹H NMR (400 MHz, DMSO-d₆) δ 0.71-0.72 (m, 2H), 0.96-0.98 (m, 2H), 1.91-1.98 (m, 1H), 4.15 (t, J=5.2 Hz, 2H), 4.87 (m, 1H), 6.34 (dt, J₁=4.8 Hz, J₂=15.6 Hz, 1H), 6.48 (s, 1H), 6.80 (d, J=16 Hz, 1H), 7.48-7.51 (m, 3H), 8.28-8.30 (m, 2H), 8.47 (s, 1H), 9.05 (s, 1H), 12.15 (s, 1H).

To a solution of (E)-3-(4-(5-cyclopropyl-1H-pyrazol-3-ylamino)-2-phenylpyrimidin-5-yl)prop-2-en-1-ol (Compound 53) (80 mg, 0.24 mmol, 1.0 equiv.) in anhydrous CH$_2$Cl$_2$ (2 mL) was added Et$_3$N (0.2 mL, 1.44 mmol, 6.0 equiv.), Ac$_2$O (0.08 mL, 0.72 mmol, 3.0 equiv.) and DMAP (8 mg, 0.048 mmol, 0.2 equiv.) at 0° C. under nitrogen atmosphere. The reaction mixture was stirred for 1 h at 0° C. and quenched with water. The aqueous layers were extracted with CH$_2$Cl$_2$ and the organic layers were washed with water, brine, dried (Na$_2$SO$_4$) and filtered. The filtrate was concentrated in vacuum to afford intermediate (E)-3-(4-(1-acetyl-5-cyclopropyl-1H-pyrazol-3-ylamino)-2-phenylpyrimidin-5-yl)allyl acetate (80 mg, 80%). LC-MS (m/z): 418.1 [M+H]$^+$.

The mixture of (E)-3-(4-(1-acetyl-5-cyclopropyl-1H-pyrazol-3-ylamino)-2-phenylpyrimidin-5-yl)allyl acetate (80 mg, 0.192 mmol, 1.0 equiv.) and NaHCO$_3$ (144 mg, 1.724 mmol, 9.0 eqiv.) in EtOH (20 mL) was stirred at room temperature for 24 h. The reaction mixture was filtered, the filtrate was concentrated. The residue was diluted with EtOAc and washed with water, brine, dried (Na$_2$SO$_4$), and filtered. The filtrate was concentrated and purified by silica gel chromatography (EtOAc/MeOH 20:1) to afford (E)-3-(4-(5-cyclopropyl-1H-pyrazol-3-ylamino)-2-phenylpyrimidin-5-yl)allyl acetate (Compound 81) (8 mg, 11.1%). LC-MS (m/z): 376.1 [M+H]$^+$. $^1$H NMR (400 MHz, DMSO-d$_6$) δ 0.72-0.73 (m, 2H), 0.96-0.98 (m, 2H), 1.91-1.98 (m, 1H), 2.07 (s, 3H), 4.70 (d, J=5.6 Hz, 2H), 6.35 (d, J=15.2 Hz, 1H), 6.46 (s, 1H), 7.10 (d, J=15.2 Hz, 1H), 7.47-7.49 (m, 3H), 8.29-8.30 (m, 2H), 8.54 (s, 1H), 9.29 (s, 1H), 12.16 (s, 1H).

(E)-N-(5-cyclopropyl-1H-pyrazol-3-yl)-5-(3-methoxyprop-1-enyl)-2-phenylpyrimidin-4-amine (Compound 39)

A mixture of tert-butyl 5-cyclopropyl-3-(5-iodo-2-phenylpyrimidin-4-ylamino)-1H-pyrazole-1-carboxylate (318 mg, 0.63 mmol, 1.0 equiv.), (E)-2-(3-methoxyprop-1-enyl)-4,4,5,5-tetramethyl-1,3,2-dioxaborolane (500 mg, 2.53 mmol, 4.0 equiv.), PdCl$_2$(dppf$_2$)'CH$_2$Cl$_2$ (155 mg, 0.19 mmol, 0.3 equiv.) and K$_2$CO$_3$ (348 mg, 2.53 mmol, 4.0 equiv.) in dry DMF (40 mL) was heated to 90° C. under a nitrogen atmosphere and stirred for 2 hours. Then, the reaction mixture was cooled down to room temperature and concentrated in vacuum. The residue was purified by Prep-HPLC to give the title compound (E)-N-(5-cyclopropyl-1H-pyrazol-3-yl)-5-(3-methoxyprop-1-enyl)-2-phenylpyrimidin-4-amine (Compound 39) (10 mg, 2%). LCMS: 348.1 [M+H]$^+$. $^1$H NMR (400 MHz, DMSO-d$_6$): 0.72-0.78 (m, 2H), 0.96-0.98 (m, 2H), 1.94-2.02 (m, 1H), 3.30 (s, 3H), 4.06 (d, J=5.2 Hz, 2H), 6.33 (m, 1H), 6.46 (s, 1H), 7.02 (d, J=15.6 Hz, 1H), 7.48 (m, 3H), 8.29 (d, J=4.4 Hz, 2H), 8.53 (s, 1H), 9.26 (s, 1H), 12.15 (s, 1H).

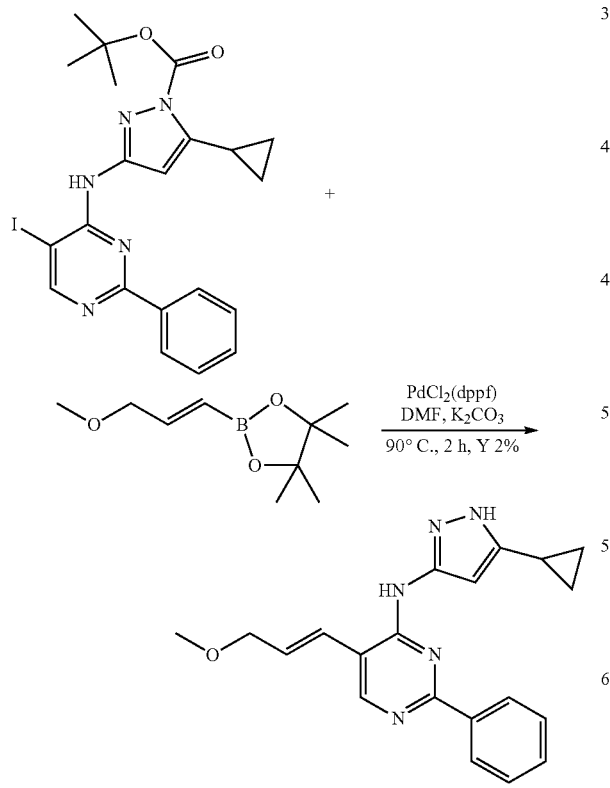

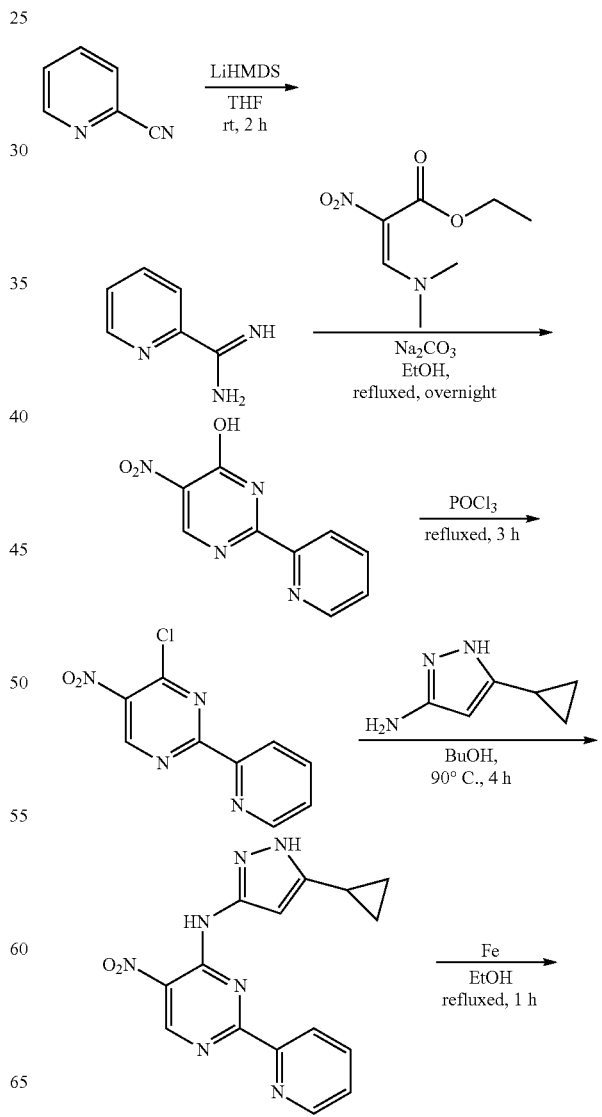

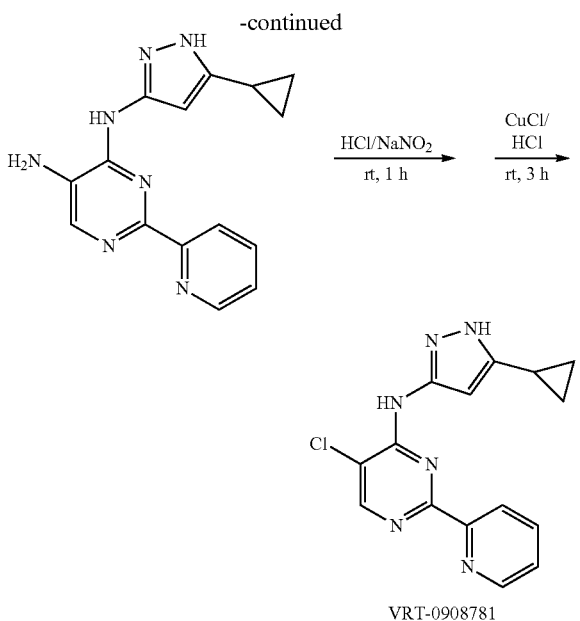

VRT-0908781

5-chloro-N-(5-cyclopropyl-1H-pyrazol-3-yl)-2-(pyridin-2-yl)pyrimidin-4-amine (Compound 182)

To the solution of LiHMDS (5.18 g, 0.026 mmol, 1.3 equiv.) was added picolinonitrile (2.08 g, 0.02 mmol, 1 equiv.) at ice-bath and kept stirred for 2 h. Then, the reaction mixture was acidified with aqueous HCl (4N) to pH2, cooled at ice-bath and kept stirred. Then, the mixture was extracted with EA (200 mL×5). The combined organic phase was washed with brine, dried (Na2SO4), and evaporated to get picolinimidamide (2.0 g, 83%). LC-MS (m/z)=122 [M+H]$^+$.

The mixture of picolinimidamide (1.2 g, 0.01 mmol, 1 equiv.), (E)-ethyl 3-(dimethylamino)-2-nitroacrylate (2.0 g, 0.0106 mmol, 1.06 equiv.), and Na2CO3 (1.05 g, 0.01 mmol, 1 equiv.) in ethanol (20 mL) was stirred and heated at reflux overnight. Then, the reaction mixture was poured into water (200 mL), extracted with EA (100 mL×3). The aqueous phase was acidified with conc.HCl to pH1. After filtration 5-nitro-2-(pyridin-2-yl)pyrimidin-4-ol was obtained as a white solid (2.0 g, 92%). LC-MS (m/z)=219 [M+H]$^+$.

A solution of 5-nitro-2-(pyridin-2-yl)pyrimidin-4-ol (1.74 g, 0.008 mmol, 1 equiv.) in POCl3 (6.12 g, 0.04 mmol, 5 equiv.) was refluxed for 3 h. Then, the mixture was poured into ice (200 g), extracted with EA (200 mL×2). The combined organic phases were evaporated to afford 4-chloro-5-nitro-2-(pyridin-2-yl)pyrimidine (1.5 g, 80%). LCMS: 237 [M+H]$^+$.

To 4-chloro-5-nitro-2-(pyridin-2-yl)pyrimidine (1.42 g, 0.006 mmol, 1 equiv.) in BuOH (20 mL) was added 5-cyclopropyl-1H-pyrazol-3-amine (1.23 g, 0.01 mmol, 1.6 equiv.) After heating at 90° C. for 4 h. the reaction mixture was filtered to produce N-(5-cyclopropyl-1H-pyrazol-3-yl)-5-nitro-2-(pyridin-2-yl)pyrimidin-4-amine (1.5 g, 79%). LC-MS (m/z)=324 [M+H]$^+$; $^1$H NMR (400 MHz, DMSO-d6): δ0.74-0.77 (m, 2H), 0.97-1.02 (m, 2H), 1.93-2.00 (m, 1H), 7.00 (s, 1H), 7.60-7.63 (m, 1H), 8.03-8.06 (m, 1H), 8.43 (d, J=7.6 Hz, 1H), 8.84 (d, J=4.0 Hz, 1H), 9.37 (s, 1H), 10.24 (s, 1H)

A mixture of N-(5-cyclopropyl-1H-pyrazol-3-yl)-5-nitro-2-(pyridin-2-yl)pyrimidin-4-amine (1.29 g, 0.004 mmol, 1 equiv.) and Fe (2.24 g, 0.04 mmol, 10 equiv.) in ethanol and aqueous NH4Cl (2.12 g, 0.04 mmol, equiv.) was bubbled with N2, and refluxed for 1 h. Then, the reaction mixture was filtered. The liquid was evaporated to afford N4-(5-cyclopropyl-1H-pyrazol-3-yl)-2-(pyridin-2-yl)pyrimidine-4,5-diamine (1.0 g, 85%). LC-MS (m/z)=294 [M+H]$^+$.

To N4-(5-cyclopropyl-1H-pyrazol-3-yl)-2-(pyridin-2-yl)pyrimidine-4,5-diamine (0.88 g, 0.003 mmol, 1 equiv.) in conc.HCl (3 mL) at ice-bath was added NaNO2 (0.23 g, 0.0033 mmol, 1.1 equiv.). After 1 h, CuCl (0.33 g, 0.0033 mmol, 1.1 equiv.) in conc.HCl (6 mL) was added at 0° C. After 30 min, the reaction mixture was allowed to stand at room temperature for further 3 h, poured into ice water and adjusted to pH10 with Na2CO3, extracted with EA (50 mL×3). The organic phase was combined, dried (Na2SO4), purified with silicon chromatography (EA: PE=2:1) to produce 5-chloro-N-(5-cyclopropyl-1H-pyrazol-3-yl)-2-(pyridin-2-yl)pyrimidin-4-amine (Compound 182) (0.47 g, 50%). LC-MS (m/z)=313 [M+H]$^+$; $^1$H NMR (400 MHz, DMSO-d6): δ 0.75-0.78 (m, 2H), 0.97-1.02 (m, 2H), 1.96-2.02 (m, 1H), 6.44-6.45 (m, 1H), 7.92-7.93 (m, 1H), 8.44 (s, 2H), 8.73 (d, J=2.8 Hz, 1H), 8.87 (d, J=3.6 Hz, 1H), 10.20 (bs, 1H)

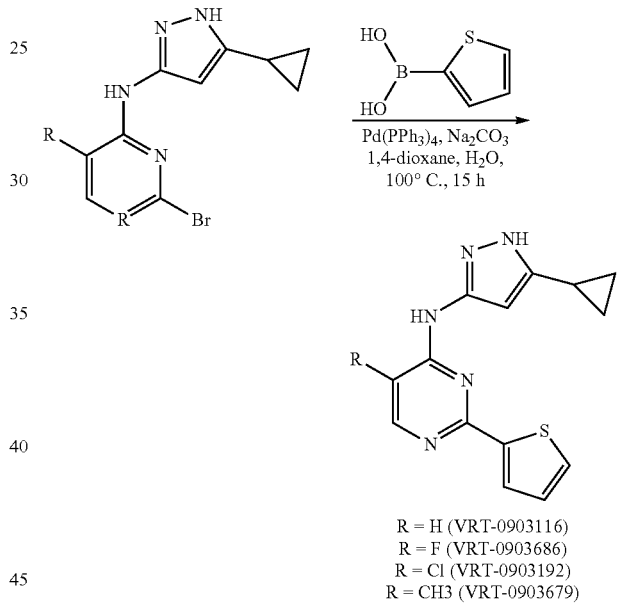

R = H (VRT-0903116)
R = F (VRT-0903686)
R = Cl (VRT-0903192)
R = CH3 (VRT-0903679)

N-(5-cyclopropyl-1H-pyrazol-3-yl)-2-(thiophen-2-yl)pyrimidin-4-amine (R═H) (Compound 27)

A mixture of 2-bromo-N-(5-cyclopropyl-1H-pyrazol-3-yl)pyrimidin-4-amine (170 mg, 0.64 mmol, 1.0 equiv.), thiophen-2-ylboronic acid (107 mg, 0.83 mmol, 1.3 equiv.), Pd(PPh3)4 (148 mg, 0.128 mmol, 0.2 equiv.), Na2CO3 (238 mg, 2 mmol, 3.5 equiv.), 1,4-dioxane (5 ml) and water (1 ml) was stirred at 100° C. under a nitrogen atmosphere for 15 h. The reaction mixture was allowed to cool down to room temperature and concentrated to give a residue. The residue was purified by silica gel chromatography (CH2Cl2/methanol 500:1 to 100:1 as eluent) to afford title compound N-(5-cyclopropyl-1H-pyrazol-3-yl)-2-(thiophen-2-yl)pyrimidin-4-amine (Compound 27)(92.2 mg, 50.9%) as solid. LC-MS (m/z)=284.0 [M+H]$^+$; $^1$H NMR (400 MHz, DMSO-d6): δ 0.71 (m, 2H), 0.95 (m, 2H), 1.94 (m, 1H), 6.35 (s, 1H), 6.87 (s, 1H), 7.17 (m, 1H), 7.70 (m, 1H), 7.83 (d, J=2.8 Hz, 1H), 8.23 (d, J=5.6 Hz, 1H), 9.91 (s, 1H), 12.08 (s, 1H).

N-(5-cyclopropyl-1H-pyrazol-3-yl)-5-fluoro-2-(thiophen-2-yl)pyrimidin-4-amine (R=F) (Compound 41)

A mixture of 2-bromo-N-(5-cyclopropyl-1H-pyrazol-3-yl)-5-fluoropyrimidin-4-amine (250 mg, 0.84 mmol, 1.0 eq), thiophen-2-ylboronic acid (150 mg, 1.18 mmol, 1.4 eq), Pd(dppf)Cl$_2$ (69 mg, 0.084 mmol, 0.1 eq), Na$_2$CO$_3$ (356 mg, 3.36 mmol, 4 eq), 1,4-dioxane (10 ml) and water (1.5 ml) was stirred at 100° C. under a nitrogen atmosphere for 15 h. The reaction mixture was allowed to cool to room temperature and concentrated to give a residue. The residue was purified by silica gel chromatography (CH$_2$Cl$_2$/methanol 500:1 to 100:1 as eluent) to afford title compound N-(5-cyclopropyl-1H-pyrazol-3-yl)-5-fluoro-2-(thiophen-2-yl)pyrimidin-4-amine (Compound 41) (71.2 mg, 28.1%) as a solid. LC-MS (m/z)=302.1 [M+H]$^+$; $^1$H NMR (400 MHz, DMSO-d$_6$): δ 0.77 (d, J=4 Hz, 2H), 1.01 (d, J=7.2 Hz, 2H), 1.97 (t, J=4.4 Hz, 1H), 6.58 (s, 1H), 7.21 (t, J=4.2 Hz, 1H), 7.76 (m, 2H), 8.32 (d, J=3.2 Hz, 1H), 10.12 (s, 1H), 12.24 (s, 1H).

5-chloro-N-(5-cyclopropyl-1H-pyrazol-3-yl)-2-(thiophen-2-yl)pyrimidin-4-amine (R=Cl) (Compound 29)

Same procedure was repeated as in Compound 27, starting from 2-bromo-5-chloro-N-(5-cyclopropyl-1H-pyrazol-3-yl)pyrimidin-4-amine to afford 5-chloro-N-(5-cyclopropyl-1H-pyrazol-3-yl)-(thiophen-2-yl)pyrimidin-4-amine (Compound 29) (16.7 mg, 8.2%). LC-MS (m/z)=318.0 [M+H]$^+$; $^1$H NMR (400 MHz, DMSO-d$_6$): δ 0.73 (s, 2H), 0.97 (s, 2H), 1.94 (s, 1H), 6.48 (s, 1H), 7.19 (s, 1H), 7.00 (d, J=20 Hz, 2H), 8.39 (s, 1H), 9.29 (s, 1H), 12.28 (s, 1H).

N-(5-cyclopropyl-1H-pyrazol-3-yl)-5-methyl-2-(thiophen-2-yl)pyrimidin-4-amine (Compound 38)

(R=Me)

Same procedure was repeated as in Compound 27, starting from 2-bromo-5-methyl-N-(5-cyclopropyl-1H-pyrazol-3-yl)pyrimidin-4-amine to afford N-(5-cyclopropyl-1H-pyrazol-3-yl)-5-methyl-2-(thiophen-2-yl)pyrimidin-4-amine (Compound 38) (62.7 mg, 15.5%) was prepared. LC-MS (m/z)=298.1 [M+H]$^+$;

$^1$H NMR (400 MHz, DMSO-d$_6$): δ 0.74 (m, 2H), 0.98-1.00 (m, 2H), 1.94 (m, 1H), 2.17 (s, 3H), 6.60 (s, 1H), 7.17 (t, J=4.4 Hz, 1H), 7.67 (d, J=4.4 Hz, 1H), 7.78 (s, 1H), 8.09 (s, 1H), 8.99 (s, 1H), 12.14 (s, 1H).

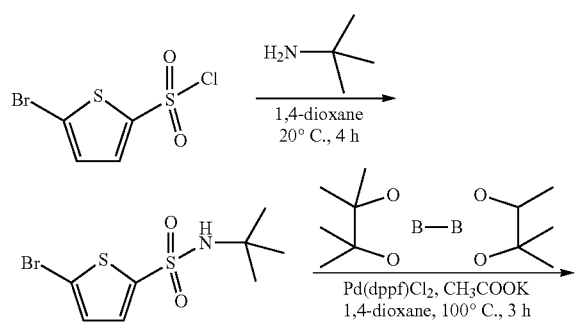

5-(4-(5-cyclopropyl-1H-pyrazol-3-ylamino)pyrimidin-2-yl)thiophene-2-sulfonamide (Compound 50)

Step 1. A mixture of 5-bromothiophene-2-sulfonyl chloride (1.5 g, 5.74 mmol, 1.0 equiv.), t-BuNH$_2$ (1.26 g, 17.22 mmol, 3.0 equiv.) in 1,4-dioxane (50 ml) was stirred at 20° C. for 4 h under nitrogen atmosphere. The reaction mixture was concentrated to give a residue, which was purified by silica gel chromatography (PE/EA 100:1 to 10:1 as eluent) to afford 5-bromo-N-tert-butylthiophene-2-sulfonamide (1.614 g, 94.3%) as solid.

Step 2. A mixture of 5-bromo-N-tert-butylthiophene-2-sulfonamide (1.614 g, 5.41 mmol, 1.0 equiv.), 4,4,4',4',5,5,5',5'-octamethyl-2,2'-bi(1,3,2-dioxaborolane) (1.65 g, 6.49 mmol, 1.2 eq), Pd(dppf)Cl$_2$ (0.442 g, 0.541 mmol, 0.1 eq), CH$_3$COOK (2.124 g, 21.64 mmol, 4.0 eq) in 1,4-dioxane (30 ml) was stirred at 100° C. under a nitrogen atmosphere for 3 h. The reaction mixture was allowed to cool to room temperature and concentrated to give a residue. The residue was purified by silica gel chromatography (PE/EA 300:1 to 40:1 as eluent) to afford N-tert-butyl-5-(4,4,5,5-tetramethyl-1,3,2-dioxaborolan-2-yl)thiophene-2-sulfonamide (1.3 g, 69.6%) as solid.

Step 3. A mixture of 2-bromo-N-(5-cyclopropyl-1H-pyrazol-3-yl)pyrimidin-4-amine (300 mg, 1.071 mmol, 1.0 eq), N-tert-butyl-5-(4,4,5,5-tetramethyl-1,3,2-dioxaborolan-2-yl)thiophene-2-sulfonamide (443.7 mg, 1.285 mmol, 1.2 eq), Pd(dppf)Cl$_2$ (87.5 mg, 0.1071 mmol, 0.1 eq), Na$_2$CO$_3$ (454.1 mg, 4.284 mmol, 4 eq) in 1,4-dioxane (20 ml) and water (4 ml) was stirred at 100° C. under a nitrogen atmosphere for 15

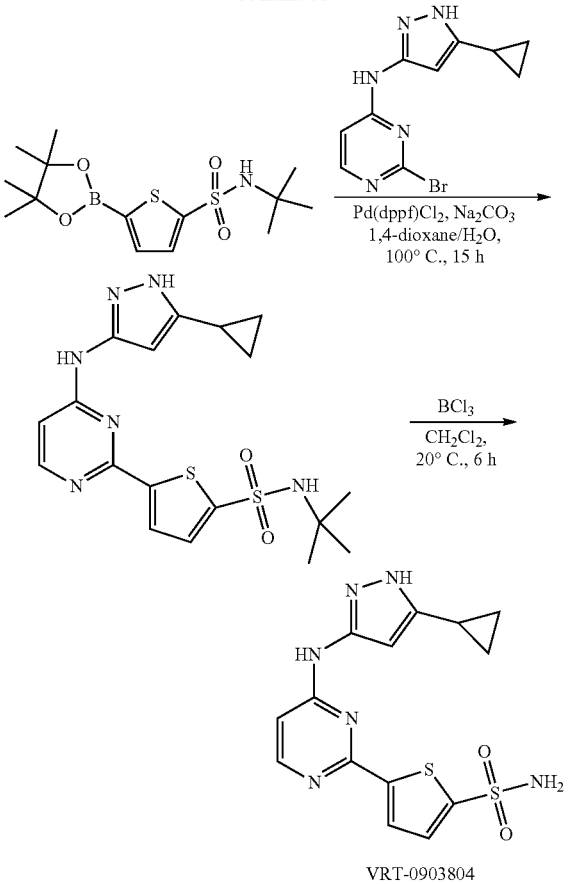

h. The reaction mixture was allowed to cool to room temperature and concentrated to give a residue, which was purified by silica gel chromatography (CH$_2$Cl$_2$/methanol 500:1 to 50:1 as eluent) to afford N-tert-butyl-5-(4-(5-cyclopropyl-1H-pyrazol-3-ylamino)pyrimidin-2-yl)thiophene-2-sulfonamide (300 mg, 66.9%) as a solid. LC-MS (m/z)=419.1 [M+H]$^+$.

Step 4. A mixture of N-tert-butyl-5-(4-(5-cyclopropyl-1H-pyrazol-3-ylamino)pyrimidin-2-yl)thiophene-2-sulfonamide (300 mg, 0.717 mmol, 1.0 eq), BCl$_3$/CH$_2$Cl$_2$ (7.17 ml, 7.17 mmol, 10 eq. 1 M) in CH$_2$Cl$_2$ (20 ml) was stirred at 20° C. under a nitrogen atmosphere for 6 h. Water (50 ml) was added into the mixture. The mixture was extracted by EA (3×50 ml). The combined organic phases were washed (sat NaHCO$_3$), brine, dried (Na$_2$SO$_4$), filtered and concentrated. The residue was purified by recrystallization (solvent: EA/PE and DIPE) to afford title compound 5-(4-(5-cyclopropyl-1H-pyrazol-3-ylamino)pyrimidin-2-yl)thiophene-2-sulfonamide (Compound 50) (50.9 mg, 19.6%) as a yellow solid. LC-MS (m/z)=363.0 [M+H]$^+$; $^1$H NMR (400 MHz, DMSO-d$_6$): 0.72-0.74 (m, 2H), 0.94-0.99 (m, 2H), 1.89-1.94 (m, 1H), 6.41 (s, 1H), 6.84 (s, 1H), 7.58 (d, J=4 Hz, 1H), 7.49-7.81 (m, 3H), 8.29 (d, J=5.2 Hz, 1H), 10.08 (s, 1H), 12.14 (s, 1H).

Compound 52

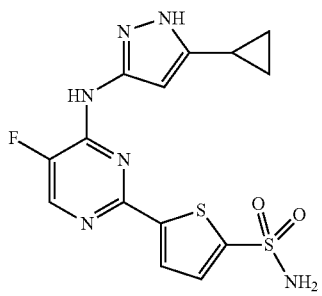

5-(4-(5-cyclopropyl-1H-pyrazol-3-ylamino)-5-fluoropyrimidin-2-yl)thiophene-2-sulfonamide (Compound 52)

Starting with 2-bromo-N-(5-cyclopropyl-1H-pyrazol-3-yl)-5-fluoropyrimidin-4-amine, 5-(4-(5-cyclopropyl-1H-pyrazol-3-ylamino)-5-fluoropyrimidin-2-yl)thiophene-2-sulfonamide (Compound 52) (51.5 mg, 17.4%) was prepared as described in Compound 50. LC-MS (m/z)=380.4 [M+H]$^+$; $^1$H NMR (400 MHz, DMSO-d$_6$): 0.75-0.76 (m, 2H), 0.98-0.99 (m, 2H), 1.94-1.97 (m, 1H), 6.49 (s, 1H), 7.57 (d, J=4 Hz, 1H), 7.71 (d, J=3.6 Hz, 1H), 7.82 (s, 2H), 8.36 (s, 1H), 10.23 (s, 1H), 12.25 (s, 1H).

Compound 42

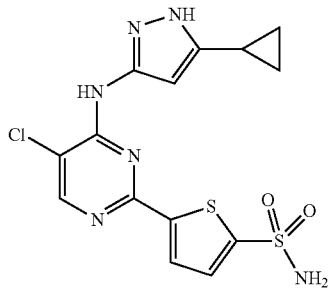

5-(5-chloro-4-(5-cyclopropyl-1H-pyrazol-3-ylamino)pyrimidin-2-yl)thiophene-2-sulfonamide) (Compound 42)

Using 2-bromo-5-chloro-N-(5-cyclopropyl-1H-pyrazol-3-yl)pyrimidin-4-amine as starting material, following same procedure as described in Compound 50, the HCl salt of 5-(5-chloro-4-(5-cyclopropyl-1H-pyrazol-3-ylamino)pyrimidin-2-yl)thiophene-2-sulfonamide (Compound 42) was prepared (92.7 mg, 33.4%). LC-MS (m/z)=397.0 [M+H]$^+$; $^1$H NMR (400 MHz, DMSO-d$_6$): 0.78-0.79 (m, 2H), 1.00-1.02 (m, 2H), 1.97-1.99 (m, 1H), 6.42 (s, 1H), 7.59 (d, J=4.4 Hz, 1H), 7.78 (d, J=3.6 Hz, 1H), 7.84 (s, 2H), 8.50 (s, 1H), 9.65 (s, 1H).

Compound 40

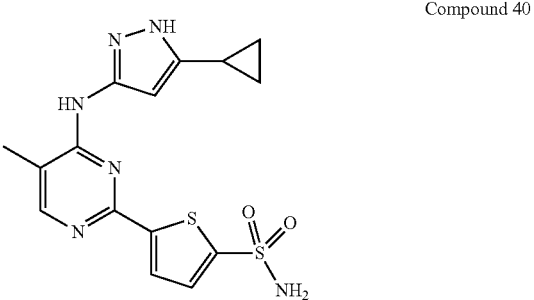 [SMILES: Cc1cnc(-c2ccc(S(N)(=O)=O)s2)nc1Nc1cc(C2CC2)[nH]n1]

5-(4-(5-cyclopropyl-1H-pyrazol-3-ylamino)-5-methylpyrimidin-2-yl)thiophene-2-sulfonamide (Compound 40)

5-(4-(5-Cyclopropyl-1H-pyrazol-3-ylamino)-5-methylpyrimidin-2-yl)thiophene-2-sulfonamide (Compound 40) (43 mg, 24.8%) was prepared following same procedure as described in Compound 50 by starting with 2-bromo-5-methyl-N-(5-cyclopropyl-1H-pyrazol-3-yl)pyrimidin-4-amine. LC-MS (m/z)=377.0 [M+H]$^+$; $^1$H NMR (400 MHz, DMSO-d$_6$): 0.75-0.76 (m, 2H), 0.97-0.99 (m, 2H), 1.93-1.95 (m, 1H), 2.18 (s, 3H), 6.51 (s, 1H), 7.57 (d, J=3.6 Hz, 1H), 7.73 (d, J=3.2 Hz, 1H), 7.78 (s, 2H), 8.14 (s, 1H), 9.13 (s, 1H), 12.17 (s, 1H).

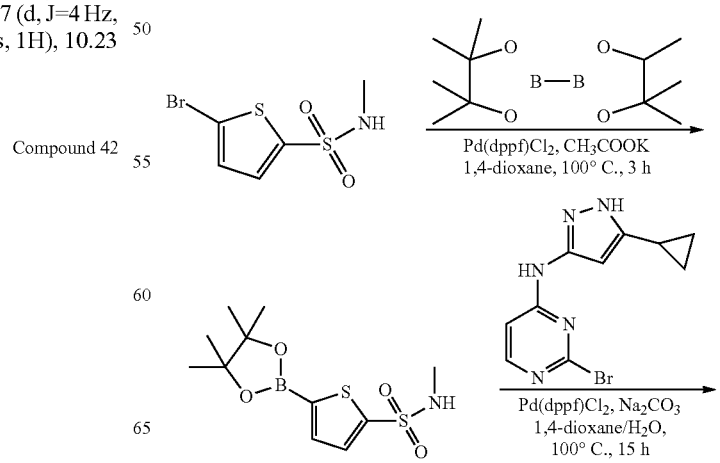

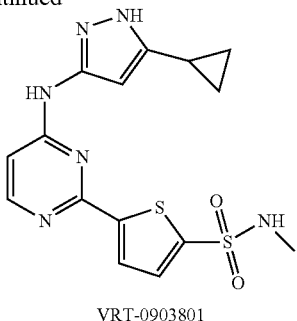

VRT-0903801

N-tert-butyl-5-(4-(5-cyclopropyl-1H-pyrazol-3-ylamino)pyrimidin-2-yl)thiophene-2-sulfonamide (Compound 48)

A mixture of compound 5-bromo-N-methylthiophene-2-sulfonamide (2.3 g, 9.05 mmol, 1.0 eq), 4,4,4',4',5,5,5',5'-octamethyl-2,2'-bi(1,3,2-dioxaborolane) (3 g, 12.35 mmol, 1.3 eq), Pd(dppf)Cl₂ (0.74 g, 0.905 mmol, 0.1 eq), CH₃COOK (3.6 g, 36.7 mmol, 4.0 eq) in 1,4-dioxane (30 ml) was stirred at 100° C. under a nitrogen atmosphere for 3 h. The reaction mixture was allowed to cool to room temperature and concentrated to give a residue. The residue was purified by silica gel chromatography (PE/CH₃COOC₂H₅ 300:1 to 40:1 as eluent) to afford title N-methyl-5-(4,4,5,5-tetramethyl-1,3,2-dioxaborolan-2-yl)thiophene-2-sulfonamide (1.5 g, 55%) as a solid.

A mixture of N-methyl-5-(4,4,5,5-tetramethyl-1,3,2-dioxaborolan-2-yl)thiophene-2-sulfonamide (422 mg, 1.39 mmol, 1.3 eq), 2-bromo-N-(5-cyclopropyl-1H-pyrazol-3-yl)-5-fluoropyrimidin-4-amine (300 mg, 1.07 mmol, 1.0 eq), Pd (dppf)Cl₂ (88 mg, 0.107 mmol, 0.1 eq), Na₂CO₃ (454 mg, 4.28 mmol, 4.0 eq) in 1,4-dioxane (20 ml) and water (4 ml) was stirred at 100° C. under a nitrogen atmosphere for 15 h. The reaction mixture was allowed to cool to room temperature and concentrated to give a residue. The residue was purified by silica gel chromatography (CH₂Cl₂/methanol 500:1 to 50:1 as eluent) to afford title compound N-tert-butyl-5-(4-(5-cyclopropyl-1H-pyrazol-3-ylamino) pyrimidin-2-yl) thiophene-2-sulfonamide (Compound 48) (35.9 mg, 8.9%) as a white solid. LC-MS (m/z)=377.0 [M+H]⁺; ¹H NMR (400 MHz, DMSO-d₆): δ 0.71 (s, 2H), 0.95 (s, 2H), 1.90 (s, 1H), 2.54 (s, 3H), 6.35 (s, 1H), 6.85 (s, 1H), 7.59 (s, 1H), 7.82 (s, 2H), 8.28 (s, 1H), 10.13 (s, 1H), 12.15 (s, 1H).

Using coupling conditions similar to the one used to prepare Compound 48, the following compounds were also made: Compounds 28, 30, 31, 32, 33, 34, 35, 37, 43, 51, 58, 61, 75, 96, 97, 104, 117, 121, 126, 127, 134, 138, 155, 161 and other structurally similar compounds.

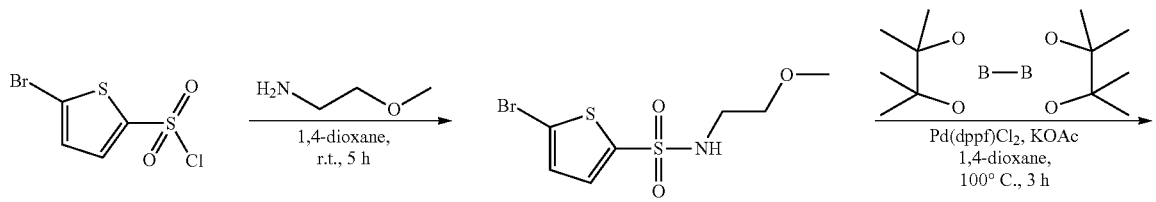

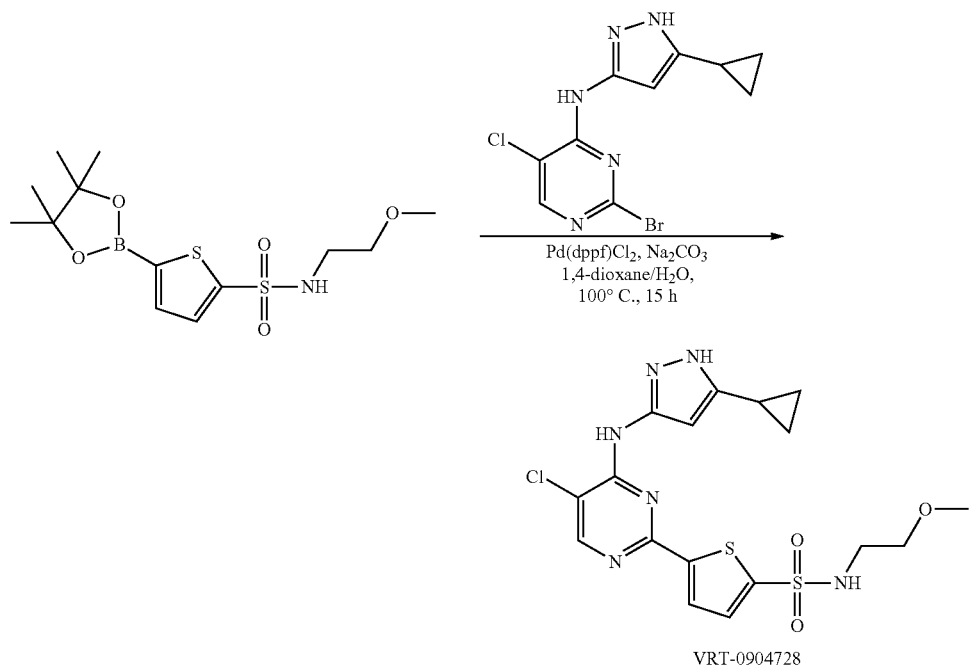

VRT-0904728

5-(5-chloro-4-(5-cyclopropyl-1H-pyrazol-3-ylamino)pyrimidin-2-yl)-N-(2-methoxyethyl)thiophene-2-sulfonamide (Compound 88)

A mixture of 5-bromothiophene-2-sulfonyl chloride (1 g, 3.82 mmol) and 2-methoxyethanamine (0.43 g, 5.73 mmol, 1.5 eq) in 1,4-dioxane (20 mL) was stirred at r.t. for 2.5 h. The mixture was evaporated under reduced pressure. The residue was purified by column chromatography (PE100%-EtOAc100%) to afford 5-bromo-N-(2-methoxyethyl)thiophene-2-sulfonamide (1 g, 87%). LC-MS (m/z)=301 [M+H]$^+$.

A mixture of 5-bromo-N-(2-methoxyethyl)thiophene-2-sulfonamide (1 g, 3.3 mmol), 4,4,4',4',5,5,5',5'-octamethyl-2,2'-bi(1,3,2-dioxaborolane) (1.1 g, 4.29 mmol, 1.3 eq), Pd(dppf)Cl$_2$ (269 mg, 0.33 mmol, 0.1 eq) and KOAc (1.13 g, 11.55 mmol, 3.5 eq) in 1,4-dioxane (20 mL) was stirred at 100° C. under a nitrogen atmosphere for 3 h. The reaction mixture was allowed to cool to room temperature and concentrated to give a residue. The residue was purified by silica gel chromatography (PE/EA 300:1 to 40:1 as eluent) to afford N-(2-methoxyethyl)-5-(4,4,5,5-tetramethyl-1,3,2-dioxaborolan-2-yl)thiophene-2-sulfonamide (712 mg, 62%) as a solid.

A mixture of 2-bromo-5-chloro-N-(5-cyclopropyl-1H-pyrazol-3-yl)pyrimidin-4-amine (250 mg, 0.795 mmol), N-(2-methoxyethyl)-5-(4,4,5,5-tetramethyl-1,3,2-dioxaborolan-2-yl)thiophene-2-sulfonamide (359 mg, 1.034 mmol, 1.3 eq), Pd(dppf)Cl$_2$ (65 mg, 0.0795 mmol, 0.1 eq) and Na$_2$CO$_3$ (295 mg, 2.783 mmol, 3.5 eq) in 1,4-dioxane (5 mL) and water (1 mL) was stirred at 100° C. under a nitrogen atmosphere for 15 h. The reaction mixture was allowed to cool to room temperature and concentrated to give a residue. The residue was purified by silica gel chromatography (CH$_2$Cl$_2$/methanol 500:1 to 50:1 as eluent) to afford title compound 5-(5-chloro-4-(5-cyclopropyl-1H-pyrazol-3-ylamino)pyrimidin-2-yl)-N-(2-methoxyethyl) thiophene-2-sulfonamide (Compound 88) (71.2 mg, 28.1%) as solid. LC-MS (m/z)=455.0 [M+H]$^+$; $^1$H NMR (400 MHz, DMSO-d$_6$): δ 0.75 (d, J=3.6 Hz, 2H), 0.99 (d, J=6.4 Hz, 2H), 1.94 (s, 1H), 3.04 (t, J=5.2 Hz, 2H), 3.20 (s, 3H), 3.37 (t, J=5.0 Hz, 2H), 6.39 (s, 1H), 7.61 (d, J=3.2 Hz, 1H), 7.77 (d, J=3.6 Hz, 1H), 8.15 (s, 1H), 8.46 (s, 1H), 9.49 (s, 1H), 12.35 (s, 1H).

Using coupling conditions similar to the one used to prepare Compound 88, the following compounds were also made: Compounds 79, 86 and other structurally similar compounds.

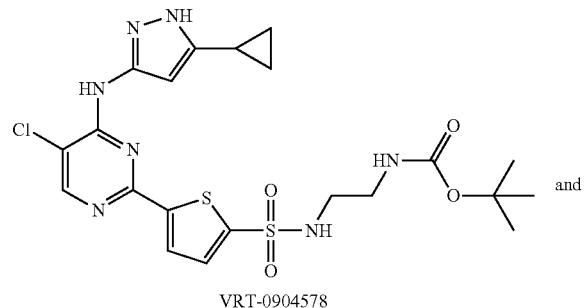

VRT-0904578

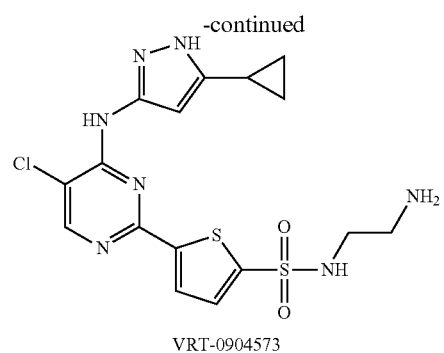

VRT-0904573 tert-Butyl 2-(5-(5-chloro-4-(5-cyclopropyl-1H-pyrazol-3-ylamino)pyrimidin-2-yl)thiophene-2-sulfonamido)ethylcarbamate (Compound 78) and N-(2-aminoethyl)-5-(5-chloro-4-(5-cyclopropyl-1H-pyrazol-3-ylamino)pyrimidin-2-yl)thiophene-2-sulfonamide (Compound 75)

tert-Butyl 2-(5-(5-chloro-4-(5-cyclopropyl-1H-pyrazol-3-ylamino)pyrimidin-2-yl)thiophene-2-sulfonamido)ethylcarbamate (Compound 78) (3.9 mg, 4%) was prepared in a similar way as described in Compound 88. LC-MS (m/z)=540 [M+H]$^+$; $^1$H NMR (400 MHz, DMSO-d$_6$): δ 0.74-0.75 (m, 2H), 0.98-0.99 (m, 2H), 1.34 (s, 9H), 1.91-1.99 (m, 1H), 2.89 (q, J=6.0 Hz, 2H), 2.99 (q, J=6.0 Hz, 2H), 6.39 (s, 1H), 6.83 (t, J=5.2 Hz, 1H), 7.60 (d, J=4.0 Hz, 1H), 7.77 (d, J=3.6 Hz, 1H), 8.03 (t, J=5.6 Hz, 1H), 8.47 (s, 1H), 9.50 (s, 1H), 12.33 (s, 1H)

tert-Butyl 2-(5-(5-chloro-4-(5-cyclopropyl-1H-pyrazol-3-ylamino)pyrimidin-2-yl)thiophene-2-sulfonamido)ethylcarbamate (Compound 78) (70 mg, 12.96 mmol, 1 equiv.) was added into HCl in MeOH and the resulting mixture was stirred at room temperature for 2 h. The mixture was adjusted pH10 with Na$_2$CO$_3$, and extracted with EA (50 mL×3). The organic phase was combined and washed with brine, dried (Na$_2$SO$_4$), evaporated to afford N-(2-aminoethyl)-5-(5-chloro-4-(5-cyclopropyl-1H-pyrazol-3-ylamino)pyrimidin-2-yl)thiophene-2-sulfonamide (Compound 75) (38.3 mg, 67%). LC-MS (m/z)=440 [M+H]$^+$; $^1$H NMR (400 MHz, DMSO-d$_6$): δ 0.81-0.82 (m, 2H), 1.03-1.05 (m, 2H), 2.01-2.03 (m, 1H), 2.90 (q, J=5.6 Hz, 2H), 3.15 (q, J=6.0 Hz, 2H), 6.43 (s, 1H), 7.71 (d, J=4.0 Hz, 1H), 7.85 (d, J=3.6 Hz, 1H), 8.18 (s, 1H), 8.48 (d, J=5.6 Hz, 1H), 8.55 (s, 1H), 9.83 (d, J=20.8 Hz, 1H)

VRT-0905081

N-(2-(5-(5-chloro-4-(5-cyclopropyl-1H-pyrazol-3-ylamino)pyrimidin-2-yl)thiophene-2-sulfonamido)ethyl)acetamide (Compound 118)

N-(2-(5-(5-chloro-4-(5-cyclopropyl-1H-pyrazol-3-ylamino)pyrimidin-2-yl)thiophene-2-sulfonamido)ethyl)acetamide (Compound 118) (9.2 mg, 6%) was prepared in a similar way as described in Compound 88. LC-MS (m/z)=482 [M+H]; $^1$H NMR (400 MHz, DMSO-$d_6$): δ 0.75-0.77 (m, 2H), 0.98-0.99 (m, 2H), 1.76 (s, 3H), 1.95-1.98 (m, 1H), 2.92 (q, J=6.4 Hz, 2H), 3.11 (q, J=6.4 Hz, 2H), 6.38 (s, 1H), 7.61 (d, J=4.0 Hz, 1H), 7.78 (d, J=4.0 Hz, 1H), 7.92 (t, J=5.6 Hz, 1H), 8.06 (t, J=5.6 Hz, 1H), 8.48 (s, 1H), 9.54 (s, 1H)

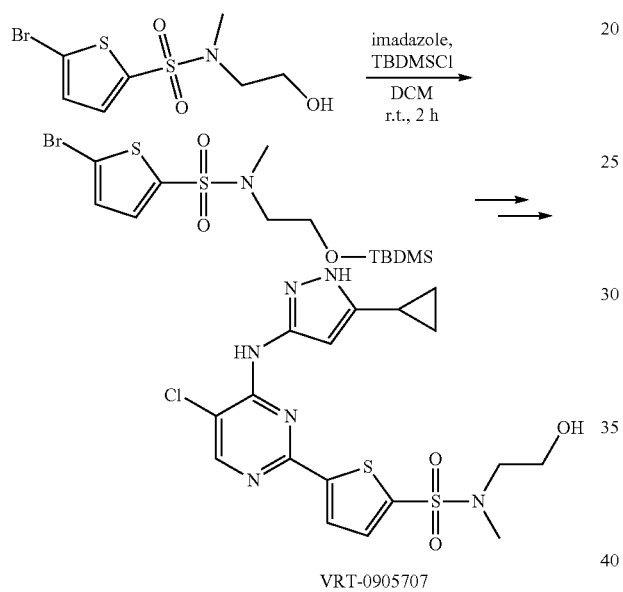

5-(5-Chloro-4-(5-cyclopropyl-1H-pyrazol-3-ylamino)pyrimidin-2-yl)-N-(2-hydroxyethyl)-N-methylthiophene-2-sulfonamide (Compound 129)

This was prepared by a similar procedure as in Compound 88 with protection and de-protection of the alcohol with TBDMS group. 74 mg of 5-(5-chloro-4-(5-cyclopropyl-1H-pyrazol-3-ylamino)pyrimidin-2-yl)-N-(2-hydroxyethyl)-N-methylthiophene-2-sulfonamide (Compound 129) was made by the 4-step procedure. LC-MS (m/z)=455 [M+H]$^+$; $^1$H NMR (400 MHz, DMSO-$d_6$): 0.73-0.74 (m, 2H), 0.98-1.00 (m, 2H), 1.90-1.98 (m, 1H), 2.82 (s, 3H), 3.08 (t, J=6.0 Hz, 2H), 3.56 (q, J=4.8 Hz, 2H), 4.87 (t, J=5.6 Hz, 1H), 6.40 (s, 1H), 7.67 (d, J=4.4 Hz, 1H), 7.82 (d, J=4.0 Hz, 1H), 8.47 (s, 1H), 9.54 (s, 1H), 12.36 (s, 1H).

The following compounds were also prepared in a similar way as described for Compound 88: Compounds 74, 98, 106, 135, 140, 148, 152, 158 and other structurally similar compounds.

2-(5-(5-chloro-4-(5-cyclopropyl-1H-pyrazol-3-ylamino)pyrimidin-2-yl)thiophen-2-yl)propan-2-ol (Compound 87)

To the solution of 1-(5-bromothiophen-2-yl)ethanone (2.05 g, 10 mmol, 1 eq) in ether (20 mL) was added methylmagnesium bromide (11 mL, 11 mmol, 1.1 eq) dropwise at ice-bath. After 0.5 h, the reaction mixture was allowed to stand at room temperature for 1.5 h. Then, the reaction was quenched with saturated aqueous NH$_4$Cl, washed with brine, dried (Na$_2$SO$_4$), and evaporated to afford 2-(5-bromothiophen-2-yl)propan-2-ol (1.97 g, 89%). LC-MS (m/z)=211 [M+H]$^+$.

2-(5-(5-chloro-4-(5-cyclopropyl-1H-pyrazol-3-ylamino)pyrimidin-2-yl)thiophen-2-yl)propan-2-ol (Compound 87) (6.0 mg, 5%) was prepared as in a similar way as described in Compound 88. LC-MS (m/z)=376 [M+H]$^+$; $^1$H NMR (400 MHz, DMSO-$d_6$): δ 0.76 (d, J=3.2 Hz, 2H), 1.00 (d, J=6.4 Hz, 2H), 1.54 (s, 6H), 1.95 (t, J=4.0 Hz, 1H), 5.60 (s, 1H), 6.51 (s, 1H), 6.98 (d, J=4.0 Hz, 1H), 7.63 (t, J=4.0 Hz, 1H), 8.38 (s, 1H), 9.26 (s, 1H), 12.30 (s, 1H).

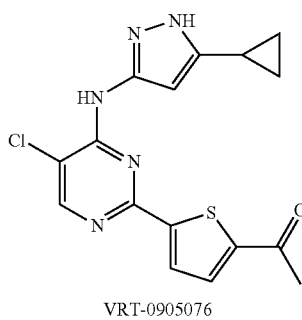

VRT-0905076

1-(5-(5-chloro-4-(5-cyclopropyl-1H-pyrazol-3-ylamino)pyrimidin-2-yl)thiophen-2-yl)ethanone (Compound 116)

This (13.2 mg, 2.9%) was prepared as in a similar way as described in Compound 88. LC-MS (m/z)=386 [M+H]+; $^1$H NMR (400 MHz, DMSO-d$_6$): δ 0.75 (d, J=3.6 Hz, 2H), 1.00 (d, J=6.8 Hz, 2H), 1.96 (d, J=4 Hz, 2H), 2.57 (s, 3H), 6.44 (s, 1H), 7.83 (d, J=3.6 Hz, 1H), 7.96 (d, J=4 Hz, 1H), 8.47 (s, 1H), 9.47 (s, 1H), 12.34 (s, 1H).

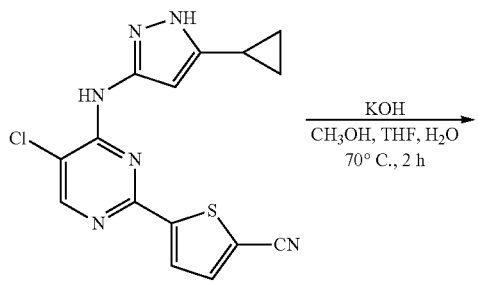

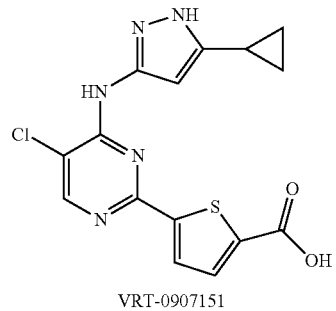

VRT-0907151

5-(5-chloro-4-(3-cyclopropyl-1H-pyrazol-5-ylamino)pyrimidin-2-yl)thiophene-2-carboxylic acid (Compound 156)

This (40 mg) was obtained by basic hydrolysis of 5-(5-chloro-4-(5-cyclopropyl-1H-pyrazol-3-ylamino)pyrimidin-2-yl)thiophene-2-carbonitrile (Compound 140). LC-MS (m/z)=362 [M+H]+; $^1$H NMR (400 MHz, DMSO-d$_6$): δ 0.75-0.78 (m, 2H), 0.97-1.01 (m, 2H), 1.92-1.99 (m, 1H), 6.44 (s, 1H), 7.73 (d, J=3.6 Hz, 1H), 7.79 (d, J=3.6 Hz, 1H), 8.46 (s, 1H), 9.47 (s, 1H), 12.84 (bs, 2H).

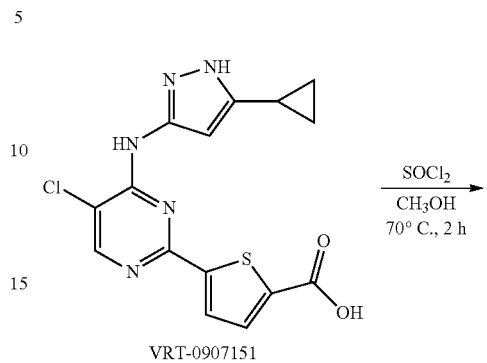

VRT-0907151

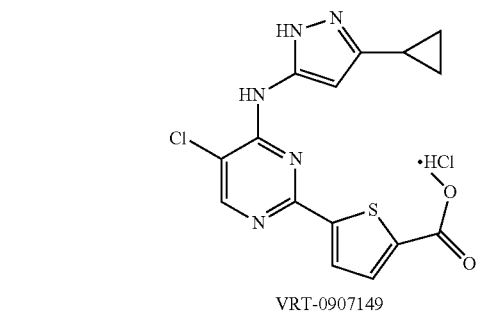

VRT-0907149

Methyl 5-(5-chloro-4-(3-cyclopropyl-1H-pyrazol-5-ylamino)pyrimidin-2-yl)thiophene-2-carboxylate hydrochloride (Compound 154)

To a solution of 5-(5-chloro-4-(3-cyclopropyl-1H-pyrazol-5-ylamino)pyrimidin-2-yl)thiophene-2-carboxylic acid (Compound 156) (50 mg, 0.138 mmol) in methanol (5 mL) was added SOCl$_2$ (0.5 mL) dropwise. The mixture was stirred at 70° C. for 2 hrs. LCMS showed that the reaction is over. The solvent was removed in vacuum to the target product Methyl 5-(5-chloro-4-(3-cyclopropyl-1H-pyrazol-5-ylamino)pyrimidin-2-yl)thiophene-2-carboxylate hydrochloride (Compound 154) as HCl salt (25 mg, 44%). LC-MS (m/z)=376 [M+H]+; 1H NMR (400 MHz, DMSO-d6): δ 0.77-0.81 (m, 2H), 1.00-1.05 (m, 2H), 1.95-2.02 (m, 1H), 3.86 (s, 3H), 6.43 (s, 1H), 7.81-7.84 (m, 2H), 8.51 (s, 1H), 9.67 (s, 1H).

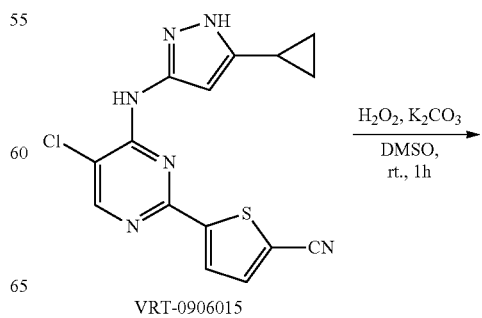

VRT-0906015

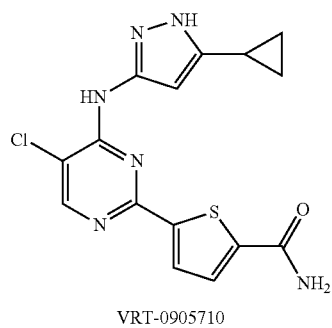

VRT-0905710

5-(5-Chloro-4-(5-cyclopropyl-1H-pyrazol-3-ylamino)pyrimidin-2-yl)thiophene-2-carboxamide (Compound 131)

A mixture of 5-(5-chloro-4-(5-cyclopropyl-1H-pyrazol-3-ylamino)pyrimidin-2-yl)thiophene-2-carbonitrile (Compound 140) (7 mg, 0.02 mmol, 1 equiv.), $H_2O_2$ (6.8 mg, 0.2 mmol, 10 equiv.) and $K_2CO_3$ (14 mg, 0.1 mmol, 5 equiv.) in DMSO (1 mL) was stirring at rt. for 1 h. The mixture was washed by water to afford 5-(5-chloro-4-(5-cyclopropyl-1H-pyrazol-3-ylamino)pyrimidin-2-yl)thiophene-2-carboxamide (Compound 131) (5 mg, 69%). LC-MS (m/z)=361 [M+H]+; 1H NMR (400 MHz, DMSO-$d_6$): δ 0.74 (d, J=14.4 Hz, 2H), 0.98 (d, J=7.6 Hz, 2H), 1.93-1.97 (m, 1H), 6.46 (s, 1H), 7.73-7.46 (m, 1H), 7.76 (s, 1H), 8.07-8.18 (m, 1H), 8.34 (d, J=12.8 Hz, 1H), 8.45 (d, J=6.4 Hz, 1H), 9.19-9.35 (m, 1H), 12.23-12.29 (m, 1H).

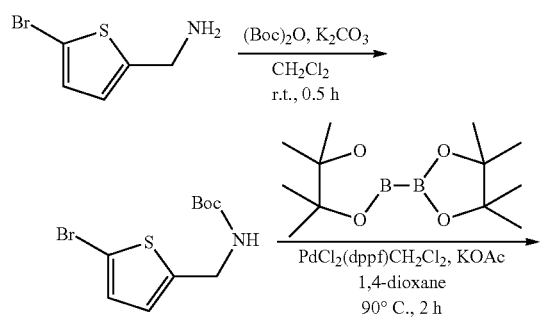

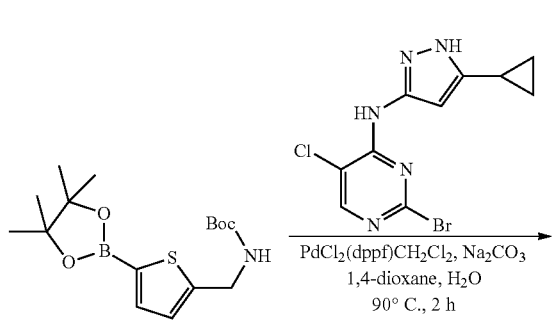

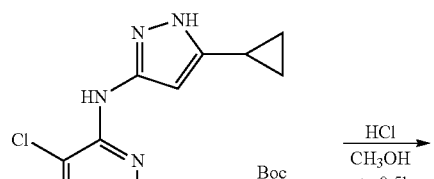

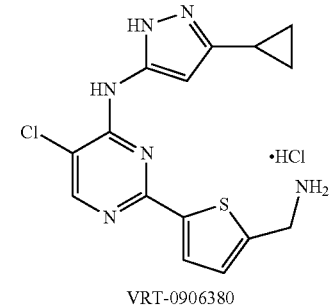

VRT-0906380

2-(5-(aminomethyl)thiophen-2-yl)-5-chloro-N-(3-cyclopropyl-1H-pyrazol-5-yl)pyrimidin-4-amine hydrochloride (Compound 141)

A mixture of (5-bromothiophen-2-yl)methanamine (3.0 g, 15.62 mmol), (Boc)$_2$O (5.1 g, 23.43 mmol, 1.5 eq) and $K_2CO_3$ (4.3 g, 31.24 mmol, 2.0 equiv) in DCM (30 mL) was stirred at room temperature for 0.5 h. Water was added and the reaction was extracted with EA. The combined organic layers were dried (Na$_2$SO$_4$), filtered. The filtrate was concentrated to afford the compound 2 (3.8 g, 83%). LC-MS (m/z)=376 [M+H]+.

2-(5-(aminomethyl)thiophen-2-yl)-5-chloro-N-(3-cyclopropyl-1H-pyrazol-5-yl)pyrimidin-4-amine hydrochloride (Compound 141) (100 mg, 19%) was prepared as in a similar way as described in Compound 138. LC-MS (m/z)=347 [M+H]+; 1H NMR (500 MHz, DMSO-$d_6$): δ 0.83-0.86 (m, 2H), 1.03-1.06 (m, 2H), 2.04-2.09 (m, 1H), 4.27 (d, J=5.0 Hz, 2H), 6.50 (s, 1H), 7.37 (d, J=3.5 Hz, 1H), 7.82 (d, J=3.5 Hz, 1H), 8.51 (s, 1H), 8.71 (s, 2H), 9.83 (s, 1H).

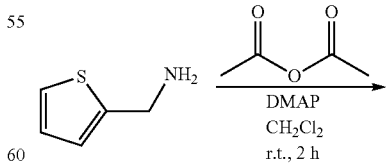

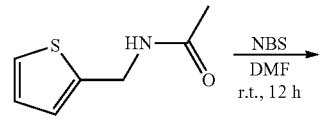

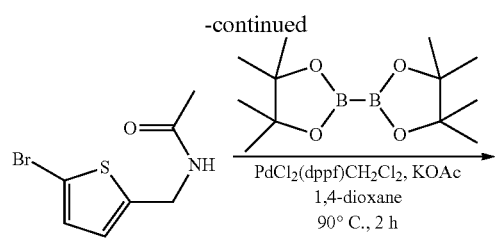

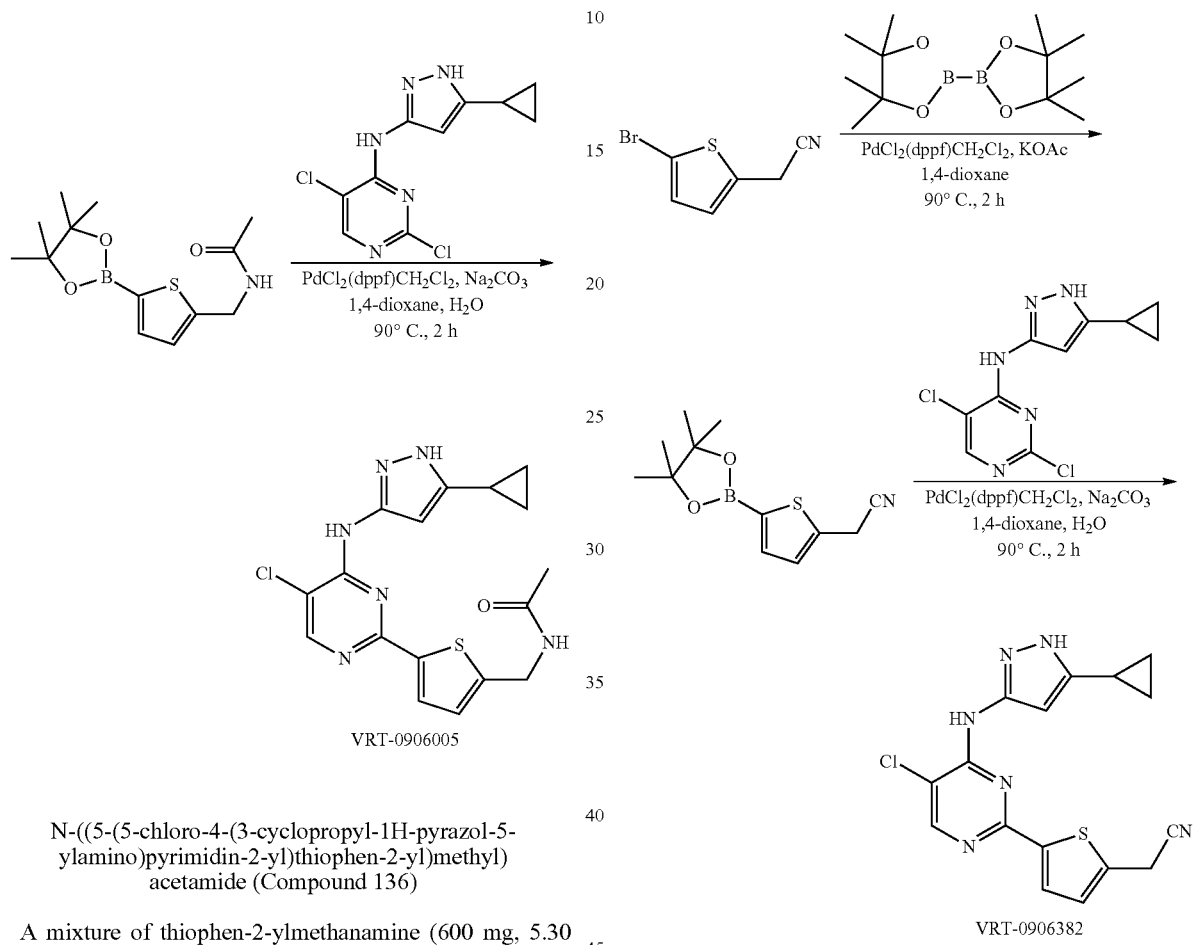

N-((5-(5-chloro-4-(3-cyclopropyl-1H-pyrazol-5-ylamino)pyrimidin-2-yl)thiophen-2-yl)methyl)acetamide (Compound 136)

A mixture of thiophen-2-ylmethanamine (600 mg, 5.30 mmol), DMAP (130 mg, 1.06 mmol, 0.2 equiv) and acetic anhydride (648 mg, 6.36 mmol, 1.2 equiv) in DCM (20 mL) was stirred at room temperature for 2 h. Water was added and the reaction was extracted with EA. The combined organic layers were dried (Na$_2$SO$_4$), filtered. The filtrate was concentrated to afford the compound N-(thiophen-2-ylmethyl)acetamide (745 mg, 91%). LC-MS (m/z)=156 [M+H]$^+$.

A mixture of N-(thiophen-2-ylmethyl)acetamide (745 mg, 4.80 mmol) and NBS (940 mg, 5.28 mmol, 1.1 equiv) in DMF (10 mL) was stirred at room temperature for 12 h. Water was added and the reaction was extracted with EA. The combined organic layers were dried (Na$_2$SO$_4$), filtered. The filtrate was concentrated to afford the compound 3 (1.0 g, 89%). LC-MS (m/z)=234 [M+H]$^+$.

N-((5-(5-chloro-4-(3-cyclopropyl-1H-pyrazol-5-ylamino)pyrimidin-2-yl)thiophen-2-yl)methyl)acetamide (Compound 136) (100 mg, 27%) was prepared using the procedure for synthesis of Compound 129. LC-MS (m/z)=389 [M+H]$^+$; $^1$H NMR (500 MHz, DMSO-d$_6$): δ 0.75-0.76 (m, 2H), 0.98-1.00 (m, 2H), 1.89 (s, 3H), 4.44 (d, J=6.0 Hz, 2H), 6.46 (s, 1H), 7.01 (d, J=3.5 Hz, 1H), 7.54 (d, J=3.0 Hz, 2H), 8.38 (s, 1H), 8.57 (t, J=5.5 Hz, 1H), 9.27 (s, 1H), 12.29 (s, 1H).

2-(5-(5-chloro-4-(3-cyclopropyl-1H-pyrazol-5-ylamino)pyrimidin-2-yl)thiophen-2-yl)acetonitrile Starting from 2-(5-bromothiophen-2-yl)acetonitrile, 2-(5-(5-chloro-4-(3-cyclopropyl-1H-pyrazol-5-ylamino)pyrimidin-2-yl)thiophen-2-yl)acetonitrile (Compound 143) (120 mg, 30%) was prepared using the procedure for synthesis of Compound 129. LC-MS (m/z)=357 [M+H]$^+$; $^1$H NMR (500 MHz, DMSO-d$_6$): δ 0.76 (m, 2H), 0.98-0.99 (m, 2H), 1.93-1.98 (m, 1H), 4.38 (s, 2H), 6.44 (s, 1H), 7.14 (d, J=4.0 Hz, 1H), 7.69 (d, J=4.0 Hz, 1H), 8.41 (s, 1H), 9.33 (s, 1H), 12.29 (s, 1H).

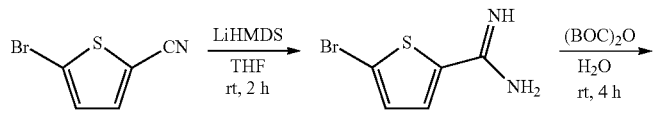

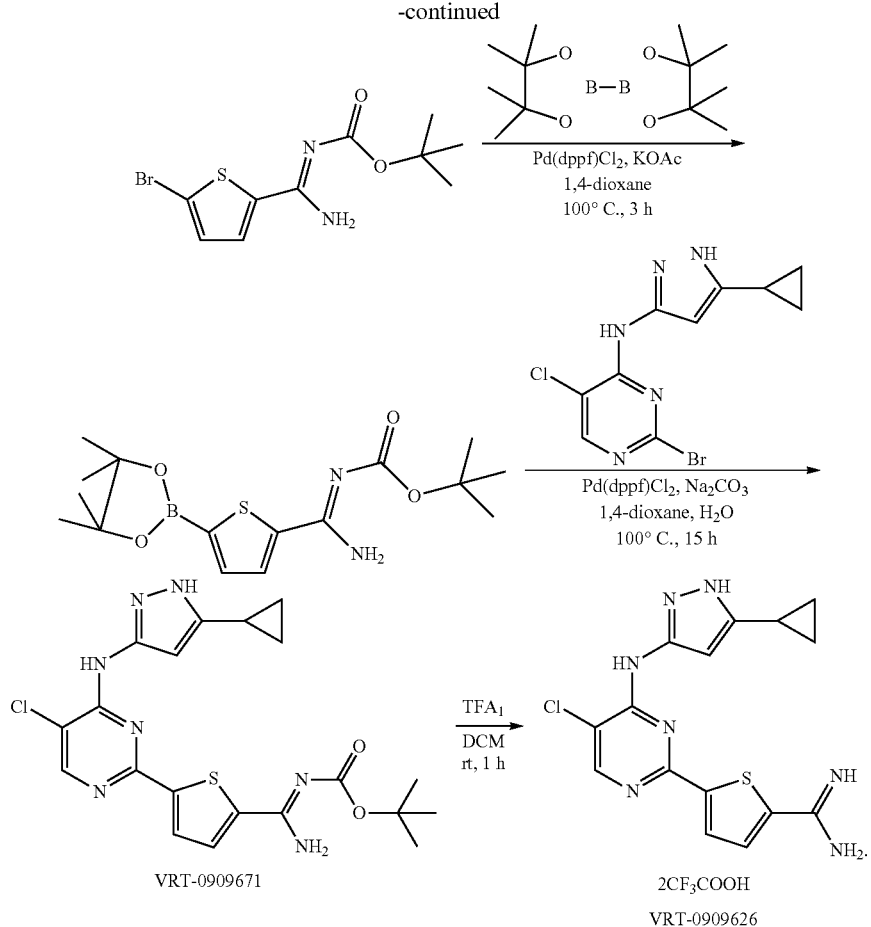

(Z)-tert-butyl amino(5-(5-chloro-4-(5-cyclopropyl-1H-pyrazol-3-ylamino)pyrimidin-2-yl)thiophen-2-yl)methylenecarbamate (Compound 328) and 5-(5-chloro-4-(5-cyclopropyl-1H-pyrazol-3-ylamino)pyrimidin-2-yl)thiophene-2-carboximidamide (Compound 205)

To a solution of LiHMDS (2.59 g, 0.013 mmol, 1.3 eq) in THF was added 5-bromo thiophene-2-carbonitrile (1.88 g, 0.01 mmol, 1 eq) dropwise at ice-bath. After 2 h, the reaction mixture was acidified with 2N HCl to pH2, and kept for 0.5 h, extracted with EA. The aqueous was adjusted to pH10, and reacted with di-tert-butyl dicarbonate (3.21 g, 0.015 mmol, 1.5 equiv.) at room temperature overnight to afford (Z)-tert-butyl amino(5-bromothiophen-2-yl)methylenecarbamate (2.3 g, 75%).

(Z)-tert-butyl amino(5-(5-chloro-4-(5-cyclopropyl-1H-pyrazol-3-ylamino)pyrimidin-2-yl)thiophen-2-yl)methylenecarbamate (Compound 328) (70.0 mg, 15.1%) was prepared as following the similar procedure as described Compound 88. LC-MS (m/z)=460 [M+H]; $^1$H NMR (400 MHz, DMSO-$d_6$): δ (400 MHz, DMSO-$d_6$); 0.80 (d, J=4.0 Hz, 2H), 1.00 (d, J=6.8 Hz, 2H), 1.49 (s, 9H), 1.94-1.97 (m, 1H), 6.47 (s, 1H), 7.80 (d, J=4.4 Hz, 1H), 8.01 (d, J=4.0 Hz, 1H), 8.46 (s, 1H), 9.09 (s, 2H), 9.39 (s, 1H), 12.33 (s, 1H)

A mixture of (Z)-tert-butyl amino(5-(5-chloro-4-(5-cyclopropyl-1H-pyrazol-3-ylamino)pyrimidin-2-yl)thiophen-2-yl)methylenecarbamate (Compound 328) (60 mg, 0.13 mmol) and TFA (2 mL) in DCM (2 mL) was stirred at room temperature for 1 h. The solvent was distilled and recrystallized with ether (2 mL) to afford get 5-(5-chloro-4-(5-cyclopropyl-1H-pyrazol-3-ylamino)pyrimidin-2-yl)thiophene-2-carboximidamide (Compound 205) as TFA salt (55 mg, 72%). LC-MS (m/z)=360 [M+H]$^+$; $^1$H NMR (400 MHz, DMSO-$d_6$): δ 0.77-0.81 (m, 2H), 0.97-1.01 (m, 2H), 1.97-2.01 (m, 1H), 6.43 (s, 1H), 7.90 (d, J=4.0 Hz, 1H), 8.01 (d, J=4.0 Hz, 1H), 8.50 (s, 1H), 9.34 (s, 2H), 9.44 (s, 2H), 9.56 (s, 1H).

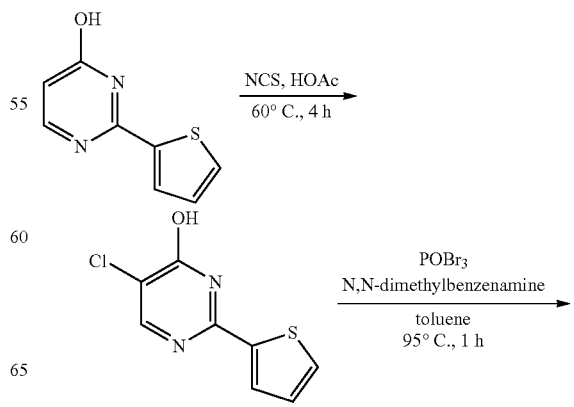

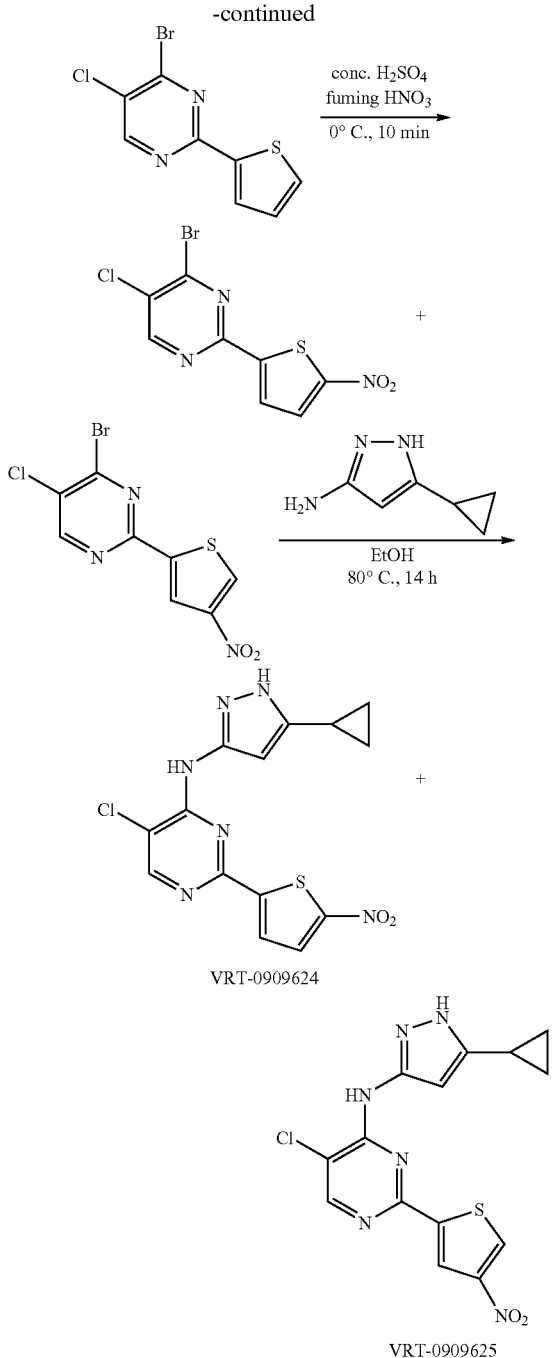

VRT-0909624

VRT-0909625

5-Chloro-N-(5-cyclopropyl-1H-pyrazol-3-yl)-2-(5-nitrothiophen-2-yl)pyrimidin-4-amine (Compound 203) and 5-chloro-N-(5-cyclopropyl-1H-pyrazol-3-yl)-2-(4-nitrothiophen-2-yl)pyrimidin-4-amine (Compound 204)

To the solution of 2-(thiophen-2-yl)pyrimidin-4-ol (100 mg, 0.56 mmol) in HOAc (3 mL) was added NCS (90 mg, 0.67 mmol, 1.2 equiv.) portionwise. The reaction mixture was stirred at 60° C. for 4 h and partitioned between brine and ethylacetate. The organic layer was washed with saturated NaHCO₃, brine, dried over Na₂SO₄, filtered and concentrated. The residue was purified by flash column chromatography to give 5-chloro-2-(thiophen-2-yl)pyrimidin-4-ol (90 mg, 75%). LC-MS (m/z)=213.0 [M+H]⁺.

A mixture of 5-chloro-2-(thiophen-2-yl)pyrimidin-4-ol (90 mg, 0.42 mmol, 1.0 equiv.), POBr₃ (364 mg, 1.27 mmol, 3.0 equiv.) and N,N-dimethylbenzenamine (103 mg, 0.85 mmol, 2.0 equiv.) in toluene (5 mL) was stirred at 100° C. for 1 h, then poured into crashed ice. The mixture was extracted with ethyl acetate. The combined organic layers were washed over saturated NaHCO₃, brine, dried over Na₂SO₄, filtered and concentrated. The residue was purified by column chromatography to afford 4-bromo-5-chloro-2-(thiophen-2-yl)pyrimidine, which was directly used for the next step. LC-MS (m/z)=275.0 [M+H]⁺.

To the solution of 4-bromo-5-chloro-2-(thiophen-2-yl)pyrimidine in conc. H₂SO₄ (1 mL) was added fuming HNO₃ (4 drops) dropwise at 0° C. The reaction mixture was stirred for 10 minutes, quenched with crashed ice. The mixture was extracted with ethyl acetate. The combined organic layers were washed over saturated NaHCO₃, brine, dried over Na₂SO₄, filtered and concentrated. The residue was purified by column chromatography to give the mixture of 4-bromo-5-chloro-2-(5-nitrothiophen-2-yl)pyrimidine and 4-bromo-5-chloro-2-(4-nitrothiophen-2-yl)pyrimidine (80 mg, 59% over 2 steps). LC-MS (m/z)=320.0 [M+H]⁺.

The mixture obtained in last step (80 mg, 0.25 mmol, 1.0 equiv.) and 5-cyclopropyl-1H-pyrazol-3-amine (62 mg, 0.50 mmol, 2.0 equiv.) in ethanol (5 mL) was stirred at 80° C. for 14 h and then concentrated. The residue was purified by prep-HPLC to afford 5-chloro-N-(5-cyclopropyl-1H-pyrazol-3-yl)-2-(5-nitrothiophen-2-yl)pyrimidin-4-amine (Compound 203) (15 mg, 33%) and 5-chloro-N-(5-cyclopropyl-1H-pyrazol-3-yl)-2-(4-nitrothiophen-2-yl)pyrimidin-4-amine (Compound 204) (15 mg, 33%).

5-chloro-N-(5-cyclopropyl-1H-pyrazol-3-yl)-2-(5-nitrothiophen-2-yl)pyrimidin-4-amine (Compound 203). LC-MS (m/z)=362.9 [M+H]⁺; ¹H NMR: (400 MHz, DMSO-d₆): δ 0.69-0.80 (m, 2H), 0.95-1.06 (m, 2H), 1.89-2.01 (m, 1H), 6.37 (s, 1H), 7.77 (d, J=4.4 Hz, 1H), 8.15 (d, J=4.4 Hz, 1H), 8.51 (s, 1H), 9.58 (s, 1H), 12.36 (s, 1H).

5-chloro-N-(5-cyclopropyl-1H-pyrazol-3-yl)-2-(4-nitrothiophen-2-yl)pyrimidin-4-amine (Compound 204). LC-MS (m/z)=363.0 [M+H]⁺; ¹H NMR: (400 MHz, DMSO-d₆): δ 0.66-0.78 (m, 2H), 0.93-1.05 (m, 2H), 1.93-1.96 (m, 1H), 6.38 (s, 1H), 8.12 (s, 1H), 8.47 (s, 1H), 8.92 (d, J=1.6 Hz, 1H), 9.52 (s, 1H), 12.36 (s, 1H).

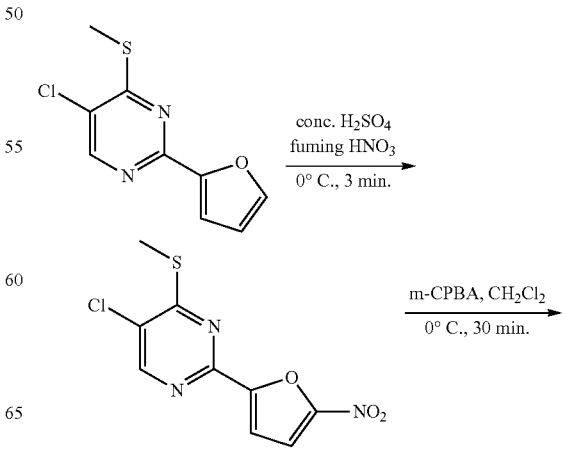

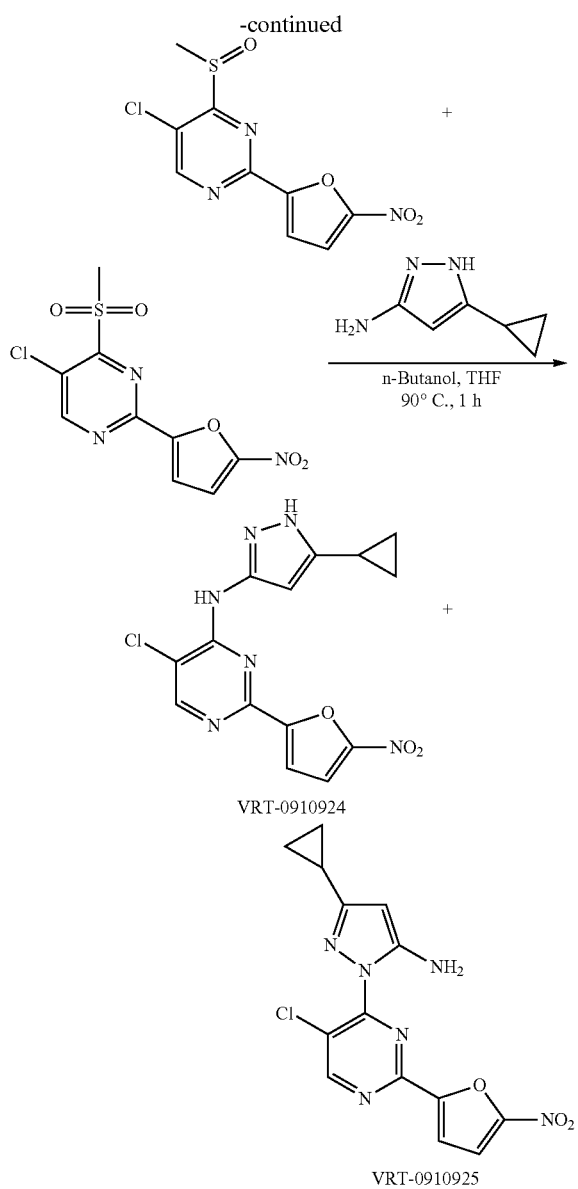

5-chloro-N-(5-cyclopropyl-1H-pyrazol-3-yl)-2-(5-nitrofuran-2-yl)pyrimidin-4-amine (Compound 222) and 1-(5-chloro-2-(5-nitrofuran-2-yl)pyrimidin-4-yl)-3-cyclopropyl-1H-pyrazol-5-amine To the solution of 5-chloro-2-(furan-2-yl)-4-(methylthio)pyrimidine (100 mg, 0.44 mmol, 1.0 equiv.) in conc. $H_2SO_4$ (2 mL) was added fuming $HNO_3$ (2 drops) dropwise at 0° C. The reaction mixture was stirred for 3 minutes, then, quenched with crashed ice. The mixture was extracted with ethyl acetate. The combined organic layers were washed with saturated $NaHCO_3$, brine, dried over $Na_2SO_4$, filtered and concentrated. The residue was purified by column chromatography to give 5-chloro-4-(methylthio)-2-(5-nitrofuran-2-yl)pyrimidine (105 mg, 88%). LC-MS (m/z)=272.0 [M+H]⁺.

To the solution of 5-chloro-4-(methylthio)-2-(5-nitrofuran-2-yl)pyrimidine (225 mg, 0.83 mmol, 1.0 equiv.) in $CH_2Cl_2$ (11 mL) was added m-CPBA (229 mg, 1.00 mmol, 1.2 equiv., 75% content) at 0° C. The reaction mixture was stirred for 30 minutes, then, concentrated to give the mixture of the sulfoxide and sulfone. The residue was directly used for the next step.

A mixture of 3 and 4 (240 mg, 2.02 mmol, 5.1 equiv.) in THF (5 mL) and n-butanol (6 mL) was stirred at 90° C. for 1 h, then, partitioned between brine and ethylacetate. The organic layer was washed over brine, dried over $Na_2SO_4$, filtered and concentrated. The residue was purified by column chromatography to afford 5-chloro-N-(5-cyclopropyl-1H-pyrazol-3-yl)-2-(5-nitrofuran-2-yl)pyrimidin-4-amine (Compound 222) (35 mg, 26% over 2 steps) and 1-(5-chloro-2-(5-nitrofuran-2-yl)pyrimidin-4-yl)-3-cyclopropyl-1H-pyrazol-5-amine (VRT-0910925) (45 mg, 34% over 2 steps).

For 5-chloro-N-(5-cyclopropyl-1H-pyrazol-3-yl)-2-(5-nitrofuran-2-yl)pyrimidin-4-amine (Compound 222): LC-MS (m/z)=347.0 [M+H]⁺; ¹H NMR: (400 MHz, DMSO-d₆): δ 0.78-0.82 (m, 2H), 0.96-1.01 (m, 2H), 1.90-1.97 (m, 1H), 6.61 (s, 1H), 7.43 (d, J=4.0 Hz, 1H), 7.82 (d, J=4.0 Hz, 1H), 8.54 (s, 1H), 9.64 (bs, 1H), 12.36 (bs, 1H).

For 1-(5-chloro-2-(5-nitrofuran-2-yl)pyrimidin-4-yl)-3-cyclopropyl-1H-pyrazol-5-amine (VRT-0910925): LC-MS (m/z)=347.0 [M+H]⁺; ¹H NMR: (400 MHz, DMSO-d₆): δ 0.67-0.71 (m, 2H), 0.86-0.90 (m, 2H), 1.78-1.82 (m, 1H), 5.23 (s, 1H), 6.36 (s, 2H), 7.66 (d, J=4.0 Hz, 1H), 7.87 (d, J=4.0 Hz, 1H), 9.07 (s, 1H).

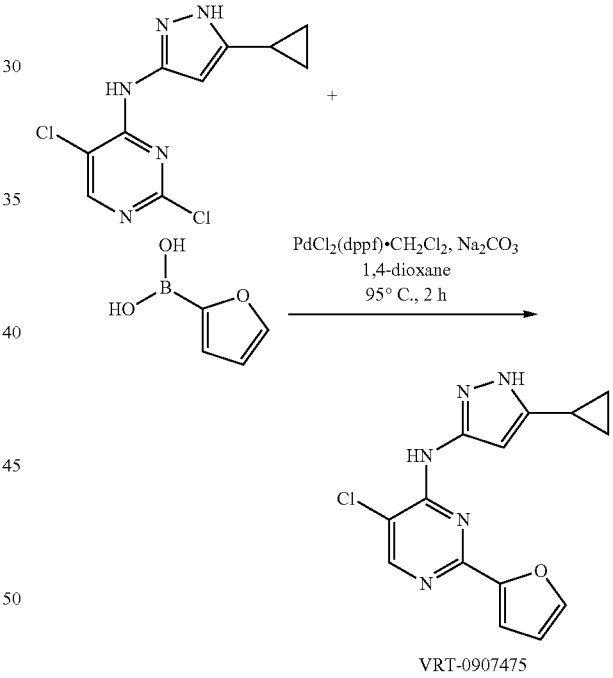

5-chloro-N-(5-cyclopropyl-1H-pyrazol-3-yl)-2-(furan-2-yl)pyrimidin-4-amine (Compound 164)

The mixture of Pd(dppf)Cl₂.CH₂Cl₂ (100 mg, 0.12 mmol, 0.15 eq), furan-2-ylboronic acid (116 mg, 1.04 mmol, 1.3 eq), 2,5-dichloro-N-(5-cyclopropyl-1H-pyrazol-3-yl)pyrimidin-4-amine (215 mg, 0.80 mmol, 1.0 eq) and aq Na₂CO₃ (10 mL) in dioxane (20 mL) was heated to 95° C. for 2 h under nitrogen atmosphere. The reaction mixture was cooled to room temperature, and extracted with THF. The combined layers were purified by prep-HPLC to afford compound 5-chloro-N-(5-cyclopropyl-1H-pyrazol-3-yl)-2-(furan-2-yl)pyrimidin-4- amine (Compound 164) (12 mg, 9%). LC-MS (m/z)=302 [M+H]+; 1H NMR (400 MHz, DMSO-d6): 0.73-0.76 (m, 2H), 0.95-0.98 (m, 2H), 1.93-1.97 (m, 1H), 6.53 (s, 1H), 6.68-6.70 (m, 1H), 7.15 (d, J=2.8 Hz, 1H), 7.91 (s, 1H), 8.41 (s, 1H), 9.24 (s, 1H), 12.24 (s, 1 Hz).

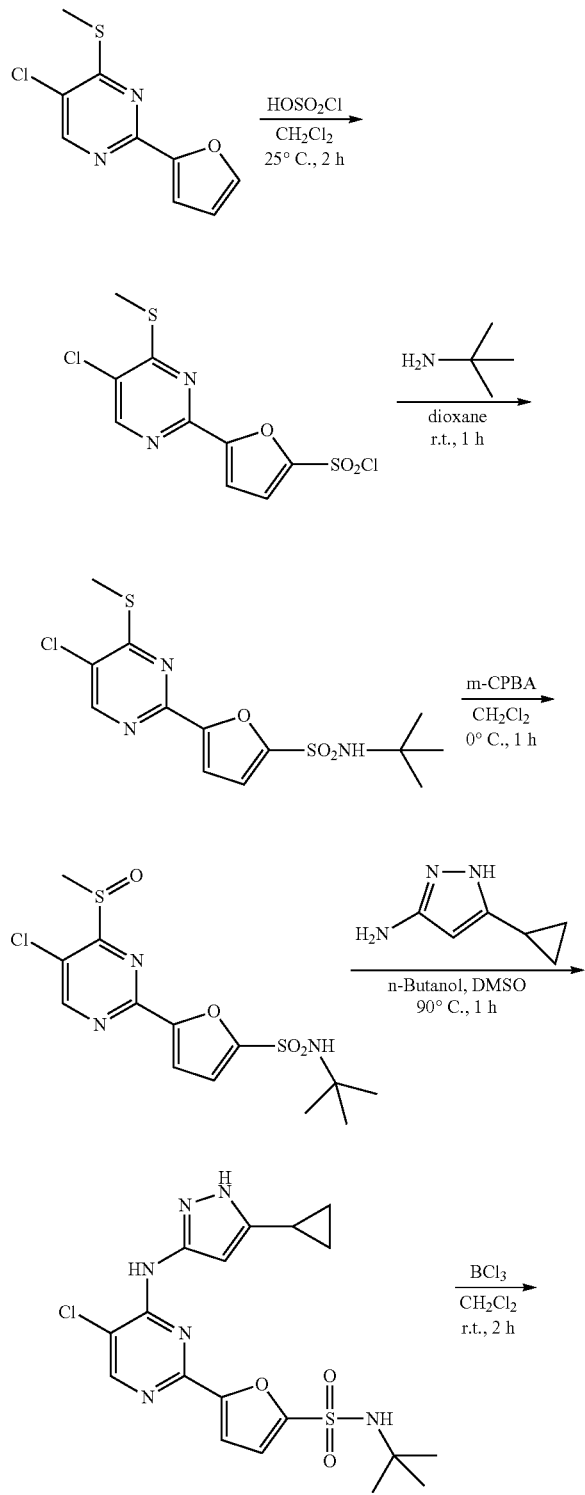

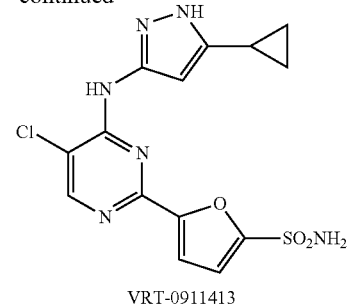

VRT-0911413

5-(5-chloro-4-(5-cyclopropyl-1H-pyrazol-3-ylamino) pyrimidin-2-yl)furan-2-sulfonamide (Compound 240)

To a solution of 5-chloro-2-(furan-2-yl)-4-(methylthio)pyrimidine (800 mg, 3.53 mmol, 1.0 equiv.) in CH2Cl2 (5 mL) was added ClSO3H (25 mL) dropwise at −20° C. The reaction mixture was stirred at 25° C. for 2 h, then, quenched with cracked ice at −20° C. The mixture was extracted with ethylacetate. The combined organic layers was dried with Na2SO4 to give a solution of 5-(5-chloro-4-(methylthio)pyrimidin-2-yl)furan-2-sulfonyl chloride in ethylacetate, to which t-butylamine (10 mL) was added. The mixture was stirred at 20° C. for 2 h, then, concentrated. The residue was purified by column chromatography to afford N-tert-butyl-5-(5-chloro-4-(methylthio)pyrimidin-2-yl)furan-2-sulfonamide (147 mg, 12% over 2 steps). LC-MS (m/z)=362.0 [M+H]+.

To the solution of N-tert-butyl-5-(5-chloro-4-(methylthio)pyrimidin-2-yl)furan-2-sulfonamide (150 mg, 0.42 mmol, 1.0 equiv.) in CH2Cl2 (3 mL) was added m-CPBA (124 mg, 0.54 mmol, 1.3 eq., 75% content) at 0° C. The reaction mixture was stirred for 30 minutes and then concentrated to produce N-tert-butyl-5-(5-chloro-4-(methyl sulfinyl)pyrimidin-2-yl)furan-2-sulfonamide. The residue was directly used for the next step. LC-MS (m/z)=378.0 [M+H]+.

The mixture of the crude N-tert-butyl-5-(5-chloro-4-(methylsulfinyl)pyrimidin-2-yl)furan-2-sulfonamide and 5-cyclopropyl-1H-pyrazol-3-amine (255 mg, 2.08 mmol, 5.0 equiv.) in n-butanol (6 mL) was stirred at 90° C. for 2 h, then, partitioned between brine and ethylacetate. The organic layer was washed over brine, dried over Na2SO4, filtered and concentrated. The residue was purified by column chromatography to afford N-tert-butyl-5-(5-chloro-4-(5-cyclopropyl-1H-pyrazol-3-ylamino)pyrimidin-2-yl)furan-2-sulfonamide (45 mg, 28% over 2 steps). LC-MS (m/z)=437.0 [M+H]+.

To a solution of compound N-tert-butyl-5-(5-chloro-4-(5-cyclopropyl-1H-pyrazol-3-ylamino)pyrimidin-2-yl)furan-2-sulfonamide (45 mg, 0.10 mmol, 1.0 equiv.) in CH2Cl2 (5 mL) was added BCl3 (1.0 mL, 1.0 mmol, 10.0 equiv.) at room temperature. The mixture was stirred for 2 hours, then, concentrated. The residue was recrystallized with methanol and isopropylether to give the title compound 5-(5-chloro-4-(5-cyclopropyl-1H-pyrazol-3-ylamino)pyrimidin-2-yl)furan-2-sulfonamide (Compound 240) (20 mg, 53%). LC-MS (m/z)=380.9 [M+H]+; 1H NMR (400 MHz, DMSO-d6): δ 0.73-0.81 (m, 2H), 0.91-1.00 (m, 2H), 1.91-1.97 (m, 1H), 6.50 (s, 1H), 7.12 (d, J=3.2 Hz, 1H), 7.21 (d, J=2.8 Hz, 1H), 7.93 (s, 2H), 8.48 (s, 1H), 9.44 (s, 1H), 12.28 (s, 1H).

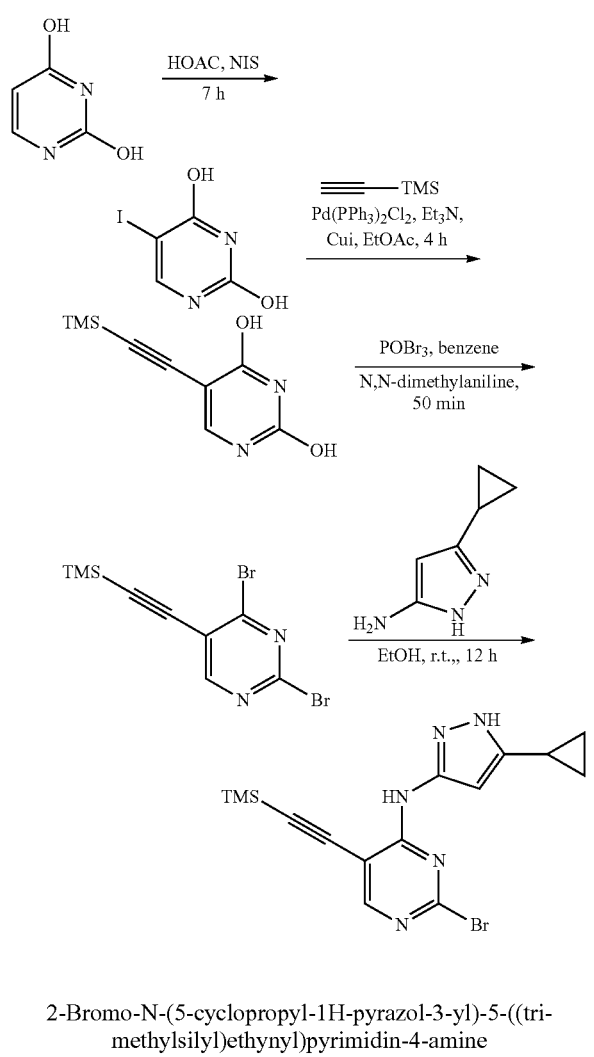

2-Bromo-N-(5-cyclopropyl-1H-pyrazol-3-yl)-5-((trimethylsilyl)ethynyl)pyrimidin-4-amine A mixture of pyrimidine-2,4-diol (100 g, 0.892 mol) and NIS (220 g, 1.981 mol, 1.1 eq) in AcOH (900 mL) was stirred for about 7 h. Solid 5-iodopyrimidine-2,4-diol (202 g, 95%) was obtained by filtration, washed with ethyl acetate. LC-MS (m/z)=238.9 [M+H]$^+$.

(Ph$_3$P)$_2$PdCl$_2$ (7.373 g, 0.0105 mol, 0.025 eq) and finely ground CuI (2.000 g, 0.0105 mol, 0.025 equiv.) were added to a well stirred suspension of 5-iodopyrimidine-2,4-diol (100 g, 0.420 mol, 1.0 eq) in ethyl acetate (800 mL) at 10-15° C. The mixture was then deoxygenated by evacuating and flushing with nitrogen three times. Triethylamine (117 mL, 0.840 mol, 2.0 eq) was added followed by trimethylsilylacetaylene (71.1 mL, 0.504 mol, 1.2 equiv). The suspension was stirred under nitrogen at 25° C. for 4 h. The solids were isolated by filtration under nitrogen and washed sequentially with ethyl acetate (2×100 mL), water (3×100 mL) and finally ethyl acetate (2×100 mL). The product was dried in the air to give 5-((trimethylsilyl)ethynyl)pyrimidine-2,4-diol (40.07 g, 46%). LC-MS (m/z)=209.0 [M+H]$^+$.

Toluene (1300 mL) was added into a well stirred mixture of compound 5-((trimethylsilyl)ethynyl) pyrimidine-2,4-diol (55.382 g, 265.89 mmol, 1.0 equiv.) and N,N-dimethyl aniline (128.1 mL, 976.18 mmol, 3.8 equiv.). Then, POBr$_3$ (671.45 g, 2260.63 mmol, 8.8 equiv.) was added. After a few minutes, the reaction was heated at 100° C. for 50 minutes. The reaction mixture was cooled down and the organic layer was washed with icy water several times till the water's pH=7. The organic phase was dried by Na$_2$SO$_4$, filtered and concentrated. The residue was purified by silica-gel column chromatography (mobile phase: petroleum ether/ethyl acetate=500/10), it a clear oily product 2,4-dibromo-5-((trimethylsilyl)ethynyl) pyrimidine (45 g, 51%). LC-MS (m/z)=334.7 [M+H]$^+$.

(Step 4) A solution of 3-cyclopropyl-1H-pyrazol-5-amine (12.241 g, 99.39 mmol, 1.5 equiv.) in EtOH was added to a solution of compound 2,4-dibromo-5-((trimethylsilyl)ethynyl) pyrimidine (22.136 g, 66.26 mmol,) in EtOH (220 mL) at 20° C. After 12 h, EtOH was evaporated under reduce pressure. The residue was purified by silica-gel column chromatography (mobile phase: petroleum ether/ethyl acetate=20/1~5/1) to afford solid product 2-Bromo-N-(5-cyclopropyl-1H-pyrazol-3-yl)-5-((trimethylsilyl)ethynyl) pyrimidin-4-amine (9.948 g, 40%). LC-MS (m/z)=377.0 [M+H]$^+$.

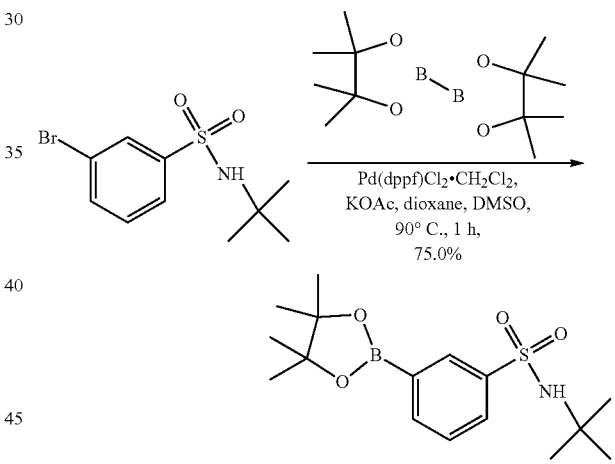

N-tert-butyl-3-(4,4,5,5-tetramethyl-1,3,2-dioxaborolan-2-yl)benzenesulfonamide

A mixture of 3-bromo-N-tert-butylbenzenesulfonamide (1.8 g, 6.17 mmol), 4,4,4',4',5,5,5',5'-octamethyl-2,2'-bi(1,3,2-dioxaborolane) (1.88 g, 7.41 mmol, 1.2 eq), KOAc (1.51 g, 15.4 mmol, 2.5 eq), PdCl$_2$(dppf)CH$_2$Cl$_2$ (504 mg, 0.62 mmol, 0.1 eq) in DMSO (1 mL) was flushed with nitrogen. 1, 4-Dioxane (40 mL) was added and the reaction mixture was stirred at 90° C. for 1 h. The reaction mixture cooled down to room temperature, filtered and the filtrate was washed with brine, dried (Na$_2$SO$_4$), filtered and concentrated. The residue was washed with isopropyl ether. The filtrate was concentrated and crystallized with petroleum ether to afford N-tert-butyl-3-(4,4,5,5-tetramethyl-1,3,2-dioxaborolan-2-yl)benzene sulfonamide (1.56 g, 75%). LC-MS (m/z)=340.0 [M+Na]$^+$.

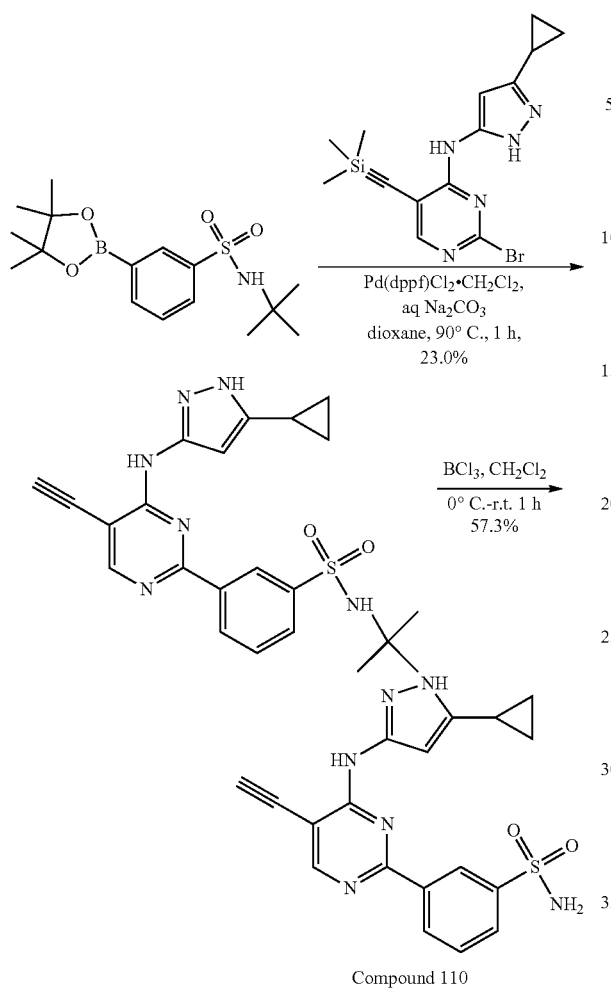

Compound 110

3-(4-(5-cyclopropyl-1H-pyrazol-3-ylamino)-5-ethynylpyrimidin-2-yl)benzene sulfonamide (Compound 110)

A mixture of Pd(dppf)Cl$_2$.CH$_2$Cl$_2$ (65.3 mg, 0.08 mmol, 0.1 equiv.), N-tert-butyl-3-(4,4,5,5-tetramethyl-1,3,2-dioxaborolan-2-yl)benzenesulfonamide (542 g, 1.60 mmol, 2.0 equiv.), 2-Bromo-N-(5-cyclopropyl-1H-pyrazol-3-yl)-5-((trimethyl silyl)ethynyl) pyrimidin-4-amine (300 mg, 0.80 mmol, 1.0 equiv.) and saturated aq Na$_2$CO$_3$ (10 mL) in dioxane (30 mL) was heated to 90° C. for 1 h under nitrogen atmosphere. The reaction mixture was cooled to room temperature and extracted with THF. The combined layers were concentrated and the residue was purified by silica gel chromatography (EtOAc/Petroleum ether from 10:1 to 1:1) to afford compound N-tert-butyl-3-(4-(3-cyclopropyl-1H-pyrazol-5-ylamino)-5-ethynylpyrimidin-2-yl)benzenesulfonamide (80 mg, 23%). LC-MS (m/z)=437.1 [M+H]$^+$.

BCl$_3$ (1 M in CH$_2$Cl$_2$, 0.92 mL, 0.92 mmol, 5 equiv.) was added to a stirred solution of N-tert-butyl-3-(4-(3-cyclopropyl-1H-pyrazol-5-ylamino)-5-ethynylpyrimidin-2-yl)benzenesulfonamide (80 mg, 0.18 mmol, 1.0 equiv.) in CH$_2$Cl$_2$ (20 mL) at room temperature under nitrogen. The reaction mixture was stirred for 30 min and quenched with aq. NaHCO$_3$ under an ice bath. The reaction mixture was extracted with ethylacetate and washed with water, brine, dried, filtered and evaporated. The crude product was crystallized with THF/isopropyl to afford the title compound 3-(4-(5-cyclopropyl-1H-pyrazol-3-ylamino)-5-ethynylpyrimidin-2-yl)benzene sulfonamide (Compound 110) (40 mg, 57%). LC-MS (m/z)=380.9 [M+H]$^+$. $^1$H NMR (400 MHz, DMSO-d$_6$): δ 0.82 (m, 2H), 0.96-0.98 (m, 2H), 1.94 (m, 1H), 4.90 (s, 1H), 6.47 (s, 1H), 7.45 (s, 2H), 7.74 (t, J=8.0 Hz, 1H), 7.97 (d, J=7.6 Hz, 1H), 8.49 (d, J=8.0 Hz, 1H), 8.62 (s, 1H), 8.70 (s, 1H), 8.82 (s, 1H), 12.31 (s, 1H).

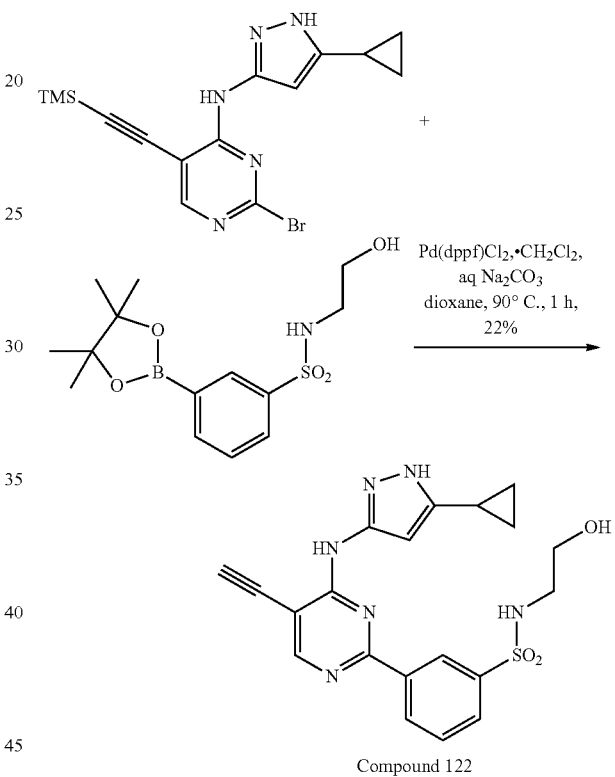

Compound 122

3-(4-(3-Cyclopropyl-1H-pyrazol-5-ylamino)-5-ethynylpyrimidin-2-yl)-N-(2-hydroxyethyl)benzene sulfonamide (Compound 122)

3-(4-(3-Cyclopropyl-1H-pyrazol-5-ylamino)-5-ethynylpyrimidin-2-yl)-N-(2-hydroxyethyl)benzene sulfonamide (Compound 122) (100 mg, 22%) was prepared from N-(2-hydroxyethyl)-3-(4,4,5,5-tetramethyl-1,3,2-dioxaborolan-2-yl)benzenesulfonamide and 2-Bromo-N-(5-cyclopropyl-1H-pyrazol-3-yl)-5-((trimethylsilyl)ethynyl) pyrimidin-4-amine using the same Pd cataliysed condition as described in Compound 110. LC-MS (m/z)=425.1 [M+H]$^+$. $^1$H NMR (400 MHz, DMSO-d$_6$): δ 0.81-0.83 (m, 2H), 0.96-0.98 (m, 2H), 1.91-1.98 (m, 1H), 2.83 (q, J=6.0 Hz, 2H), 3.37 (q, J=6.0 Hz, 2H), 4.70 (t, J=5.6 Hz, 1H), 4.91 (s, 1H), 6.46 (s, 1H), 7.71 (t, J=5.6 Hz, 1H), 7.94 (d, J=8.0 Hz, 1H), 8.52 (d, J=7.6 Hz, 1H), 8.62 (s, 1H), 8.73 (s, 1H), 8.76 (s, 1H), 12.32 (s, 1H).

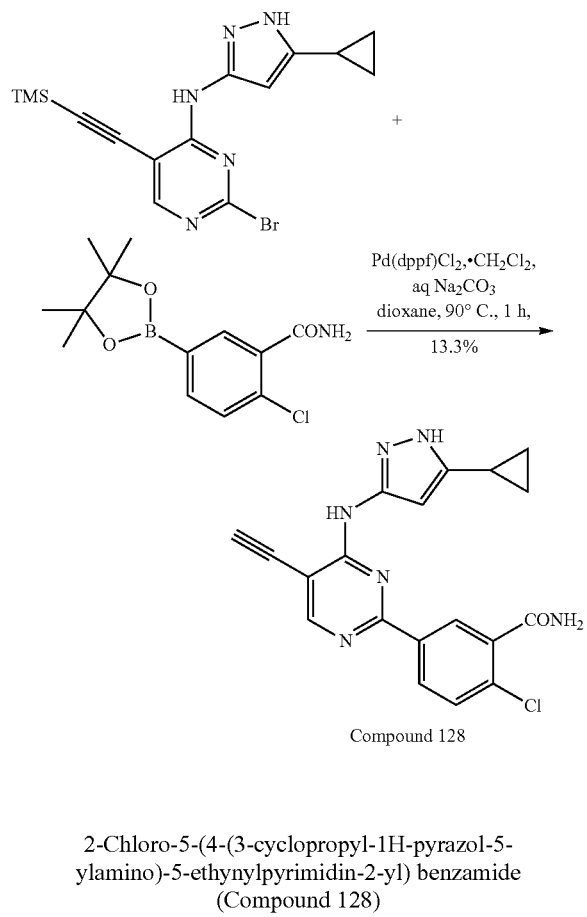

Compound 128

2-Chloro-5-(4-(3-cyclopropyl-1H-pyrazol-5-ylamino)-5-ethynylpyrimidin-2-yl) benzamide (Compound 128)

2-chloro-5-(4-(3-cyclopropyl-1H-pyrazol-5-ylamino)-5-ethynylpyrimidin-2-yl) benzamide (Compound 128) (40 mg, 13%) was prepared from 2-chloro-5-(4,4,5,5-tetramethyl-1,3,2-dioxaborolan-2-yl)benzamide and 2-bromo-N-(5-cyclopropyl-1H-pyrazol-3-yl)-5-((trimethylsilyl)ethynyl) pyrimidin-4-amine using the same Pd catalysed condition as described in Compound 110. LC-MS (m/z)=378.9 [M+H¹H NMR (400 MHz, DMSO-d$_6$): δ 0.75-0.76 (m, 2H), 0.98-0.99 (m, 2H), 1.89-1.97 (m, 1H), 4.87 (s, 1H), 6.41 (s, 1H), 7.65 (d, J=8.4 Hz, 1H), 7.72 (s, 1H), 8.05 (s, 1H), 8.31 (d, J=8.4 Hz, 1H), 8.33 (d, J=1.6 Hz, 1H), 8.58 (s, 1H), 8.75 (s, 1H), 12.33 (s, 1H).

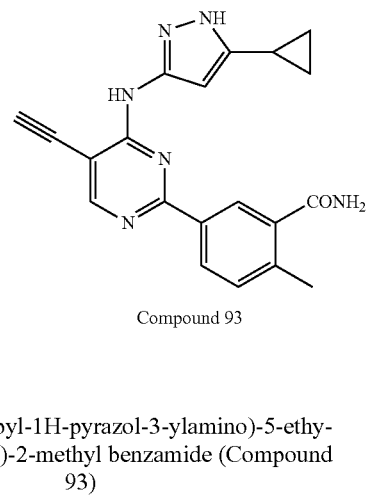

Compound 93

5-(4-(5-Cyclopropyl-1H-pyrazol-3-ylamino)-5-ethynylpyrimidin-2-yl)-2-methyl benzamide (Compound 93)

Using the same coupling procedure as described in Compound 110, 5-(4-(5-cyclopropyl-1H-pyrazol-3-ylamino)-5-ethynylpyrimidin-2-yl)-2-methyl benzamide (Compound 110) (7.4 mg, 2.6%) was prepared from 2-bromo-N-(5-cyclopropyl-1H-pyrazol-3-yl)-5-((trimethylsilyl)ethynyl) pyrimidin-4-amine and 2-methyl-5-(4,4,5,5-tetramethyl-1,3,2-dioxaborolan-2-yl)benzamide. LC-MS (m/z)=359.1 [M+H]⁺. ¹H NMR (400 MHz, DMSO-d$_6$): δ 0.74-0.78 (m, 2H), 0.95-1.00 (m, 2H), 1.91-1.95 (m, 1H), 2.43 (s, 3H), 4.88 (s, 1H), 6.47 (s, 1H), 7.39 (d, J=8.0 Hz, 1H), 7.49 (s, 1H), 7.91 (s, 1H), 8.24 (d, J=8.0 Hz, 1H), 8.33 (d, J=1.2 Hz, 1H), 8.57 (s, 1H), 8.73 (s, 1H), 12.37 (bs, 1H).

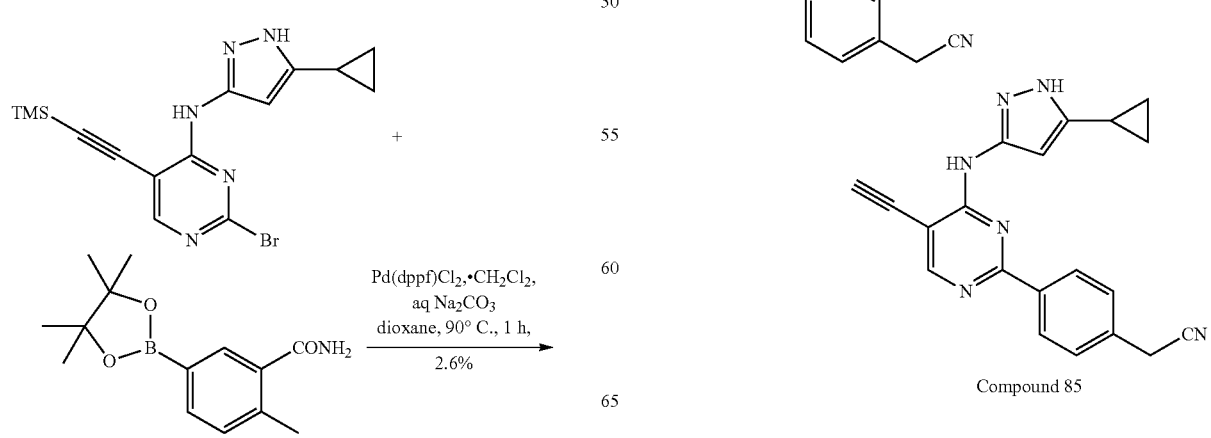

Compound 85

2-(4-(4-(5-cyclopropyl-1H-pyrazol-3-ylamino)-5-ethynylpyrimidin-2-yl)phenyl) acetonitrile (Compound 85)

Using the same coupling procedure as described in Compound 110, 2-(4-(4-(5-cyclopropyl-1H-pyrazol-3-ylamino)-5-ethynylpyrimidin-2-yl)phenyl) acetonitrile (Compound 85) (6.3 mg, 2.3%) was prepared from 2-bromo-N-(5-cyclopropyl-1H-pyrazol-3-yl)-5-((trimethylsilyl)ethynyl) pyrimidin-4-amine and 2-(4-(4,4,5,5-tetramethyl-1,3,2-dioxaborolan-2-yl)phenyl)acetonitrile. LC-MS (m/z)=341.1 [M+H]$^+$. $^1$H NMR (400 MHz, DMSO-d$_6$): δ 0.75-0.76 (m, 2H), 0.98-1.06 (m, 2H), 1.96-2.00 (m, 1H), 4.15 (s, 2H), 4.87 (s, 1H), 6.47 (s, 1H), 7.51 (d, J=8.4 Hz, 2H), 8.32 (d, J=8.0 Hz, 2H), 8.57 (s, 1H), 8.65 (s, 1H), 12.29 (s, 1H).

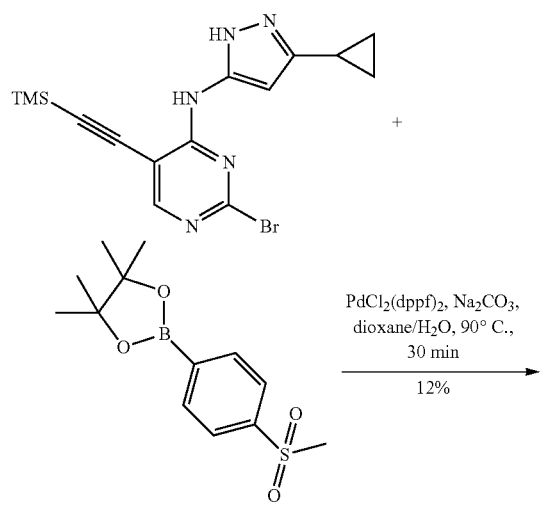

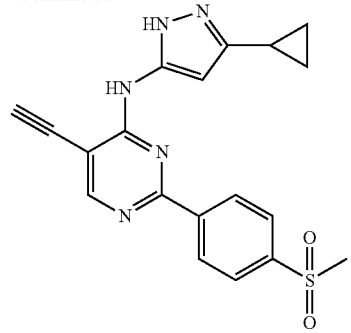

Compound 153

N-(5-Cyclopropyl-1H-pyrazol-3-yl)-5-ethynyl-2-(4-(methylsulfonyl)phenyl) pyrimidin-4-amine (Compound 153)

Using the same coupling procedure as described in Compound 110, N-(5-cyclopropyl-1H-pyrazol-3-yl)-5-ethynyl-2-(4-(methylsulfonyl)phenyl) pyrimidin-4-amine (Compound 153) (50 mg, 12%) was prepared from 2-bromo-N-(5-cyclopropyl-1H-pyrazol-3-yl)-5-((trimethylsilyl)ethynyl) pyrimidin-4-amine and 4,4,5,5-tetramethyl-2-(4-(methylsulfonyl)phenyl)-1,3,2-dioxaborolane. LC-MS (m/z)=380.1 [M+H]$^+$. $^1$H NMR (400 MHz, DMSO-d$_6$): δ 0.78-0.79 (m, 2H), 0.99-1.01 (m, 2H), 1.95-2.02 (m, 1H), 3.29 (s, 3H), 4.91 (s, 1H), 6.45 (s, 1H), 8.09 (d, J=8.4 Hz, 2H), 8.51 (d, J=8.4 Hz, 2H), 8.63 (s, 1H), 8.78 (s, 1H), 12.31 (s, 1H).

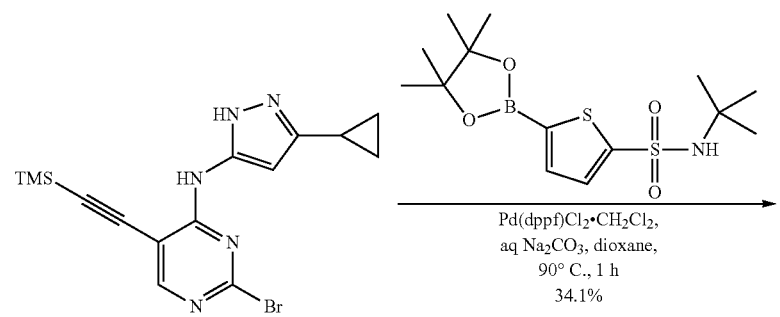

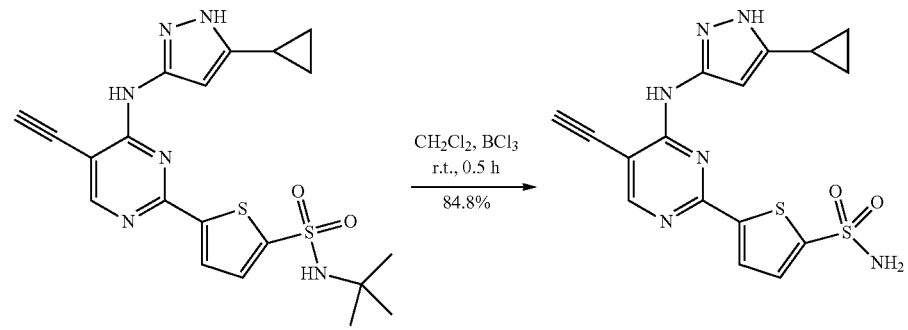

Compound 115  Compound 114

317

N-tert-butyl-5-(4-(5-cyclopropyl-1H-pyrazol-3-ylamino)-5-ethynylpyrimidin-2-yl)thiophene-2-sulfonamide (Compound 115) and 5-(4-(3-Cyclopropyl-1H-pyrazol-5-ylamino)-5-ethynylpyrimidin-2-yl)thiophene-2-sulfonamide (Compound 114)

Using the same coupling procedure as described in Compound 110, N-tert-butyl-5-(4-(5-cyclopropyl-1H-pyrazol-3-ylamino)-5-ethynylpyrimidin-2-yl)thiophene-2-sulfonamide (Compound 115) (200 mg, 34%) was prepared from 2-bromo-N-(5-cyclopropyl-1H-pyrazol-3-yl)-5-((trimethylsilyl)ethynyl) pyrimidin-4-amine and N-tert-butyl-5-(4,4,5,5-tetramethyl-1,3,2-dioxaborolan-2-yl)thiophene-2-sulfonamide. LC-MS (m/z)=442.9 [M+H]+. 1H NMR (400 MHz, DMSO-d6): δ 0.75-0.76 (m, 2H), 0.97-1.00 (m, 2H), 1.20 (s, 9H), 1.91-1.98 (m, 1H), 4.89 (s, 1H), 6.45 (s, 1H), 7.61 (d, J=3.6 Hz, 1H), 7.79 (d, J=4.0 Hz, 1H), 7.93 (s, 1H), 8.51 (s, 1H), 8.78 (s, 1H), 12.31 (s, 1H).

318

5-(4-(3-cyclopropyl-1H-pyrazol-5-ylamino)-5-ethynylpyrimidin-2-yl)thiophene-2-sulfonamide (Compound 114) (59.2 mg, 84.8%) was prepared using the procedure for synthesis of Compound 110. LC-MS (m/z)=386.9 [M+H]+. 1H NMR (400 MHz, DMSO-d6): δ 0.73-0.77 (m, 2H), 0.97-0.99 (m, 2H), 1.91-1.98 (m, 1H), 4.90 (s, 1H), 6.44 (s, 1H), 7.60 (d, J=4.0 Hz, 1H), 7.81 (d, J=4.0 Hz, 1H), 7.84 (s, 2H), 8.52 (s, 1H), 8.80 (bs, 1H), 12.30 (bs, 1H).

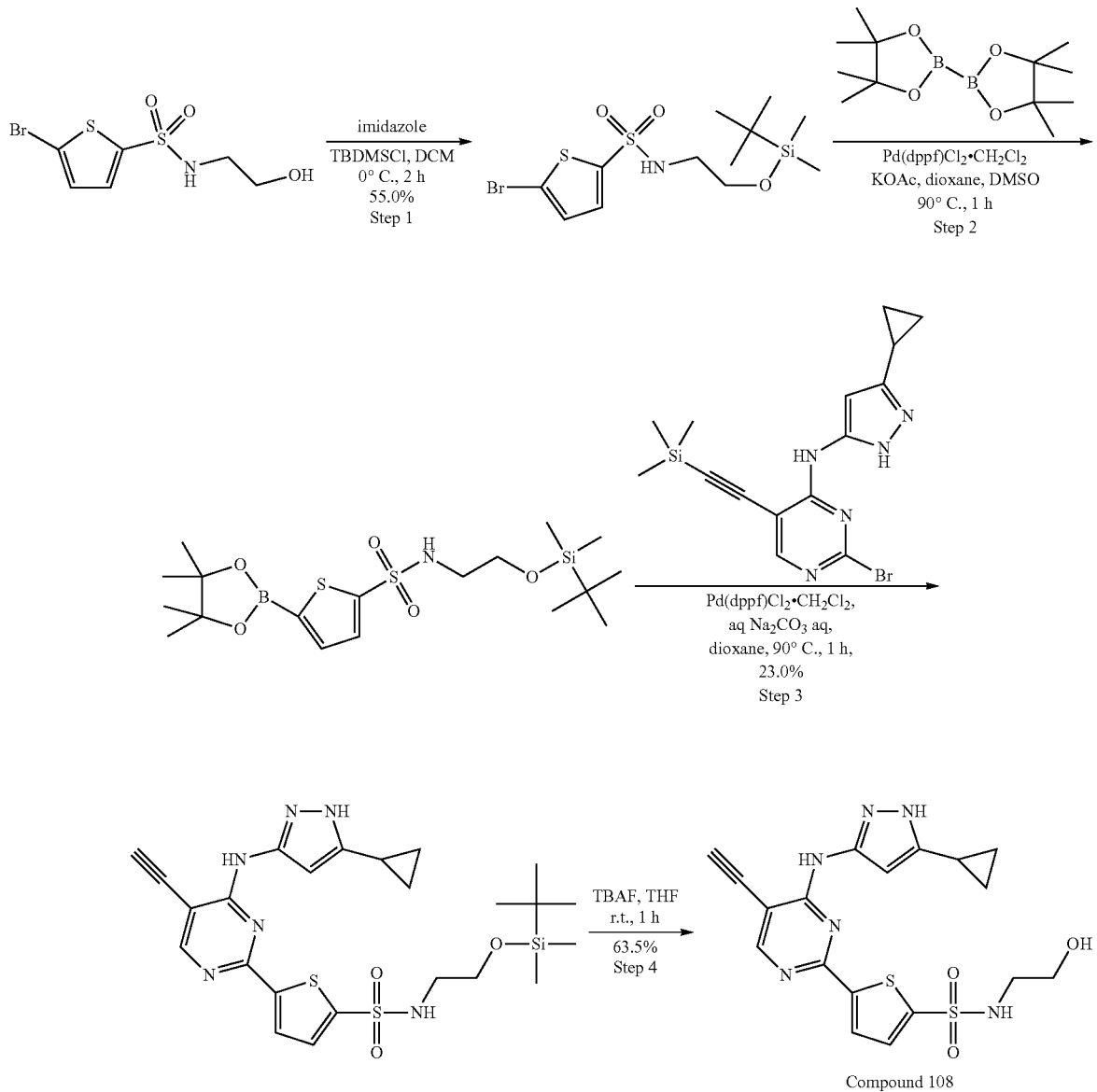

Compound 108

5-(4-(3-cyclopropyl-1H-pyrazol-5-ylamino)-5-ethynylpyrimidin-2-yl)-N-(2-hydroxyethyl)thiophene-2-sulfonamide (Compound 108)

Step 1. To a solution of 5-bromo-N-(2-hydroxyethyl) thiophene-2-sulfonamide (1.3 g, 4.54 mmol) in dry CH2Cl2 (40 mL) was added imidazole (0.371 g, 5.45 mmol, 1.2 eq). The reaction mixture was stirred at 0° C. for 5 min and tert-butylchlorodimethylsilane (0.82 g, 5.45 mmol, 1.2 eq) was added in one portion. The solution was stirred at 0° C. for another 1 h and allowed to warm to room temperature within 2 h. The reaction mixture was evaporated under reduced pressure and the resulting residue was dissolved in EtOAc. The EtOAc solution was washed with 1 N HCl, saturated $NaHCO_3$, and brine, dried ($Na_2SO_4$) and filtered. The filtrate was concentrated by evaporation to afford 5-bromo-N-(2-(tert-butyldimethyl silyloxy)ethyl) thiophene-2-sulfonamide (600 mg, 55%). LC-MS (m/z)=400.0 [M+H]$^+$.

Step 2 and step 3. Following the similar procedures as described in Compound 110, N-(2-(tert-butyldimethyl silyloxy)ethyl)-5-(4-(5-cyclopropyl-1H-pyrazol-3-ylamino)-5-ethynylpyrimidin-2-yl)thiophene-2-sulfonamide (100 mg, 23.0%) was prepared. LC-MS (m/z)=545.0 [M+H]$^+$ Step 4. To a solution of N-(2-(tert-butyldimethylsilyloxy)ethyl)-5-(4-(5-cyclopropyl-1H-pyrazol-3-ylamino)-5-ethynylpyrimidin-2-yl)thiophene-2-sulfonamide (100 mg, 0.18 mmol, 1 equiv.) in dry THF (4 mL) was added tetrabutylammonium fluoride (0.54 mL, 0.54 mmol, 3.0 equiv., 1.0 M solution in THF) dropwise. The reaction mixture was allowed to stir for 1 h. The reaction mixture was washed with $NaHCO_3$ and water. The organic layer was dried ($MgSO_4$) and filtered. The filtrate was concentrated and resulting residue was crystallized with THF, ether and ethanol to give title compound 5-(4-(3-cyclopropyl-1H-pyrazol-5-ylamino)-5-ethynylpyrimidin-2-yl)-N-(2-hydroxyethyl)thiophene-2-sulfonamide (Compound 108) as pale solid (50 mg, 64%). LC-MS (m/z)=430.9 [M+H]$^+$. $^1$H NMR (400 MHz, DMSO-d$_6$): δ 0.75-0.76 (m, 2H), 0.98-1.00 (m, 2H), 1.95 (m, 1H), 2.95 (q, J=5.2 Hz, 2H), 3.42 (q, J=6.0 Hz, 2H), 4.75 (t, J=5.2 Hz, 1H), 4.89 (s, 1H), 6.44 (s, 1H), 7.62 (d, J=3.6 Hz, 1H), 7.83 (d, J=3.6 Hz, 1H), 8.02 (s, 1H), 8.52 (s, 1H), 8.81 (s, 1H), 12.32 (s, 1H).

ethynylpyrimidin-2-yl)-N-methylthiophene-2-sulfonamide (Compound 113) (70 mg, 22%) was prepared from 2-bromo-N-(5-cyclopropyl-1H-pyrazol-3-yl)-5-((trimethylsilyl)ethynyl) pyrimidin-4-amine and N-methyl-5-(4,4,5,5-tetramethyl-1,3,2-dioxaborolan-2-yl)thiophene-2-sulfonamide. LC-MS (m/z)=401.0 [M+H]$^+$. $^1$H NMR (400 MHz, DMSO-d$_6$): δ 0.76 (m, 2H), 0.98-1.00 (m, 2H), 1.90-1.98 (m, 1H), 2.56 (d, J=4.0 Hz, 3H), 4.89 (s, 1H), 6.44 (s, 1H), 7.62 (d, J=4.0 Hz, 1H), 7.84 (d, J=2.8 Hz, 2H), 8.52 (s, 1H), 8.81 (s, 1H), 12.32 (s, 1H).

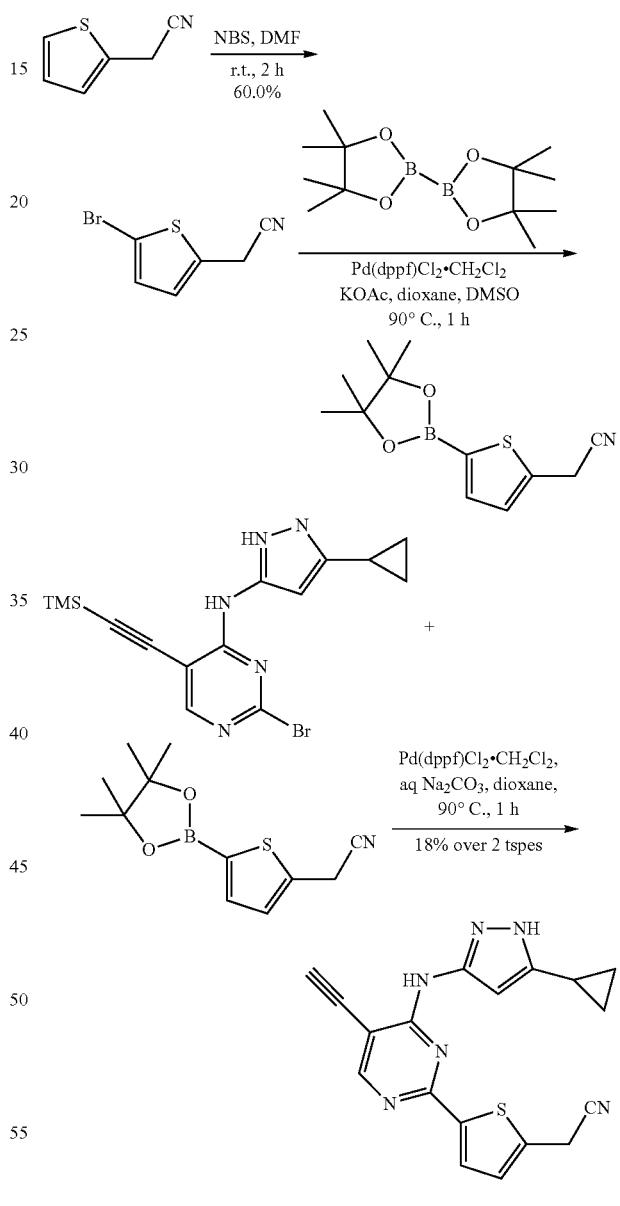

Compound 130

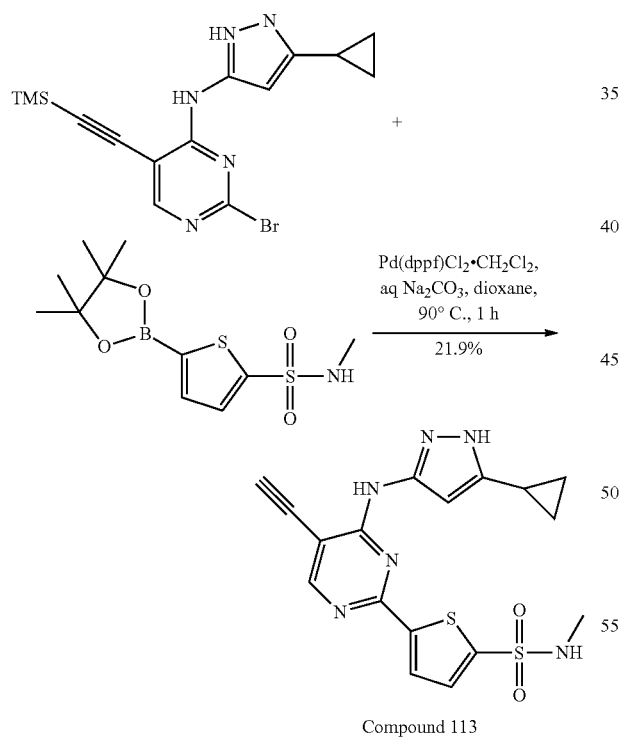

Compound 113

5-(4-(3-cyclopropyl-1H-pyrazol-5-ylamino)-5-ethynylpyrimidin-2-yl)-N-methylthiophene-2-sulfonamide (Compound 113)

Using the same coupling procedure as described in Compound 110, 5-(4-(3-cyclopropyl-1H-pyrazol-5-ylamino)-5-

2-(5-(4-(3-Cyclopropyl-1H-pyrazol-5-ylamino)-5-ethynylpyrimidin-2-yl)thiophen-2-yl)acetonitrile (Compound 130)

To a solution of 2-(thiophen-2-yl)acetonitrile (1.23 g, 10 mmol, 1.0 eq) in DMF (10 mL), NBS (1.96 g, 11 mmol, 1.1 eq) was added. The mixture was stirred at room temperature for 2 h. Water was added to the reaction mixture. After extraction with EtOAc (3×), the organic layers were washed with water, brine, dried ($Na_2SO_4$) and filtered. The filtrate was concentrated and the resulting residue was purified by silica gel chromatography (petroleum/EtOAc from 100:1 to 10:1) to affords 2-(5-bromothiophen-2-yl)acetonitrile (738 mg, 60%). LC-MS (m/z)=202 $[M+H]^+$ The following steps were conducted as described in Compound 110. 2-(5-(4-(3-cyclopropyl-1H-pyrazol-5-ylamino)-5-ethynylpyrimidin-2-yl)thiophen-2-yl)acetonitrile (Compound 130) (50 mg, 18%) was obtained. LC-MS (m/z)=346.9 $[M+H]^+$. $^1H$ NMR (400 MHz, DMSO-$d_6$): δ 0.75-0.77 (m, 2H), 0.98-0.99 (m, 2H), 1.92-1.98 (m, 1H), 4.39 (s, 2H), 4.86 (s, 1H), 6.49 (s, 1H), 7.16 (d, J=3.6 Hz, 1H), 7.74 (d, J=3.6 Hz, 1H), 8.46 (s, 1H), 8.61 (s, 1H), 12.28 (s, 1H).

Step 3 and Step 4. Tert-butyldimethyl((5-(4,4,5,5-tetramethyl-1,3,2-dioxaborolan-2-yl)thiophen-2-yl)methoxy)silane (500 mg, 60%) and 2-(5-((tert-butyldimethylsilyloxy)methyl)thiophen-2-yl)-N-(3-cyclopropyl-1H-pyrazol-5-yl)-5-ethynylpyrimidin-4-amine (240 mg, 55%) were prepared using the procedures for synthesis of Compound 110.

Step 5. A mixture of 2-(5-((tert-butyldimethylsilyloxy)methyl)thiophen-2-yl)-N-(3-cyclopropyl-1H-pyrazol-5-yl)-5-ethynylpyrimidin-4-amine (240 mg, 0.53 mmol, 1.0 eq), TBAF (694 mg, 2.66 mmol, 5.0 eq) in THF (20 ml) was stirred at room temperature for 30 min. The reaction mixture was evaporated under reduce pressure and the resulting residue was dissolved in EtOAc. The organic layers were washed with water, brine, dried ($Na_2SO_4$) and filtered. The filtrate was concentrated the residue was recrystalized by ether to give title compound (5-(4-(5-cyclopropyl-1H-pyrazol-3-

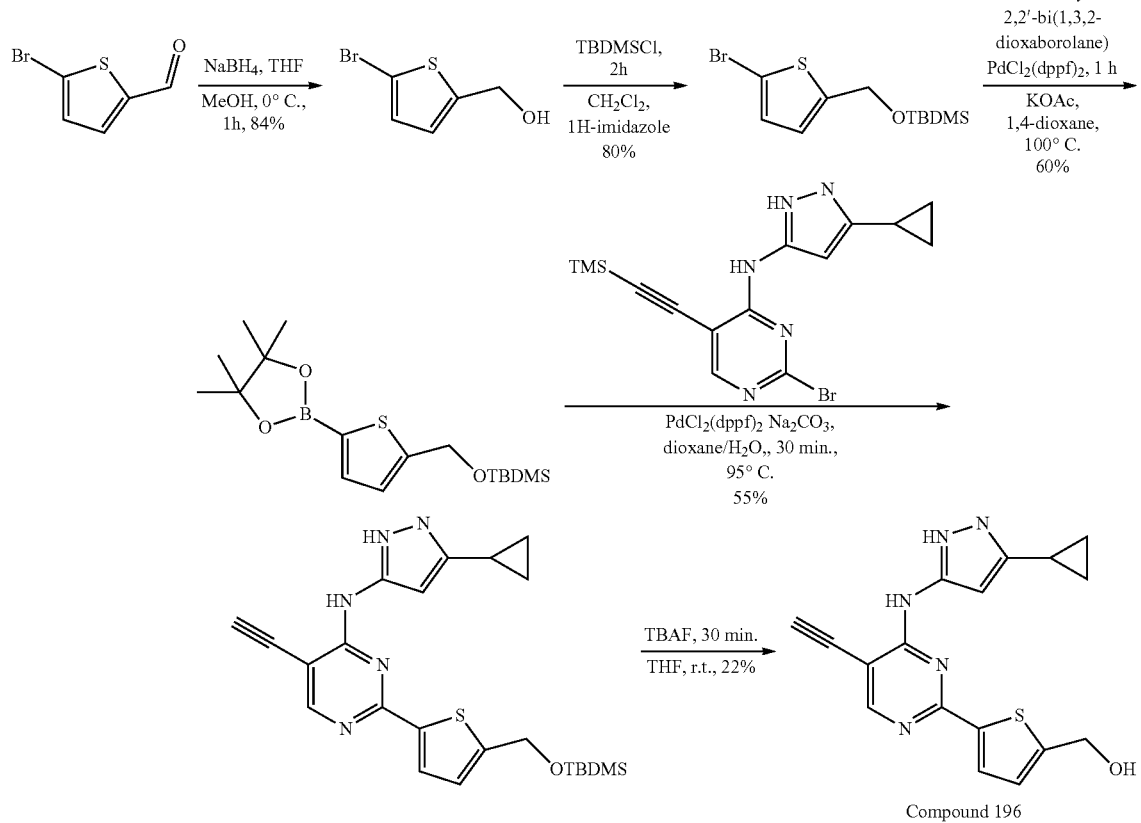

5-(4-(5-Cyclopropyl-1H-pyrazol-3-ylamino)-5-ethynylpyrimidin-2-yl)thiophen-2-yl)methanol (Compound 196)

Step 1. $NaBH_4$ (1.98 g, 52.35 mmol, 5.0 eq) was added to a solution of compound 5-bromothiophene-2-carbaldehyde (2 g, 10.47 mmol, 1.0 equiv.) in dry THF (100 mL) and methanol (50 mL) at 0° C. The mixture was stirred for 1 hour. Then, the reaction was quenched (cracked ice) and concentrated. The residue was recrystallized with methanol and isopropylether to give the compound (5-bromothiophen-2-yl)methanol (1.70 g, 84%).

Step 2. The TBDMS protection was conducted in the same condition as in step 1 of Compound 108.

ylamino)-5-ethynylpyrimidin-2-yl)thiophen-2-yl)methanol (Compound 196) (39 mg, 22%). LC-MS (m/z)=338.0 $[M+H]^+$. $^1H$ NMR (400 MHz, DMSO-$d_6$): δ 0.74 (s, 2H), 0.92-0.97 (m, 2H), 1.94 (s, 1H), 4.67 (d, J=5.2 Hz, 2H), 4.83 (s, 1H), 5.61-5.63 (m, 1H), 6.52 (s, 1H), 7.03 (d, J=1.2 Hz, 1H), 7.72 (d, J=2.4 Hz, 1H), 8.45-8.50 (m, 2H), 12.24 (s, 1H).

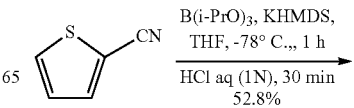

-continued

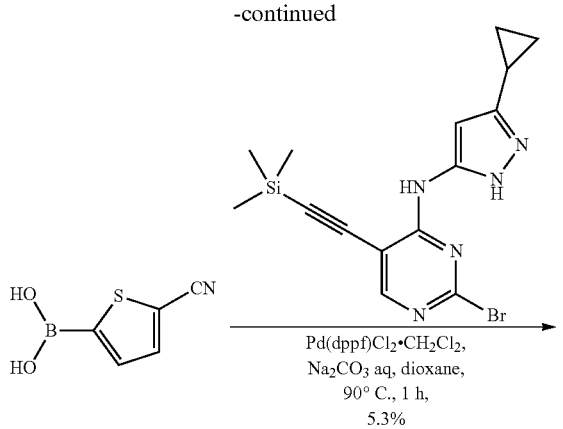

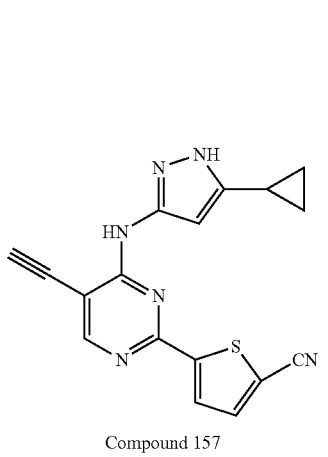

Compound 157

5-(4-(5-Cyclopropyl-1H-pyrazol-3-ylamino)-5-ethynylpyrimidin-2-yl)thiophene-2-carbonitrile (Compound 157)

To a solution of compound thiophene-2-carbonitrile (10 g, 9.16 mmol, 1.0 eq) and tri-iso-propylborate (23 mL, 100 mmol, 1.09 eq) in dry THF (300 mL) under nitrogen at −78° C., potassium hexamethyldisilazide (1 M in THF, 100 mL, 100 mmol, 1.09 eq) was added dropwise. After 1 h, the reaction was quenched with 1 N HCl (200 mL), stirred for 30 min and extracted with ethyl acetate. The combined organic layers were washed with water, dried ($Na_2SO_4$), filtered and evaporated and crystallized with petroleum ether/ethyl acetate to afford the product compound 5-cyanothiophen-2-ylboronic acid (7.4 g, 53%). LC-MS (m/z)=153.9 [M+H]$^+$ 5-(4-(5-cyclopropyl-1H-pyrazol-3-ylamino)-5-ethynylpyrimidin-2-yl)thiophene-2-carbonitrile (Compound 157) (16.8 mg, 5.3%) was prepared using the 1st step procedure for synthesis of Compound 110. LC-MS (m/z)=333.0 [M+H]$^+$. $^1$H NMR (400 MHz, DMSO-d$_6$): δ 0.75-0.76 (m, 2H), 0.97-0.99 (m, 2H), 1.96-1.99 (m, 1H), 4.91 (s, 3H), 6.43 (s, 1H), 7.88 (d, J=4.0 Hz, 1H), 8.03 (d, J=4.0 Hz, 1H), 8.52 (s, 1H), 8.86 (s, 1H), 12.30 (s, 1H).

Compound 157

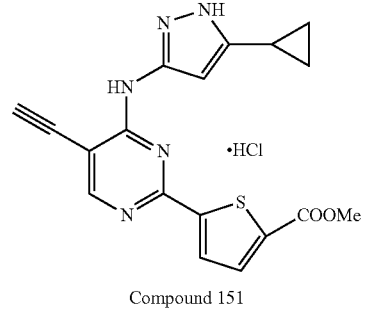

Compound 151

Methyl 5-(4-(5-cyclopropyl-1H-pyrazol-3-ylamino)-5-ethynylpyrimidin-2-yl)thiophene-2-carboxylate hydrochloride (Compound 151)

To a solution of 5-(4-(5-cyclopropyl-1H-pyrazol-3-ylamino)-5-ethynylpyrimidin-2-yl)thiophene-2-carbonitrile (80 mg, 0.24 mmol, 1.0 equiv.) in MeOH (5 mL) was added $K_2CO_3$ (133 mg, 0.96 mmol, 4.0 eq). After being stirred at 20° C. for 4 h, HCl (10%, 5 mL) was added, and the reaction mixture was stirred at 20° C. for 30 min. The reaction mixture was extracted with ethyl acetate, the organic layer was washed with water, dried ($Na_2SO_4$) and evaporated and crystallized with petroleum ether/ethyl acetate to afford the product compound methyl 5-(4-(5-cyclopropyl-1H-pyrazol-3-ylamino)-5-ethynylpyrimidin-2-yl)thiophene-2-carboxylate hydrochloride (Compound 151) (21.2 mg, 22%). LC-MS (m/z)=366 [M+H]$^+$. $^1$H NMR (400 MHz, DMSO-d$_6$): δ 0.75-0.79 (m, 2H), 0.99-1.02 (m, 2H), 1.95-1.99 (m, 1H), 3.87 (s, 3H), 4.92 (s, 1H), 6.46 (s, 1H), 7.85 (dd, J=4.0 Hz, J=3.6 Hz, 2H), 8.54 (s, 1H), 8.99 (s, 1H).

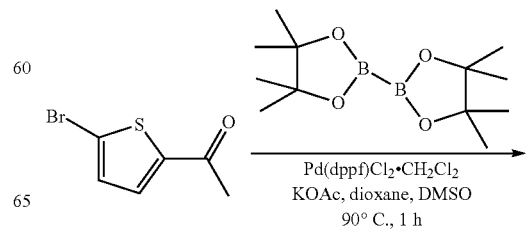

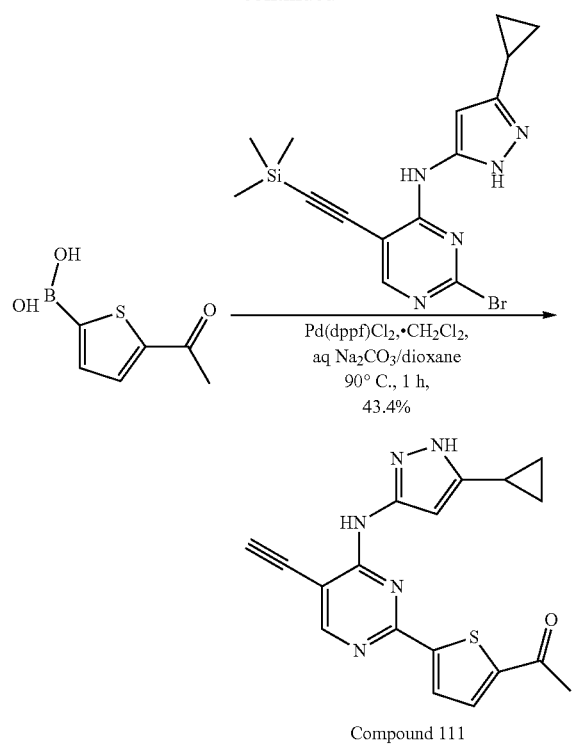

1-(5-(4-(5-Cyclopropyl-1H-pyrazol-3-ylamino)-5-ethynylpyrimidin-2-yl)thiophen-2-yl)ethanone (Compound 111)

1-(5-(4-(5-cyclopropyl-1H-pyrazol-3-ylamino)-5-ethynylpyrimidin-2-yl)thiophen-2-yl)ethanone (Compound 111) (120 mg, 43%) was prepared using the procedure for synthesis of Compound 110. LC-MS (m/z)=349.9 [M+H]$^+$. $^1$H NMR (400 MHz, DMSO-d$_6$): δ 0.74-0.75 (m, 2H), 0.98-0.99 (m, 2H), 1.90-1.98 (m, 1H), 2.57 (s, 3H), 4.90 (s, 1H), 6.46 (s, 1H), 7.87 (d, J=3.6 Hz, 1H), 7.97 (d, J=4.0 Hz, 1H), 8.52 (s, 1H), 8.78 (bs, 1H), 12.31 (s, 1H).

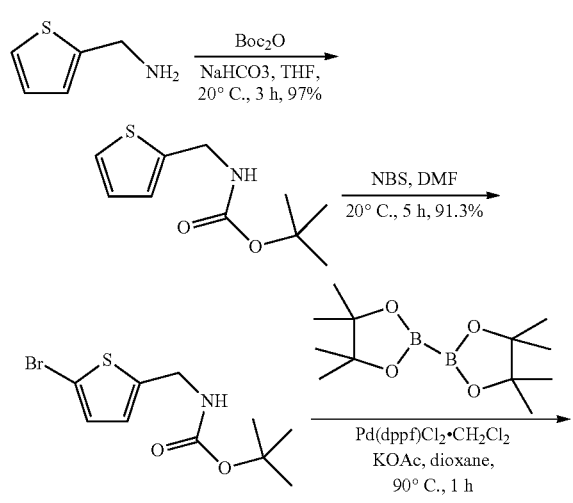

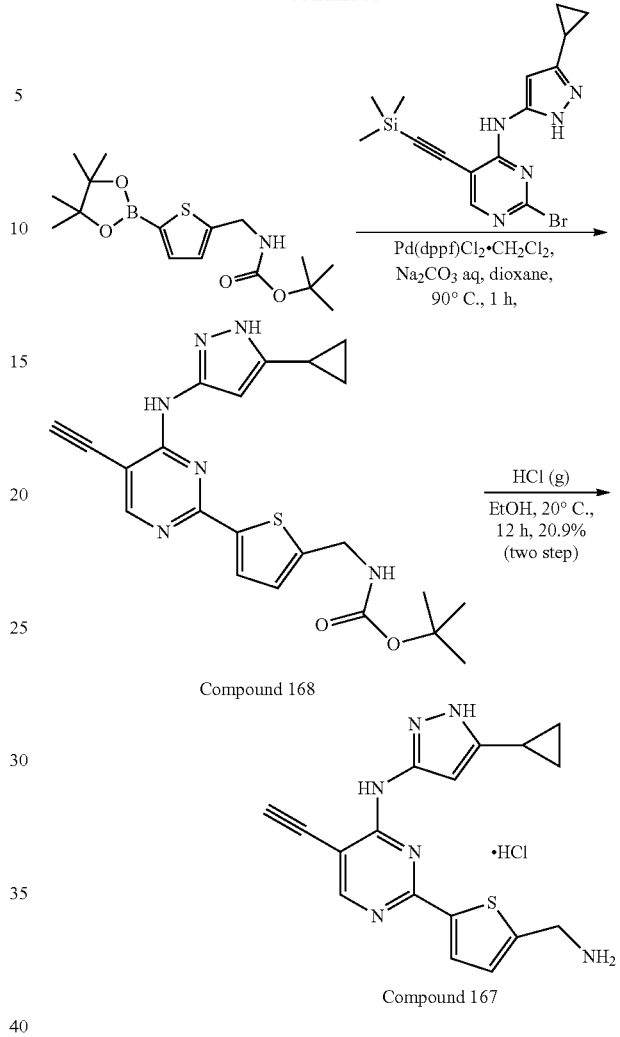

Tert-butyl (5-(4-(5-cyclopropyl-1H-pyrazol-3-ylamino)-5-ethynylpyrimidin-2-yl)thiophen-2-yl)methylcarbamate (Compound 168) and 2-(5-(aminomethyl)thiophen-2-yl)-N-(5-cyclopropyl-1H-pyrazol-3-yl)-5-ethynylpyrimidin-4-amine hydrochloride (Compound 167)

To a solution of compound thiophen-2-ylmethanamine (0.7 g, 6.18 mmol, 1.0 eq) in THF (10 mL) was added NaHCO$_3$ (519 mg, 6.18 mmol, 1.0 equiv.) and (Boc)$_2$O (1.482 g, 6.8 mmol, 1.1 eq) slowly. The resulting mixture was stirred at 20° C. for 3 h. TLC showed that the starting material was disappeared. The reaction was filtrated through silica and concentrated to produce tert-butyl thiophen-2-ylmethylcarbamate (1.28 g, 97%).

To a solution of produce tert-butyl thiophen-2-ylmethylcarbamate (1.28 g, 6 mmol, 1.0 equiv.) in DMF (4 mL) was added NBS (1.17 g, 6.6 mmol, 1.1 eq). After stirring at 20° C. for 5 h, the reaction mixture was diluted with ethyl acetate and washed with water for three times. The organic layer was dried (MgSO$_4$) and concentrated in vacua. The residue was purified by silica gel column chromatography (PE/EtOAc=100:1 to 5:1) to afford tert-butyl (5-bromothiophen-2-yl)methylcarbamate (1.6 g, 91%). LC-MS (m/z)=235.9 [M−55]$^+$. $^1$H NMR (400 MHz, DMSO-d$_6$): δ 1.39 (s, 9H), 4.20 (d, J=6.0 Hz, 2H), 6.76 (d, J=4.0 Hz, 1H), 7.03 (d, J=3.6 Hz, 1H), 7.52 (t, J=5.6 Hz, 1H).

Tert-butyl (5-(4,4,5,5-tetramethyl-1,3,2-dioxaborolan-2-yl)thiophen-2-yl)methylcarbamate (800 mg, 43%) was prepared using the procedure for synthesis of N-tert-butyl-3-(4,4,5,5-tetramethyl-1,3,2-dioxaborolan-2-yl)benzenesulfonamide.

Tert-butyl (5-(4-(5-cyclopropyl-1H-pyrazol-3-ylamino)-5-ethynylpyrimidin-2-yl)thiophen-2-yl)methyl carbamate (Compound 168) was prepared using the procedure for synthesis of Compound 110. LC-MS (m/z)=437.1 [M+H]$^+$. δ (400 MHz, DMSO-d$_6$); 0.76-0.77 (m, 2H), 0.97-0.98 (m, 2H), 1.05 (s, 9H), 1.92-1.96 (m, 1H), 4.32 (d, J=5.6 Hz, 2H), 4.84 (s, 1H), 6.51 (s, 1H), 7.00 (d, J=3.2 Hz, 1H), 7.57 (t, J=5.6 Hz, 1H), 7.71 (d, J=3.6 Hz, 1H), 8.45 (s, 1H), 8.51 (bs, 1H), 12.24 (bs, 1H).

To a solution of tert-butyl (5-(4-(5-cyclopropyl-1H-pyrazol-3-ylamino)-5-ethynylpyrimidin-2-yl)thiophen-2-yl)methylcarbamate (Compound 168) (100 mg, 0.23 mmol, 1.0 equiv.) in EtOH (3 mL) was added HCl(g)/EtOH (saturated, 3 mL). After stirred at 20° C. for 12 h, the reaction mixture was concentrated in vacuum. The crude product was crystallized with THF/isopropyl to afford 2-(5-(aminomethyl)thiophen-2-yl)-N-(5-cyclopropyl-1H-pyrazol-3-yl)-5-ethynylpyrimidin-4-amine hydrochloride (Compound 167) (41.4 mg, 20.9%, two steps). LC-MS (m/z)=337.0 [M+H]$^+$. $^1$H NMR (400 MHz, DMSO-d$_6$): δ 0.80-0.84 (m, 2H), 1.00-1.05 (m, 2H), 2.01-2.04 (m, 1H), 4.28 (d, J=5.2 Hz, 2H), 4.92 (s, 1H), 6.52 (s, 1H), 7.38 (d, J=3.6 Hz, 1H), 7.87 (d, J=4.0 Hz, 1H), 8.53 (s, 1H), 8.65 (bs, 2H), 9.13 (s, 1H).

2-(5-(4-(5-Cyclopropyl-1H-pyrazol-3-ylamino)-5-ethynylpyrimidin-2-yl)thiophen-2-yl)propan-2-ol
(Compound 180)

2-(5-(4-(3-Cyclopropyl-1H-pyrazol-5-ylamino)-5-((trimethyl silyl)ethynyl)pyrimidin-2-yl)thiophen-2-yl)propan-2-ol was prepared according to the coupling procedure in Compound 110. LC-MS (m/z)=438.1 [M+H]$^+$ A mixture of 2-(5-(4-(3-cyclopropyl-1H-pyrazol-5-ylamino)-5-((trimethylsilyl)ethynyl)pyrimidin-2-yl)thiophen-2-yl)propan-2-ol (115 mg, 0.26 mmol), K$_2$CO$_3$ (72 mg, 0.52 mmol, 2.0 equiv.) in CH$_3$OH (10 ml) was stirred at room temperature for 1 h. The mixture was filtered. The solid was washed with water and extracted with EtOAc. The extract was washed by brine, dried (Na$_2$SO$_4$), filtered and concentrated. The residue was recrystalized by ether to give compound 2-(5-(4-(5-cyclopropyl-1H-pyrazol-3-ylamino)-5-ethynylpyrimidin-2-yl)thiophen-2-yl)propan-2-ol (Compound 180) (53 mg, 55%). LC-MS (m/z)=366.1 [M+H]$^+$. $^1$H NMR (400 MHz, DMSO-d$_6$): δ 0.73-0.77 (m, 2H), 0.96-1.01 (m, 2H), 1.54 (s, 6H), 1.91-1.97 (m, 1H), 4.83 (s, 1H), 5.60 (s, 1H), 6.52 (s, 1H), 7.01 (d, J=4.0 Hz, 1H), 7.69 (d, J=4.0 Hz, 1H), 8.63 (s, 1H), 8.45 (s, 1H), 8.56 (bs, 1H), 12.24 (s, 1H).

Following the Suzuki coupling condition, the following compound was also made: \

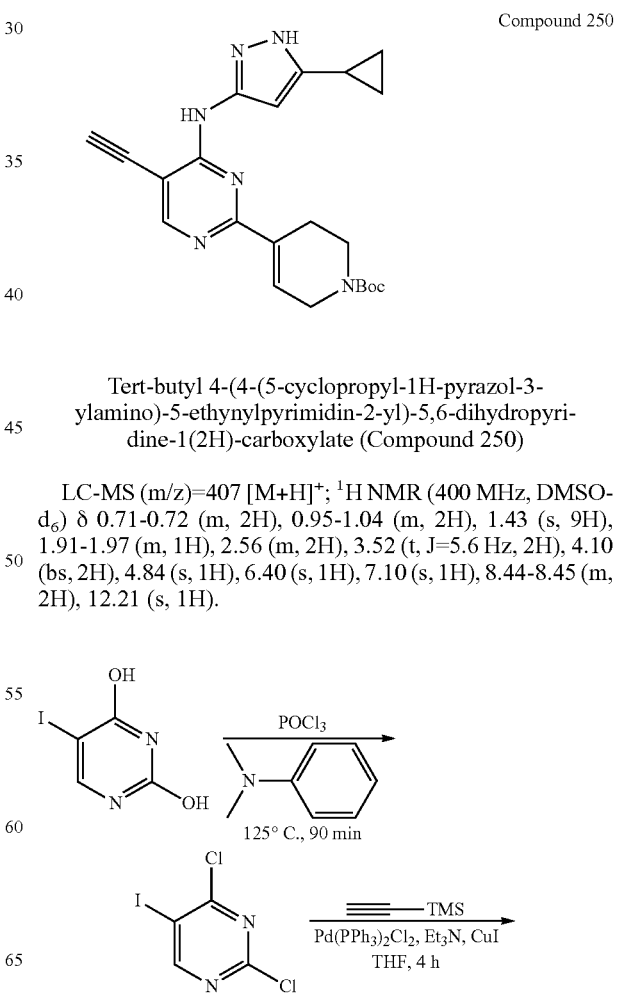

Tert-butyl 4-(4-(5-cyclopropyl-1H-pyrazol-3-ylamino)-5-ethynylpyrimidin-2-yl)-5,6-dihydropyridine-1(2H)-carboxylate (Compound 250)

LC-MS (m/z)=407 [M+H]$^+$; $^1$H NMR (400 MHz, DMSO-d$_6$) δ 0.71-0.72 (m, 2H), 0.95-1.04 (m, 2H), 1.43 (s, 9H), 1.91-1.97 (m, 1H), 2.56 (m, 2H), 3.52 (t, J=5.6 Hz, 2H), 4.10 (bs, 2H), 4.84 (s, 1H), 6.40 (s, 1H), 7.10 (s, 1H), 8.44-8.45 (m, 2H), 12.21 (s, 1H).

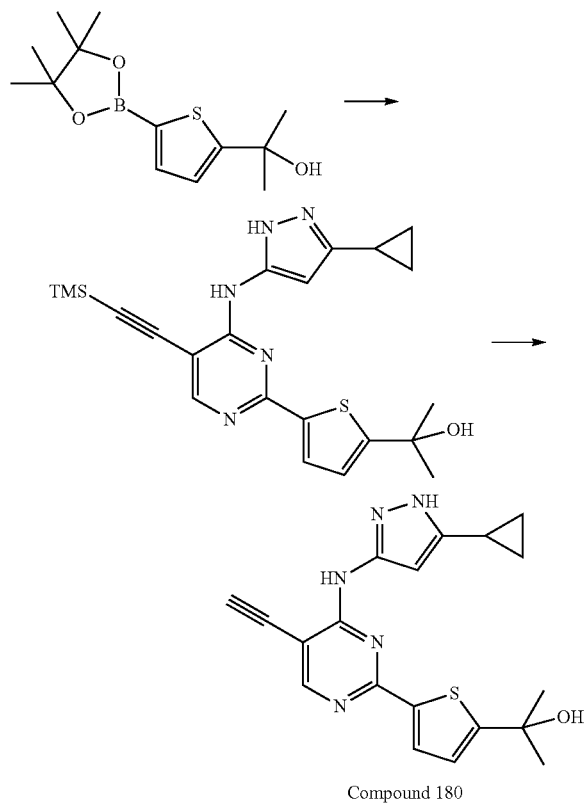

Compound 180

329
-continued

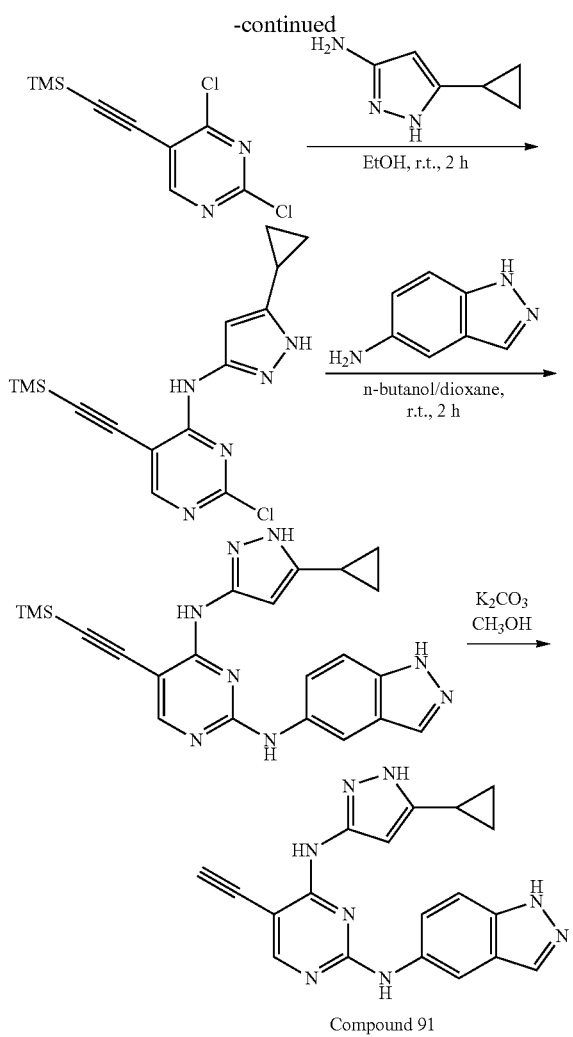

Compound 91

N[4]-(5-cyclopropyl-1H-pyrazol-3-yl)-5-ethynyl-N[2]-(1H-indazol-5-yl)pyrimidine-2,4-diamine (Compound 91)

5-Iodopyrimidine-2,4-diol (10.0 g, 42 mmol, 1.0 eq) was suspended in N,N-dimethylaniline (11 ml), treated with POCl$_3$ (39 mL, 420 mmol, 10.0 eq) and stirred for 90 min at 125° C. After cooling to room temperature, the mixture was poured into ice-water and extracted with EtOAc. The extract were washed with brine, dried (Na$_2$SO$_4$) and concentrated. The residue was purified by silica gel column chromatography (PE/EtOAc=100:1) to afford compound 2,4-dichloro-5-iodopyrimidine (2.0 g, 17%).

Under nitrogen atmosphere, a mixture of 2,4-dichloro-5-iodopyrimidine (2.0 g, 7.3 mmol, 1.0 eq), Pd(PPh$_3$)$_2$Cl$_2$ (256 mg, 0.37 mmol, 0.05 eq), CuI (139 mg, 0.73 mmol, 0.1 eq) Et$_3$N (2.2 g, 21.9 mmol, 3.0 eq) and ethynyltrimethylsilane (1.4 g, 14.6 mmol, 1.2 eq) in THF (20 ml) was stirred at 35° C. for 4 h. The mixture was filtered and concentrated. The residue was purified by silica gel column chromatography (PE/EtOAc=200:1) to give compound 2,4-dichloro-5-((trimethylsilyl)ethynyl)pyrimidine (1.0 g, 56%).

330

A mixture of 2,4-dichloro-5-((trimethylsilyl)ethynyl)pyrimidine (1.0 g, 4.1 mmol, 1.0 eq) and 5-cyclopropyl-1H-pyrazol-3-amine (756 mg, 6.2 mmol, 1.5 eq) in EtOH (4 ml) was stirred at room temperature for 2 h. The mixture was purified by silica gel column chromatography (PE/EtOAc=5:1 to 2:1) to afford 2-chloro-N-(5-cyclopropyl-1H-pyrazol-3-yl)-5-((trimethylsilyl)ethynyl)pyrimidin-4-amine (900 mg, 66%).

A mixture of 2-chloro-N-(5-cyclopropyl-1H-pyrazol-3-O-5-((trimethylsilyl)ethynyl)pyrimidin-4-amine (300 mg, 0.9 mmol, 1.0 eq) and 1H-indazol-5-amine (361 mg, 2.7 mmol, 3.0 eq) in n-butanol (4 ml) and 1,4-dioxane (4 ml) was stirred at 70° C. for 2 h. Then the mixture was washed with water, extracted with EtOAc, dried (Na$_2$SO$_4$) and filtered. EtOAc was removed by evaporation and the residue was recrystalized by PE to give compound N[4]-(5-cyclopropyl-1H-pyrazol-3-yl)-N[2]-(1H-indazol-5-yl)-5-((trimethylsilyl)ethynyl) pyrimidine-2,4-diamine (100 mg, 26%).

N[4]-(5-cyclopropyl-1H-pyrazol-3-yl)-5-ethynyl-N[2]-(1H-indazol-5-yl)pyrimidine-2,4-diamine (Compound 91) (40 mg, 55%) was prepared using the procedure for synthesis of Compound 180. LC-MS (m/z)=357.1 [M+H]$^+$. $^1$H NMR (400 MHz, DMSO-d$_6$): δ 0.57 (s, 2H), 0.86 (s, 2H), 1.82 (s, 1H), 4.60 (s, 1H), 5.63-6.23 (m, 1H), 7.47 (s, 2H), 7.99-8.21 (m, 4H), 9.46 (s, 1H), 12.20 (s, 1H), 12.95 (s, 1H).

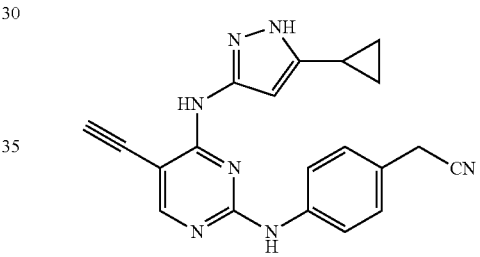

Compound 101

2-(4-(4-(5-Cyclopropyl-1H-pyrazol-3-ylamino)-5-ethynylpyrimidin-2-ylamino)phenyl) acetonitrile (Compound 101)

2-(4-(4-(5-Cyclopropyl-1H-pyrazol-3-ylamino)-5-ethynylpyrimidin-2-ylamino)phenyl) acetonitrile (Compound 101) (50 mg, 58%) was prepared as described in Compound 91. LC-MS (m/z)=356.1 [M+H]$^+$ $^1$H NMR (400 MHz, DMSO-d$_6$): δ 0.68 (s, 2H), 0.94 (s, 2H), 1.89 (s, 1H), 3.97 (s, 2H), 4.61 (s, 1H), 6.31 (bs, 1H), 7.24 (d, J=7.2 Hz, 2H), 7.68 (d, J=7.6 Hz, 2H), 8.16 (bs, 1H), 8.23 (s, 1H), 9.57 (s, 1H), 12.24 (s, 1H).

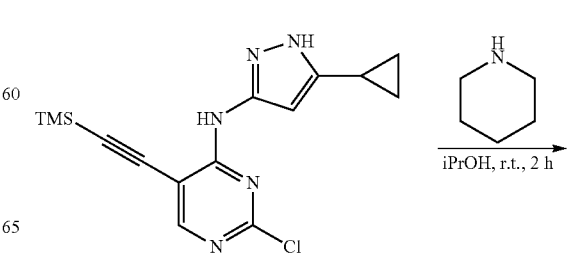

331

-continued

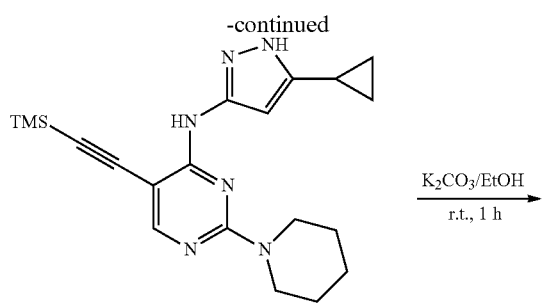

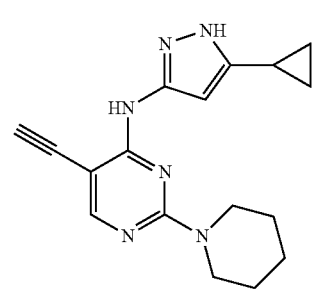

Compound 172

332

N-(5-Cyclopropyl-1H-pyrazol-3-yl)-5-ethynyl-2-(piperidin-1-yl)pyrimidin-4-amine (Compound 172)

A mixture of 2-chloro-N-(5-cyclopropyl-1H-pyrazol-3-yl)-5-((trimethylsilyl)ethynyl) pyrimidin-4-amine (200 mg, 0.6 mmol, 1.0 eq), piperidine (102.7 mg, 1.2 mmol, 2.0 eq) in iPrOH (4 ml) was stirred at room temperature for 2 h. Then the mixture was washed with water, extracted with EtOAc, dried ($Na_2SO_4$). EtOAc was removed by evaporation and the residue was recrystalized by PE to give compound N-(5-cyclopropyl-1H-pyrazol-3-yl)-2-(piperidin-1-yl)-5-((trimethylsilyl)ethynyl)pyrimidin-4-amine (101 mg, 44.3%).

A mixture of N-(5-cyclopropyl-1H-pyrazol-3-yl)-2-(piperidin-1-yl)-5-((trimethylsilyl)ethynyl)pyrimidin-4-amine (101 mg, 0.27 mmol), $K_2CO_3$ (74.5 mg, 0.54 mmol, 2.0 eq) in EtOH (4 ml) was stirred at room temperature for 1 h. The mixture was filtered, the filtration was washed with water, extracted with EtOAc, dried ($Na_2SO_4$). EtOAc was removed by evaporation, the residue was recrystalized from ether to afford compound N-(5-cyclopropyl-1H-pyrazol-3-yl)-5-ethynyl-2-(piperidin-1-yl)pyrimidin-4-amine (Compound 172) (68 mg, 81.9%). MS (m/z): 309.1 [M+H]$^+$. $^1$H NMR (400 MHz, DMSO-$d_6$): δ 0.66-0.68 (m, 2H), 0.95 (d, J=6.8 Hz, 2H), 1.53 (d, J=3.6 Hz, 4H), 1.63-1.66 (m, 2H), 1.89-1.93 (m, 1H), 3.75 (t, J=5.4 Hz, 4H), 4.54 (s, 1H), 6.25 (bs, 1H), 7.94 (bs, 1H), 8.14 (s, 1H), 12.17 (bs, 1H).

This procedure was used for the following amino compounds: Compounds 244, 177, 178, 200, 188, 175 and 174.

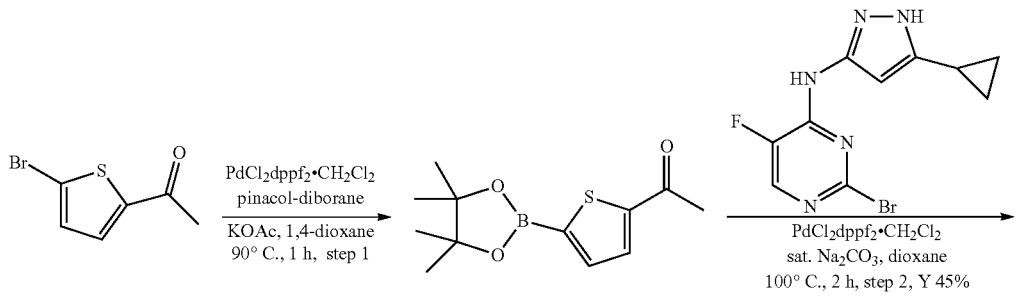

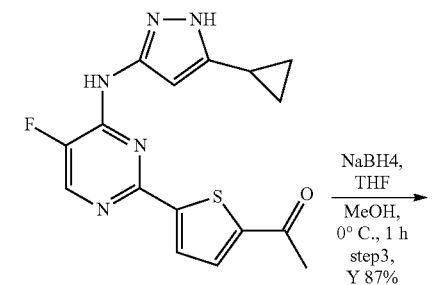

Compound 137

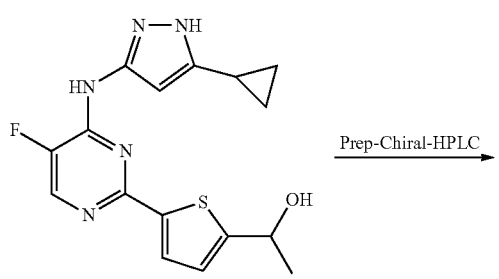

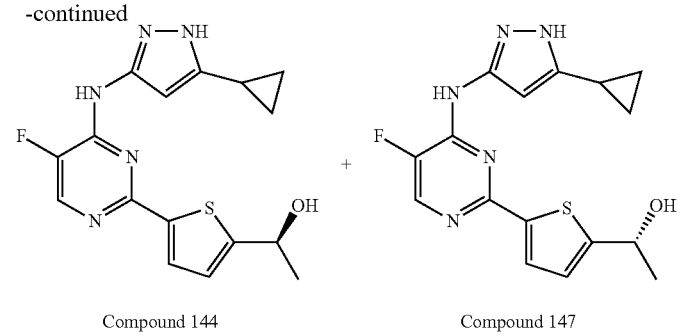

Compound 144            Compound 147

1-(5-(4-(5-cyclopropyl-1H-pyrazol-3-ylamino)-5-fluoropyrimidin-2-yl)thiophen-2-yl)ethanone (Compound 137) and (S and R)-1-(5-(4-(5-cyclopropyl-1H-pyrazol-3-ylamino)-5-fluoropyrimidin-2-yl)thiophen-2-yl)ethanol (Compound 144 and Compound 147)

Step 1. A flask charged with 1-(5-bromothiophen-2-yl)ethanone (1.95 g, 9.56 mmol), pinacol-dibrane (4.86 g, 19.13 mmol, 2.0 eq), KOAc (2.82 g, 28.68 mmol, 3.0 eq) and Pd(dppf)$_2$Cl$_2$ (546 mg, 0.67 mmol, 0.07 eq) was flushed with nitrogen followed by the addition of 1,4-dioxane (30 mL) and DMSO (2 mL). The mixture was stirred at 90° C. for 2 h and cooled to rt. The reaction mixture was filtered and the filtrate was concentrated. The residue was triturated with isopropyl ether and the solid was filtered off. The filtrate was concentrated and the residue 1-(5-(4-(5-cyclopropyl-1H-pyrazol-3-ylamino)-5-fluoropyrimidin-2-yl)thiophen-2-yl)ethanone was used all for the next step. LC-MS (m/z)=171.0 [M+H]$^+$.

Step 2. The mixture of 1-(5-(4-(5-cyclopropyl-1H-pyrazol-3-ylamino)-5-fluoropyrimidin-2-yl)thiophen-2-yl)ethanone, 2-bromo-N-(5-cyclopropyl-1H-pyrazol-3-yl)-5-fluoropyrimidin-4-amine (825 mg, 2.77 mmol, 1.0 eq), Pd(dppf)$_2$Cl$_2$ (226 mg, 0.28 mmol, 0.1 eq) and saturated Na$_2$CO$_3$ aqueous (8 mL) in 1,4-dioxane (60 mL) was stirred at 100° C. for 2 hours under N$_2$. Then, the reaction mixture was cooled down to rt and partitioned between EtOAc and water. The organic layer was concentrated and the residue was purified by column chromatography to give the compound 1-(5-(4-(5-cyclopropyl-1H-pyrazol-3-ylamino)-5-fluoropyrimidin-2-yl)thiophen-2-yl)ethanone (Compound 137) (450 mg, 45%). LC-MS (m/z)=344.0 [M+H]$^+$. $^1$H NMR (400 MHz, DMSO-d$_6$): δ 0.74-0.77 (m, 2H), 0.99-1.02 (m, 2H), 1.94-1.97 (m, 1H), 2.57 (s, 3H), 6.52 (s, 1H), 7.79 (d, J=3.2 Hz, 1H), 7.96 (d, J=3.6 Hz, 1H), 8.36 (d, J=3.2 Hz, 1H), 10.23 (s, 1H), 12.27 (s, H).

Step 3. NaBH$_4$ (220 mg, 5.82 mmol, 5.0 equiv.) was added to a solution of 1-(5-(4-(5-cyclopropyl-1H-pyrazol-3-ylamino)-5-fluoropyrimidin-2-yl)thiophen-2-yl)ethanone (Compound 137) (400 mg, 1.17 mmol, 1.0 equiv.) in dry THF (10 mL) and methanol (10 mL) at 0° C. The mixture was stirred for 1 hour, quenched (crashed ice) and concentrated. The residue was recrystallized with methanol and isopropyl ether to give the racemic 1-(5-(4-(5-cyclopropyl-1H-pyrazol-3-ylamino)-5-fluoropyrimidin-2-yl)thiophen-2-yl)ethanol (350 mg, 87%). LC-MS (m/z)=346.1 [M+H]$^+$.

Step 4. (S)-1-(5-(4-(5-cyclopropyl-1H-pyrazol-3-ylamino)-5-fluoropyrimidin-2-yl)thiophen-2yl)ethanol (Compound 144) (80 mg) and (R)-1-(5-(4-(5-cyclopropyl-1H-pyrazol-3-ylamino)-5-fluoropyrimidin-2-yl)thiophen-2-yl)ethanol (Compound 147) (75 mg) were obtained by Prep-Chiral-HPLC from the above racemic 1-(5-(4-(5-cyclopropyl-1H-pyrazol-3-ylamino)-5-fluoropyrimidin-2-yl)thiophen-2-yl)ethanol (350 mg). The stereostructure of and (R)-1-(5-(4-(5-cyclopropyl-1H-pyrazol-3-ylamino)-5-fluoropyrimidin-2-yl)thiophen-2-yl)ethanol (Compound 147) was confirmed by the comparable sample prepared from 1-(5-(4-(5-cyclopropyl-1H-pyrazol-3-ylamino)-5-fluoropyrimidin-2-yl)thiophen-2-yl)ethanone with BH$_3$/S-CBS-Me. Synthetic procedures described as following:

A solution of compound 1-(5-(4-(5-cyclopropyl-1H-pyrazol-3-ylamino)-5-fluoropyrimidin-2-yl)thiophen-2-yl)ethanone (50 mg, 0.15 mmol, 1.0 eq) in dry THF (5 mL) was added dropwise to the mixture of (S)-1-methyl-3,3-diphenyl-hexahydropyrrolo[1,2-c][1,3,2] oxazaborole (0.22 mL, 0.22 mmol, 1.5 eq) and BH$_3$.THF (0.44 mL, 0.44 mmol, 3.0 eq) in dry THF (2 mL) at 0° C. The mixture was stirred for 3 h, quenched with isopropylalcohol and concentrated. The residue was purified by silica gel column chromatography, then, recrystallized with THF/CH$_2$Cl$_2$/Petroleum ether to afford (R)-1-(5-(4-(5-cyclopropyl-1H-pyrazol-3-ylamino)-5-fluoropyrimidin-2-yl)thiophen-2-yl)ethanol (Compound 147) (21 mg, 42%).

For (S)-1-(5-(4-(5-cyclopropyl-1H-pyrazol-3-ylamino)-5-fluoropyrimidin-2-yl)thiophen-2yl)ethanol (Compound 144): LC-MS: 346.1 [M+H]$^+$. $^1$H NMR (500 MHz, DMSO-d$_6$): δ 0.72-0.76 (m, 2H), 0.96-1.00 (m, 2H), 1.44 (d, J=6.0 Hz, 3H), 1.91-1.97 (m, 1H), 4.93-4.97 (m, 1H), 5.66 (d, J=5.0 Hz, 1H), 6.54 (bs, 1H), 6.96 (d, J=4.0 Hz, 1H), 7.59 (d, J=4.0 Hz, 1H), 8.27 (d, J=3.5 Hz, 1H), 10.04 (bs, 1H), 12.20 (bs, 1H).

For (R)-1-(5-(4-(5-cyclopropyl-1H-pyrazol-3-ylamino)-5-fluoropyrimidin-2-yl)thiophen-2-yl)ethanol (Compound 147): LC-MS: 346.1 [M+H]$^+$. $^1$H NMR (500 MHz, DMSO-d$_6$): δ 0.73-0.76 (m, 2H), 0.97-1.01 (m, 2H), 1.45 (d, J=6.5 Hz, 3H), 1.92-1.96 (m, 1H), 4.95-4.98 (m, 1H), 5.66 (d, J=4.5 Hz, 1H), 6.55 (bs, 1H), 6.97 (d, J=3.5 Hz, 1H), 7.59 (d, J=3.5 Hz, 1H), 8.28 (d, J=3.5 Hz, 1H), 10.05 (bs, 1H), 12.20 (bs, 1H).

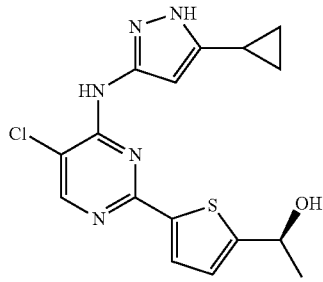

Compound 132

-continued

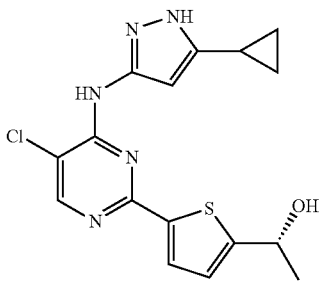

Compound 131

(S and R)-1-(5-(4-(5-cyclopropyl-1H-pyrazol-3-ylamino)-5-chloropyrimidin-2-yl)thiophen-2-yl)ethanol (Compounds 132 and 131)

Following the 5-fluoro analogs, (S)-1-(5-(4-(5-cyclopropyl-1H-pyrazol-3-ylamino)-5-chloropyrimidin-2-yl)thiophen-2-yl)ethanol (Compound 132) (4 mg) and (R)-1-(5-(4-(5-cyclopropyl-1H-pyrazol-3-ylamino)-5-chloropyrimidin-2-yl)thiophen-2-yl)ethanol (Compound 131) (3.7 mg) were prepared. Both had LC-MS: 362.1 [M+H]$^+$.

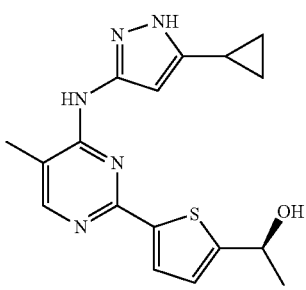

Compound 146

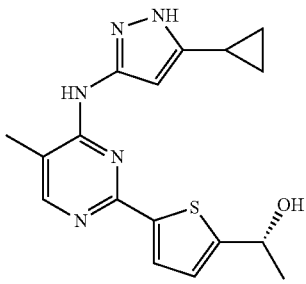

Compound 145

(S and R)-1-(5-(4-(5-cyclopropyl-1H-pyrazol-3-ylamino)-5-methylpyrimidin-2-yl)thiophen-2-yl)ethanol (Compounds 146 and 145)

Following the 5-fluoro analogs, these two enantiomers were prepared:

(S)-1-(5-(4-(5-cyclopropyl-1H-pyrazol-3-ylamino)-5-methylpyrimidin-2-yl)thiophen-2-yl)ethanol (70 mg) (Compound 146), LC-MS: 342.1 [M+H]$^+$. $^1$H NMR (500 MHz, DMSO-d$_6$): δ 0.74-0.77 (m, 2H), 0.97-1.00 (m, 2H), 1.45 (d, J=6.0 Hz, 3H), 1.92-1.95 (m, 1H), 2.16 (s, 1H), 4.93-4.98 (m, 1H), 5.63 (d, J=4.5 Hz, 1H), 6.56 (bs, 1H), 6.96 (d, J=3.5 Hz, 1H), 7.62 (d, J=4.0 Hz, 1H), 8.08 (s, 1H), 8.99 (bs, 1H), 12.10 (bs, 1H).

For (R)-1-(5-(4-(5-cyclopropyl-1H-pyrazol-3-ylamino)-5-methylpyrimidin-2-yl)thiophen-2-yl)ethanol (55 mg) (Compound 145), LC-MS: 342.1 [M+H]$^+$. $^1$H NMR (500 MHz, DMSO-d$_6$): δ 0.72-0.75 (m, 2H), 0.96-0.99 (m, 2H), 1.44 (d, J=6.0 Hz, 3H), 1.90-1.95 (m, 1H), 2.15 (s, 1H), 4.92-4.97 (m, 1H), 5.62 (d, J=4.5 Hz, 1H), 6.55 (bs, 1H), 6.95 (d, J=4.0 Hz, 1H), 7.60 (d, J=3.5 Hz, 1H), 8.07 (s, 1H), 8.97 (bs, 1H), 12.09 (bs, 1H).

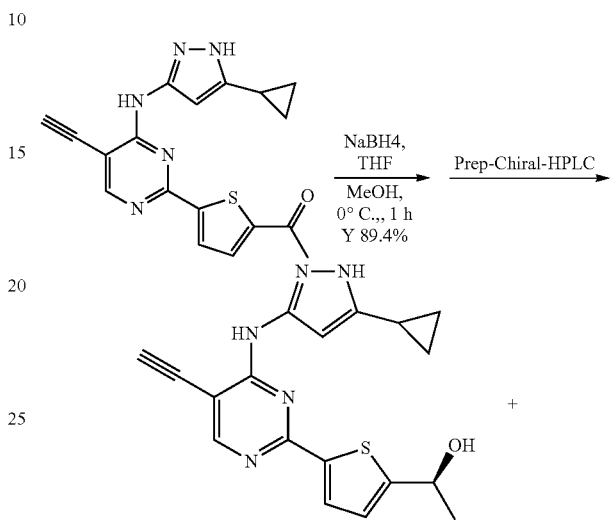

Compound 198

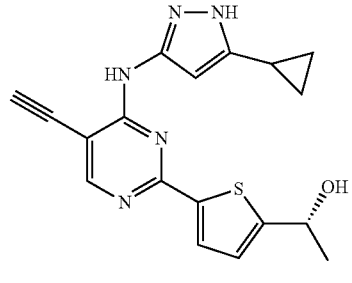

Compound 212

(S or R)-1-(5-(4-(3-cyclopropyl-1H-pyrazol-5-ylamino)-5-ethynylpyrimidin-2-yl) thiophen-2-yl)ethanol (Compounds 198 and 212)

Following the 5-flouo analog, reduction of 1-(5-(4-(5-cyclopropyl-1H-pyrazol-3-ylamino)-5-ethynyl pyrimidin-2-yl)thiophen-2-yl)ethanone (245 mg) afforded the racemic alcohol 1-(5-(4-(3-cyclopropyl-1H-pyrazol-5-ylamino)-5-ethynylpyrimidin-2-yl) thiophen-2-yl)ethanol (220 mg, 89.4%) (LC-MS (m/z)=352.0 [M+H]$^+$), which was separated by a preparative chiral HPLC as described in the 5-fluoro analog to produce the following two enantiomers:

(S)-1-(5-(4-(3-cyclopropyl-1H-pyrazol-5-ylamino)-5-ethynylpyrimidin-2-yl) thiophen-2-yl)ethanol (Compound 198) (31 mg). LC-MS (m/z)=352.0 [M+H]$^+$. $^1$H NMR (400 MHz, DMSO-d$_6$): δ 0.74-0.75 (m, 2H), 0.98-1.03 (m, 2H), 1.45 (d, J=6.4 Hz, 3H), 1.94 (m, 1H), 4.83 (s, 1H), 4.94-5.00 (m, 1H), 5.70 (t, J=4.8 Hz, 1H), 6.54 (s, 1H), 7.01 (d, J=3.6 Hz, 1H), 7.71 (t, J=3.6 Hz, 1H), 8.46 (s, 1H), 8.52 (s, 1H), 12.26 (s, 1H).

(R)-1-(5-(4-(3-cyclopropyl-1H-pyrazol-5-ylamino)-5-ethynylpyrimidin-2-yl) thiophen-2-yl)ethanol (Compound 212) (21 mg). LC-MS (m/z)=352.0 [M+H]+. 1H NMR (400 MHz, DMSO-d6): δ 0.75-0.76 (m, 2H), 0.98-1.00 (m, 2H), 1.45 (d, J=6.4 Hz, 3H), 1.94-1.95 (m, 1H), 4.83 (s, 1H), 4.94-5.00 (m, 1H), 5.70 (d, J=4.8 Hz, 1H), 6.54 (s, 1H), 7.01 (d, J=3.6 Hz, 1H), 7.71 (t, J=3.2 Hz, 1H), 8.45 (s, 1H), 8.52 (s, 1H), 12.26 (s, 1H).

Following the similar procedures for the chiral alcohols, the following enantiomers were also made: Compounds 199 and 213; and Compounds 210 and 214;

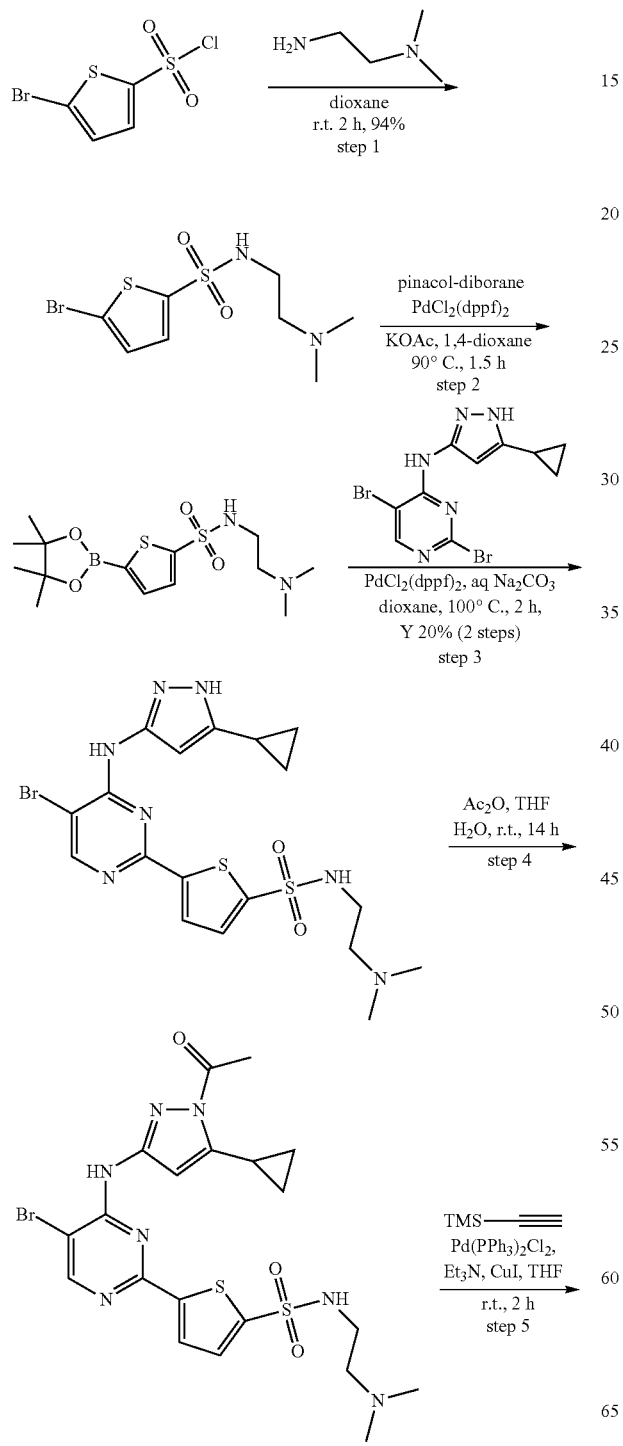

Compound 160

N-(2-(5-(5-bromo-4-(5-cyclopropyl-1H-pyrazol-3-ylamino)pyrimidin-2-yl)thiophene-2-sulfonamido)ethyl)acetamide (Compound 160)

Step 1. A mixture of 5-bromothiophene-2-sulfonyl chloride (2.0 g, 7.6 mmol, 1.0 eq) and N,N-dimethyl ethane-1,2-diamine (1.0 g, 11.5 mmol, 1.5 eq) in dioxane (20 mL) was stirred at room temperature for 2 h. Water was added and the reaction was extracted with dichloromethane. The combined organic layers were dried (Na2SO4), filtered, evaporated and purified by silica gel chromatography to afford 5-bromo-N-(2-(dimethylamino)ethyl)thiophene-2-sulfonamide (1.35 g, 94%). LC-MS (m/z)=313.0, 315.0 [M+H]+.

Step 2. A mixture of 5-bromo-N-(2-(dimethylamino)ethyl)thiophene-2-sulfonamide (768 mg, 2.45 mmol, 1.1 eq), pinacol-dibrane (736 mg, 2.90 mmol, 1.3 eq), KOAc (656 mg, 6.68 mmol, 3.0 eq) and PdCl2(dppf)CH2Cl2 (182 mg, 0.22 mmol, 0.1 eq) was flushed with nitrogen. 1, 4-Dioxane (15 mL) was added and the reaction mixture was stirred at 90° C. for 1.5 h. The reaction mixture was cooled to room temperature, filtered and the filtrate was used for the next step without further purification as the crude N-(2-(dimethylamino)ethyl)-5-(4,4,5,5-tetramethyl-1,3,2-dioxaborolan-2-yl)thiophene-2-sulfonamide. LC-MS (m/z)=361.0 [M+H]+.

Step 3. A mixture of Pd(dppf)Cl2.CH2Cl2 (182 mg, 0.22 mmol, 0.1 equiv.), the crude N-(2-(dimethyl amino)ethyl)-5-(4,4,5,5-tetramethyl-1,3,2-dioxaborolan-2-yl)thiophene-2-sulfonamide and 2,5-dibromo-N-(5-cyclopropyl-1H-pyrazol-3-yl)pyrimidin-4-amine (700 mg, 1.95 mmol, 1.0 eq) in dioxane (20 mL) and saturated Na$_2$CO$_3$ aqueous (2 mL) was heated at 100° C. for 2 h under nitrogen atmosphere. The reaction mixture was cooled to room temperature, and extracted with THF. The combined organic layers were purified by silica gel chromatography to afford compound 5-(5-bromo-4-(5-cyclopropyl-1H-pyrazol-3-ylamino)pyrimidin-2-yl)-N-(2-(dimethylamino)ethyl)thiophene-2-sulfonamide (200 mg, 20% over 2 steps). LC-MS (m/z)=512.0, 514.0 [M+H]$^+$.

Step 4. To the mixture of 5-(5-bromo-4-(5-cyclopropyl-1H-pyrazol-3-ylamino)pyrimidin-2-yl)-N-(2-(dimethylamino)ethyl)thiophene-2-sulfonamide (200 mg, 0.39 mmol) in THF/H$_2$O (2 mL/2 mL), Ac$_2$O (0.2 mL, 1.95 mmol, 5.0 eq) was added dropwise. The reaction mixture was stirred at room temperature for 14 h. The reaction mixture was filtered, and the solid was concentrated with ethanol to bring residual water off to afford crude 5-(4-(1-acetyl-5-cyclopropyl-1H-pyrazol-3-ylamino)-5-bromopyrimidin-2-yl)-N-(2-(dimethylamino)ethyl)thiophene-2-sulfonamide (used for the next step without further purification). LC-MS (m/z)=556.0, 558.0 [M+H]$^+$ Step 6. The mixture of crude 5-(4-(1-acetyl-5-cyclopropyl-1H-pyrazol-3-ylamino)-5-bromopyrimidin-2-yl)-N-(2-(dimethylamino)ethyl)thiophene-2-sulfonamide (from step 4), Pd(PPh$_3$)$_2$Cl$_2$ (14 mg, 0.02 mmol, 0.05 eq) and CuI (8 mg, 0.04 mmol, 0.1 eq) was flushed with nitrogen. Anhydrous THF (12 mL) and Et$_3$N (121 mg, 1.2 mmol, 3.0 eq) were added and the reaction mixture was flushed with nitrogen. Ethynyl-trimethylsilane (118 mg, 1.2 mmol, 3.0 eq) was added and the reaction mixture was stirred at rt for 1 h. Then, the reaction mixture was concentrated to about 5 mL, which was taken in EtOAc and was washed with water, brine. The combined organic layers were concentrated to afford crude 5-(4-(1-acetyl-5-cyclopropyl-1H-pyrazol-3-ylamino)-5-((trimethylsilyl)ethynyl)pyrimidin-2-yl)-N-(2-(dimethylamino)ethyl) thiophene-2-sulfonamide, which was used for the next step without further purification). LC-MS (m/z)=572.0 [M+H]$^+$ Step 7. The crude 5-(4-(1-acetyl-5-cyclopropyl-1H-pyrazol-3-ylamino)-5-((trimethylsilyl) ethynyl) pyrimidin-2-yl)-N-(2-(dimethylamino)ethyl)thiophene-2-sulfonamide mixture (from step 5) and K$_2$CO$_3$ (160 mg, 1.2 mmol, 3.0 eq) in EtOH (20 mL) was stirred at room temperature for 1 h. The reaction mixture was filtered. The filtrate was concentrated to 2 mL. The conc. liquid was extracted with EtOAc and washed with water, brine and dried (Na$_2$SO$_4$) and filtered. The filtrate was concentrated and the residue was purified by silica gel chromatography to afford N-(2-(5-(5-bromo-4-(5-cyclopropyl-1H-pyrazol-3-ylamino)pyrimidin-2-yl)thiophene-2-sulfonamido)ethyl)acetamide (Compound 160)(30 mg, 17% over 3 steps). LC-MS (m/z)=458.0 [M+H]$^+$. $^1$H NMR (400 MHz, DMSO-d$_6$): δ 0.68-0.77 (m, 2H), 0.91-0.99 (m, 2H), 1.88-1.97 (m, 1H), 2.09 (s, 6H), 2.30 (t, J=7.2 Hz, 2H), 2.97 (t, J=7.2 Hz, 2H), 4.85 (bs, 1H), 6.39 (bs, 1H), 7.62 (d, J=4.0 Hz, 1H), 7.80 (d, J=3.2 Hz, 1H), 8.46 (bs, 1H), 8.80 (bs, 1H), 12.40 (bs, 1H).

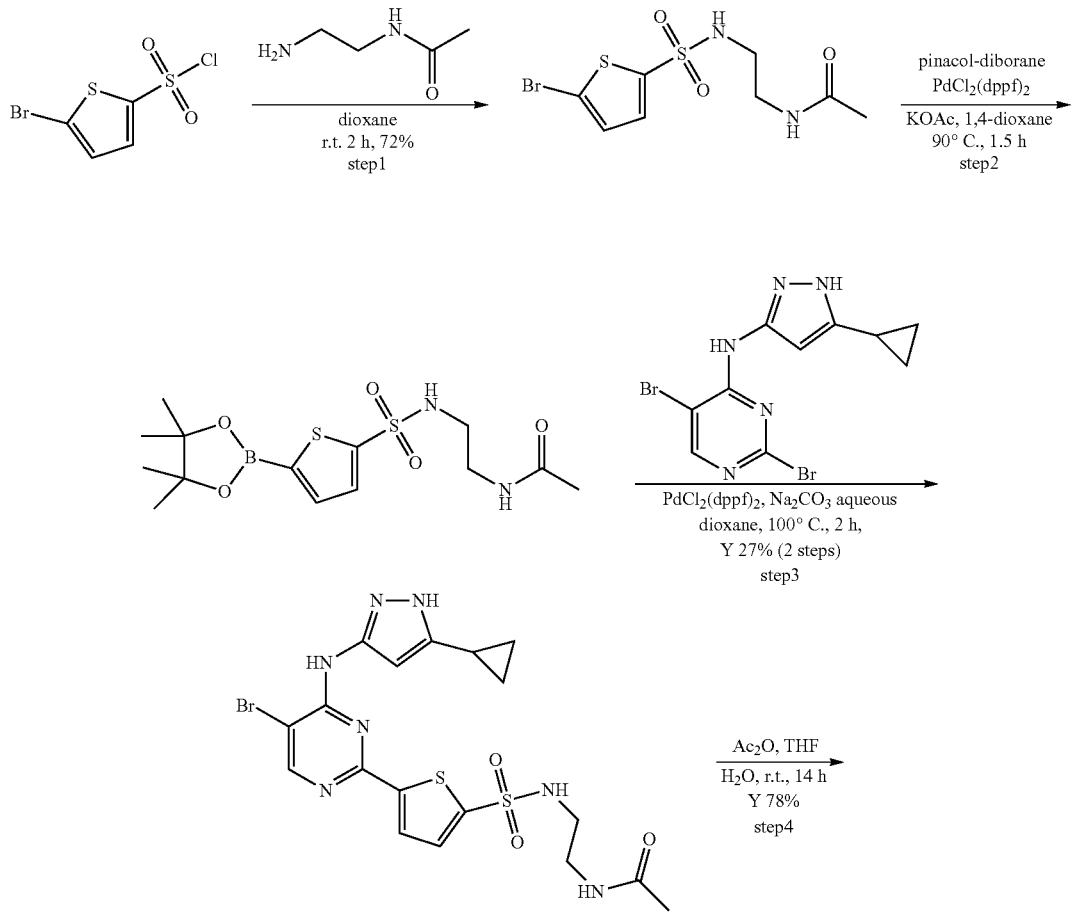

Compound 166

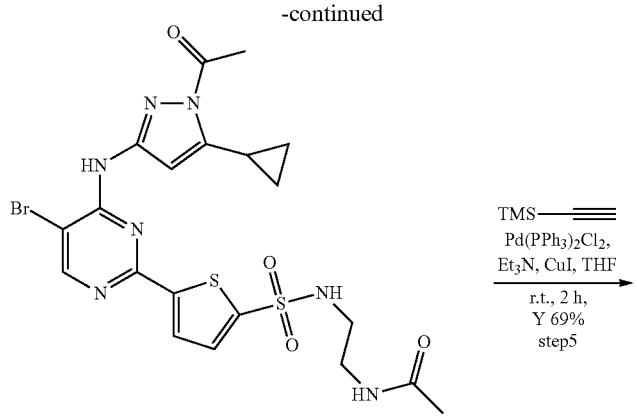

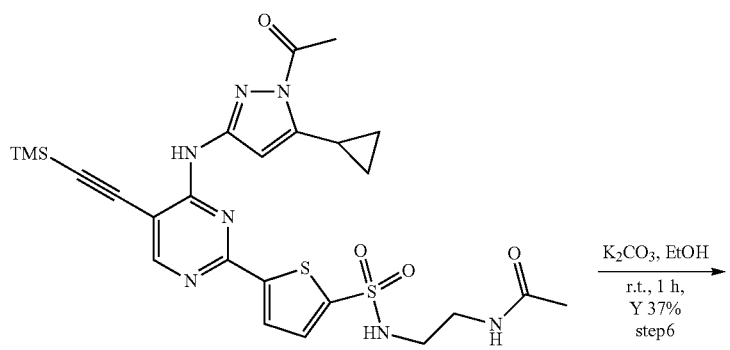

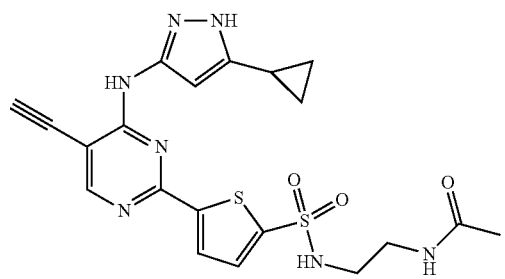

Compound 181

N-(2-(5-(5-bromo-4-(5-cyclopropyl-1H-pyrazol-3-ylamino)pyrimidin-2-yl)thiophene-2-sulfonamido)ethyl)acetamide (Compound 166) and N-(2-(5-(4-(5-cyclopropyl-1H-pyrazol-3-ylamino)-5-ethynyl pyrimidin-2-yl)thiophene-2-sulfonamido)ethyl)acetamide (Compound 188)

Step 1 to step 3: Similar as the precedent example, N-(2-(5-(5-bromo-4-(5-cyclopropyl-1H-pyrazol-3-ylamino)pyrimidin-2-yl)thiophene-2-sulfonamido)ethyl)acetamide (Compound 166) (280 mg, 27% over 2 steps) was prepared as described. LC-MS (m/z)=526.0, 528.0 [M+H]+. $^1$H NMR (400 MHz, DMSO-$d_6$): δ 0.73-0.76 (m, 2H), 0.97-1.02 (m, 2H), 1.76 (s, 3H), 1.93-1.97 (m, 1H), 2.89-2.94 (m, 2H), 3.09-3.13 (m, 2H), 6.38 (s, 1H), 7.60 (d, J=4.0 Hz, 1H), 7.78 (d, J=4.0 Hz, 1H), 7.91 (t, J=6.0 Hz, 1H), 8.05 (t, J=6.0 Hz, 1H), 8.57 (s, 1H), 9.04 (s, 1H), 12.35 (s, 1H).

Step 4 (78%), Step 5 (69%) and step 6: Similar as the precedent example. N-(2-(5-(4-(5-cyclopropyl-1H-pyrazol-3-ylamino)-5-ethynyl pyrimidin-2-yl)thiophene-2-sulfonamido)ethyl)acetamide (Compound 188) (60 mg, 37%) was prepared. LC-MS (m/z)=472.0 [M+H]+. $^1$H NMR (400 MHz, DMSO-$d_6$): δ δ 0.75-0.76 (m, 2H), 0.98-1.00 (m, 2H), 1.76 (s, 3H), 1.94-1.95 (m, 1H), 2.90-2.93 (m, 2H), 3.09-3.14 (m, 2H), 4.90 (s, 1H), 6.44 (s, 1H), 7.62 (d, J=4.0 Hz, 1H), 7.83 (d, J=4.0 Hz, 1H), 7.92 (t, J=5.6 Hz, 1H), 8.07 (t, J=4.0 Hz, 1H), 8.52 (s, 1H), 8.83 (s, 1H), 12.32 (s, 1H).

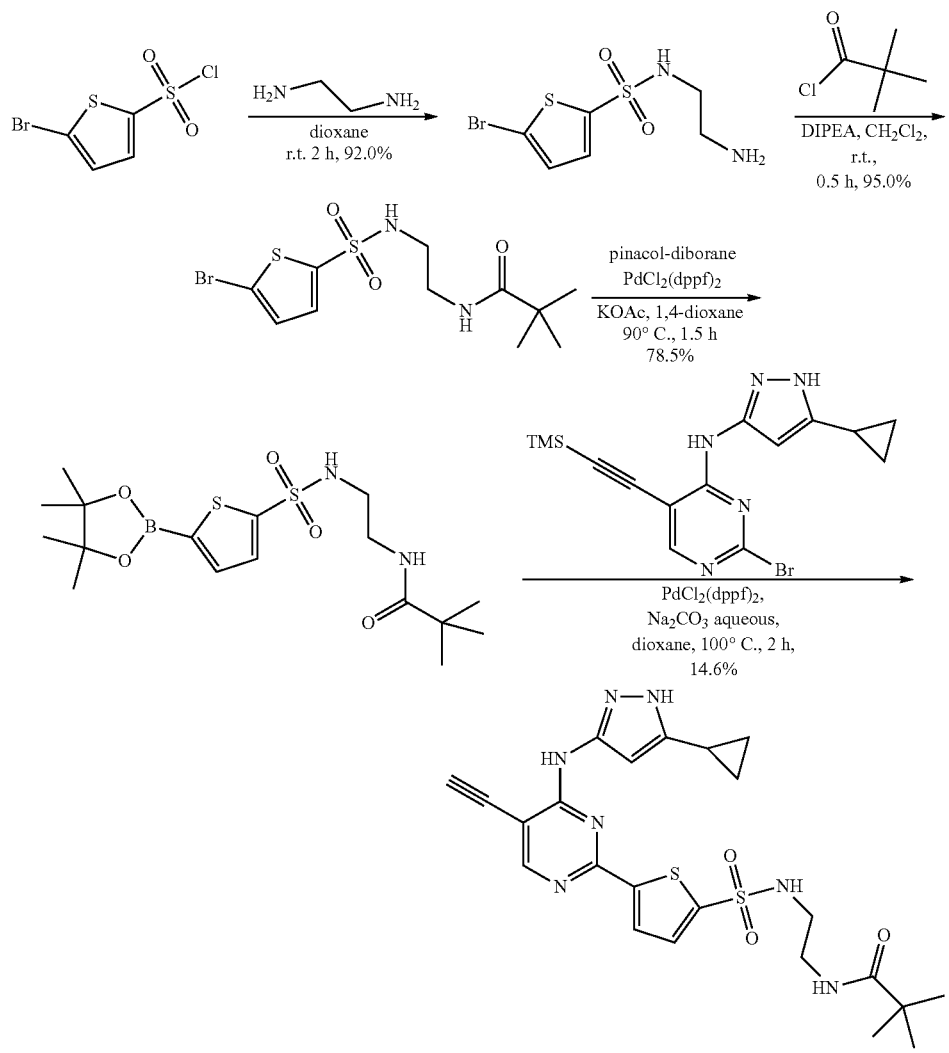

Compound 183

N-(2-(5-(4-(5-cyclopropyl-1H-pyrazol-3-ylamino)-5-ethynylpyrimidin-2-yl)thiophene-2-sulfonamido)ethyl)pivalamide (Compound 183)

Step 1. A mixture of 5-bromothiophene-2-sulfonyl chloride (2.5 g, 9.6 mmol, 1.0 eq) in CH$_2$Cl$_2$ (100 mL) was stirred at 0° C., ethane-1, 2-diamine (2.3 g, 38.24 mmol, 4 eq) was added drop-wise. Then, the mixture was stirred at 0° C. for 0.5 h. Water was added and extracted with EA (6×80 ml). The combined organic layers were dried (Na$_2$SO$_4$), filtered and concentrated to give N-(2-aminoethyl)-5-bromothiophene-2-sulfonamide (2.51 g, 92.0%). LC-MS (m/z)=284.1 [M+H]$^+$.

Step 2. A mixture of N-(2-aminoethyl)-5-bromothiophene-2-sulfonamide (2.5 g, 8.77 mmol, 1.0 eq) and DIPEA (3.4 g, 26.3 mmol, 3.0 eq) in CH$_2$Cl$_2$ (100 mL) was stirred at 0° C., pivaloyl chloride (2.1 g, 17.5 mmol, 2 equiv.) was added drop-wise. Then, the mixture was stirred at 0° C. for 0.5 h. Water was added and the reaction was extracted with EA (3×80 ml). The combined organic layers were dried (Na$_2$SO$_4$), filtered, evaporated and purified by silica gel chromatography (PE/EA=10:1 as eluant) to afford N-(2-(5-bromothiophene-2-sulfonamido)ethyl)pivalamide (3.07 g, 95.0%). LC-MS (m/z)=368.9 [M+H]$^+$.

Step 3. A mixture of N-(2-(5-bromothiophene-2-sulfonamido)ethyl)pivalamide (3.0 g, 8.3 mmol, 1 eq), bis(pinacolato)diborn (4.2 g, 16.7 mmol, 2.0 eq), KOAc (3.3 g, 33.4 mmol, 4 eq), PdCl$_2$(dppf)CH$_2$Cl$_2$ (677.3 mg, 0.83 mmol, 0.1 eq) in 1, 4-dioxane (20 mL) was stirred at 100° C. for 2 h under nitrogen atmosphere. The solvent was removed and the residue was purified by silica gel chromatography (PE/EA=2:1 as eluant) to generate N-(2-(5-(4,4,5,5-tetramethyl-1,3,2-dioxaborolan-2-yl)thiophene-2-sulfonamido)ethyl)pivalamide (2.2 g, 78.5%) as yellow oil. LC-MS (m/z)=334.1 [M+H]$^+$;

Step 4. Starting with 2-bromo-N-(5-cyclopropyl-1H-pyrazol-3-yl)-5-((trimethylsilyl)ethynyl)pyrimidin-4-amine and N-(2-(5-(4,4,5,5-tetramethyl-1,3,2-dioxaborolan-2-yl)thiophene-2-sulfonamido)ethyl)pivalamide with the procedure in step 3 of Compound 160, N-(2-(5-(4-(5-cyclopropyl-1H-pyrazol-3-ylamino)-5-ethynylpyrimidin-2-yl)thiophene-2-sulfonamido)ethyl)pivalamide (Compound 183) (60.0 mg, 14.6%) was prepared. LC-MS (m/z)=513.9 [M+H]$^+$; $^1$H NMR (400 MHz, DMSO-d$_6$): δ 0.75 (m, 2H), 0.98-1.00 (m, 2H), 1.04 (s, 9H), 2.90-2.93 (m, 2H), 3.14 (dd, J=6.4 Hz, 12.4 Hz, 2H), 4.88 (s, 1H), 6.44 (s, 1H), 7.48 (t, J=5.2 Hz, 1H), 7.62 (d, J=4.0 Hz, 1H), 7.83 (d, J=3.6 Hz, 1H), 8.06 (s, 1H), 8.52 (s, 1H), 8.79 (s, 1H), 12.30 (s, 1H).

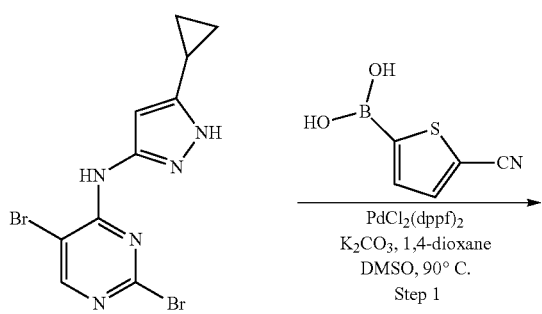

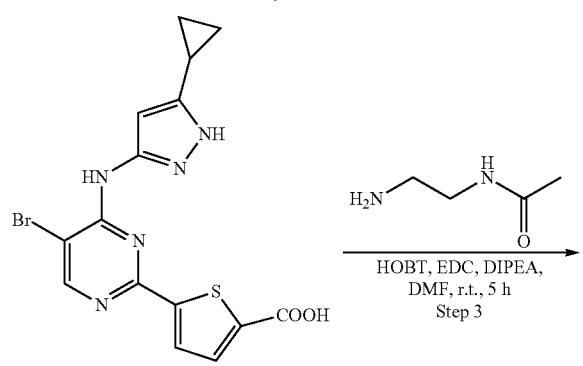

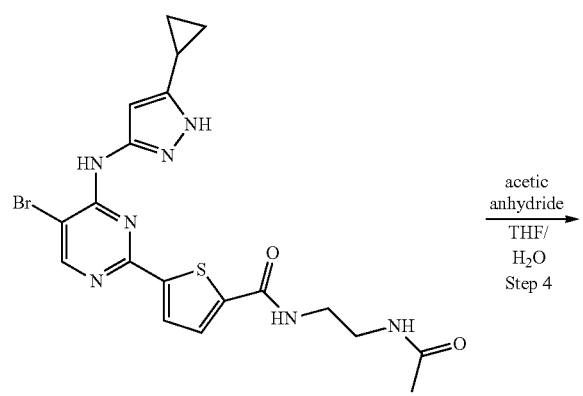

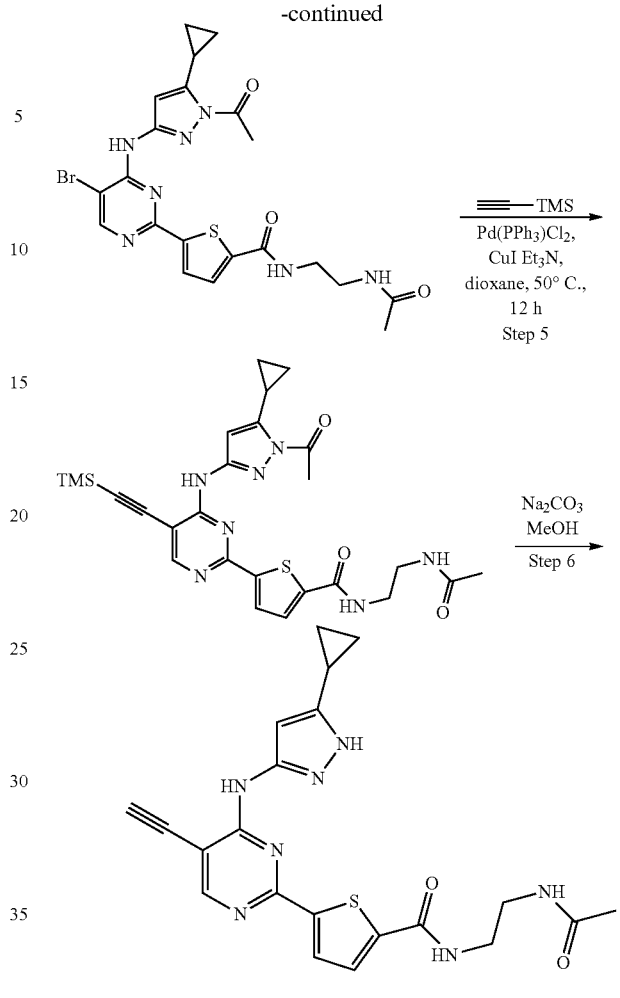

Compound 206

N-(2-acetamidoethyl)-5-(4-(5-cyclopropyl-1H-pyrazol-3-ylamino)-5-ethynylpyrimidin-2-yl)thiophene-2-carboxamide (Compound 206)

Step 1. Compound 5-(5-bromo-4-(5-cyclopropyl-1H-pyrazol-3-ylamino)pyrimidin-2-yl)thiophene-2-carbonitrile (800 mg, 48.6%) was prepared using the procedure in step 3 of Compound 160. LC-MS (m/z)=387.9 [M+H]$^+$.

Step 2. A 100 mL round bottomed flask was charged with anhydrous methanol (50 mL). Then, SOCl$_2$ (20 mL) was added dropwise with ice bath. After addition, the mixture was stirred for 1 h at 0° C. Then, the ice bath was removed and 5-(5-bromo-4-(5-cyclopropyl-1H-pyrazol-3-ylamino)pyrimidin-2-yl)thiophene-2-carbonitrile (800 mg, 2.1 mmol, 1.0 equiv.) was added. The mixture was stirred overnight at rt and the solvent was removed. Then, methanol (10 mL) and 1 N HCl aqueous (5 mL) was added. The mixture was stirred for 1 h and the solvent was removed to give a residue, which was purified by silica gel column chromatography (PE/EA/MeOH=2:1:0.06 as eluant) to give a yellow solid. This solid and NaOH (6N, 3 mL) was dissolved in methanol/THF (10 mL/10 mL). The mixture was stirred for 2 h. The solvent was removed and water (10 mL) was added. Then, 1 N HCl was added until the pH of the solution reach 2-3. The mixture was filtered and the solid was collected as acid 5-(5-bromo-4-(5- cyclopropyl-1H-pyrazol-3-ylamino)pyrimidin-2-yl)thiophene-2-carboxylic acid (332.5 mg, yield: 38.9%). LC-MS (m/z)=407.1 [M+H]$^+$.

Step 3. A 100 mL round bottomed flask was charged with 5-(5-bromo-4-(5-cyclopropyl-1H-pyrazol-3-ylamino)pyrimidin-2-yl)thiophene-2-carboxylic acid (332.5 mg, 0.82 mmol, 1 eq), N-(2-aminoethyl)acetamide (125.3 mg, 1.23 mol, 1.5 eq), EDCI (313.0 mg, 1.6 mmol, 2 eq), HOBt (221.1 mg, 1.6 mmol, 2 eq) and DIPEA (635.4 mg, 4.9 mmol, 6 equiv) in DMF (5 mL). The mixture was stirred for 12 h at 23° C. and extracted with THF (3×70 mL). The organic layers were dried (Na$_2$SO$_4$), filtered and concentrated. The residue was purified by silica gel column chromatography (PE/EA/MeOH=1:1:0.05 as eluant) to give pale-yellow solid N-(2-acetamidoethyl)-5-(5-bromo-4-(5-cyclopropyl-1H-pyrazol-3-ylamino)pyrimidin-2-yl)thiophene-2-carboxamide (273.8 mg, 68.3%). LC-MS (m/z)=491.1 [M+H]$^+$.

Step 4. To N-(2-acetamidoethyl)-5-(5-bromo-4-(5-cyclopropyl-1H-pyrazol-3-ylamino)pyrimidin-2-yl)thiophene-2-carboxamide (273.8 mg, 0.56 mmol, 1.0 equiv.), acetic anhydride (114.2 mg, 1.1 mmol, 2.0 equiv.) in THF/H$_2$O (10 ml/1 mL) was stirred at 23° C. for 2 hour. Then the mixture was extracted with THF (6×40 ml). The combined organic layers were dried (Na$_2$SO$_4$), filtered and concentrated give N-(2-acetamidoethyl)-5-(4-(1-acetyl-5-cyclopropyl-1H-pyrazol-3-ylamino)-5-bromopyrimidin-2-yl)thiophene-2-carboxamide (294.0 mg, 98.5%) as pale yellow solid. LC-MS (m/z) =533.1 [M+H]$^+$;

Step 5 A mixture of N-(2-acetamidoethyl)-5-(4-(1-acetyl-5-cyclopropyl-1H-pyrazol-3-ylamino)-5-bromopyrimidin-2-yl)thiophene-2-carboxamide (294.0 mg, 0.5 mmol, 1.0 eq), Pd(PPh$_3$)$_2$Cl$_2$ (40.8 mg, 0.5 mmol, 0.1 eq) and CuI (9.5 mg, 0.05 mmol, 0.1 eq) was flushed with nitrogen. Anhydrous THF (10 mL) and Et$_3$N (154.5 mg, 1.5 mmol, 3.0 eq) were added and the reaction mixture was flushed with nitrogen. Ethynyltrimethylsilane (149.9 mg, 1.5 mmol, 3.0 equiv.) was added and the reaction mixture was stirred at room temperature for 1 h. Then, the reaction mixture was concentrated to 5 mL. The conc. liquid was extracted with EtOAc and washed with water, brine. The organic layers were concentrated to afford the residue, which was purified by silica gel chromatography (PE/EA/MeOH=2:1:0.06 as eluant) to afford N-(2-acetamidoethyl)-5-(4-(1-acetyl-5-cyclopropyl-1H-pyrazol-3-ylamino)-5-((trimethylsilyl)ethynyl) pyrimidin-2-yl)thiophene-2-carboxamide (96.1 mg, 35.2%) as pale yellow solid. LC-MS (m/z)=549.9 [M+H]$^+$ Step 6. The mixture of N-(2-acetamidoethyl)-5-(4-(1-acetyl-5-cyclopropyl-1H-pyrazol-3-ylamino)-5-((trimethylsilyl)ethynyl)pyrimidin-2-yl)thiophene-2-carboxamide (96.1 mg, 0.17 mmol, 1.0 eq) and K$_2$CO$_3$ (70.4 mg, 0.51 mmol, 3.0 eq) in EtOH (10 mL) was stirred at room temperature for 1 h. The reaction mixture was filtered. The filtrate was concentrated to 2 mL. The conc. liquid was extracted with EtOAc and washed with water, brine and dried (Na$_2$SO$_4$) and filtered. The filtrate was concentrated to generate N-(2-acetamidoethyl)-5-(4-(5-cyclopropyl-1H-pyrazol-3-ylamino)-5-ethynylpyrimidin-2-yl)thiophene-2-carboxamide (Compound 206) (53.2 mg, 72.1%) as pale yellow solid. LC-MS (m/z)=436.1 [M+H]$^+$. $^1$H NMR (400 MHz, DMSO-d$_6$): δ 0.74-0.78 (m, 2H), 0.97-1.01 (m, 2H), 1.82 (s, 3H), 1.93-1.99 (m, 1H), 3.20-3.23 (m, 2H), 3.27-3.30 (m, 2H), 4.87 (m, 1H), 6.49 (m, 1H), 7.76 (d, J=4.4 Hz, 1H), 7.84 (d, J=4.0 Hz, 1H), 8.01 (t, J=5.2 Hz, 1H), 8.50 (s, 1H), 8.70 (t, J=5.2 Hz, 1H), 8.76 (s, 1H)

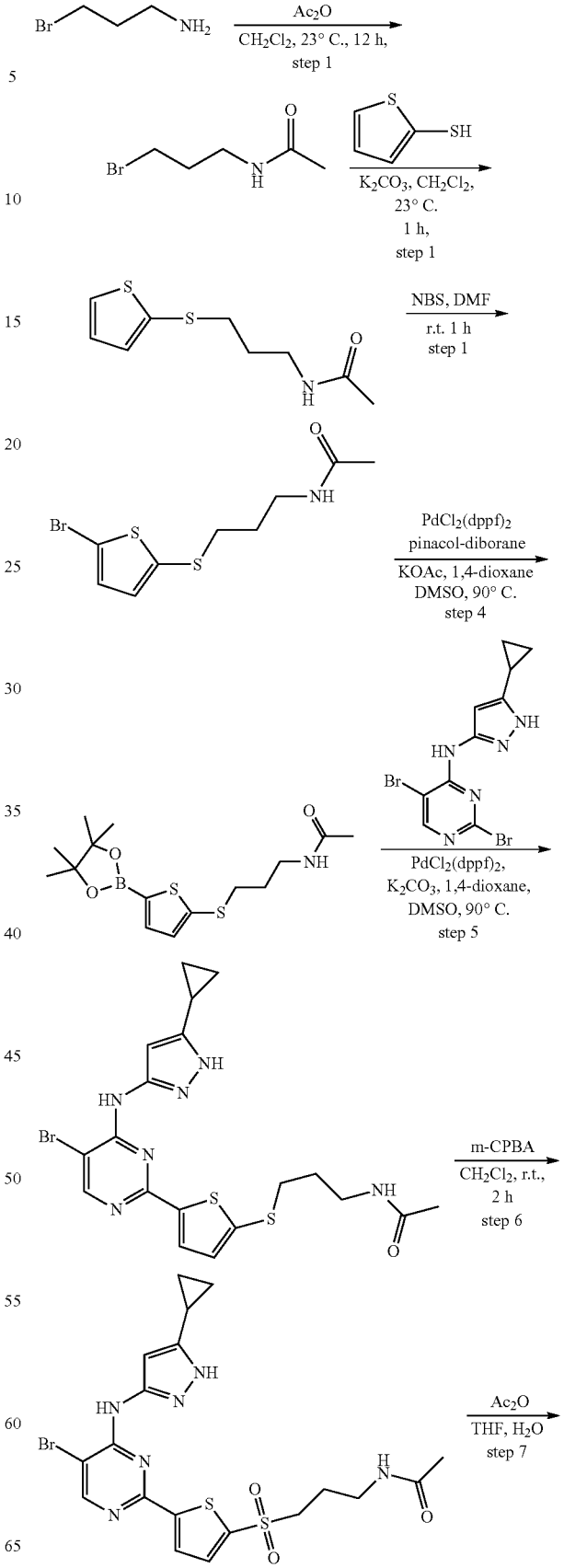

-continued

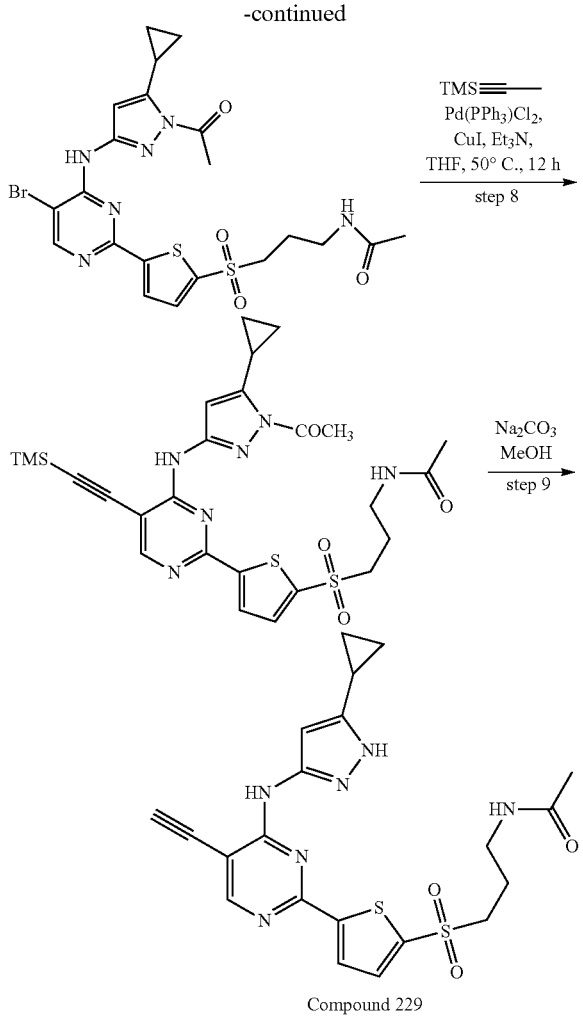

Compound 229

N-(3-(5-(4-(5-cyclopropyl-1H-pyrazol-3-ylamino)-5-ethynylpyrimidin-2-yl)thiophen-2-ylsulfonyl)propyl)acetamide (Compound 229)

Step 1. To the mixture of 3-bromopropan-1-amine (6.0 g, 43.4 mmol, 1.0 eq) in CH$_2$Cl$_2$ (50 mL) was added acetic anhydride (8.8 g, 86.8 mmol, 2.0 eq). The mixture was extracted with CH$_2$Cl$_2$. The combined organic layers were dried (MgSO$_4$), filtered and concentrated to give white solid N-(3-bromopropyl) acetamide (5.0 g, 65.2%); LC-MS (m/z)=180.1 [M+H]$^+$.

Step 2. A mixture of thiophene-2-thiol (1.8 g, 15.9 mmol, 1.0 eq), N-(3-bromopropyl) acetamide (4.3 g, 23.9 mmol, 1.5 eq) and K$_2$CO$_3$ (4.4 g, 31.8 mmol, 2.0 eq) in CH$_2$Cl$_2$ (50 mL) was stirred at 23° C. for 1 hour. Then the mixture was extracted with CH$_2$Cl$_2$. (3×). The combined organic layers were dried (Na$_2$SO$_4$), filtered and concentrated to give white solid N-(3-(thiophen-2-ylthio)propyl)acetamide (2.5 g, 72.8%); LC-MS (m/z)=215.9 [M+H]$^+$.

Step 3. A mixture of N-(3-(thiophen-2-ylthio)propyl)acetamide (2.5 g, 11.6 mmol, 1.0 eq), NBS (2.1 g, 11.6 mmol, 1.0 eq) in DMF (5 mL) was stirred at 23° C. for 1 hour. The mixture was extracted with CH$_2$Cl$_2$. The combined organic layers were dried (Na$_2$SO$_4$), filtered and concentrated to give yellow oil N-(3-(5-bromothiophen-2-ylthio)propyl)acetamide (1.6 g, 46.8%);

Step 4. A mixture of N-(3-(5-bromothiophen-2-ylthio)propyl)acetamide (1.2 g, 4.08 mmol, 1 eq), bis(pinacolato)diborn (2.07 g, 9.16 mmol, 2.0 eq), KOAc (1.6 g, 16.3 mmol, 4 eq), PdCl$_2$(dppf)CH$_2$Cl$_2$ (334.8 mg, 0.41 mmol, 0.1 eq) in 1,4-dioxane (20 mL) was stirred at 100° C. for 2 h under nitrogen atmosphere. The solvent was removed and the residue was purified by silica gel chromatography (PE/EA=2:1 as eluant) to afford N-(3-(5-(4,4,5,5-tetramethyl-1,3,2-dioxaborolan-2-yl)thiophen-2-ylthio)propyl)acetamide (1.4 g, 97.6%) as a yellow oil. LC-MS (m/z)=342.1 [M+H]$^+$;

Step 5. N-(3-(5-(5-bromo-4-(5-cyclopropyl-1H-pyrazol-3-ylamino)pyrimidin-2-yl)thiophen-2-ylthio)propyl)acetamide (500 mg, 26.7%) prepared using the procedure in step 3 of Compound 160
LC-MS (m/z)=494.1 [M+H]$^+$;

Step 6. The mixture of N-(3-(5-(5-bromo-4-(5-cyclopropyl-1H-pyrazol-3-ylamino)pyrimidin-2-yl)thiophen-2-ylthio)propyl)acetamide (500 mg, 1.0 mmol, 1.0 eq), m-CPBA (524 mg, 3.03 mmol, 1.0 eq) in THF (10 mL) was stirred at 23° C. for 2 hour. The mixture was extracted with THF (6×40 ml). The combined organic layers were dried (Na$_2$SO$_4$), filtered and concentrated to give the residue, which was purified by silica gel chromatography (PE/EA/MeOH=2:1:0.06 as eluant) to give N-(3-(5-(5-bromo-4-(5-cyclopropyl-1H-pyrazol-3-ylamino)pyrimidin-2-yl)thiophen-2-ylsulfonyl)propyl)acetamide (200 mg, 37.7%) as pale yellow solid. LC-MS (m/z)=526.1 [M+H]+;

Step 7. N-(3-(5-(4-(1-acetyl-5-cyclopropyl-1H-pyrazol-3-ylamino)-5-bromopyrimidin-2-yl)thiophen-2-ylsulfonyl)propyl)acetamide (212 mg, 98.5%) was prepared using the procedure of step 4 for Compound 206. LC-MS (m/z)=568.1 [M+H]$^+$;

Step 8. N-(3-(5-(4-(1-acetyl-5-cyclopropyl-1H-pyrazol-3-ylamino)-5-((trimethylsilyl)ethynyl)pyrimidin-2-yl)thiophen-2-ylsulfonyl)propyl)acetamide (65.0 mg, 37.1%) was prepared using the procedure of step 5 for Compound 206. LC-MS (m/z)=585.1 [M+H]$^+$ Step 9. N-(3-(5-(4-(5-cyclopropyl-1H-pyrazol-3-ylamino)-5-ethynylpyrimidin-2-yl)thiophen-2-ylsulfonyl)propyl)acetamide (Compound 229) (35.3 mg, 68.2%) was prepared using the procedure of step 6 for Compound 206. LC-MS (m/z)=471.1 [M+H]$^+$. $^1$H NMR (400 MHz, DMSO-d$_6$): δ 0.74-0.75 (m, 2H), 0.98-1.00 (m, 2H), 1.72-1.79 (m, 5H), 1.92-1.99 (m, 1H), 3.10 (dd, J=7.2 Hz, 12.8 Hz, 2H), 3.47 (t, J=8.0 Hz, 2H), 4.90 (s, 1H), 6.43 (s, 1H), 7.82 (d, J=4.0 Hz, 1H), 7.87-7.90 (m, 2H), 8.54 (s, 1H), 8.87 (s, 1H), 12.32 (s, 1H).

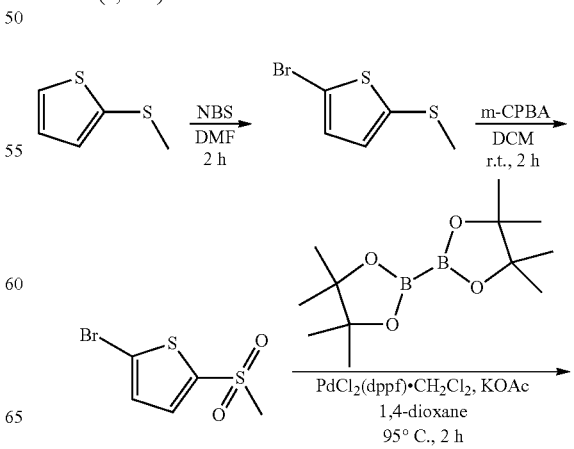

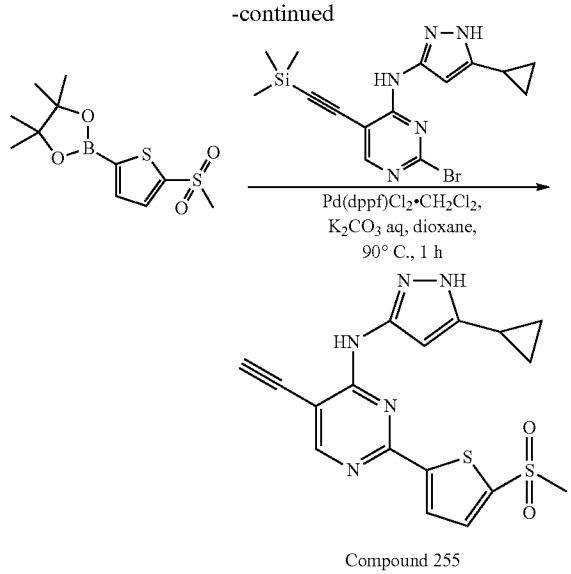

Compound 255

N-(5-cyclopropyl-1H-pyrazol-3-yl)-5-ethynyl-2-(5-(methylsulfonyl)thiophen-2-yl)pyrimidin-4-amine (Compound 255)

A mixture of 2-(methylthio)thiophene (1 g, 6.8 mmol, 1.0 eq), NBS (469 mg, 8.2 mmol, 1.2 eq) in DMF (30 mL) was stirred at r.t. for 2 h under $N_2$, then partitioned between EtOAc and water. The organic layer was concentrated and purified by silica gel chromatography to afford 2-bromo-5-(methylthio)thiophene (1.2 g, 82%). LC-MS (m/z)=209 [M+H]+

A solution of 2-bromo-5-(methylthio)thiophene (1 g, 4.8 mmol, 1.0 eq), m-CPBA (2 g, 12 mmol, 2.5 eq) in DMF (30 mL) was stirred at r.t. for 2 h under $N_2$, then partitioned between EtOAc and water. The organic layer was concentrated and purified by silica gel chromatography to afford 2-bromo-5-(methylsulfonyl)thiophene (1 g, 90%). LC-MS (m/z)=241 [M+H]+

A mixture of 2-bromo-5-(methylsulfonyl)thiophene (800 mg, 3.35 mmol, 1 eq), bis(pinacolato)diborn (1.7 g, 6.7 mmol, 2.0 eq), KOAc (1.3 g, 13.3 mmol, 4 eq), PdCl$_2$(dppf) CH$_2$Cl$_2$ (277 mg, 0.34 mmol, 0.1 eq) and 1 in 4-dioxane (20 mL) was stirred at 100° C. for 2 h under nitrogen atmosphere. The solvent was removed and the residue was purified by silica gel chromatography (PE/EA=1:2 as eluant) to give 4,4,5,5-tetramethyl-2-(5-(methylsulfonyl)thiophen-2-yl)-1,3,2-dioxaborolane (770 mg, 80%).

LC-MS (m/z)=289 [M+H]+

A mixture of 4,4,5,5-tetramethyl-2-(5-(methylsulfonyl) thiophen-2-yl)-1,3,2-dioxaborolane (550 mg, 1.92 mmol, 1.5 eq), 2-bromo-N-(5-cyclopropyl-1H-pyrazol-3-yl)-5-((trimethylsilyl)ethynyl)pyrimidin-4-amine (480 mg, 1.28 mmol, 1.0 eq), PdCl$_2$(dppf)CH$_2$Cl$_2$ (106.1 mg, 0.13 mmol, 0.1 eq), K$_2$CO$_3$ (529.0 mg, 3.84 mmol, 3.0 equiv.), dioxane (20 mL) and water (2 mL) was heated for 1 h at 90° C. under nitrogen atmosphere. The solvent was removed and the residue was purified by silica gel chromatography (PE/EtOAc=4:12:1 as eluant) to yield N-(5-cyclopropyl-1H-pyrazol-3-yl)-5-ethynyl-2-(5-(methyl sulfonyl) thiophen-2-yl)pyrimidin-4-amine (Compound 255) (246 mg, 50%). LC-MS (m/z)=386 [M+H]+; $^1$H NMR (400 MHz, DMSO-d$_6$): 0.73-0.77 (m, 2H), 0.96-1.01 (m, 2H), 1.93-1.99 (m, 1H), 3.41 (s, 3H), 4.91 (s, 1H), 6.42 (s, 1H), 7.87 (dd, J1=4.0 Hz, J2=7.2 Hz, 2H), 8.54 (s, 1H), 8.94 (s, 1H).

-continued

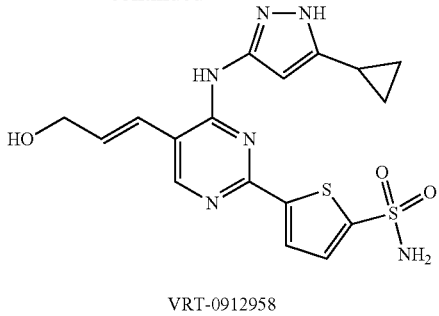 [SMILES: NS(=O)(=O)c1ccc(-c2ncc(/C=C/CO)c(Nc3cc(C4CC4)[nH]n3)n2)s1]

VRT-0912958

N-tert-butyl-5-(4-(5-cyclopropyl-1H-pyrazol-3-ylamino)-5-(3-hydroxyprop-1-ynyl)pyrimidin-2-yl)thiophene-2-sulfonamide (Compound 216), (E)-N-tert-butyl-5-(4-(5-cyclopropyl-1H-pyrazol-3-ylamino)-5-(3-hydroxyprop-1-enyl)pyrimidin-2-yl)thiophene-2-sulfonamide (Compound 218) and (E)-5-(4-(5-cyclopropyl-1H-pyrazol-3-ylamino)-5-(3-hydroxyprop-1-enyl)pyrimidin-2-yl)thiophene-2-sulfonamide (Compound 281)

The mixture of Pd(dppf)Cl$_2$.CH$_2$Cl$_2$ (457 mg, 0.56 mmol, 0.1 eq), 5-(N-tert-butylsulfamoyl)thiophen-2-ylboronic acid (2.95 g, 11.2 mmol, 2.0 eq), 2,5-dibromo-N-(5-cyclopropyl-1H-pyrazol-3-yl)pyrimidin-4-amine (2 g, 5.6 mmol, 1.0 eq) and saturate Na$_2$CO$_3$ (5 mL) in dioxane (30 mL) was heated to 90° C. for 1 h under nitrogen atmosphere. The reaction mixture was cooled to room temperature, and extracted with THF. The combined layers were evaporated and residue purified by silica gel chromatography (EtOAc/Petroleum ether from 10:1 to 2:1) to afford compound 5-(5-bromo-4-(5-cyclopropyl-1H-pyrazol-3-ylamino)pyrimidin-2-yl)-N-tert-butylthiophene-2-sulfonamide (1.6 g, 59%). LC-MS (m/z)=497 [M+H]$^+$.

$^1$H NMR (400 MHz, DMSO-d$_6$): δ 0.74-0.76 (m, 2H), 0.98-1.00 (m, 2H), 1.20 (s, 9H), 1.92-1.97 (m, 1H), 6.38 (s, 1H), 7.60 (d, J=4.4 Hz, 1H), 7.75 (d, J=4.0 Hz, 1H), 7.91 (s, 1H), 8.56 (s, 1H), 9.00 (s, 1H), 12.34 (s, 1H).

To 5-(5-bromo-4-(5-cyclopropyl-1H-pyrazol-3-ylamino)pyrimidin-2-yl)-N-tert-butylthiophene-2-sulfonamide (1.6 g, 3.21 mmol, 1.0 eq) in THF/H$_2$O (30 mL/15 mL), Ac$_2$O (0.64 g, 6.42 mmol, 2.0 eq) was added dropwise. The reaction mixture was stirred at room temperature for 1 h. The reaction mixture was filtered to afford compound 5-(4-(1-acetyl-5-cyclopropyl-1H-pyrazol-3-ylamino)-5-bromopyrimidin-2-yl)-N-tert butylthiophene-2-sulfonamide (1.6 g, 92%). LC-MS (m/z)=539 [M+H]$^+$ To a mixture of 5-(4-(1-acetyl-5-cyclopropyl-1H-pyrazol-3-ylamino)-5-bromopyrimidin-2-yl)-N-tert butylthiophene-2-sulfonamide (1 g, 1.85 mmol, 1.0 eq), Pd(PPh3)$_2$Cl$_2$ (389 mg, 0.56 mmol, 0.3 eq.) and CuI (70.5 mg, 0.37 mmol, 0.2 equiv.), anhydrous THF (60 mL) and Et$_3$N (560 mg, 5.55 mmol, 3.0 equiv.) were added under nitrogen atmosphere. Prop-2-yn-1-ol (310 mg, 5.55 mmol, 3.0 eq) was added and the reaction mixture was stirred at room temperature for 1 h. The reaction mixture was evaporated to 5 mL, then was extracted with EtOAc and washed with water and brine. The organic layers were purified by chromatography (Petroleum/EtOAc from 5:1 to 0:1) to afford crude product. The crude product was crystallized with isopropyl ether to afford purified compound N-tert-butyl-5-(4-(5-cyclopropyl-1H-pyrazol-3-ylamino)-5-(3-hydroxyprop-1-ynyl)pyrimidin-2-yl)thiophene-2-sulfonamide (Compound 216) (400 mg, 46%). LC-MS (m/z)=473 [M+H]$^+$. $^1$H NMR (400 MHz, DMSO-d$_6$): δ 0.75-0.76 (m, 2H), 0.98-1.00 (m, 2H), 1.20 (s, 9H), 1.92-1.99 (m, 1H), 4.40 (d, J=5.6 Hz, 2H), 5.43 (t, J=5.6 Hz, 1H), 6.46 (s, 1H), 7.61 (d, J=4.0 Hz, 1H), 7.77 (d, J=3.6 Hz, 1H), 7.91 (s, 1H), 8.43 (s, 1H), 8.98 (s, 1H), 12.32 (s, 1H).

A solution of N-tert-butyl-5-(4-(5-cyclopropyl-1H-pyrazol-3-ylamino)-5-(3-hydroxyprop-1-ynyl) pyrimidin-2-yl)thiophene-2-sulfonamide (250 mg, 0.53 mmol, 1.0 eq) in dry THF (2 mL) was added dropwise over 10 min to a mixture of LiAlH$_4$ (250 mg, 6.58 mmol, 12.4 eq) in THF (20 mL) under nitrogen. The reaction mixture was maintained 0° C. during the addition. The reaction mixture was heated to reflux for 10 min. Then the reaction mixture was cooled to 0° C., while vigorous stirring was maintained, carefully treated with Na$_2$SO$_4$.10H$_2$O (10 g) in portion and then stirred at room temperature for 10 min. The reaction mixture was filtered. The filtrate was concentrated and purified by silica gel chromatography (EtOAc/MeOH/THF from 10:0:0 to 20:1:2) to afford (E)-N-tert-butyl-5-(4-(5-cyclopropyl-1H-pyrazol-3-ylamino)-5-(3-hydroxyprop-1-enyl)pyrimidin-2-yl)thiophene-2-sulfonamide (Compound 218) (100 mg, 40.0%). LC-MS (m/z)=475 [M+H]$^+$. $^1$H NMR (400 MHz, DMSO-d$_6$): δ 0.74-0.75 (m, 2H), 0.96-0.97 (m, 2H), 1.20 (s, 9H), 1.90-1.95 (m, 1H), 4.16 (m, 2H), 4.85 (s, 1H), 6.38 (d, J=16.0 Hz, 1H), 6.46 (s, 1H), 6.89 (d, J=15.2 Hz, 1H), 7.59 (d, J=3.6 Hz, 1H), 7.73 (d, J=4.0 Hz, 1H), 7.87 (bs, 1H), 8.42 (s, 1H), 9.26 (bs, 1H), 12.18 (bs, 1H).

BCl$_3$ (1 M in CH$_2$Cl$_2$, 0.5 mL, 6.0 mmol, 20 eq) was added to a stirred solution of (E)-N-tert-butyl-5-(4-(5-cyclopropyl-1H-pyrazol-3-ylamino)-5-(3-hydroxyprop-1-enyl)pyrimidin-2-yl)thiophene-2-sulfonamide (Compound 214) (40 mg, 0.08 mmol) in CH$_2$Cl$_2$ (10 mL) at room temperature under nitrogen. The reaction mixture was stirred for 30 min and then quenched with aq. NaHCO$_3$ in ice bath. The reaction mixture was extracted with ethyl acetate and washed with water, brine, dried and evaporated. The crude product was crystallized with THF/isopropyl to afford (E)-5-(4-(5-cyclopropyl-1H-pyrazol-3-ylamino)-5-(3-hydroxyprop-1-enyl)pyrimidin-2-yl)thiophene-2-sulfonamide (Compound 281) (4 mg, 11%). LC-MS (m/z)=419 [M+H]$^+$. $^1$H NMR (400 MHz, DMSO-d$_6$): δ 0.73-0.77 (m, 2H), 0.95-1.00 (m, 2H), 1.90-1.96 (m, 1H), 4.16 (d, J=4.4 Hz, 2H), 6.37 (dt, J=15.6 Hz, 4.8 Hz, 1H), 6.45 (s, 1H), 6.88 (d, J=15.6 Hz, 1H), 7.57 (d, J=4.4 Hz, 1H), 7.76 (d, J=4.0 Hz, 1H), 7.78 (s, 2H), 8.43 (s, 1H), 9.27 (s, 1H).

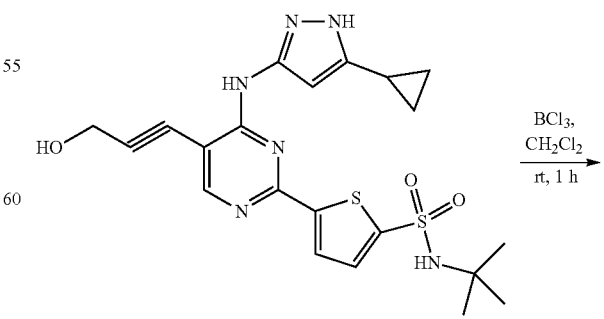

Compound 216

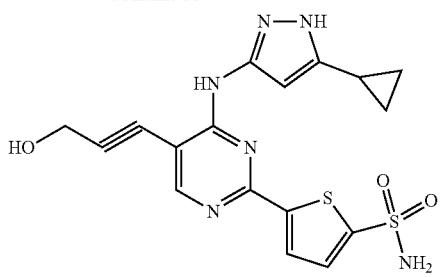

Compound 217

5-(4-(5-cyclopropyl-1H-pyrazol-3-ylamino)-5-(3-hydroxyprop-1-ynyl)pyrimidin-2-yl)thiophene-2-sulfonamide (Compound 218)

5-(4-(5-Cyclopropyl-1H-pyrazol-3-ylamino)-5-(3-hydroxyprop-1-ynyl)pyrimidin-2-yl)thiophene-2-sulfonamide (Compound 217) (5 mg, 11.4%) was prepared using the procedure for synthesis of (E)-N-tert-butyl-5-(4-(5-cyclopropyl-1H-pyrazol-3-ylamino)-5-(3-hydroxyprop-1-enyl)pyrimidin-2-yl)thiophene-2-sulfonamide (Compound 218). LC-MS (m/z)=417 [M+H]$^+$. $^1$H NMR (400 MHz, DMSO-d$_6$): 0.76-0.77 (m, 2H), 0.98-1.00 (m, 2H), 1.94-1.98 (m, 1H), 4.40 (d, J=5.6 Hz, 2H), 5.43 (t, J=5.6 Hz, 1H), 6.47 (s, 1H), 7.60 (d, J=4.4 Hz, 1H), 7.79 (d, J=4.0 Hz, 1H), 7.83 (s, 2H), 8.44 (s, 1H), 8.97 (s, 1H), 12.31 (s, 1H).

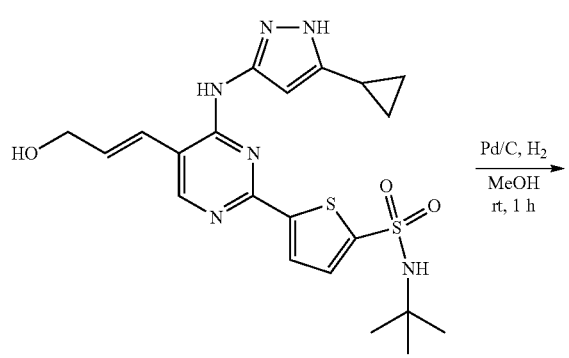

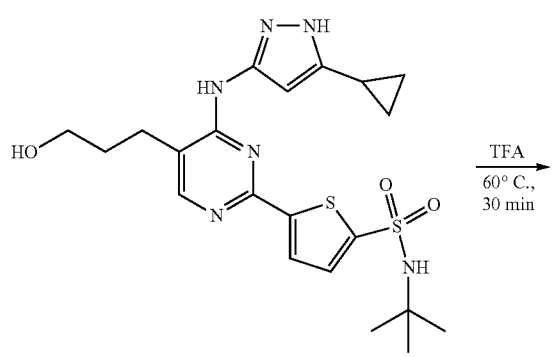

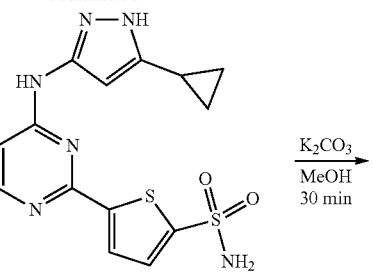

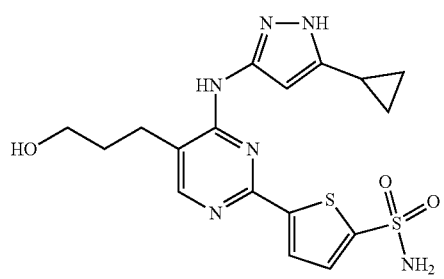

Compound 319

5-(4-(5-Cyclopropyl-1H-pyrazol-3-ylamino)-5-(3-hydroxypropyl)pyrimidin-2-yl)thiophene-2-sulfonamide (Compound 311)

To a solution of (E)-N-tert-butyl-5-(4-(5-cyclopropyl-1H-pyrazol-3-ylamino)-5-(3-hydroxyprop-1-enyl)pyrimidin-2-yl)thiophene-2-sulfonamide (10 mg, 0.02 mmol, 1.0 equiv.) in MeOH (2 mL) was added Pd/C (1 mg, 10%). The flask was then evacuated and filled with H2. The reaction mixture was stirred for 1 h at rt and then Pd/C was removed by filtered. The filtrate was concentrated to offered desire compound N-tert-butyl-5-(4-(5-cyclopropyl-1H-pyrazol-3-ylamino)-5-(3-hydroxypropyl)pyrimidin-2-yl)thiophene-2-sulfonamide (10 mg, 99%). LC-MS (m/z)=476 [M+H]$^+$ A solution of N-tert-butyl-5-(4-(5-cyclopropyl-1H-pyrazol-3-ylamino)-5-(3-hydroxypropyl)pyrimidin-2-yl)thiophene-2-sulfonamide (10 mg, 0.02 mmol) in TFA (1 mL) was heated to reflux for 0.5 h. The reaction was removed in vacuo, to which K$_2$CO$_3$ (43 mg, 0.31 mmol) in MeOH (5 mL) was added. After stirring at room temperature for 1 h the reaction mixture was filtered, the filtrate was concentrated and purified by HPLC-prepare to afford the desired compound 5-(4-(5-cyclopropyl-1H-pyrazol-3-ylamino)-5-(3-hydroxy propyl)pyrimidin-2-yl)thiophene-2-sulfonamide (Compound 311) (6 mg, 66.7%, two step). LC-MS (m/z)=421 [M+H]$^+$; $^1$H NMR (400 MHz, DMSO-d$_6$) δ: 0.75-0.79 (m, 2H), 0.99-1.03 (m, 2H), 1.71 (q, J=6.4 Hz, 2H), 1.94-1.99 (m, 1H), 2.71 (t, J=6.4 Hz, 2H), 3.47 (t, J=6.4 Hz, 2H), 6.45 (s, 1H), 7.64 (d, J=4.0 Hz, 1H), 7.80 (s, 2H), 8.05 (d, J=3.2 Hz, 1H), 8.22 (s, 1H), 10.06 (bs, 1H).

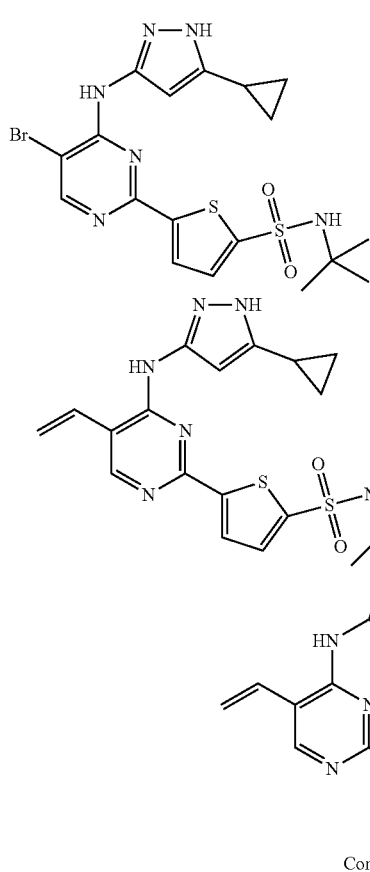

Compound 209

5-(4-(5-Cyclopropyl-1H-pyrazol-3-ylamino)-5-vinylpyrimidin-2-yl)thiophene-2-sulfonamide (Compound 209)

The mixture of 5-(5-bromo-4-(5-cyclopropyl-1H-pyrazol-3-ylamino)pyrimidin-2-yl)-N-tert-butylthiophene-2-sulfonamide (1 g, 2.0 mmol, 1.0 eq), tributyl(vinyl)stannane (956 mg, 3.01 mmol, 1.5 eq), Pd (PPh$_3$)$_2$Cl$_2$ (200 mg, 0.28 mmol, 0.14 eq) and Bu$_4$NBr (642 mg, 2.0 mmol, 1.0 eq) in 1,4-dioxane (30 mL) was stirred at 100° C. for 2 h under N$_2$, cooled to room temperature and partitioned between EtOAc and water. The organic layer was concentrated and purified by silica gel chromatography to afford N-tert-butyl-5-(4-(5-cyclopropyl-1H-pyrazol-3-ylamino)-5-vinylpyrimidin-2-yl)thiophene-2-sulfonamide (755 mg, 80%). LC-MS (m/z)=444 [M+H]$^+$ A mixture of N-tert-butyl-5-(4-(5-cyclopropyl-1H-pyrazol-3-ylamino)-5-vinylpyrimidin-2-yl)thiophene-2-sulfonamide (80 mg, 0.17 mmol) and BCl$_3$ (3 mL) in DCM (10 mL) was stirred for 0.5 h, Water was added and extracted with EA. The combined organic layers were dried (NaHSO$_4$), filtered. The filtrate was concentrated to afford the compound 5-(4-(5-cyclopropyl-1H-pyrazol-3-ylamino)-5-vinylpyrimidin-2-yl)thiophene-2-sulfonamide (Compound 209) (70 mg, 90%). LC-MS (m/z)=389 [M+H]$^+$; $^1$H NMR (400 MHz, DMSO-d$_6$): 0.80-0.81 (m, 2H), 1.01-1.04 (m, 2H), 1.96-2.02 (m, 1H), 5.50 (d, J=11.6 Hz, 1H), 5.96 (d, J=17.2 Hz, 1H), 6.43 (s, 1H), 7.08-7.15 (m, 1H), 7.63 (d, J=4 Hz, 1H), 7.87 (bs, 2H), 8.00 (bs, 1H), 8.56 (s, 1H), 10.13 (bs, 1H).

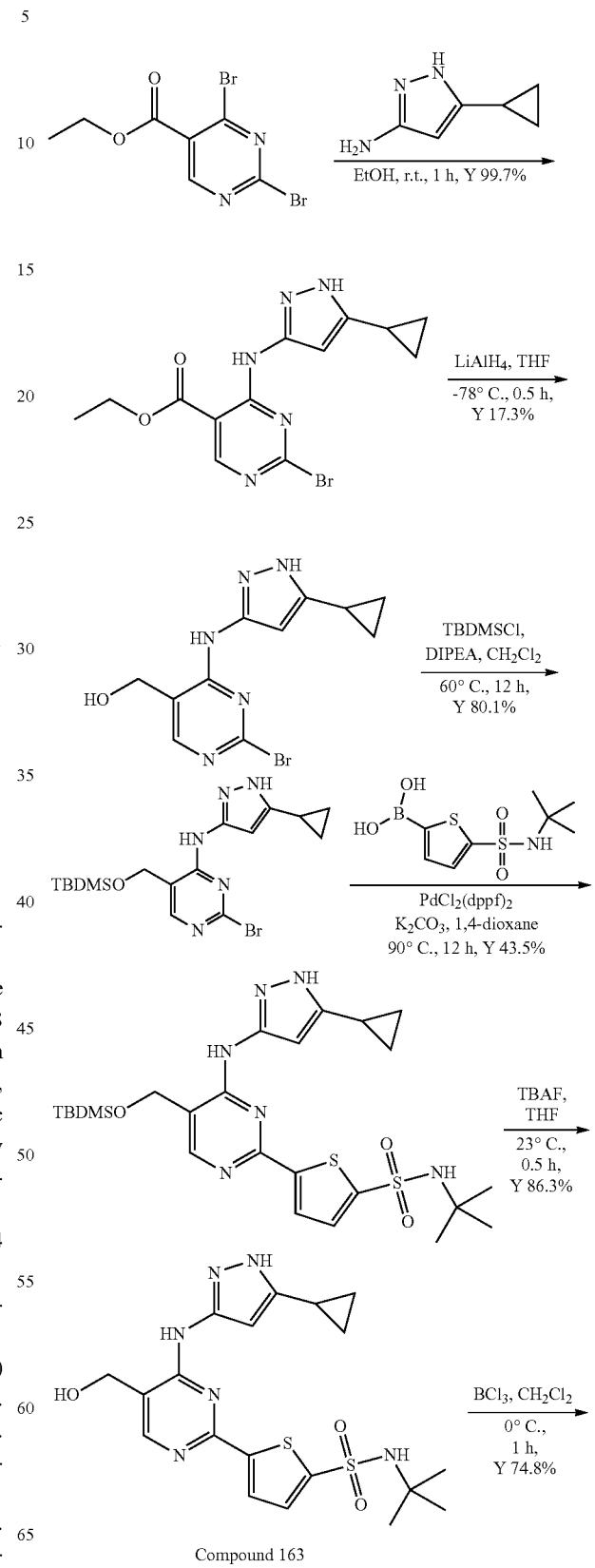

Compound 163

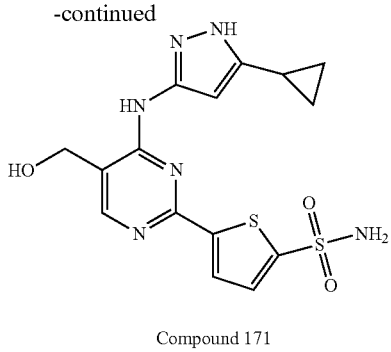

Compound 171

N-tert-butyl-5-(4-(5-cyclopropyl-1H-pyrazol-3-ylamino)-5-(hydroxymethyl)pyrimidin-2-yl) thiophene-2-sulfonamide (Compound 163) and 5-(4-(5-cyclopropyl-1H-pyrazol-3-ylamino)-5-(hydroxymethyl)pyrimidin-2-yl)thiophene-2-sulfonamide (Compound 171

Step 1. A mixture of ethyl 2,4-dibromopyrimidine-5-carboxylate (3.0 g, 10.1 mmol, 1.0 eq) and 5-cyclopropyl-1H-pyrazol-3-amine (1.87 g, 15.2 mmol, 1.5 eq) in EtOH (5 mL) was stirred at 23° C. for 1 h. Filtration then afforded ethyl 2-bromo-4-(5-cyclopropyl-1H-pyrazol-3-ylamino)pyrimidine-5-carboxylate (3.4 g, 99.7%) as white solid. LC-MS (m/z)=353.1 [M+H]$^+$ Step 2. To the solution of ethyl 2-bromo-4-(5-cyclopropyl-1H-pyrazol-3-ylamino)pyrimidine-5-carboxylate (3.0 g, 8.5 mmol, 1 eq) in THF (300 ml) at −78° C., LiAlH$_4$ (3.0 g) was added slowly. After stirring at RT for 1 h, Na$_2$SO$_4$.H$_2$O was added and stirred at 23° C. for 0.5 h. The mixture was filtered and extracted with EtOAc (3×50 ml). The combined organic phases were washed (brine), dried (Na$_2$SO$_4$), filtered and concentrated to give a residue. The residue was purified by silica gel column chromatography (PE/EtOAc=1:1 as eluant) to give (2-bromo-4-(5-cyclopropyl-1H-pyrazol-3-ylamino) pyrimidin-5-yl)methanol (450 mg, 17.03%) as white solid. LC-MS (m/z)=311.15 [M+H]$^+$ Step 3. A solution of (2-bromo-4-(5-cyclopropyl-1H-pyrazol-3-ylamino)pyrimidin-5-yl)methanol (420 mg, 1.35 mmol, 1.0 equiv.), TBDMSCl (244.9 mg, 1.63 mmol, 1.2 equiv.) and DIPEA (522.45 mg, 4.05 mmol, 3.0 equiv.) in CH$_2$Cl$_2$ (50 mL) was stirred for 12 h at 60° C. Water was added, and the mixture was extracted with EtOAc (3×50 ml). The combined organic phases were washed (brine), dried (Na$_2$SO$_4$), filtered and concentrated to 2-bromo-5-((tert-butyldimethylsilyloxy)methyl)-N-(5-cyclopropyl-1H-pyrazol-3-yl)pyrimidin-4-amine (457.9 mg, 80.1%) as white solid. LC-MS (m/z): 424.1 [M+H]$^+$;

Step 4. A mixture of 2-bromo-5-((tert-butyldimethylsilyloxy)methyl)-N-(5-cyclopropyl-1H-pyrazol-3-yl)pyrimidin-4-amine (210 mg, 0.49 mmol, 1.0 equiv.), 5-(N-tert-butylsulfamoyl)thiophen-2-ylboronic acid (260.4 mg, 0.99 mmol, 2 equiv.), PdCl$_2$(dppf)CH$_2$Cl$_2$ (120.0 mg, 0.15 mmol, 0.3 equiv.), K$_2$CO$_3$ (236.67 mg, 1.72 mmol, 3.5 equiv.) in dioxane (10 mL) and water (2 mL) was heated for 12 h at 90° C. under nitrogen atmosphere. The solvent was removed and the residue was purified by silica gel chromatography (PE/EtOAc=5:12:1 as eluant) to give N-tert-butyl-5-(5-((tert-butyldimethylsilyloxy)methyl)-4-(5-cyclopropyl-1H-pyrazol-3-ylamino)pyrimidin-2-yl)thiophene-2-sulfonamide (120.0 mg, 43.5%) as white solid. LC-MS (m/z)=563.1 [M+H]$^+$;

Step 5. A solution of N-tert-butyl-5-(5-((tert-butyldimethylsilyloxy)methyl)-4-(5-cyclopropyl-1H-pyrazol-3-ylamino)pyrimidin-2-yl)thiophene-2-sulfonamide (120 mg, 0.24 mmol, 1.0 equiv.) and TBAF (0.3 ml, 0.29 mmol, 1.2 equiv.) in THF (5 mL) was stirred for 0.5 h at 23° C. Water was added and the reaction was extracted with EtOAc (3×50 ml). The combined organic phases were washed (brine), dried (Na$_2$SO$_4$), filtered and concentrated to afford N-tert-butyl-5-(4-(5-cyclopropyl-1H-pyrazol-3-ylamino)-5-(hydroxymethyl)pyrimidin-2-yl) thiophene-2-sulfonamide (Compound 163) (89.0 g, 86.34%) as white solid. LC-MS (m/z)=449.1 [M+H]$^+$; $^1$H NMR (400 MHz, DMSO-d$_6$): δ 0.75 (m, 2H), 0.96-0.98 (m, 2H), 1.20 (s, 9H), 1.93 (m, 1H), 4.56 (d, 4.4 Hz, 2H), 5.62 (s, 1H), 6.52 (s, 1H), 7.59 (d, J=3.6 Hz, 1H), 7.76 (d, J=3.6 Hz, 1H), 7.86 (s, 1H), 8.23 (s, 1H), 8.96 (s, 1H), 12.18 (s, 1H)

Step 6. A solution of N-tert-butyl-5-(4-(5-cyclopropyl-1H-pyrazol-3-ylamino)-5-(hydroxymethyl) pyrimidin-2-yl) thiophene-2-sulfonamide (89 mg, 0.17 mmol, 1.0 eq) and BCl$_3$ (1.0 ml, 1.0 mmol, 6.0 equiv.) in CH$_2$Cl$_2$ (5 mL) was stirred for 1 h at 0° C. After addition od water and extraction with EtOAc (3×50 ml), the combined organic phases were washed (brine), dried (Na$_2$SO$_4$), filtered and concentrated to produce 5-(4-(5-cyclopropyl-1H-pyrazol-3-ylamino)-5-(hydroxymethyl)pyrimidin-2-yl)thiophene-2-sulfonamide (Compound 171) (50.0 mg, 74.8%) as white solid. LC-MS (m/z)=393.0 [M+H]$^+$; $^1$H $^1$H NMR (400 MHz, DMSO-d$_6$): δ 0.75-0.76 (m, 2H), 0.97-0.99 (m, 2H), 1.92-1.96 (m, 1H), 4.56 (d, J=5.2 Hz, 2H), 5.61 (t, J=5.2 Hz, 1H), 6.53 (d, J=10.4 Hz, 1H), 7.58 (d, J=3.6 Hz, 1H), 7.78 (s, 3H), 8.24 (s, 1H), 8.95 (s, 1H), 12.16 (s, 1H).

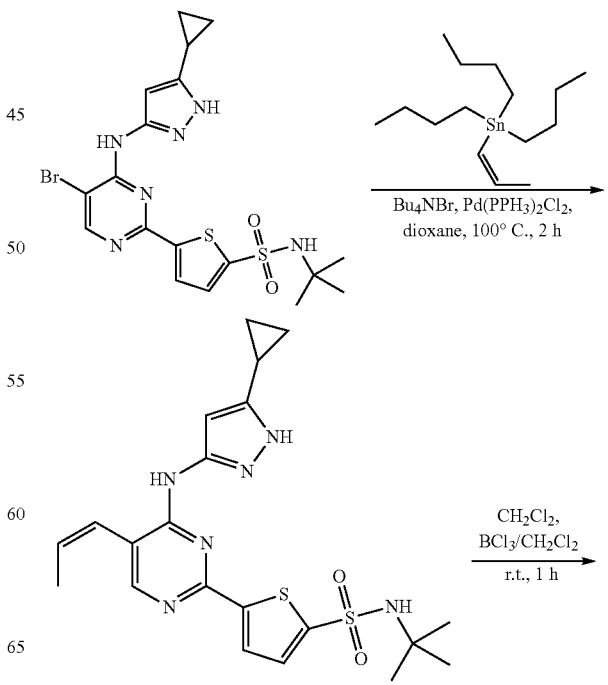

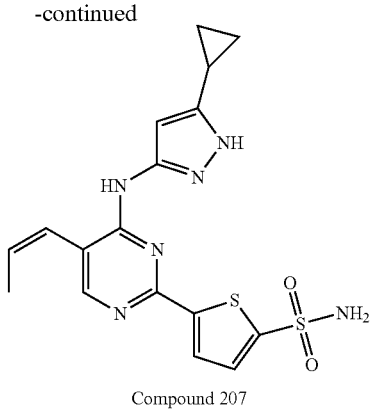

Compound 207

(Z)-5-(4-(5-cyclopropyl-1H-pyrazol-3-ylamino)-5-(prop-1-enyl)pyrimidin-2-yl)thiophene-2-sulfonamide (Compound 207)

A mixture of 5-(5-bromo-4-(5-cyclopropyl-1H-pyrazol-3-ylamino)pyrimidin-2-yl)-N-tert-butylthiophene-2-sulfonamide (497.4 mg, 1.0 mmol, 1.0 eq), Pd(PPh$_3$)$_2$Cl$_2$ (28.0 mg, 0.1 mmol, 0.1 eq) and Bu$_4$NBr (321.1 mg, 0.1 mmol, 1.0 equiv.) was flushed with nitrogen. Anhydrous dioxane (10 mL) was added and the reaction mixture was flushed with nitrogen. (Z)-tributyl(prop-1-enyl)stannane (475.4 mg, 1.5 mmol, 1.5 eq) was added and the reaction mixture was stirred at rt for 2 h. The mixture was extracted with EtOAc and washed with water, brine. The organic layers were concentrated to afford the residue, which was purified by silica gel chromatography (PE/EA/MeOH=2:1:0.06 as eluant) to afford (Z)—N-tert-butyl-5-(4-(5-cyclopropyl-1H-pyrazol-3-ylamino)-5-(prop-1-enyl)pyrimidin-2-yl)thiophene-2-sulfonamide (375.6 mg, 82.1%) as white solid. LC-MS (m/z)=459 [M+H]$^+$.

BCl$_3$ (1 M in CH$_2$Cl$_2$, 3.28 mL, 3.28 mmol, 4.0 equiv.) was added to a stirred solution of (Z)—N-tert-butyl-5-(4-(5-cyclopropyl-1H-pyrazol-3-ylamino)-5-(prop-1-enyl)pyrimidin-2-yl)thiophene-2-sulfonamide (375.6 mg, 0.82 mmol, 1.0 equiv.) in CH$_2$Cl$_2$ (20 mL) at room temperature under nitrogen. The reaction mixture was stirred for 30 min and then quenched with aq. NaHCO$_3$ in ice bath. The reaction mixture was extracted with ethyl acetate and washed with water, brine, dried and evaporated. The crude product was crystallized with THF/isopropyl to afford (Z)-5-(4-(5-cyclopropyl-1H-pyrazol-3-ylamino)-5-(prop-1-enyl)pyrimidin-2-yl)thiophene-2-sulfonamide (Compound 207) (255.1 mg, 77.4%). LC-MS (m/z)=403 [M+H]$^+$. $^1$H NMR (400 MHz, DMSO-d$_6$): δ 0.75-0.76 (m, 2H), 0.95-1.00 (m, 2H), 1.79-1.81 (m, 2H), 1.90 (d, J=6.0 Hz, 1H), 1.93-1.97 (m, 1H), 5.60-6.04 (m, 0.6H), 6.26-6.31 (m, 0.4H), 6.46-6.49 (s, 1.5H), 6.79 (d, J=15.2 Hz, 0.4H), 7.57-7.59 (m, 1H), 7.74-7.79 (m, 3H), 8.19 (s, 0.6H), 8.39 (s, 0.4H), 8.94 (s, 0.5H), 9.33 (s, 0.3H).

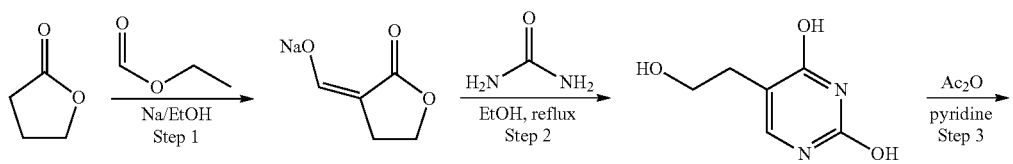

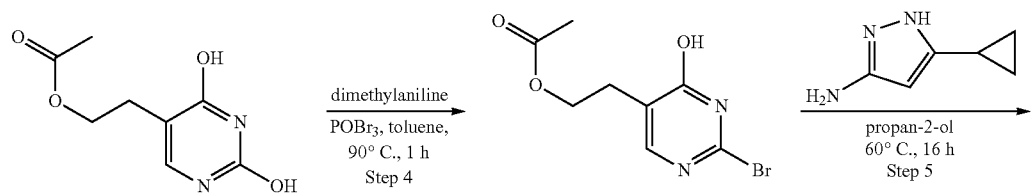

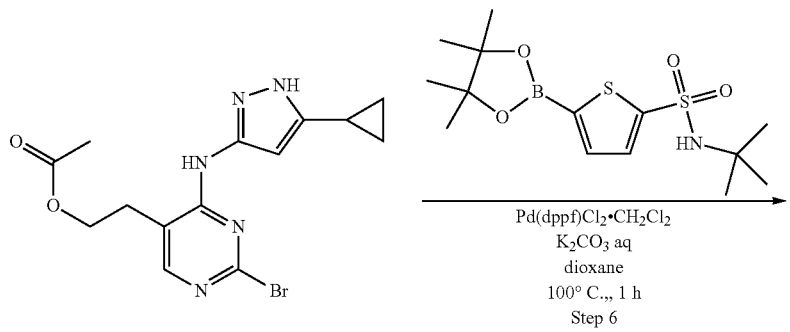

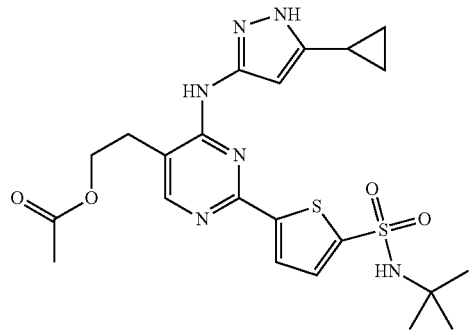

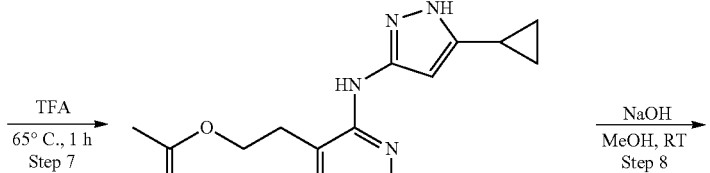

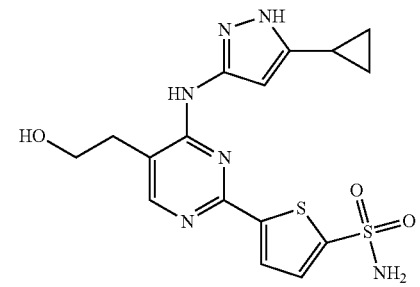

Compound 313

Compound 239

2-(4-(5-cyclopropyl-1H-pyrazol-3-ylamino)-2-(5-sulfamoylthiophen-2-yl)pyrimidin-5-yl)ethyl acetate (Compound 313) and 5-(4-(5-cyclopropyl-1H-pyrazol-3-ylamino)-5-(2-hydroxyethyl)pyrimidin-2-yl)thiophene-2-sulfonamide (Compound 239)

Step 1. To a cooled suspension of 54.0 g. (1 mole) of sodium methoxide in a liter of dry ether, a mixture of 80 ml. (1.3 moles) of methylformate and 76 ml. (1 mole) of y-butyrolactone was added dropwise with stirring over a 2-h period. The stirring was continued at room temperature overnight. The reaction mixture was then cooled in an ice bath for 1 hr. to complete the separation of the cream-colored product which was then collected, washed with dry ether, and dried under vacuum to yield sodium (Z)-(2-oxodihydrofuran-3(2H)-ylidene)methanolate (123 g, 90%)

Step 2. Sodium (Z)-(2-oxodihydrofuran-3(2H)-ylidene)methanolate (1.36 g, 10 mmole) was added to a solution of 600 mg. (10 mmole) of urea in 50 ml. of absolute ethanol, and the reaction mixture was boiled under reflux for 5 h with stirring. Concentration under vacuum gave a residue, which was crystallized from ethanol to yield 5-(2-hydroxyethyl)pyrimidine-2,4-diol (290 mg, 18.5%). LC-MS (m/z)=157 [M+H]$^+$ Step 3. Mixture of 5-(2-hydroxyethyl)pyrimidine-2,4-diol (1.0 g, 6.4 mmole), 5 ml. of acetic anhydride, and ca. 30 ml. of dry pyridine was stirred for 1 hr. under anhydrous condition. The clear solution was treated with water and evaporated under vacuum to leave a white residue that was recrystallized from water to yield the monoacetate as white powder 2-(2,4-dihydroxypyrimidin-5-yl)ethyl acetate (0.95 g, 74%). LC-MS (m/z)=199 [M+H]$^+$.

Step 4. A mixture of 2-(2,4-dihydroxypyrimidin-5-yl)ethyl acetate (198 mg, 1 mmol), POBr$_3$ (0.85 g, 3 equiv.) and N,N-dimethylbenzenamine (243 mg, 2 mmol, 2 equiv.) in toluene (8 mL) was stirred at rt for 0.5 h then heated to 90° C. for 1 h. The solution was cooled down to 55° C. and poured into ice-water while stirring vigorously. The mixture was maintained below 25° C. during the quenching, the reaction mixture was extracted with CH$_2$Cl$_2$, the organic layer was washed (cold water), dried (Na$_2$SO4), evaporated and purified by silica gel chromatography (EA/PE from 1:10 to 1:5) to afford 2-(2,4-dibromopyrimidin-5-yl)ethyl acetate (150 mg, 46%). LC-MS (m/z)=324 [M+H]$^+$.

Step 5. A mixture of 2-(2,4-dibromopyrimidin-5-yl)ethyl acetate (650 mg, 2.0 mmol, 1.0 eq), 5-cyclopropyl-1H-pyrazol-3-amine (296 mg, 2.4 mmol, 1.2 eq) and DIPEA (387 mg, 3.0 mmol, 1.5 eq) in propan-2-ol (10 mL) was stirred at 60° C. for 16 h. The mixture was extracted with EtOAc. The combined organic phases were washed (brine), dried (Na$_2$SO$_4$), filtered and concentrated to give a residue, which was purified by silica gel column chromatography (PE/EtOAc=1:2) to give 2-(2-bromo-4-(5-cyclopropyl-1H-pyrazol-3-ylamino)pyrimidin-5-yl)ethyl acetate (390 mg, 53%) as a white solid. LC-MS (m/z)=366 [M+H]$^+$ Step 6. A mixture of 2-(2-bromo-4-(5-cyclopropyl-1H-pyrazol-3-ylamino)pyrimidin-5-yl)ethyl acetate (366 mg, 1.0 mmol, 1.0 eq), N-tert-butyl-5-(4,4,5,5-tetramethyl-1,3,2-dioxaborolan-2-yl)thiophene-2-sulfonamide (517 mg, 1.5 mmol, 1.5 eq), PdCl$_2$(dppf) (81.6 mg, 0.1 mmol, 0.1 eq), K$_2$CO$_3$ (417 mg, 3.0 mmol, 3.0 eq), dioxane (15 mL) and water (2 mL) was heated for 1 h at 90° C. under nitrogen atmosphere. The solvent was removed and the residue was purified by silica gel chromatography (PE/EtOAc=1:1) to yield 2-(2-(5-(N-tert-butylsulfamoyl)thiophen-2-yl)-4-(5-cyclopropyl-1H-pyrazol-3-ylamino)pyrimidin-5-yl)ethyl acetate (300 mg, 60%). LC-MS (m/z)=505.1 [M+H]$^+$; $^1$H NMR (400 MHz, DMSO-d$_6$): δ 0.73-0.74 (m, 2H), 0.96-0.97 (m, 2H), 1.16 (s, 9H), 1.90-1.94 (m, 1H), 1.97 (s, 3H), 2.96 (t, J=5.6 Hz, 2H), 4.17 (d, J=5.6 Hz, 2H), 6.47 (s, 1H), 7.58 (d, J=4.0 Hz, 1H), 7.72 (d, J=4.0 Hz, 1H), 7.87 (s, 1H), 8.13 (s, 1H), 9.37 (s, 1H), 12.19 (s, 1H)

Step 7. The solution of 2-(2-(5-(N-tert-butylsulfamoyl) thiophen-2-yl)-4-(5-cyclopropyl-1H-pyrazol-3-ylamino)pyrimidin-5-yl)ethyl acetate (300 mg, 0.6 mmol) in CF$_3$COOH (5 mL) was stirred at 60° C. After 1 h, the solution was evaporated to afford 2-(4-(5-cyclopropyl-1H-pyrazol-3-ylamino)-2-(5-sulfamoylthiophen-2-yl)pyrimidin-5-yl)ethyl acetate (Compound 313) (250 mg, 93%). LC-MS (m/z)=449 [M+H]$^+$; $^1$H NMR (400 MHz, DMSO-d$_6$): δ 0.76 (m, 2H), 0.98-0.99 (m, 2H), 1.94 (m, 1H), 1.99 (s, 3H), 2.98 (s, 2H), 4.20 (s, 2H), 6.47 (s, 1H), 7.59 (s, 1H), 7.76 (d, J=2.8 Hz, 1H), 7.81 (s, 2H), 8.16 (s, 1H), 9.44 (s, 1H).

Step 8. A solution of 2-(4-(5-cyclopropyl-1H-pyrazol-3-ylamino)-2-(5-sulfamoylthiophen-2-yl)pyrimidin-5-yl)ethyl acetate (Compound 313) (200 mg, 0.45 mmol, 1.0 equiv.) and NaOH.aq (2 mL) in MeOH (5 mL) was stirred for 1 h at rt. Water was added and the mixture was extracted with EtOAc. The combined organic phases were washed (brine), dried (Na$_2$SO$_4$), filtered and concentrated to yield 5-(4-(5-cyclopropyl-1H-pyrazol-3-ylamino)-5-(2-hydroxyethyl)pyrimidin-2-yl)thiophene-2-sulfonamide (Compound 239) (120 mg, 66%). LC-MS (m/z)=407.1 [M+H]$^+$; $^1$H NMR (400 MHz, DMSO-d$_6$): δ 0.77-0.81 (m, 2H), 1.01-1.06 (m, 2H), 1.97-2.01 (m, 1H), 2.89 (t, J=5.6 Hz, 2H), 3.69 (d, J=5.6 Hz, 2H), 6.47 (s, 1H), 7.69 (d, J=4.0 Hz, 1H), 7.98 (s, 2H), 8.23 (s, 1H), 8.34 (d, J=3.2 Hz, 1H), 10.67 (s, 1H)

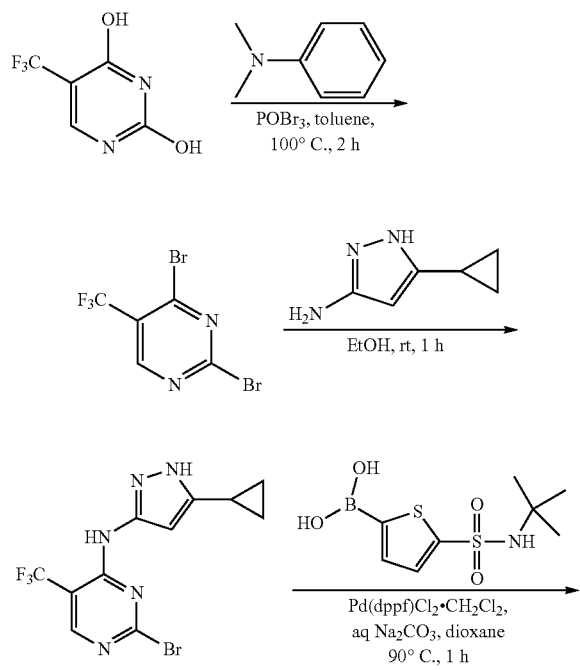

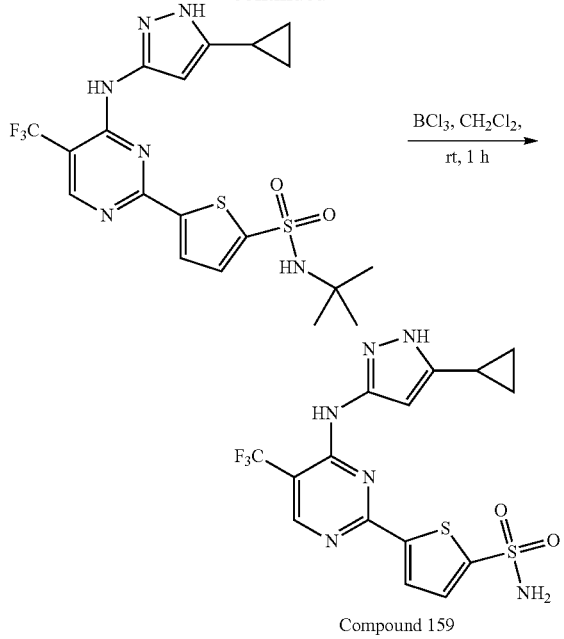

Compound 159

5-(4-(5-cyclopropyl-1H-pyrazol-3-ylamino)-5-(trifluoromethyl)pyrimidin-2-yl)thiophene-2-sulfonamide (Compound 159)

A mixture of 5-(trifluoromethyl)pyrimidine-2,4-diol (500 mg, 2.78 mmol), POBr$_3$ (2.38 g) and N, N-dimethylbenzenamine (67 mg, 0.55 mmol, 0.2 equiv.) in toluene (10 mL) was heated to 100° C. for 2 h. The solution was cooled down to 55° C. and poured into ice-water while stirring vigorously. The mixture was maintained below 25° C. during the quench, the reaction mixture was extracted with CH$_2$Cl$_2$, the organic layer was washed (cold water), dried (Na$_2$SO4), evaporated and purified by silica gel chromatography (EA/PE from 1:10 to 1:5) to afford 2,4-dibromo-5-(trifluoromethyl)pyrimidine (500 mg, 65%). LC-MS (m/z)=305 [M+H]$^+$. To a suspension of 2,4-dibromo-5-(trifluoromethyl)pyrimidine (500 mg, 1.63 mmol) in ethanol (80 mL) was added 3-cyclopropyl-1H-pyrazol-5-amine (0.811 g, 6.58 mmol, 2 eq) in ethanol (30 mL). The suspension was stirred for 8 h and filtered to afford 2,6-dichloro-N-(3-cyclopropyl-1H-pyrazol-5-yl)quinazolin-4-amine (0.9 g, 85%). LC-MS (m/z)=348 [M+H]$^+$ N-tert-butyl-5-(4-(5-cyclopropyl-1H-pyrazol-3-ylamino)-5-(trifluoromethyl)pyrimidin-2-yl)thiophene-2-sulfonamide (60 mg, 21.58%) was prepared using the step 4 procedure for the precedent example. LC-MS (m/z)=487 [M+H]$^+$. $^1$H NMR (400 MHz, DMSO-d$_6$): δ 0.74-0.76 (m, 2H), 0.98-1.00 (m, 2H), 1.19 (s, 9H), 1.91-1.97 (m, 1H), 6.28 (s, 1H), 7.62 (d, J=4.0 Hz, 1H), 7.80 (d, J=4.0 Hz, 1H), 7.95 (s, 1H), 8.69 (s, 1H), 9.22 (s, 1H), 12.41 (s, 1H).

5-(4-(5-Cyclopropyl-1H-pyrazol-3-ylamino)-5-(trifluoromethyl)pyrimidin-2-yl)thiophene-2-sulfonamide (Compound 159) (33 mg, 75%) was prepared using the last step procedure for synthesis of Compound 171. LC-MS (m/z)=431 [M+H]$^+$. $^1$H NMR (400 MHz, DMSO-d$_6$): δ 0.75-0.76 (m, 2H), 0.98-1.00 (m, 2H), 1.91-1.98 (m, 1H), 6.28 (s, 1H), 7.61 (d, J=4.0 Hz, 1H), 7.82 (d, J=4.4 Hz, 1H), 7.86 (s, 2H), 8.69 (s, 1H), 9.23 (s, 1H), 12.41 (s, 1H).

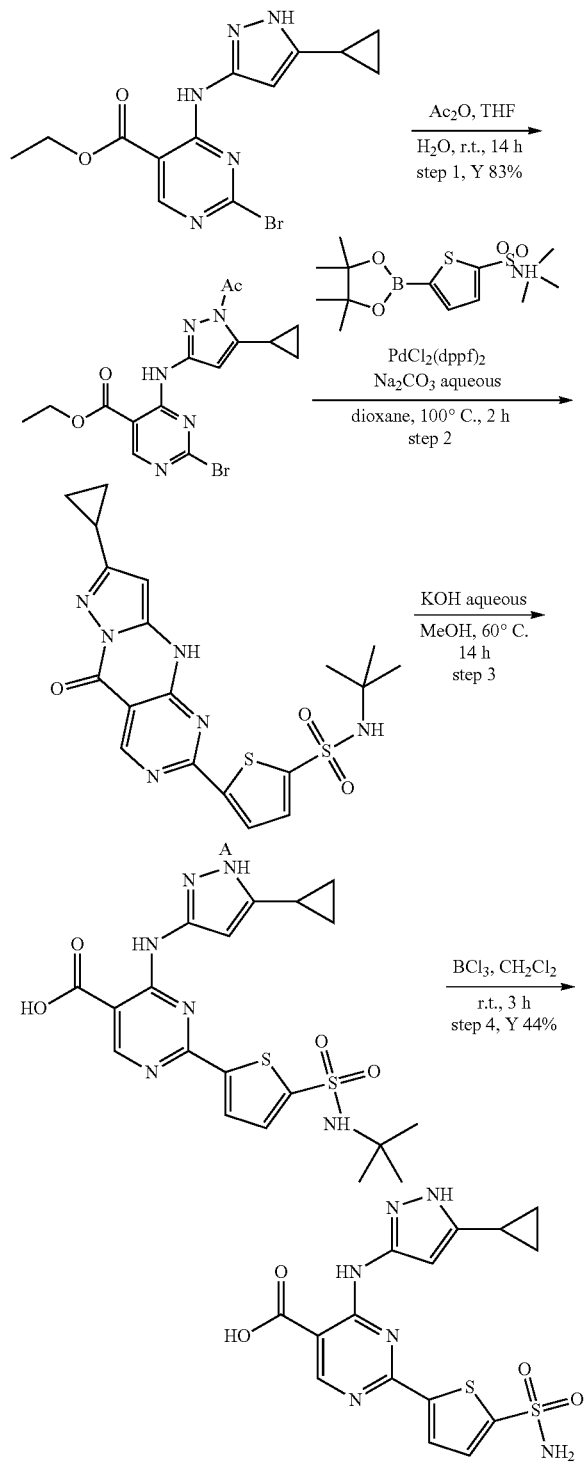

Ac₂O (2.0 mL). The reaction mixture was stirred for 2 h and water was added. The mixture was filtered and the solid was washed with water and concentrated with ethanol to remove the residual water to obtain ethyl 4-(1-acetyl-5-cyclopropyl-1H-pyrazol-3-ylamino)-2-bromopyrimidine-5-carboxylate (460 mg, 83%). LC-MS (m/z)=394.0 [M+H]⁺.

Step 2. The mixture of ethyl 4-(1-acetyl-5-cyclopropyl-1H-pyrazol-3-ylamino)-2-bromopyrimidine-5-carboxylate (360 mg, 0.91 mmol), N-tert-butyl-5-(4,4,5,5-tetramethyl-1,3,2-dioxaborolan-2-yl)thiophene-2-sulfonamide (947 mg, 2.73 mmol, 3.0 equiv.), Pd (dppf)₂Cl₂ (220 mg, 0.27 mmol, 0.3 equiv.) and saturated Na₂CO₃ aqueous (2 mL) in 1,4-dioxane (15 mL) was stirred at 100° C. for 2 h under N₂, cooled to room temperature and partitioned between EtOAc and water. The organic layer was concentrated to give the compound A and was used for the next step without further purification.

Step 3. The compound A was dissolved in methanol (20 mL) and 40% KOH aqueous (5 mL). The mixture was stirred at 60° C. for 14 h, then, partitioned between EtOAc and brine. The organic layer was washed (brine), dried (Na₂SO₄) and concentrated. The residue was purified by Prep-HPLC to give the compound 2-(5-(N-tert-butylsulfamoyl)thiophen-2-yl)-4-(5-cyclopropyl-1H-pyrazol-3-ylamino)pyrimidine-5-carboxylic acid (80 mg, 19% over 2 steps). LC-MS (m/z)=418.0 [M+H]⁺.

Step 4. To a solution of 2-(5-(N-tert-butylsulfamoyl)thiophen-2-yl)-4-(5-cyclopropyl-1H-pyrazol-3-ylamino)pyrimidine-5-carboxylic acid (80 mg, 0.17 mmol, 1.0 eq) in CH₂Cl₂ (20 mL) was added 1N BCl₃ (3.4 mL, 3.4 mmol, 20.0 eq) at rt. The mixture was stirred for 3 h and concentrated. The residue was purified by recrystallization with methanol and isopropylether to 4-(5-cyclopropyl-1H-pyrazol-3-ylamino)-2-(5-sulfamoylthiophen-2-yl)pyrimidine-5-carboxylic acid (Compound 179) (30 mg, 44%). LC-MS (m/z)=407.0 [M+H]⁺. ¹H NMR (400 MHz, DMSO-d₆): δ 0.77-0.80 (m, 2H), 0.98-1.03 (m, 2H), 1.95-2.00 (m, 1H), 6.60 (s, 1H), 7.65 (d, J=4.0 Hz, 1H), 7.92 (s, 2H), 7.95 (d, J=4.0 Hz, 1H), 8.92 (s, 1H), 10.74 (s, 1H).

4-(5-cyclopropyl-1H-pyrazol-3-ylamino)-2-(5-sulfamoylthiophen-2-yl)pyrimidine-5-carboxylic acid (Compound 179)

Step 1. To the mixture of ethyl 2-bromo-4-(5-cyclopropyl-1H-pyrazol-3-ylamino)pyrimidine-5-carboxylate (495 mg, 1.41 mmol) in THF (100 mL) and water (10 mL) was added

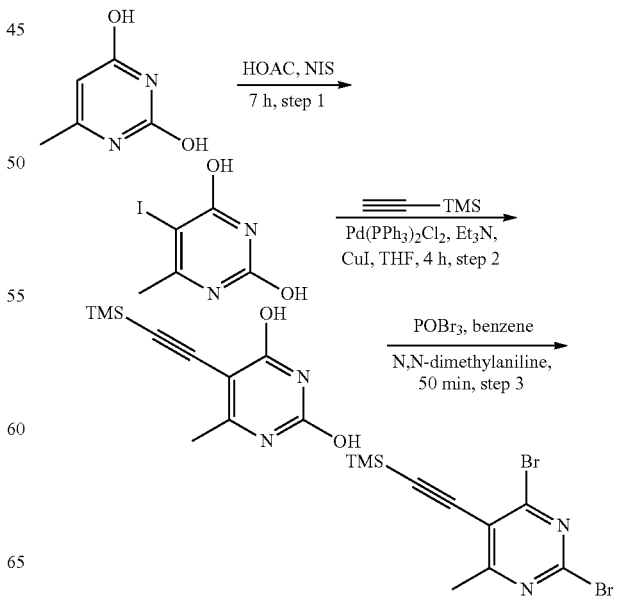

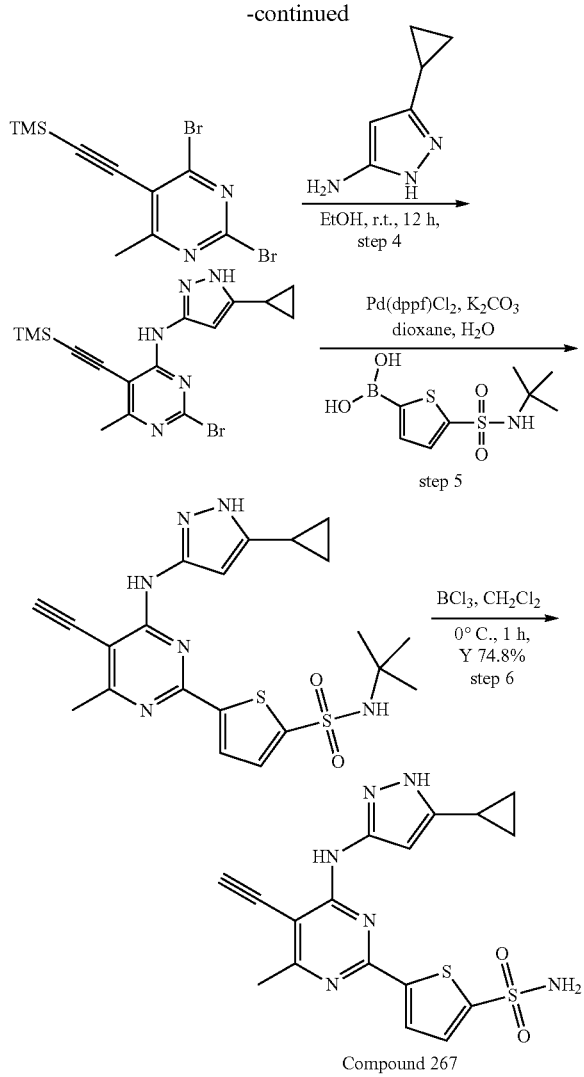

Compound 267

5-(4-(3-cyclopropyl-1H-pyrazol-5-ylamino)-5-ethynyl-6-methylpyrimidin-2-yl)thiophene-2-sulfonamide (Compound 267)

Step 1. The mixture of all materials (6-methylpyrimidine-2,4-diol, 20.00 g, 0.159 mol, 1.0 eq; NIS, 39.25 g, 0.174 mol, 1.1 eq; AcOH, 150 mL) was stirred well for about 7 h. It affords white solid product 5-iodo-6-methylpyrimidine-2,4-diol (37.93 g, 95%), isolated by filtration, washed with ethyl acetate. LC-MS (m/z)=252.9 [M+H]$^+$.

Step 2. $(Ph_3P)_2PdCl_2$ (0.700 g, 0.001 mol, 0.05 eq.) and finely ground CuI (0.190 g, 0.001 mol, 0.05 eq.) were added to a well stirred suspension of 5-iodo-6-methylpyrimidine-2,4-diol (5.040 g, 0.02 mol, 1.0 eq) in ethyl acetate (100 mL) at 10-15° C. The mixture was then deoxygenated by evacuating and flushing with nitrogen three times. Trimethylsilylacetaylene (8.0 mL, 0.056 mol, 2.8 eq) followed by triethylamine (4.2 mL, 0.03 mol, 1.5 eq) was added. The suspension was stirred under nitrogen at 25° C. for 16 h. The solids were isolated by filtration under nitrogen and washed sequentially with ethyl acetate (2×10 mL), water (3×10 mL) and finally ethyl acetate (2×10 mL) to the prodcut 6-methyl-5-((trimethylsilyl)ethynyl) pyrimidine-2,4-diol (3.92 g, 88%). LC-MS (m/z)=223.1 [M+H]$^+$.

Step 3. Toluene was added (100 mL) into a well stirred mixture of compound 6-methyl-5-((trimethylsilyl)ethynyl) pyrimidine-2,4-diol (3.92 g, 17.6 mmol, 1.0 equiv.) and N,N-dimethyl aniline (8.9 mL, 70.5 mmol, 4.0 equiv.). Then $POBr_3$ (45.0 g, 158.7 mmol, 9.0 eq) was added dropwise. After a few min, the reaction was heated to 100° C. for 50 minutes. The cooled solvent was washed with icy water several times till the water's pH=7. Dried by $Na_2SO_4$ and purified by silica-gel column chromatography (mobile phase: petroleum ether to petroleum ether/ethyl acetate=500/10), oil product 2,4-dibromo-6-methyl-5-((trimethylsilyl)ethynyl) pyrimidine was obtained (1.2 g, 20%). LC-MS (m/z)=348.8 [M+H]$^+$.

Step 4. At 20° C. (using an ice bath for the temperature control), 3-cyclopropyl-1H-pyrazol-5-amine (1.192 g, 9.68 mmol, 1.5 eq) in ethanol (15 ml) was added into a solution of compound 2,4-dibromo-6-methyl-5-((trimethylsilyl)ethynyl)pyrimidine (2.246 g, 6.45 mmol, 1.0 equiv.) in ethanol (15 mL). The reaction was stirred at for 20 h at 20-23° C. Ethanol was removed under reduced pressure 10-20° C. Purified by silica-gel column chromatography (mobile phase: petroleum ether/ethyl acetate=20/1; 5/1) afforded solid product 2-bromo-N-(5-cyclopropyl-1H-pyrazol-3-yl)-6-methyl-5-((trimethylsilyl)ethynyl)pyrimidin-4-amine (500 mg, 22%). LC-MS (m/z)=392.0 [M+2H]$^+$.

Step 5. N-tert-butyl-5-(4-(5-cyclopropyl-1H-pyrazol-3-ylamino)-5-ethynyl-6-methylpyrimidin-2-yl)thiophene-2-sulfonamide (230 mg, 50.3%) was prepared using the procedure for synthesis of Compound 183. LC-MS (m/z)=457.1 [M+H]$^+$. δ (400 MHz, DMSO-$d_6$): 0.75-0.76 (m, 2H), 0.98-1.00 (m, 2H), 1.20 (s, 9H), 1.92-1.97 (m, 1H), 2.51 (s, 3H), 5.10 (s, 1H), 6.46 (s, 1H), 7.61 (d, J=4.4 Hz, 1H), 7.79 (d, J=4.4 Hz, 1H), 7.92 (s, 1H), 8.51 (s, 1H), 12.29 (s, 1H)

Step 6. $BCl_3$ (1 M in $CH_2Cl_2$, 2.5 mL, 2.5 mmol, 5 eq) was added to a stirred solution of N-tert-butyl-5-(4-(5-cyclopropyl-1H-pyrazol-3-ylamino)-5-ethynyl-6-methyl pyrimidin-2-yl)thiophene-2-sulfonamide (230 mg, 0.50 mmol, 1.0 eq) in $CH_2Cl_2$ (10 mL) at rt under nitrogen. The reaction mixture was stirred for 30 min and then quenched with aq. $NaHCO_3$ in ice bath. The reaction mixture was extracted with ethyl acetate and washed with water, brine, dried and evaporated. The crude product was crystallized with THF/isopropanol to afford the title compound 5-(4-(3-cyclopropyl-1H-pyrazol-5-ylamino)-5-ethynyl-6-methylpyrimidin-2-yl)thiophene-2-sulfonamide (Compound 267) (175.0 mg, 87.5%). LC-MS (m/z)=401.1 [M+H]$^+$. δ (400 MHz, DMSO-$d_6$): 0.81-0.85 (m, 2H), 1.03-1.07 (m, 2H), 1.99-2.04 (m, 1H), 2.55 (s, 3H), 5.17 (s, 1H), 6.49 (s, 1H), 7.61 (d, J=3.6 Hz, 1H), 7.88 (s, 2H), 7.91 (d, J=3.6 Hz, 1H), 9.21 (s, 1H)

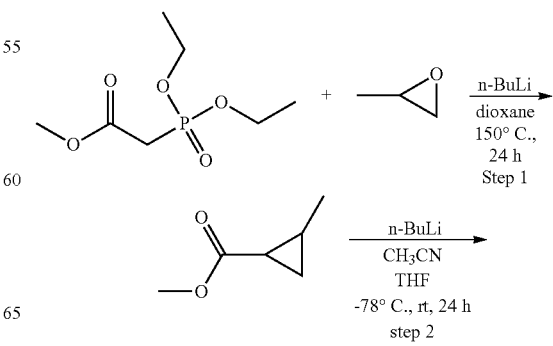

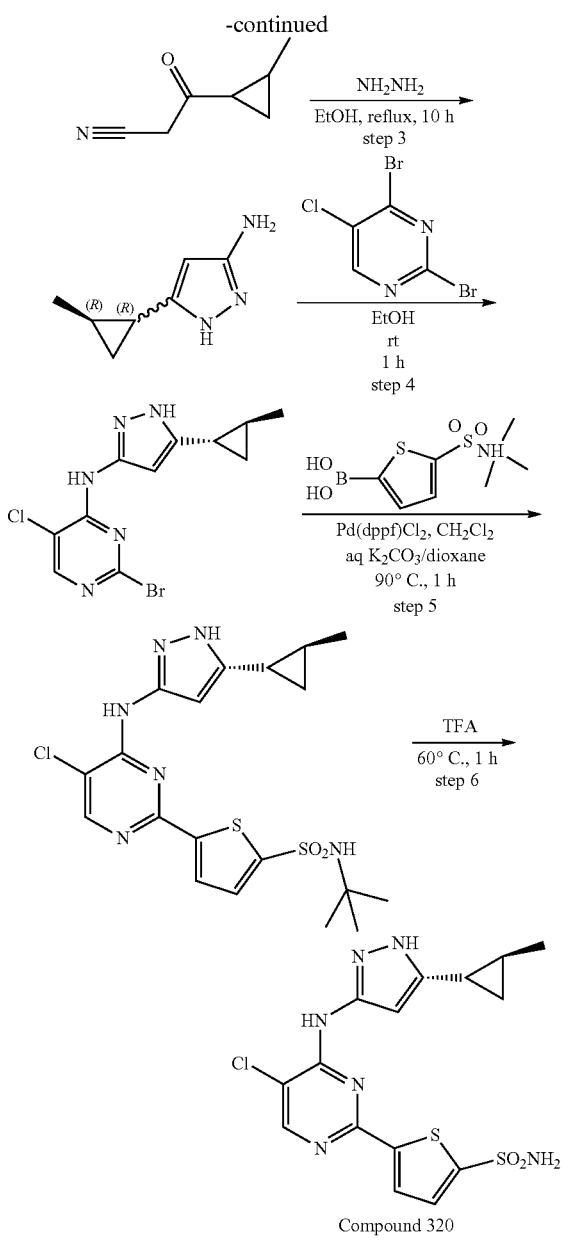

Compound 320

5-(5-chloro-4-(5-(trans-2-methylcyclopropyl)-1H-pyrazol-3-ylamino)pyrimidin-2-yl)thiophene-2-sulfonamide (Compound 320)

Step 1. Under a nitrogen atmosphere, n-BuLi (2.5 M in hexanes, 36.8 mL, 92 mmol, 1.0 equiv.) was added dropwise over 20 min to methyl 2-(diethoxyphosphoryl)acetate (4.5 g, 19.67 mmol) in anhydrous dioxane (200 mL) at 19 to 25° C. After 30 min, 2-methyloxirane (7 g, 120.15 mmol, 1.31 eq) was added, and the mixture was transferred into a 500 mL Stainless Steel pressure (Parr) reactor. The mixture is heated to 150° C. within 15 min and stirred at this temperature for 24 h. The reaction mixture was treated with 1 N HCl and extracted with Et$_2$O.

The organic layers were dried by Na2SO4 for 12 h and filtered. The filtrate was concentrated in vacuo (at <30° C.). The resulting residue methyl 2-methylcyclopropanecarboxylate was used all for next step.

Step 2. At −60 C., butyllithium in hexane (10 mL, 2.5M in hexane, 25 mmol, 1.47 equiv.) was added to 30 ml of tetrahydrofuran. At −60° C., acetonitrile (700 mg, 17.0 mmol, 1.0 equiv.) and the 1/10 of crude methyl 2-methylcyclopropanecarboxylate were then added successively. After the cooling bath was removed, the resulting white suspension was stirred at rt for 24 h. The reaction mixture was poured into about the same amount of 2N hydrochloric acid and then extracted three times with methylene chloride. The organic extract solutions were combined, dried with sodium sulphate and filtered. The solvents were carefully distilled off from the filtrate under water pump vacuum and the resulting residue 3-(2-methylcyclopropyl)-3-oxopropanenitrile was used for next step.

Step 3. The crude 3-(2-methylcyclopropyl)-3-oxopropanenitrile was dissolved in ethanol (50 mL) and hydrazine hydrate (0.83 mL, 17 mmol) was added. The solution was maintained at reflux for 10 hours and then the solvent evaporated under vacuum. The residue was redissolved in methylene chloride and washed several times with brine. The organic layer was dried over anhydrous sodium sulfate and the solvent evaporated to give compound trans 5-(−2-methylcyclopropyl)-1H-pyrazol-3-amine (1 g, 79%, three step). LC-MS (m/z)=138 [M+H]$^+$; $^1$H NMR (400 MHz, DMSO-d$_6$) δ 0.59 (m, 1H), 0.73-0.74 (m, 1H), 0.90-0.93 (m, 1H), 1.07 (d, J=5.6 Hz, 3H), 1.39-1.41 (m, 1H), 4.32 (bs, 2H), 5.01 (s, 1H), 11.03 (bs, 1H).

Step 4. To a suspension of trans 5-(−2-methylcyclopropyl)-1H-pyrazol-3-amine (400 mg, 1.47 mmol, 1.0 eq) in ethanol (5 mL) was added 2,4-dibromo-5-chloropyrimidine (402 mg, 2.94 mmol, 2.0 eq) in ethanol (30 mL). The suspension was stirred for 1 hour and filtered to afford compound 2-bromo-5-chloro-N-(5-((trans-2-methylcyclopropyl)-1H-pyrazol-3-yl)pyrimidin-4-amine (400 mg, 83%). LC-MS (m/z)=328 [M+H]$^+$; $^1$H NMR (400 MHz, DMSO-d$_6$) δ 0.72-0.76 (m, 1H), 0.86-0.92 (m, 1H), 1.03-1.11 (m, 1H), 1.13 (d, J=5.2 Hz, 3H), 1.16-1.66 (m, 1H), 6.16 (s, 1H), 8.26 (s, 1H), 9.68 (s, 1H), 12.29 (bs, 1H).

Step 5. The mixture of Pd(dppf)Cl$_2$.CH$_2$Cl$_2$ (74 mg, 0.09 mmol, 0.15 eq.), 2-bromo-5-chloro-N-(5-(trans-2-methylcyclopropyl)-1H-pyrazol-3-yl)pyrimidin-4-amine (200 mg, 0.61 mmol, 1.0 eq), 5-(N-tert-butylsulfamoyl)thiophen-2-yl-boronic acid (192 mg, 0.73 mmol, 1.2 equiv.) and saturate Ka$_2$CO$_3$ (5 mL) in dioxane (10 mL) was heated to 90° C. for 1 h under nitrogen atmosphere. The reaction mixture was cooled to rt, and extracted with THF. The combined layers were purified by silica gel chromatography (EtOAc/Petroleum ether from 10:1 to 2:1) to afford compound N-tert-butyl-5-(5-chloro-4-(5-(trans-2-methylcyclopropyl)-1H-pyrazol-3-ylamino)pyrimidin-2-yl)thiophene-2-sulfonamide (180 mg, 63%).

LC-MS (m/z)=467 [M+H]% $^1$H NMR (400 MHz, DMSO-d$_6$) δ 0.78-0.81 (m, 1H), 0.93-0.94 (m, 1H), 1.16 (m, 4H), 1.20 (s, 9H), 1.64-1.66 (m, 1H), 6.38 (s, 1H), 7.60 (d, J=3.6 Hz, 1H), 7.74 (d, J=4.0 Hz, 1H), 7.90 (s, 1H), 8.45 (s, 1H), 9.44 (s, 1H), 12.27 (s, 1H).

Step 6. The solution of N-tert-butyl-5-(5-chloro-4-(5-(trans-2-methylcyclopropyl)-1H-pyrazol-3-ylamino)pyrimidin-2-yl)thiophene-2-sulfonamide (90 mg, 0.19 mmol) in TFA (5 mL) was heated to reflux for 0.5 h. After concentration, the resulting residue was dilute with EtOAc and washed with water, saturate NaHCO$_3$, brine, dried (Na$_2$SO$_4$) and filtered. The filtrate was concentrated to afford the title compound 5-(5-chloro-4-(5-(trans-2-methylcyclopropyl)-1H-pyrazol-3-ylamino)pyrimidin-2-yl)thiophene-2-sulfonamide (Compound 320) (70 mg, 89%). LC-MS (m/z)=411 [M+H]% $^1$H NMR (400 MHz, DMSO-d$_6$) δ 0.78-0.81 (m, 1H), 0.92-0.95 (m, 1H), 1.16 (m, 4H), 1.64-1.65 (m, 1H), 6.37 (s, 1H), 7.58 (d, J=4.0 Hz, 1H), 7.75 (d, J=3.6 Hz, 1H), 7.81 (s, 2H), 8.45 (s, 1H), 9.42 (s, 1H), 12.26 (s, 1H).

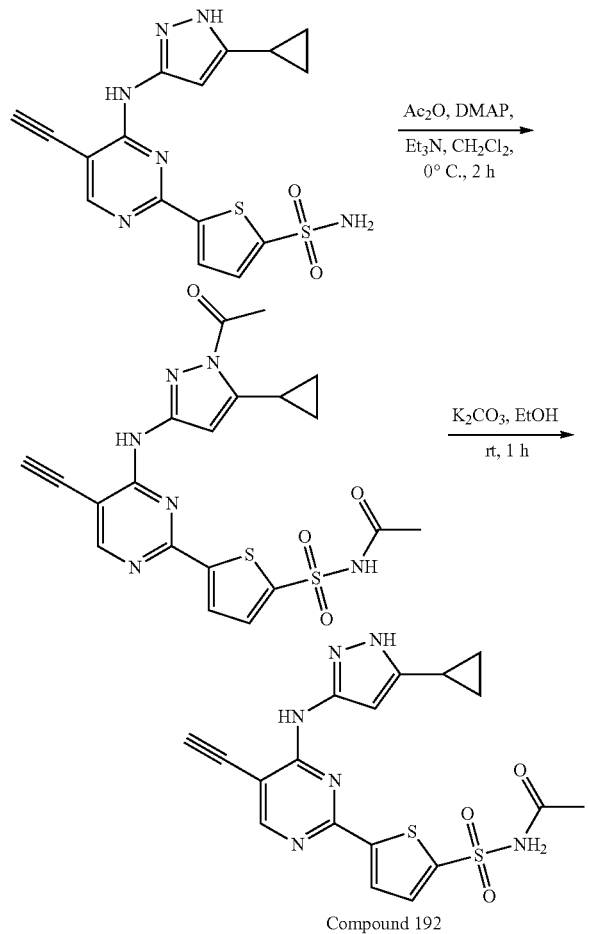

Compound 192

N-(5-(4-(5-cyclopropyl-1H-pyrazol-3-ylamino)-5-ethynylpyrimidin-2-yl)thiophen-2 ylsulfonyl) acetamide (Compound 192)

To a solution of 5-(4-(5-cyclopropyl-1H-pyrazol-3-ylamino)-5-ethynylpyrimidin-2-yl)thiophene-2-sulfonamide (70 mg, 0.13 mmol, 1.0 eq) in anhydrous $CH_2Cl_2$ (2 mL) was added $Et_3N$ (78 mg, 0.78 mmol, 6.0 eq), $Ac_2O$ (40 mg, 0.39 mmol, 3.0 eq) and DMAP (3 mg, 0.03 mmol, 0.2 equiv.) at 0° C. under nitrogen atmosphere. The reaction mixture was stirred for 1 h at 0° C. and quenched with water. The aqueous layers were extracted with $CH_2Cl_2$ and the organic layers were washed with water, brine, dried ($Na_2SO_4$) and filtered. The filtrate was concentrated in vacuum to afford N-(5-(4-(1-acetyl-5-cyclopropyl-1H-pyrazol-3-ylamino)-5-ethynylpyrimidin-2-yl)thiophen-2-ylsulfonyl)acetamide all for next step. LC-MS (m/z)=471 [M+H]$^+$.

The mixture of crude N-(5-(4-(1-acetyl-5-cyclopropyl-1H-pyrazol-3-ylamino)-5-ethynylpyrimidin-2-yl)thiophen-2-ylsulfonyl)acetamide and $K_2CO_3$ (43 mg, 0.31 mmol, 2.4 eq) in EtOH (10 mL) was stirred at room temperature for 1 h. The reaction mixture was filtered, the filtrate was concentrated. The residue was diluted with EtOAc and washed with water, brine, dried ($Na_2SO_4$), and filtered. The filtrate was concentrated and crystallized with ether to yield N-(5-(4-(5-cyclopropyl-1H-pyrazol-3-ylamino)-5-ethynylpyrimidin-2-yl)thiophen-2-ylsulfonyl)acetamide (Compound 192) (65 mg, 84%). LC-MS (m/z)=429 [M+H]$^+$; $^1$H NMR (400 MHz, DMSO-$d_6$) δ 0.74-0.77 (m, 2H), 0.97-0.99 (m, 2H), 1.71 (s, 3H), 1.92-1.99 (m, 1H), 4.87 (s, 1H), 6.49 (s, 1H), 7.41 (d, J=4.0 Hz, 1H), 7.66 (d, J=3.6 Hz, 1H), 8.47 (s, 1H), 8.57 (bs, 1H), 12.31 (bs, 1H)

Following same procedure as Compound 192, the following two compounds were made: Compounds 201, 194 and other structurally similar compounds.

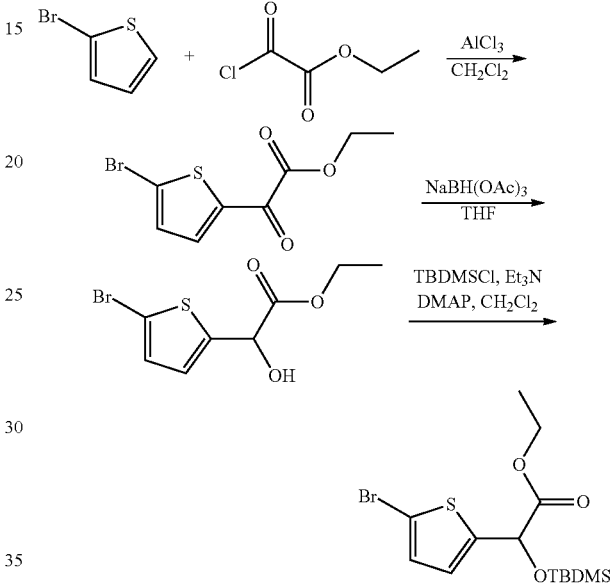

Ethyl 2-(5-bromothiophen-2-yl)-2-(tert-butyldimethylsilyloxy)acetate

To a solution of 2-bromothiophene (10 mL, 103.3 mmol, 1.0 eq) in dichloromethane (200 mL) was added ethyl 2-chloro-2-oxoacetate (13.8 mL, 123.9 mmol, 1.2 eq) and aluminum trichloride (16.5 g, 123.9 mmol, 1.2 eq) at 0° C. After stirring for 10 minutes, the reaction mixture was diluted with dichloromethane and poured into ice. The combined organic phase was washed (brine), dried ($MgSO_4$), filtered and concentrated to give a residue, the residue was purified by silica gel column chromatography to yield ethyl 2-(5-bromothiophen-2-yl)-2-oxoacetate (7.0 g, 25.8%). LC-MS (m/z): 262.8 [M+H]$^+$. $^1$H NMR (400 MHz, DMSO-$d_6$): δ 1.33 (t, J=7.2 Hz, 3H), 4.33-4.39 (m, 2H), 7.48 (d, J=3.6 Hz, 1H), 7.94 (d, J=4.4 Hz, 1H).

To a solution of ethyl 2-(5-bromothiophen-2-yl)-2-oxoacetate (2.5 g, 9.5 mmol) in tetrahydrofuran (50 mL) was added sodium triacetoxy borohydride (2.5 g, 11.8 mmol, 1.2 eq). After stirring for 1 hour at 60° C., the reaction mixture was diluted with ethyl acetate, washed (brine), dried ($Na_2SO_4$), filtered and concentrated to provide ethyl 2-(5-bromothiophen-2-yl)-2-hydroxyacetate (2.5 g, 99.24%). $^1$H NMR (400 MHz, DMSO-$d_6$): δ 1.19 (t, J=7.0 Hz, 3H), 4.11-4.16 (m, 2H), 5.34 (d, J=5.6 Hz, 1H), 6.50 (d, J=6.0 Hz, 1H), 6.91 (d, J=4.0 Hz, 1H), 7.09 (d, J=4.0 Hz, 1H).

To a solution of ethyl 2-(5-bromothiophen-2-yl)-2-hydroxyacetate (2.5 g, 9.43 mmol, 1.0 eq), DMAP (115 mg, 0.94 mmol, 0.1 eq) in dichloromethane (30 mL) was added TBDMSCl (2.85 g, 18.91 mmol, 2.0 eq) and triethylamine (5.0 mL, 35.97 mmol, 3.8 eq) at 0° C. After addition, the ice-water bath is removed and the mixture is allowed to reach room temperature overnight. The reaction mixture was diluted with ethyl acetate, washed (brine), dried (Na$_2$SO$_4$), filtered and concentrated to give a residue, which was purified by silica gel column chromatography (PE:EA=50:1) to produce ethyl 2-(5-bromothiophen-2-yl)-2-(tert-butyldimethylsilyloxy)acetate (2.5 g, 69.9%). $^1$H NMR (400 MHz, DMSO-d$_6$): δ 0.03 (s, 3H), 0.07 (s, 3H), 0.85 (s, 9H), 1.16 (t, J=7.0 Hz, 3H), 4.09-4.15 (m, 2H), 5.56 (d, J=0.8 Hz, 1H), 6.91-6.92 (m, 1H), 7.08 (d, J=4.0 Hz, 1H).

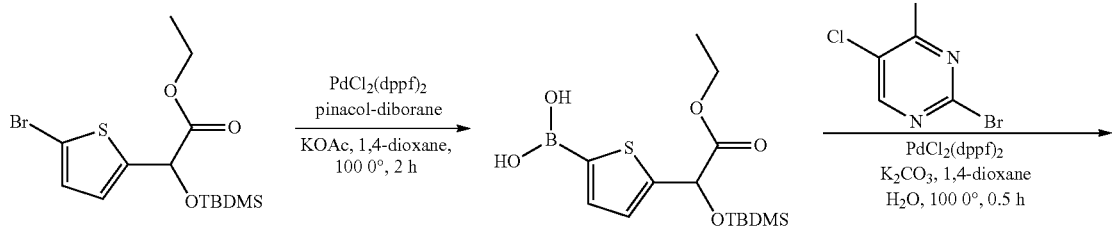

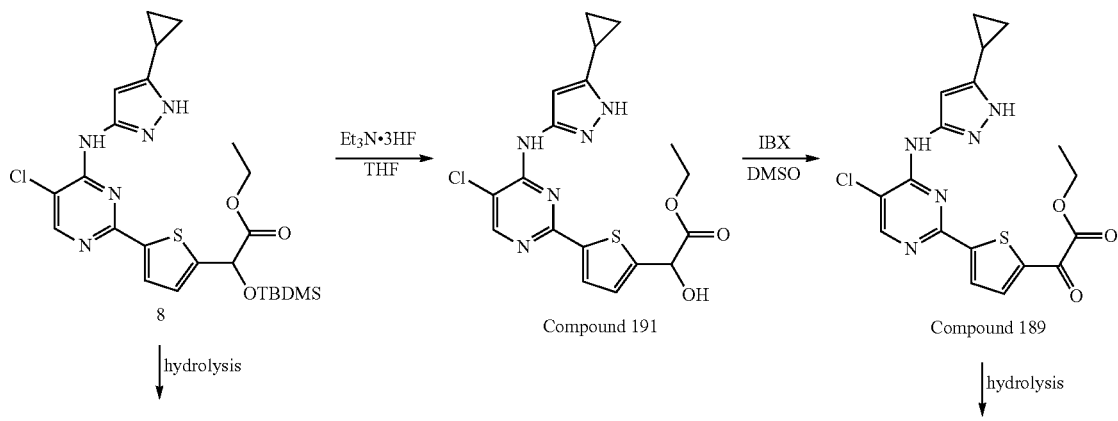

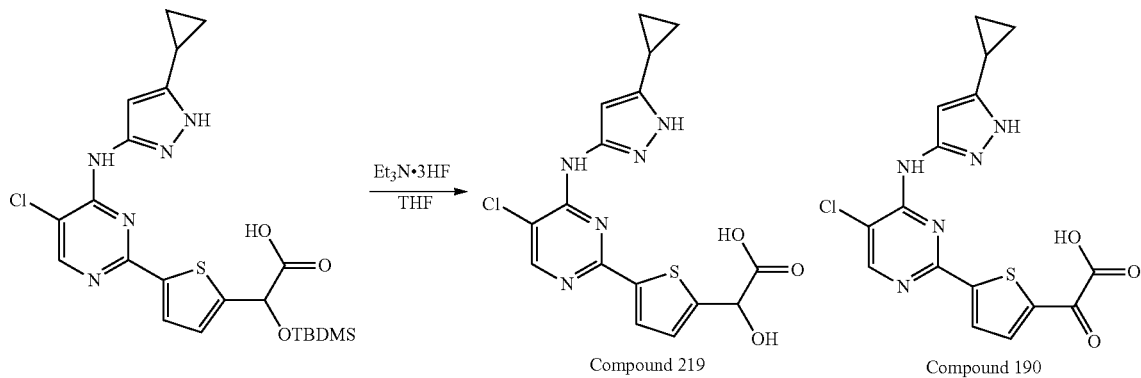

Ethyl 2-(5-(5-chloro-4-(5-cyclopropyl-1H-pyrazol-3-ylamino)pyrimidin-2-yl)thiophen-2-yl)-2-hydroxyacetate (Compound 191), ethyl 2-(5-(5-chloro-4-(5-cyclopropyl-1H-pyrazol-3-ylamino)pyrimidin-2-yl) thiophen-2-yl)-2-oxoacetate (Compound 189), 2-(5-(5-chloro-4-(5-cyclopropyl-1H-pyrazol-3-ylamino) pyrimidin-2-yl)thiophen-2-yl)-2-oxoacetic acid Compound 190) and 2-(5-(5-chloro-4-(5-cyclopropyl-1H-pyrazol-3-ylamino)pyrimidin-2-yl)thiophen-2-yl)-2-hydroxyacetic acid (Compound 219)

A solution of ethyl 2-(5-bromothiophen-2-yl)-2-(tert-butyldimethylsilyloxy)acetate (2.0 g, 5.27 mmol, 1.0 eq), pinacol-diborane (1.6 g, 6.32 mmol, 1.2 eq), Pd(dppf)Cl$_2$ (430 mg, 0.53 mmol, 0.1 eq) and KOAc (2.06 g, 21.08 mmol, 4.0 eq) in 1,4-dioxane (30 mL) was stirred at 100° C. under a nitrogen atmosphere for 2 h. The reaction mixture was allowed to cool to room temperature and extracted with ethyl acetate. The combined organic phases were washed (brine), dried (Na$_2$SO$_4$), filtered and concentrated to give a residue. The residue was washed with 2-isopropoxypropane and filtered, concentrated to provide the crude 5-(1-(tert-butyldimethylsilyloxy)-2-ethoxy-2-oxoethyl)thiophen-2-ylboronic acid for next step without further purification (1.6 g, 72.3%).

To a mixture of 5-(1-(tert-butyldimethylsilyloxy)-2-ethoxy-2-oxoethyl)thiophen-2-ylboronic acid (1.0 g, 3.18 mmol, 1.0 eq), 2-bromo-5-chloro-N-(5-cyclopropyl-1H-pyrazol-3-yl)pyrimidin-4-amine (1.6 g, 3.82 mmol, 1.2 eq) and Pd(dppf)Cl$_2$ (260 mg, 0.32 mmol, 0.1 eq) in 1,4-dioxane (30 mL) was added aq K$_2$CO$_3$ (1.75 g, 12.72 mmol, 4.0 eq., in 6 mL of water). The reaction mixture was stirred at 100° C. under a nitrogen atmosphere for 1 hour. The reaction mixture was allowed to cool to room temperature and diluted with ethyl acetate. The combined organic phases were washed (brine), dried (Na$_2$SO$_4$), filtered and concentrated to give a residue, the residue was purified by silica gel column chromatography (PE:EA=2:1) to generate ethyl 2-(tert-butyldimethylsilyloxy)-2-(5-(5-chloro-4-(5-cyclopropyl-1H-pyrazol-3-ylamino)pyrimidin-2-yl)thiophen-2-yl)acetate (750 mg, 44.2%). LC-MS (m/z): 534.1 [M+H]$^+$.

To a solution of ethyl 2-(tert-butyldimethylsilyloxy)-2-(5-(5-chloro-4-(5-cyclopropyl-1H-pyrazol-3-ylamino)pyrimidin-2-yl)thiophen-2-yl)acetate (200 mg, 0.37 mmol, 1.0 eq) in tetrahydrofuran (10 mL) was added Et$_3$N.3HF (0.2 mL, 1.11 mmol, 3.0 eq). The reaction mixture was stirred at room temperature overnight. The mixture was diluted with ethyl acetate, washed (brine), dried (Na$_2$SO$_4$), filtered and concentrated to give a residue, which was purified by silica gel column chromatography (PE:EA=1:1) to give Ethyl 2-(5-(5-chloro-4-(5-cyclopropyl-1H-pyrazol-3-ylamino)pyrimidin-2-yl)thiophen-2-yl)-2-hydroxyacetate (Compound 191) (123 mg, 78.6%). LC-MS (m/z): 420.0 [M+H]$^+$. $^1$H NMR (400 MHz, DMSO-d$_6$): δ 0.73-0.77 (m, 2H), 0.96-1.01 (m, 2H), 1.21 (t, J=7.0 Hz, 3H), 1.91-1.98 (m, 1H), 4.14-4.19 (m, 2H), 5.42 (d, J=4.8 Hz, 1H), 6.44 (s, 1H), 6.52 (d, J=5.6 Hz, 1H), 7.13 (d, J=4.0 Hz, 1H), 7.67 (d, J=4.0 Hz, 1H), 8.40 (s, 1H), 9.29 (s, 1H), 12.30 (bs, 1H).

To a solution of Ethyl 2-(5-(5-chloro-4-(5-cyclopropyl-1H-pyrazol-3-ylamino)pyrimidin-2-yl)thiophen-2-yl)-2-hydroxyacetate (Compound 191), (100 mg, 0.24 mmol, 1.0 eq) in DMSO (10 mL) was added IBX (168 mg, 0.6 mmol, 2.5 eq). The reaction mixture was stirred at room temperature overnight. The mixture was diluted with ethyl acetate, washed (brine), dried (Na$_2$SO$_4$), filtered and concentrated to give a residue, the residue was purified by silica gel column chromatography (PE:EA=2:1) to give ethyl 2-(5-(5-chloro-4-(5-cyclopropyl-1H-pyrazol-3-ylamino)pyrimidin-2-yl) thiophen-2-yl)-2-oxoacetate (Compound 189) (90 mg, 90.8%). LC-MS (m/z): 418.0 [M+H]$^+$. $^1$H NMR (400 MHz, DMSO-d$_6$): δ 0.75-0.79 (m, 2H), 0.99-1.01 (m, 2H), 1.35 (t, J=7.0 Hz, 3H), 1.93-1.97 (m, 1H), 4.37-4.42 (m, 2H), 6.43 (s, 1H), 7.89 (d, J=3.6 Hz, 1H), 8.14 (d, J=3.6 Hz, 1H), 8.51 (s, 1H), 9.50 (s, 1H), 12.35 (s, 1H).

To a solution of ethyl 2-(5-(5-chloro-4-(5-cyclopropyl-1H-pyrazol-3-ylamino)pyrimidin-2-yl)thiophen-2-yl)-2-oxoacetate (Compound 189) (50 mg, 0.12 mmol, 1.0 eq) in ethanol (15 mL) was added 1 N NaOH (0.5 mL, 0.48 mmol, 4.0 eq). The mixture was stirred at room temperature for 1 hour, then, concentrated and the residue was redissolved in water. To the solution was added 1N HCl (0.5 mL) and the mixture was stirred for 0.5 h at 23° C. The solution was filtered to afford 2-(5-(5-chloro-4-(5-cyclopropyl-1H-pyrazol-3-ylamino)pyrimidin-2-yl)thiophen-2-yl)-2-oxoacetic acid Compound 190) (30 mg, 64.3%). LC-MS (m/z): 390.0 [M+]$^+$. $^1$H NMR (400 MHz, DMSO-d$_6$): δ 0.74-0.78 (m, 2H), 0.96-1.01 (m, 2H), 1.92-1.96 (m, 1H), 6.42 (s, 1H), 7.87 (d, J=4.0 Hz, 1H), 8.07 (d, J=4.4 Hz, 1H), 8.49 (s, 1H), 9.51 (s, 1H), 13.28 (bs, 1H).

To a mixture of ethyl 2-(tert-butyldimethylsilyloxy)-2-(5-(5-chloro-4-(5-cyclopropyl-1H-pyrazol-3-ylamino)pyrimidin-2-yl)thiophen-2-yl)acetate (100 mg, 0.19 mmol, 1.0 eq.) in ethanol (10 mL) was added 1 N NaOH (0.8 mL, 0.76 mmol, 4.0 eq). The mixture was stirred at room temperature for 1 hour, then, concentrated and the residue was redissolved in water. To the solution was added 1N HCl (0.8 mL) and the mixture was stirred for 0.5 h at 23° C. The solution was filtered to give 2-(tert-butyldimethylsilyloxy)-2-(5-(5-chloro-4-(5-cyclopropyl-1H-pyrazol-3-ylamino)pyrimidin-2-yl)thiophen-2-yl)acetic acid (60 mg, 63.3%). LC-MS (m/z): 506.0 [M+H]$^+$.

To a solution of 2-(tert-butyldimethylsilyloxy)-2-(5-(5-chloro-4-(5-cyclopropyl-1H-pyrazol-3-ylamino) pyrimidin-2-yl)thiophen-2-yl)acetic acid (60 mg, 0.12 mmol, 1.0 equiv.) in tetrahydrofuran (10 mL) was added Et$_3$N.3HF (0.06 mL, 0.36 mmol, 3.0 equiv.). The reaction mixture was stirred at room temperature overnight. The mixture was diluted with ethyl acetate, washed (brine), dried (Na$_2$SO$_4$), filtered and concentrated to give a residue, the residue was purified by silica gel column chromatography (PE:EA=1:1) to afford 2-(5-(5-chloro-4-(5-cyclopropyl-1H-pyrazol-3-ylamino)pyrimidin-2-yl)thiophen-2-yl)-2-hydroxyacetic acid (Compound 219) (30 mg, 64.6%). LC-MS (m/z): 392.0 [M+H]$^+$. $^1$H NMR (400 MHz, DMSO-d$_6$): δ 0.75-0.76 (m, 2H), 0.97-0.99 (m, 2H), 1.92-1.96 (m, 1H), 5.31 (s, 1H), 6.45 (s, 1H), 7.13 (d, J=3.2 Hz, 1H), 7.67 (d, J=3.6 Hz, 1H), 8.39 (s, 1H), 9.30 (s, 1H), 12.59 (bs, 1H).

The following acetylene analogs were also made using such procedures: Compounds 233, 202, 246, 231 and other structurally similar compounds.

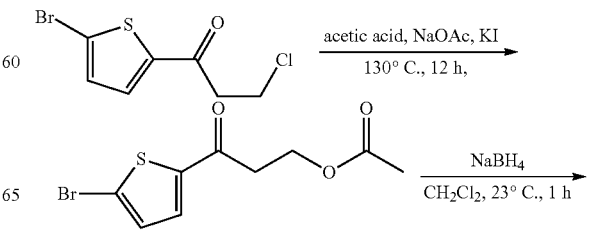

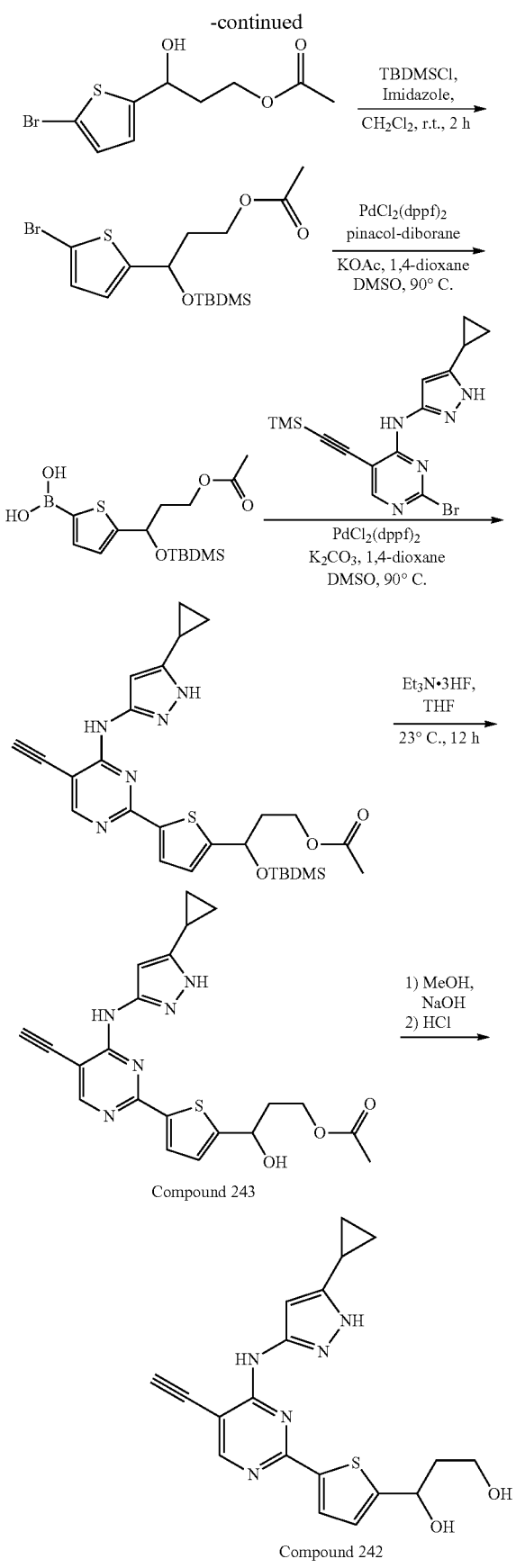

Compound 243

Compound 242

3-(5-(4-(5-cyclopropyl-1H-pyrazol-3-ylamino)-5-ethynylpyrimidin-2-yl)thiophen-2-yl)-3-hydroxy propyl acetate (Compound 243) and 1-(5-(4-(5-cyclopropyl-1H-pyrazol-3-ylamino)-5-ethynylpyrimidin-2-yl)thiophen-2-yl)propane-1,3-diol (Compound 242)

To the mixture of 1-(5-bromothiophen-2-yl)-3-chloropropan-1-one (2.8 g, 1.6 mmol, 1.0 eq), NaOAc (4.5 g, 55.3 mmol, 5 eq) and KI (200 mg) in acetic acid (16 mL) was stirred at 130° C. for overnight. The mixture was extracted with $CH_2Cl_2$ (3×40 ml). The combined organic layers were washed (brine), dried ($Na_2SO_4$), filtered and concentrated to give yellow oil 3-(5-bromothiophen-2-yl)-3-oxopropyl acetate (2.4 g, 76.2%). LC-MS (m/z)=278.1 [M+H]$^+$ A mixture of 3-(5-bromothiophen-2-yl)-3-oxopropyl acetate (2.4 g, 8.8 mmol, 1 eq) in THF (150 ml) was stirred at 0° C., and $NaBH_4$ (401.2 mg, 10.6 mmol, 2 eq) was added slowly and the reaction was stirred at 23° C. After 1 hour, $Na_2CO_3 \cdot H_2O$ was added. After 30 min the mixture was filtered and extracted with EtOAc (3×50 ml). The combined organic phases were washed (brine), dried ($Na_2SO_4$), filtered and concentrated to give a residue. The residue was purified by silica gel column chromatography (PE/EtOAc=5:1 as eluant) to give 3-(5-bromothiophen-2-yl)-3-hydroxypropyl acetate (1.92 g, 78.2%) as white solid. LC-MS (m/z)=279.1 [M+H]$^+$ A solution of 3-(5-bromothiophen-2-yl)-3-hydroxypropyl acetate (1.92 g, 6.9 mmol, 1.0 equiv.), TBDMSCl (1.24 g, 8.3 mmol, 1.2 eq) and 1H-imidazol (1.4 g, 20.7 mmol, 3.0 eq) in $CH_2Cl_2$ (50 mL) was stirred for 4 h at 60° C. Water was added and the reaction was extracted with EtOAc (3×200 ml). The combined organic phases were washed (brine), dried ($Na_2SO_4$), filtered and concentrated to give a residue, which was purified by silica gel column chromatography (PE/EA=100:1 as eluant) to produce 3-(5-bromothiophen-2-yl)-3-(tert-butyldimethylsilyloxy)propyl acetate (2.6 g, 97.6%) as yellow oil. LC-MS (m/z): 393.1 [M+H]$^+$;

Following procedure from Compound 191, 3-(5-Bromothiophen-2-yl)-3-(tert-butyldimethylsilyloxy)propyl acetate was converted to 5-(3-acetoxy-1-(tert-butyldimethylsilyloxy)propyl)thiophen-2-ylboronic acid (2.7 g, 94.5%) (LC-MS (m/z)=441.0 [M+H]$^+$), which was condensed with 2-bromo-N-(5-cyclopropyl-1H-pyrazol-3-yl)-5-((trimethylsilyl)ethynyl)pyrimidin-4-amine to produce 3-(tert-butyldimethylsilyloxy)-3-(5-(4-(5-cyclopropyl-1H-pyrazol-3-ylamino)-5-ethynylpyrimidin-2-yl)thiophen-2-yl)propyl acetate (500 mg, 50.0%). LC-MS (m/z)=538.1 [M+H]$^+$ $Et_3N3HF$ (1 M in $CH_2Cl_2$, 2.7 mL, 2.7 mmol, 3 equiv.) was added to a stirred solution of 6 (500 mg, 0.93 mmol, 1.0 equiv.) in THF (5 mL) at room temperature under nitrogen. The reaction mixture was stirred for 30 min and then quenched with aq. $NaHCO_3$ in ice bath. The reaction mixture was extracted with ethyl acetate and washed with water, brine, dried and evaporated. The crude product was crystallized with THF/isopropyl to afford 3-(5-(4-(5-cyclopropyl-1H-pyrazol-3-ylamino)-5-ethynylpyrimidin-2-yl)thiophen-2-yl)-3-hydroxypropyl acetate (Compound 243) (390 mg, 99.1%). LC-MS (m/z)=424.1 [M+H]$^+$. $^1$H NMR (400 MHz, DMSO-$d_6$): δ 0.74-0.75 (m, 2H), 0.98-0.99 (m, 2H), 1.91-1.97 (m, 1H), 2.01-2.06 (m, 5H), 4.06-4.17 (m, 2H), 4.85 (s, 1H), 4.85-4.94 (m, 1H), 5.94 (d, J=4.8 Hz, 1H), 6.53 (s, 1H), 7.05 (d, J=3.6 Hz, 1H), 7.72 (d, J=4.0 Hz, 1H), 8.46 (s, 1H), 8.57 (s, 1H), 12.27 (s, 1H)

A solution of 3-(5-(4-(5-cyclopropyl-1H-pyrazol-3-ylamino)-5-ethynylpyrimidin-2-yl)thiophen-2-yl)-3-hydroxypropyl acetate C-243 (390 mg, 0.92 mmol, 1.0 equiv.) in MeOH (10 mL) was stirred at 23° C., 1 NNaOH was added until the PH of the solution reached 11~12. After 1 hour, H₂O (20 mL) and 1 NHCl were added until the PH of the solution reached 3-4. The reaction mixture was extracted with THF and washed with water, brine, dried and evaporated. The crude product was crystallized with THF/isopropyl to afford 1-(5-(4-(5-cyclopropyl-1H-pyrazol-3-ylamino)-5-ethynylpyrimidin-2-yl)thiophen-2-yl)propane-1,3-diol (Compound 242) (250 mg, 71.3%). LC-MS (m/z)=382.1 [M+H]⁺. ¹H NMR (400 MHz, DMSO-d₆): δ 0.75 (m, 2H), 0.98-1.00 (m, 2H), 1.84-1.88 (m, 2H), 1.93-1.98 (m, 1H), 3.47-3.59 (m, 2H), 4.53 (t, J=4.8 Hz, 1H), 4.84 (s, 1H), 4.92-4.96 (m, 1H), 5.72 (d, J=4.8 Hz, 1H), 6.54 (s, 1H), 7.02 (d, J=3.6 Hz, 1H), 7.72 (d, J=3.2 Hz, 1H), 8.45 (s, 1H), 8.55 (s, 1H), 12.27 (s, 1H).

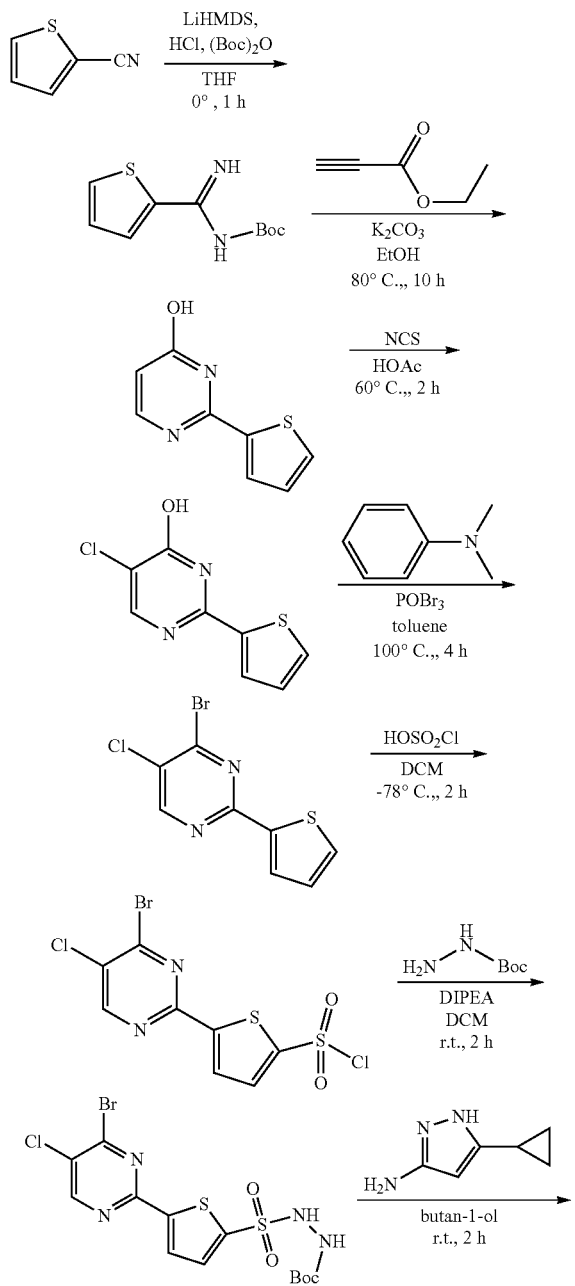

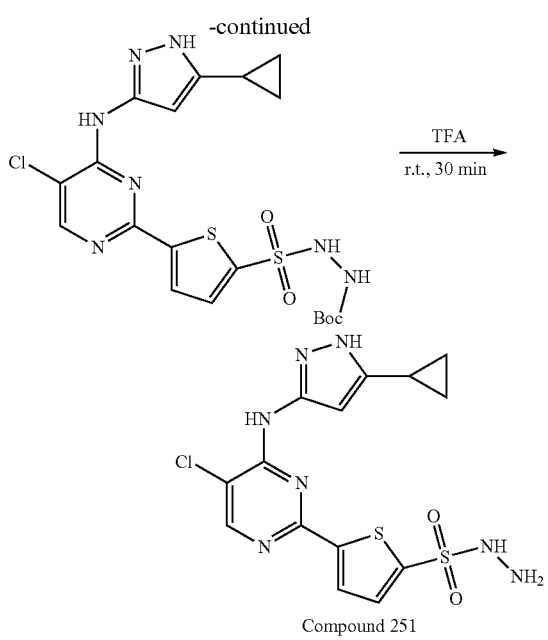

5-(5-chloro-4-(5-cyclopropyl-1H-pyrazol-3-ylamino)pyrimidin-2-yl)thiophene-2-sulfonohydrazide (Compound 251)

To a solution of LiHMDS (20 mL od 1N, 20 mmol) in THF was stirred at 0° C. was added then thiophene-2-carbonitrile (2.2 g, 20 mmol, 1.0 equiv.) dropwise. After 1 h, the mixture was adjusted to PH 2.5 with 2N HCl, extracted with EA and to the aqueous phase was added (Boc)₂O (13 g, 60 mmol, 3.0 equiv.) and DIPEA (20 mL). After 12 h, the mixture was filtered to afford crude tert-butylimino(thiophen-2-yl)methylcarbamate (2.2 g, 50%) which was used directly for next step. LC-MS (m/z)=227 [M+H]⁺

A mixture of tert-butylimino(thiophen-2-yl)methylcarbamate (2 g, 12 mmol, 1.0 eq), ethyl propiolate (1.4 g, 13 mmol, 1.1 eq.) and K₂CO₃ (1.7 g, 12 mmol, 1.0 eq) in EtOH (60 mL) was stirred at 80° C. overnight. The solid was collected and washed with ether to provide 2-(thiophen-2-yl)pyrimidin-4-ol (1.1 g, 53%) for the next step. LC-MS (m/z)=179 [M+H]⁺

Conversion of 2-(thiophen-2-yl)pyrimidin-4-ol (1 g) to 5-chloro-2-(thiophen-2-yl)pyrimidin-4-ol (0.772 g, 65%) with NCS can be found in an earlier example Compound 203. LC-MS (m/z)=213 [M+H]⁺.

5-Chloro-2-(thiophen-2-yl)pyrimidin-4-ol (0.6 g) was converted to 5-(4-bromo-5-chloropyrimidin-2-yl)thiophene-2-sulfonyl chloride (0.164 g, 16% over 2 steps, LC-MS (m/z)=373 [M+H]⁺) following procedures (2 steps) in example Compound 203.

A mixture of 5-(4-bromo-5-chloropyrimidin-2-yl)thiophene-2-sulfonyl chloride (164 mg, 0.45 mmol, 1.0 equiv.), tert-butyl hydrazinecarboxylate (119 mg, 0.9 mmol, 2.0 equiv.) and DIPEA (5 mL) was stirred in DCM at r.t. for 2 h, The reaction was extracted with EA and the combined layers were dried (Na₂SO₄), filtered. The filtrate was concentrated to afford tert-butyl 2-(5-(4-bromo-5-chloropyrimidin-2-yl)thiophen-2-ylsulfonyl)hydrazinecarboxylate (179 mg, 85%). LC-MS (m/z)=469 [M+H]⁺

A mixture of tert-butyl 2-(5-(4-bromo-5-chloropyrimidin-2-yl)thiophen-2-ylsulfonyl)hydrazinecarboxylate (179 mg, 0.38 mmol, 1.0 eq) and 5-cyclopropyl-1H-pyrazol-3-amine (92 mg, 0.76 mmol, 2.0 equiv.) in n-butanol was refluxed for 2 h, The reaction was cooled down and extracted with EA and the combined layers were dried ($Na_2SO_4$), filtered and purified by silica gel chromatography (EA/PE 1:2) to afford tert-butyl 2-(5-(5-chloro-4-(5-cyclopropyl-1H-pyrazol-3-ylamino)pyrimidin-2-yl)thiophen-2-ylsulfonyl)hydrazinecarboxylate (23 mg, 12%). LC-MS (m/z)=512 $[M+H]^+$.

Tert-butyl 2-(5-(5-chloro-4-(5-cyclopropyl-1H-pyrazol-3-ylamino)pyrimidin-2-yl)thiophen-2-ylsulfonyl)hydrazinecarboxylate (23 mg, 0.05 mmol, 1.0 equiv.) was stirred in TFA at r.t. for 30 min. The reaction was concentrated and to the residue was added aqueous $NaHCO_3$ and extracted with EA (3×). The combined EA layers were dried ($Na_2SO_4$), filtered, concentrated and washed with ether to afford the 5-(5-chloro-4-(5-cyclopropyl-1H-pyrazol-3-ylamino)pyrimidin-2-yl)thiophene-2-sulfonohydrazide (Compound 251) (8 mg, 44%). LC-MS (m/z)=412 $[M+H]^+$; $^1$H NMR (400 MHz, DMSO-$d_6$): 0.75-0.76 (m, 2H), 0.98-0.99 (m, 2H), 1.91-1.95 (m, 1H), 4.23 (d, J=7.2 Hz, 2H), 6.41 (s, 1H), 7.94 (s, 1H), 8.30 (d, J=1.2 Hz, 1H), 8.46 (s, 2H), 9.47 (d, J=7.6 Hz, 1H), 12.37 (s, 1H).

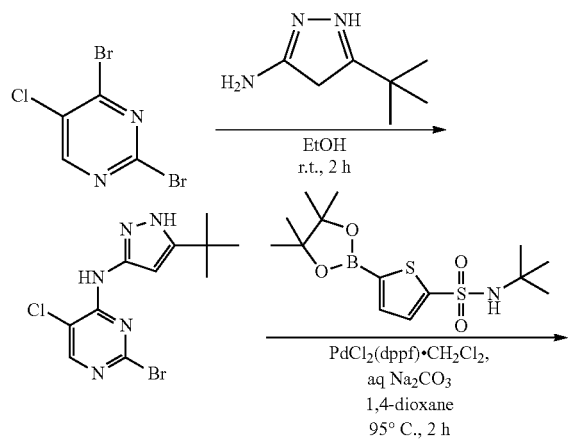

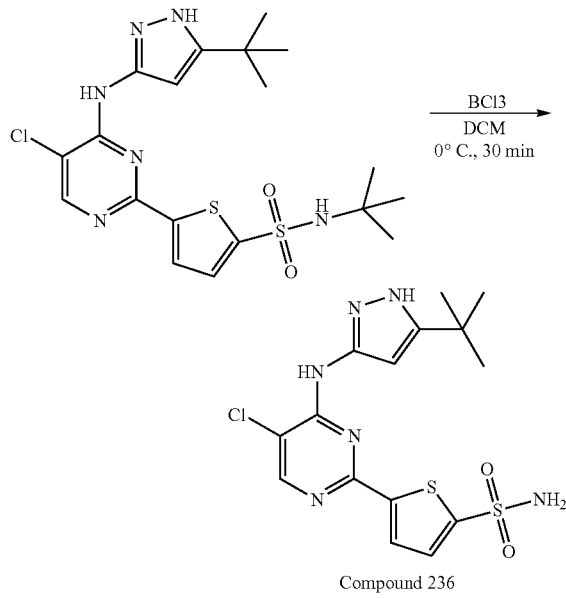

Compound 236

5-(4-(5-tert-butyl-1H-pyrazol-3-ylamino)-5-chloropyrimidin-2-yl)thiophene-2-sulfonamide (Compound 236)

A mixture of 2,4-dibromo-5-chloropyrimidine (500 mg, 1.85 mmol) and 5-tert-butyl-1H-pyrazol-3-amine (216 mg, 2.2 mmol, 1.2 eq) in EtOH (100 mL) was stirred at rt for 2 h. After addition of water and extraction with EA (3×), the combined organic layers were dried ($Na_2SO_4$), filtered, concentrated and purified by silica gel chromatography (EA/PE 1:2) to afford 2-bromo-N-(5-tert-butyl-1H-pyrazol-3-yl)-5-chloropyrimidin-4-amine (450 mg, 85%). LC-MS (m/z)=288 $[M+H]^+$ A mixture of 2-bromo-N-(5-tert-butyl-1H-pyrazol-3-yl)-5-chloropyrimidin-4-amine (250 mg, 0.87 mmol), $PdCl_2$(dppf)$CH_2Cl_2$ (106 mg, 0.13 mmol, 0.15 eq), N-tert-butyl-5-(4,4,5,5-tetramethyl-1,3,2-dioxaborolan-2-yl)thiophene-2-sulfonamide (336 mg, 1.13 mmol, 1.3 eq), $Na_2CO_3$ (323 mg, 3.18 mmol, 3.5 equiv.) in dioxane was heated at 95° C. for 2 h under N. The reaction mixture was cooled to room temperature, and extracted with THF. The combined layers were concentrated and purified by silica gel chromatography (EA/PE 1:2) to afford N-tert-butyl-5-(4-(5-tert-butyl-1H-pyrazol-3-ylamino)-5-chloropyrimidin-2-yl)thiophene-2-sulfonamide (95 mg, 21%). LC-MS (m/z)=427 $[M+H]^+$ A mixture of N-tert-butyl-5-(4-(5-tert-butyl-1H-pyrazol-3-ylamino)-5-chloropyrimidin-2-yl)thiophene-2-sulfonamide (95 mg, 0.22 mmol) and $BCl_3$ (4 mL of 1N solution in DCM) in DCM (8 mL) was stirred for 0.5 h, After addition of water and extraction with EA (3×), the combined organic layers were dried ($NaHSO_4$), filtered. The filtrate was concentrated to afford the title compound 5-(4-(5-tert-butyl-1H-pyrazol-3-ylamino)-5-chloropyrimidin-2-yl)thiophene-2-sulfonamide (C-236) (50 mg, 62%). LC-MS (m/z)=413 $[M+H]^+$; $^1$H NMR (400 MHz, DMSO-$d_6$): 1.34 (s, 9H), 6.57 (s, 1H), 7.58 (d, J=4.0 Hz, 1H), 7.75 (d, J=3.6 Hz, 1H), 7.81 (s, 2H), 8.47 (s, 1H), 9.52 (s, 1H).

Using these procedures the following analogs were made: Compounds 224, 221, 235, 225, 220.

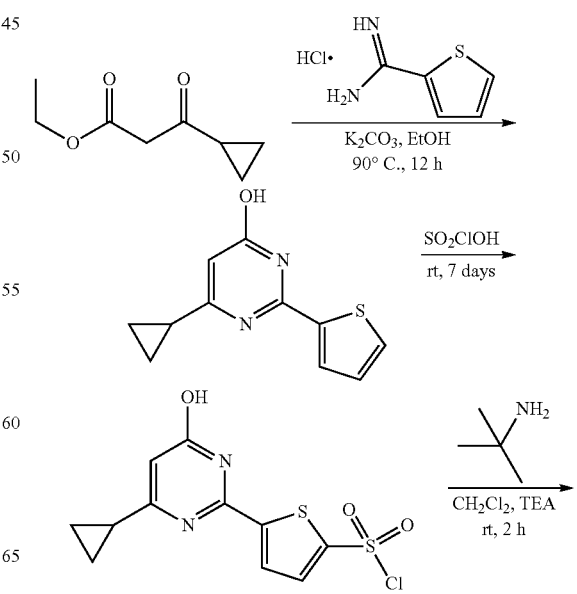

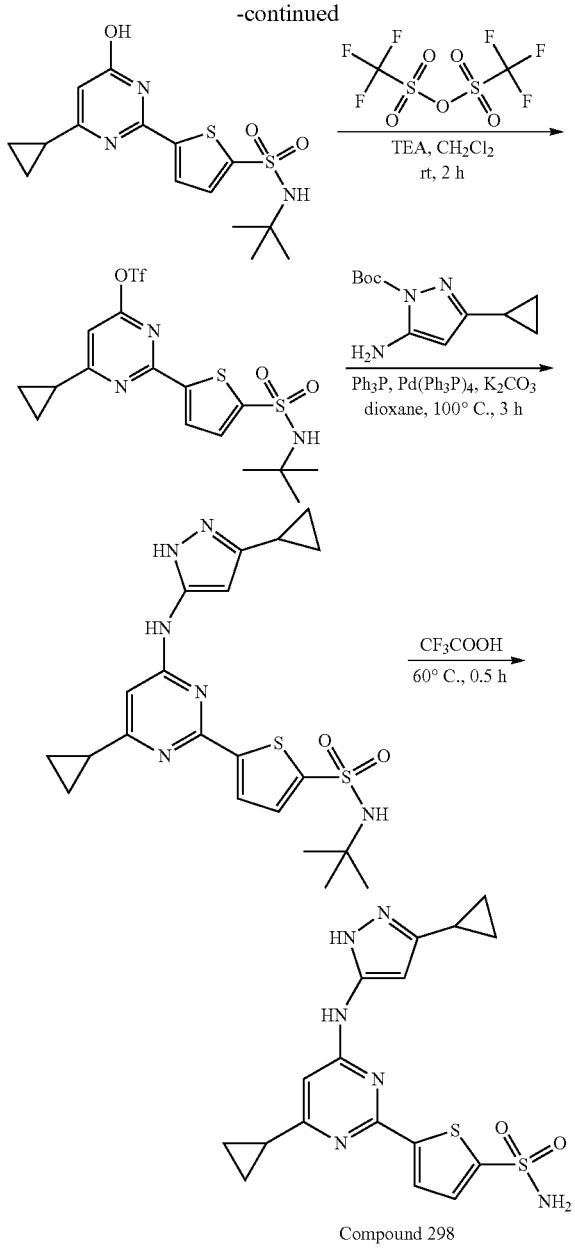

5-(4-cyclopropyl-6-(3-cyclopropyl-1H-pyrazol-5-ylamino)pyrimidin-2-yl)thiophene-2-sulfonamide (Compound 298)

The mixture of ethyl 3-cyclopropyl-3-oxopropanoate (13.64 g, 87.4 mmol), thiophene-2-carboximidamide hydrochloride (14.21 g, 87.4 mmol, 1.0 eq) and K₂CO₃ (30.1 g, 174.8 mmol, 2.0 equiv.) in ethanol (210 mL) was stirred and heated overnight. The reaction mixture was poured into water (1 L), washed with EA (200 mL×1). The aqueous layer was acidified with 1N HCl to PH 4-5. The resulting solid was collected as 6-cyclopropyl-2-(thiophen-2-yl)pyrimidin-4-ol. LC-MS (m/z)=219.1 [M+H]⁺

6-Cyclopropyl-2-(thiophen-2-yl)pyrimidin-4-ol (2.5 g, 11.46 mmol) in sulfurochloridic acid (30 mL) was stirred at rt for 7 days. The solution was poured into ice-water while stirring vigorously. The mixture was maintained below 25° C. during the quenching, the reaction mixture was extracted with EA (3) and the combined organic layers were washed (cold water), dried (Na₂SO4) and concentrated to provide the crude product 5-(4-cyclopropyl-6-hydroxypyrimidin-2-yl) thiophene-2-sulfonyl chloride which is used for the subsequent step without further purification. LC-MS (m/z)=316.1 [M+H]⁺

A mixture of crude 5-(4-cyclopropyl-6-hydroxypyrimidin-2-yl)thiophene-2-sulfonyl chloride (1.9 g, 6.0 mmol, 1.0 equiv.), t-butylamine (25 mL) and TEA (10 mL) in CH₂Cl₂ (500 mL) was stirred at rt for 2 h. The reaction mixture was diluted with water, the organic layer was washed (brine), dried (Na₂SO4), evaporated and purified by silica gel chromatography (EA/PE 1:1) to afford N-tert-butyl-5-(4-cyclopropyl-6-hydroxypyrimidin-2-yl)thiophene-2-sulfonamide (500 mg, 24%). LC-MS (m/z)=354.1 [M+H]⁺

A mixture of N-tert-butyl-5-(4-cyclopropyl-6-hydroxypyrimidin-2-yl)thiophene-2-sulfonamide (200 mg, 0.56 mmol), trifluoromethanesulfonic anhydride (192 mg, 0.38 mmol, 1.2 eq) and TEA (78 mg, 0.72 mmol, 1.3 eq) in CH₂Cl₂ (20 mL) was stirred at rt for 2 h. The reaction mixture was diluted with CH₂Cl₂ and washed (brine), dried (Na₂SO₄) and concentrated to provide the crude 2-(5-(N-tert-butyl sulfamoyl) thiophen-2-yl)-6-cyclopropylpyrimidin-4-yl trifluoromethanesulfonate (242 mg, 83%) which was used for the subsequent step without further purification. LC-MS (m/z) =486.0 [M+H]⁺

A mixture of crude 2-(5-(N-tert-butylsulfamoyl)thiophen-2-yl)-6 cyclopropylpyrimidin-4-yl trifluoromethanesulfonate 220 mg, 0.41 mmol, 1.0 equiv.), tert-butyl 5-amino-3-cyclopropyl-1H-pyrazole-1-carboxylate (138 mg, 0.62 mmol, 1.2 equiv.), Ph₃P (33 mg, 0.12 mmol, 0.3 equiv.), Ph(Ph₃P)₄ (47 mg, 0.041 mmol, 0.1 equiv.) and K₂CO₃ (170 mg, 1.23 mmol, 3 equiv.) in dioxane (5 mL) was stirred at 100° C. for 3 h. The mixture was extracted with EtOAc. The combined organic phase was washed (brine), dried (Na₂SO₄), filtered and concentrated to give a residue, which was purified by silica gel column chromatography (PE/EtOAc/MeOH=1: 1:0.1) to provide N-tert-butyl-5-(4-cyclopropyl-6-(3-cyclopropyl-1H-pyrazol-5-ylamino)pyrimidin-2-yl)thiophene-2-sulfonamide (50 mg, 27%) as a white solid. LC-MS (m/z) =459.1 [M+H]⁺

The solution of N-tert-butyl-5-(4-cyclopropyl-6-(3-cyclopropyl-1H-pyrazol-5-ylamino)pyrimidin-2-yl)thiophene-2-sulfonamide (50 mg, 0.1 mmol) in trifluoroacetic acid (5 mL) was stirred at 60° C. After 0.5 h, the solution was evaporated to give a residue which was recrystallized from ether to afford 5-(4-cyclopropyl-6-(3-cyclopropyl-1H-pyrazol-5-ylamino) pyrimidin-2-yl)thiophene-2-sulfonamide (VRCompound 298) (21 mg, 52%). LC-MS (m/z)=403.1 [M+H]⁺; δ (400 MHz, DMSO-d₆); 0.71-0.74 (m, 2H), 0.93-1.02 (m, 6H), 1.88-2.00 (m, 2H), 6.19 (bs, 1H), 6.93 (bs, 1H), 7.46 (s, 2H), 8.01 (s, 1H), 8.14 (b, 1H), 9.86 (s, 1H).

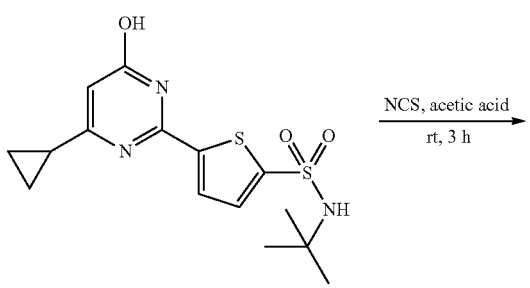

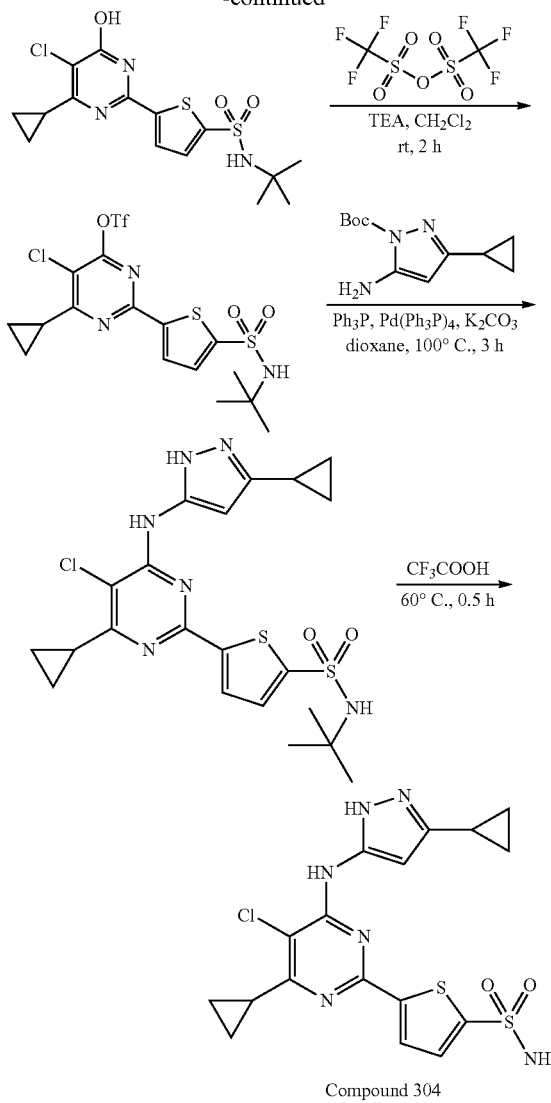

Compound 304

5-(5-chloro-4-cyclopropyl-6-(3-cyclopropyl-1H-pyrazol-5-ylamino)pyrimidin-2-yl)thiophene-2-sulfonamide (Compound 304)

A mixture of N-tert-butyl-5-(4-cyclopropyl-6-hydroxypyrimidin-2-yl)thiophene-2-sulfonamide (353 mg, 1.0 mmol) and NCS (139 mg, 1.05 mmol, 1.0 equiv.) in acetic acid (5 mL) was stirred at rt for 1 h. The reaction was extracted with EA, the organic layer was washed with (brine), dried (Na$_2$SO4) and concentrated to provide N-tert-butyl-5-(5-chloro-4-cyclopropyl-6-hydroxypyrimidin-2-yl)thiophene-2-sulfonamide (341 mg, 88%). LC-MS (m/z)=388.1 [M+H]$^+$ A mixture of N-tert-butyl-5-(5-chloro-4-cyclopropyl-6-hydroxypyrimidin-2-yl)thiophene-2-sulfonamide (341 mg, 0.87 mmol, 1.0 eq), trifluoromethanesulfonic anhydride (294 mg, 1.04 mmol, 1.2 eq) and TEA (121 mg, 1.13 mmol, 1.3 equiv.) in CH$_2$Cl$_2$ (20 mL) was stirred at rt for 2 h. The reaction mixture was extracted with CH$_2$Cl$_2$ and the organic layer was washed (brine), dried (Na$_2$SO4) and concentrated to provide the crude product 2-(5-(N-tert-butylsulfamoyl)thiophen-2-yl)-5-chloro-6-cyclopropylpyrimidin-4-yl trifluoromethane sulfonate (210 mg, 47%) which is used for the subsequent step without further purification. LC-MS (m/z) =520.0 [M+H]$^+$ A mixture of 2-(5-(N-tert-butylsulfamoyl)thiophen-2-yl)-5-chloro-6-cyclopropylpyrimidin-4-yl trifluoromethane sulfonate (200 mg, 0.38 mmol, 1.0 eq), tert-butyl 5-amino-3-cyclopropyl-1H-pyrazole-1-carboxylate (129 mg, 0.58 mmol, 1.2 eq), Ph$_3$P (30 mg, 0.11 mmol, 0.3 eq), Ph(Ph$_3$P)$_4$ (44 mg, 0.038 mmol, 0.1 eq) and K$_2$CO$_3$ (158 mg, 1.14 mmol, 3 eq) in dioxane (5 mL) was stirred at 100° C. for 3 h. The mixture was extracted with EtOAc. The combined organic phases were washed (brine), dried (Na$_2$SO$_4$), filtered and concentrated to give a residue, which was purified by silica gel column chromatography (PE/EtOAc/MeOH=1:1:0.1) to provide N-tert-butyl-5-(5-chloro-4-cyclopropyl-6-(3-cyclopropyl-1H-pyrazol-5-ylamino)pyrimidin-2-yl)thiophene-2-sulfonamide (60 mg, 32%) as a white solid. LC-MS (m/z)=493.9 [M+H]$^+$ The solution of N-tert-butyl-5-(5-chloro-4-cyclopropyl-6-(3-cyclopropyl-1H-pyrazol-5-ylamino)pyrimidin-2-yl) thiophene-2-sulfonamide (60 mg, 0.12 mmol) in trifluoroacetic acid (5 mL) was stirred at 60° C. After 0.5 h, the solution was evaporated to give the crude product, which was recrystallized from ether to afford 5-(5-chloro-4-cyclopropyl-6-(3-cyclopropyl-1H-pyrazol-5-ylamino)pyrimidin-2-yl)thiophene-2 sulfonamide (Compound 304) (25 mg, 48%). LC-MS (m/z)=436.9 [M+H]$^+$; δ (400 MHz, DMSO-d$_6$); 0.73-0.77 (m, 2H), 0.96-0.99 (m, 2H), 1.12-1.14 (m, 4H), 1.91 (m, 1H), 2.43-2.47 (m, 1H), 6.39 (s, 1H), 7.48 (s, 2H), 7.96 (d, J=1.6 Hz, 1H), 8.18 (d, J=1.2 Hz, 1H), 9.18 (s, 1H)

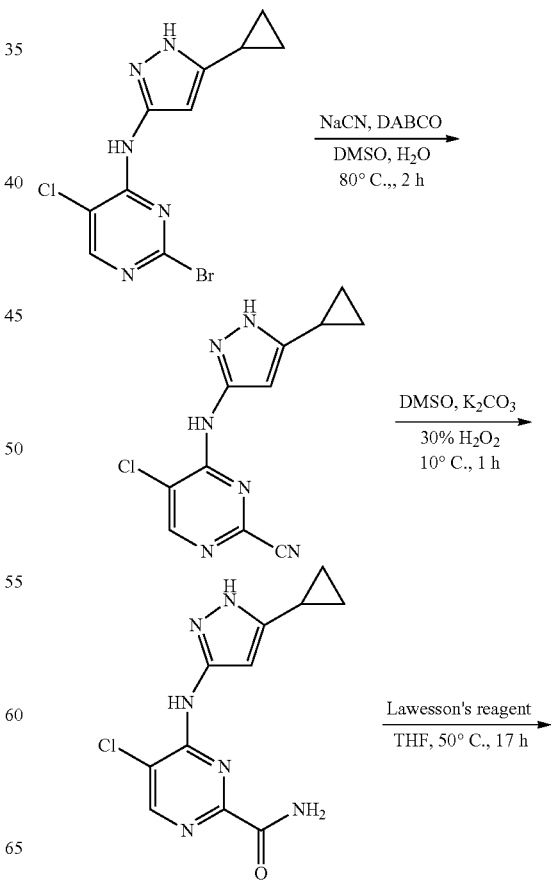

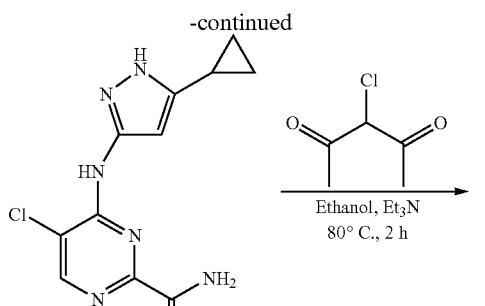

Compound 297

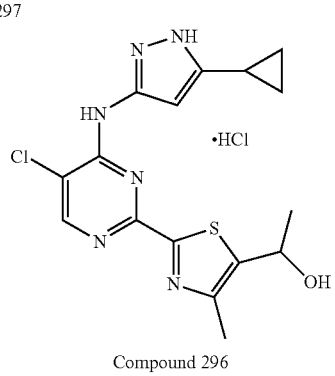

Compound 296

1-(2-(5-Chloro-4-(5-cyclopropyl-1H-pyrazol-3-ylamino)pyrimidin-2-yl)-4-methylthiazol-5-yl)ethanone (Compound 297) and 1-(2-(5-chloro-4-(5-cyclopropyl-1H-pyrazol-3-ylamino)pyrimidin-2-yl)-4-methylthiazol-5-yl)ethanol (Compound 296)

A mixture of 2-bromo-5-chloro-N-(5-cyclopropyl-1H-pyrazol-3-yl)pyrimidin-4-amine (3.0 g, 9.54 mmol, 1.0 eq), KCN (1.24 g, 19.07 mmol, 2.0 eq) and 1,4-diazobicyclo[2,2,2]octan (DABCO.6H$_2$O) (4.20 g, 19.07 mmol, 2.0 eq) in DMSO (50 mL) and H$_2$O (10 mL) was stirred at 80° C. for 4 h. The reaction mixture was diluted with H$_2$O (50 mL) and extracted with EtOAc (3×100 mL). The combined organic phases were washed (brine), dried (Na$_2$SO$_4$), filtered and concentrated. The residue was purified by silica gel chromatography (CH$_2$Cl$_2$/MeOH 500:1 to 50:1 as eluent) to afford 5-chloro-4-(5-cyclopropyl-1H-pyrazol-3-ylamino)pyrimidine-2-carbonitrile (1.9 g, 77%) as a solid. LC-MS (m/z)=261.0 [M+H]$^+$.

The mixture of 5-chloro-4-(5-cyclopropyl-1H-pyrazol-3-ylamino)pyrimidine-2-carbonitrile (1.0 g, 3.85 mmol, 1.0 eq) and K$_2$CO$_3$ (2.0 g, 14.49 mmol, 3.8 eq) in DMSO (20 mL) was stirred at room temperature, and 30% hydrogen peroxide (3 mL) was added dropwise. The reaction mixture was stirred at rt for 1 h, water was added and the suspension was filtered to afford 5-chloro-4-(5-cyclopropyl-1H-pyrazol-3-ylamino)pyrimidine-2-carboxamide (950 mg, 89%). LC-MS (m/z)=279.0 [M+H]$^+$.

A mixture of 5-chloro-4-(5-cyclopropyl-1H-pyrazol-3-ylamino)pyrimidine-2-carboxamide (500 mg, 1.79 mmol) and Lawesson's reagent (1.45 g, 3.58 mmol, 2.0 eq) in toluene (30 ml) and THF (20 ml) was stirred at 50° C. for 17 h, and then, concentrated. The residue was recrystallized with toluene to give the crude 5-chloro-4-(5-cyclopropyl-1H-pyrazol-3-ylamino)pyrimidine-2-carbothioamide (2.3 g, directly used for the next step). LC-MS (m/z)=295.0 [M+H]$^+$.

A mixture of crude 5-chloro-4-(5-cyclopropyl-1H-pyrazol-3-ylamino)pyrimidine-2-carbothioamide (1.2 g, 4.1 mmol), 3-chloropentane-2,4-dione (548 mg, 4.1 mmol, 1.0 eq) and Et$_3$N (1.0 mL) in EtOH (30 mL) was stirred at 80° C. for 2 h, then, concentrated. The residue was recrystallized with EtOH to produce 1-(2-(5-Chloro-4-(5-cyclopropyl-1H-pyrazol-3-ylamino)pyrimidin-2-yl)-4-methylthiazol-5-yl)ethanone (Compound 297) (300 mg, 20%). LC-MS (m/z) =375.0 [M+H]$^+$; $^1$H NMR (400 MHz, DMSO-d$_6$): δ 0.67-0.80 (m, 2H), 0.92-1.05 (m, 2H), 1.91-1.97 (m, 1H), 2.60 (s, 3H), 2.73 (s, 3H), 6.60 (s, 1H), 8.54 (s, 1H), 9.69 (s, 1H), 12.37 (s, 1H).

NaBH$_4$ (46 mg, 1.2 mmol, 3.0 equiv.) was added to a solution of 1-(2-(5-Chloro-4-(5-cyclopropyl-1H-pyrazol-3-ylamino)pyrimidin-2-yl)-4-methylthiazol-5-yl)ethanone (Compound 297 (150 mg, 0.4 mmol, 1.0 equiv.) in THF (2 mL) and methanol (2 mL) at rt. The mixture was stirred for 0.5 h, then, concentrated. The residue was partitioned between ethyl acetate and water. The organic layer was dried and concentrated. The residue was recrystallized with methanol and isopropyl ether to afford 1-(2-(5-chloro-4-(5-cyclopropyl-1H-pyrazol-3-ylamino)pyrimidin-2-yl)-4-methylthiazol-5-yl)ethanol (Compound 296) (120 mg, 80%). LC-MS (m/z)=377.0 [M+H]$^+$. $^1$H NMR (400 MHz, DMSO-d$_6$): δ 0.70-0.78 (m, 2H), 0.95-1.03 (m, 2H), 1.41 (d, J=5.2 Hz, 3H), 1.89-1.96 (m, 1H), 2.38 (s, 3H), 5.04-5.08 (m, 1H), 5.75 (d, J=2.8 Hz, 1H), 6.62 (s, 1H), 8.47 (s, 1H), 9.51 (s, 1H), 12.33 (s, 1H).

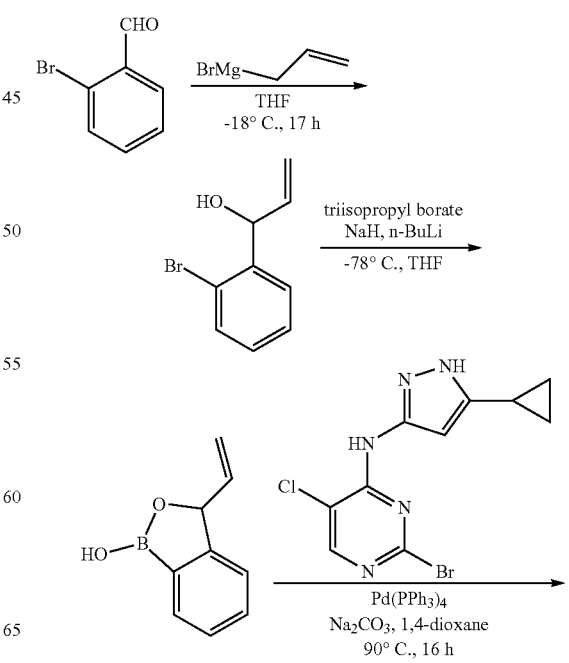

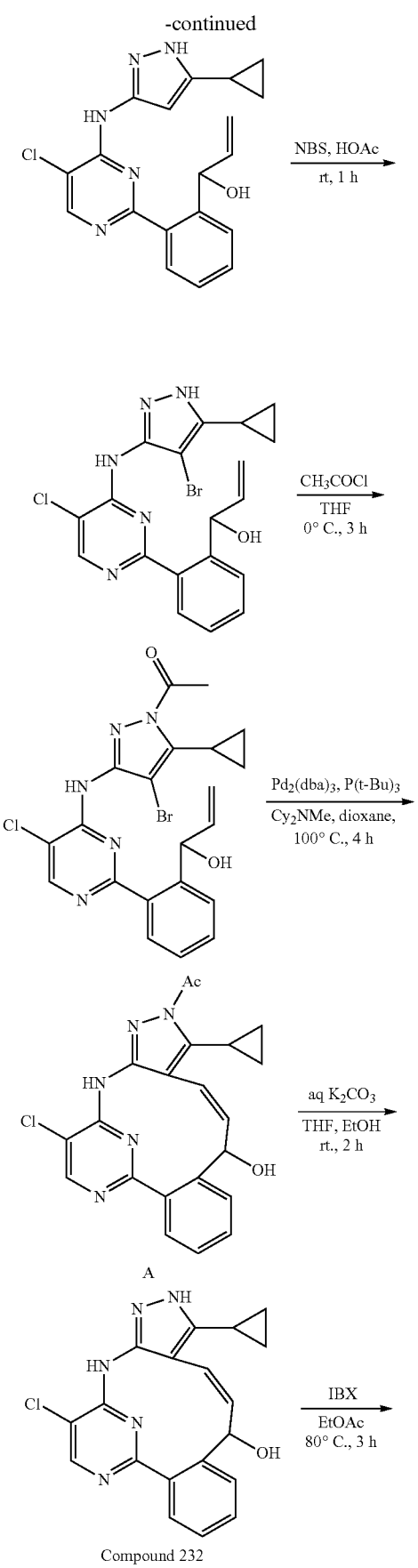
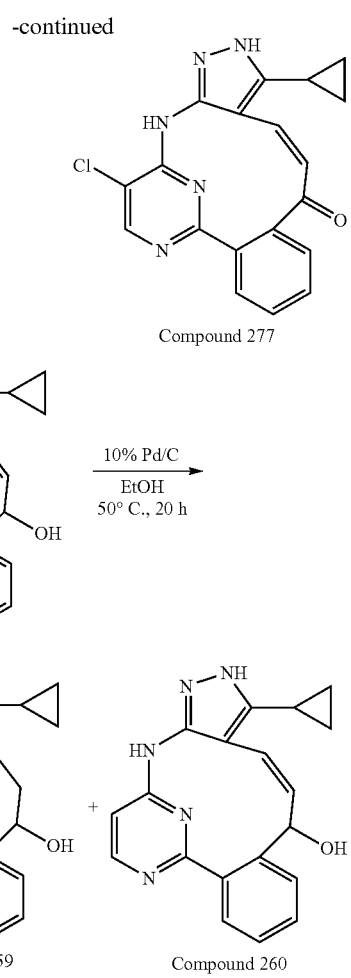

Compounds 232, 277, 259 and 260

To a solution of allylmagnesium bromide (108 mL, 108 mmol, 2.0 eq) in THF was added a solution of 2-bromobenzaldehyde (10 g, 54 mmol, 1.0 eq) in THF (20 mL) dropwise at −18° C. The mixture was allowed to reach room temperature for 17 h, then, quenched with saturated NH$_4$Cl aqueous. The mixture was partitioned between brine and ethyl acetate. The organic layer was washed with brine, dried over Na$_2$SO$_4$, filtered and concentrated. The residue was purified by column chromatography to provide 1-(2-bromophenyl)prop-2-en-1-ol (10.5 g, 91%). LC-MS (m/z)=213.0 [M+H]$^+$.

To a suspension of NaH (1.23 g, 28.2 mmol, 1.2 equiv., 60% content) in THF (10 mL) was added a solution of 1-(2-bromophenyl)prop-2-en-1-ol (5.0 g, 23.5 mmol, 1.0 eq) in THF (10 mL) dropwise at 0° C. The mixture was stirred for 1 h, then, cooled to −70° C. n-BuLi (11.3 mL, 28.2 mmol, 1.2 eq., 2.5M in THF) was added. The mixture was stirred for 1 h, then, triisopropyl borate (5.3 g, 28.2 mmol, 1.2 equiv.) was added. The mixture was stirred for 5 h, then, quenched with 2N H$_2$SO$_4$. The mixture was partitioned between brine and ethylacetate. The organic layer was washed over brine, dried over Na$_2$SO$_4$, filtered and concentrated. The residue was purified by column chromatography to yield 3-vinylbenzo[c][1,2]oxaborol-1(3H)-ol (2.2 g, 57%). LC-MS (m/z)=158.9, 160.9 [M+H]$^+$.

The mixture of 3-vinylbenzo[c][1,2]oxaborol-1(3H)-ol (2.2 g, 13.4 mmol, 1.3 eq), 2-bromo-5-chloro-N-(5-cyclopropyl-1H-pyrazol-3-yl)pyrimidin-4-amine (3.3 g, 10.5 mmol, 1.0 eq), Pd(PPh$_3$)$_4$ (1.3 g, 1.1 mmol, 0.11 equiv.) and saturated aq Na₂CO₃ (5 mL) in 1,4-dioxane (30 mL) was stirred at 90° C. for 3 h under N₂, then, cooled to rt and partitioned between EtOAc and water. The organic layer was washed with brine, dried over Na₂SO₄, filtered and concentrated. The residue was purified by column chromatography to give 1-(2-(5-chloro-4-(5-cyclopropyl-1H-pyrazol-3-ylamino)pyrimidin-2-yl)phenyl)prop-2-en-1-ol (1.8 g, 47%). LC-MS (m/z)=368.0 [M+H]⁺.

To a mixture of 1-(2-(5-chloro-4-(5-cyclopropyl-1H-pyrazol-3-ylamino)pyrimidin-2-yl)phenyl)prop-2-en-1-ol (920 mg, 2.5 mmol, 1.0 eq) in AcOH (15 mL), NBS (490 mg, 2.8 mmol, 1.1 equiv.) was added portionwise. The mixture was stirred at 0° C. for 1 h, then, partitioned between EtOAc and water. The organic layer was washed with brine and saturated NaHCO₃, dried over Na₂SO₄, filtered and concentrated. The residue was purified by column chromatography to afford (750 mg, 67%). LC-MS (m/z)=446.0, 448.0 [M+H]⁺.

To a mixture of 1-(2-(4-(4-bromo-5-cyclopropyl-1H-pyrazol-3-ylamino)-5-chloropyrimidin-2-yl)phenyl)prop-2-en-1-ol (550 mg, 1.2 mmol, 1.0 eq) in THF (20 mL), a solution of acetyl chloride (966 mg, 12 mmol, 10 eq) in THF (2 mL) was added. The mixture was stirred at 0° C. for 4 h, then, partitioned between EtOAc and water. The organic layer was washed with brine, dried over Na₂SO₄, filtered and concentrated. The residue was purified by column chromatography to provide 1-(4-bromo-3-(5-chloro-2-(2-(1-hydroxyallyl)phenyl)pyrimidin-4-ylamino)-5-cyclopropyl-1H-pyrazol-1-yl)ethanone (310 mg, 52%). LC-MS (m/z)=488.0, 490.0 [M+H]⁺.

A flask charged wit1-(4-bromo-3-(5-chloro-2-(2-(1-hydroxyallyl)phenyl)pyrimidin-4-ylamino)-5-cyclopropyl-1H-pyrazol-1-yl)ethanone (1.3 g, 2.7 mmol, 1.0 eq), Pd₂(dba)₃ (487 mg, 0.53 mmol, 0.2 eq), P(t-Bu)₃ (377 mg, 1.9 mmol, 0.7 eq) and Cy₂NMe (1.7 mL, 8.0 mmol, 3.0 eq) in dioxane (35 mL) was flushed with nitrogen. The mixture was stirred and heated to 100° C. for 4 h. Then, the reaction mixture was cooled down to rt and filtered over a pad of silica gel. The filtrate was concentrated and the residue was purified by column chromatography to give the compound A (557 mg, 51%). LC-MS (m/z)=408.1 [M+H]⁺.

To a solution of compound A (70 mg, 0.17 mmol, 1.0 equiv.) in THF (10 mL) and ethanol (5 mL) was added saturated aqueous K₂CO₃ (3 mL). The mixture was stirred at rt for 2 h, then, partitioned between EtOAc and water. The organic layer was washed (brine), dried (Na₂SO₄), filtered and concentrated. The residue was recrystallized with methanol and isopropyl ether to give the compound Compound 232 (40 mg, 64%). LC-MS (m/z)=366.0 [M+H]⁺. ¹H NMR (400 MHz, DMSO-d₆): δ 0.81-0.86 (m, 2H), 1.01-1.04 (m, 2H), 2.02-2.06 (m, 1H), 5.18 (d, J=6.4 Hz, 1H), 5.46 (dd, J=9.2 Hz, 10.0 Hz, 1H), 6.07-6.12 (m, 2H), 7.33-7.38 (m, 1H), 7.49-7.53 (m, 1H), 8.01 (d, J=7.6 Hz, 1H), 8.40 (s, 1H), 8.49 (dd, J=1.2 Hz, 8.0 Hz, 1H), 9.41 (s, 1H), 12.17 (s, 1H).

To a mixture of Compound 232 (290 mg, 0.71 mmol, 1.0 equiv.) in ethyl acetate (10 mL), IBX (597 mg, 2.13 mmol, 3.0 equiv.) was added. The mixture was stirred at 80° C. for 2 h, then, filtered. The filtrate was concentrated and recrystallized with isopropylether to give the compound Compound 277 (160 mg, 62%). LC-MS (m/z)=364.0 [M+H]⁺. ¹H NMR (400 MHz, DMSO-d₆): δ 0.75-0.81 (m, 1H), 0.83-0.94 (m, 2H), 0.98-1.04 (m, 1H), 1.89-1.96 (m, 1H), 6.54 (s, 2H), 7.32-7.35 (m, 1H), 7.57-7.61 (m, 2H), 8.34-8.36 (m, 1H), 8.48 (s, 1H), 9.45 (s, 1H), 12.29 (s, 1H).

A mixture of Compound 232 (100 mg, 0.27 mmol, 1.0 equiv.) and 10% Pd/C (100 mg) in ethanol (10 mL) was stirred under H₂ atmosphere (1 atm) at 50° C. for 20 h, then, filtered. The filtrate was concentrated and purified by Prep-HPLC to afford the compound Compound 259 (10 mg, 11%) and C-260 (12 mg, 13%).

Compound 259: LC-MS (m/z)=334.0 [M+H]⁺. ¹H NMR (400 MHz, DMSO-d₆): δ 0.60-0.63 (m, 1H), 0.65-0.75 (m, 1H), 0.80-0.88 (m, 2H), 1.60-1.63 (m, 1H), 1.78-1.84 (m, 2H), 1.95-1.97 (m, 2H), 2.63 (s, 1H), 6.60 (d, J=6.0 Hz, 1H), 7.22 (t, J=7.6 Hz, 1H), 7.37 (t, J=7.6 Hz, 1H), 7.63 (d, J=7.6 Hz, 1H), 7.68 (bs, 1H), 8.18 (d, J=6.0 Hz, 1H).

Compound 260: LC-MS (m/z)=332.0 [M+H]⁺. ¹H NMR (400 MHz, DMSO-d₆): δ 0.75-0.81 (m, 2H), 0.87-0.93 (m, 2H), 1.90-1.93 (m, 1H), 5.31-5.34 (m, 0.5H), 6.66 (d, J=5.6 Hz, 1H), 7.26-7.28 (m, 1H), 7.49-7.51 (m, 2H), 8.17

In general, compounds of the invention, including compounds in Table 1, are effective for the inhibition of PknB. Selectivity for inhibition of PknB by the compounds of the invention was tested and the results are shown in the following Example. The data obtained shows values for PknB isoform selectivity by showing Ki potencies.

Example 2

PknB Assay

The compounds of the invention were screened for their ability to inhibit PknB kinase using a standard radiometric assay. Briefly, in this kinase assay the transfer of the terminal ³³P-phosphate in ³³P-ATP to substrate GarA is interrogated. The assay was carried out in 96-well plates to a final volume of 100 μL per well containing 3 nM PknB, 100 mM HEPES (pH 7.5), 10 mM MgCl₂, 25 mM NaCl, 0.01% BSA, 1 mM DTT, 6 uM GarA, and 3 μM ATP. Accordingly, compounds of the invention were dissolved in DMSO to make 10 mM initial stock solutions. Serial dilutions in DMSO were then made to obtain the final solutions for the assay. A 1.5 μL aliquot of DMSO or inhibitor in DMSO was added to each well, followed by the addition of ³³P-ATP, and finally the addition of PknB and GarA (both from internal sources). After 30 min, the reaction was quenched with 50 μL of 30% trichloroacetic acid (TCA) containing 4 mM ATP. The reaction mixture was transferred to the 0.66 mm GF filter plates (Corning) and washed three times with 5% TCA. Following the addition of 50 μL of Ultimate Gold™ high efficiency scintillant (Packard Bioscience), the samples were counted in a Packard Top-Count NXT Microplate Scintillation and Luminescence Counter (Packard BioScience). The K$_i$ values were calculated using the graphing software Prism (GraphPad) to fit the data to the kinetic model for competitive tight-binding inhibition. Ki values are represented as the following values, shown in Table 3:

A** 0.001 μM>0.01 μM

A* 0.01 μM-0.05 μM

A 0.05 μM-0.1 μM

B** 0.1 μM-0.5 μM

B* 0.5-1.0 μM

B 1.0 μM-2.0 μM

C 2.0 μM-4.0 μM

D >4.0 μM

TABLE 3

| Compound # | Ki Values | Compound # | Ki Values | Compound # | Ki Values |
|---|---|---|---|---|---|
| 1 | A* | 51 | A | 101 | A*, A*, A |
| 2 | A | 52 | A** | 102 | A |
| 3 | D | 53 | A, B**, B** | 103 | A**, A* |
| 4 | B** | 54 | B | 104 | A*, A |
| 5 | A*, A | 55 | B | 105 | A* |
| 6 | D | 56 | B | 106 | A*, A |
| 7 | D | 57 | B** | 107 | A |
| 8 | B** | 58 | B, C, C | 108 | A** |
| 9 | D | 59 | B**, B*, B* | 109 | B, B* |
| 10 | B | 60 | C, C, D | 110 | A* |
| 11 | B** | 61 | A, C, D | 111 | A**, A* |
| 12 | A** | 62 | D | 112 | A* |
| 13 | A* | 63 | D | 113 | A** |
| 14 | A*, A | 64 | A*, B** | 114 | A** |
| 15 | A*, A | 65 | C, D, D | 115 | A* |
| 16 | A*, A | 66 | B | 116 | A**, A* |
| 17 | A* | 67 | A* | 117 | A*, A |
| 18 | A**, A* | 68 | A, B** | 118 | A* |
| 19 | A** | 69 | D | 119 | A* |
| 20 | B** | 70 | D | 120 | B** |
| 21 | B* | 71 | B | 121 | A* |
| 22 | A* | 72 | D | 122 | A* |
| 23 | A, B** | 73 | B** | 123 | B** |
| 24 | A* | 74 | A** | 124 | A |
| 25 | A* | 75 | A** | 125 | B* |
| 26 | A* | 76 | A* | 126 | A* |
| 27 | A* | 77 | B** | 127 | A* |
| 28 | A* | 78 | B** | 128 | A* |
| 29 | A | 79 | A* | 129 | A** |
| 30 | A* | 80 | A, B** | 130 | A** |
| 31 | A* | 81 | B** | 131 | A** |
| 32 | A | 82 | A | 132 | A**, A* |
| 33 | A* | 83 | A**, A* | 133 | A**, A* |
| 34 | A* | 84 | A* | 134 | A* |
| 35 | A* | 85 | A* | 135 | A* |
| 36 | A | 86 | A** | 136 | A* |
| 37 | A** | 87 | A**, A* | 137 | A* |
| 38 | A*, A | 88 | A* | 138 | A* |
| 39 | B* | 89 | B** | 139 | A* |
| 40 | A** | 90 | A* | 140 | A* |
| 41 | A* | 91 | A* | 141 | A, A, B** |
| 42 | A** | 92 | A* | 142 | A*, A, B**, B** |
| 43 | A** | 93 | A* | 143 | A** |
| 44 | C, D | 94 | A** | 144 | A* |
| 45 | C, D | 95 | A*, A | 145 | A |
| 46 | D | 96 | A* | 146 | A*, A** |
| 47 | D | 97 | A* | 147 | A* |
| 48 | A** | 98 | A** | 148 | A, B** |
| 49 | D | 99 | A* | 149 | D |
| 50 | A** | 100 | B** | 150 | D |
| 151 | A**, A* | 211 | A**, A*, A* | 271 | A* |
| 152 | A* | 212 | A**, A**, A* | 272 | A** |
| 153 | A* | 213 | A** | 273 | A* |
| 154 | A* | 214 | A**, A**, A* | 274 | A |
| 155 | D | 215 | A**, A**, A* | 275 | A** |
| 156 | A | 216 | B | 276 | A** |
| 157 | A** | 217 | A**, A* | 277 | D |
| 158 | A* | 218 | A | 278 | B** |
| 159 | B** | 219 | B** | 279 | B |
| 160 | B** | 220 | D | 280 | A* |
| 161 | A | 221 | A** | 281 | A** |
| 162 | B* | 222 | A** | 282 | C |
| 163 | B** | 223 | A** | 283 | B** |
| 164 | B** | 224 | A** | 284 | B** |
| 165 | A**, A* | 225 | A** | 285 | A** |
| 166 | A* | 226 | A* | 286 | A* |
| 167 | A, A, A, B** | 227 | A** | 287 | A* |
| 168 | B**, B**, B | 228 |  | 288 | B** |
| 169 | C, D | 229 | A* | 289 | B** |
| 170 | A*, A | 230 | A | 290 | B* |
| 171 | A, B**, B** | 231 | A | 291 | B** |
| 172 | A, B**, B** | 232 | D | 292 | D |
| 173 | B, C | 233 | A* | 293 | B** |
| 174 | C | 234 | D | 294 | C |
| 175 | C | 235 | A* | 295 | A**, B** |
| 176 | A** | 236 | B** | 296 | B** |
| 177 | C | 237 | A** | 297 | A* |

TABLE 3-continued

| Compound # | Ki Values | Compound # | Ki Values | Compound # | Ki Values |
|---|---|---|---|---|---|
| 178 | B** | 238 | A** | 298 | A |
| 179 | B* | 239 | A*, B** | 299 | A* |
| 180 | A* | 240 | A* | 300 | A |
| 181 | A* | 241 | A | 301 | A |
| 182 | B | 242 | A* | 302 | A* |
| 183 | A | 243 | A* | 303 | C |
| 184 | D | 244 | D | 304 | A** |
| 185 | B* | 245 | D | 305 | B* |
| 186 | A** | 246 | A* | 306 | A* |
| 187 | D | 247 | B** | 307 | A* |
| 188 | D | 248 | D | 308 | A* |
| 189 | A | 249 | D | 309 | B** |
| 190 | A* | 250 | B** | 310 | B** |
| 191 | A*, B** | 251 | A* | 311 | A* |
| 192 | B** | 252 | A* | 312 | A* |
| 193 | B, C | 253 | B** | 313 | A* |
| 194 | A, B** | 254 | B** | 314 | A** |
| 195 | C | 255 | A** | 315 | A** |
| 196 | A* | 256 | B* | 316 | A* |
| 197 | B* | 257 | D | 317 | A* |
| 198 | A** | 258 | B** | 318 | A* |
| 199 | A**, A* | 259 |  | 319 | A** |
| 200 | B, D, D | 260 |  | 320 | A** |
| 201 | B*, B*, B | 261 | B** | 321 | B** |
| 202 | A* | 262 | B | 322 | A** |
| 203 | A** | 263 | D | 323 | A* |
| 204 | A* | 264 | A** | 324 | B** |
| 205 | A, B** | 265 | A** | 325 | B** |
| 206 | B**, B**, B* | 266 | A** | 326 | A* |
| 207 | A** | 267 | A** | 327 | A* |
| 208 | B**, B**, B*, B | 268 | A* | 328 | A, A, B** |
| 209 | A** | 269 | B** |  |  |
| 210 | A* | 270 | B**, B*, B*, B* |  |  |

Example 3

*Mycobacterium tuberculosis* Inhibition Assay

Compounds were screened for their ability to inhibit the growth of *Mycobacterium tuberculosis* H37R$_a$ using a standard microtiter dilution method with reduction of the dye resazurin as an indicator of growth. The growth assay was carried out in standard *Mycobacterium* liquid growth medium, 7H9 Broth (BD Biosciences, Franklin Lakes, N.J.) supplemented with 10% ADC enrichment (BD Biosciences, Franklin Lakes, N.J.). The medium was inoculate with ~1×10$^6$ cells/milliliter of *Mycobacterium tuberculosis* H37R$_a$ grown on a the surface of a growth medium solid medium (7H11 agar [BD Biosciences, Franklin Lakes, N.J.] supplemented with 10% OADC enrichment [BD Biosciences, Franklin Lakes, N.J.]).

Two-fold serial dilutions (either 7 or 11-step series) of test compounds in DMSO were dispensed into 96-well assay plates (sterile, black sided, clear bottom wells) in a volume of 1 microliter. One microliter of DMSO was dispensed into a control well at the end of each series. One-hundred microliters of the bacterial cell suspension in growth medium was dispensed into each test well containing a DSMO solution of compound. The assay plates were covered with a fitted lid and incubated at 37° C. in a humidified chamber for 9 days. On the ninth day 30 microliters of a 0.01% solution of resazurin (Sigma Chemical Co., St. Louis, Mo.) in distilled water was added to each well and the baseline fluorescence of resazurin was determined by measuring well fluorescence at an excitation wavelength of 492 nm and an emission wavelength of 595 nm on a Spectrafluor Plus (Tecan, Durham, N.C.) instrument. The assay plates were returned to the incubation chamber for 24 hours. After 24 hours, the fluorescence of the wells (resulting from the reduction of resazurin dye) was measured at an excitation wavelength of 492 nm and an emission wavelength of 595 nm on the Spectrafluor Plus instrument. The minimum inhibitory concentration (MIC) was called as the lowest concentration of compound that inhibited the reduction of resazurin by >70%, as compared to the DMSO (untreated) control wells. MIC values are represented as the following values:

A* <1.6 µM
A 1.6 µM<12.5 µM
B** 12.5 µM-25.0 µM
B* 25.0 µM-50.0 µM
B 50.0 µM-100.0 µM
C >100.0 µM

TABLE 4

| Compound # | MIC values | Compound # | MIC values | Compound # | MIC values |
|---|---|---|---|---|---|
| 1 | BM, B | 51 | B++ | 101 | C |
| 2 | C | 52 | A | 102 | B |
| 3 | C | 53 | B+ | 103 | B++, B+ |
| 4 | C | 54 | B | 104 | B++, C |
| 5 | B | 55 | B | 105 | B+ |
| 6 | C | 56 | C | 106 | B++, C |

TABLE 4-continued

| Compound # | MIC values | Compound # | MIC values | Compound # | MIC values |
|---|---|---|---|---|---|
| 7 | C | 57 | C | 107 | B++, B+ |
| 8 | B | 58 | C | 108 | B+ |
| 9 | C | 59 | C | 109 | B |
| 10 | C | 60 | A | 110 | A |
| 11 | B+ | 61 | A | 111 | B++, B |
| 12 | B+ | 62 | A+ | 112 | B+ |
| 13 | B | 63 | B+ | 113 | B+ |
| 14 | B+, B | 64 | B | 114 | A+, A |
| 15 | B | 65 | C | 115 | B++, B+ |
| 16 | C | 66 | B+ | 116 | B++, C |
| 17 | B | 67 | A+ | 117 | A, C, C |
| 18 | B, B, C | 68 | C | 118 | C |
| 19 | B, B, C, C | 69 | C | 119 | C |
| 20 | B | 70 | C | 120 | C |
| 21 | B+, B, B | 71 | C | 121 | C |
| 22 | B | 72 | C | 122 | B |
| 23 | C | 73 | C | 123 | B, C |
| 24 | B | 74 | A, B++, C | 124 | A, B++ |
| 25 | B+ | 75 | C | 125 | C |
| 26 | B+ | 76 | B | 126 | B++, B+ |
| 27 | B | 77 | B, C | 127 | B |
| 28 | A | 78 | A, B++, C, C | 128 | B+, C |
| 29 | B | 79 | B+, B | 129 | B++ |
| 30 | A | 80 | B, C | 130 | A |
| 31 | A | 81 | B++, B+ | 131 | B |
| 32 | B+ | 82 | B | 132 | A |
| 33 | B+ | 83 | B+ | 133 | B++ |
| 34 | C | 84 | C | 134 | A |
| 35 | A | 85 | C | 135 | A |
| 36 | B++, B+ | 86 | B++ | 136 | B+ |
| 37 | B+ | 87 | A | 137 | C |
| 38 | B | 88 | B+, C | 138 | B, C |
| 39 | B | 89 | C | 139 | B+, C |
| 40 | A | 90 | B+ | 140 | C |
| 41 | B+ | 91 | B+ | 141 | B, C, C |
| 42 | A | 92 | B | 142 | C |
| 43 | B++ | 93 | B, C | 143 | A |
| 44 | C | 94 | B++, B+ | 144 | B++ |
| 45 | C | 95 | C | 145 | B++, B+ |
| 46 | C | 96 | C | 146 | B++ |
| 47 | C | 97 | B | 147 | B++ |
| 48 | A | 98 | B, C | 148 | B, C |
| 49 | C | 99 | B+, B | 149 | B+ |
| 50 | A | 100 | C | 150 | C |
| 151 | C | 211 | A | 271 | B |
| 152 | B | 212 | A, B++ | 272 | A |
| 153 | C | 213 | A | 273 | B+ |
| 154 | C | 214 | B++ | 274 | C |
| 155 | C | 218 | B++ | 275 | B++ |
| 156 | C | 216 | B+ | 276 | A |
| 157 | C | 217 | A | 277 | C |
| 158 | C | 218 | B++ | 278 | C |
| 159 | B+ | 219 | C | 279 | B++ |
| 160 | C | 220 | C | 280 | A |
| 161 | A | 221 | C | 281 | A |
| 162 | C | 222 | A+, A | 282 | A |
| 163 | B | 223 | B++ | 283 | C |
| 164 | C | 224 | B++ | 284 | B++ |
| 165 | C | 225 | B++ | 285 | A |
| 166 | B | 226 | B++ | 286 | B |
| 167 | B++ | 227 | B++ | 287 | B+ |
| 168 | B | 228 | B+ | 288 | C |
| 169 | B | 229 | C | 289 | B |
| 170 | B+ | 230 | A | 290 | B++ |
| 171 | B++ | 231 | C | 291 | A |
| 172 | B | 232 | B, C | 292 | C |
| 173 | B+ | 233 | B | 293 | B++ |
| 174 | C | 234 | C | 294 | B+ |
| 175 | C | 235 | A | 295 | A |
| 176 | C | 236 | A+, A, A, A, A | 296 | A |
| 177 | C | 237 | B++ | 297 | C |
| 178 | B | 238 | B++ | 298 | A |
| 179 | C | 239 | A | 299 | C |
| 180 | B++ | 240 | B++ | 300 | B+ |
| 181 | C | 241 | B | 301 | B+ |
| 182 | A | 242 | A | 302 | C |
| 183 | B | 243 | A | 303 | B+ |
| 184 | C | 244 | C | 304 | A |

TABLE 4-continued

| Compound # | MIC values | Compound # | MIC values | Compound # | MIC values |
|---|---|---|---|---|---|
| 185 | C | 245 | C | 305 | A, B++ |
| 186 | A | 246 | C | 306 | B+ |
| 187 | C | 247 | C | 307 | B+ |
| 188 | C | 248 | C | 308 | B+ |
| 189 | C | 249 | C | 309 | C |
| 190 | C | 250 | B+ | 310 | A |
| 191 | B, C | 251 | C | 311 | A |
| 192 | B, C | 252 | B+ | 312 | B+ |
| 193 | C | 253 |  | 313 | A+ |
| 194 | B | 254 | B, C | 314 | A |
| 195 | C | 255 | A | 315 | A |
| 196 | B | 256 | B+ | 316 | B+ |
| 197 | B+ | 257 | B++ | 317 | B+ |
| 198 | A, A, A, B++ | 258 | C | 318 | A |
| 199 | B+ | 259 |  | 319 | A |
| 200 | B, C | 260 |  | 320 | A |
| 201 | B | 261 | B++ | 321 | A |
| 202 | C | 262 | A | 322 | B++ |
| 203 | A+, A | 263 | C | 323 | B++ |
| 204 | B+ | 264 | A | 324 |  |
| 205 | B, C | 265 | B++ | 325 | B |
| 206 | C | 266 | A+, A, A, C | 326 | A |
| 207 | A | 267 | A+, A | 327 | A |
| 208 | B | 268 | B++ | 328 | B, C |
| 209 | A | 269 | C |  |  |
| 210 | A | 270 | C |  |  |

Example 4

In-Vivo Inhibition of *M. tuberculosis*

Six-week old female C57BL/6 mice were used in the experiment. All animal procedures were approved by the Subcommittee for Animal Studies (SAS).

INH (Sigma Chemical Co., St. Louis, Mo.) was dissolved in distilled water and dosed at 25 mg/kg. The following Vertex inhibitors were dissolved in 10% VitE-TPGS for oral delivery or a mixture of PEG, cremaphor EL, propylene glycol and sodium phosphate buffer: Compounds 42, 52, 207 and 217.

*M. tuberculosis* ATCC 35801 (strain Erdman) was obtained from the American Type Culture Collection (ATCC) Manassas, Va. The organism was grown in modified 7H10 broth (pH 6.6; 7H10 agar formulation with agar and malachite green omitted) with 10% OADC (oleic acid, albumin, dextrose, catalase) enrichment (BBL Microbiology Systems, Cockeysville, Md.) and 0.05% Tween 80 for 5-10 days on a rotary shaker at 37° C. The culture was diluted to 100 Klett units (equivalent to $5 \times 10^7$ colony forming units (CFU)) per ml (Photoelectric Colorimeter; Manostat Corp., New York, N.Y.). The culture was frozen at −70° C. until use. On the day of infection the culture was thawed and sonicated. The final inoculum size was determined by titration, in triplicate, on 7H10 agar plates supplemented with 10% OADC enrichment. The plates were incubated at 37° C. in ambient air for 4 weeks.

Six-week old female C57BL/6 mice were infected intranasally with ~$1 \times 10^6$ CFU of *M tuberculosis* Erdman. Mice were randomly assigned to groups of 6 mice: Early Control and INH, of groups of 9 mice: Late Control and Vertex inhibitors.

One day post-infection mice were treated with the above agents twice per day (except for INH, which was given once) orally by gavage in a 0.2 ml volume for 10 consecutive days. The Early Control group was euthanized at the initiation of therapy to determine the infection load. A Late Control group was euthanized at the end of the treatment timepoint to determine the level of infection without therapy.

Six mice per group were sacrificed by $CO_2$ inhalation after the completion of 10 days of therapy. Right lungs were aseptically removed and ground in a sealed tissue homogenizer. The number of viable organisms was determined by serial dilution and titration on 7H10 agar plates. Plates were incubated at 37° C. in ambient air for 4 weeks prior to counting.

Three mice in the Late Control and 3 mice in each of the Vertex inhibitor group were used for PK analysis. On the 10th day of treatment mice were treated once and one-hour post-treatment mice were euthanized by $CO_2$ inhalation. Mice were bleed immediately and spun in a centrifuge to collect the plasma. The plasma was then frozen at −70° C. The lungs were then removed, washed in saline, dried and immediately frozen.

The plasma was thawed and mixed 1:4 with acetonitrile containing the internal standard. This was then vortexed for 2 minutes, allowed to sit for 5 minutes and then centrifuged at 3,000×g for 20 minutes. Approximately 250 μl of supernatant was collected into a microfuge tube and then frozen at −70° C. The lungs were weighed, thawed and homogenized in 2 parts saline to one part lung tissue. The homogenate was mixed 1:4 with acetonitrile containing the internal standard. This was vortexed for 2 minuted, allowed to sit for 5 minutes and centrifuged at 3,000×g for 20 minutes. Approximately 250 μl of supernatant was collected into a microfuge tube and then frozen at −70° C. P value of the bacterial lung burden reduction compared the late control by the Vertex compounds are reported herein:

Compound 42—P value<0.0050
Compound 52—0.1<P value<0.15
Compound 207—0.01<P value<0.05
Compound 217—0.05<P value<0.07

While we have described a number of embodiments of this invention, it is apparent that our basic examples may be altered to provide other embodiments that utilize the compounds, methods, and processes of this invention. Therefore, it will be appreciated that the scope of this invention is to be defined by the appended claims rather than by the specific embodiments that have been represented by way of example herein.

We claim:
1. A method of treating tuberculosis, comprising the step of administering to a patient a therapeutically effective amount of a compound of formula I:

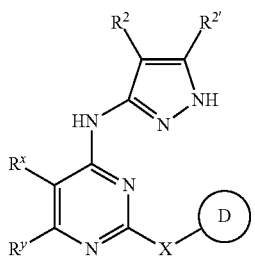

I or a pharmaceutically acceptable salt thereof, wherein:
X is a bond or —N(R)—;
Ring D is a 5-7 membered monocyclic ring or 8-10 membered bicyclic ring selected from aryl, heteroaryl, heterocyclyl or carbocyclyl, said heteroaryl or heterocyclyl ring having 1-4 ring heteroatoms selected from nitrogen, oxygen or sulfur, wherein Ring D is independently substituted at any substitutable ring carbon by oxo or —$R^5$, and at any substitutable ring nitrogen by —$R^4$;
$R^x$ and $R^y$ are independently selected from T-$R^3$, or $R^x$ and $R^y$ are taken together with their intervening atoms to form a fused, unsaturated or partially unsaturated, 5-8 membered ring having 1-3 ring heteroatoms selected from oxygen, sulfur, or nitrogen, wherein any substitutable carbon on said fused ring is optionally and independently substituted by T-$R^3$, and any substitutable nitrogen on said ring is substituted by $R^4$;
T is a valence bond or a $C_{1-4}$ alkylidene chain;
$R^2$ and $R^{2'}$ are independently selected from —R, -T-W—$R^6$, or $R^2$ and $R^{2'}$ are taken together with their intervening atoms to form a fused, 5-8 membered, unsaturated or partially unsaturated, ring containing 0-3 ring heteroatoms selected from nitrogen, oxygen, or sulfur, wherein said fused ring is optionally substituted by up to three groups independently selected from halo, oxo, —CN, —$NO_2$, —$R^7$, or —V—$R^6$;
$R^3$ is selected from —R, -halo, =O, —OR, —C(=O)R, —$CO_2R$, —COCOR, —$COCH_2COR$, —$NO_2$, —CN, —S(O)R, —$S(O)_2R$, —SR, —$N(R^4)_2$, —$CON(R^4)_2$, —$SO_2N(R^4)_2$, —OC(=O)R, —$N(R^4)COR$, —$N(R^4)CO_2$ (optionally substituted $C_{1-6}$ aliphatic), —$N(R^4)N(R^4)_2$, —C=$NN(R^4)_2$, —C=N—OR, —$N(R^4)CON(R^4)_2$, —$N(R^4)SO_2N(R^4)_2$, —$N(R^4)SO_2R$, or —OC(=O)$N(R^4)_2$;
each R is independently selected from hydrogen or an optionally substituted group selected from $C_{1-6}$ aliphatic, $C_{6-10}$ aryl, a heteroaryl ring having 5-10 ring atoms, or a heterocyclyl ring having 5-10 ring atoms;
each $R^4$ is independently selected from —$R^7$, —$COR^7$, —$CO_2$ (optionally substituted $C_{1-6}$ aliphatic), —CON($R^7)_2$, or —$SO_2R^7$, or two $R^4$ on the same nitrogen are taken together to form a 5-8 membered heterocyclyl or heteroaryl ring;
each $R^5$ is independently selected from —R, halo, —OR, —C(=O)R, —$CO_2R$, —COCOR, —$NO_2$, —CN, —S(O)R, —$SO_2R$, —SR, —$N(R^4)_2$, —$CON(R^4)_2$, —$SO_2N(R^4)_2$, —OC(=O)R, —$N(R^4)COR$, —$N(R^4)CO_2$ (optionally substituted $C_{1-6}$ aliphatic), —$N(R^4)N(R^4)_2$, —C=$NN(R^4)_2$, —C=N—OR, —$N(R^4)CON(R^4)_2$, —$N(R^4)SO_2N(R^4)_2$, —$N(R^4)SO_2R$, or —OC(=O)$N(R^4)_2$;
V is —O—, —S—, —SO—, —$SO_2$—, —$N(R^6)SO_2$—, —$SO_2N(R^6)$—, —$N(R^6)$—, —CO—, —$CO_2$—, —$N(R^6)CO$—, —$N(R^6)C(O)O$—, —$N(R^6)CON(R^6)$—, —$N(R^6)SO_2N(R^6)$—, —$N(R^6)N(R^6)$—, —C(O)$N(R^6)$—, —OC(O)$N(R^6)$—, —C($R^6)_2O$—, —C($R^6)_2S$—, —C($R^6)_2SO$—, —C($R^6)_2SO_2$—, —C($R^6)_2SO_2N(R^6)$—, —C($R^6)_2N(R^6)$—, —C($R^6)_2N(R^6)C(O)$—, —C($R^6)_2N(R^6)C(O)O$—, —C($R^6$)=NN($R^6$)—, —C($R^6$)=N—O—, —C($R^6)_2N(R^6)N(R^6)$—, —C($R^6)_2N(R^6)SO_2N(R^6)$—, or —C($R^6)_2N(R^6)CON(R^6)$—;
W is —C($R^6)_2O$—, —C($R^6)_2S$—, —C($R^6)_2SO$—, —C($R^6)_2SO_2$—, —C($R^6)_2SO_2N(R^6)$—, —C($R^6)_2N(R^6)$—, —CO—, —$CO_2$—, —C($R^6$)OC(O)—, —C($R^6$)OC(O)N($R^6$)—, —C($R^6)_2N(R^6)CO$—, —C($R^6)_2N(R^6)C(O)O$—, —C($R^6$)=NN($R^6$)—, —C($R^6$)=N—O—, —C($R^6)_2N(R^6)N(R^6)$—, —C($R^6)_2N(R^6)SO_2N(R^6)$—, —C($R^6)_2N(R^6)CON(R^6)$—, or —CON($R^6$)—;
each $R^6$ is independently selected from hydrogen or an optionally substituted $C_{1-4}$ aliphatic group, or two $R^6$ groups on the same nitrogen atom are taken together with the nitrogen atom to form a 5-6 membered heterocyclyl or heteroaryl ring; and
each $R^7$ is independently selected from hydrogen or an optionally substituted $C_{1-6}$ aliphatic group, or two $R^7$ on the same nitrogen are taken together with the nitrogen to form a 5-8 membered heterocyclyl ring or heteroaryl.

2. The method of claim 1, wherein the compound is selected from the following compounds, or a pharmaceutically acceptable salt thereof:

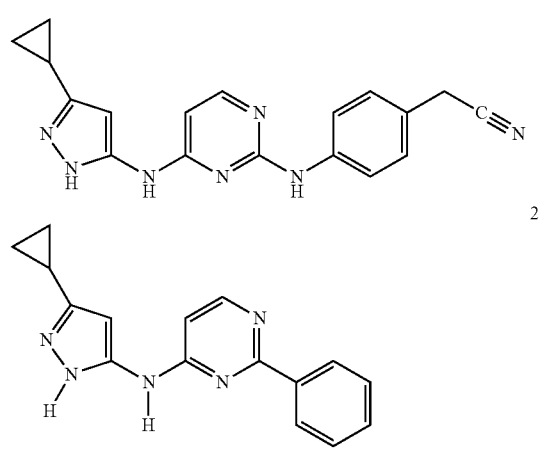

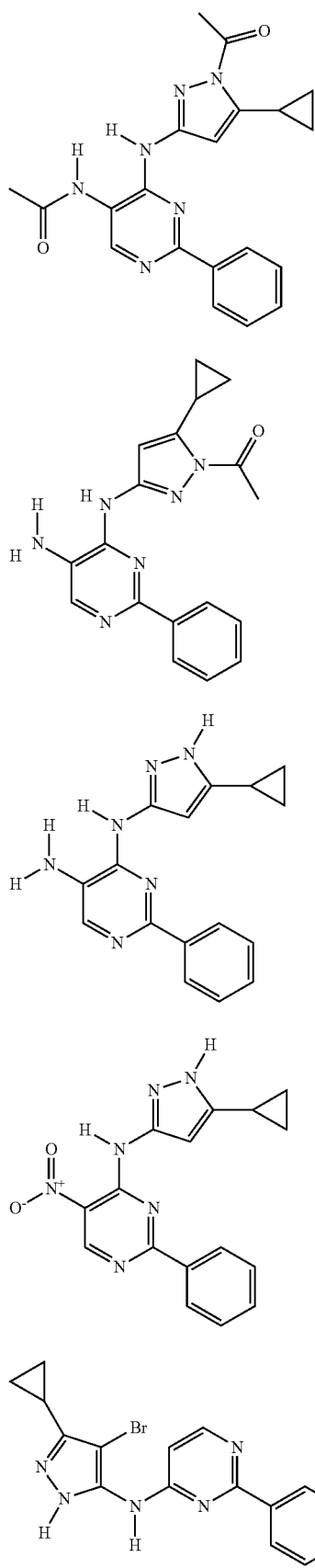
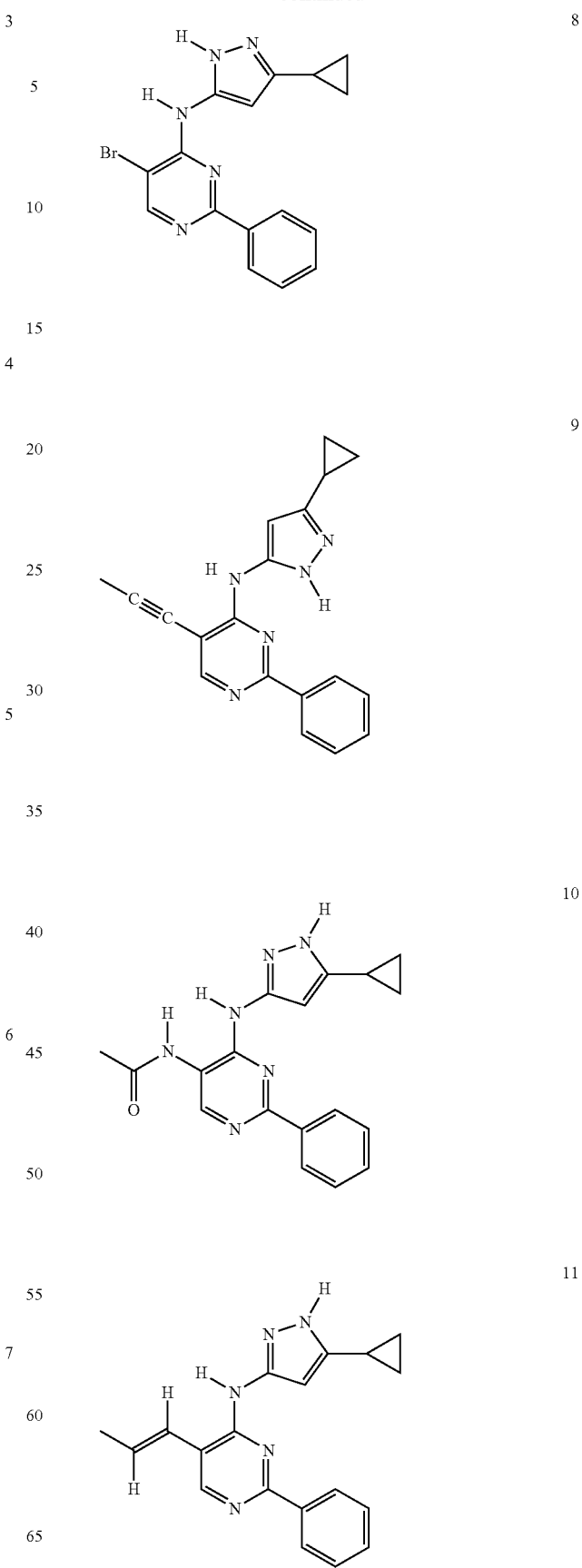

12
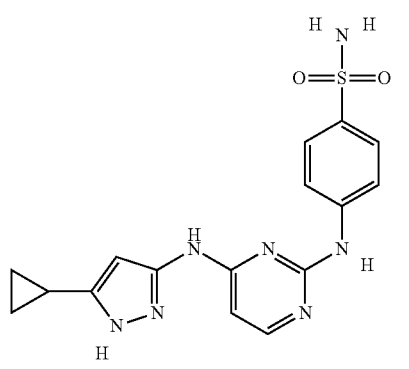
13
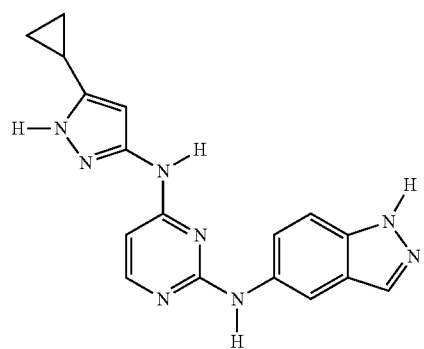
14
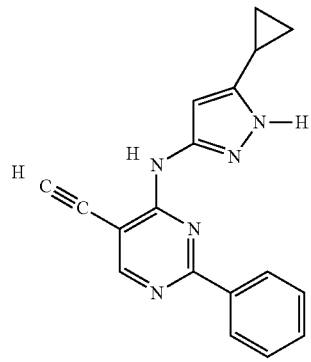
15
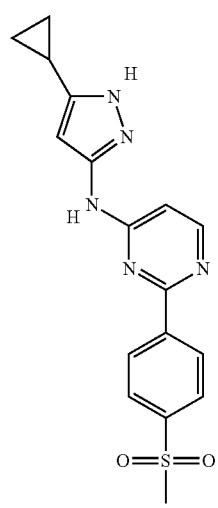
16
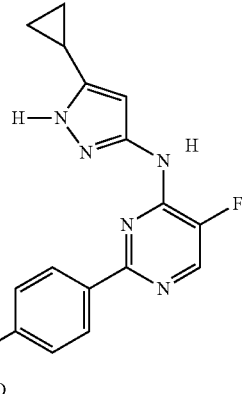
17
18
19

20
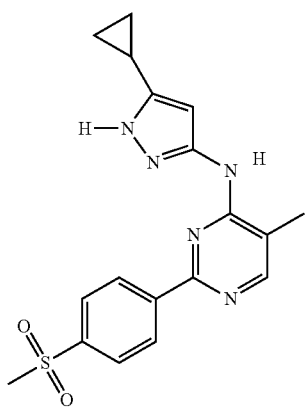
21
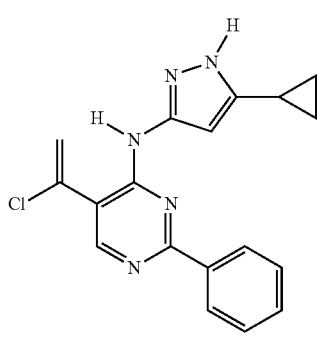
22
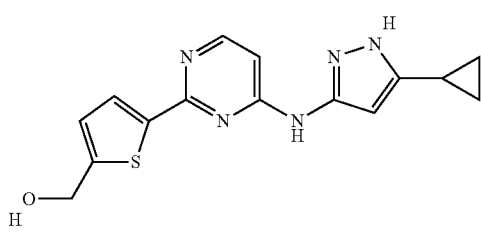
23
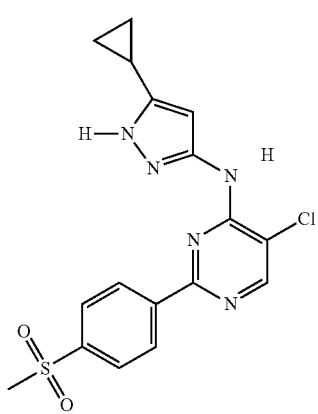
24
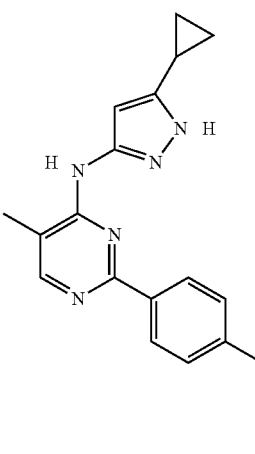
25
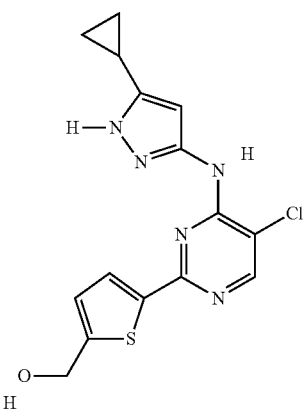
26
27
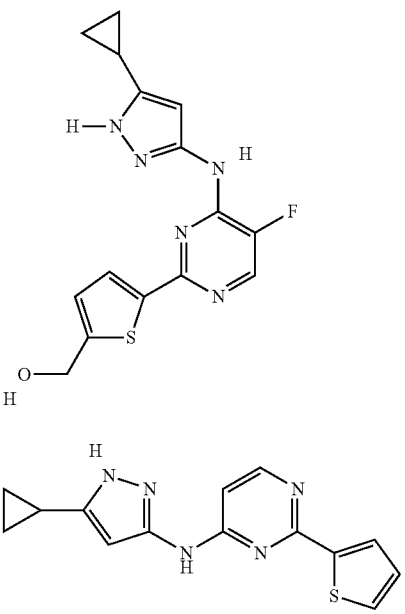

-continued
28
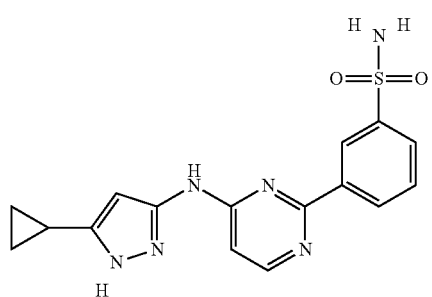
29
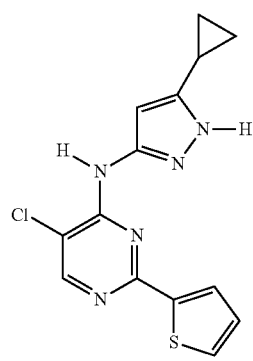
30
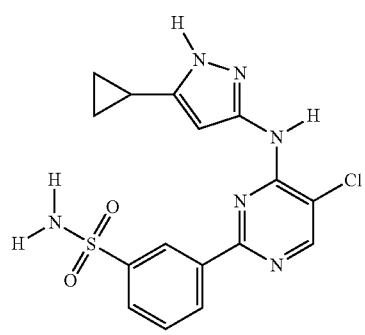
31
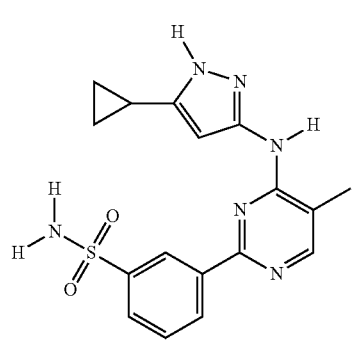
-continued
32
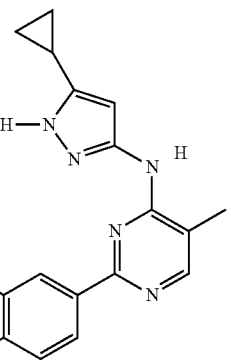
33
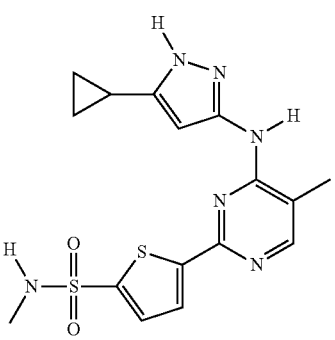
34
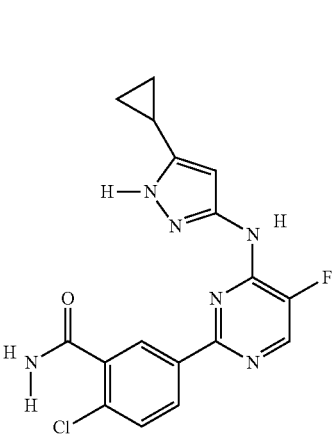
35
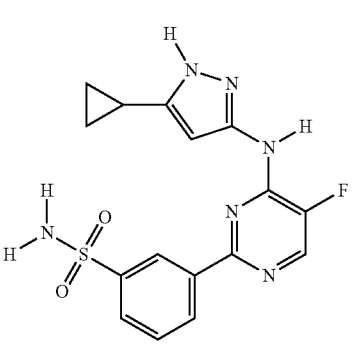

36
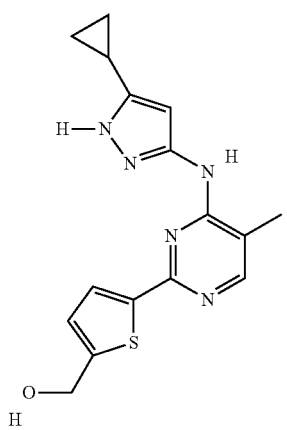
37
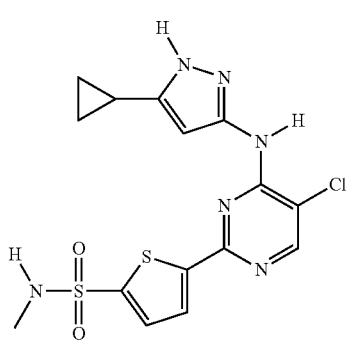
38
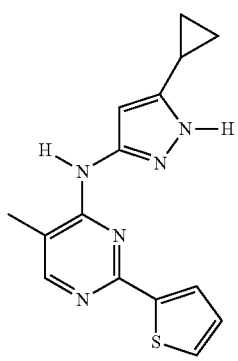
39
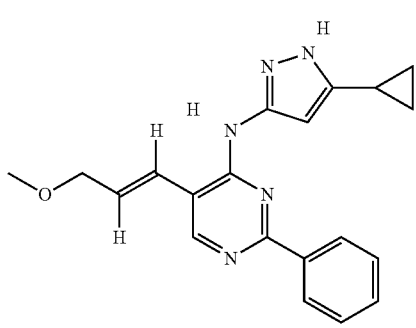
40
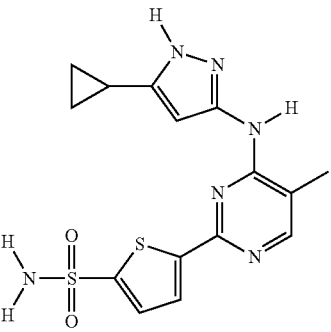
41
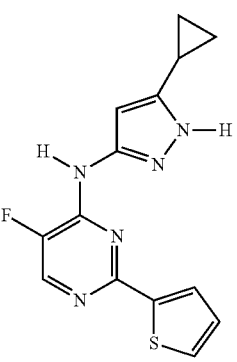
42
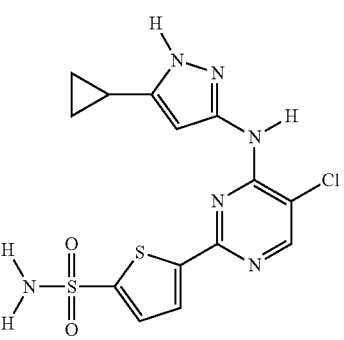
43
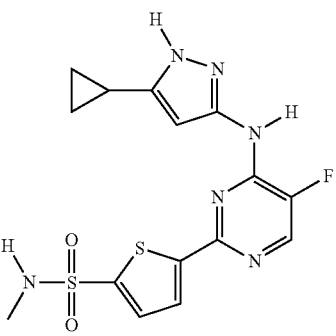

44
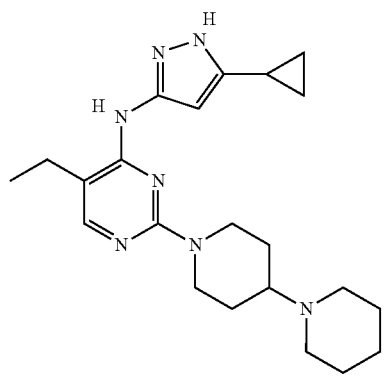
45
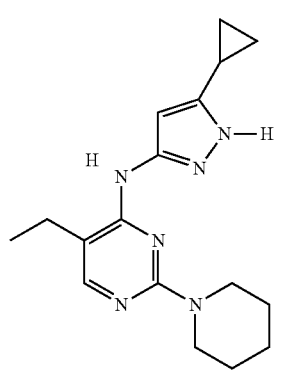
46
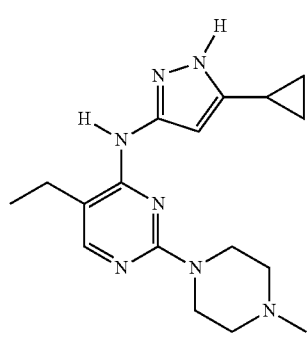
47
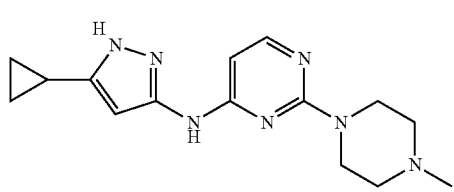
48
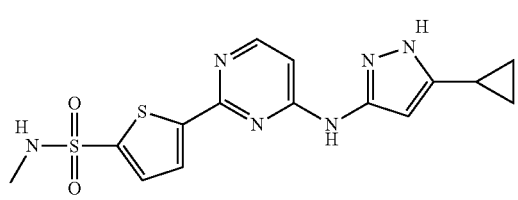
49
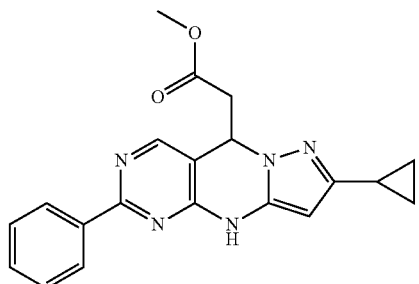
50
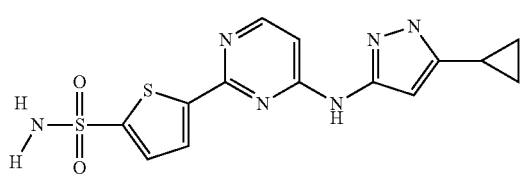
51
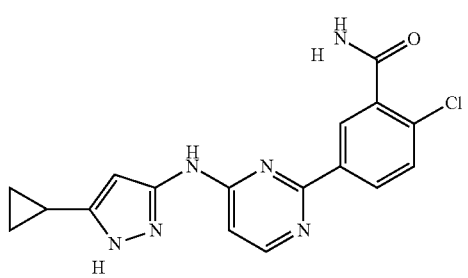
52
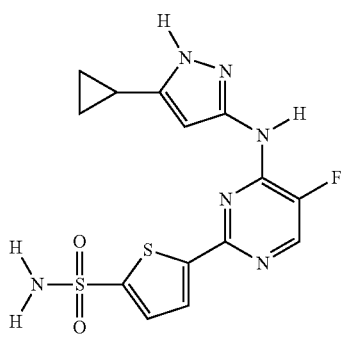
53
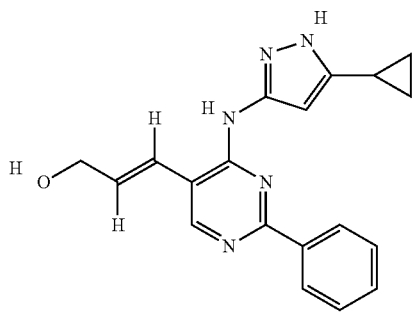

55
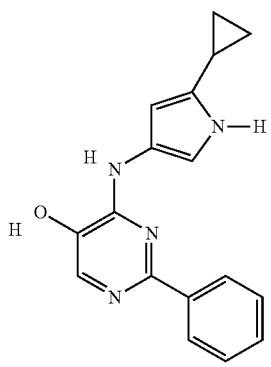
56
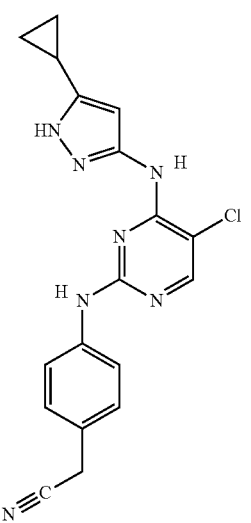
57
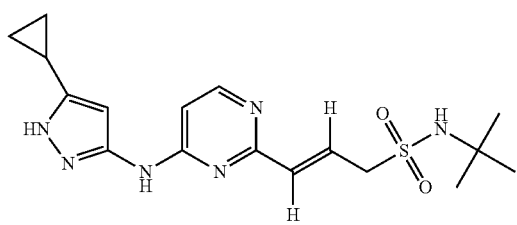
58
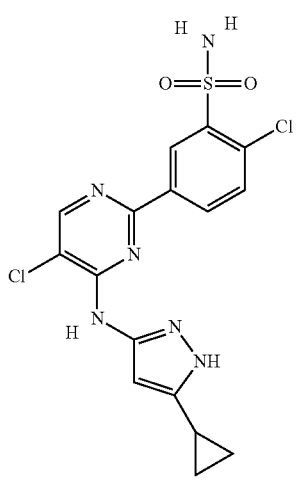
59
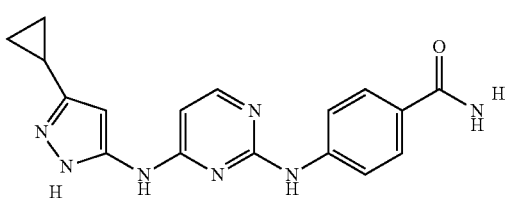
60
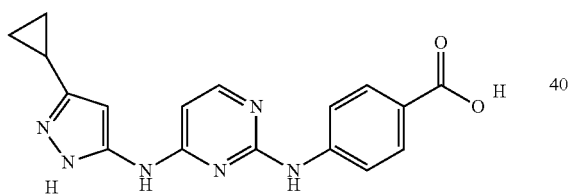
61
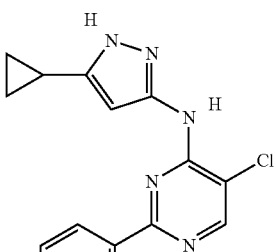
62
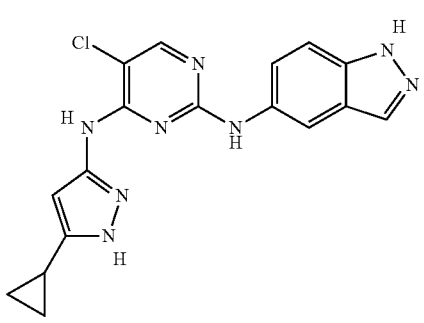

63
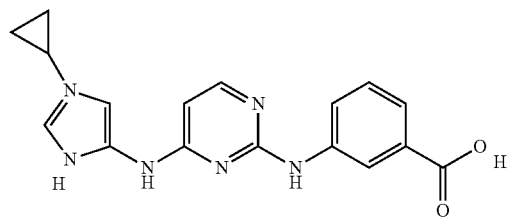
64
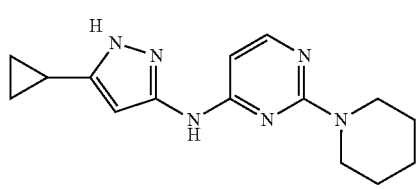
65
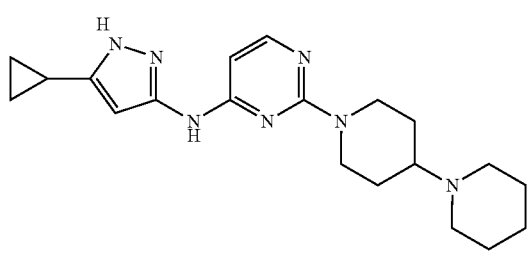
66
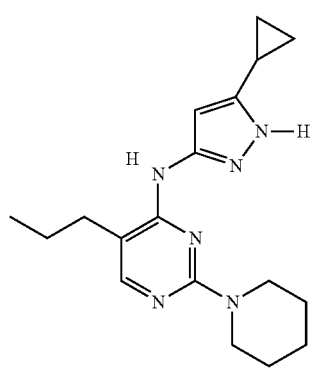
67
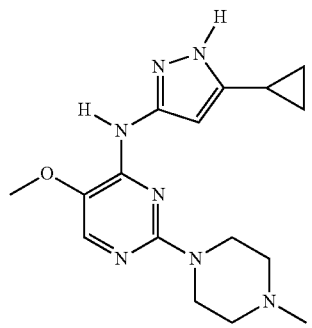
68
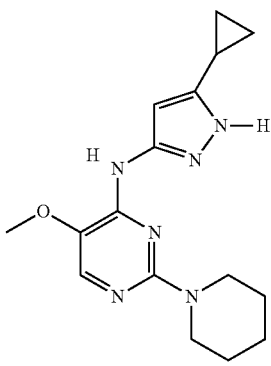
69
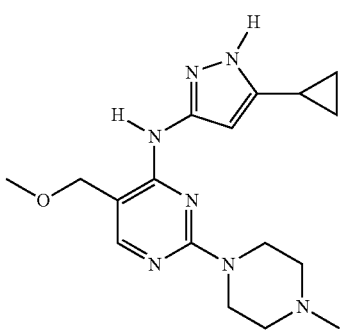
70
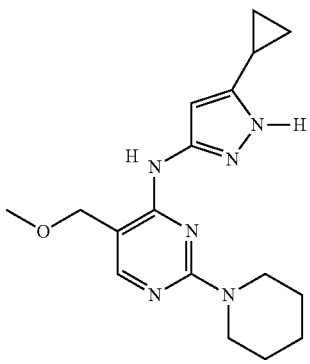
71
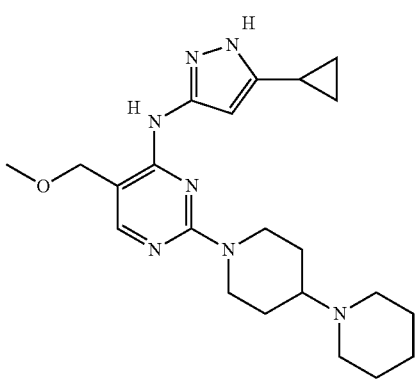

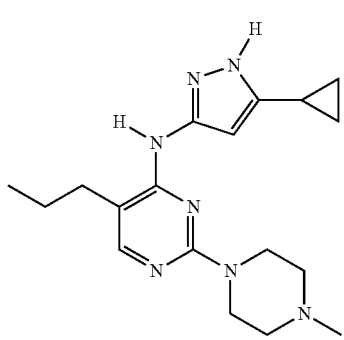
72
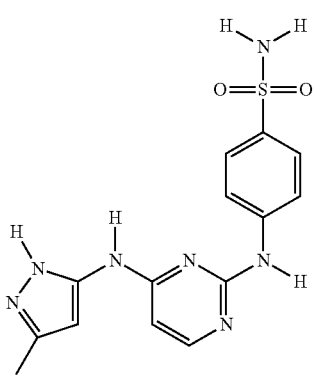
76
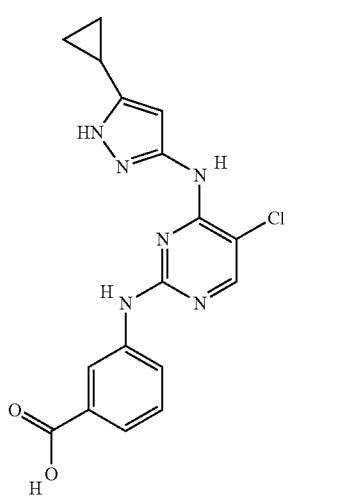
73
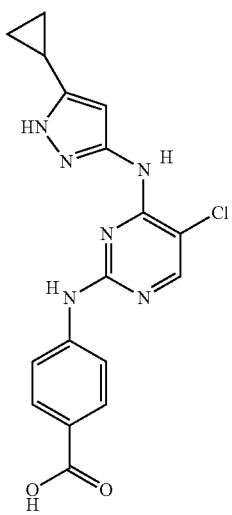
77
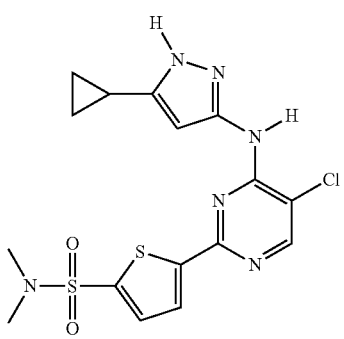
74
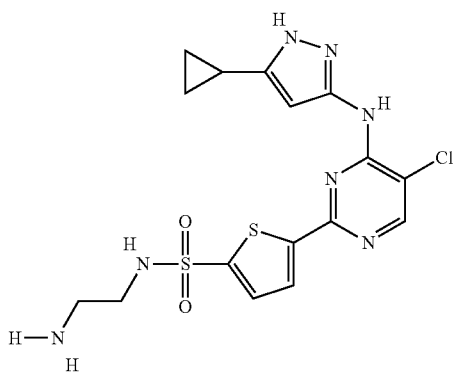
75
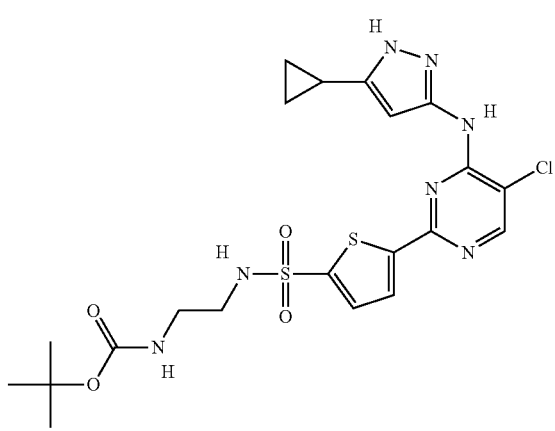
78

79
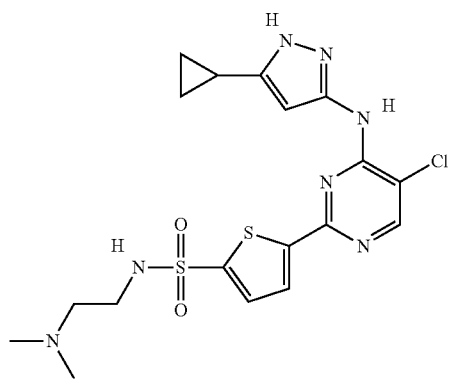
80
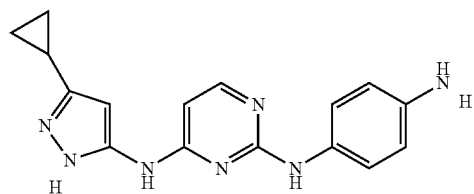
81
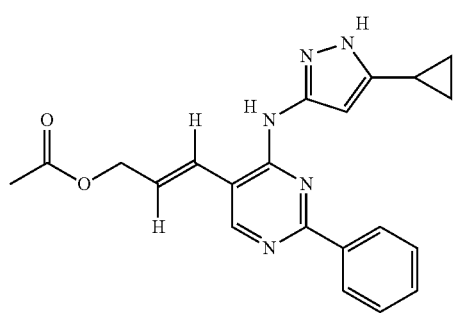
82
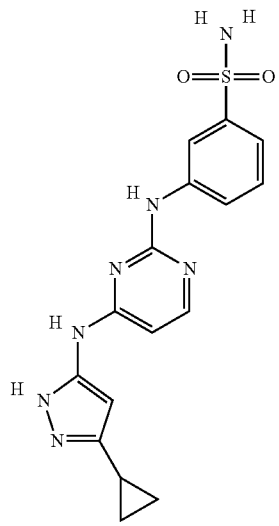
83
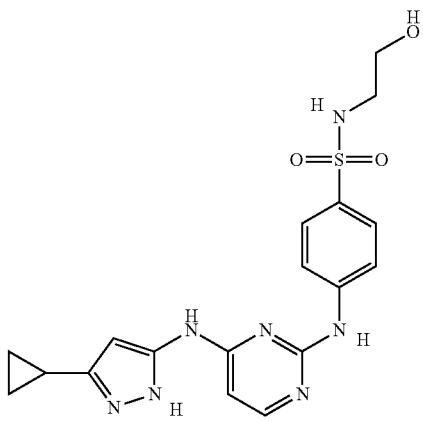
84
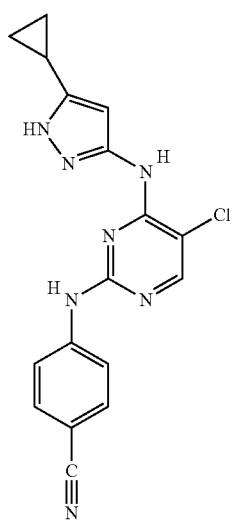
85
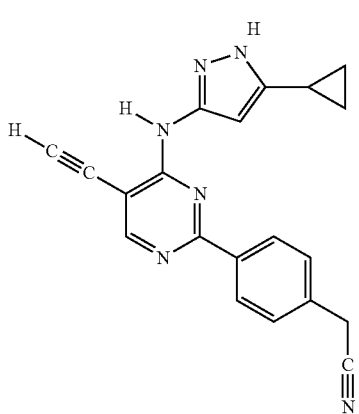

86
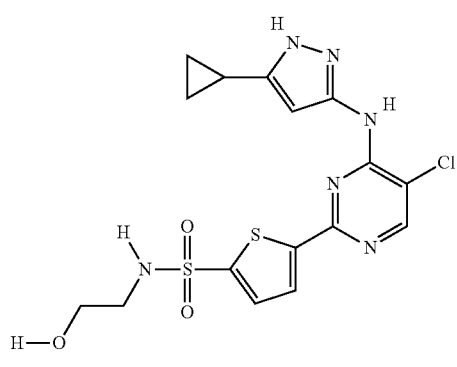
87
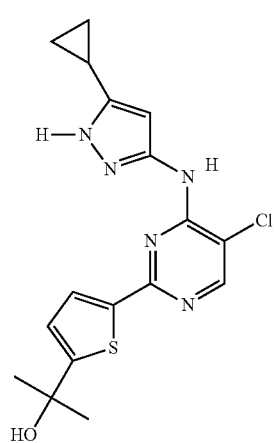
88
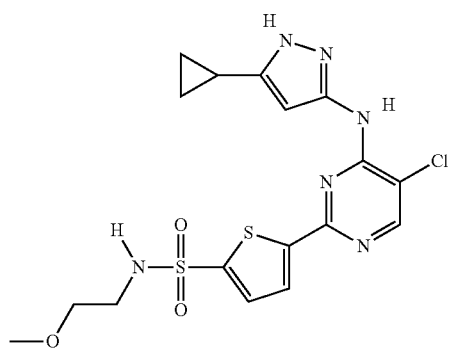
89
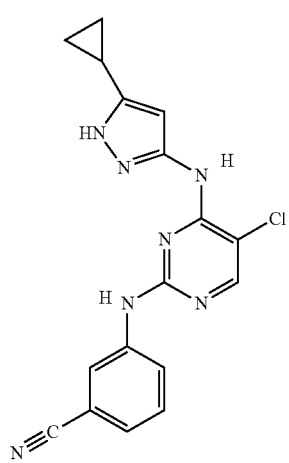
90
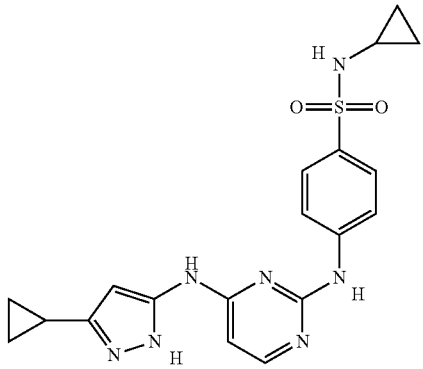
91
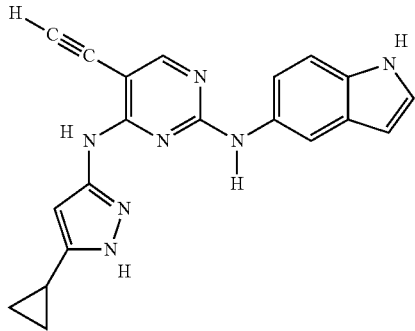
92
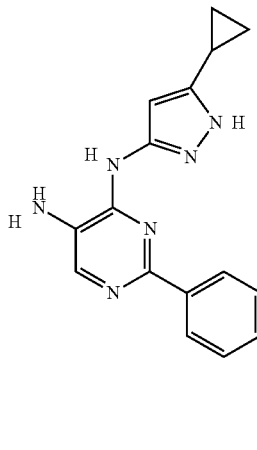
93
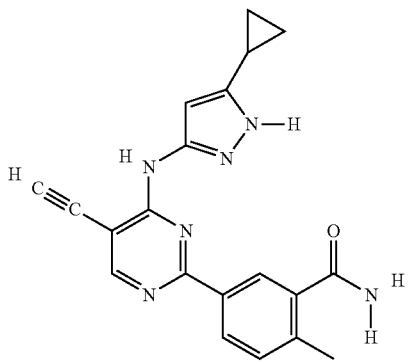

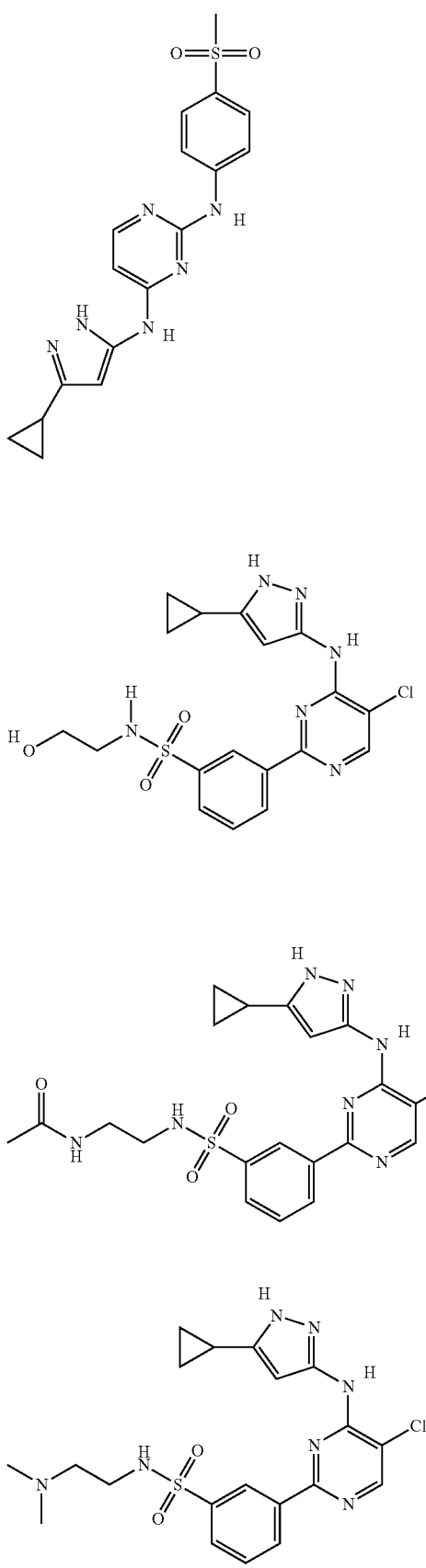
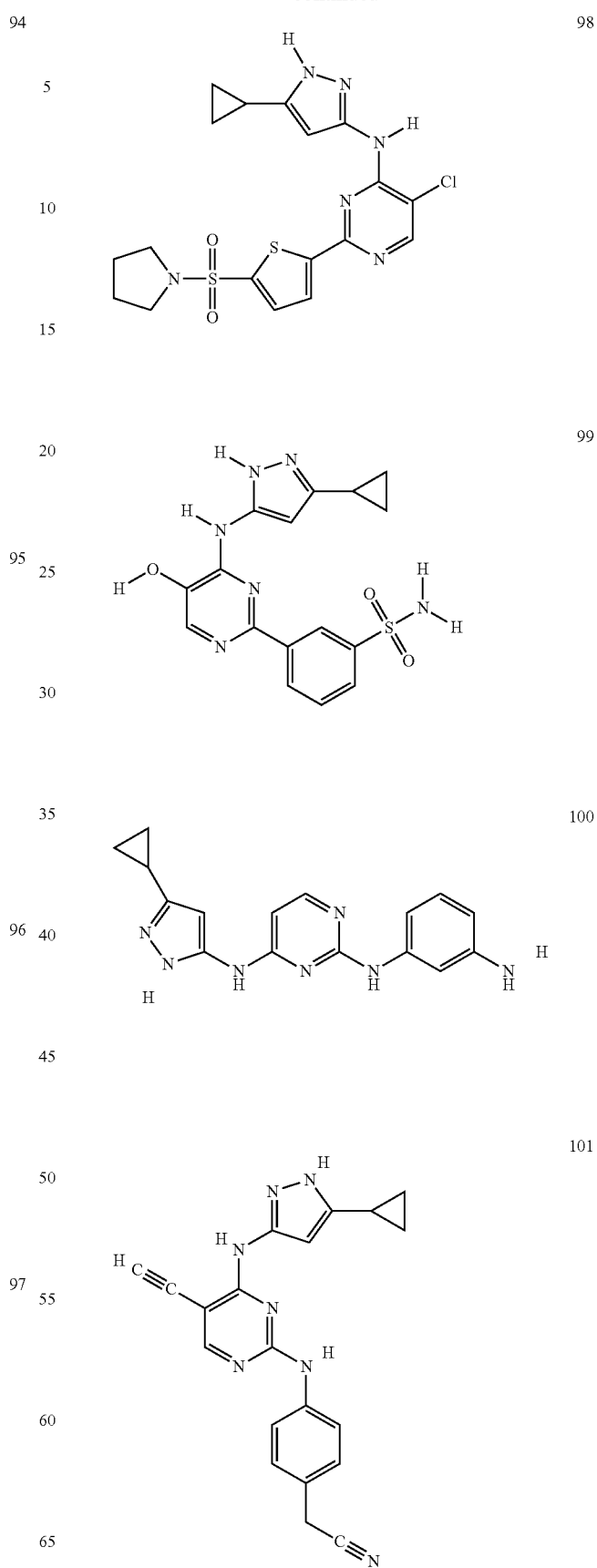

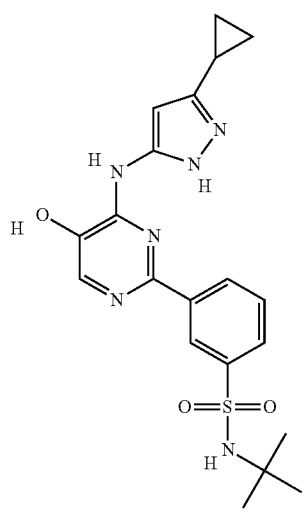
102
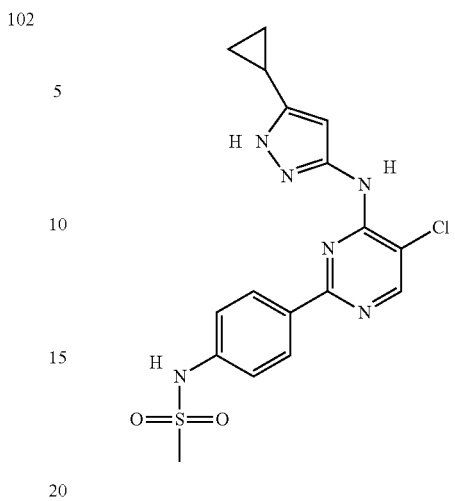
105
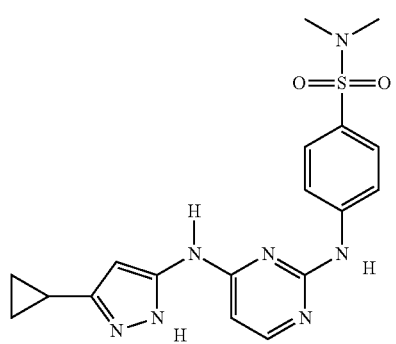
103
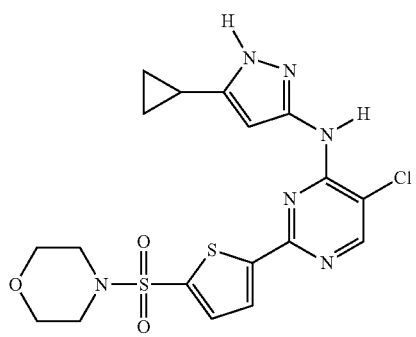
106
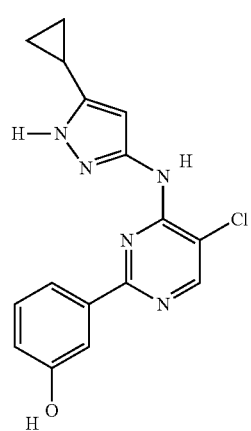
104
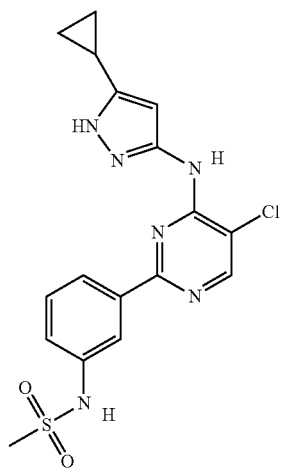
107

| 108 | 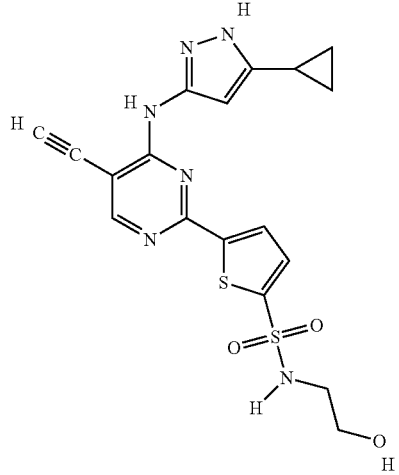 |
| 109 | 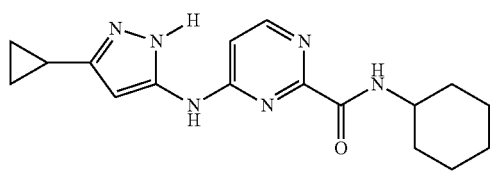 |
| 110 | 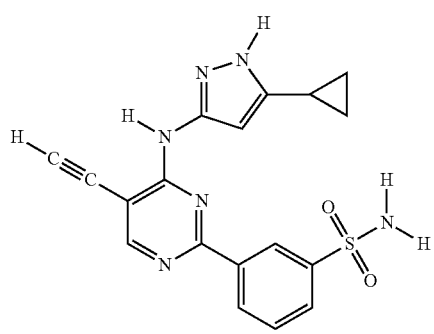 |
| 111 | 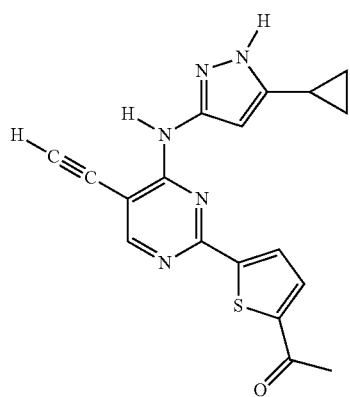 |
| 112 | 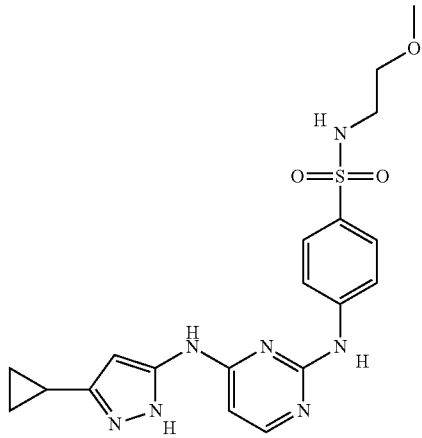 |
| 113 | 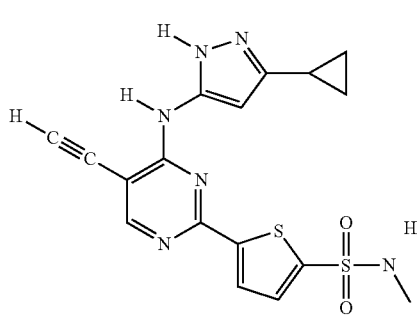 |
| 114 | 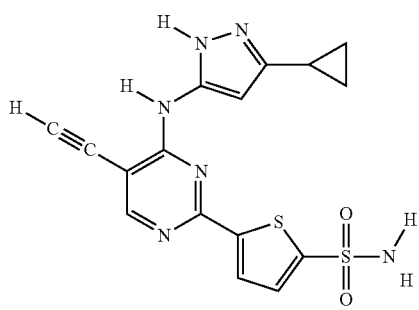 |
| 115 | 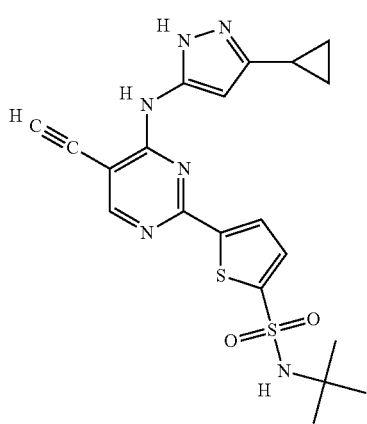 |

433
-continued
434
-continued
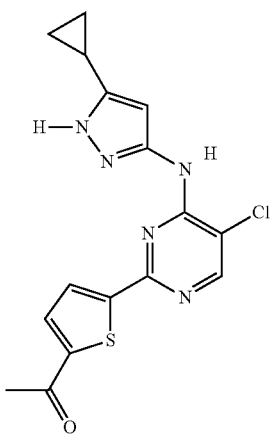
116
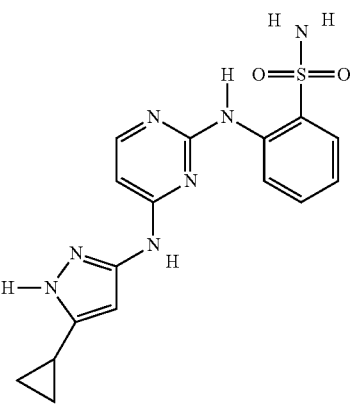
120
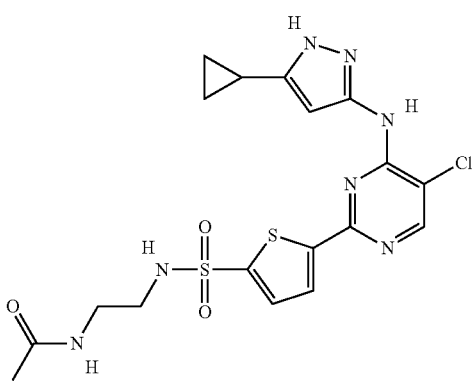
117, 118
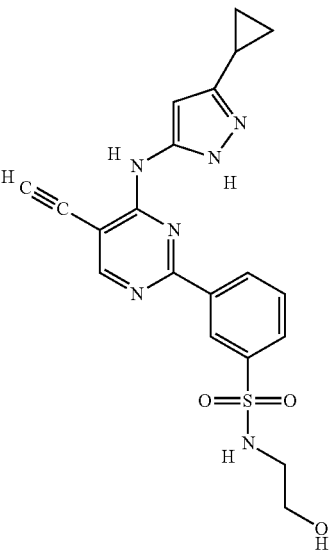
121, 122
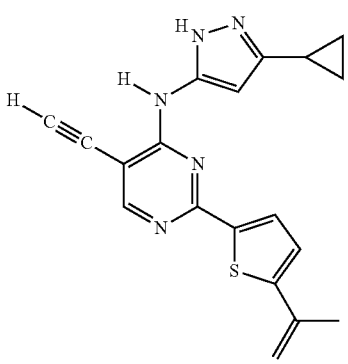
119

123
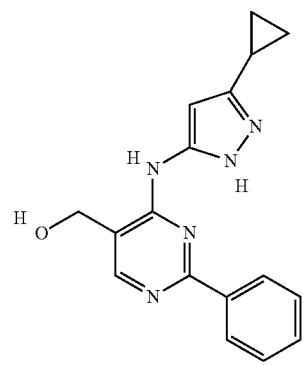
124
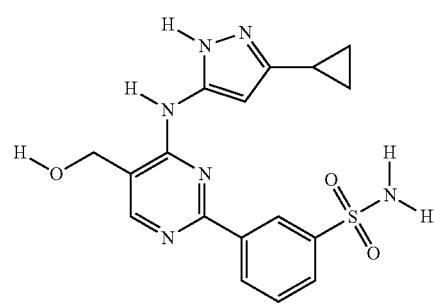
125
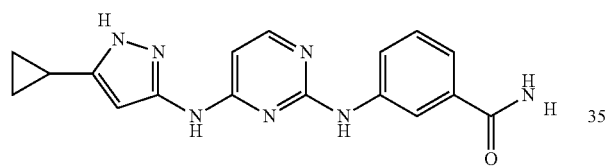
126
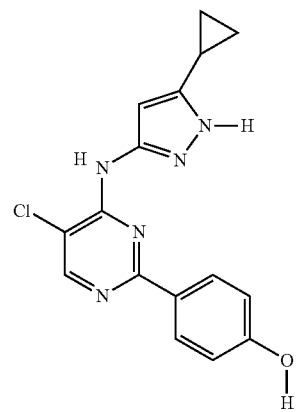
127
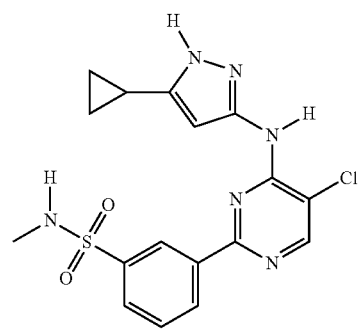
128
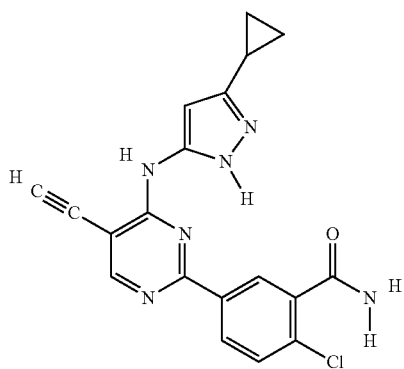
129
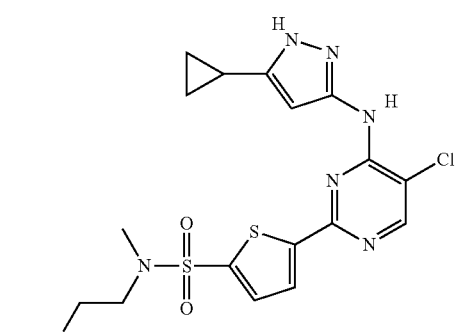
130
131

| | |
|---|---|
| 132 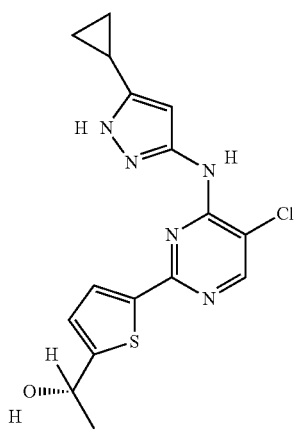 | 136 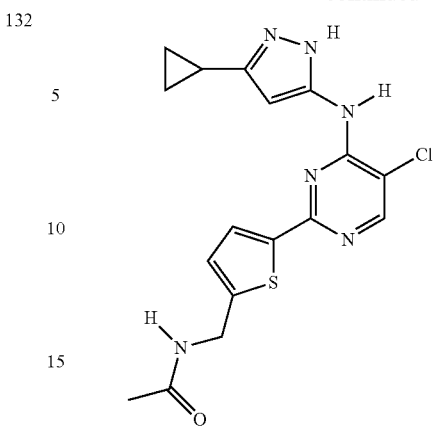 |
| 133 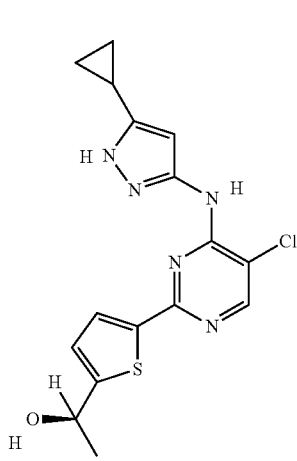 | 137 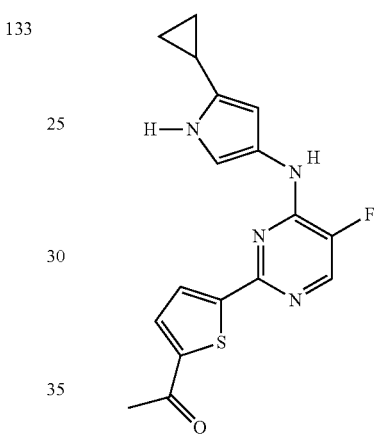 |
| 134 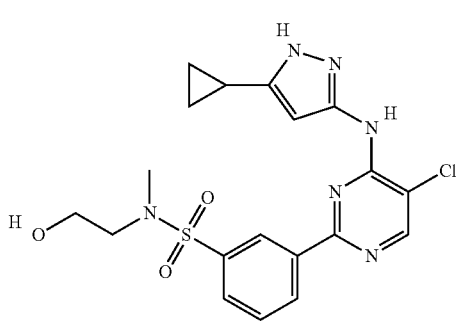 | 138 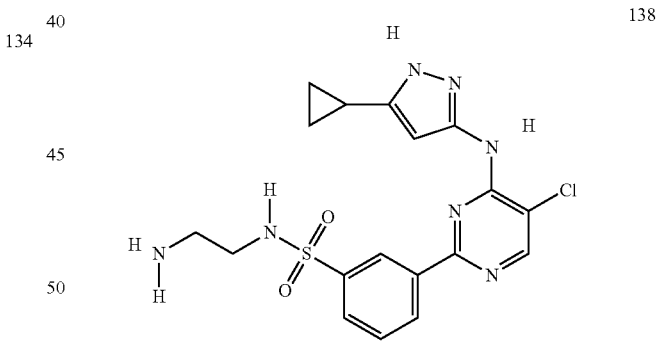 |
| 135 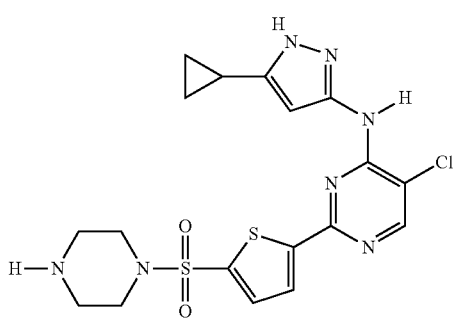 | 139 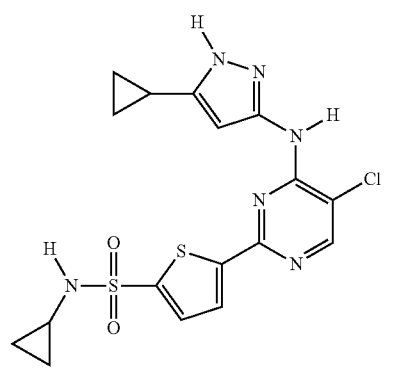 |

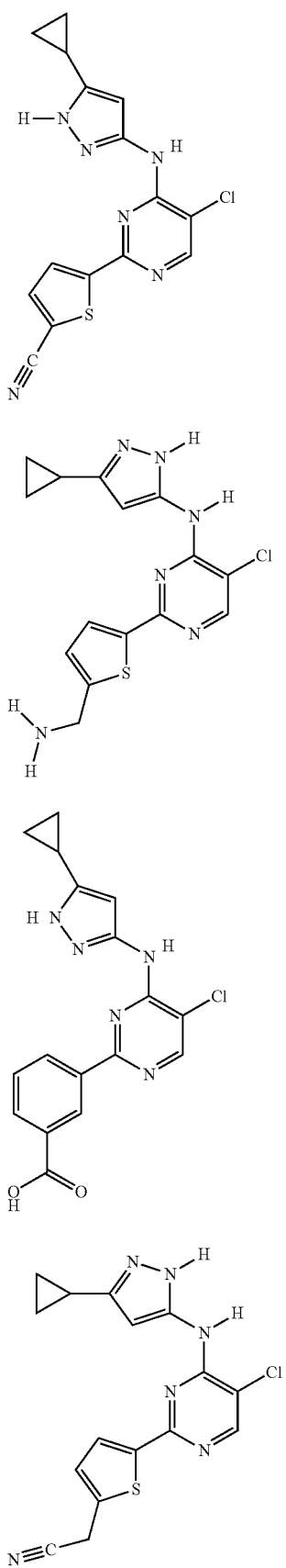
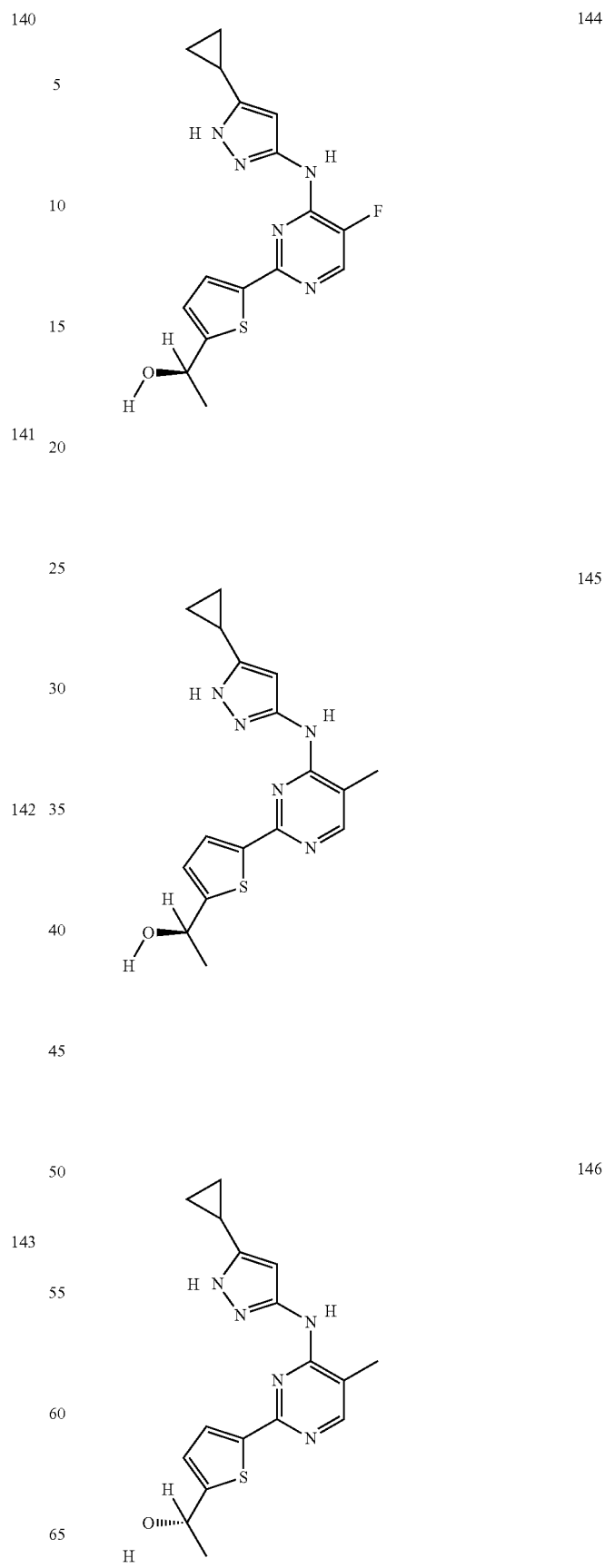

147 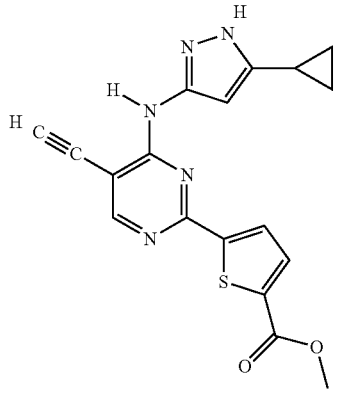
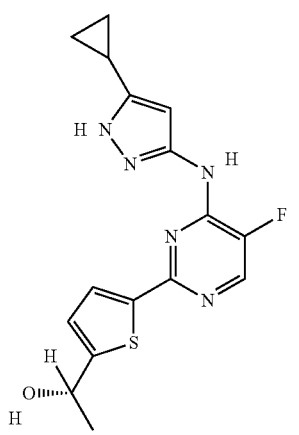
148 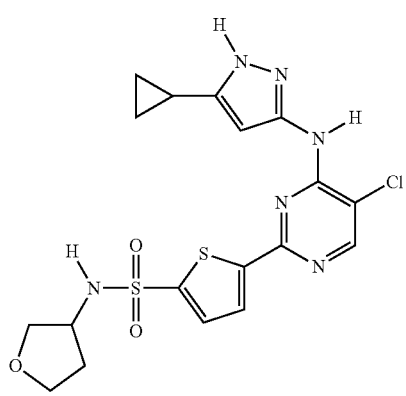
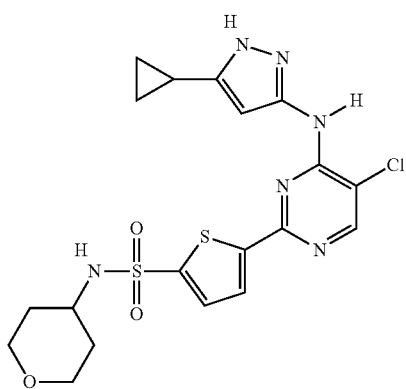
152 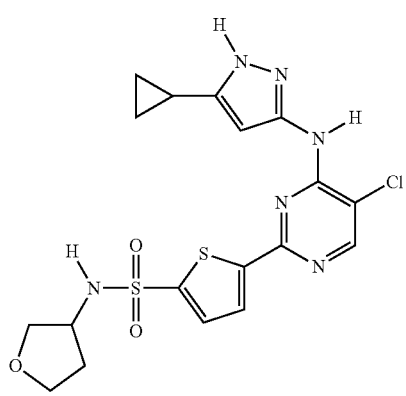
149 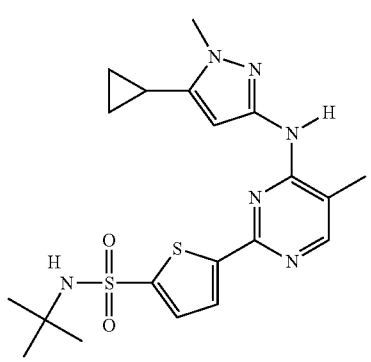
153 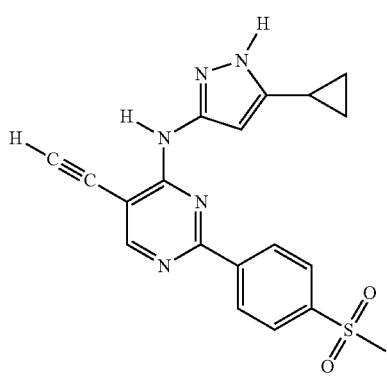
150 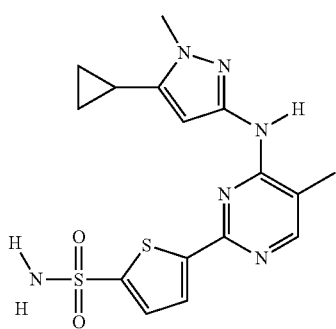
154 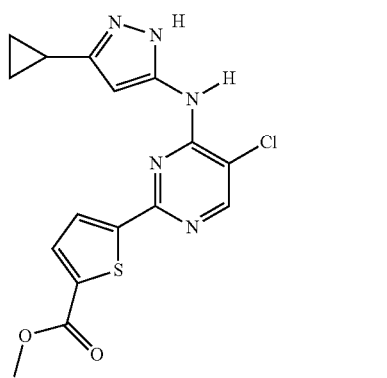

| 155 | 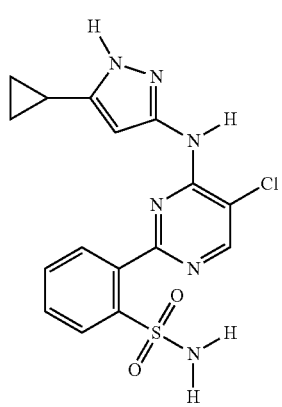 | 159 | 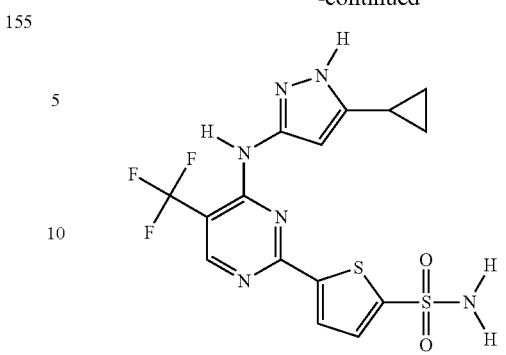 |
| --- | --- | --- | --- |
| 156 | 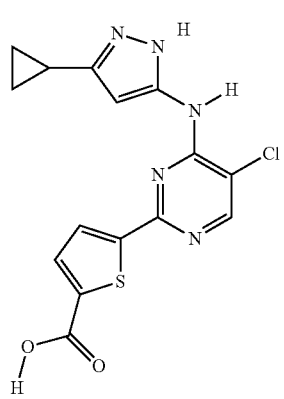 | 160 | 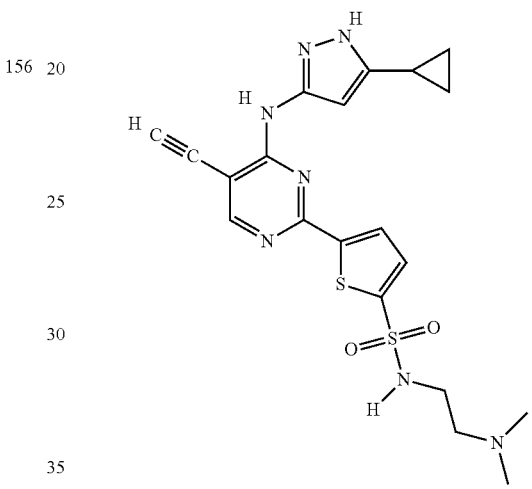 |
| 157 | 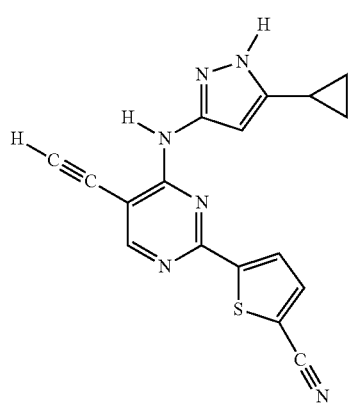 | 161 | 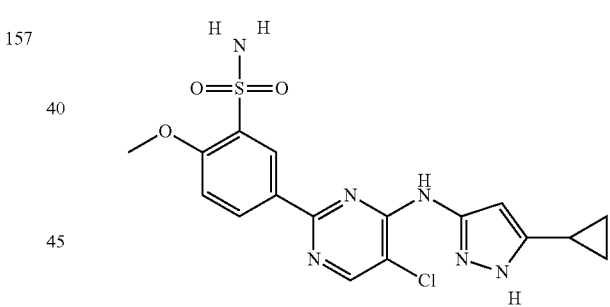 |
| 158 | 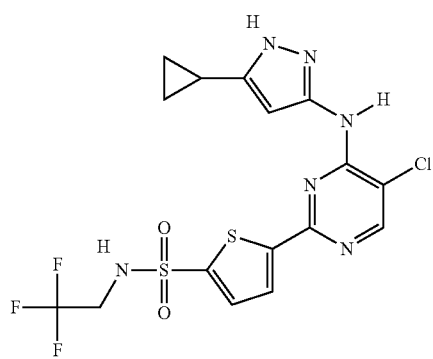 | 162 | 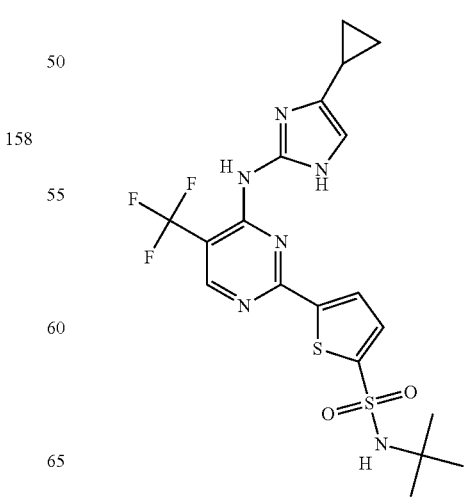 |

163
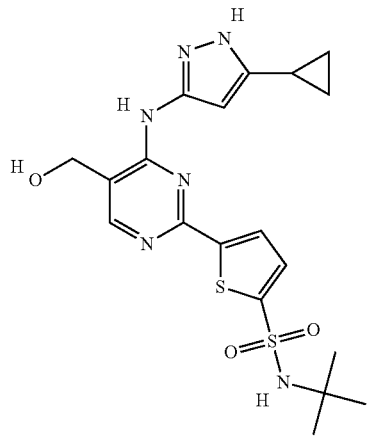
164
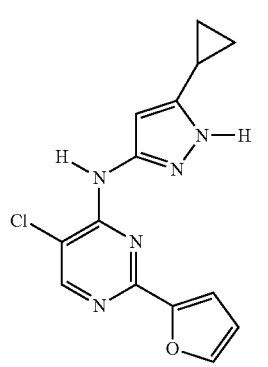
165
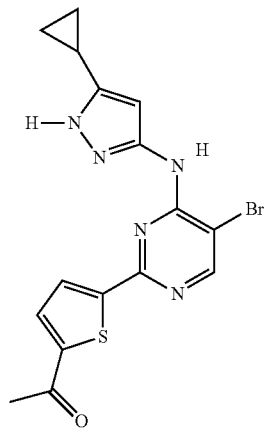
166
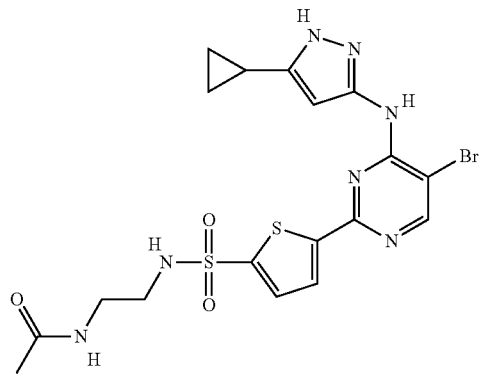
167
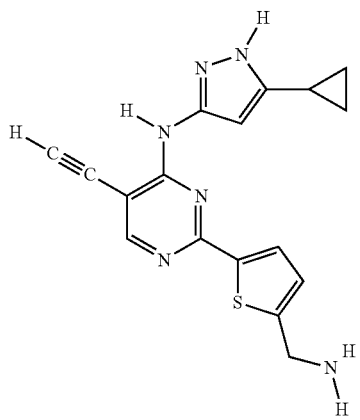
168
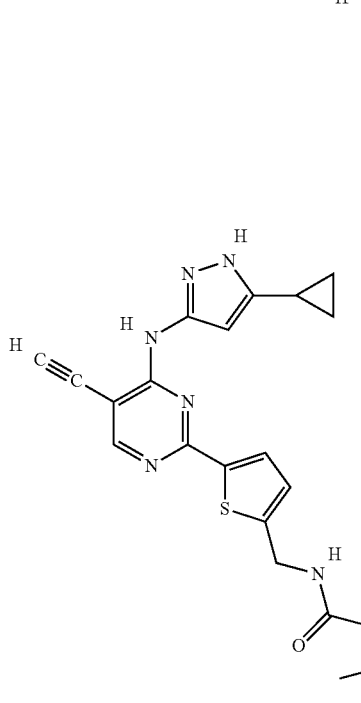
169
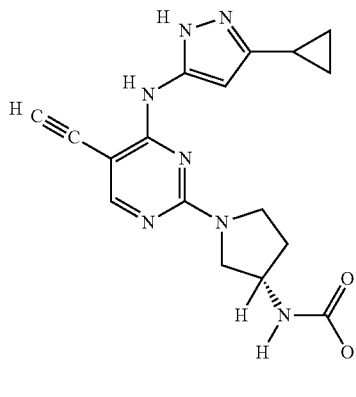

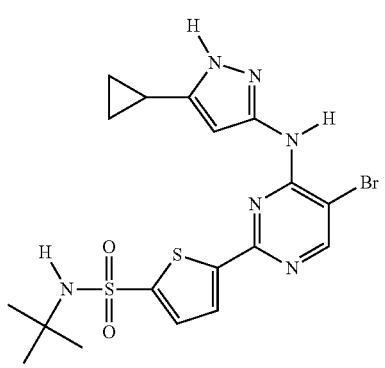
170
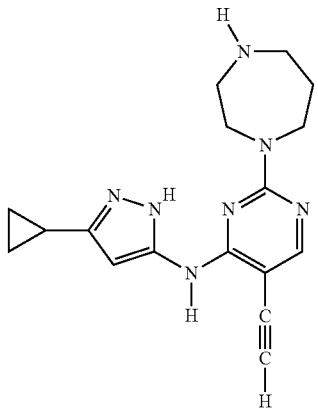
174
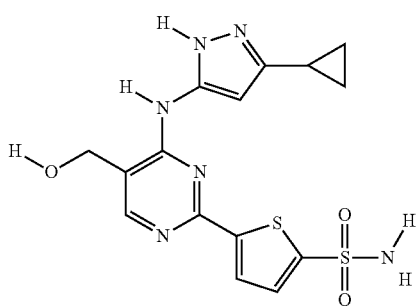
171
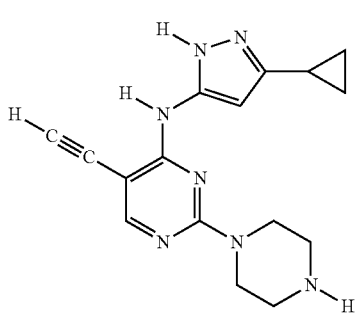
175
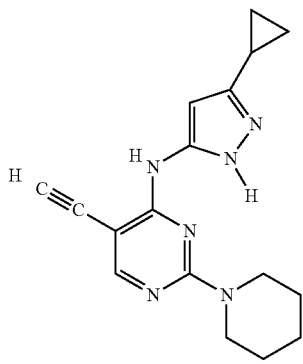
172
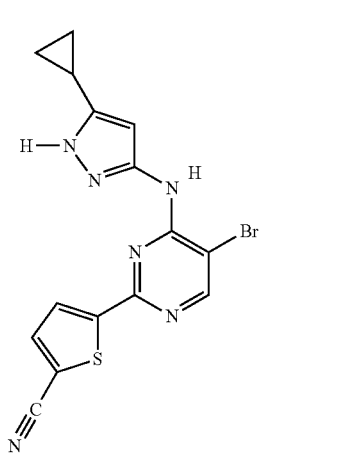
176
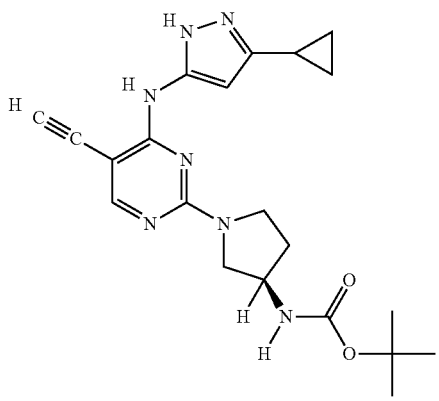
173
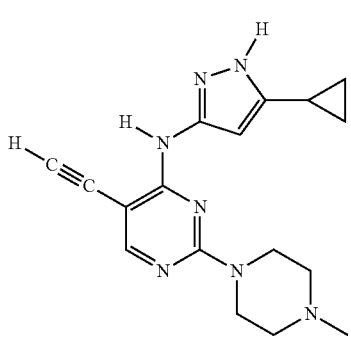
177

| 178 | 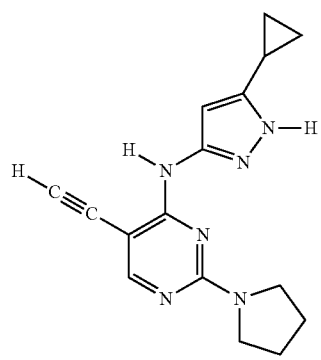 | 182 | 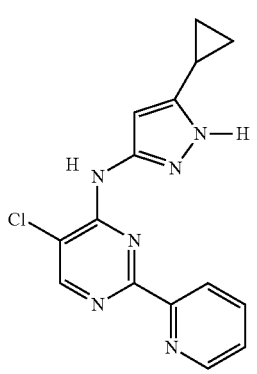 |
| 179 | 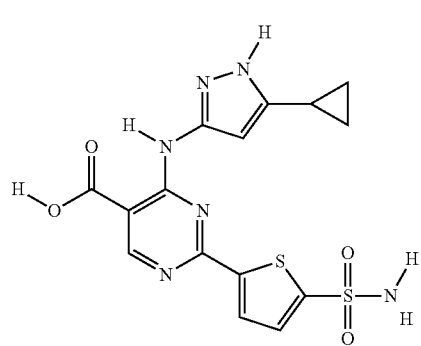 | 183 | 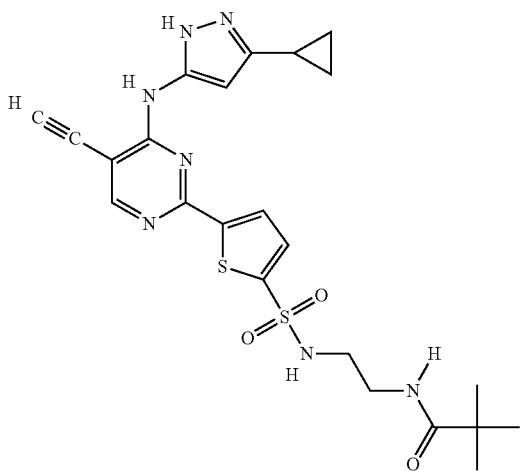 |
| 180 | 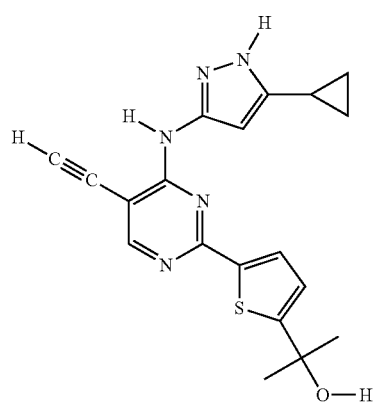 | 184 | 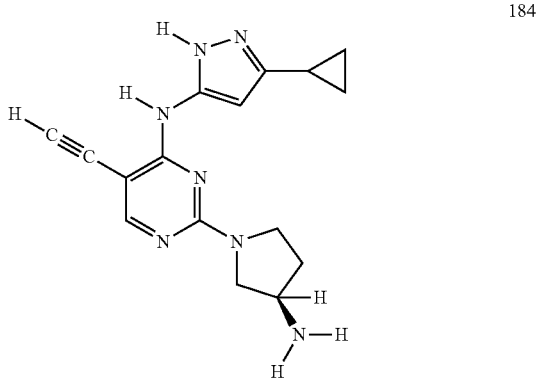 |
| 181 | 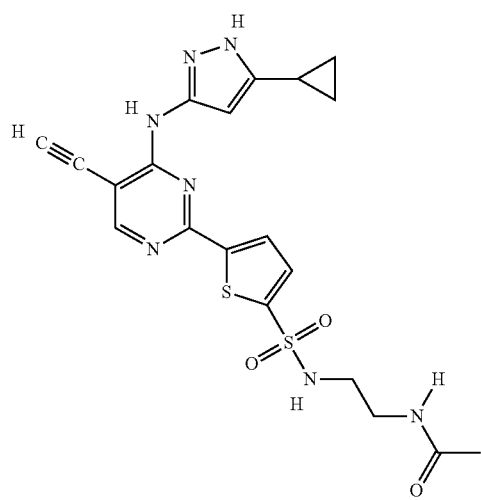 | 185 | 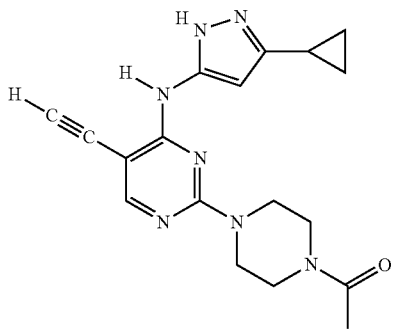 |

451
-continued
186
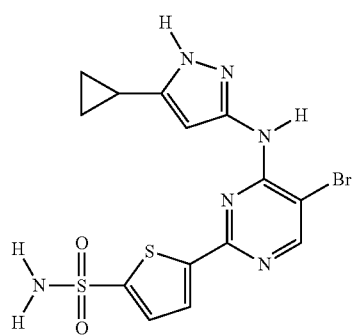
187
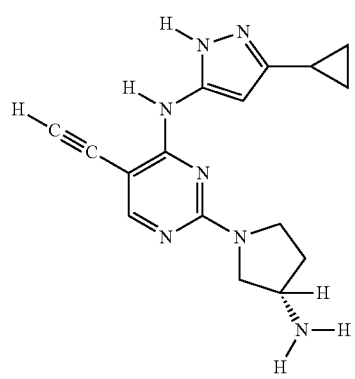
188
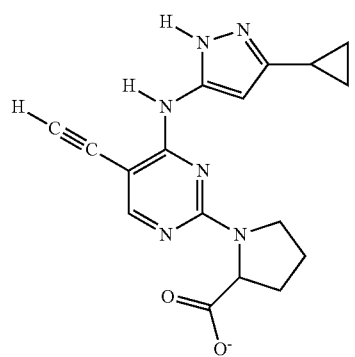
189
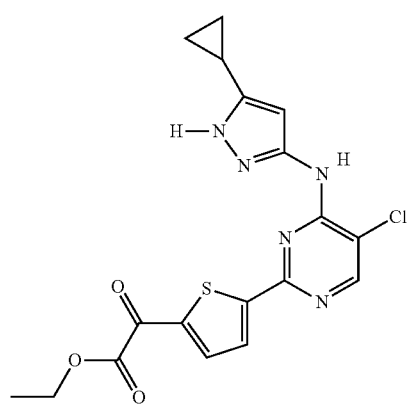
452
-continued
190
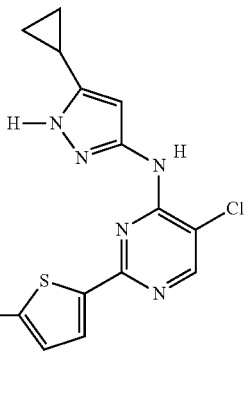
191
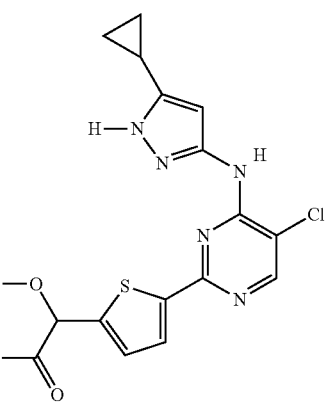
192
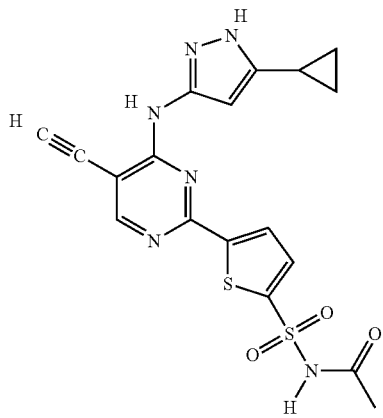
193
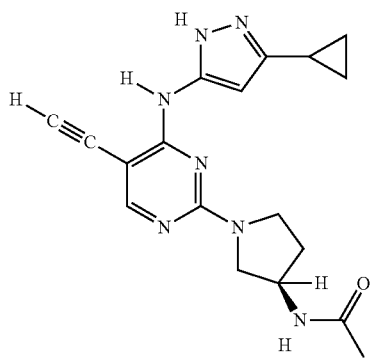

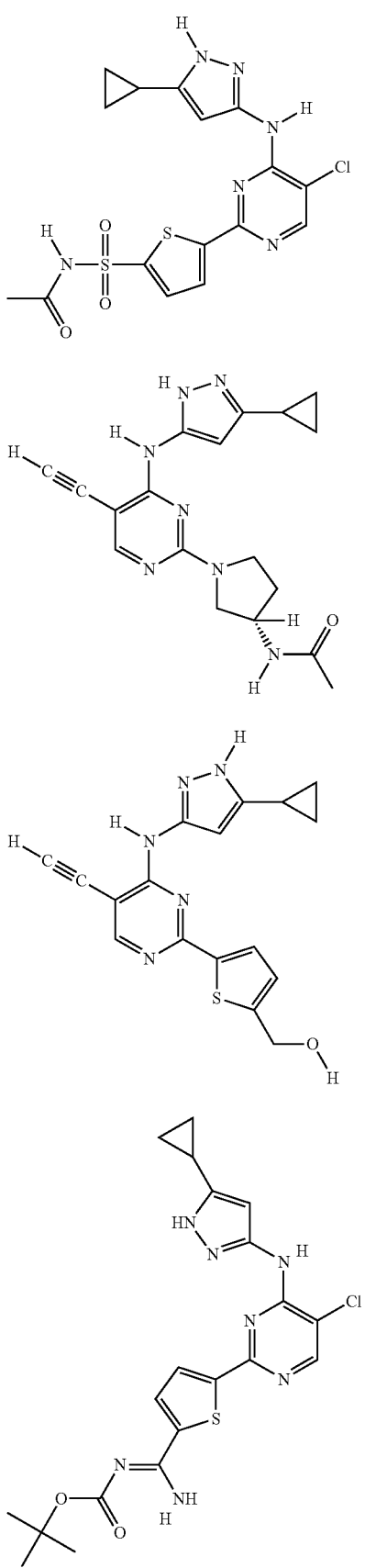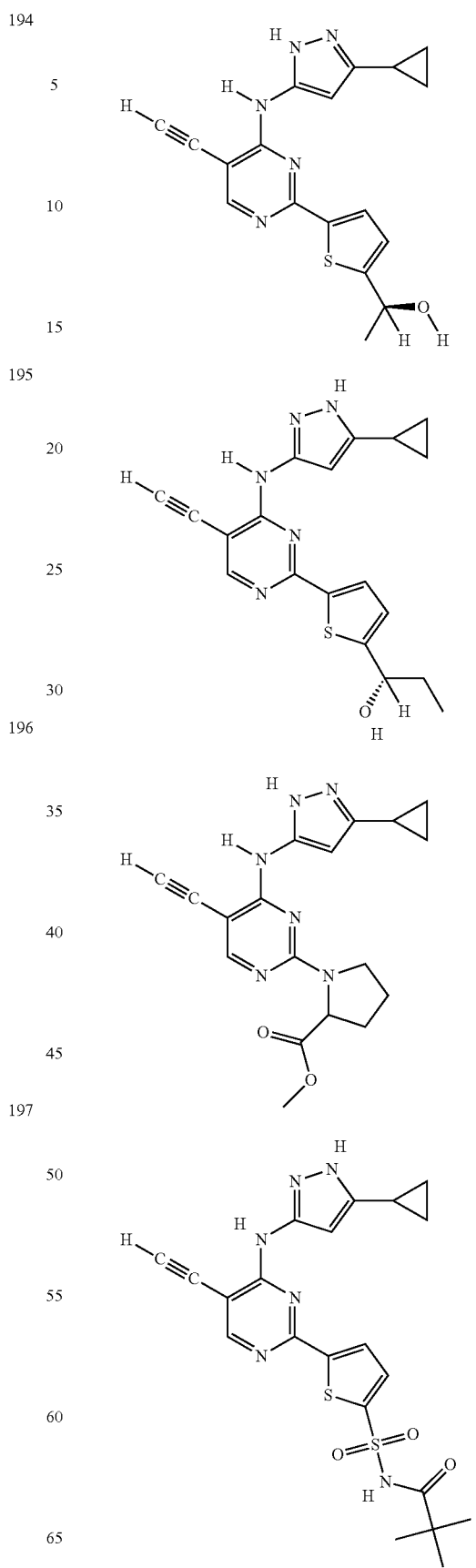

| 202 | 206 |
|---|---|
| 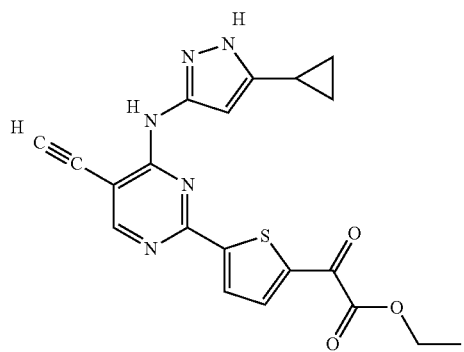 | 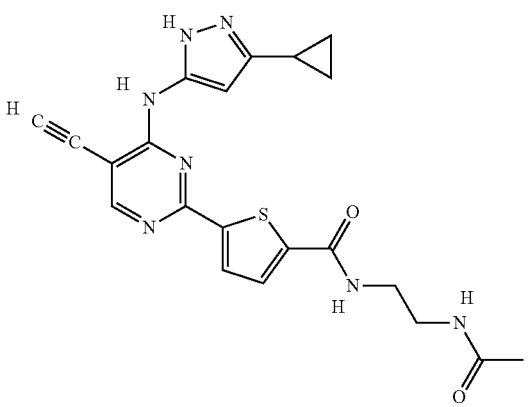 |
| 203 | 207 |
| 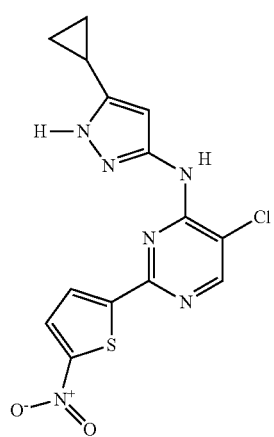 | 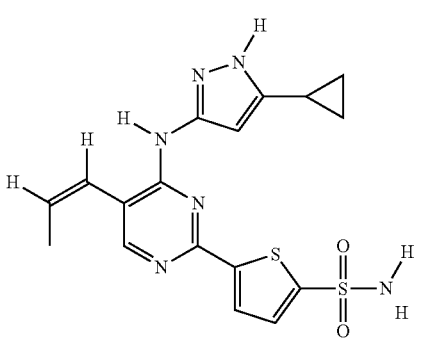 |
| 204 | 208 |
| 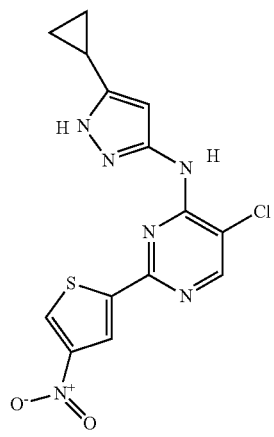 | 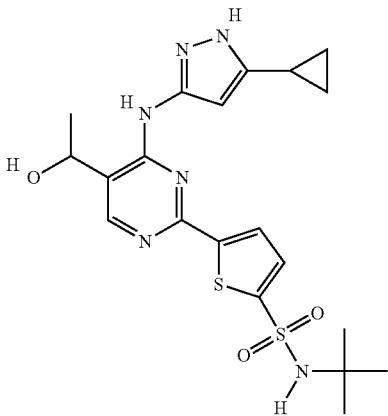 |
| 205 | 209 |
| 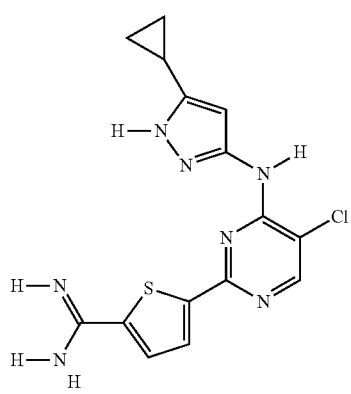 | 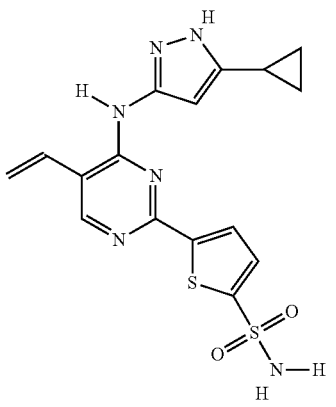 |

210 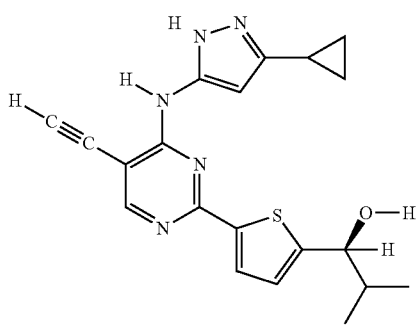
211 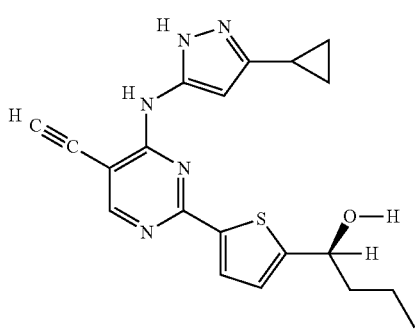
212 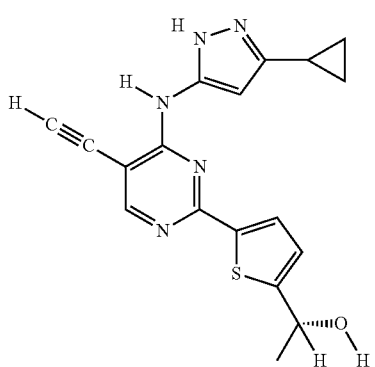
213 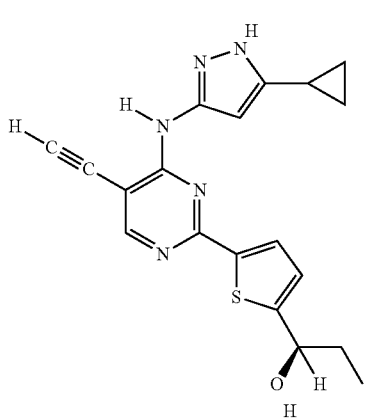
214 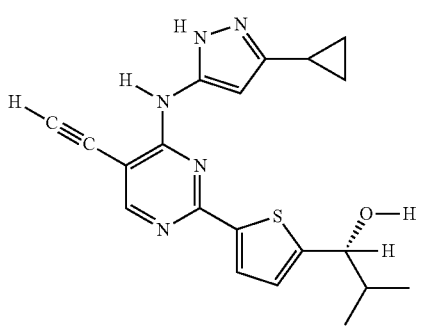
215 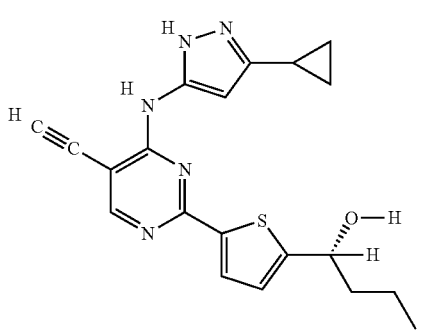
216 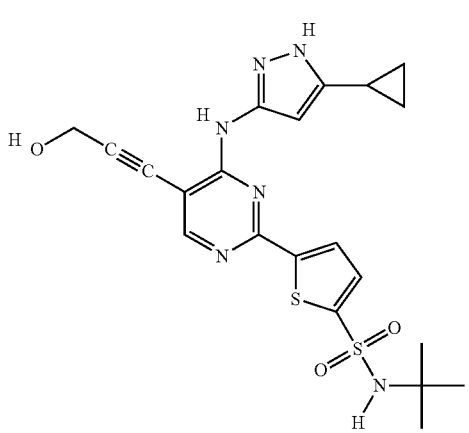
217 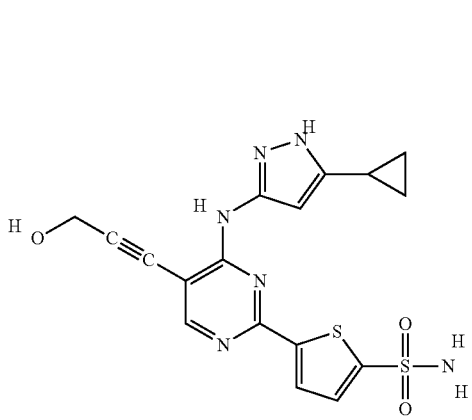

218 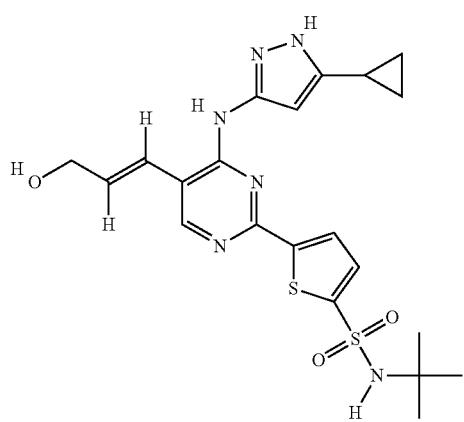
5 222 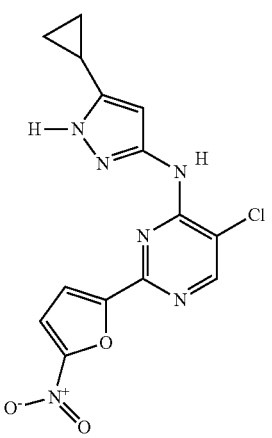
219 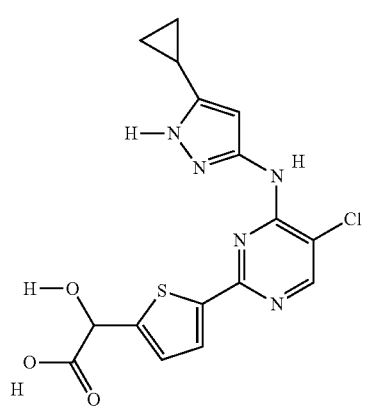
223 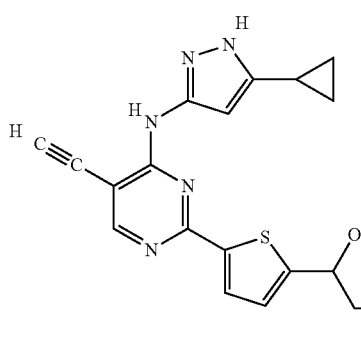
220 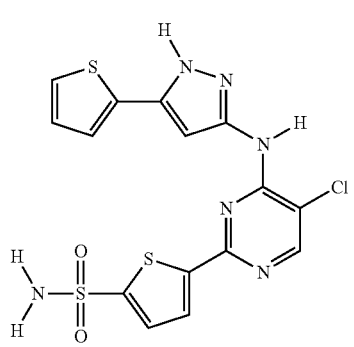
224 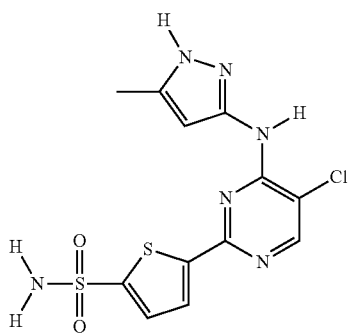
221 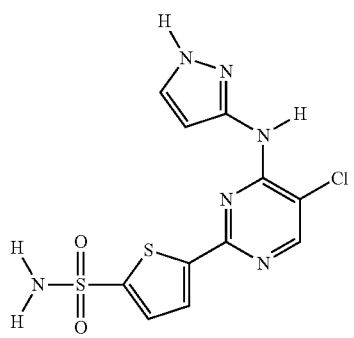
225 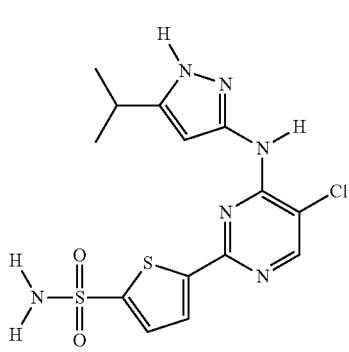

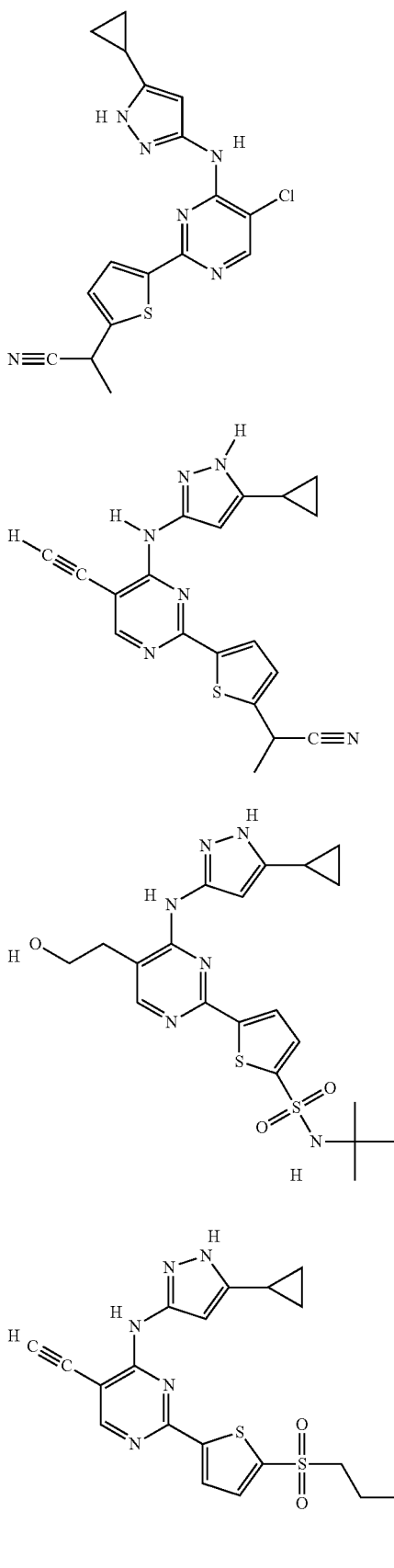
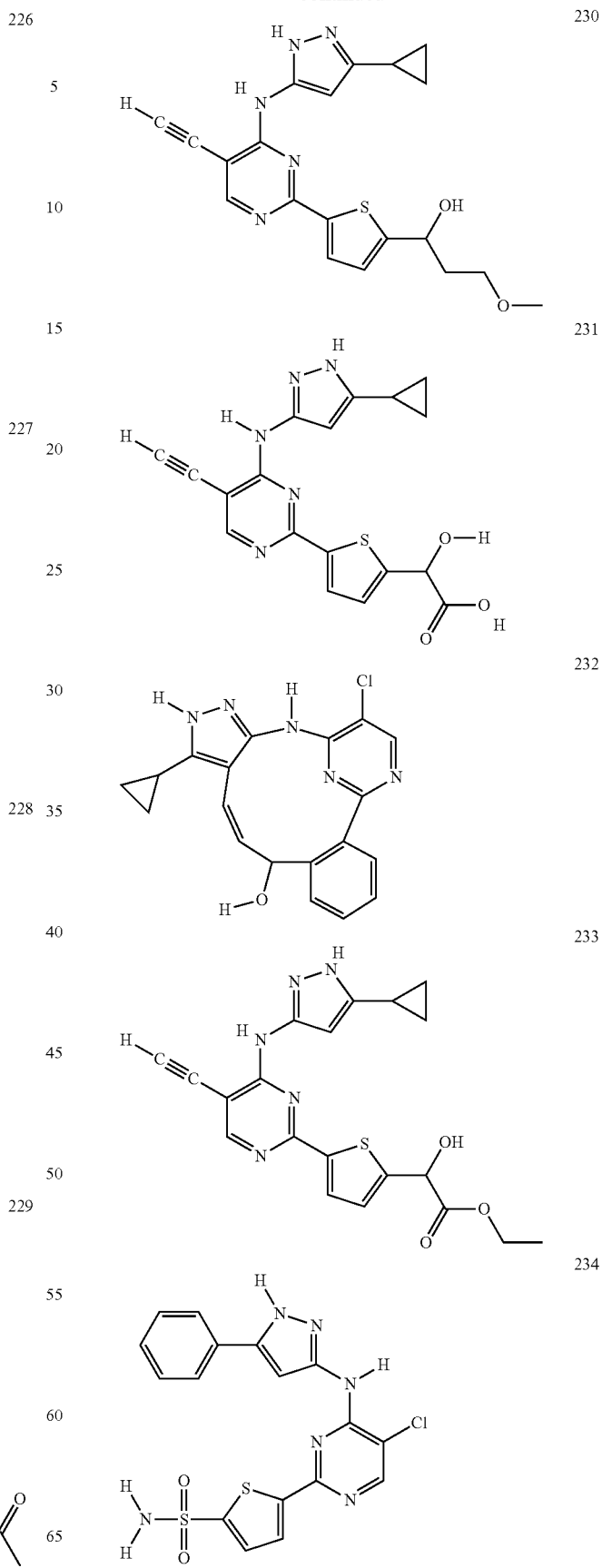

463 -continued
235 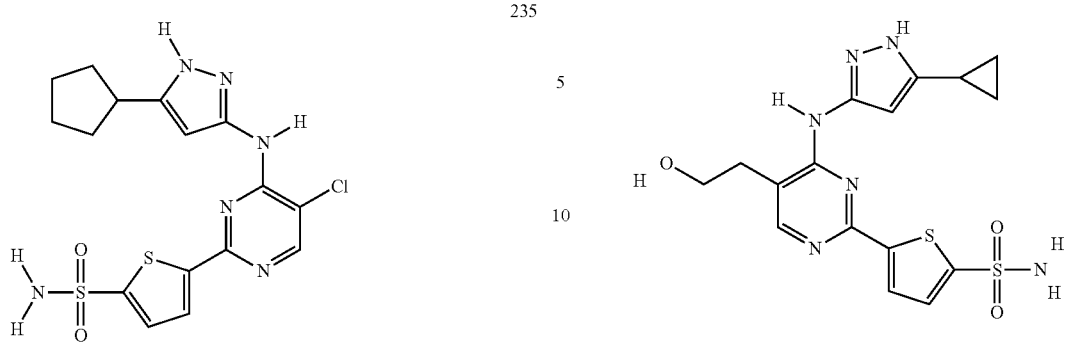
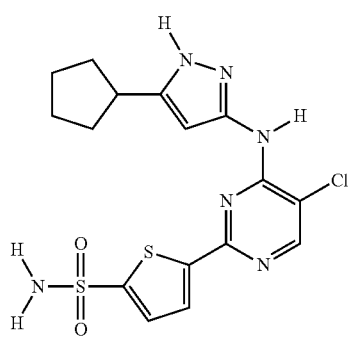
236 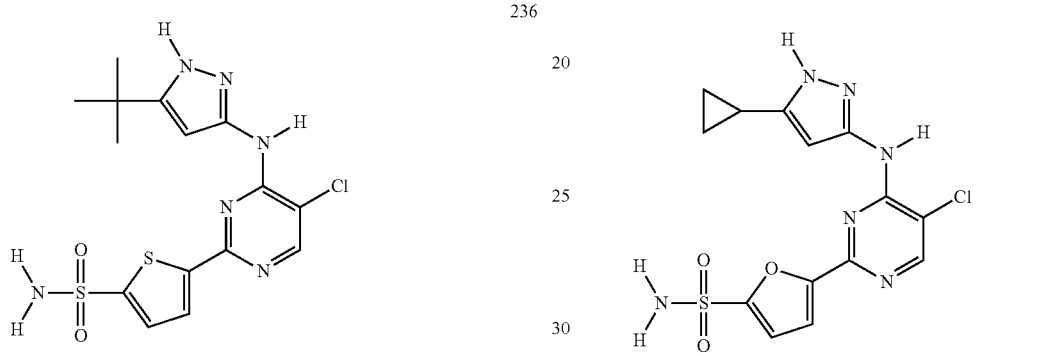
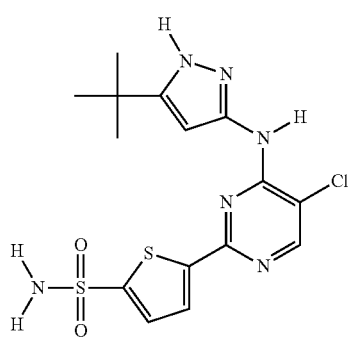
237
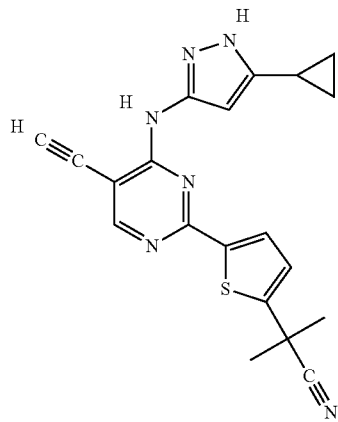
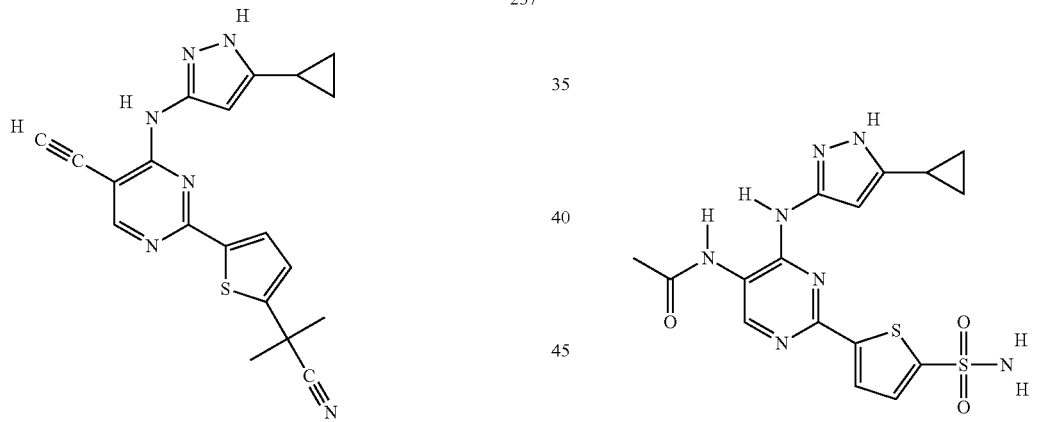
238
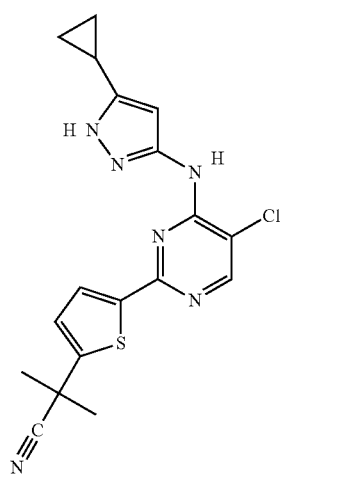
464 -continued
239
240
241
242

| 243 | 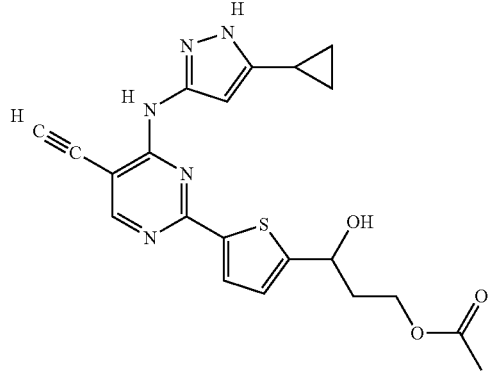 | 247 | 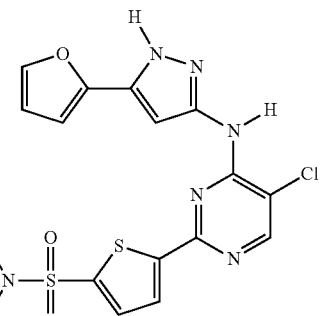 |
| 244 | 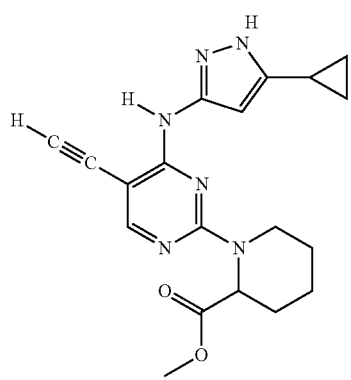 | 248 | 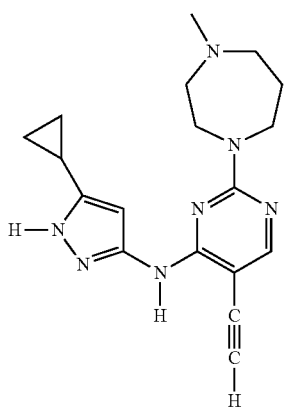 |
| 245 | 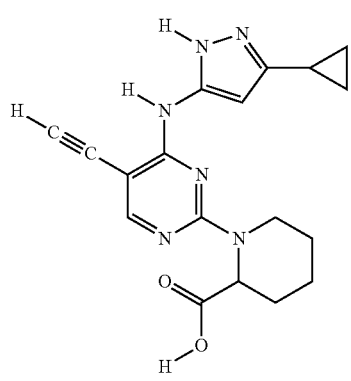 | 249 | 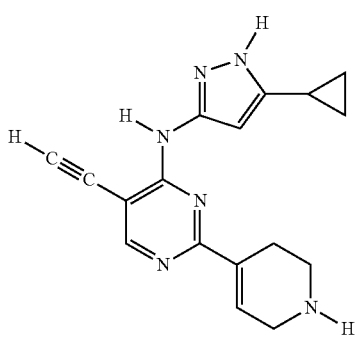 |
| 246 | 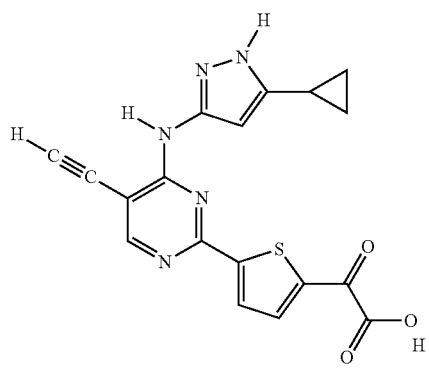 | 250 | 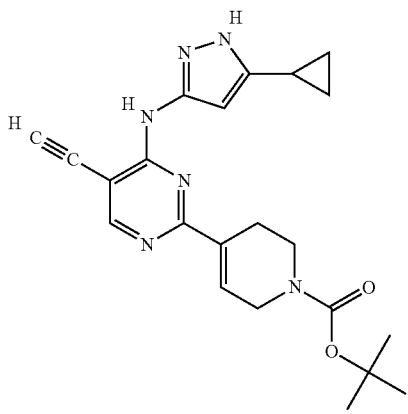 |

251 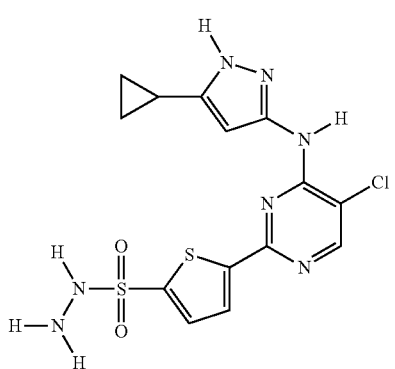
252 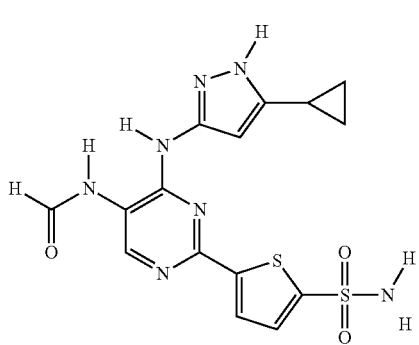
253 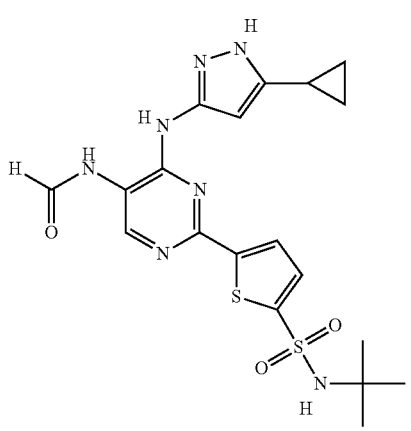
254 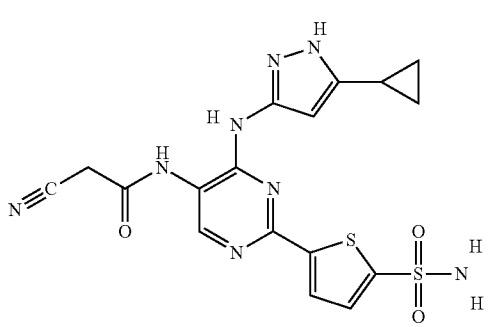
255 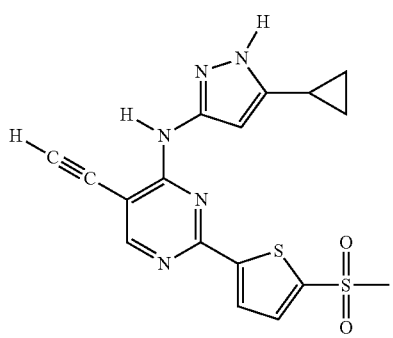
256 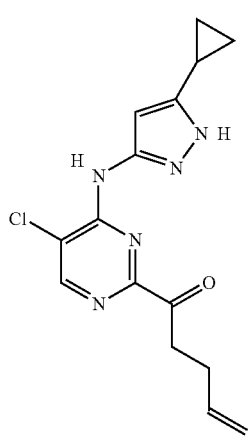
257 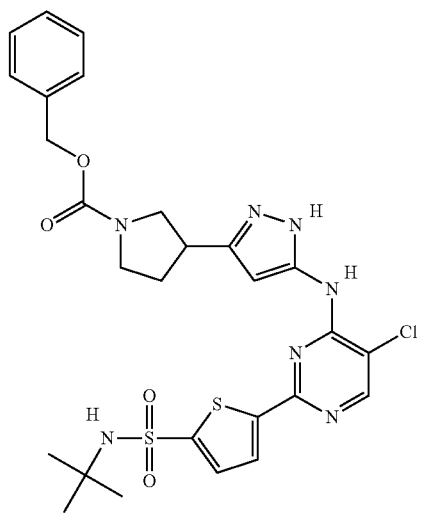

| 258 | 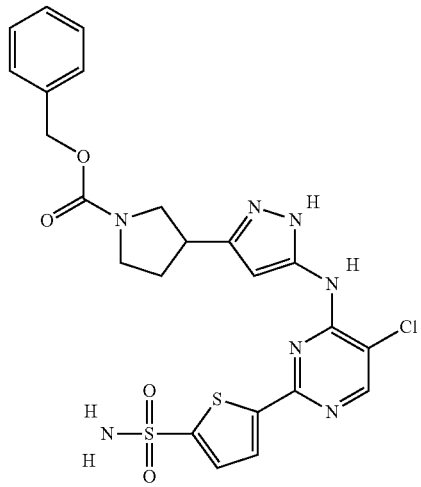 |
|---|---|
| | 262 |
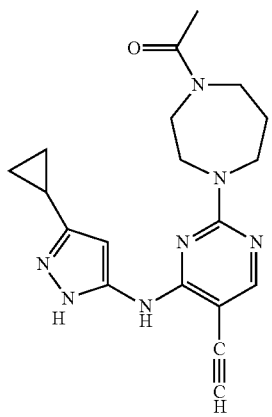
259
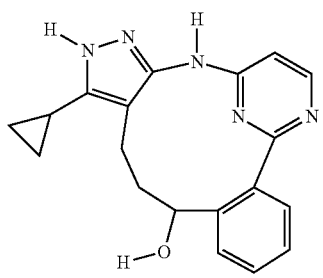
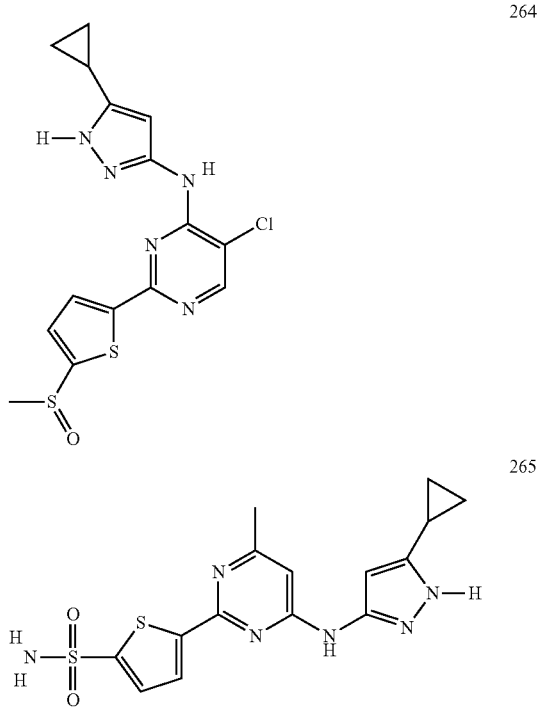
260
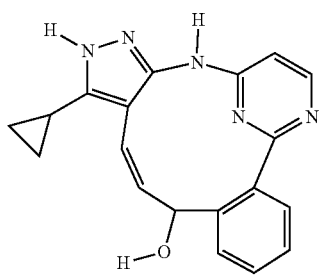
261
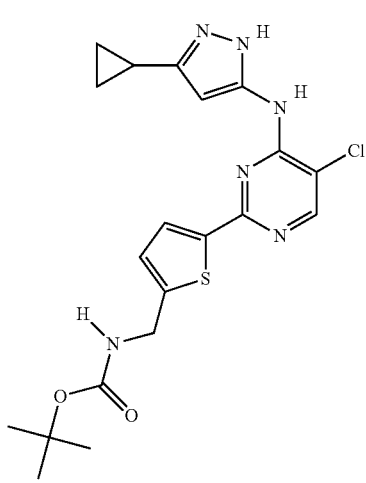

| 266 | 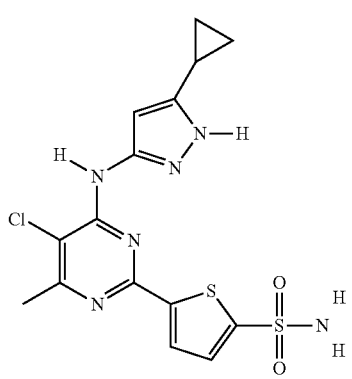 |
| 267 | 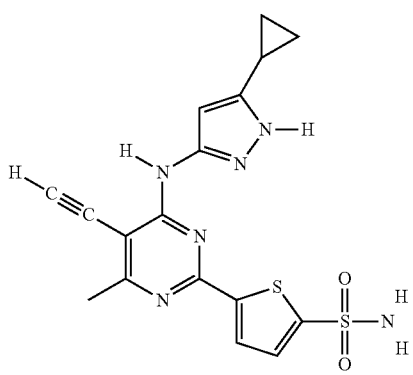 |
| 268 | 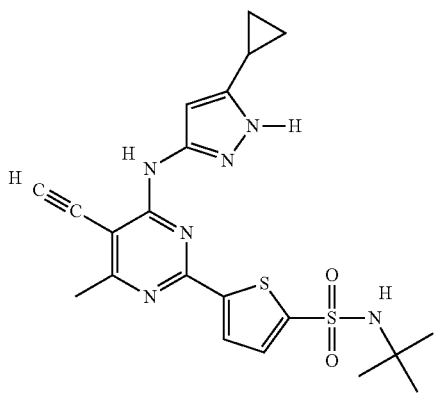 |
| 269 | 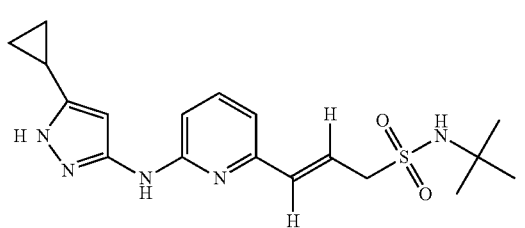 |
| 270 | 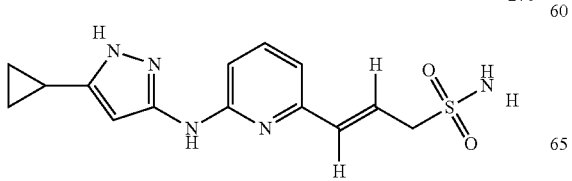 |
| 271 | 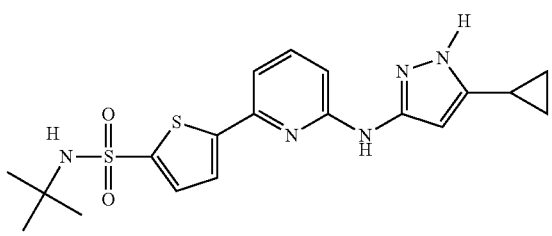 |
| 272 | 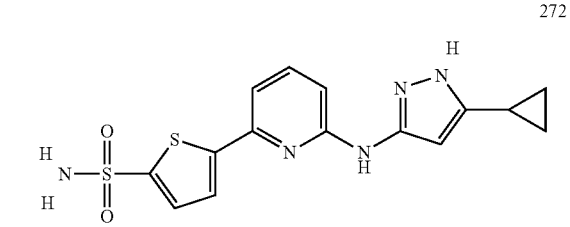 |
| 273 | 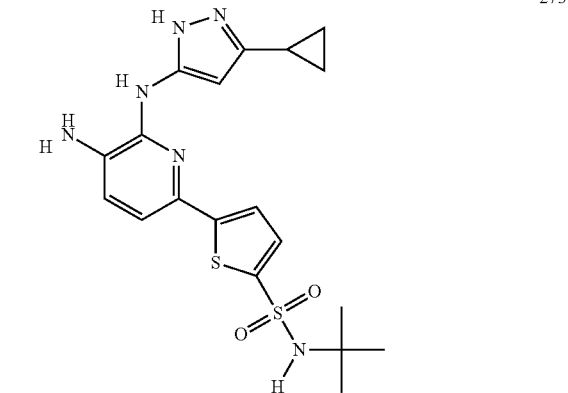 |
| 274 | 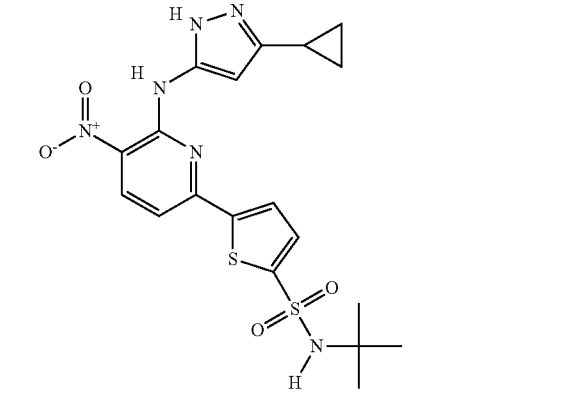 |
| 275 | 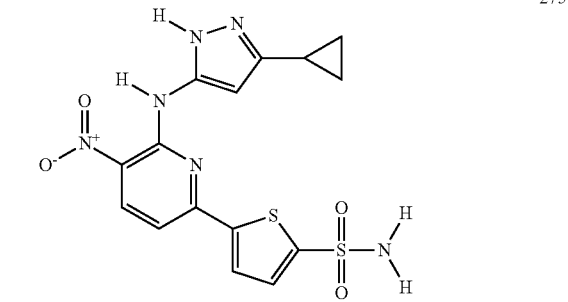 |

| 276 | 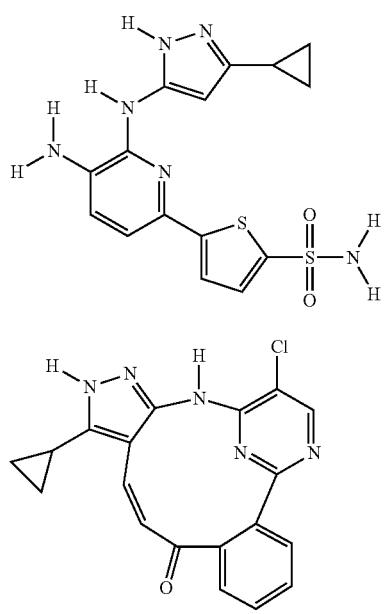 | 280 | 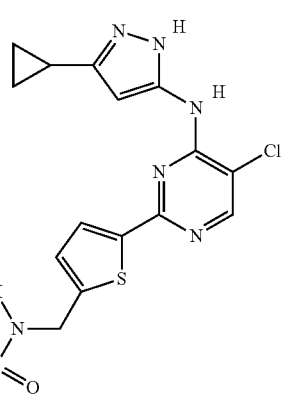 |
| 277 | | | |
| 278 | 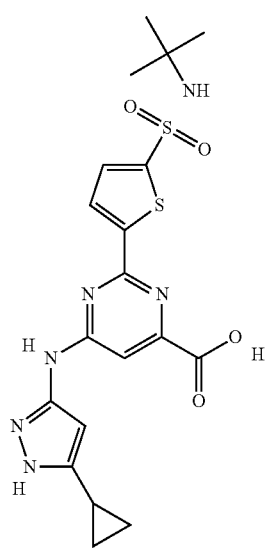 | 281 | 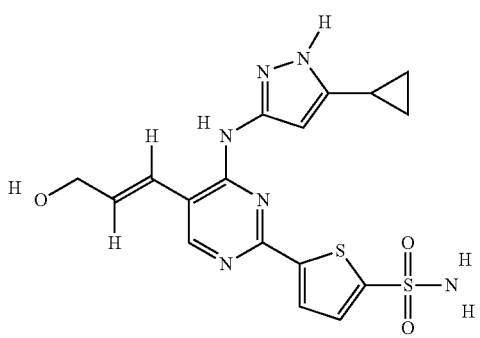 |
| 279 | 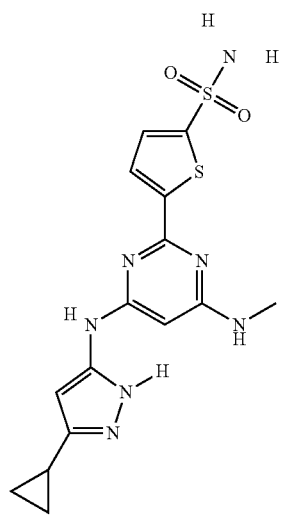 | 282 | 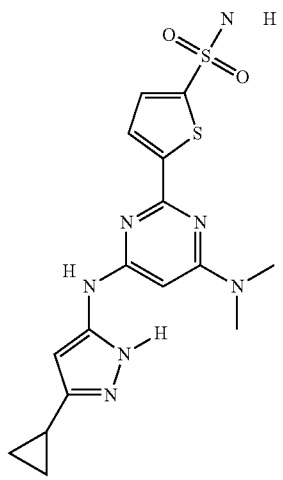 |

475
-continued
283
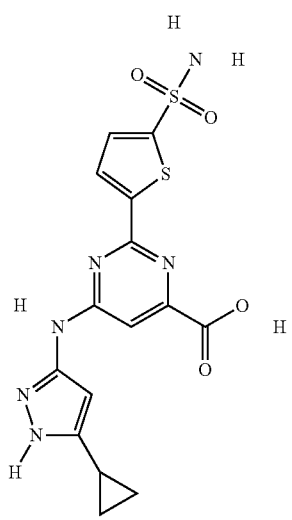
284
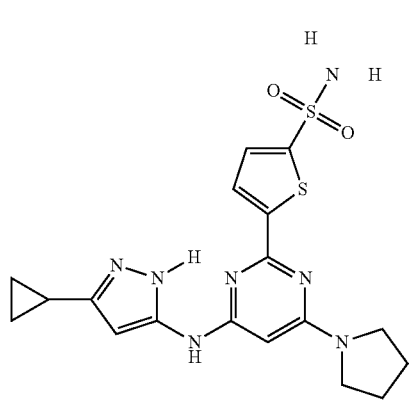
285
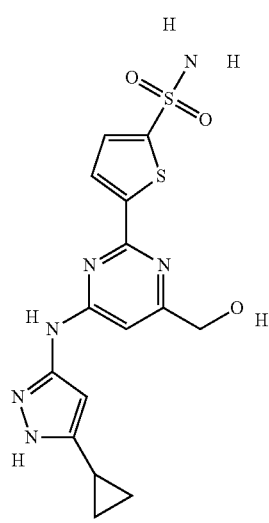
476
-continued
286
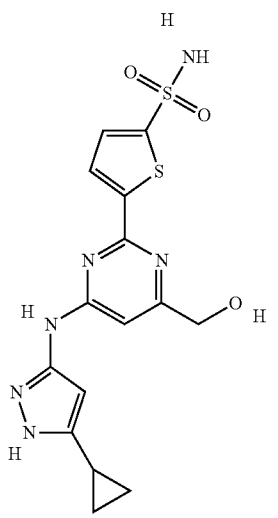
287
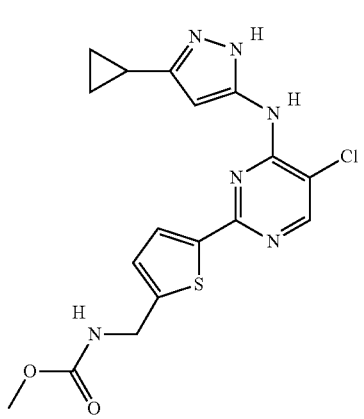
288
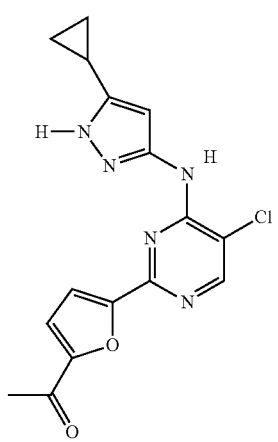

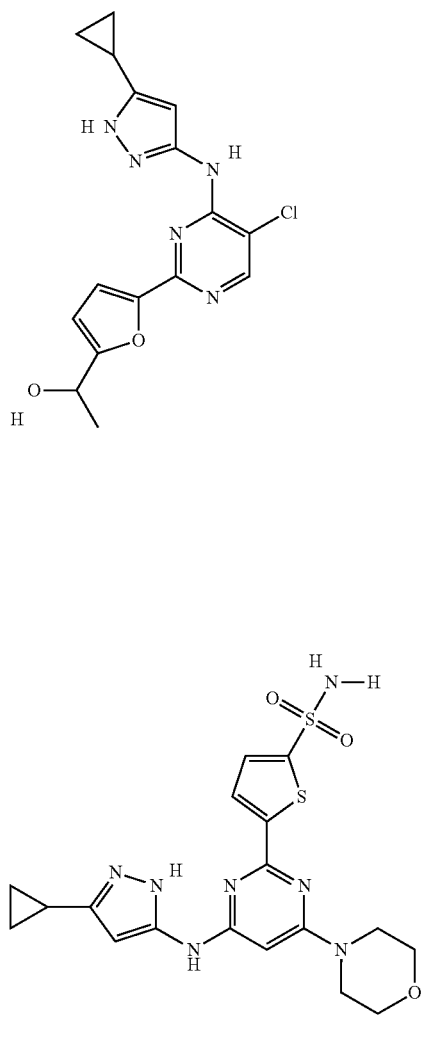
289
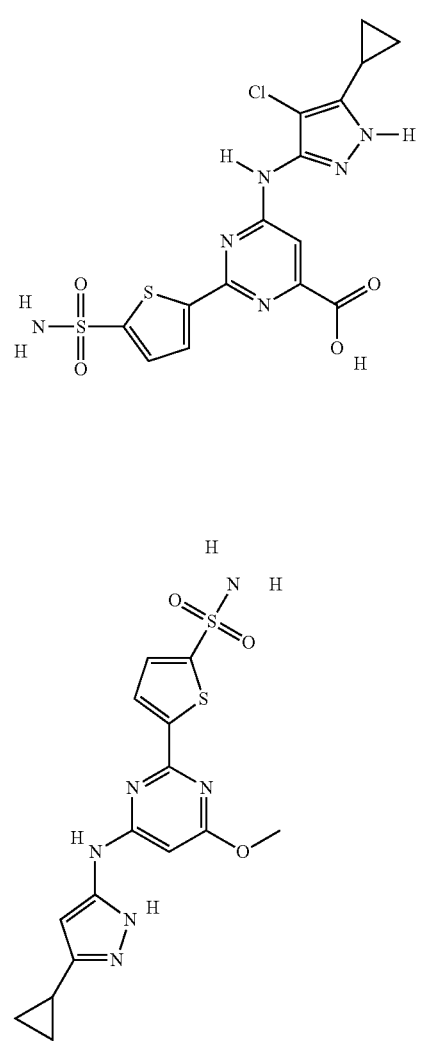
292
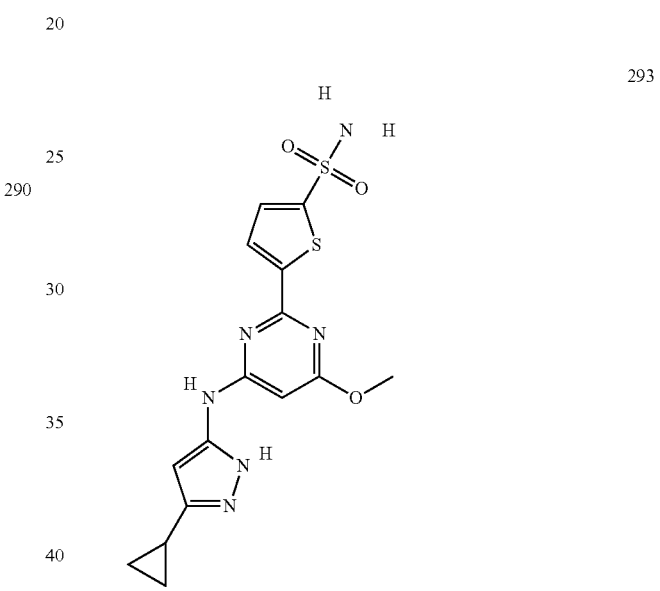
293
290
291
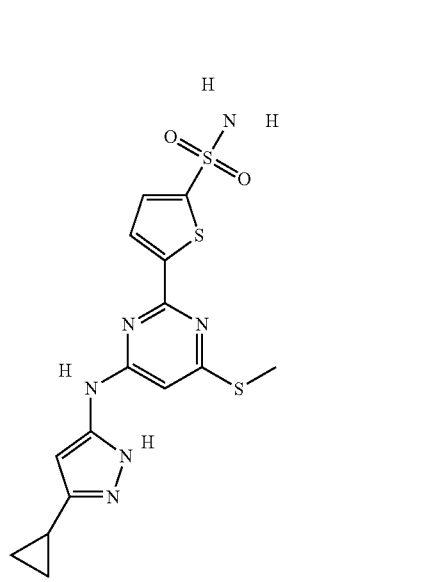
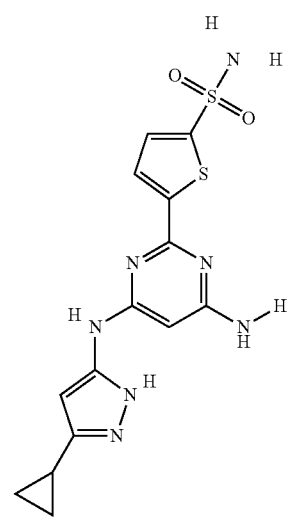
294

295 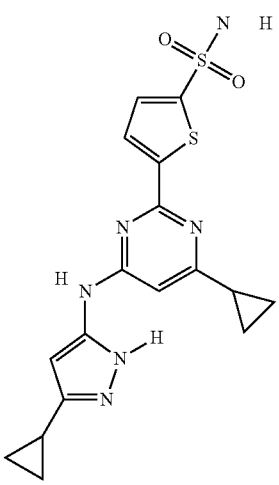
296 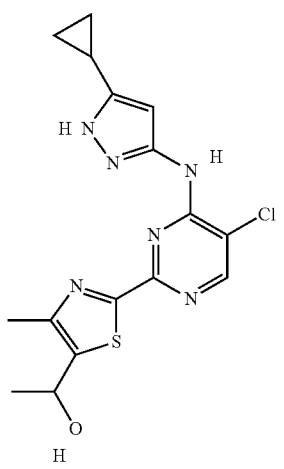
297 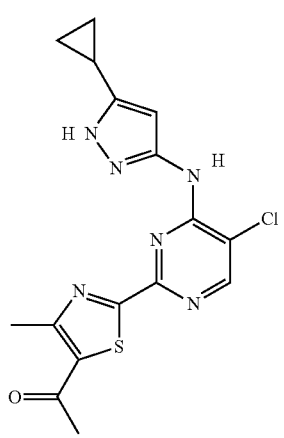
298 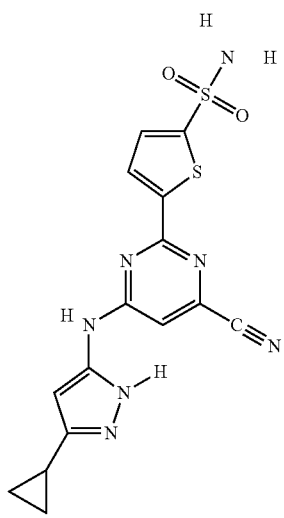
299 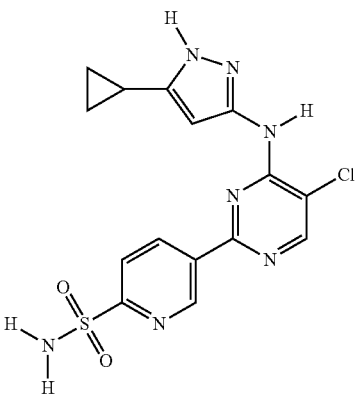
300 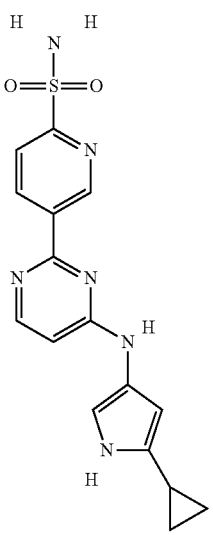

301 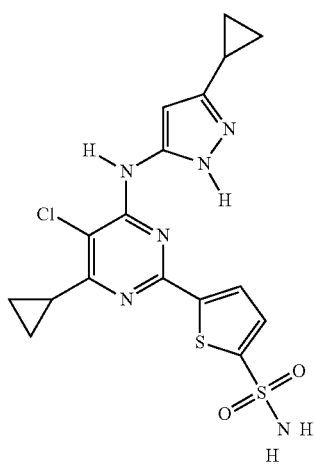
302 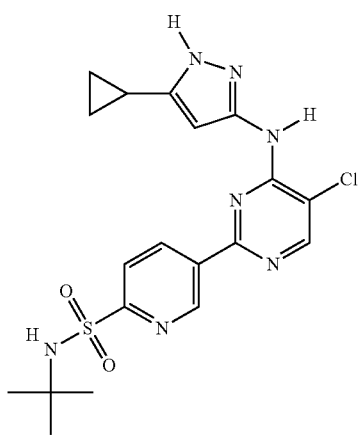
303 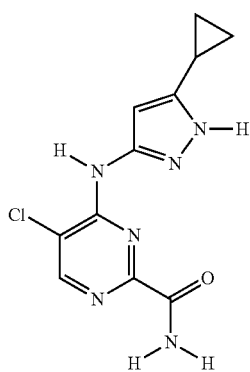
304 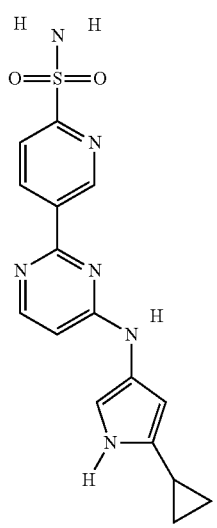
305 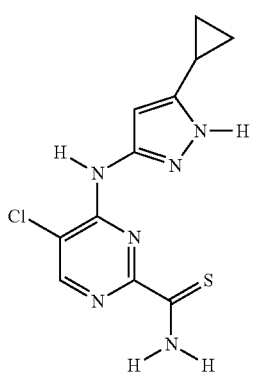
306 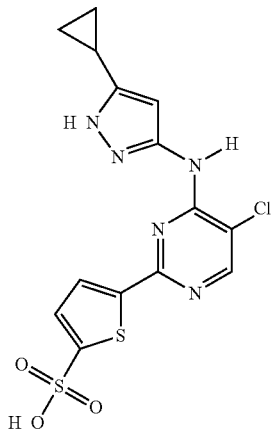
307 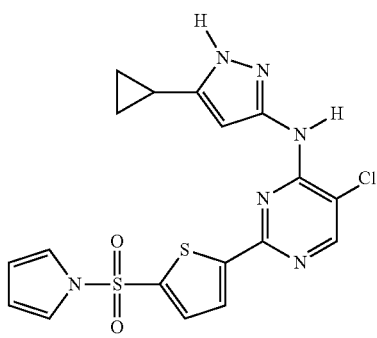

483
-continued
308
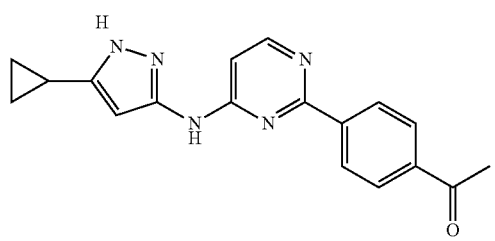
309
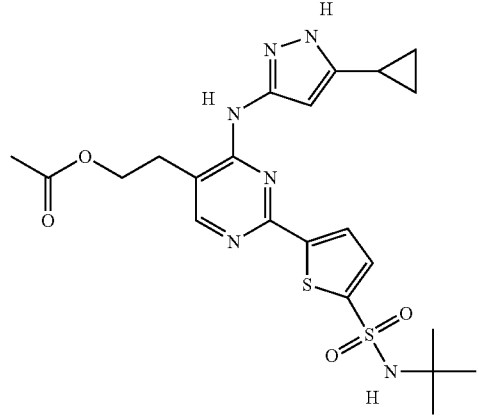
310
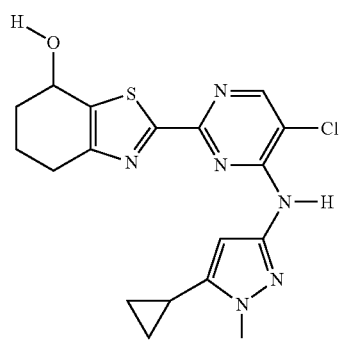
311
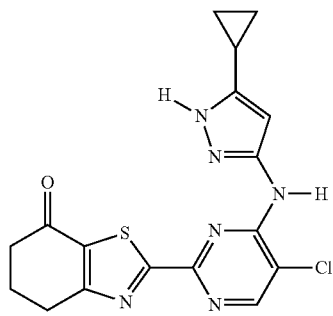
312
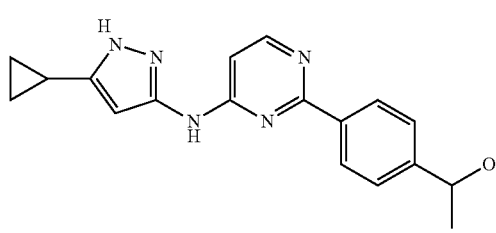
484
-continued
313
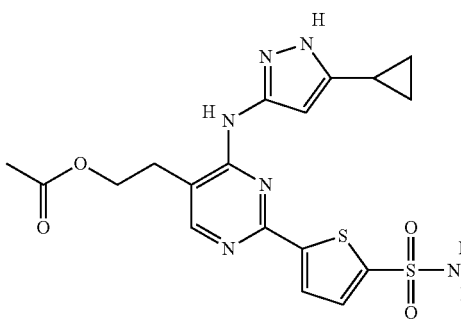
314
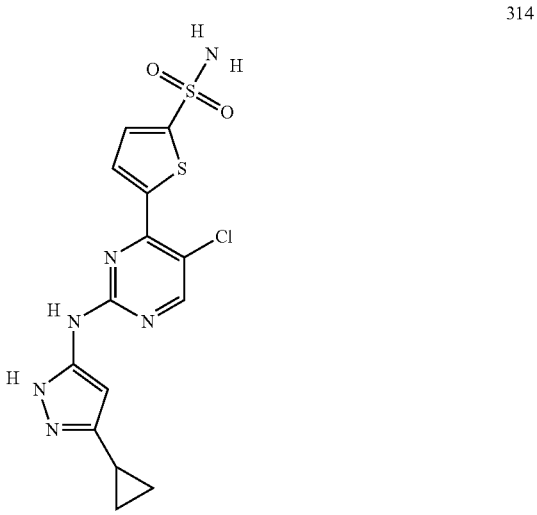
315
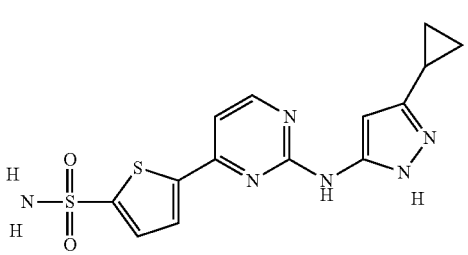
316
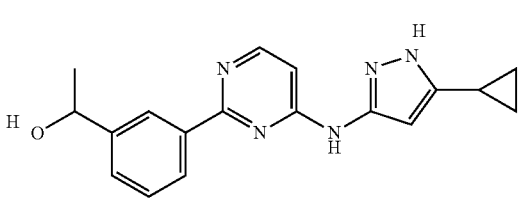
317
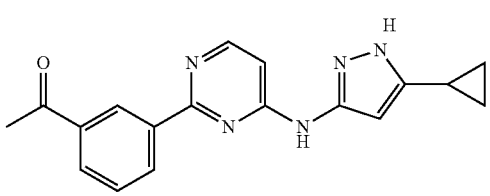

-continued
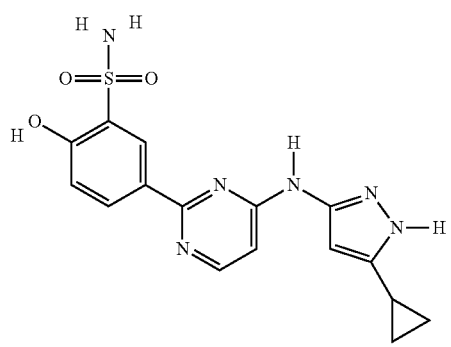
318
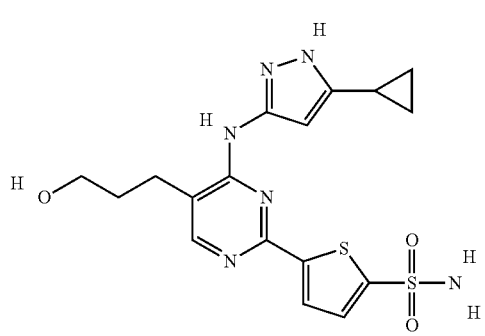
319
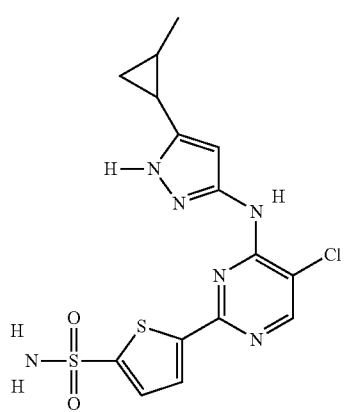
320
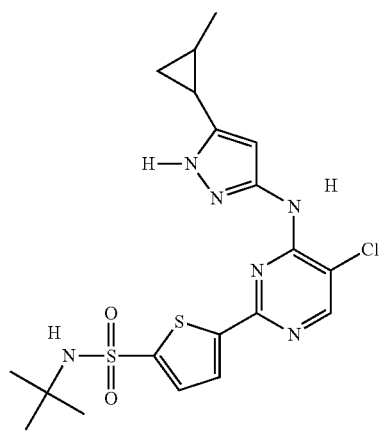
321
-continued
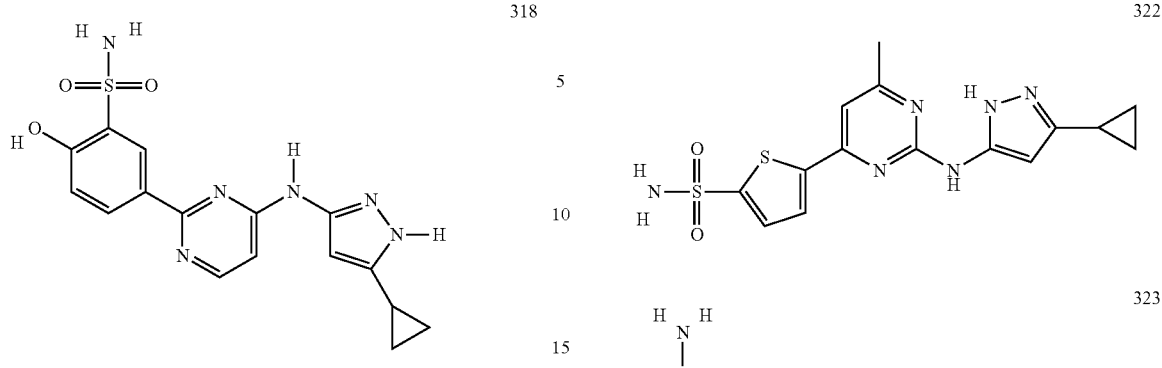
322
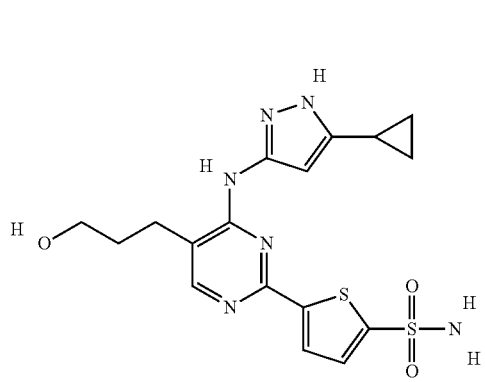
323
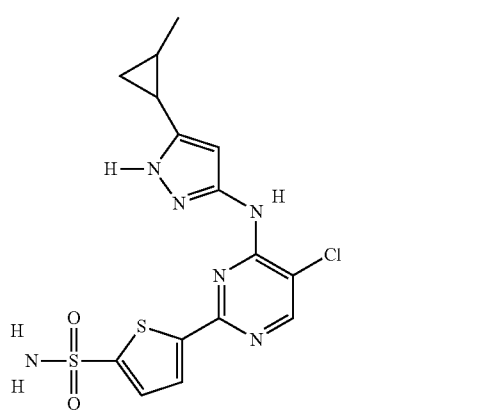
324
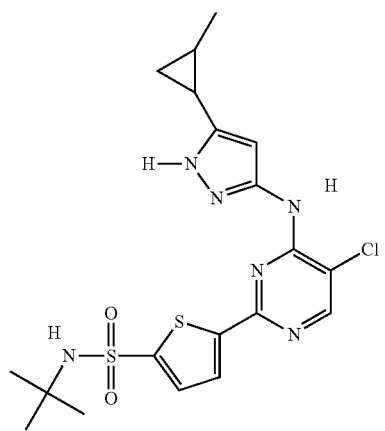
325

326

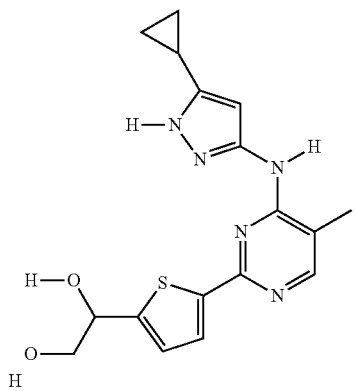

327

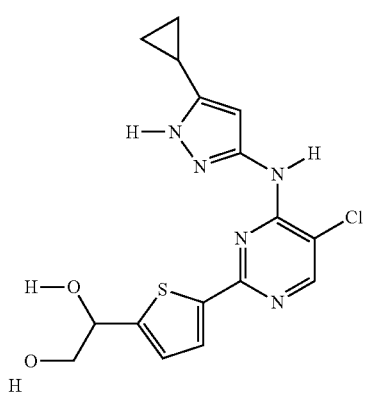

328

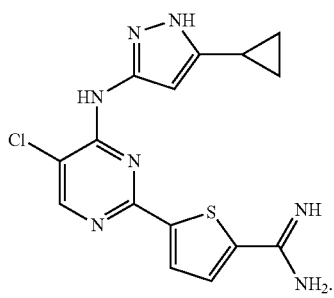

3. A compound of formula II:

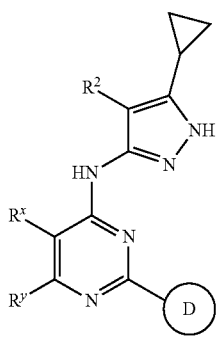

II or a pharmaceutically acceptable salt thereof, wherein:
Ring D is substituted at any substitutable ring carbon by $R^5$;
$R^x$ and $R^y$ are independently selected from T-$R^3$, or $R^x$ and $R^y$ are taken together with their intervening atoms to form a fused, unsaturated or partially unsaturated, 5-8 membered ring having 1-3 ring heteroatoms selected from oxygen, sulfur, or nitrogen, wherein any substitutable carbon on said fused ring is optionally and independently substituted by T-$R^3$, and any substitutable nitrogen on said ring is substituted by $R^4$;

T is a valence bond or a $C_{1-4}$ alkylidene chain;

$R^2$ is independently selected from —R, -T-W—$R^6$;

$R^3$ is selected from —R, -halo, =O, —OR, —C(=O)R, —CO$_2$R, —COCOR, —COCH$_2$COR, —NO$_2$, —CN, —S(O)R, —S(O)$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$ (optionally substituted $C_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$;

each R is independently selected from hydrogen or an optionally substituted group selected from $C_{1-6}$ aliphatic, $C_{6-10}$ aryl, a heteroaryl ring having 5-10 ring atoms, or a heterocyclyl ring having 5-10 ring atoms;

each $R^4$ is independently selected from —$R^7$, —COR$^7$, —CO$_2$ (optionally substituted $C_{1-6}$ aliphatic), —CON(R$^7$)$_2$, or —SO$_2$R$^7$, or two $R^4$ on the same nitrogen are taken together to form a 5-8 membered heterocyclyl or heteroaryl ring;

each $R^5$ is independently selected from —R, halo, —OR, —C(=O)R, —CO$_2$R, —COCOR, —NO$_2$, —CN, —S(O)R, —SO$_2$R, —SR, —N(R$^4$)$_2$, —CON(R$^4$)$_2$, —SO$_2$N(R$^4$)$_2$, —OC(=O)R, —N(R$^4$)COR, —N(R$^4$)CO$_2$ (optionally substituted $C_{1-6}$ aliphatic), —N(R$^4$)N(R$^4$)$_2$, —C=NN(R$^4$)$_2$, —C=N—OR, —N(R$^4$)CON(R$^4$)$_2$, —N(R$^4$)SO$_2$N(R$^4$)$_2$, —N(R$^4$)SO$_2$R, or —OC(=O)N(R$^4$)$_2$;

V is —O—, —S—, —SO—, —N(R$^6$)SO$_2$—, —SO$_2$N(R$^6$)—, —N(R$^6$)—, —CO—, —CO$_2$—, —N(R$^6$)CO—, —N(R$^6$)C(O)O—, —N(R$^6$)CON(R$^6$)—, —N(R$^6$)SO$_2$N(R$^6$)—, —N(R$^6$)N(R$^6$)—, —C(O)N(R$^6$)—, —OC(O)N(R$^6$)—, —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —C(R$^6$)$_2$N(R$^6$)C(O)—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, or —C(R$^6$)$_2$N(R$^6$)CON(R$^6$)—;

W is —C(R$^6$)$_2$O—, —C(R$^6$)$_2$S—, —C(R$^6$)$_2$SO—, —C(R$^6$)$_2$SO$_2$—, —C(R$^6$)$_2$SO$_2$N(R$^6$)—, —C(R$^6$)$_2$N(R$^6$)—, —CO—, —C(R$^6$)OC(O)—, —C(R$^6$)OC(O)N(R$^6$)—, —C(R$^6$)$_2$N(R$^6$)CO—, —C(R$^6$)$_2$N(R$^6$)C(O)O—, —C(R$^6$)=NN(R$^6$)—, —C(R$^6$)=N—O—, —C(R$^6$)$_2$N(R$^6$)N(R$^6$)—, —C(R$^6$)$_2$N(R$^6$)SO$_2$N(R$^6$)—, —C(R$^6$)$_2$N(R$^6$)CON(R$^6$)—, or —CON(R$^6$)—;

each $R^6$ is independently selected from hydrogen or an optionally substituted $C_{1-4}$ aliphatic group, or two $R^6$ groups on the same nitrogen atom are taken together with the nitrogen atom to form a 5-6 membered heterocyclyl or heteroaryl ring; and each $R^7$ is independently selected from hydrogen or an optionally substituted $C_{1-6}$ aliphatic group, or two $R^7$ on the same nitrogen are taken together with the nitrogen to form a 5-8 membered heterocyclyl ring or heteroaryl.

4. The compound in the method of claim 1, wherein:
Ring D is a phenyl, pyridinyl, piperidinyl, piperazinyl, furanyl, pyrrolidinyl, thienyl, 1,4-diazepane, 1,2,3,4-tetrahydropyridinyl, azepanyl, morpholinyl, thiazolyl, 1,2,3,4-tetrahydroisoquinolinyl, 1,2,3,4-tetrahydroquinolinyl, 2,3-dihydro-1H-isoindolyl, 1H-indolyl, 2,3-dihydro-1H-indolyl, isoquinolinyl, quinolinyl, or naphthyl ring.

5. The compound in the method of claim 1, wherein:

Ring D is pyridinyl, piperidinyl, piperazinyl, furanyl, pyrrolidinyl, thienyl, 1,4-diazepane, 1,2,3,4-tetrahydropyridinyl, azepanyl, morpholinyl, thiazolyl, 1,2,3,4-tetrahydroisoquinolinyl, 1,2,3,4-tetrahydroquinolinyl, 2,3-dihydro-1H-isoindolyl, 1H-indolyl, 2,3-dihydro-1H-indolyl, isoquinolinyl, quinolinyl, or naphthyl ring.

6. The compound in the method of claim 1, wherein: Ring D is a 5-7 membered monocyclic ring selected from heteroaryl, heterocyclyl or carbocyclyl, said heteroaryl or heterocyclyl ring having 1-4 ring heteroatoms selected from nitrogen, oxygen or sulfur, wherein Ring D is independently substituted at any substitutable ring carbon by oxo or —$R^5$, and at any substitutable ring nitrogen by —$R^4$.

7. The compound in the method of claim 1 or the compound of claim 3, wherein Ring D is substituted with —($C_{1-6}$ aliphatic), —$R^8SO_2N(R^1)_2$, —$R^8SO_2N(R^1)_2NR$, —$R^8SO_2OR$, —$R^8SO_2R$, —$R^8SOR$, —$R^8NR_2$, —C(O)R, —C(R)$_2$—OH, —C(OH)($C_{1-6}$ aliphatic)C(O)$_2$R, —C(=O)$R^8N(R)_2$, —($C_{1-3}$ aliphatic)-O—C(O)R, —NO$_2$, —$R^8C(O)_2R$, —C(NH)(NH$_2$), —$R^3$, —C(=O)C(=O)$R^4$R and —C(=O)C(=O)OR, wherein $R^8$ is a bond, —NR— or —($C_{1-6}$ aliphatic)N(R)—.

8. The compound of claim 3, wherein:
a) Ring D is substituted with —$R^8SO_2N(R^1)_2$, —C(O)R or —C(R)$_2$—OH; and
b) $R^8$ is a bond.

9. The compound of claim 3, wherein:
a) Ring D is substituted with —$R^8SO_2N(R^1)_2$; and
b) $R^8$ is a bond.

10. The compound of claim 3, wherein:
a) Ring D is substituted with —C(R)$_2$—OH; and
b) $R^8$ is a bond.

11. A composition for treating tuberculosis comprising a compound in the method of claim 1 and a pharmaceutically acceptable excipient.

12. The composition according to claim 11 further comprising a second therapeutic agent.

13. A method for treating tuberculosis, comprising administering to a subject a therapeutically effective amount of the compound in the method of claim 1, the compound of claim 3 or the composition according to claim 11, wherein the compound or the composition inhibits PknB kinase activity.

14. The compound of claim 3, selected from the following compounds, or a pharmaceutically acceptable salt thereof:

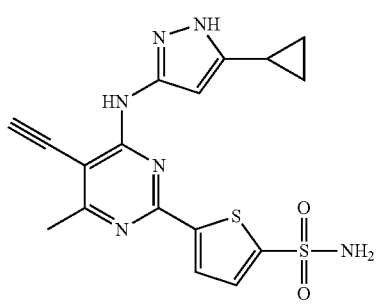

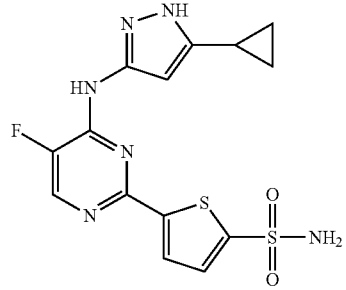

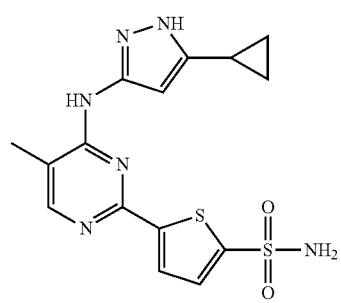

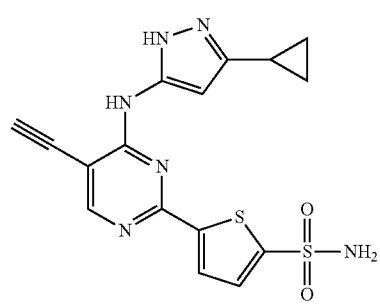

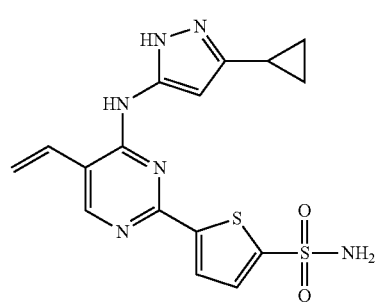

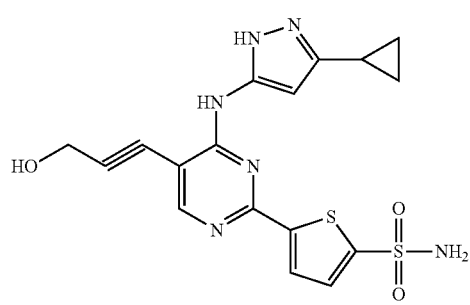

-continued
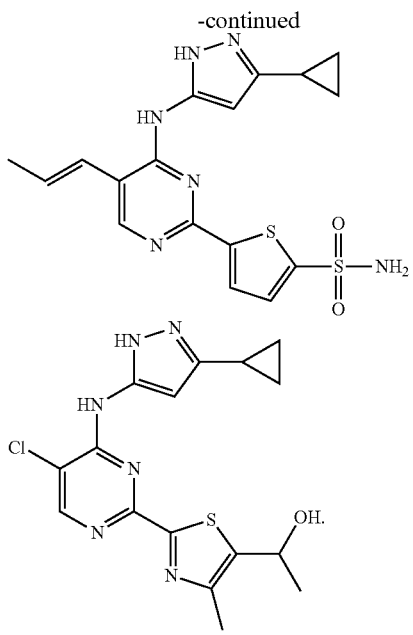
15. A composition for treating tuberculosis comprising a compound in claim 3 and a pharmaceutically acceptable excipient.
16. The composition according to claim 15, further comprising a second therapeutic agent.